(12) United States Patent
Andrews et al.

(10) Patent No.: US 12,037,346 B2
(45) Date of Patent: Jul. 16, 2024

(54) AMINO-SUBSTITUTED HETEROARYLS FOR TREATING CANCERS WITH EGFR MUTATIONS

(71) Applicant: Nuvalent, Inc., Cambridge, MA (US)

(72) Inventors: Kristin Lynne Andrews, Concort, MA (US); Baudouin Gerard, Arlington, MA (US); Joshua Courtney Horan, Somerville, MA (US); Scot Richard Mente, Arlington, MA (US); Henry Efrem Pelish, Newton, MA (US); Matthew D. Shair, Lexington, MA (US); Yuting Sun, Wellesley, MA (US); Anupong Tangpeerachaikul, Cambridge, MA (US)

(73) Assignee: Nuvalent, Inc., Cambridge, MA (US)

( * ) Notice: Subject to any disclaimer, the term of this patent is extended or adjusted under 35 U.S.C. 154(b) by 0 days.

(21) Appl. No.: 17/718,381

(22) Filed: Apr. 12, 2022

(65) Prior Publication Data
US 2022/0363696 A1    Nov. 17, 2022

Related U.S. Application Data

(60) Provisional application No. 63/292,605, filed on Dec. 22, 2021, provisional application No. 63/242,837, filed on Sep. 10, 2021, provisional application No. 63/239,089, filed on Aug. 31, 2021, provisional application No. 63/174,177, filed on Apr. 13, 2021.

(51) Int. Cl.
| | | |
|---|---|---|
| *A61K 31/4353* | (2006.01) | |
| *A61K 31/519* | (2006.01) | |
| *C07D 471/04* | (2006.01) | |
| *C07D 487/04* | (2006.01) | |
| *C07D 519/00* | (2006.01) | |

(52) U.S. Cl.
CPC ......... *C07D 519/00* (2013.01); *C07D 487/04* (2013.01)

(58) Field of Classification Search
CPC .............. A61K 31/4353; A61K 31/519; C07D 471/04; C07D 487/04
USPC ......... 514/262.1, 264.11, 300; 544/256, 279; 546/122
See application file for complete search history.

(56) References Cited

U.S. PATENT DOCUMENTS

| | | |
|---|---|---|
| 2,779,780 A | 1/1957 | Middleton |
| 4,172,896 A | 10/1979 | Uno et al. |
| 5,034,393 A | 7/1991 | Hackler et al. |
| 5,346,772 A | 9/1994 | Akiyama et al. |
| 5,350,749 A | 9/1994 | Hackler et al. |
| 5,358,970 A | 10/1994 | Ruff et al. |
| 5,407,938 A | 4/1995 | Fisher et al. |
| 5,427,798 A | 6/1995 | Ludwig et al. |
| 5,534,520 A | 7/1996 | Fisher et al. |
| 5,541,231 A | 7/1996 | Ruff et al. |
| 5,621,002 A | 4/1997 | Bosslet et al. |
| 5,654,307 A | 8/1997 | Bridges et al. |
| 5,679,683 A | 10/1997 | Bridges et al. |
| 5,707,989 A | 1/1998 | Himmelsbach et al. |
| 5,731,000 A | 3/1998 | Ruff et al. |
| 5,763,493 A | 6/1998 | Ruff et al. |
| 5,821,240 A | 10/1998 | Himmelsbach et al. |
| 5,852,029 A | 12/1998 | Fisher et al. |
| 5,861,510 A | 1/1999 | Piscopio et al. |
| 5,977,102 A | 11/1999 | Himmelsbach et al. |
| 6,084,095 A | 7/2000 | Bridges et al. |
| 6,110,973 A | 8/2000 | Young |
| 6,169,091 B1 | 1/2001 | Cockerill et al. |
| 6,174,889 B1 | 1/2001 | Cockerill et al. |
| 6,207,669 B1 | 3/2001 | Cockerill et al. |
| 6,232,312 B1 | 5/2001 | Pamukcu et al. |
| 6,265,410 B1 | 7/2001 | Bridges et al. |
| 6,284,764 B1 | 9/2001 | Kath et al. |

(Continued)

FOREIGN PATENT DOCUMENTS

| | | |
|---|---|---|
| AU | 2022271388 A1 | 12/2022 |
| CN | 1157619 A | 8/1997 |

(Continued)

OTHER PUBLICATIONS

US 9,062,058 B2, 06/2015, Chen et al. (withdrawn)
Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag Gmbh & Co. KGaA, 2005, Preface.*
Abuhelwa et al., 2022, "A comprehensive review on antibody-drug conjugates (ADCs) in the treatment landscape of non-small cell lung cancer (NSCLC)," Cancer Treatment Reviews, 106:102393.

(Continued)

*Primary Examiner* — Douglas M Willis
(74) *Attorney, Agent, or Firm* — Jones Day

(57) ABSTRACT

Disclosed are amino-substituted heteroaromatic compounds such as a compound of Formula (I):

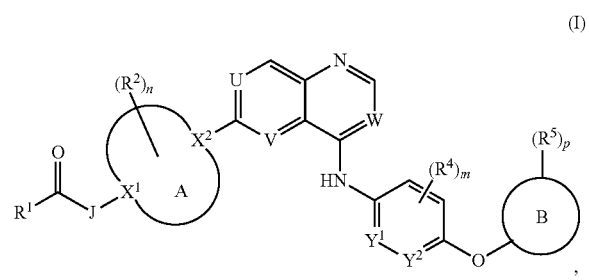

pharmaceutically acceptable salts of the compounds, and pharmaceutical compositions thereof. Also disclosed are methods of treating or preventing cancer using the amino-substituted heteroaromatic compounds, pharmaceutically acceptable salts of the compounds, and pharmaceutical compositions thereof.

43 Claims, 18 Drawing Sheets

(56) References Cited

U.S. PATENT DOCUMENTS

| | | |
|---|---|---|
| 6,313,292 B1 | 11/2001 | Showalter et al. |
| 6,395,733 B1 | 5/2002 | Arnold et al. |
| 6,413,971 B1 | 7/2002 | Arnold et al. |
| 6,455,534 B2 | 9/2002 | Bridges et al. |
| 6,465,449 B1 | 10/2002 | Kath et al. |
| 6,521,620 B1 | 2/2003 | Bridges et al. |
| 6,541,481 B2 | 4/2003 | Kath et al. |
| 6,583,124 B2 | 6/2003 | Asgharian |
| 6,589,947 B1 | 7/2003 | Hamanaka et al. |
| 6,596,726 B1 | 7/2003 | Bridges et al. |
| 6,680,384 B2 | 1/2004 | Belzer et al. |
| 6,713,484 B2 | 3/2004 | Bridges et al. |
| 6,713,485 B2 | 3/2004 | Carter et al. |
| 6,723,726 B1 | 4/2004 | Cockerill et al. |
| 6,727,256 B1 | 4/2004 | Carter et al. |
| 6,777,404 B2 | 8/2004 | Hamanaka et al. |
| 6,784,174 B1 | 8/2004 | Cumming |
| 6,849,734 B2 | 2/2005 | Belzer et al. |
| 6,867,201 B2 | 3/2005 | Kath et al. |
| 6,927,220 B2 | 8/2005 | Morris et al. |
| 7,030,242 B2 | 4/2006 | Noe et al. |
| 7,109,333 B2 | 9/2006 | Carter et al. |
| 7,132,438 B2 | 11/2006 | Frenkel et al. |
| 7,141,576 B2 | 11/2006 | Lackey et al. |
| 7,332,582 B2 | 2/2008 | Hardy et al. |
| 7,351,434 B2 | 4/2008 | Chern et al. |
| 7,488,802 B2 | 2/2009 | Collins et al. |
| 7,547,782 B2 | 6/2009 | Borzilleri et al. |
| 7,585,869 B2 | 9/2009 | Bhattacharya et al. |
| 7,632,947 B2 | 12/2009 | Jeong et al. |
| 7,648,986 B2 | 1/2010 | Nagarathnam et al. |
| 7,695,715 B2 | 4/2010 | Hardy et al. |
| 7,776,857 B2 | 8/2010 | Cee et al. |
| 7,829,574 B2 | 11/2010 | Su et al. |
| 7,858,623 B2 | 12/2010 | Kim et al. |
| 7,880,004 B2 | 2/2011 | Borzilleri et al. |
| 7,915,411 B2 | 3/2011 | Betebenner et al. |
| 7,943,743 B2 | 5/2011 | Korman et al. |
| 7,981,891 B2 | 7/2011 | Deak et al. |
| 7,982,036 B2 | 7/2011 | Singh et al. |
| 7,989,465 B2 | 8/2011 | Singh et al. |
| 8,008,449 B2 | 8/2011 | Korman et al. |
| 8,088,794 B2 | 1/2012 | Kim et al. |
| 8,129,357 B2 | 3/2012 | Chern et al. |
| 8,168,179 B2 | 5/2012 | Honjo et al. |
| 8,217,149 B2 | 7/2012 | Irving et al. |
| 8,236,950 B2 | 8/2012 | Betebenner et al. |
| 8,293,897 B2 | 10/2012 | Xi |
| 8,299,117 B2 | 10/2012 | Tokahiki et al. |
| 8,329,901 B2 | 12/2012 | Singh et al. |
| 8,354,509 B2 | 1/2013 | Carven et al. |
| 8,426,585 B2 | 4/2013 | Xi |
| 8,444,988 B2 | 5/2013 | Lackey et al. |
| 8,445,498 B2 | 5/2013 | Singh et al. |
| 8,460,927 B2 | 6/2013 | Chen |
| 8,513,262 B2 | 8/2013 | Carter et al. |
| 8,541,424 B2 | 9/2013 | DeGoey et al. |
| 8,552,154 B2 | 10/2013 | Freeman et al. |
| 8,552,156 B2 | 10/2013 | Takayanagi et al. |
| 8,557,816 B2 | 10/2013 | Geuns-Meyer et al. |
| 8,569,316 B2 | 10/2013 | Ettmayer et al. |
| 8,648,087 B2 | 2/2014 | Lyssikatos et al. |
| 8,653,087 B2 | 2/2014 | Mantoulidis et al. |
| 8,680,114 B2 | 3/2014 | Mitchell et al. |
| 8,685,983 B2 | 4/2014 | Kim et al. |
| 8,686,119 B2 | 4/2014 | Rotem-Yehudar et al. |
| 8,703,771 B2 | 4/2014 | Yang et al. |
| 8,735,553 B1 | 5/2014 | Li et al. |
| 8,748,601 B2 | 6/2014 | Taunton et al. |
| 8,748,606 B2 | 6/2014 | Singh et al. |
| 8,779,108 B2 | 7/2014 | Queva et al. |
| 8,841,418 B2 | 9/2014 | Karsunky et al. |
| 8,889,666 B2 | 11/2014 | Sagara et al. |
| 8,907,053 B2 | 12/2014 | Sasikumar et al. |
| 8,912,205 B2 | 12/2014 | Carter et al. |
| 8,927,697 B2 | 1/2015 | Davis et al. |
| 8,993,731 B2 | 3/2015 | Tyson |
| 9,040,541 B2 | 5/2015 | Singh et al. |
| 9,102,727 B2 | 8/2015 | Freeman et al. |
| 9,163,017 B2 | 10/2015 | Degoey et al. |
| 9,163,087 B2 | 10/2015 | Kuchroo et al. |
| 9,175,082 B2 | 11/2015 | Zhou et al. |
| 9,199,973 B2 | 12/2015 | Carter et al. |
| 9,205,148 B2 | 12/2015 | Langermann et al. |
| 9,242,991 B2 | 1/2016 | Hu et al. |
| 9,244,059 B2 | 1/2016 | Triebel et al. |
| 9,296,704 B2 | 3/2016 | Singh et al. |
| 9,393,246 B2 | 7/2016 | Singh et al. |
| 9,500,790 B2 | 11/2016 | Fujisawa et al. |
| 9,505,839 B2 | 11/2016 | Lonberg et al. |
| 9,650,386 B2 | 5/2017 | Uno et al. |
| 9,693,989 B2 | 7/2017 | Lyssikatos et al. |
| 9,758,526 B2 | 9/2017 | Uno et al. |
| 9,815,797 B2 | 11/2017 | Alexander et al. |
| 10,077,271 B2 | 9/2018 | Grembecka et al. |
| 10,174,041 B2 | 1/2019 | Grembecka et al. |
| 10,435,402 B2 | 10/2019 | Mukhopadhyay et al. |
| 10,519,193 B2 | 12/2019 | Wang et al. |
| 10,683,304 B2 | 6/2020 | Long |
| 10,711,000 B2 | 7/2020 | Jin et al. |
| 10,780,073 B2 | 9/2020 | Lyssikatos et al. |
| 10,822,334 B2 | 11/2020 | Li et al. |
| 10,828,305 B2 | 11/2020 | Xia et al. |
| 10,829,491 B2 | 11/2020 | Zhang et al. |
| 11,040,972 B2 | 6/2021 | Jin et al. |
| 11,466,000 B2 | 10/2022 | Lee et al. |
| 11,542,278 B1 | 1/2023 | Horan et al. |
| 2001/0041673 A1 | 11/2001 | Fossa |
| 2002/0082420 A1 | 11/2002 | Himmelsbach et al. |
| 2003/0207878 A1 | 11/2003 | Hennequin |
| 2004/0038856 A1 | 2/2004 | Chakravarty et al. |
| 2004/0146509 A1 | 7/2004 | Li et al. |
| 2005/0004074 A1 | 1/2005 | Lyons et al. |
| 2005/0031697 A1 | 2/2005 | Vehige et al. |
| 2005/0059744 A1 | 3/2005 | Donello et al. |
| 2005/0080056 A1 | 4/2005 | Horn |
| 2005/0101617 A1 | 5/2005 | Wallace et al. |
| 2006/0074102 A1 | 4/2006 | Cusack et al. |
| 2006/0148819 A1 | 7/2006 | Hennequin |
| 2006/0167026 A1 | 7/2006 | Nawa et al. |
| 2006/0188498 A1 | 8/2006 | Ashkenazi |
| 2009/0155247 A1 | 6/2009 | Ashkenazi |
| 2010/0216788 A1 | 8/2010 | Ishikawa et al. |
| 2010/0234351 A1 | 9/2010 | Seto et al. |
| 2011/0104161 A1 | 5/2011 | Burgess et al. |
| 2011/0224155 A1 | 9/2011 | Tachdjian et al. |
| 2011/0281908 A1 | 11/2011 | Sun et al. |
| 2012/0189573 A1 | 7/2012 | Ashkenazi |
| 2013/0023531 A1 | 1/2013 | Mantoulidis et al. |
| 2014/0243339 A1 | 8/2014 | Burgess et al. |
| 2014/0336182 A1 | 11/2014 | Cee et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2016/0108123 A1 | 4/2016 | Freeman et al. |
| 2017/0174679 A1 | 6/2017 | Lajkiewicz et al. |
| 2017/0174695 A1 | 6/2017 | Gollner et al. |
| 2018/0093955 A1 | 4/2018 | Jones et al. |
| 2019/0262345 A1 | 8/2019 | Miyadera et al. |
| 2019/0290637 A1 | 9/2019 | Engelhardt et al. |
| 2019/0352420 A1 | 11/2019 | Hofmann et al. |
| 2019/0358230 A1 | 11/2019 | Gmachl et al. |
| 2020/0085944 A1 | 3/2020 | Heidenreich et al. |
| 2020/0190091 A1 | 6/2020 | Xia et al. |
| 2020/0253975 A1 | 8/2020 | Abe et al. |
| 2020/0290978 A1 | 9/2020 | Nathanson et al. |
| 2020/0291020 A1 | 9/2020 | Engelhardt et al. |
| 2020/0291024 A1 | 9/2020 | Gallatin et al. |
| 2020/0377476 A1 | 12/2020 | Boese et al. |
| 2020/0407357 A1 | 12/2020 | Lajkiewicz et al. |
| 2021/0008023 A1 | 1/2021 | Lyssikatos et al. |
| 2021/0009581 A1 | 1/2021 | Routier et al. |
| 2021/0040099 A1 | 2/2021 | Bannen et al. |
| 2021/0040114 A1 | 2/2021 | Zhang et al. |

(56) References Cited

U.S. PATENT DOCUMENTS

| | | |
|---|---|---|
| 2021/0085796 A1 | 3/2021 | Deacon et al. |
| 2021/0261532 A1 | 8/2021 | Lennek et al. |
| 2021/0308134 A1 | 10/2021 | Hata et al. |
| 2021/0347785 A1 | 11/2021 | Zhang et al. |
| 2021/0359226 A1 | 11/2021 | Ko et al. |
| 2021/0386742 A1 | 12/2021 | Zhou et al. |
| 2022/0088162 A1 | 3/2022 | Wollmann et al. |
| 2022/0098212 A1 | 3/2022 | Horan et al. |
| 2022/0111028 A1 | 4/2022 | Rossi et al. |
| 2022/0133734 A1 | 5/2022 | Engelhardt et al. |
| 2023/0012273 A1 | 1/2023 | Boettcher et al. |
| 2023/0043863 A1 | 2/2023 | Zeng et al. |
| 2023/0076627 A1 | 3/2023 | Horan et al. |
| 2023/0107663 A1 | 4/2023 | Horan et al. |
| 2023/0124705 A1 | 4/2023 | Chen et al. |
| 2023/0227470 A1 | 7/2023 | Broeker et al. |
| 2023/0322753 A1 | 10/2023 | Lee et al. |

FOREIGN PATENT DOCUMENTS

| | | |
|---|---|---|
| CN | 101575333 A | 11/2009 |
| CN | 102086211 A | 6/2011 |
| CN | 102558147 A | 7/2012 |
| CN | 104876912 A | 9/2015 |
| CN | 102887891 B | 3/2016 |
| CN | 107141293 A | 9/2017 |
| CN | 108490184 A | 9/2018 |
| CN | 109422755 A | 3/2019 |
| CN | 109912572 A | 6/2019 |
| CN | 112079830 A | 12/2020 |
| CN | 112105618 A | 12/2020 |
| CN | 112574208 A | 3/2021 |
| CN | 113861195 A | 12/2021 |
| CN | 114539226 A | 5/2022 |
| CN | 114621207 A | 6/2022 |
| CN | 115052878 A | 9/2022 |
| CN | 115052881 A | 9/2022 |
| EP | 405602 A | 1/1991 |
| EP | 0606046 A1 | 7/1994 |
| EP | 0780386 A1 | 6/1997 |
| EP | 0818442 A2 | 1/1998 |
| EP | 0931788 A2 | 7/1999 |
| EP | 0945864 A2 | 9/1999 |
| EP | 1004578 A2 | 5/2000 |
| EP | 1971601 B1 | 10/2009 |
| EP | 3101032 A1 | 12/2016 |
| EP | 3424928 A1 | 9/2019 |
| FR | 3713 M | 1/1996 |
| GB | 9912961 A | 6/1999 |
| JP | 2009-046453 A | 3/2009 |
| WO | WO 1990/005719 | 5/1990 |
| WO | WO 1993/017681 A1 | 9/1993 |
| WO | WO 1993/017682 A1 | 9/1993 |
| WO | WO 1995/003303 A2 | 2/1995 |
| WO | WO 1995/019774 A1 | 7/1995 |
| WO | WO 1995/019970 A1 | 7/1995 |
| WO | WO 1996/007657 A1 | 3/1996 |
| WO | WO 1996/027583 | 9/1996 |
| WO | WO 1996/040142 A1 | 12/1996 |
| WO | WO 1997/013771 A1 | 4/1997 |
| WO | WO-1997/013771 A1 | 4/1997 |
| WO | WO 1997/026259 A1 | 7/1997 |
| WO | WO 1997/032880 A1 | 9/1997 |
| WO | WO 1997/032881 A1 | 9/1997 |
| WO | WO 1997/032882 A1 | 9/1997 |
| WO | WO-1998/002437 A1 | 1/1998 |
| WO | WO 1998/002437 A1 | 1/1998 |
| WO | WO 1998/002438 A1 | 1/1998 |
| WO | WO 1998/003516 | 1/1998 |
| WO | WO 1998/007697 | 2/1998 |
| WO | WO 1998/023613 A1 | 6/1998 |
| WO | WO 1998/027061 A1 | 6/1998 |
| WO | WO 1998/030566 | 7/1998 |
| WO | WO 1998/033768 | 8/1998 |
| WO | WO 1998/034915 | 8/1998 |
| WO | WO 1998/034918 | 8/1998 |
| WO | WO 1999/007675 | 2/1999 |
| WO | WO 1999/029667 | 6/1999 |
| WO | WO 1999/033172 | 7/1999 |
| WO | WO 1999/035146 A1 | 7/1999 |
| WO | WO 1999/052889 | 10/1999 |
| WO | WO 1999/052910 | 10/1999 |
| WO | WO 2000/035436 | 6/2000 |
| WO | WO 2000/044728 A1 | 8/2000 |
| WO | WO 2000/055162 A2 | 9/2000 |
| WO | WO 2000/056738 A1 | 9/2000 |
| WO | WO 2002/006213 | 1/2002 |
| WO | WO 2002/012227 A2 | 2/2002 |
| WO | WO 2002/056912 A2 | 7/2002 |
| WO | WO 2002/066470 | 8/2002 |
| WO | WO 2002/079202 A1 | 10/2002 |
| WO | WO 2003/059913 A1 | 7/2003 |
| WO | WO 2003/064383 | 8/2003 |
| WO | WO 2003/076424 | 9/2003 |
| WO | WO 2003/077914 | 9/2003 |
| WO | WO 2003/097615 A1 | 11/2003 |
| WO | WO 2004/010929 A2 | 2/2004 |
| WO | WO 2004/060400 A1 | 7/2004 |
| WO | WO 2004/106308 A1 | 12/2004 |
| WO | WO 2005/080377 A1 | 9/2005 |
| WO | WO 2005/110410 A2 | 11/2005 |
| WO | WO 2006/089015 A2 | 8/2006 |
| WO | WO 2006/116713 A1 | 11/2006 |
| WO | WO 2006/121168 | 11/2006 |
| WO | WO 2006/129199 A1 | 12/2006 |
| WO | WO 2007/014011 | 2/2007 |
| WO | WO 2007/035428 A1 | 3/2007 |
| WO | WO 2007/041379 A1 | 4/2007 |
| WO | WO 2007/059257 A2 | 5/2007 |
| WO | WO 2007/064045 A1 | 6/2007 |
| WO | WO 2007/081517 A2 | 7/2007 |
| WO | WO 2007/084786 | 7/2007 |
| WO | WO 2007/097470 A2 | 8/2007 |
| WO | WO 2008/086462 | 7/2008 |
| WO | WO 2008/124083 A2 | 10/2008 |
| WO | WO 2008/132601 | 11/2008 |
| WO | WO 2008/133753 A2 | 11/2008 |
| WO | WO 2009/036082 | 3/2009 |
| WO | WO 2009/044273 | 4/2009 |
| WO | WO 2009/055730 | 4/2009 |
| WO | WO 2009/114335 | 9/2009 |
| WO | WO 2009/137797 A2 | 11/2009 |
| WO | WO 2009/140549 A1 | 11/2009 |
| WO | WO 2010/019570 | 2/2010 |
| WO | WO 2010/026262 A1 | 3/2010 |
| WO | WO 2010/027827 | 3/2010 |
| WO | WO 2010/042489 A2 | 4/2010 |
| WO | WO 2010/045095 A1 | 4/2010 |
| WO | WO 2010/051373 | 5/2010 |
| WO | WO 2010/075376 A2 | 7/2010 |
| WO | WO 2010/094695 A1 | 8/2010 |
| WO | WO 2010/123870 A1 | 10/2010 |
| WO | WO 2011/066342 | 6/2011 |
| WO | WO 2011/146401 A1 | 11/2011 |
| WO | WO 2011/159297 A1 | 12/2011 |
| WO | WO 2012/006960 A1 | 1/2012 |
| WO | WO 2012/101238 A1 | 8/2012 |
| WO | WO-2012/125668 A1 | 9/2012 |
| WO | WO 2012/125668 A1 | 9/2012 |
| WO | WO 2012/145493 | 10/2012 |
| WO | WO 2013/033981 A1 | 3/2013 |
| WO | WO 2013/079174 | 6/2013 |
| WO | WO 2013/118817 A1 | 8/2013 |
| WO | WO 2014/022758 | 2/2014 |
| WO | WO 2014/055897 | 4/2014 |
| WO | WO 2014/100079 | 6/2014 |
| WO | WO 2014/140180 | 9/2014 |
| WO | WO 2014/179664 | 11/2014 |
| WO | WO 2014/194302 | 12/2014 |
| WO | WO 2014/209804 | 12/2014 |
| WO | WO 2015/061668 | 4/2015 |
| WO | WO 2015/081158 | 6/2015 |
| WO | WO 2015/085238 A1 | 6/2015 |
| WO | WO 2015/085847 | 6/2015 |

(56) References Cited

FOREIGN PATENT DOCUMENTS

| | | |
|---|---|---|
| WO | WO 2015/086523 A1 | 6/2015 |
| WO | WO 2015/109124 | 7/2015 |
| WO | WO 2015/112800 | 7/2015 |
| WO | WO 2015/112805 | 7/2015 |
| WO | WO 2015/116539 | 8/2015 |
| WO | WO 2015/175632 A1 | 11/2015 |
| WO | WO 2015/181342 | 12/2015 |
| WO | WO 2015/195163 | 12/2015 |
| WO | WO 2015/195228 A1 | 12/2015 |
| WO | WO 2015/200119 | 12/2015 |
| WO | WO 2016/000619 | 1/2016 |
| WO | WO 2016/028672 | 2/2016 |
| WO | WO 2016/071448 | 5/2016 |
| WO | WO 2016/092419 | 6/2016 |
| WO | WO 2016/110821 A1 | 7/2016 |
| WO | WO 2016/111947 | 7/2016 |
| WO | WO 2016/128908 A1 | 8/2016 |
| WO | WO 2016/144803 | 9/2016 |
| WO | WO 2016/161270 | 10/2016 |
| WO | WO 2016/183278 A1 | 11/2016 |
| WO | WO 2016/191471 A1 | 12/2016 |
| WO | WO 2016/195776 A1 | 12/2016 |
| WO | WO 2017/070565 A1 | 4/2017 |
| WO | WO 2017/112730 A1 | 6/2017 |
| WO | WO 2017/148391 A1 | 9/2017 |
| WO | WO 2018/200412 A1 | 11/2018 |
| WO | WO 2018/215557 A1 | 11/2018 |
| WO | WO 2018/228275 A1 | 12/2018 |
| WO | WO 2019/042409 A1 | 3/2019 |
| WO | WO 2019/046775 A1 | 3/2019 |
| WO | WO 2019/046778 A1 | 3/2019 |
| WO | WO 2019/067543 A1 | 4/2019 |
| WO | WO 2019/081486 A1 | 5/2019 |
| WO | WO-2019/122129 A1 | 6/2019 |
| WO | WO 2019/148036 A1 | 8/2019 |
| WO | WO 2019/149164 A1 | 8/2019 |
| WO | WO 2019/163865 | 8/2019 |
| WO | WO 2019/165358 A1 | 8/2019 |
| WO | WO 2019/170088 A1 | 9/2019 |
| WO | WO 2019/177374 A1 | 9/2019 |
| WO | WO 2019/177375 A1 | 9/2019 |
| WO | WO 2019/214634 A1 | 11/2019 |
| WO | WO 2019/222093 A1 | 11/2019 |
| WO | WO 2019/226991 A1 | 11/2019 |
| WO | WO 2019/228403 A1 | 12/2019 |
| WO | WO 2019/241715 A1 | 12/2019 |
| WO | WO 2020/009156 A1 | 1/2020 |
| WO | WO 2020/025030 A1 | 2/2020 |
| WO | WO 2020/033413 A2 | 2/2020 |
| WO | WO 2020/057511 A1 | 3/2020 |
| WO | WO 2020/061470 A1 | 3/2020 |
| WO | WO 2020/068867 A1 | 4/2020 |
| WO | WO 2020/068873 A1 | 4/2020 |
| WO | WO 2020/098723 A1 | 5/2020 |
| WO | WO 2020/138400 A1 | 7/2020 |
| WO | WO 2020/190119 A1 | 9/2020 |
| WO | WO 2020/190765 A2 | 9/2020 |
| WO | WO 2020/216781 A1 | 10/2020 |
| WO | WO 2020/219904 A1 | 10/2020 |
| WO | WO 2020/260252 A1 | 12/2020 |
| WO | WO 2021/030711 A1 | 2/2021 |
| WO | WO 2021/057796 A1 | 4/2021 |
| WO | WO 2021/057877 A1 | 4/2021 |
| WO | WO 2021/062327 A1 | 4/2021 |
| WO | WO 2021/127397 A1 | 6/2021 |
| WO | WO 2021/127456 A1 | 6/2021 |
| WO | WO 2021/133809 A1 | 7/2021 |
| WO | WO 2021/156178 A1 | 8/2021 |
| WO | WO 2021/156180 A1 | 8/2021 |
| WO | WO 2021/164697 A1 | 8/2021 |
| WO | WO 2021/179274 A1 | 9/2021 |
| WO | WO 2021/185348 A1 | 9/2021 |
| WO | WO 2021/198020 A1 | 10/2021 |
| WO | WO 2021/213800 A1 | 10/2021 |
| WO | WO 2021/226208 | 11/2021 |
| WO | WO 2021/226269 | 11/2021 |
| WO | WO 2021/231400 A1 | 11/2021 |
| WO | WO 2021/243596 A1 | 12/2021 |
| WO | WO 2022/002100 A1 | 1/2022 |
| WO | WO 2022/003575 A1 | 1/2022 |
| WO | WO 2022/006386 A1 | 1/2022 |
| WO | WO 2022/007841 A1 | 1/2022 |
| WO | WO 2022/012593 A1 | 1/2022 |
| WO | WO 2022/033410 A1 | 2/2022 |
| WO | WO 2022/033416 A1 | 2/2022 |
| WO | WO 2022/033455 A1 | 2/2022 |
| WO | WO 2022/037568 A1 | 2/2022 |
| WO | WO 2022/042755 A1 | 3/2022 |
| WO | WO 2022/055895 A1 | 3/2022 |
| WO | WO 2022/060196 A1 | 3/2022 |
| WO | WO 2022/066734 A1 | 3/2022 |
| WO | WO 2022/072632 A1 | 4/2022 |
| WO | WO 2022/072634 A1 | 4/2022 |
| WO | WO 2022/072645 A2 | 4/2022 |
| WO | WO 2022/076304 A1 | 4/2022 |
| WO | WO 2022/076671 A1 | 4/2022 |
| WO | WO 2022/076831 A2 | 4/2022 |
| WO | WO 2022/090481 A1 | 5/2022 |
| WO | WO 2022/094271 A1 | 5/2022 |
| WO | WO 2022/094354 A1 | 5/2022 |
| WO | WO 2022/094355 A1 | 5/2022 |
| WO | WO 2022/098992 A1 | 5/2022 |
| WO | WO 2022/101184 A1 | 5/2022 |
| WO | WO 2022/105882 A1 | 5/2022 |
| WO | WO 2022/105908 A1 | 5/2022 |
| WO | WO 2022/116995 A1 | 6/2022 |
| WO | WO 2022/139386 A1 | 6/2022 |
| WO | WO 2022/140769 A1 | 6/2022 |
| WO | WO 2022/146027 A1 | 7/2022 |
| WO | WO 2022/147150 A1 | 7/2022 |
| WO | WO 2022/166916 | 8/2022 |
| WO | WO 2022/170043 | 8/2022 |
| WO | WO 2022/170052 | 8/2022 |
| WO | WO 2022/171138 | 8/2022 |
| WO | WO 2022/191664 | 9/2022 |
| WO | WO 2022/192431 | 9/2022 |
| WO | WO 2022/194257 | 9/2022 |
| WO | WO 2022/194265 | 9/2022 |
| WO | WO 2022/197913 | 9/2022 |
| WO | WO 2022/206929 | 10/2022 |
| WO | WO 2022/212538 | 10/2022 |
| WO | WO 2022/221227 A1 | 10/2022 |
| WO | WO 2022/225238 | 10/2022 |
| WO | WO-2022221227 A1 * 10/2022 ........... C07D 487/04 |
| WO | WO 2022/234965 | 11/2022 |
| WO | WO 2022/237825 | 11/2022 |
| WO | WO 2022/245085 | 11/2022 |
| WO | WO 2022/251095 | 12/2022 |
| WO | WO 2022/266425 | 12/2022 |
| WO | WO 2022/266426 | 12/2022 |
| WO | WO 2022/266427 | 12/2022 |
| WO | WO 2022/266458 | 12/2022 |
| WO | WO 2022/269531 | 12/2022 |
| WO | WO 2022/271612 | 12/2022 |
| WO | WO 2022/271613 | 12/2022 |
| WO | WO 2022/271630 | 12/2022 |
| WO | WO 2022/271749 | 12/2022 |
| WO | WO 2022/271801 | 12/2022 |
| WO | WO 2022/271846 | 12/2022 |
| WO | WO 2023/287130 | 1/2023 |
| WO | WO 2023/011505 | 2/2023 |
| WO | WO 2023/014022 | 2/2023 |
| WO | WO 2023/015240 | 2/2023 |
| WO | WO 2023/028054 | 3/2023 |
| WO | WO 2023/056405 | 4/2023 |
| WO | WO 2023/056431 | 4/2023 |
| WO | WO 2023/066296 | 4/2023 |
| WO | WO 2023/077259 | 5/2023 |
| WO | WO 2023/081637 | 5/2023 |
| WO | WO 2023/099608 A1 | 6/2023 |
| WO | WO 2023/099612 A1 | 6/2023 |
| WO | WO 2023/099624 A1 | 6/2023 |
| WO | WO 2023/154124 A1 | 8/2023 |

(56) References Cited

FOREIGN PATENT DOCUMENTS

| | | |
|---|---|---|
| WO | WO 2023/173083 A1 | 9/2023 |
| WO | WO 2023/185793 A1 | 10/2023 |
| WO | WO 2023/195773 A1 | 10/2023 |

OTHER PUBLICATIONS

Adamo, et al., 1999, "An Improved Resolution of 2-Methyl Piperidine and Its Use in the Synthesis of Homochiral Trans-2,6-Dialkyl Piperidines," Synthetic Communications, 29(10): 1747-1756.
Aertgeerts et al., 2011, "Structural Analysis of the Mechanism of Inhibition and Allosteric Activation of the Kinase Domain of HER2 Protein," Journal of Biological Chemsistry, 286(21): 18756-18765.
Arcila et al., 2012, "Prevalence, Clinicopathologic Associations, and Molecular Spectrum of ERBB2 (HER2) Tyrosine Kinase Mutations in Lung Adenocarcinomas," Clinical Cancer Research, 18:4910-4918.
Arcila et al., 2013, "EGFRExon 20 Insertion Mutations in Lung Adenocarcinomas: Prevalence, Molecular Heterogeneity, and Clinicopathologic Characteristics," Molecular Cancer Therapeutics, 12(2).
Auliac et al., 2019, "Non-Small Cell Lung Cancer Patients Harboring HER2 Mutations: Clinical Characteristics and Management in a Real-Life Setting. Cohort HER2 Explore GFPC 02-14," Adv. Ther., 36(8):2161-2166.
Azar et al., 2021, "Spotlight on Trastuzumab Deruxteean (DS-8201, T-DXd) for HER2 Mutation Positive Non-Small Cell Lung Cancer," Lung Cancer: Targets and Therapy, 12:103-104.
Ben-Baruch et al., 2015, "HER2 mutated breast cancer responds to treatment with single agent neratinib, a second generation HER2/EGFR tyrosine kinase inhibitor," J. Natl. Comp. Cancer Netw., 13(9):1061-1064.
Bertotti et al., 2015, "The Genomic Landscape of Response to EGFR Blockade in Colorectal Cancer," Nature, 526(7572):263-267.
Borges et al., 2018, "Tucatinib Combined With Ado-Trastuzumab Emtansine in Advanced ERBB2/HER2-PositiveMetastatic Breast Cancer: A Phase 1b Clinical Trial," JAMA Oncol., 4(9):1214-1220.
Bose et al., 2013, "Activating HER2 Mutations in HER2 Gene Amplification Negative Breast Cancer," Cancer Discovery, 3(2): 224-237.
Burgos et al., 2006, "Significantly Improved Method for the Pd-Catalyzed Coupling of Phenols with Alyl Halides: Understanding Ligand Effects," Angew. Chem., 118:4427-4432.
Calikusu et al., 2009, "The effect of HER2 expression on cisplatin-based chemotherapy in advanced non-small cell lung cancer patients," Journal of Experimental & Clinical Cancer Research, 28:97.
Cao et al., 2022, "CHMFL-26 is a highly potent irreversible HER2 inhibitor for use in the treatment of HER2-positive and HER2-mutant cancers," Acta Pharmacologica Sinica, 0:1-9.
Castellano et al., 2019, "A Novel Acquired Exon 20 EGFR M766Q Mutation in Lung Adenocarcinoma Mediates Osimertinib Resistance but is Sensitive to Neratinib and Poziotinib," Journal of Thoracic Oncology, 14(11): 1982-1988.
Certified Copy of Priority Document, U.S. Appl. No. 63/208,901, filed Jun. 30, 2020.
Certified Copy of Priority Document, U.S. Appl. No. 63/046,506, filed Jun. 30, 2020.
Chmielecki et al., 2015, "OncogenicAlterations in ERBB2/HER2Represent Potential Therapeutic Targets Across Tumors From Diverse Anatomic Sites of Origin," The Oncologist, 20:7-12.
Cocco et al., 2018 "Neratinib is effective in breast tumors bearing both amplification and mutation of ERBB2 (HER2)," Science Signaling, 11:eaat9773.
Cocco et al., 2019, "Prevalence and role of HER2 mutations in cancer," Pharmacology & Therapeutics, 199: 188-196.
Collins et al., 2019, "Preclinical Characteristics of the Irreversible Pan-HER Kinase Inhibitor Neratinib Compared with Lapatinib: Implications for the Treatment of HER2-Positive and HER2-Mutated Breast Cancer," Cancers, 11:737.
Conlon et al., 2020, "Comparative analysis of drug response and gene profiling of HER2-targeted tyrosine kinase inhibitors," British Journal of Cancer, 124:1249-1259.
Connell and Doherty, 2017, "Activating HER2 mutations as emerging targets in multiple solid cancers," ESMO Open, 2:e000279.
Cooper and Gainor, 2022, "Human Epidermal Growth Factor Receptor 2—Mutant Non-Small-Cell Lung Cancer: Continued Progress But Challenges Remain," Journal of Clinical Oncology, 40(7):693-697.
Cornelissen, 2021, "Efficacy and Safety of Poziotinib in Treatment-naïve NSCLC Harboring HER2 exon 20 Mutations: A Multinational Phase 2 Study (ZENITH20-4)," Presentation at ESMO Congress, Erasmus MC.
Cortes et al., 2022, "Trastuzumab Deruxteean versus Trastuzumab Emtansine for Breast Cancer," New England Journal of Medicine, 386:1143-1154.
Costales et al., 2019, "A Designed Small Molecule Inhibitor of a Non-Coding RNA Sensitizes HER2 Negative Cancers to Herceptin," J. Am. Chem. Soc., 141(7):2960-2974.
Cristalli et al., 1995, "Synthesis and Biological Evaluation of N6-Cycloalkyl Derivatives of 1-Deazaadenine Nucleosides: A New Class of Anti-Human Immunodeficiency Virus Agents," J. Med. Chem., 38:4019-4025.
Cristau, et al., 2004, "A General and Mild UllmannType Synthesis of Diaryl Ethers," Organic Letters, 6(6): 913-916.
Croessmann et al., 2019, "Combined Blockade of Activating ERBB2 Mutations and ER Results in Synthetic Lethality of ER+/HER2 Mutant Breast Cancer," Clin. Cancer Res., 25(1):277-289.
D'Amato et al., 2015, "Mechanisms of lapatinib resistance in HER2-driven breast cancer," Cancer Treatment Reviews, 41:877-883.
Dantoing et al., 2021, "Anti-PD1/PD-L1 Immunotherapy for Non-Small Cell Lung Cancer with Actionable Oncogenic Driver Mutations," Int. J. Mol. Sci., 22:6288.
Doi et al., 2017, "Safety, pharmacokinetics, and antitumour activity of trastuzumab deruxtecan (DS-8201), a HER2-targeting antibody—drug conjugate, in patients with advanced breast and gastric or gastro-oesophageal tumours: a phase 1 dose-escalation study," Lancet Oncol., 18:1512-1522.
Dziadziuszko et al., 2019, "Afatinib in NSCLC With HER2 Mutations: Results of the Prospective, Open-Label Phase II Niche Trial of European Thoracic Oncology Platform (ETOP),"Journal of Throacic Oncology, 14(6):1086-1094.
Elamin et al., 2021, "Poziotimin for Patients With HER2 Exon 20 Mutant Non-Small-Cell Lung Cancer: Results From a Phase II Trial," Journal of Clinical Oncology, 40(7):702-709.
Elitzin et al., 2010, "Development of a New Synthesis for the Large-Scale Preparation of Triple Reuptake Inhibitor (−)-GSK1360707," Organic Process Research & Development, 14:912-917.
Elwaie et al., 2020, "HER2 Kinase-Targeted Breast Cancer Therapy: Design, Synthesis, and In Vitro and In Vivo Evaluation of Novel Lapatinib Congeners as Selective and Potent HER2 Inhibitors with Favorable Metabolic Stability," Journal of Medical Chemistry, 63(24): 15906-15945.
Estrada-Bernal et al., 2020, "Tarloxotinib Is a Hypoxia-Activated Pan-HER Kinase Inhibitor Active Against a Broad Range of HER-Family Oncogenes," Clinical Cancer Research, 27(5): 1463-1475.
Floc'h et al., 2018, "Anti-tumor activity of osimertinib, an irreversible mutant-selective EGFR tyrosine kinase inhibitor, in NSCLC harboring EGFR Exon 20 Insertions," Mol. Cancer Ther., 17(5): 885-896.
Friedlaender et al., 2022, "EGFR and HER2 exon 20 insertions in solid tumours: from biology to treatment," Nature Reviews, 19: 51-69.
Fui et al., 2020, "Recent Advancement of Ullmann Condensation Coupling Reaction in the Formation of Aryl-Oxygen(C—O) Bonding by Copper-Mediated Catalyst," Catalysts, 10:1103.
Gaibar et al., 2020, "Somatic Mutations in HER2 and Implications for Current Treatment Paradigms in HER2-Positive Breast Cancer," Journal of Oncology, 6375956.

(56) References Cited

OTHER PUBLICATIONS

Gontcharov et al., 2019, "Development of a Scalable Synthesis for an Inhaled pan-JAK Inhibitor," Org. Process Res. Dev., 23:1990-2000.
Greulich et al., 2012, "Functional analysis of receptor tyrosine kinase mutations in lung cancer identifies oncogenic extracellular domain mutations of ERBB2," PNAS, 109(36):14476-14481.
Hallberg and Palmer, 2013, "Mechanistic insight into ALK receptor tyrosine kinase in human cancer biology," Nature Reviews, 13:685-700.
Han et al., 2021, "Targeting HER2 Exon 20 Insertion-Mutant Lung Adenocarcinoma with a Novel Tyrosine Kinase Inhibitor Mobocertinib," Cancer Research, 81(20):5311-5324.
Hanker et al., 2017, "An Acquired HER2$^{T798I}$ Gatekeeper Mutation Induces Resistance to Neratinib in a Patient with HER2 Mutant-Driven Breast Cancer," Cancer Discovery, 7(6): 575-585.
Hanker et al., 2019, "Correction: An Acquired HER2T798I Gatekeeper Mutation Induces Resistance to Neratinib in a Patient with HER2 Mutant-Driven Breast Cancer," Cancer Discovery, 9(2): 303.
Hanker et al., 2020, "Overcoming Endocrine Resistance in Breast Cancer," Cancer Cell, 37: 496-513.
Hanker et al., 2021, "Co-occurring gain-of-function mutations in HER2 and HER3 modulate HER2/HER3 activation, oncogenesis, and HER2 inhibitor sensitivity," Cancer Cell, 39:1-16.
Harding et al., 2019, "Treating HER2-mutant advanced biliary tract cancer with neratinib: benefits of HER2-directed targeted therapy in the phase 2 Summit 'basket' trial," Presentation.
Hasako et al., 2018, "TAS6417, A Novel EGFR Inhibitor Targeting Exon 20 Insertion Mutations," Mol. Cancer Ther, 17(8): 1648-1658.
He et al., 2021, "Mechanisms and management of 3rd-generation EGFR-TKI resistance in advanced non-small cell lung cancer (Review)," International Journal of Oncology, 59(90).
Hirano, 2015, "In Vitro modeling to determine mutation specificity of EGFR tyrosine kinase inhibitors against clinically relevant EGFR mutants in non-small-cell lung cancer," Oncotarget, 6(36).
Humphrey, 2021, "BDTX-189: A MasterKey Inhibitor of EGFR and HER2 Exon 20 Insertion Mutations and Allosteric HER2 Mutations," Presentation at HER2-Targeted Therapies Summit, Jun. 2021, Black Diamond Therapeutics.
Hyman et al., 2018, "HER kinase inhibition in patients with HER2- and HER3-mutant cancers," Nature, 554.
Ishiyama et al., 2022, "Computational and Functional Analyses of HER2 Mutations Reveal Allosteric Activation Mechanisms and Altered Pharmacologic Effects," MAP Manuscript, Abstract.
Ishiyama et al., 2022, "Computational and Functional Analyses of HER2 Mutations Reveal Allosteric Activation Mechanisms and Altered Phatmacologic Effects," MAP Manuscript, Supplementary Information.
Janne et al., 2011, "Phase I Dose-Escalation Study of the Pan-HER Inhibitor, PF299804, in Patients with Advanced Malignant Solid Tumors," Clin. Cancer Res, 17(5): 1131-1139.
Jebbink et al., 2020, "The force of HER2—A druggable target in NSCLC?," Cancer Treatment Reviews, 86:101996.
Jeong et al., 2016, "PMCA2 regulates HER2 protein kinase localization and signaling and promotes HER2-mediated breast cancer," PNAS, 113(3):E282-E290.
Kancha et al., 2011, "Differential Sensitivity of ERBB2 Kinase Domain Mutations towards Lapatinib," PLoS One, 6(10):e26760.
Kavuri et al., 2015, "HER2 Activating Mutations Are Targets for Colorectal Cancer Treatment," Cancer Discov., 5(8): 832-841.
Kinzel et al., 2010, "A New Palladium Precatalyst Allows for the Fast Suzuki-Miyaura Coupling Reactions of Unstable Polyfluorophenyl and 2-Heteroaryl Boronic Acids," J. Am. Chem. Soc., 132:14073-14075.
Kosaka et al., 2017, "Response Heterogeneity of EGFR and HER2 Exon 20 Insertions to Covalent EGFR and HER2 Inhibitors," Cancer Research, 77(10): 2712-2721.
Kris et al., 2014, "Using Multiplexed Assays of Oncogenic Drivers in Lung Cancers to Select Targeted Drugs," JAMA, 311(19): 1998-2006.
Kulukian et al., 2020, "Preclinical Activity of HER2-Selective Tyrosine Kinase Inhibitor Tucatinib as a Single Agent or in Combination with Trastuzumab or Docetaxel in Solid Tumor Models," Mol. Cancer Ther., 19:976-987.
Lategahn et al., 2020, "Targeting Her2-insYVMA with Covalent Inhibitors—A Focused Compound Screening and Structure-Based Design Approach," Journal of Medical Chemistry, 22;63(20):11725-11755.
Li et al., 2016, "HER2 Amplification and HER2 Mutation Are Distinct Molecular Targets in Lung Cancers," Journal of Thoracic Oncology, 11(3): 414-419.
Li et al., 2017, "Discovery and development of pyrotinib: A novel irreversible EGFR/HER2 dual tyrosine kinase inhibitor with favorable safety profiles for the treatment of breast cancer," European Journal of Pharmaceutical Sciences, 110: 51-61.
Li et al., 2018, "Ado-Trastuzumab Emtansine for Patients With HER2-Mutant Lung Cancers: Results From a Phase II Basket Trial," Journal of Clinical Oncology, 36(24).
Li et al., 2019, "HER2-L755S mutation induces hyperactive MAPK and PI3K-mTOR signaling, leading to resistance to HER2 tyrosine kinase inhibitor treatment," Cell Cycle, 18(13): 1513-1522.
Li et al., 2020, "HER2-Mediated Internalization of Cytotoxic Agents in ERBB2 Amplified or Mutant Lung Cancers," Cancer Discovery, 10(5): 674-687.
Li et al., 2021, "Trastuzumab Deruxteean in HER2-Mutant Non-Small-Cell Lung Cancer," New England Journal of Medicine, 386:241-251.
Li et al., 2021, "Trastuzumab Deruxteean in HER2-Mutant Non-Small-Cell Lung Cancer," New England Journal of Medicine, 386:241-251, Supplementary Appendix.
Li et al., 2022, "Trastuzumab Deruxteean in Non-Small-Cell Lung Cancer," Letter to the Editor, New England Journal of Medicine, 368(18): 1769-1771.
Li et al., 2022, "Discovery of SPH5030, a Selective, Potent, and Irreversible Tyrosine Kinase Inhibitor for HER2-Amplified and HER2-Mutant Cancer Treatment," Journal of Medical Chemistry, 1:c00710.
Lin and Sun, 2013, "Recent Synthetic Developments and Applications of the Ullmann Reaction. A Review," Org. Prep. Proced. Int., 45(5).
Lin et al., 2019, "Discovery of a Furanopyrimidine-Based Epidermal Growth Factor Receptor Inhibitor (DBPR112) as a Clinical Candidate for the Treatment of Non-Small Cell Lung Cancer," J. Med. Chem., 62:10108-10123.
Lucas et al., 2021, "BDTX-1535, a CNS penetrant MasterKey inhibitor of common, uncommon and resistant EGFR mutations, demonstrates in vivo efficacy and has potential to treat patients with NSCLC harboring osimertinib-resistant mutations with or without brain metastases," Presentation at AACR-NCI-EORTC Virtual International Conference on Molecular Targets and Cancer Therapeutics.
Ma et al., 2017, "Neratinib Efficacy and Circulating Tumor DNA Detection of HER2 Mutations in HER2 Nonamplified Metastatic Breast Cancer," Clin. Cancer Res., 23(19):5687-5695.
Ma et al., 2022, "The Phase II MutHER Study of Neratinib Alone and in Combination with Fulvestrant in HER2-Mutated, Non-amplified Metastatic Breast Cancer," Clinical Cancer Research, 28:1258-1267.
Maiti and Buchwald, 2010, "Cu-Catalyzed Arylation of Phenols: Synthesis of Sterically Hindered and Heteroaryl Dialyl Ethers," Journal of Organic Chemistry, 75: 1791-1794.
Maryanoff et al., 2012, "Pyrimidinopyrimidine Inhibitors of Ketohexokinase: Exploring the Ring C2 Group that Interacts with Asp-27B in the Ligand Binding Pocket," Bioorganic & Medicinal Chemistry Letters, 22:5326-5329.
Mazieres et al., 2016, "Lung cancer patients with HER2 mutations treated with chemotherapy and HER2-targeted drugs: results from the European EUHER2 cohort," Annals of Oncology, 27:281-286.
Medford et al., 2019, "Blood-based monitoring identifies acquired and targetable driver HER2 mutations in endocrine-resistant metastatic breast cancer," Precision Oncology, 18.
Meric-Bernstam et al., 2019, "Advances in HER2-Targeted Therapy: Novel Agents and Opportunities Beyond Breast and Gastric Cancer," Clin. Cancer Res., 25(7):2033-2041.

(56) References Cited

OTHER PUBLICATIONS

Mishra et al., 2017, "Genomic alterations of ERBB receptors in cancer: clinical implications," Oncotarget, 8(69):114371-114392.
Mitsudomi and Yatabe, 2007, "Mutations of the epidermal growth factor receptor gene and related genes as determinants of epidermal growth factor receptor tyrosine kinase inhibitors sensitivity in lung cancer," Cancer Sci, 98(12): 1817-1824.
Modi et al., 2020, "Trastuzumab Deruxtecan in Previously Treated HER2-Positive Breast Cancer," New England Journal of Medicine, 382(7):610-621.
Modi et al., 2022, "Trastuzumab deruxtecan (T-DXd) versus treatment of physician's choice (TPC) in patients (pts) with HER2-low unresectable and/or metastatic breast cancer (mBC): Results of DESTINY-Breast04, a randomized, phase 3 study," Abstract to LBA3—Plenary Sesssion.
Modi et al., 2022, "Trastuzumab Deruxtecan in Previously Treated HER2-Low Advanced Breast Cancer," New England Journal of Medicine, 387(1): 9-20.
Moss et al., 2022, "Multifocal and pathologically-confirmed brain metastasis complete response to trastuzumab deruxtecan," CNS Oncol., 1;11(3):CNS90.
Moulder et al., 2017, "Phase I Study of ONT-380, a HER2 Inhibitor, in Patients with HER2þ -Advanced Solid Tumors, with an Expansion Cohort in HER2þ Metastatic Breast Cancer (MBC)," Clin. Cancer Res., 23(14): 3529-3536.
Murthy et al., 2020, "Tucatinib, Trastuzumab, and Capecitabine for HER2-Positive Metastatic Breast Cancer," New England Journal of Medicine, 382(7): 597-609.
Nagamoto et al., 2020, "Preclinical evaluation of DS-2087b, a novel and selective inhibitor of EGFR/HER2 exon 20 insertion," Presentation at 2020 Annual Meeting of the European Society for Medical Oncology.
Nagasaka et al., 2021, "The Effects of HER2 Alterations in EGFR Mutant Non-small Cell Lung Cancer," Clinical Lung Cancer, 23(1):52-59.
Nayar et al., 2019, "Acquired HER2 mutations in ER+ metastatic breast cancer confer resistance to estrogen receptor—directed therapies," Nature Genetics, 51:207-216.
Nayar et al., 2019, "Acquired HER2 mutations in ER+ metastatic breast cancer confer resistance to estrogen receptor—directed therapies," Nature Genetics, 51:207-216, Supplemental Information.
NCCN, 2019, "Clinical Practice Guidelines in Oncology: Non-Small Cell Lung Cancer."
NCCN, 2021, "Clinical Practice Guidelines in Oncology: Breast Cancer."
Neal et al., 2018, "Safety, PK, and Preliminary Antitumor Activity of the Oral EGFR/HER2 Exon 20 Inhibitor TAK-788 in NSCLC," Presentation at 19th World Conference on Lung Cancer, Sep. 2018, Toronto, Canada.
Nokin et al., 2021, "Targeting Infrequent Driver Alterations in Non-Small Cell Lung Cancer," Trends in Cancer, 7(5):410-429.
O'Brien et al., 2022, "Tucatinib has Selective Activity in HER2-Positive Cancers and Significant Combined Activity with Approved and Novel Breast Cancer—Targeted Therapies," Mol. Cancer Ther., 4;21(5):751-761.
Offin et al., 2019, "Frequency and Outcomes of Brain Metastases in Patients With HER2-Mutant Lung Cancers," Cancer, 125:4380-4387.
Ogitani et al., 2016, "Bystander killing effect of DS-8201a, a novel anti-human epidermal growth factor receptor 2 antibody-drug conjugate, in tumors with human epidermal growth factor receptor 2 heterogeneity," Cancer Science, 107(7):1039-1046.
Ogitani et al., 2016, "DS-8201a, A Novel HER2-Targeting ADC with a Novel DNA Topoisomerase I Inhibitor, Demonstrates a Promising Antitumor Efficacy with Differentiation from T-DM1," Clin. Cancer Res., 15;22(20):5097-5108.
Oh and Bang, 2020, "HER2-targeted therapies—a role beyond breast cancer," Nature Reviews, 17:33-48.
Ou et al., Undated, "Characterization of 648 non-small cell lung cancer (NSCLC) cases with 28 unique HER2 exon 20 insertions," Presentation of Chao Family Comprehensive Cancer Center, Univ. of CA Irvine.
Oxnard et al., 2013, "Natural History and Molecular Characteristics of Lung Cancers Harboring EGFR Exon 20 Insertions," Journal of Thoracic Oncology, 8(2): 179-184.
Perez-Garcia et al., 2022, "Trastuzumab Deruxteean in Patients with Central Nervous System Involvement from HER2-Positive Breast Cancer: The DEBBRAH Trial," Neuro Oncol., 144.
Pfizer, 2019, "Oncology [Key Post-POC Updates Since June 2019]."
Pillai et al., 2017, "HER2 Mutations in Lung Adenocarcinomas: A Report From the Lung Cancer Mutation Consortium," Cancer, 123 (21):4099-4105.
Ren et al., 2022, "Consensus for HER2 alterations testing in non-small-cell lung cancer," ESMO, 7(1).
Robichaux et al., 2018, "Mechanisms and clinical activity of an EGFR and HER2 exon 20—selective kinase inhibitor in non-small cell lung cancer," Nature Medicine, 24:638-646.
Robichaux et al., 2018, "Mechanisms and clinical activity of an EGFR and HER2 exon 20—selective kinase inhibitor in non-small cell lung cancer," Nature Medicine, 24:638-646, Supplementary Information.
Robichaux et al., 2019, "Pan-Cancer Landscape and Analysis of ERBB2 Mutations Identifies Poziotinib as a Clinically Active Inhibitor and Enhancer of T-DM1 Activity," Cancer Cell, 36:1-14.
Rolfo and Russo, 2020, "HER2 Mutations in non-small Cell Lung Cancer: A Herculean effort to Hit the Target," Cancer Discovery, 10(5): 643-645.
Salvi et al., 2012, "A New Biarylphosphine Ligand for the Pd-Catalyzed Synthesis of Diaryl Ethers under Mild Conditions," Organic Letters, 14(1):170-173.
Saura et al., 2019, "Neratinib plus capecitabine versus lapatinib plus capecitabine in patients with HER2-positve metastaic breast cancer previously treated with ≥2 HER2-directed regimens: Findings from the multnational, randomized, phase 3 NALA trial," Presentation at 2019 ASCO Annual Meeting.
Schram et al., 2021, "Safety and Preliminary Efficacy From the Phase 1 Portion of MasterKey-01: A First-in-Human Dose-Escalation Study to Determine the Recommended Phase 2 Dose, Pharmacokinetics and Preliminary Antitumor Activity of BDTX-189, and Inhibitor of Allosteric EGFR/HER2 Mutations, in Patients With Advanced Solid Malignancies," Presentation at American Society of Clinical Oncology (ASCO) Annual Meeting.
Smaill et al., 1999, "Tyrosine Kinase Inhibitors. 15. 4-(Phenylamino)quinazoline and 4-(Phenylamino)pyrido[d]pyrimidine Acrylamides as Irreversible Inhibitors of the ATP Binding Site of the Epidermal Growth Factor Receptor," J. Med. Chem., 42:1803-1815.
Smaill et al., 2016, "Tyrosine Kinase Inhibitors. 20. Optimization of Substituted Quinazoline and Pyrido[3,4-d]pyrimidine Derivatives as Orally Active, Irreversible Inhibitors of the Epidermal Growth Factor Receptor Family," J. Med. Chem., 59:8103-8124.
Smyth et al., 2020, "Efficacy and Determinants of Response to HER Kinase Inhibition in HER2—Mutant Metastatic Breast Cancer," Cancer Discovery, 10(2):198-213.
Solca et al., 2004, "Inhibition of Epidermal Growth Factor Receptor Activity by Two Pyrimidopyrimidine Derivatives," Journal of Pharm. Exp. Ther, 311(2): 502-509.
Son et al., 2022, "A novel HER2-selective kinase inhibitor is effective in HER2 mutant and amplified non-small cell lung cancer," The Journal of Cancer Research, 82(8).
Song et al., 2022, "Efficacy and safety of pyrotinib in advanced lung adenocarcinoma with HER2 mutations: a multicenter, single-aim, phase II trial," BMC Medicine, 20:42.
Stinchcombe et al., 2021, "SGNTUC-019: Phase 2 Basket Study of Tucatinib and Transtubumab in Previously Treated Solid Tumors with HER2 Alterations," Abstract in Amer. Soc. of Clin. Oncology presentation, Jun. 2021.
Subramanian et al., 2019, "Emergence of ERBB2 Mutation as a Biomarker and an Actionable Target in Solid Cancers," The Oncologist, 24:e1303-e1314.

(56) References Cited

OTHER PUBLICATIONS

Sun et al., 2019, "Analysis of different HER-2 mutations in breast cancer progression and drug resistance," J. Cell. Mol. Med., 19(12):2691-2701.
Sun, 2022, "Efficacy and Safety of Poziotinib in Treatment-Naïve HER2 Exon 20 Insertion Mutated Non-Small Cell Lung Cancer; Zenith20-4," ESMO TAT presentation, Div. Medical Oncology.
Takegawa et al., 2017, "DS-8201a, a new HER2-targeting antibody—drug conjugate incorporating a novel DNA topoisomerase I inhibitor, overcomes HER2-positive gastric cancer T-DM1 resistance," Int. J. Cancer, 141:1682-1689.
Takise et al., 2017, "Decarbonylative Diaryl Ether Synthesis by Pd and Ni Catalysis," Journal of the American Chemcial Society, 139: 3340-3343.
Toolabi et al., 2020, "6-Cinnamoyl-4-arylaminothienopyrimidines as highly potent cytotoxic agents: Design, synthesis and structure-activity relationship studies," European Journal of Medicinal Chemistry, 185:111786.
Tsurutani et al., 2020, "Targeting HER2 with Trastuzumab Deruxtecan: A Dose-Expansion, Phase I Study in Multiple Advanced Solid Tumors," Cancer Discovery, 10(5):688-701.
Turgeon, Spectrum Pharmaceuticals Investor Presentation, Mar. 2018.
Turgeon, Spectrum Pharmaceuticals Investor Presentation, Jan. 2019.
Turgeon, Spectrum Pharmaceuticals Investor Presentation, Mar. 2019.
Udagawa et al., 2019, "TAS6417/CLN-081 Is a Pan-Mutation—Selective EGFR Tyrosine Kinase Inhibitor with a Broad Spectrum of Preclinical Activity against Clinically Relevant EGFR Mutations," Molecular Cancer Research, 17(11): 2233-2243.
Ueda et al., 2012, "Me3(OMe)tBuXPhos: A Surrogate Ligand for Me4tBuXPhos in Palladium-Catalyzed C—N and C—O Bond Forming Reactions," Journal of Organic Chemistry, 77:2543-2547.
Van Veggel et al., 2020, "Osimertinib treatment for patients with EGFR exon 20 mutation positive non-small cell lung cancer," Lung Cancer, 141:9-13.
Verma et al., 2018, "Structural investigations on mechanism of lapatinib resistance caused by HER-2 mutants," PLoS One, 13(2):e0190942.
Wang et al., 2022, "Sunvozertinib, a selective EGFR inhibitor for previously treated non-small cell lung cancer with EGFR exon 20 insertion mutations," Cancer Discov., 12(7):1676-1689.
Wanner et al., 2015, "Catalytic Kinetic Resolution of Disubstituted Piperidines by Enantioselective Acylation: Synthetic Utility and Mechanistic Insights," Journal of the American Chemical Society, 137:11491-11497.
Waters et al., 2021, "Clinical Pharmacokinetics of BDTX-189, an Inhibitor of Allosteric ErbB Mutations, in Patients With Advanced Solid Malignancies in MasterKey-01 Study," Presentation at American Society of Clinical Oncology (ASCO) Annual Meeting.
Weigelt and Reis-Filho, 2012, "Activating Mutations in HER2: Neu Opportunities and Neu Challenges," Cancer Discov., 3(2):145-147.
Wen et al., 2015, "Mutations in the Kinase Domain of the HER2/ERBB2 Gene Identified in a Wide Variety of Human Cancers," Journal of Molecular Diagnostics, 17(5):487-495.
Wildiers et al., 2019, "Neratinib + trastuzumab + fulvestrant for HER2-mutant, hormone receptor-positive, metastatic breast cancer: updated results from the phase 2 Summit 'basket' trial," Presentation at San Antonio Breat Cancer Symposium, Puma Biotechnology.
Wilding et al., 2022, "Discovery of potent and selective HER2 inhibitors with efficacy against HER2 exon 20 insertion-driven tumors, which preserve wild-type EGFR signaling," Nature Cancer, 3:821-836.
Woodward et al., 2016, "Management of Patients Treated with Pertuzumab in the Australian Clinical Practice Setting," Asia-Pacific Journal of Clinical Oncology, 12(Suppl.2):5-15.
Written Opinion of the International Searching Authority, PCT/IB2021/055832, dated Jan. 6, 2022.
Wu et al., 2022, "Efficacy of targeted therapy in patients with HER2-positive non-small cell lung cancer: A systematic review and meta-analysis," Br. J. Clin. Pharmacol., 88:2019-2034.
Xu et al., 2017, "HER2 Reactivation through Acquisition of the HER2 L755S Mutation as a Mechanism of Acquired Resistance to HER2-targeted Therapy in HER2þ Breast Cancer," Clin. Cancer Res., 23(17):5123-5134.
Xu et al, 2020, "Treatment Outcome and Clinical Characteristics of HER2 Mutated Advanced Non-Small Cell Lung Cancer Patients in China," Thorasic Cancer, 11:679-685.
Yang et al., 2016, "AZD3759, a BBB-penetrating EGFR Inhibitor for the Treatment of EGFR Mutant NSCLC with CNS Metastasees," Sci. Transl. Med., 8(368ra172).
Yang et al., 2021, "Exon 20 YVMA insertion is associated with high incidence of brain metastasis and inferior outcome of chemotherapy in advanced non-small cell lung cancer patients with HER2 kinase domain mutations," Transl. Lun Cancer Res. 10(2):753-765.
Yasuda et al., 2013, "Structural, Biochemical and Clinical Characterization of Epidermal Growth Factor Receptor (EGFR) Exon 20 Insertion Mutations in Lung Cancer," Sci. Transl. Med. 5(6).
Zabransky et al., 2015, "HER2 missense mutations have distinct effects on oncogenic signaling and migration," PNAS, e6205-e6214.
Zeng et al., 2015, "Discovery and Evaluation of Clinical Candidate AZD3759, a Potent, Oral Active, Central Nervous System-Penetrant, Epidermal Growth Factor Receptor Tyrosine Kinase Inhibitor," Journal of Medical Chemistry, 58:8200-8215.
Zhang et al, 2009, "(2-Pyridyl)acetone-Promoted Cu-Catalyzed OArylation of Phenols with Aryl Iodides, Broides, and Chlorides," Journal of Organic Chemistry, 74: 7187-7190.
Zhang et al., 2016, "Ullmann Diaryl Ether Synthesis Catalyzed by Copper (I)/Pyridine-Functionalized Silane," Phosphorus, Sulfur, and Silicon and the Related Elements, 191(6):930-932.
Zhao and Xia, 2020, "Targeting HER2 Alterations in Non-Small Cell Lung Cancer: A Comprehensive Review," JCO Precision Oncology, 4:411-425.
Zhao et al., 2020, "Conformational Landscapes of HER2 Exon 20 Insertions Explain Their Sensitivity to Kinase Inhibitors in Lung Adenocarcinoma," Journal of Thoracic Oncology, 15(6): 962-972.
Zhou et al., 2020, "Pyrotinib in HER2-Mutant Advanced Lung Adenocarcinoma After Platinum-Based Chemotherapy: A Multicenter, Open-Label, Single-Arm, Phase II Study," Journal of Clinical Oncology, 38(24): 2753-2761.
Zhou et al., 2020, "Pyrotinib in HER2-Mutant Advanced Lung Adenocarcinoma After Platinum-Based Chemotherapy: A Multicenter, Open-Label, Single-Arm, Phase II Study," Journal of Clinical Oncology, 38(24): 2753-2761, Supplement.
Abuhelwa et al., 2022, "Trastuzumab Deruxtecan-Induced Interstitial Lung Disease/Pneumonitis in ERBB2-Positive Advanced Solid Malignancies: A Systematic Review," Drugs, 82(9):979-987.
Agostinetto et al., 2022, "Immunotherapy for HER2-Positive Breast Cancer: Clinical Evidence and Future Perspectives," Cancers, 14(9):2136.
Andrews et al., 2022, "NVL-330 is a Selective, Brain-penetrant Inhibitor of Oncogenic HER2 Exon 20 Insertion Mutations in Preclinical Models," Nuvalent, Abstract #212 from the 34th EORTC-NCI-AACR Symposium (ENA), Oct. 26-28, 2022, Barcelona, Spain.
Baihong, Xie, Sep. 28, 2021, "The Golden Triangle joins hands with startup Anbang to target the precise development of cancer drugs," World Journal News (17 pages).
Chen et al., 2021, "Immune microenvironment features and efficacy of PD-1/PD-L1 blockade in non-small cell lung cancer patients with EGFR or HER2 exon 20 insertions," Thoracic Cancer, 12(2):218-226.
Chu et al., 2022, "Treatment efficacy of HER2-mutant lung adenocarcinoma by immune checkpoint inhibitors: a multicenter retrospective study," Cancer Immunology, Immunotherapy, 71(7):1625-1631.
Chumsri et al., 2018, "High p95HER2/HER2 Ratio Associated With Poor Outcome in Trastuzumab-Treated HER2-Positive Metastatic

(56) References Cited

OTHER PUBLICATIONS

Breast Cancer NCCTG N0337 and NCCTG 98-32-52 (Alliance)," Clinical Cancer Research, 24(13):3053-3058.

Cui et al., 2023, "Structure optimization and discovery of novel compound for the treatment of insertion mutations within exon 20 of EGFR and HER2," Bioogranic & Medicinal Chemistry, 81:117202.

Gandhi et al., 2018, "Pembrolizumab plus Chemotherapy in Metastatic Non-Small-Cell Lung Cancer," The New England Journal of Medicine, 378(22):2078-2092.

Goel et al., 2023, "Dual kinase inhibitor for EGFR mutants and ErbB2 limit breast cancer," Biochemical and Biophysical Research Communications, 651:39-46.

Guisier et al., 2019, "Efficacy and Safety of Anti-PD-1 Immunotherapy in Patients With Advanced NSCLC With BRAF, HER2, or MET Mutations or RET Translocation: GFPC Jan. 2018," Journal of Thoracic Oncology, 15(4):628-636.

Harding et al., 2023, "Antitumour activity of neratinib in patients with HER2-mutant advanced biliary tract cancers, " Nature Communications, 14(1):630.

Henegouwen et al., 2022, "Trastuzumab and pertuzumab combination therapy for advanced pre-treated HER2 exon 20-mutated non-small cell lung cancer," European Journal of Cancer, 171:114-123.

International Search Report and Written Opinion dated Aug. 22, 2022 for PCT/US2022/024334 (14 pages).

International Search Report and Written Opinion dated Dec. 30, 2022 for PCT/CN2022/124864 (18 pages).

Le et al., 2021, "Poziotinib in Non-Small-Cell Lung Cancer Harboring HER2 Exon 20 Insertion Mutations After Prior Therapies: ZENITH20-2 Trial," American Society of Clinical Oncology, 40(7):710-718.

Morfouace et al., 2022, "Results of screening in early and advanced thoracic malignancies in the EORTC pan-European SPECTAlung platform," Scientific Reports, 12(1):8342.

Negrao et al., 2021, "Oncogene-specific differences in tumor mutational burden, PD-L1 expression, and outcomes from immunotherapy in non-small cell lung cancer," Journal for ImmunoTherapy of Cancer, 9(8):e002891.

Oguchi et al., 2023, "TAS2940, a novel brain-penetrable pan-ERBB inhibitor, for tumors with HER2 and EGFR aberrations," Cancer Science, 114(2):654-664.

Okamoto et al., 2020, "Pharmacokinetics of trastuzumab deruxtecan (TDXd), a novel anti-HER2 antibody-drug conjugate, in HER2-positive tumour-bearing mice," Xenobiotica, 50(10):1242-1250.

Perera et al., 2009, "HER2YVMA drives rapid development of adenosquamous lung tumors in mice that are sensitive to BIBW2992 and rapamycin combination therapy," PNAS, 106(2):474-479.

Prescribing Information for ENHERTU® (fam-trastuzumab—deruxtecan-nxki), 2019.

Prescribing Information for NERLYNX® (neratinib) tablets, 2017.

Saalfeld et al., 2021, "Efficacy of Immune Checkpoint Inhibitors Alone or in Combination With Chemotherapy in NSCLC Harboring ERBB2 Mutations," Journal of Thoracic Oncology, 16(11):1952-1958.

Shaw et al., 2020, "First-Line Lorlatinib or Crizotinib in Advanced ALK-Positive Lung Cancer," The New England Journal of Medicine, 383(21):2018-2029.

Tsang et al., 2017, "PD-L1 expression and tumor infiltrating PD-1+ lymphocytes associated with outcome in HER2+ breast cancer patients," Breast Cancer Research and Treatment, 162(1):19-30.

Uehara et al., 2022, "Efficacy of first-line immune checkpoint inhibitors in patients with advanced NSCLC with KRAS, MET, FGFR, RET, BRAF, and HER2 alterations," Thoracic Cancer, 13(11):1703-1711.

Yang et al., 2022, "First-line immunotherapy or angiogenesis inhibitor plus chemotherapy for HER2-altered NSCLC: a retrospective real-world POLISH study," Therapeutic Advances in Medical Oncology, 14:1-13.

Yang et al., 2022, "Pyrotinib combined with apatinib for targeting metastatic non-small cell lung cancer with HER2 alterations: a prospective, open-label, single-arm phase 2 study (PATHER2)," BMC Medicine, 20(1):277.

Zhang et al., 2023, "Chinese expert consensus on the diagnosis and treatment of HER2-altered non-small cell lung cancer," Thoracic Cancer, 14(1):91-104.

Neumuller et al., "Novel EGFR(WT)-Sparing, HER2 Selective Inhibitors for the Treatment of HER2 Exon 20 Insertion Driven Tumors Address a Clear Unmet Medical Need," Presented at the AACR Annual Meeting 2021, Virtual Conference, Apr. 9-14, 2021.

Berge et al., 1977, "Pharmaceutical salts," Journal of Pharmaceutical Sciences, 66(1):1-19.

Brunetto et al., 2013, "First-in-human, pharmacokinetic and pharmacodynamic phase I study of Resminostat, an oral histone deacetylase inhibitor, in patients with advanced solid tumors," Clinical Cancer Research, 19(19):5494-5504.

Buggy et al., 2006, "CRA-024781: a novel synthetic inhibitor of histone deacetylase enzymes with antitumor activity in vitro and in vivo," Molecular Cancer Therapeutics, 5(5):1309-1317.

Ember et al., 2014, "Acetyl-lysine binding site of bromodomain-containing protein 4 (BRD4) interacts with diverse kinase inhibitors," ACS Chemical Biology, 9(5):1160-1171.

Filippakopoulos et al., 2010, "Selective inhibition of BET bromodomains," Nature, 468(7327):1067-1073.

Fish et al., 2012, "Identification of a chemical probe for bromo and extra C-terminal bromodomain inhibition through optimization of a fragment-derived hit," Journal of Medicinal Chemistry, 55(22):9831-9837.

Giles et al., 2006, "A phase I study of intravenous LBH589, a novel cinnamic hydroxamic acid analogue histone deacetylase inhibitor, in patients with refractory hematologic malignancies," Clinical Cancer Research, 12(15):4628-4635.

Göttlicher et al., 2001, "Valproic acid defines a novel class of HDAC inhibitors inducing differentiation of transformed cells," The EMBO Journal, 20(24):6969-6978.

Hamid et al., 2013, "Safety and tumor responses with lambrolizumab (anti-PD-1) in melanoma," New England Journal of Medicine, 369(2):134-144.

Heymach et al., "Updated data from the Phase I Beamion Lung 1 trial of the HER2 tyrosine kinase inhibitor, BI 1810631, as monotherapy in patients with advanced/metastatic solid tumors with HER2 aberrations," Presented at the American Association for Cancer Research Congress (AACR), Orlando, FL, USA, Apr. 14-19, 2023 (1 page).

Karachaliou et al., 2015, "Real-time liquid biopsies become a reality in cancer treatment," Annals of Translational Medicine, 3(3):36.

Knutson et al., 2014, "Synergistic Anti-Tumor Activity of EZH2 Inhibitors and Glucocorticoid Receptor Agonists in Models of Germinal Center Non-Hodgkin Lymphomas," PLoS One, 9(12):e111840.

Noel et al., 2013, "Abstract C244: Development of the BET bromodomain inhibitor OTX015," Molecular Cancer Therapeutics, 12(Suppl. 11):c244.

Picaud et al., 2013, "PFI-1, a highly selective protein interaction inhibitor, targeting BET Bromodomains," Cancer Research, 73(11):3336-3346.

Piekarz et al., 2001, "Inhibitor of histone deacetylation, depsipeptide (FR901228), in the treatment of peripheral and cutaneous T-cell lymphoma: a case report," Blood, 98(9):2865-2868.

Plumb et al., 2003, "Pharmacodynamic response and inhibition of growth of human tumor xenografts by the novel histone deacetylase inhibitor PXD101," Molecular Cancer Therapeutics, 2(8):721-728.

Richon et al., 1998, "A class of hybrid polar inducers of transformed cell differentiation inhibits histone deacetylases," Proceedings of the National Academy of Sciences (PNAS), 95(6):3003-3007.

Rosenblatt et al., 2011, "PD-1 blockade by CT-011, anti-PD-1 antibody, enhances ex vivo T-cell responses to autologous dendritic cell/myeloma fusion vaccine," Journal of Immunotherapy, 34(5):409-418.

Saito et al., 1999, "A synthetic inhibitor of histone deacetylase, MS-27-275, with marked in vivo antitumor activity against human tumors," Proceedings of the National Academy of Sciences (PNAS), 96(8):4592-4597.

(56) References Cited

OTHER PUBLICATIONS

Seal et al., 2012, "Identification of a novel series of BET family bromodomain inhibitors: binding mode and profile of I-BET151 (GSK1210151A)," Bioorganic & Medicinal Chemistry Letters, 22(8):2968-2972.
Temperini et al., 2008, "Carbonic anhydrase inhibitors. Interaction of 2-N,N-dimethylamino-1,3,4-thiadiazole-5-methanesulfonamide with 12 mammalian isoforms: kinetic and X-ray crystallographic studies," Bioorganic & Medicinal Chemistry Letters, 18(3):999-1005.
Venugopal et al., 2013, "A phase I study of quisinostat (JNJ-26481585), an oral hydroxamate histone deacetylase inhibitor with evidence of target modulation and antitumor activity, in patients with advanced solid tumors," Clinical Cancer Research, 19(15):4262-4272.
Vippagunta et al., 2001, "Crystalline solids," Advanced Drug Delivery Reviews, 48(1):3-26.
Walczak et al., 2019, "The Role of the ER-Induced UPR Pathway and the Efficacy of Its Inhibitors and Inducers in the Inhibition of Tumor Progression," Oxidative Medicine and Cellular Longevity, vol. 2019, Article ID 5729710.
Wilen et al., 1977, "Strategies in optical resolutions," Tetrahedron, 33(21):2725-2736.
Yu, L, et al., 2001, "Amorphous pharmaceutical solids: preparation, characterization and stabilization," Advanced Drug Delivery Reviews, 48(1):27-42.
Zhao et al., 2013, "The making of I-BET762, a BET bromodomain inhibitor now in clinical development," Journal of Medicinal Chemistry, 56(19):7498-7500.
Bartsch at al., 2022, "Trastuzumab deruxtecan in HER2-positive breast cancer with brain metastases: a single-arm, phase 2 trial," Nature Medicine, 28(9):1840-1847.
Cancer Genome Atlas Research Network. Comprehensive molecular profiling of lung adenocarcinoma. Nature. Jul. 3, 20141;511(7511):543-50.
Ghosh et al., 2023, "Irreversible tyrosine kinase inhibitors induce the endocytosis and downregulation of ErbB2," Biochemistry and Biophysics Reports, 34:101436.
Heymach et al., 2022, "A Phase I, open-label, dose-escalation, confirmation, and expansion trial of BI 1810631, a HER2 inhibitor, as monotherapy in patients with advanced or metastatic solid tumors with HER2 aberrations," presented at the American Society for Clinical Oncology (ASCO) Meeting in Chicago, Illinois (1 page).
International Application Status Report for PCT/CN2023/084265 generated Oct. 6, 2023 (2 pages).
Ishiyama, et al., 2023, "Computational and Functional Analyses of HER2 Mutations Reveal Allosteric Activation Mechanisms and Altered Pharmacologic Effects," Cancer Research, 83(9):1531-1542.
Li et al., 2022, "Trastuzumab Deruxtecan in HER2-Mutant Non-Small-Cell Lung Cancer," The New England Journal of Medicine, 386(3):241-251 (including supplementary appendix).
Liu et al., 2018, "Targeting HER2 Aberrations in Non-Small Cell Lung Cancer with Osimertinib," Clin Cancer Res, 24(11):2594-2604.
Liu et al., 2023, "First-line pyrotinib in advanced HER2-mutant non-small-cell lung cancer: a patient-centric phase 2 trial," Nature Medicine, 29:2079-2086.
Nützinger et al., 2023, "Management of HER2 alterations in non-small cell lung cancer—The past, present, and future," Lung Cancer, 186:107385.
Opdam et al., 2022, "A Phase I trial of BI 1810631, a HER2 tyrosine kinase inhibitor, as monotherapy in patients with advanced/metastatic solid tumors with HER2 aberrations," presented at the AACR-NCI-EORTC Molecular Targets and Cancer Therapeutics Symposium in Barcelona, Spain (15 pages).
Prescribing Information for ENHERTU® (fam-trastuzumab - deruxtecan-nxki), 2022 (35 pages).
Ruiter et al., 2023, "Beamion LUNG-1, an ongoing Phase la/lb trial of the HER2 Tki, zongertinib (BI 1810631) in patients with advanced solid tumors with HER2 aberrations: latest data," presented at the European Society of Medical Oncology in Madrid, Spain (1 page).
Song et al., 2022, "Pyrotinib in Patients with HER2-Amplified Advanced Non-Small Cell Lung Cancer: A Prospective, Multicenter, Single-Arm Trial," Clin Cancer Res, 28:461-467.
Taniguchi et al., 2023, "Tissue-agnostic efficacy of trastuzumab deruxtecan (T-DXd) in advanced solid tumors with HER2 amplification identified by plasma cell-free DNA (cfDNA) testing: Results from a phase 2 basket trial (HERALD/EPOC1806)," Abstract 3014 for presentation at the ASCO Annual Meeting in Chicago, Illinois (1 page).
Yun et al., 2023, "Metastatic HER2-amplified non-small-cell lung cancer treated with trastuzumab deruxtecan," BMJ Case Rep, 16:e253260.
Yun et al., 2023, "A Case of Metastatic HER2-Amplified Non-Small-Cell Lung Cancer (NSCLC) Treated with Trastuzumab Deruxtecan," Journal of Thoracic Oncology, 18(35):e38.
Bose et al., 2021, "Breast Cancer, HER2 Mutations, and Overcoming Drug Resistance," N Engl J Med 385:1241-1243.
Bose, et al., "Gene expression and mutations profiles in HER2-mutated metastatic breast cancer", San Antonio Breast Cancer Symposium 2022.
Christgen et al., 2018, "Activating human epidermal growth factor receptor 2 (HER2) gene mutation in bone metastases from breast cancer," Virchows Arch., 473:577-582.
Cornelissen, 2023, "Poziotinib in Treatment-Naive NSCLC Harboring HER2 Exon 20 Mutations: ZENITH20-4, A Multicenter, Multicohort, Open-Label, Phase 2 Trial (Cohort 4)," J Thor Onc.
Dematteo et al., 2022, "Clinical outcomes of immune checkpoint inhibitors in HER2-amplified non-small cell lung cancers," Journal of Clinical Oncology, 40(16 Supp): e21098- e21098.
Feng et al., 2023, "Prognostic effects of TP53 variants co-occurring in patients with HER2-mutated non-small cell lung cancer (NSCLC)," Journal of Clinical Oncology, 41(16 Supp): e21065-e21065.
Flaherty et al., 2020, "Molecular Landscape and Actionable Alterations in a Genomically Guided Cancer Clinical Trial: National Cancer Institute Molecular Analysis for Therapy Choice (NCI-MATCH)," J Clin Oncol 38:3883-3894.
Kalra et al., 2022, "Poziotinib Inhibits HER2-Mutant-Driven Therapeutic Resistance and Multiorgan Metastasis in Breast Cancer," Cancer Res, 82(16):2928-2939.
Lai et al., 2019, "Afatinib in patients with metastatic or recurrent HER2-mutant lung cancers: a retrospective international multicentre study," European Journal of Cancer, 109:28-35.
Liu et al., 2020, "First analysis of RAIN-701: Study of tarloxotinib in patients with non- small cell lung cancer (NSCLC) EGFR Exon 20 insertion, HER2-activating mutations & other solid tumours with NRG1/ERBB gene fusions," 31(3):S1189.
Liu et al., 2023, "Prognostic and predictive implications of plasma ctDNA in guiding first-line targeted therapy for metastatic HER2-mutant non-small cell lung cancer (NSCLC)," ASCO.
Nguyen et al., 2022, "Genomic characterization of metastatic patterns from prospective clinical sequencing of 25,000 patients," Cell, 185:563-575.
O'Leary et al., 2018, "The Genetic Landscape and Clonal Evolution of Breast Cancer Resistance to Palbociclib plus Fulvestrant in the PALOMA-3 Trial," Cancer Discov, 8(11); 1390-1403.
Petrelli et al., 2017, "Clinical and pathological characterization of HER2 mutations in human breast cancer: a systemic review of the literature," Breast Cancer Res Treat, 166:339-349.
Razavi et al., 2018, "The Genomic Landscape of Endocrine-Resistant Advanced Breast Cancers," Cancer Cell, 34:427-438.
Smith et al., 2021, "HER2 + breast cancers evade anti-HER2 therapy via a switch in driver pathway," Nat Comm, 12(1):6667.
Tan et al., 2022, "Clinical and Genomic Features of HER2 Exon 20 Insertion Mutations and Characterization of HER2 Expression by Immunohistochemistry in East Asian Non-Small-Cell Lung Cancer," JCO Precision Oncology.

(56) References Cited

OTHER PUBLICATIONS

Tian et al., 2021, "Lung adenocarcinoma with ERBB2 exon 20 intersections: Comutations and immunogenomic features related to chemoimmunotherapy," Lung Cancer, 160:50-58.

Tu et al., 2023, "Genomic and immune characteristics of HER2-mutated non-small-cell lung cancer and response to immune checkpoint inhibitor-based therapy," Molecular Oncology.

Turner et al., 2020 "Circulating tumour DNA analysis to direct therapy in advanced breast cancer (plasmaMATCH): a multicentre, multicohort, phase 2a, platform trial," Lancet Oncol 12:1296-308.

Waliany, et al., 2022, "Characterization of ERBB2 (HER2) Alterations in Metastatic Non-small Cell Lung Cancer and Comparison of Outcomes of Different Trastuzumab-based Regimens," Clin Lung Can, 23(6):498-509.

Wander et al., 2020, "The Genomic Landscape of Intrinsic and Acquired Resistance to Cyclin-Dependent Kinase 4/6 Inhibitors in Patients with Hormone Receptor-Positive Metastatic Breast Cancer," Cancer Discov, 10:1174-1193.

Wang et al., 2022, "Molecular Landscape of ERBB2 Alterations in 14,956 Solid Tumors," Pathol. Oncol. Res. 28:1610360.

Yan et al., 2022, "Response of Leptomeningeal Metastasis of Breast Cancer with a HER2/neu Activating Variant to Tucatinib: A Case Report," J Natl Compr Canc Netw 20(7):745-752.

Zhou et al., 2023, "Clinical characteristics and prognostic factors of patients with non-small cell lung cancer having HER2 alterations," Journal of Cancer Research and Clinical Oncology, 149(5):2029-2039.

Zuo, et al., 2016 "Dual Characteristics of Novel HER2 Kinase Domain Mutations in Response to HER2-Targeted Therapies in Human Breast Cancer," Clinical Cancer Research, 22(19).

Bose, et al., 2022, "Gene expression and mutations profiles in HER2-mutated metastatic breast cancer," presentation at San Antonio Breast Cancer Symposium.

Ishiyama, N. et al., 2023 "Computational and Functional Analyses of HER2 Mutations Reveal Allosteric Activation Mechanisms and Altered Pharmacological Effects," Cancer Res., 83(9):1531-1542.

Jhaveri, K., 2022, "Neritinib + fulvestrant + trastuzumab for hormone-receptor positive, HER2-negative, HER2-mutant metastatic breast cancer: outcomes and biomarker analysis from the SUMMIT trial," 2022 ASCO Annual Meeting (Jun. 3-7, 2022; San Diego, CA, USA).

* cited by examiner

AMINO-SUBSTITUTED HETEROARYLS FOR TREATING CANCERS WITH EGFR MUTATIONS

RELATED APPLICATIONS

This application claims the benefit of priority to U.S. Provisional Patent Application Nos. 63/174,177, filed Apr. 13, 2021; 63/239,089, filed Aug. 31, 2021; 63/242,837, filed Sep. 10, 2021; and 63/292,605, filed Dec. 22, 2021, the content of which are incorporated by reference herein.

BACKGROUND

Receptor tyrosine kinases (RTKs) are cell surface proteins that transmit extracellular signals, such as growth signals, into the cell through kinase activity. RTKs regulate many crucial biological processes including development, proliferation, and cell homeostasis. Aberrations in RTK signaling may cause uncontrolled cell proliferation that ultimately leads to cancer.

The human epidermal growth factor receptor (HER)-family proteins are among the first RTKs to be identified and associated with cancer. HER is also known as ErbB, a name derived from the viral homolog erythroblastosis oncogene B. The HER family comprises 4 members: EGFR/HER1/ErbB1, HER2/ErbB2, HER3/ErbB3, and HER4/ErbB4. They share highly related structures involving an extracellular domain that binds ligands, a single-pass transmembrane domain, and an intracellular kinase domain. Several ligands have been identified for EGFR (such as EGF and TGF-α) and HER3/IER4 (such as neuregulins), whereas no ligands are known for HER2. Upon activation, the HER receptors form homo- or heterodimers to catalyze downstream signal transduction through the mitogen-activated protein kinase (MAPK), the phosphoinositide 3-kinase (PI3K), and other pathways.

EGFR dysregulation is a hallmark of many cancers. Cancer cells overactivate EGFR through various mechanisms including overexpression, missense mutations, insertions, and deletions. EGFR is frequently overexpressed in many solid tumors such as non-small cell lung cancer (NSCLC), breast cancer, glioblastoma, prostate cancer, colorectal cancer, head-and-neck cancer, and many others. EGFR variant 3 (EGFR vIII), which bears a large deletion of exons 2-7, is found in about 30% of glioblastoma. A variety of activating mutations in EGFR drive around 30% of NSCLC, with higher prevalence associated with adenocarcinoma histology, non-smokers, Asians, and women. These activating mutations are further divided into point mutations (predominantly L858R in exon 21), short deletions in exon 19 (predominantly E746_A750del), short insertions in exon 20, and other rarer mutations not specified here. L858R, E746_A750del, and exon 20 insertions account for about 35-40%, 40-45%, and 5-10% of all EGFR-mutant NSCLC cases, respectively.

HER2 dysregulation is also a well-documented cause of cancer. HER2 overexpression is found in 15-25% of breast cancer cases, representing one of the major molecular subtypes of breast cancer, as well as in ovarian cancer, gastric cancer, esophageal cancer, endometrial cancer, and lung cancer. HER2 mutations are found in about 2% of NSCLC patients but, unlike EGFR, are largely restricted to exon 20 insertions (predominantly A775_G776insYVMA).

Known agents used to treat oncogenic EGFR or HER2 have significant deficiencies including one or more of the following: toxicity arising from wild-type EGFR inhibition, limited activity in the central nervous system (CNS), and inadequate activity against exon 20 insertions and drug resistance mutations. EGFR has important epithelial functions in the gastrointestinal lining and on the skin of adult humans, so inhibition of non-mutated EGFR is believed to cause adverse reactions such as diarrhea and rash, which are common safety signals for many existing EGFR inhibitors. Up to 60% of EGFR-mutant and 45% of HER2-mutant NSCLC patients will develop brain metastases over the course of the disease; therefore, CNS activity is an important consideration for future therapeutic development. Among the major forms of EGFR and HER2 mutations, exon 20 insertions represent an unmet need as no targeted therapies have been FDA-approved for these indications. For these reasons, there is a need for development of a new generation of inhibitors that spare wild-type EGFR, penetrate the blood-brain barrier, and show specific activity against exon 20 insertions and/or drug-resistance mutations.

SUMMARY

In certain aspects, the present disclosure provides compounds of Formula (I), or a pharmaceutically acceptable salt, a stereoisomer, or a tautomer thereof:

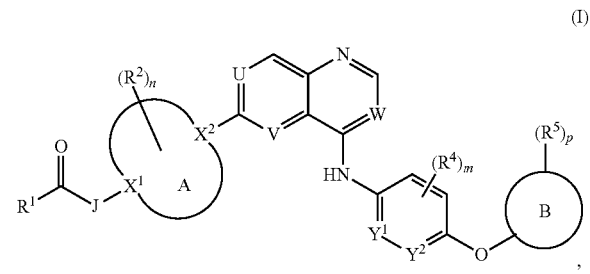

(I)

wherein:
ring

is 3- to 10-membered heterocyclyl;
ring

is 6- to 10-membered aryl or 5- to 10-membered heteroaryl;
$R^1$ is CN, $C_{1-5}$ alkyl, $C_{1-5}$ haloalkyl, C2-5 alkenyl, C2-5 alkynyl, or 3- to 6-membered heterocyclyl, wherein the alkyl, alkenyl, alkynyl, or heterocyclyl is optionally substituted by one or more occurrences of $R^a$;
$R^a$, independently for each occurrence, is halo, CN, $N(R^{n1})_2$, optionally substituted C1-5 alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;

$R^b$ is hydrogen or optionally substituted $C_{1-5}$ alkyl;

$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;

n is 0 or an integer from 1 to 3, inclusive, as permitted by valence;

$X^2$ is —C=, —CH—, or N;

U is $CR^c$ or N;

$R^c$ is hydrogen, halo, or optionally substituted $C_{1-5}$ alkoxy;

V is $CR^d$ or N;

$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;

W is N or $CR^e$;

$R^e$ is hydrogen, halo (e.g., fluoro), or cyano;

$Y^1$ and $Y^2$ are each independently CH, $CR^4$ or N, provided that at least one of $Y^1$ and $Y^2$ is CH or $CR^4$;

$R^4$, independently for each occurrence, is halo, optionally substituted $C_{1-5}$ alkyl, or optionally substituted $C_{1-5}$ alkoxy;

m is 0 or an integer from 1 to 4, inclusive, as permitted by valence;

$R^5$, independently for each occurrence, is halo, optionally substituted $C_{1-5}$ alkyl, or optionally substituted $C_{1-5}$ alkoxy; and p is 0 or an integer from 1 to 3, inclusive, as permitted by valence.

In some embodiments of Formula (I) (or a subformula thereof), it's provided that V is N; or ring

B is

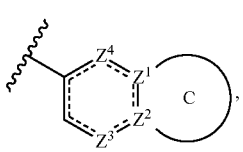

wherein

C is 5- or 6-membered heteroaryl; $Z^1$, $Z^2$, $Z^3$, and $Z^4$ are each independently C or N; and any atom of ring

B may be substituted by $R^5$ as permitted by valence.

In one embodiment of Formula (I) (or a sub-formula thereof), it is provided that when

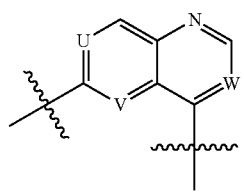

is

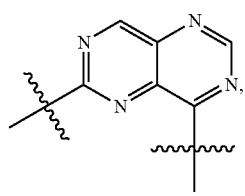

ring

A is

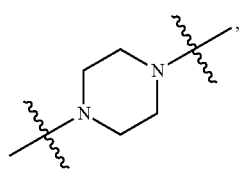

$Y^1$ and $Y^2$ are each independently $CR^4$, then $R^4$ in $Y^2$ is $C_{1-5}$ alkyl and $R^4$ in $Y^1$ is halo. In one embodiment, $R^4$ in $Y^2$ is methyl. In one embodiment, $R^4$ in $Y^1$ is fluoro. In one embodiment, $R^4$ in $Y^2$ is methyl, and $R^4$ in $Y^1$ is fluoro.

In one embodiment of Formula (I) (or a sub-formula thereof), ring

A is 6- to 10-membered bicyclic heterocyclyl or 3- to 5- or 7- to 8-membered monocyclic heterocyclyl.

In certain aspects, the present disclosure provides compounds of Formula (II), or a pharmaceutically acceptable salt, a stereoisomer, or a tautomer thereof:

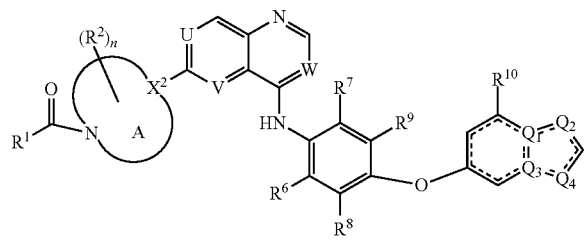

(II)

wherein:
ring 

is 4- to 7-membered heterocyclyl;
R$^1$ is

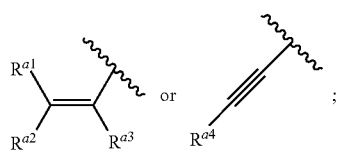

each of R$^{a1}$, R$^{a2}$, R$^{a3}$, and R$^{a4}$ is independently hydrogen, halo, CN, N(R$^{n1}$)$_2$, optionally substituted C$_{1-5}$ alkyl, optionally substituted —CH$_2$O—C$_{1-5}$ alkyl, optionally substituted —CH$_2$O—(CH$_2$)$_{1-2}$—O—C$_{1-5}$ alkyl, optionally substituted —CO$_2$—C$_{1-5}$ alkyl, or optionally substituted 3- to 6-membered heterocyclyl; or R$^{a1}$ and R$^{a2}$ are joined together to form an alkenyl group;
each instance of R$^{n1}$ is independently hydrogen or C$_{1-5}$ alkyl;
or R$^{a1}$ and R$^{a2}$ are joined together to form an alkenyl group;
R$^2$, independently for each occurrence, is optionally substituted C$_{1-5}$ alkyl; or taken together two geminal occurrences of R$^2$ form an oxo moiety; or two non-geminal occurrences of R$^2$ taken together form a C$_1$-C$_4$ (e.g., C$_1$-C$_2$) alkylene bridge; or R$^d$ and an occurrence of R$^2$ taken together with the intervening atoms form a 5- to 8-membered heterocyclic ring;
n is 0 or an integer from 1 to 3, inclusive, as permitted by valence;
X$^2$ is —C=, —CH—, or N;
U is CR$^c$ or N;
R$^c$ is hydrogen, halo, or optionally substituted C$_{1-5}$ alkoxy;
V is CR$^d$ or N;
R$^d$ is hydrogen, halo, optionally substituted C$_{1-5}$ alkyl, or optionally substituted C$_{1-5}$ alkoxy, or R$^d$ and an occurrence of R$^2$ taken together with the intervening atoms form a 3- to 6-membered heterocyclic ring;
W is N or CR$^e$;
R$^e$ is hydrogen, halo (e.g., fluoro), or cyano;
R$^6$, R$^7$, R$^8$, and R$^9$ are each independently hydrogen, halo, optionally substituted C$_{1-5}$ alkyl, or optionally substituted C$_{1-5}$ alkoxy;
R$^{10}$ is hydrogen, halo, or optionally substituted C$_{1-5}$ alkyl;

Q$^1$, Q$^2$, Q$^3$, and Q$^4$ are each independently NR$^f$ or CR$^g$, provided that at least one of Q$^1$, Q$^2$, Q$^3$, and Q$^4$ is CR$^g$;
R$^f$, independently for each occurrence, is hydrogen, optionally substituted C$_{1-5}$ alkyl, or absent; and
R$^g$, independently for each occurrence, is hydrogen, optionally substituted C$_{1-5}$ alkyl, or absent.

In one embodiment of Formula (II) (or a sub-formula thereof), it is provided that when

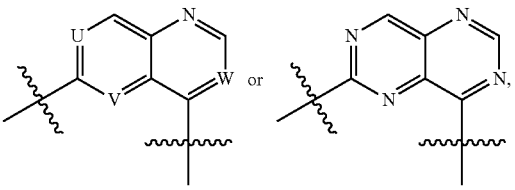

ring 

is

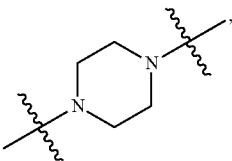 [SMILES: *N1CCN(*)CC1]

then R$^8$ is C$_{1-5}$ alkyl and R$^6$ is halo. In one embodiment, R$^8$ is methyl. In one embodiment, R$^6$ is fluoro. In one embodiment, R$^8$ is methyl, and R$^6$ is fluoro.

In certain embodiments, the compounds of Formula (II) are compounds of Formula (III), or a pharmaceutically acceptable salt, a stereoisomer, or a tautomer thereof:

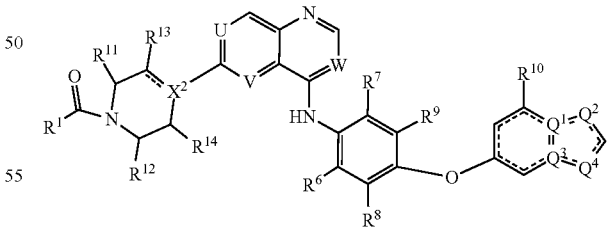

(III)

wherein:
R$^{11}$, R$^{12}$, R$^{13}$, and R$^{14}$ are each independently hydrogen or optionally substituted C$_{1-5}$ alkyl; or two non-geminal occurrences of R$^{11}$, R$^{12}$, R$^{13}$, and R$^{14}$ taken together form a C$_1$-C$_4$ (e.g., C$_1$-C$_2$) alkylene bridge.

In certain aspects, the present disclosure provides compounds of Formula (a-I), or a pharmaceutically acceptable salt, a stereoisomer, or a tautomer thereof:

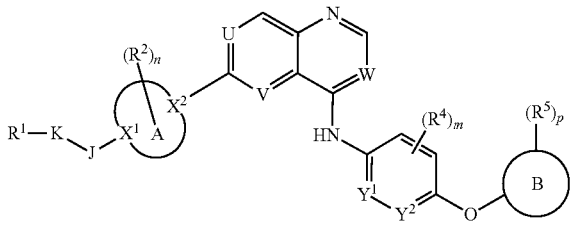
(a-1)

wherein:
ring

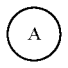

is 3- to 10-membered heterocyclyl;
ring

is 6- to 10-membered aryl or 5- to 10-membered heteroaryl;
- $R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$;
- $R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
- each instance of $R^{n1}$ is independently hydrogen or $C_{1-5}$ alkyl;
- J is $NR^b$ and $X^1$ is CH; or J is a bond and $X^1$ is N;
- $R^b$ is hydrogen or optionally substituted $C_{1-4}$ alkyl;
- K is a bond, C=O, or $SO_2$;
- $R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;
- n is 0 or an integer from 1 to 3, inclusive, as permitted by valence;
- $X^2$ is —C=, —CH—, or N;
- U is $CR^c$ or N;
- $R^c$ is hydrogen, halo, or optionally substituted $C_{1-5}$ alkoxy;
- V is $CR^d$ or N;
- $R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
- W is N or $CR^e$;
- $R^e$ is hydrogen, halo (e.g., fluoro), or cyano;
- $Y^1$ and $Y^2$ are each independently CH, $CR^4$ or N, provided that at least one of $Y^1$ and $Y^2$ is CH or $CR^4$;
- $R^4$, independently for each occurrence, is halo, optionally substituted $C_{1-5}$ alkyl, or optionally substituted $C_{1-5}$ alkoxy;
- m is 0 or an integer from 1 to 4, inclusive, as permitted by valence;
- $R^5$, independently for each occurrence, is halo, optionally substituted $C_{1-5}$ alkyl, or optionally substituted $C_{1-5}$ alkoxy; and
- p is 0 or an integer from 1 to 3, inclusive, as permitted by valence.

In some embodiments of Formula (a-I) (a subformula thereof), it is provided that when K is C=O; V is N or ring

is

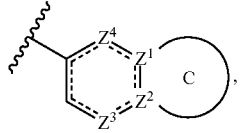

wherein

is 5- or 6-membered heteroaryl; $Z^1$, $Z^2$, $Z^3$, and $Z^4$ are each independently C or N; and any atom of ring

may be substituted by $R^5$ as permitted by valence.

In one embodiment of Formula (a-I) (or a sub-formula thereof), K is a bond. In one embodiment of Formula (a-I) (or a sub-formula thereof), K is a C=O. In one embodiment of Formula (a-I) (or a sub-formula thereof), K is a $SO_2$.

In certain aspects, the present disclosure provides compounds of Formula (I-i), or a pharmaceutically acceptable salt, a stereoisomer, or a tautomer thereof:

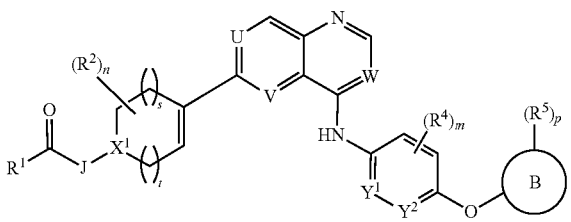
(I-i)

or a pharmaceutically acceptable salt, a stereoisomer, or a tautomer thereof,
wherein:
ring

is 6- to 10-membered aryl or 5- to 10-membered heteroaryl;
$R^1$ is $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, optionally substituted —O—$C_{1-5}$ alkyl, optionally substituted —O—$C_{1-5}$ alkylene-O—$C_{1-5}$ alkyl, optionally substituted —$CO_2$—$C_{1-5}$ alkyl, or optionally substituted 3- to 6-membered heterocyclyl; each instance of $R^{n1}$ is independently hydrogen or $C_{1-5}$ alkyl;
J is $NR^b$ and $X^1$ is CH; or J is a bond and $X^1$ is N;
s is 0, 1, or 2;
t is 1 or 2;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge;
n is 0 an integer from 1 to 3, inclusive, as permitted by valence;
U is $CR^c$ or N;
V is $CR^d$ or N; provided that at least one of U and V is N;
$R^c$ is hydrogen, halo, or optionally substituted $C_{1-5}$ alkoxy;
$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 5- to 6-membered heterocyclic ring;
W is N or $CR^e$;
$R^e$ is hydrogen, halo, or cyano;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.

In certain embodiments, the compounds of Formula (I-i) are of Formula (I-i-a), or a pharmaceutically acceptable salt, a stereoisomer, or a tautomer thereof:

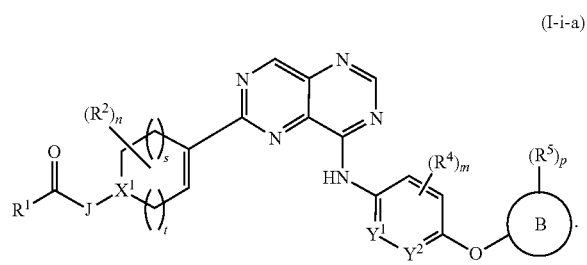

(I-i-a)

In certain embodiments, the compounds of Formula (I-i) are of Formula (I-i-a0), or a pharmaceutically acceptable salt, a stereoisomer, or a tautomer thereof:

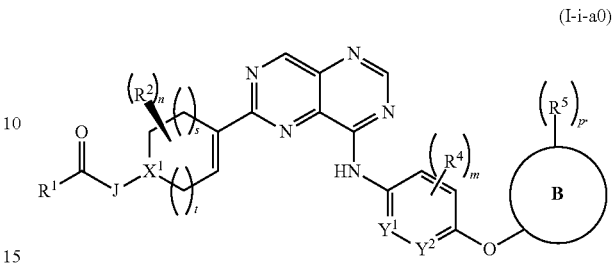

(I-i-a0)

In certain embodiments, the compounds of Formula (I-i) are of Formula (I-i-a1):

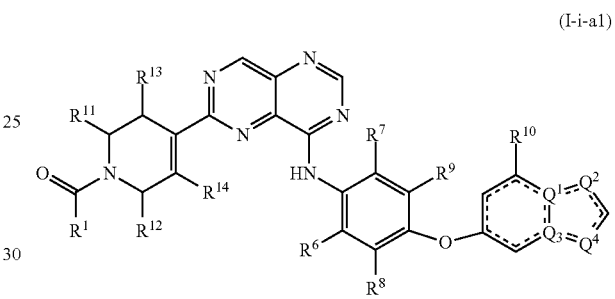

(I-i-a1)

or a pharmaceutically acceptable salt, a stereoisomer, or a tautomer thereof,
wherein:
$R^6$, $R^7$, $R^8$, and $R^9$ are each independently hydrogen, halo, optionally substituted $C_{1-5}$ alkyl, or optionally substituted $C_{1-5}$ alkoxy;
$R^{10}$ is hydrogen, halo, or optionally substituted $C_{1-5}$ alkyl;
$Q^1$, $Q^2$, $Q^3$, and $Q^4$ are each independently $NR^f$ or $CR^g$ as valency permits, provided that at least one of $Q^1$, $Q^2$, $Q^3$, and $Q^4$ is $CR^g$;
$R^f$, independently for each occurrence, is hydrogen, optionally substituted $C_{1-5}$ alkyl, or absent;
$R^g$, independently for each occurrence, is hydrogen, optionally substituted $C_{1-5}$ alkyl, or absent; and
$R^{11}$, $R^{12}$, $R^{13}$, and $R^{14}$ are each independently hydrogen or optionally substituted $C_{1-5}$ alkyl, or two of $R^{11}$, $R^{12}$, $R^{13}$, and $R^{14}$ taken together form a $C_{1-4}$ alkylene bridge.

In certain embodiments, the compounds of Formula (I-i-a1) are of the following formula, or a pharmaceutically acceptable salt, a stereoisomer, or a tautomer thereof:

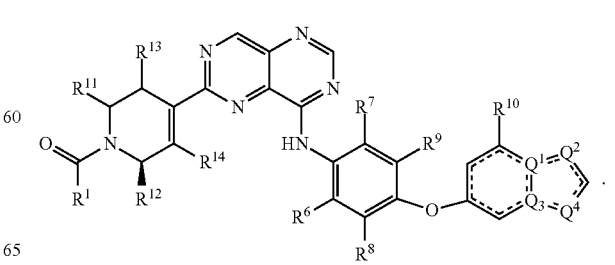

In certain embodiments, the compounds of Formula (I-i-a1) are of the following formula, or a pharmaceutically acceptable salt, a stereoisomer, or a tautomer thereof:

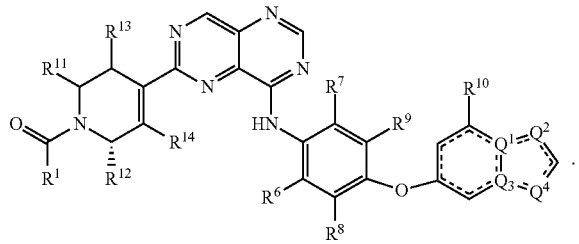

In certain embodiments, the compounds of Formula (I-i-a1) are of the following formula, or a pharmaceutically acceptable salt, a stereoisomer, or a tautomer thereof:

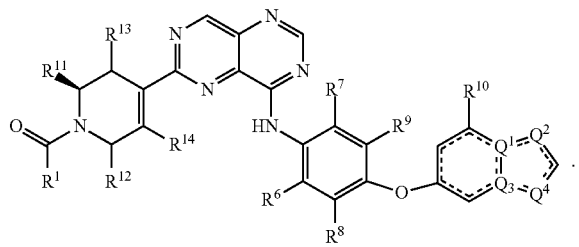

In certain embodiments, the compounds of Formula (I-i-a1) are of the following formula, or a pharmaceutically acceptable salt, a stereoisomer, or a tautomer thereof:

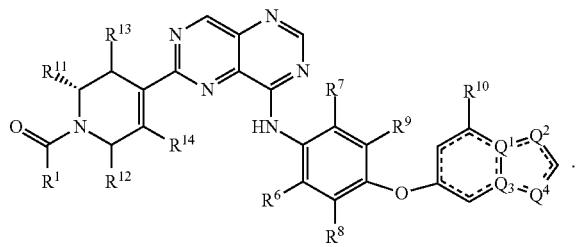

In certain embodiments, the compounds of Formula (I-i-a1) are of Formula (I-i-a2):

(I-i-a2)

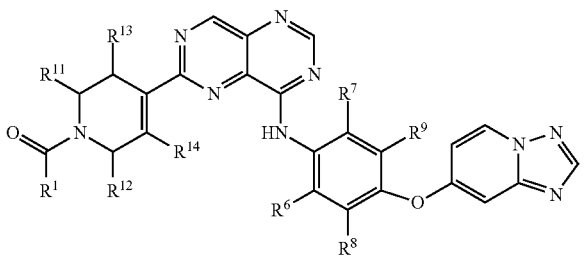

or a pharmaceutically acceptable salt, a stereoisomer, or a tautomer thereof.

In certain embodiments, the present disclosure provides a pharmaceutical composition suitable for use in a subject in the treatment or prevention of cancer comprising an effective amount of any of the compounds described herein (such as a compound of any of Formula (I), (I-i), (I-i-a), (I-i-a1), (I-i-a2), (a-I), (II), or (III), or subformulae thereof) or a pharmaceutically acceptable salt, a stereoisomer, or a tautomer thereof, and one or more pharmaceutically acceptable excipients. In certain embodiments, the pharmaceutical preparations may be for use in treating or preventing a condition or disease as described herein.

An aspect of the disclosure is methods of treating cancer, comprising administering to a mammal (e.g. a human subject) in need thereof an effective amount of a compound as disclosed herein (e.g., a compound of Formula (I), (I-i), (I-i-a), (I-i-a1), (I-i-a2), (a-I), (II), or (III), or any of the embodiments thereof disclosed herein) or a pharmaceutical composition as provided herein. In certain embodiments, provided herein are methods of treating HER2-associated cancer, comprising administering to a mammal (e.g. a human subject) in need thereof an effective amount of a compound as disclosed herein (e.g., a compound of Formula (I), (I-i), (I-i-a), (I-i-a1), (I-i-a2), (a-I), (II), or (III), or any of the embodiments thereof disclosed herein) or a pharmaceutical composition as provided herein. In certain embodiments, the human subject is in need of such treatment. In certain embodiments, the human subject is identified or diagnosed as having a HER2-associated cancer. In certain embodiments, HER2-associated cancer is associated with a dysregulation of a HER2 gene, a HER2 kinase, or expression or activity or level of any of the same. In certain embodiments, HER2-associated cancer is associated with HER2 overexpression, and/or HER2 amplification, and/or HER2 mutation(s). In certain embodiments, the cancer is solid tumor. In certain embodiments, the HER2-associated cancers include, but are not limited to, non-small cell lung cancer, breast cancer, ovarian cancer, brain cancer, biliary cancer, cervical cancer, gastric cancer, esophageal cancer, endometrial cancer, glioblastoma, prostate cancer, skin cancer, esophagus tumor, colorectal cancer, bladder cancer, gastrointestinal cancer, gallbladder tumor, kidney cancer, liver cancer, prostate cancer, and head-and-neck cancer. In some embodiments, the HER2-associated cancer is non-small cell lung cancer. In some embodiments, the HER2-associated cancer is breast cancer. In certain embodiments, HER2-associated cancer is brain cancer. In certain embodiments, the HER2 exon 20 mutation is one or more selected from YVMA insertion, VC insertion, and GSP insertion. In certain embodiments, the HER2 exon 20 mutation is one or more selected from A775_G776insYVMA, P780_Y781insGSP, G776>VC, G776>IC, G776>LC, G778_S779insCPG, G780_P781dupGSP, Y772_A775dup, G778_P780dup, E770_A771insGIRD, G778_S779insLPS, M774_A775insAYVM, G778_S779insLPG, G778dup, G776delinsVC, M774delinsWLV, A775 G776insSVMA, and A775_G776insI. In certain embodiments, the HER2 exon 20 mutation is one or more selected from A775_G776insYVMA, P780_Y781insGSP, G776>VC, G776>IC, G776>LC, G778_S779insCPG, and G780_P781dupGSP. In certain embodiments, the HER2 exon 20 mutation is one or more selected from A775_G776insYVMA, P780_Y781insGSP, G776>VC, G776>IC, G776>LC, and G778_S779insCPG.

In some embodiments, the method of treating or preventing cancer may comprise administering a compound of Formula (I), (I-i), (I-i-a), (I-i-a1), (I-i-a2), (a-I), (II), (III), or and subformulae thereof by administering with a second therapeutic agent (e.g. immunomodulator or platinum analog).

DETAILED DESCRIPTION

Definitions

Figure 1:
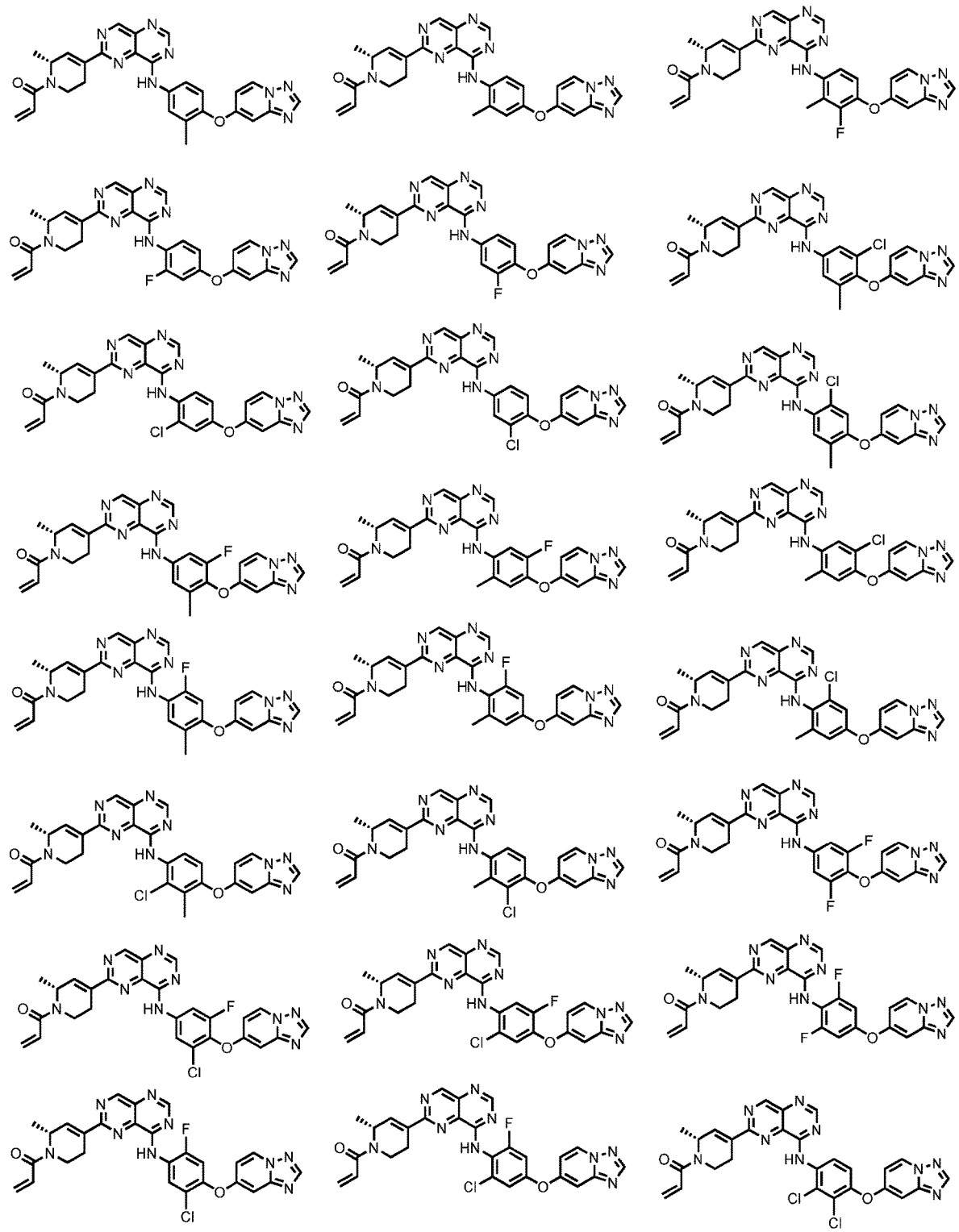
FIGS. 1-17 show certain exemplified compounds encompassed by the present invention.

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In some embodiments, chemical structures are disclosed with a corresponding chemical name. In case of conflict, the chemical structure controls the meaning, rather than the name.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited are not substantially changed by the presence of more than that which is recited, but excludes prior art embodiments.

Unless specifically stated or obvious from context, as used herein, the term "or" is understood to be inclusive. Unless specifically stated or obvious from context otherwise, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

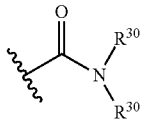

wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

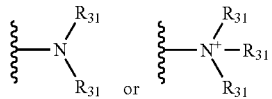

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

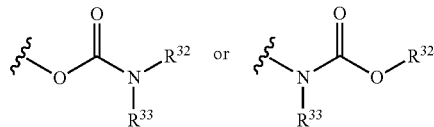

wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2—R^{34}$, wherein $R^{34}$ represents a hydrocarbyl group.

The term "carboxy", as used herein, refers to a group represented by the formula $—CO_2H$.

The term "ester", as used herein, refers to a group $—C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems, such as bicyclic ring systems (e.g., fused or spiro bicyclic heterocyclyl), having two or more cyclic rings in which one or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. The terms "heterocyclyl" and "heterocyclic" also include substituted or unsubstituted partially unsaturated non-aromatic ring structures. In some embodiments, the heterocyclyl is a 3- to 10-membered monocyclic or bicyclic ring system with at least one double bond. In some embodiments, the heterocyclyl is a 3- to 10-membered monocyclic or bicyclic ring system with only one double bond. In some embodiments, the heterocyclyl is a 6-membered heterocyclyl ring having at least one double bond. In some embodiments, the heterocyclyl is a 6-membered heterocyclyl ring having only one double bond. the Heterocyclyl groups include, for example, piperidine, piperazine, pyrrolidine, morpholine, lactones, lactams, tetrahydrofurans, 1,4-diazabicyclo[2.2.2]octane (DABCO), tetrahydroquinoline, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

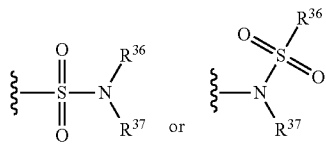

wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group $SO_3H$, or a pharmaceutically acceptable salt thereof.

The term "sulfone" is art-recognized and refers to the group —S(O)$_2$—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)$SR^{40}$ or —SC(O)$R^{40}$ wherein $R^{40}$ represents a hydrocarbyl.

The term "thioether", as used herein, is equivalent to an ether, wherein the oxygen is replaced with a sulfur.

The term "urea" is art-recognized and may be represented by the general formula

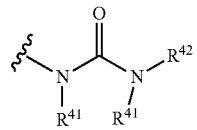

wherein $R^{41}$ and $R^{42}$ independently represent hydrogen or a hydrocarbyl, such as alkyl, or either occurrence of $R^{41}$ taken together with $R^{42}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the disclosure may be racemic. In certain embodiments, compounds of the disclosure may be enriched in one enantiomer. For example, a compound of the disclosure may have greater than about 30% ee, about 40% ee, about 50% ee, about 60% ee, about 70% ee, about 80% ee, about 90% ee, or even about 95% or greater ee. In certain embodiments, compounds of the disclosure may have more than one stereocenter. In certain such embodiments, compounds of the disclosure may be enriched in one or more diastereomer. For example, a compound of the disclosure may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I) or (II) or (III)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I) or (II) or (III)). A diastereomerically enriched mixture may comprise, for example, at least about 60 mol percent of one diastereomer, or more preferably at least about 75, about 90, about 95, or even about 99 mol percent.

As used herein, the term "stereoisomers" refer to isomeric molecules that have the same molecular constitution and connectivity, but a different three-dimensional spatial arrangement of the atoms. Stereoisomers are isomers that differ in spatial arrangement of atoms, rather than order of atomic connectivity. In some embodiments, "stereoisomers" refer to the various stereoisomeric forms of a compound that comprises one or more asymmetric centers or stereohindrance in the structure. In some embodiments, a stereoisomer is an enantiomer, a mixture of enantiomers, an atropisomer, or a tautomer thereof. In some embodiments, the compounds described herein can be in the form of an individual enantiomer, diastereomer or geometric isomer (e.g. an atropisomer), or can be in the form of a mixture of stereoisomers, including racemic mixtures and mixtures enriched in one or more stereoisomer. In some embodiments, a stereoisomer includes diastereoisomer(s), enantiomer(s), a mixture of diastereoisomers, and a mixture of enantiomers. In some embodiments, compounds provided herein may be atropisomers. In certain embodiments, atropisomers are stereoisomers arising because of hindered rotation about a single bond, where energy differences due to steric strain or other contributors create a barrier to rotation that is high enough to allow for isolation of individual conformers. Stereoisomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972).

In some embodiments, a moiety in a compound exists as a mixture of tautomers. A "tautomer" is a structural isomer of a moiety or a compound that readily interconverts with another structural isomer. For example, a pyrazole ring has two tautomers:

which differ in the positions of the pi-bonds and a hydrogen atom. Unless explicitly stated otherwise, a drawing of one tautomer of a moiety or a compound encompasses all of the possible tautomers.

The term "mammal" includes human subjects, primates, and commercially relevant mammals such as cattle, pigs, horses, sheep, goats, cats, and/or dogs; and/or birds, including commercially relevant birds such as chickens, ducks, geese, quail, and/or turkeys. The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys). In certain embodiments, the mammal is a human subject.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present disclosure. A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present disclosure. In certain embodiments, some or all of the compounds as disclosed herein in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein, refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

In certain embodiments, the pharmaceutically acceptable salt of the compound is selected from the group consisting of alkyl ammonium salts, dialkyl ammonium salts, trialkyl ammonium salts, tetra-alkyl ammonium salts, L-arginine salts, benenthamine salts, benzathine salts, betaine salts, calcium hydroxide salts, choline salts, deanol salts, diethanolamine salts, diethylamine salts, 2-(diethylamino)ethanol salts, ethanolamine salts, ethylenediamine salts, N-methylglucamine salts, hydrabamine salts, 1H-imidazole salts, lithium salts, L-lysine salts, magnesium salts, 4-(2-hydroxyethyl)morpholine salts, piperazine salts, potassium salts, 1-(2-hydroxyethyl)pyrrolidine salts, sodium salts, triethanolamine salts, tromethamine salts, Na salts, Ca salts, K salts, Mg salts, and Zn salts.

In specific embodiments, the pharmaceutically acceptable salt is a solvate selected from the group consisting of water, methanol, ethanol, and dimethylformamide.

In certain embodiments the compound is a pharmaceutical composition including a pharmaceutically acceptable carrier or excipient.

In specific embodiments, the composition is in a form selected from the group consisting of a tablet, a capsule, a granule, a lyophile for reconstitution, a powder, a solution, a syrup, a suppository, an injection, a suspension, an infusion, a transdermal delivery system (such as cream, gel, ointment), and a solution suitable for topical administration.

Compounds

The present disclosure provides a compound of Formula (I), or a pharmaceutically acceptable salt, a stereoisomer, or a tautomer thereof:

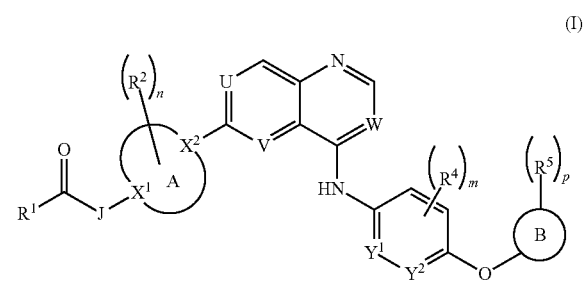

(I)

wherein:

ring

is 3- to 10-membered heterocyclyl;
ring

is 6- to 10-membered aryl or 5- to 10-membered heteroaryl;
- $R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$;
- $R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
- each instance of $R^{n1}$ is independently hydrogen or $C_{1-5}$ alkyl;
- J is $NR^b$ and $X^1$ is CH; or J is a bond and $X^1$ is N;
- $R^b$ is hydrogen or optionally substituted $C_{1-5}$ alkyl;
- $R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;
- n is 0 or an integer from 1 to 3, inclusive, as permitted by valence;
- $X^2$ is —C=, —CH—, or N;
- U is $CR^c$ or N;
- $R^c$ is hydrogen, halo, or optionally substituted $C_{1-5}$ alkoxy;
- V is $CR^d$ or N;
- $R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
- W is N or $CR^e$;
- $R^e$ is hydrogen, halo (e.g., fluoro), or cyano;
- $Y^1$ and $Y^2$ are each independently CH, $CR^4$ or N, provided that at least one of $Y^1$ and $Y^2$ is CH or $CR^4$;
- $R^4$, independently for each occurrence, is halo, optionally substituted $C_{1-5}$ alkyl, or optionally substituted $C_{1-5}$ alkoxy;
- m is 0 or an integer from 1 to 4, inclusive, as permitted by valence;
- $R^5$, independently for each occurrence, is halo, optionally substituted $C_{1-5}$ alkyl, or optionally substituted $C_{1-5}$ alkoxy; and
- p is 0 or an integer from 1 to 3, inclusive, as permitted by valence.

In some embodiments of Formula (I), it's provided when V is N; or ring

is

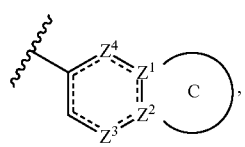

wherein

is 5- or 6-membered heteroaryl; $Z^1$, $Z^2$, $Z^3$, and $Z^4$ are each independently C or N; and any atom of ring

may be substituted by $R^5$ as permitted by valence.

In some aspects, the present disclosure provides a compound of Formula (II), or a pharmaceutically acceptable salt, a stereoisomer, or a tautomer thereof:

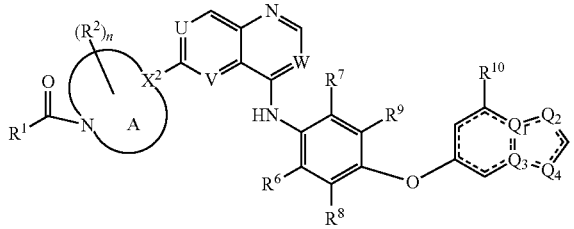

(II)

wherein.
ring

is 4- to 7-membered heterocyclyl;
$R^1$ is

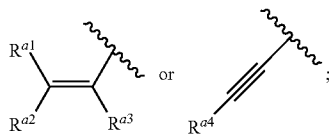

- $R^{a1}$, $R^{a2}$, $R^{a3}$, and $R^{a4}$ are each independently hydrogen, halo, CN, $N(R^{n1})_2$, optionally substituted $C_{1-5}$ alkyl, optionally substituted —$CH_2O$—$C_{1-5}$ alkyl, optionally substituted —$CH_2O$—$(CH_2)_{1-2}$—O—$C_{1-5}$ alkyl, optionally substituted —$CO_2$—$C_{1-5}$ alkyl, or optionally substituted 3- to 6-membered heterocyclyl;
- each instance of $R^{n1}$ is independently hydrogen or $C_{1-5}$ alkyl;
- $R^2$, independently for each occurrence, is optionally substituted $C_{1-5}$ alkyl; or taken together two geminal occurrences of $R^2$ are an oxo moiety; or two non-geminal occurrences of $R^2$ taken together form a $C_1$-$C_4$ (e.g., $C_1$-$C_2$) alkylene bridge;
- n is 0 or an integer from 1 to 3, inclusive, as permitted by valence;
- $X^2$ is —C=, —CH—, or N;

U is $CR^c$ or N;
$R^c$ is hydrogen, halo, or optionally substituted $C_{1-5}$ alkoxy;
V is $CR^d$ or N;
$R^d$ is hydrogen, halo, optionally substituted $C_{1-5}$ alkyl, optionally substituted $C_{1-5}$ alkoxy, or $R^d$ and an occurrence of $R^2$ taken together with the intervening atoms form a heterocyclic ring;
W is N or $CR^e$;
$R^e$ is hydrogen, halo (e.g., fluoro), or cyano;
$R^6$, $R^7$, $R^8$, and $R^9$ are each independently hydrogen, halo, optionally substituted $C_{1-5}$ alkyl, or optionally substituted $C_{1-5}$ alkoxy;
$R^{10}$ is hydrogen, halo, or optionally substituted $C_{1-5}$ alkyl;
$Q^1$, $Q^2$, $Q^3$, and $Q^4$ are each independently NR or $CR^g$, provided that at least one of $Q^1$, $Q^2$, $Q^3$, and $Q^4$ is $CR^g$;
$R^f$, independently for each occurrence, is hydrogen, optionally substituted $C_{1-5}$ alkyl, or absent; and
$R^g$, independently for each occurrence, is hydrogen, optionally substituted $C_{1-5}$ alkyl, or absent.

In some aspects, the present disclosure provides a compound of Formula (I-i), or a pharmaceutically acceptable salt, a stereoisomer, or a tautomer thereof:

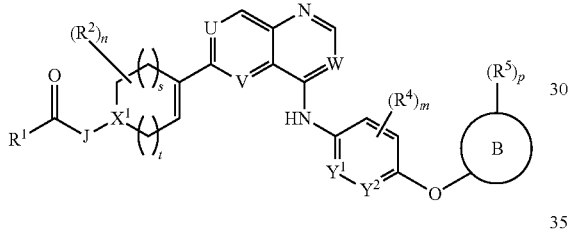

(I-i)

or a pharmaceutically acceptable salt, a stereoisomer, or a tautomer thereof,
wherein:
ring

is 6- to 10-membered aryl or 5- to 10-membered heteroaryl;
$R^1$ is $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, optionally substituted —O—$C_{1-5}$ alkyl, optionally substituted —O—$C_{1-5}$ alkylene-O—$C_{1-5}$ alkyl, optionally substituted —$CO_2$—$C_{1-5}$ alkyl, or optionally substituted 3- to 6-membered heterocyclyl;
each instance of $R^{n1}$ is independently hydrogen or $C_{1-5}$ alkyl;
J is $NR^b$ and $X^1$ is CH; or J is a bond and $X^1$ is N;
s is 0, 1, or 2;
t is 1 or 2;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge;

n is 0 or an integer from 1 to 3, inclusive, as permitted by valence;
U is $CR^c$ or N;
V is $CR^d$ or N; provided that at least one of U and V is N;
$R^c$ is hydrogen, halo, or optionally substituted $C_{1-5}$ alkoxy;
$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 5- to 6-membered heterocyclic ring;
W is N or $CR^e$;
$R^e$ is hydrogen, halo, or cyano;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.

In certain aspects, the compound of Formula (I-i) is a compound of Formula (I-i-a):

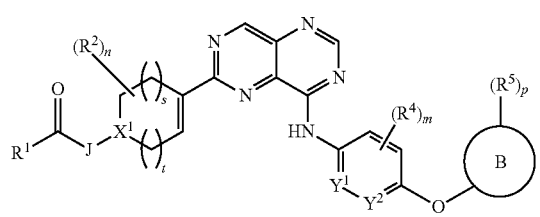

(I-i-a)

or a pharmaceutically acceptable salt, a stereoisomer, or a tautomer thereof.

In certain aspects, the compound of Formula (I-i-a) is a compound of Formula (I-i-a1):

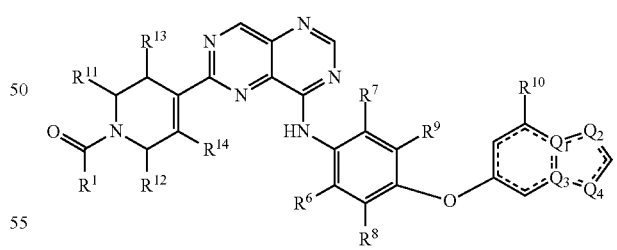

(I-i-a1)

or a pharmaceutically acceptable salt, a stereoisomer, or a tautomer thereof,
wherein:
$R^6$, $R^7$, $R^8$, and $R^9$ are each independently hydrogen, halo, optionally substituted $C_{1-5}$ alkyl, or optionally substituted $C_{1-5}$ alkoxy;
$R^{10}$ is hydrogen, halo, or optionally substituted $C_{1-5}$ alkyl;
$Q^1$, $Q^2$, $Q^3$, and $Q^4$ are each independently NR or $CR^g$ as valency permits, provided that at least one of $Q^1$, $Q^2$, $Q^3$, and $Q^4$ is $CR^g$;

$R^f$, independently for each occurrence, is hydrogen, optionally substituted $C_{1-5}$ alkyl, or absent;

$R^g$, independently for each occurrence, is hydrogen, optionally substituted $C_{1-5}$ alkyl, or absent; and $R^{11}$, $R^{12}$, $R^{13}$, and $R^{14}$ are each independently hydrogen or optionally substituted $C_{1-5}$ alkyl, or two of $R^{11}$, $R^{12}$, $R^{13}$, and $R^{14}$ taken together form a $C_{1-4}$ alkylene bridge.

In certain aspects, the compound of Formula (I-i) is a compound of Formula (I-i-a0), or a pharmaceutically acceptable salt, a stereoisomer, or a tautomer thereof:

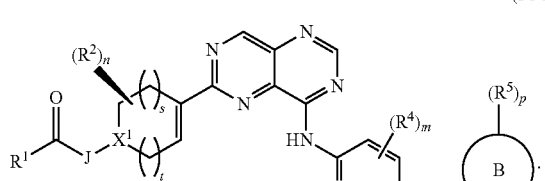

(I-i-a0)

In certain embodiments, the compounds of Formula (I-i-a1) are of the following formula, or a pharmaceutically acceptable salt, a stereoisomer, or a tautomer thereof:

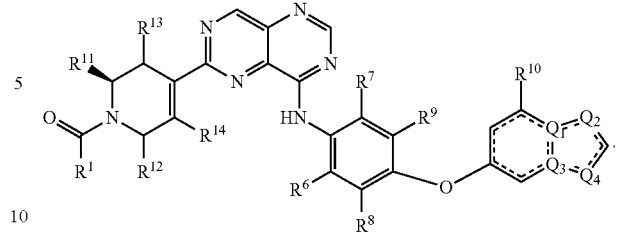

In certain embodiments, the compounds of Formula (I-i-a1) are of the following formula, or a pharmaceutically acceptable salt, a stereoisomer, or a tautomer thereof:

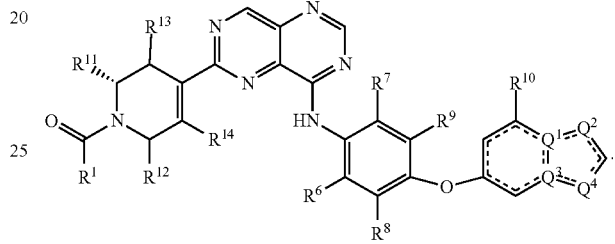

In certain embodiments, the compounds of Formula (I-i-a1) are of the following formula, or a pharmaceutically acceptable salt, a stereoisomer, or a tautomer thereof:

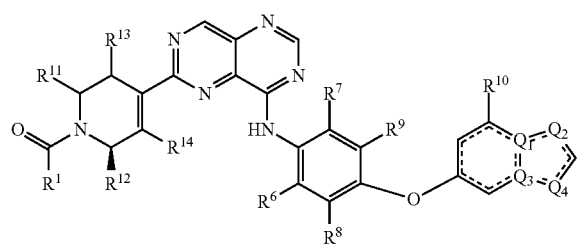

In certain embodiments, the compounds of Formula (I-i-a1) are of the following formula, or a pharmaceutically acceptable salt, a stereoisomer, or a tautomer thereof:

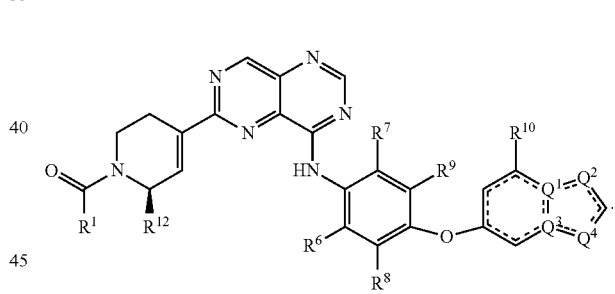

In certain embodiments, the compounds of Formula (I-i-a1) are of the following formula, or a pharmaceutically acceptable salt, a stereoisomer, or a tautomer thereof:

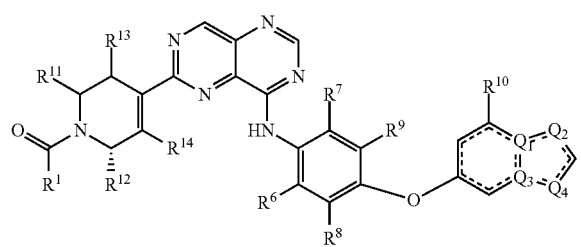

In certain embodiments, the compounds of Formula (I-i-a1) are of the following formula, or a pharmaceutically acceptable salt, a stereoisomer, or a tautomer thereof:

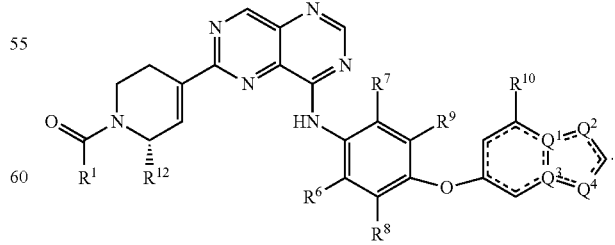

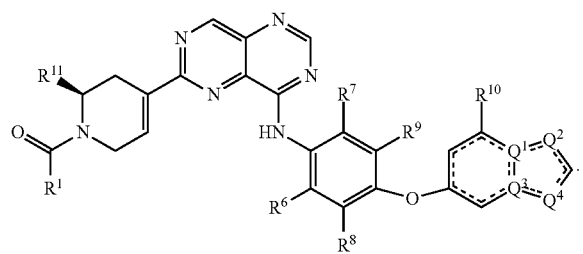

(I-i-a4)

or a pharmaceutically acceptable salt, a stereoisomer, or a tautomer thereof.

In certain aspects, the compound of Formula (I-i-a1) is a compound of Formula (I-i-a5):

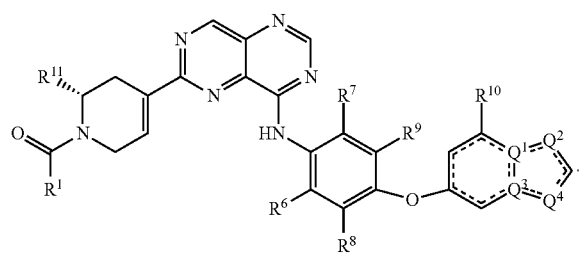

(I-i-a5)

or a pharmaceutically acceptable salt, a stereoisomer, or a tautomer thereof.

In certain aspects, the compounds of Formula (I-i-a1) is a compound of Formula (I-i-a6):

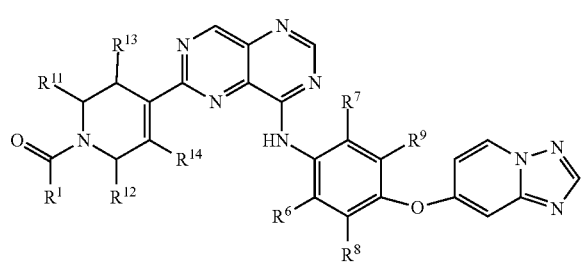

(I-i-a6)

or a pharmaceutically acceptable salt, a stereoisomer, or a tautomer thereof.

In certain aspects, the compounds of Formula (I-i) is a compound of Formula (I-i-b):

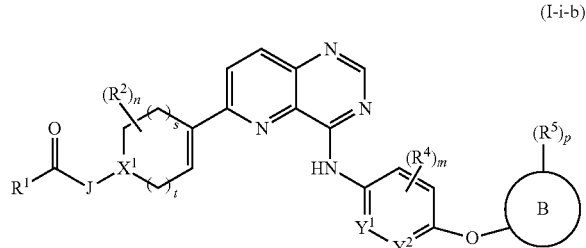

(I-i-b)

In certain embodiments, the compounds of Formula (I-i-a1) are of the following formula, or a pharmaceutically acceptable salt, a stereoisomer, or a tautomer thereof:

In certain aspects, the compound of Formula (I-i-a1) is a compound of Formula (I-i-a2):

(I-i-a2)

or a pharmaceutically acceptable salt, a stereoisomer, or a tautomer thereof.

In certain aspects, the compound of Formula (I-i-a1) is a compound of Formula (I-i-a3):

(I-i-a3)

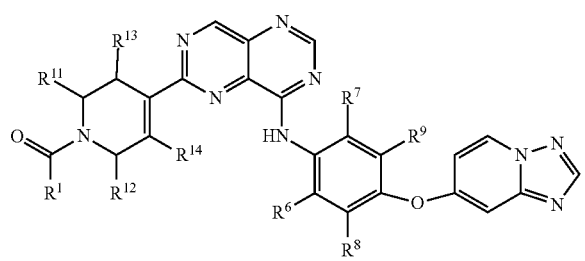

or a pharmaceutically acceptable salt, a stereoisomer, or a tautomer thereof. In certain aspects, the compound of Formula (I-i-a1) is a compound of Formula (I-i-a4):

or a pharmaceutically acceptable salt, a stereoisomer, or a tautomer thereof.

In certain aspects, the compounds of Formula (I-i) is a compound of Formula (I-i-c):

(I-i-c)

or a pharmaceutically acceptable salt, a stereoisomer, or a tautomer thereof.

In one embodiment of any one of Formula (I-i), (I-i-a), (I-i-a1), (I-i-a2), (I-i-a3), (I-i-a4), (I-i-a5), (I-i-a6), (I-i-b), (I-i-c), wherein s is 0 and t is 1 or 2. In one embodiment of any one of Formula (I-i), (I-i-a), (I-i-a1), (I-i-a2), (I-i-a3), (I-i-a4), (I-i-a5), (I-i-a6), (I-i-b), (I-i-c), wherein s is 1 and t is 1 or 2. In one embodiment of any one of Formula (I-i), (I-i-a), (I-i-a1), (I-i-a2), (I-i-a3), (I-i-a4), (I-i-a5), (I-i-a6), (I-i-b), (I-i-c), wherein s is 2 and t is 1 or 2. In one embodiment of any one of Formula (I-i), (I-i-a), (I-i-a1), (I-i-a2), (I-i-a3), (I-i-a4), (I-i-a5), (I-i-a6), (I-i-b), (I-i-c), wherein s is 1 and t is 1. In one embodiment of any one of Formula (I-i), (I-i-a), (I-i-a1), (I-i-a2), (I-i-a3), (I-i-a4), (I-i-a5), (I-i-a6), (I-i-b), (I-i-c), wherein s is 1 and t is 2.

In one embodiment of any one of Formula (I-i), (I-i-a), (I-i-a1), (I-i-a2), (I-i-a3), (I-i-a4), (I-i-a5), (I-i-a6), (I-i-b), (I-i-c), $R^{11}$ is optionally substituted $C_{1-5}$ alkyl. In one embodiment of any one of Formula (I-i), (I-i-a), (I-i-a1), (I-i-a2), (I-i-a3), (I-i-a4), (I-i-a5), (I-i-a6), (I-i-b), (I-i-c), $R^{11}$ is methyl. In one embodiment of any one of Formula (I-i), (I-i-a), (I-i-a1), (I-i-a2), (I-i-a3), (I-i-a4), (I-i-a5), (I-i-a6), (I-i-b), (I-i-c), $R^{11}$ is optionally substituted $C_{1-5}$ alkyl. In one embodiment of any one of Formula (I-i), (I-i-a), (I-i-a1), (I-i-a2), (I-i-a3), (I-i-a4), (I-i-a5), (I-i-a6), (I-i-b), (I-i-c), $R^{12}$ is methyl.

In certain aspects, the present disclosure provides compounds of Formula (I):

(I)

or a pharmaceutically acceptable salt, a stereoisomer, or a tautomer thereof,
wherein:
ring

A is 6- to 10-membered bicyclic heterocyclyl or 3- to 5- or 7- to 8-membered monocyclic heterocyclyl;
ring

B is 6- to 10-membered aryl or 5- to 10-membered heteroaryl;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —CO$_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge; or $R^d$ and an occurrence of $R^2$ taken together with the intervening atoms form a 5- to 8-membered heterocyclic ring;
n is 0 or an integer from 1 to 3, inclusive, as permitted by valence;
$X^2$ is —C=, —CH—, or N;
U is $CR^c$ or N;
V is $CR^d$ or N;
W is N or $CR^e$;
$R^c$ is hydrogen, halo, or optionally substituted $C_{1-5}$ alkoxy;
$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
$R^e$ is hydrogen, halo (e.g., fluoro), or cyano;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.-

In certain aspects, the present disclosure provides compounds of Formula (a-I), or a pharmaceutically acceptable salt, a stereoisomer, or a tautomer thereof:

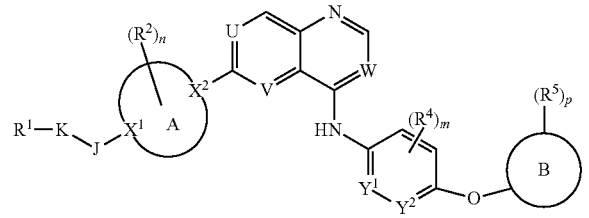

(a-I)

wherein:
ring

is 3- to 10-membered heterocyclyl;
ring

is 6- to 10-membered aryl or 5- to 10-membered heteroaryl;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$.
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —CO$_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted $C_{1-4}$ alkyl;
K is a bond, C=O, or SO$_2$;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;
n is 0 or an integer from 1 to 3, inclusive, as permitted by valence;
$X^2$ is —C=, —CH—, or N;
U is $CR^c$ or N;
$R^c$ is hydrogen, halo, or optionally substituted $C_{1-5}$ alkoxy;
V is $CR^d$ or N;
$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
W is N or $CR^e$;
$R^e$ is hydrogen, halo (e.g., fluoro), or cyano;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence;
provided that when K is C=O; V is N or ring

is

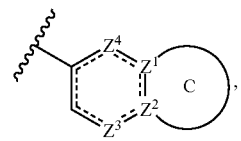

wherein

is 5- or 6-membered heteroaryl; $Z^1$, $Z^2$, $Z^3$, and $Z^4$ are each independently C or N; and any atom of ring

may be substituted by $R^5$ as permitted by valence.

In certain aspects, the present disclosure provides compounds of Formula (a-I), or a pharmaceutically acceptable salt, a stereoisomer, or a tautomer thereof:

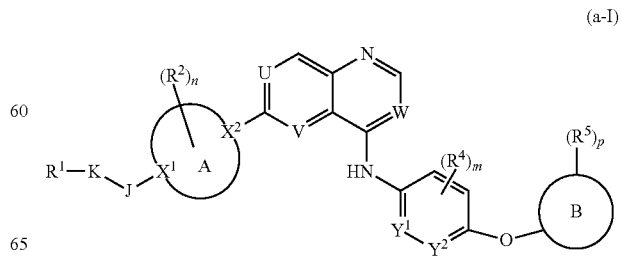

(a-I)

or a pharmaceutically acceptable salt, a stereoisomer, or a tautomer thereof,
wherein:
ring

is 3- to 10-membered heterocyclyl;
ring

is 6- to 10-membered aryl or 5- to 10-membered heteroaryl;
K is a bond or $SO_2$;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;
n is 0 or an integer from 1 to 3, inclusive, as permitted by valence;
$X^2$ is —C=, —CH—, or N;
U is $CR^c$ or N;
V is $CR^d$ or N;
W is N or $CR^e$;
$R^c$ is hydrogen, halo, or optionally substituted $C_{1-5}$ alkoxy;
$R^d$ is hydrogen, halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
$R^e$ is hydrogen, halo (e.g., fluoro), or cyano;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.

In one embodiment of Formula (a-I) (or a sub-formula thereof), K is a bond. In one embodiment of Formula (a-I) (or a sub-formula thereof), K is C=O. In one embodiment of Formula (a-I) (or a sub-formula thereof), K is S02. In one embodiment of Formula (a-I) (or a sub-formula thereof), J is a bond; $X^1$ is N; and K is C=O. In other embodiments of Formula (a-I) (or a sub-formula thereof), J is a bond; $X^1$ is N; and K is S02. In other embodiments of Formula (a-I) (or a sub-formula thereof), J is a bond; $X^1$ is N; and K is a bond. In other embodiments of Formula (a-I) (or a sub-formula thereof), J is a bond; $X^1$ is N; K is a bond; and $R^1$ is CN.

In one embodiment of Formula (I), (II), (I-i), or a-I) or a sub-formula thereof), it is provided that when

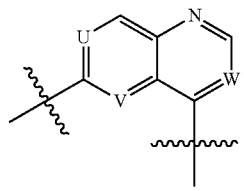

is

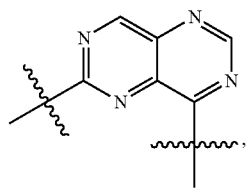 [SMILES: *c1ncc2ncnc(*)c2n1]

ring

is

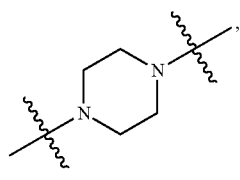 [SMILES: *N1CCN(*)CC1]

$Y^1$ and $Y^2$ are each independently $CR^4$, then $R^4$ in $Y^2$ is alkyl and $R^4$ in $Y^1$ is halo. In one embodiment, $R^4$ in $Y^2$ is methyl. In one embodiment, $R^4$ in $Y^1$ is fluoro. In one embodiment, $R^4$ in $Y^2$ is methyl, and $R^4$ in $Y^1$ is fluoro.-

In certain aspects, the present disclosure provides compounds of Formula (B):

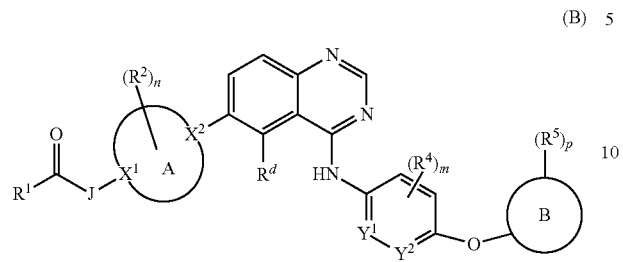

(B)

or a pharmaceutically acceptable salt, a stereoisomer, or a tautomer thereof,
wherein:
ring

is 3- to 10-membered heterocyclyl;
ring

is 6- to 10-membered aryl or 5- to 10-membered heteroaryl;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_1$-$C_4$ (e.g., $C_1$-$C_2$) alkylene bridge; or $R^d$ and an occurrence of $R^2$ taken together with the intervening atoms form a 5- to 8-membered heterocyclic ring;
n is 0 or an integer from 1 to 3, inclusive, as permitted by valence;
$X^2$ is —C═, —CH—, or N;
$R^d$ is halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring;
$Y^1$ and $Y^2$ are each independently CH, $CR^4$ or N, provided that at least one of $Y^1$ and $Y^2$ is CH or $CR^4$;
$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.

In certain aspects, the compounds of Formula (B) is a compound of Formula (B-i):

(B-i)

or a pharmaceutically acceptable salt, a stereoisomer, or a tautomer thereof,
wherein each of $R^{4a}$ and $R^{4b}$ is independently halo, optionally substituted $C_{1-5}$ alkyl, or optionally substituted $C_{1-5}$ alkoxy.

In certain embodiments of Formula (B-i) (or a sub-formula thereof), $R^{4a}$ is halo and $R^{4b}$ is optionally substituted $C_{1-5}$ alkyl. In certain embodiments of Formula (B-i) (or a sub-formula thereof), $R^{4a}$ is F or Cl and $R^{4b}$ is methyl. In certain embodiments of Formula (B-i) (or a sub-formula thereof), $R^{4b}$ is halo and $R^{4a}$ is optionally substituted $C_{1-5}$ alkyl. In certain embodiments of Formula (B-i) (or a sub-formula thereof), $R^{4b}$ is F or Cl and $R^{4a}$ is methyl. In certain embodiments of Formula (B-i) (or a sub-formula thereof), each of $R^{4a}$ and $R^{4b}$ is independently halo, optionally substituted $C_{1-5}$ alkyl, or optionally substituted $C_{1-5}$ alkoxy; and $R^d$ is halo, optionally substituted $C_{1-5}$ alkyl, or optionally substituted $C_{1-5}$ alkoxy, or $R^d$ and an occurrence of $R^2$ taken together with the intervening atoms form a 3- to 6-membered heterocyclic ring. In certain embodiments, each of $R^{4a}$ and $R^{4b}$ is independently halo (e.g., F or Cl), optionally substituted $C_{1-5}$ alkyl (e.g., methyl), $R^d$ is halo (e.g., F). In certain embodiments, each of $R^{4a}$ and $R^{4b}$ is independently halo (e.g., F or Cl), optionally substituted $C_{1-5}$ alkyl (e.g., methyl), $R^d$ is optionally substituted $C_{1-5}$ alkoxy. In certain embodiments, each of $R^{4a}$ and $R^{4b}$ is independently halo (e.g., F or Cl), optionally substituted $C_{1-5}$ alkyl (e.g., methyl), $R^d$ is optionally substituted $C_{1-5}$ alkyl or optionally substituted $C_{1-5}$ alkoxy, and an occurrence of $R^2$ taken together with the intervening atoms form a 3- to 6-membered heterocyclic ring.-

In certain aspects, the present disclosure provides compounds of Formula (C):

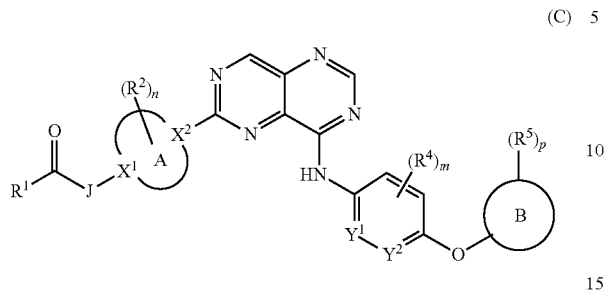

(C)

or a pharmaceutically acceptable salt, a stereoisomer, or a tautomer thereof,
wherein:
ring

is 3- to 10-membered heterocyclyl;
ring

is 6- to 10-membered aryl or 5- to 10-membered heteroaryl;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted $C_{1-5}$ alkyl;
$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge;
n is 0 or an integer from 1 to 3, inclusive, as permitted by valence, provided that when ring

is 6-membered monocyclic heterocyclyl with one or two N ring atoms, n is 2 or 3;
$X^2$ is —C=, —CH—, or N;
$Y^1$ and $Y^2$ are each independently CH, $CR^4$ or N, provided that at least one of $Y^1$ and $Y^2$ is CH or $CR^4$;

$R^4$, independently for each occurrence, is halo, optionally substituted $C_{1-5}$ alkyl, or optionally substituted $C_{1-5}$ alkoxy;
m is 0 or an integer from 1 to 4, inclusive, as permitted by valence;
$R^5$, independently for each occurrence, is halo, optionally substituted $C_{1-5}$ alkyl, or optionally substituted $C_{1-5}$ alkoxy; and
p is 0 or an integer from 1 to 3, inclusive, as permitted by valence.

In certain aspects, the present disclosure provides compounds of Formula (D):

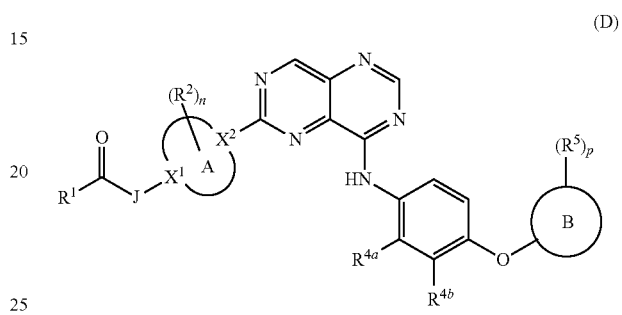

(D)

or a pharmaceutically acceptable salt, a stereoisomer, or a tautomer thereof,
wherein:
ring

is 3- to 10-membered heterocyclyl;
ring

is 6- to 10-membered aryl or 5- to 10-membered heteroaryl;
$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;
$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;
each instance of $R^{n1}$ is independently hydrogen or $C_{1-5}$ alkyl;
J is $NR^b$ and $X^1$ is CH; or J is a bond and $X^1$ is N;
$R^b$ is hydrogen or optionally substituted alkyl;
$R^2$, independently for each occurrence, is optionally substituted alkyl; or taken together two geminal occurrences of $R^2$ are an oxo moiety; or two non-geminal occurrences of $R^2$ taken together form a $C_1$-$C_4$ (e.g., $C_1$-$C_2$) alkylene bridge;
n is 0 or an integer from 1 to 3, inclusive, as permitted by valence;
$X^2$ is —C=, —CH—, or N;

each of $R^{4a}$ and $R^{4b}$ is independently halo, optionally substituted $C_{1-5}$ alkyl, or optionally substituted $C_{1-5}$ alkoxy;

$R^5$, independently for each occurrence, is halo, optionally substituted alkyl, or optionally substituted alkoxy; and p is 0 or an integer from 1 to 3, inclusive, as permitted by valence.

In certain aspects, the present disclosure provides compounds of Formula (E):

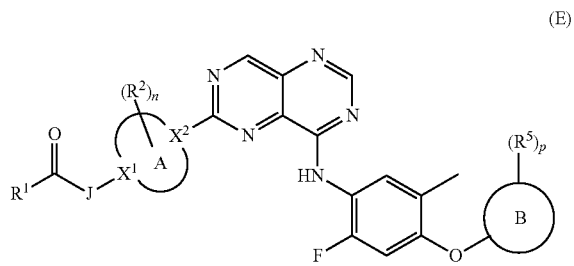

(E)

or a pharmaceutically acceptable salt, a stereoisomer, or a tautomer thereof,
wherein:
ring

is 3- to 10-membered heterocyclyl;
ring

is 6- to 10-membered aryl or 5- to 10-membered heteroaryl;

$R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkenyl, alkynyl, or heterocyclyl is optionally substituted by one or more occurrences of $R^a$;

$R^a$, independently for each occurrence, is halo, CN, $N(R^{n1})_2$, optionally substituted $C_{1-5}$ alkyl, —O—$C_{1-5}$ alkyl, —O—$C_{1-5}$ alkylene-O—$C_{1-5}$ alkyl, —$CO_2$—$C_{1-5}$ alkyl, or optionally substituted 3- to 6-membered heterocyclyl, or two $R^a$ taken together form an optionally substituted alkenyl group;

each instance of $R^{n1}$ is independently hydrogen or $C_{1-5}$ alkyl;

J is $NR^b$ and $X^1$ is CH; or J is a bond and $X^1$ is N;

$R^b$ is hydrogen or optionally substituted $C_{1-5}$ alkyl;

$R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge;

n is 0 or an integer from 1 to 3, inclusive, as permitted by valence;

$X^2$ is —C=, —CH—, or N;

$R^5$, independently for each occurrence, is halo, optionally substituted $C_{1-5}$ alkyl, or optionally substituted $C_{1-5}$ alkoxy; and p is 0 or an integer from 1 to 3, inclusive, as permitted by valence.

In certain embodiments of any of Formulae (I), (a-I), (B), (B-i), (C), (D), and (E), and subformulea thereof, ring

is a heterocyclyl comprising at least one nitrogen atom. In some embodiments, ring

is a 3- to 10-membered heterocyclyl. In some embodiments, ring

is 6- to 10-membered bicyclic heterocyclyl or 3- to 5- or 7- to 8-membered monocyclic heterocyclyl. In some embodiments, ring

is a 4- to 7-membered monocyclic heterocyclyl containing at least one nitrogen (e.g., one or two nitrogen) ring atom. In some embodiments, ring

is 6-membered monocyclic heterocyclyl. In some embodiments, ring

is 6-membered monocyclic heterocyclyl with one or two nitrogen. In some embodiments, ring

is 6- to 10-membered spiro bicyclic heterocyclyl. In some embodiments, ring

is 6- to 10-membered fused bicyclic heterocyclyl. In some embodiments, ring

is partially unsaturated heterocyclyl. In certain embodiments, ring

comprises one and only one double bond. In certain embodiments, ring

is azetidinyl, spirocyclic bis-azetidinyl, pyrrolidinyl, pyrrolinyl, piperidinyl, piperazinyl, tetrahydropyridinyl, azepanyl, or tetrahydroazepinyl. In certain such embodiments, ring

is piperazinyl or tetrahydropyridinyl. In some embodiments, ring

is tetrahydropyridinyl. In other embodiments, ring

is piperazinyl. In still other embodiments, ring

is spirocyclic bis-azetidinyl.

In certain embodiments of any of Formulae (I), (I-i), (I-i-a), (I-i-b), (I-i-c), (a-I), (B), (B-i), (C), (D), and (E) and subformulae thereof, ring

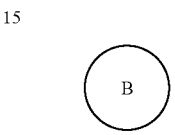

is 6- to 10-membered aryl. In some embodiments, ring

is 5-membered to 10-membered heteroaryl. In certain embodiments, ring

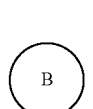

comprises 1 to 3 nitrogen atoms. In certain such embodiments, ring

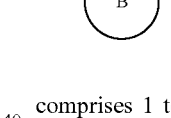

comprises three and only three nitrogen atoms. In some embodiments, ring

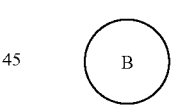

is a bicyclic heteroaryl. In certain embodiments, ring

is a 9- or 10-membered bicyclic heteroaryl. In certain such embodiments, ring

is a 9-membered bicyclic heteroaryl.

In certain embodiments of any of Formulae (I), (I-i), (I-i-a), (I-i-b), (I-i-c), (a-I), (B), (B-i), (C), (D), and (E) and subformulae thereof, ring

is

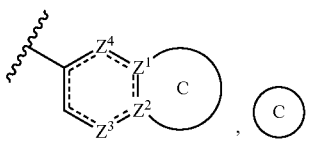

is 5- or 6-membered heteroaryl; $Z^1$, $Z^2$, $Z^3$, and $Z^4$ are each independently C or N; and any atom of ring

may be substituted by $R^5$ as permitted by valence. In some embodiments, at least one of $Z^1$, $Z^2$, $Z^3$, and $Z^4$ is N. In some embodiments, one and only one of $Z^1$, $Z^2$, $Z^3$, and $Z^4$ is N. In certain embodiments, $Z^1$ or $Z^2$ is N. In some embodiments, $Z^1$ is C and $Z^2$ is N. In certain embodiments, ring

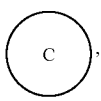

inclusive of $Z^1$ and $Z^2$, comprises 1 to 3 nitrogen atoms. In certain such embodiments, ring

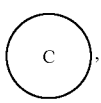

inclusive of $Z^1$ and $Z^2$, comprises three and only three nitrogen atoms.

In certain embodiments of any of Formulae (I), (I-i), (I-i-a), (I-i-b), (I-i-c), (a-I), (B), (B-i), (C), (D), and (E) and subformulae thereof, ring

is

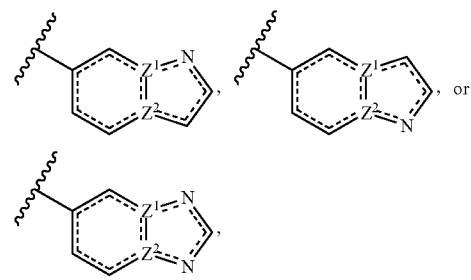

and any atom of ring

may be substituted by $R^5$ as permitted by valence. In some embodiments, ring

is

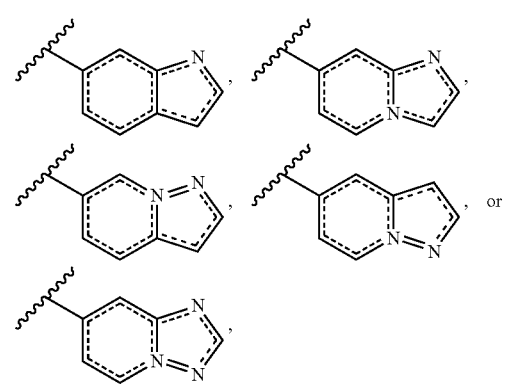

and any atom of ring

may be substituted by R⁵ as permitted by valence. In certain embodiments, ring

is

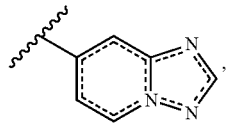, and any atom of ring

may be substituted by R⁵ as permitted by valence.

In some embodiments, $R^5$, independently for each occurrence, is halo, optionally substituted $C_{1-5}$ alkyl, or optionally substituted $C_{1-5}$ alkoxy. In some embodiments, $R^5$, independently for each occurrence, is optionally substituted $C_{1-5}$ alkyl.

In some embodiments, p is 0. In some embodiments, p is 1. In some embodiments, p is 2. In some embodiments, p is 3.

In some embodiments, $R^1$ is CN, $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$. In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^1$ is $C_{1-5}$ alkyl, $C_{1-5}$ haloalkyl, $C_{2-5}$ alkenyl, $C_{2-5}$ alkynyl, or 3- to 6-membered heterocyclyl, wherein the alkyl, alkenyl, alkynyl, or heterocyclyl is optionally substituted by one or more occurrences of $R^a$. In some embodiments, $R^1$ is $C_{2-5}$ alkenyl or $C_{2-5}$ alkynyl, wherein the alkenyl or alkynyl is optionally substituted by one or more occurrences of $R^a$.

In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^1$ is $C_{1-5}$ alkyl optionally substituted by one or more occurrences of R. In some embodiments, $R^1$ is $C_{1-5}$ alkyl. In some embodiments, $R^1$ is $C_{1-5}$ haloalkyl. In some embodiments, $R^1$ is $C_{2-5}$ alkenyl optionally substituted by one or more occurrences of $R^a$. In some embodiments, $R^1$ is $C_2$-5 alkynyl optionally substituted by one or more occurrences of R. In some embodiments, $R^1$ is ethenyl, ethynyl, methyl, ethyl, or oxiranyl. In some embodiments, $R^1$ is ethenyl. In some embodiments, $R^1$ is ethenyl. In some embodiments, $R^1$ is ethynyl.

In some embodiments, $R^a$, independently for each occurrence, is halo, CN, $N(R^{n1})_2$, optionally substituted $C_{1-5}$ alkyl, optionally substituted —O—$C_{1-5}$ alkyl, optionally substituted —O—$C_{1-5}$ alkylene-O—$C_{1-5}$ alkyl, optionally substituted —$CO_2$—$C_{1-5}$ alkyl, or optionally substituted 3- to 6-membered heterocyclyl; and each instance of $R^{n1}$ is independently hydrogen or $C_{1-5}$ alkyl. In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^a$ is $C_{1-5}$ alkyl (e.g., methyl or ethyl). In certain embodiments, $R^a$ is $C_{1-5}$ haloalkyl. In certain embodiments, $R^a$ is —O—$C_{1-5}$ alkyl (e.g., methoxy). In certain embodiments, $R^a$ is halogen (e.g., F or Cl). In certain embodiments, $R^a$ is CN. In certain embodiments, $R^a$ is $N(R^{n1})_2$. In certain embodiments, $R^a$ is $N(CH_3)_2$.

In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^1$ is substituted by at least one $R^a$ that is optionally substituted $C_{1-5}$ alkyl. In certain such embodiments, $R^a$ is optionally substituted by an amine or a heterocyclic ring, and the amine or the heterocyclic ring is optionally substituted by an alkyl. In some embodiments, $R^1$ is substituted by at least one $R^a$ that is dialkylaminomethyl. In certain embodiments, $R^1$ is substituted by one and only one $R^a$ that is dialkylaminomethyl. In certain such embodiments, the dialkylaminomethyl is dimethylaminomethyl. In other embodiments, $R^1$ is substituted by at least one $R^a$ that is fluoro, methyl, morpholinomethyl, or pyrrolidinyl. In further embodiments, $R^1$ is not substituted by $R^a$. In one embodiment, $R^1$ is unsubstituted.

In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^1$ is alkynyl. In certain embodiments, $R^a$ is optionally substituted alkyl. In certain such embodiments, $R^a$ is methyl.

In some embodiments of any of Formulae (I), (I-i), (I-i-a), (I-i-a1), (I-i-a2), (I-i-a3), (I-i-a4), (I-i-a5), (I-i-a6), (I-i-b), (I-i-c), (a-I), (B), (B-i), (C), (D), and (E) (and subformulae thereof), $R^1$ is ethenyl, ethynyl, methyl, ethyl, or oxiranyl and is substituted by at least one $R^a$ that is CN, F, Cl, —$CH_3$, —$CH_2OCH_3$, —$CH_2O(CH_2)_2OCH_3$, —$CO_2CH_3$, —$N(CH_3)_2$, —$CH_2N(CH_3)_2$, —$(CH_2)_2N(CH_3)_2$, morpholinomethyl, or pyrrolidinyl. In some embodiments, $R^1$ is ethenyl or ethynyl and is substituted by at least one $R^a$ that is CN, F, Cl, —$CH_3$, —$CH_2OCH_3$, —$CH_2O(CH_2)_2OCH_3$, —$CO_2CH_3$, —$N(CH_3)_2$, —$CH_2N(CH_3)_2$, —$(CH_2)_2N(CH_3)_2$, morpholinomethyl, or pyrrolidinyl. In some embodiments, $R^1$ is methyl, ethyl, or oxiranyl and is substituted by at least one $R^a$ that is CN, F, Cl, —$CH_3$, —$CH_2OCH_3$, —$CH_2O(CH_2)_2OCH_3$, —$CO_2CH_3$, —$N(CH_3)_2$, —$CH_2N(CH_3)_2$, —$(CH_2)_2N(CH_3)_2$, morpholinomethyl, or pyrrolidinyl.

In some embodiments of any of Formulae (I), (I-i), (I-i-a), (I-i-b), (I-i-c), (a-I), (B), (B-i), (C), (D), and (E) (and subformulae thereof), J is NR; and $X^1$ is CH. In some embodiments of any of Formulae (I), (I-i), (I-i-a), (I-i-b), (I-i-c), (a-I), (B), (B-i), (C), (D), and (E) (and subformulae thereof), $R^b$ is hydrogen or methyl. In some embodiments of any of Formulae (I), (I-i), (I-i-a), (I-i-b), (I-i-c), (a-I), (B), (B-i), (C), (D), and (E) (and subformulae thereof), $R^b$ is hydrogen. In some embodiments of any of Formulae (I), (I-i), (I-i-a), (I-i-b), (I-i-c), (a-I), (B), (B-i), (C), (D), and (E) (and subformulae thereof), J is a bond and $X^1$ is N.

In some embodiments, $R^2$, independently for each occurrence, is optionally substituted $C_{1-5}$ alkyl; or taken together two geminal occurrences of $R^2$ form an oxo moiety; or two non-geminal occurrences of $R^2$ taken together form a $C_{1-4}$ alkylene bridge. In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is $C_{1-5}$ alkyl. In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is methyl. In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is $C_{1-5}$ haloalkyl. In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is $CH_2F$. In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is $CHF_2$. In some embodiments of any of Formulae (I), (I-i), (I-i-a), (I-i-b), (I-i-c), (a-I), (B), (B-i), (C), (D), and (E) (and subformulae thereof), taken together two geminal occurrences of $R^2$ are an oxo moiety.

In some embodiments of any of Formulae (I), (I-i), (I-i-a), (I-i-b), (I-i-c), (a-I), (B), (B-i), (C), (D), and (E) (and subformulae thereof), $R^2$, independently for each occurrence, is methyl or $CH_2F$ or taken together two geminal occurrences of $R^2$ are an oxo moiety. In some embodiments of any of Formulae (I), (I-i), (I-i-a), (I-i-b), (I-i-c), (a-I), (B), (B-i), (C), (D), and (E) (and subformulae thereof), two non-geminal occurrences of $R^2$ taken together form a methylene or ethylene bridge. In some embodiments of any of Formulae (I), (I-i), (I-i-a), (I-i-b), (I-i-c), (a-I), (B), (B-i), (C), (D), and (E) (and subformulae thereof), $R^d$ and an occurrence of $R^2$ taken together with the intervening atoms form a heterocyclic ring.

In some embodiments of any of Formulae (I), (I-i), (I-i-a), (I-i-b), (I-i-c), (a-I), (B), (B-i), (C), (D), and (E) (and subformulae thereof), n is 0 or an integer from 1 to 2, inclusive, as permitted by valence. In some embodiments of any of Formulae (I), (I-i), (I-i-a), (I-i-b), (I-i-c), (a-I), (B), (B-i), (C), (D), and (E) (and subformulae thereof), n is 0. In some embodiments of any of Formulae (I), (I-i), (I-i-a), (I-i-b), (I-i-c), (a-I), (B), (B-i), (C), (D), and (E) (and subformulae thereof), n is 1. In other embodiments, n is 2.

In some embodiments of any of Formulae (I), (I-i), (I-i-a), (I-i-b), (I-i-c), (a-I), (B), (B-i), (C), (D), and (E) (and subformulae thereof), n is 1, and $R^2$ is attached to an atom adjacent to $X^1$ (e.g., $R^2$ is at ortho-position to $X^1$ in a 6-membered ring A). In some embodiments of any of Formulae (I), (I-i), (I-i-a), (I-i-b), (I-i-c), (a-I), (B), (B-i), (C), (D), and (E) (and subformulae thereof), n is 1, and $R^2$ is attached to an atom adjacent to $X^2$ (e.g., $R^2$ is at ortho-position to $X^2$ in a 6-membered ring A). The presence of $R^2$ may result in a chiral center at the atom to which $R^2$ is attached. In one embodiment, the compound has a R-configuration at the atom to which $R^2$ is attached. In one embodiment, the compound has a S-configuration at the atom to which $R^2$ is attached. In one embodiment, the compound is a racemic mixture at the atom to which $R^2$ is attached.

In some embodiments of any of Formulae (I), (I-i), (I-i-a), (I-i-b), (I-i-c), (a-I), (B), (B-i), (C), (D), and (E) (and subformulae thereof), n is 1, and $R^2$ is attached to an atom adjacent to N—C(=O)—$R^1$ (e.g., $R^2$ is at ortho-position to N—C(=O)—$R^1$ in a 6-membered ring A). In one embodiment, n is 1, and $R^2$ is attached to an atom adjacent to $X^2$ (e.g., $R^2$ is at ortho-position to $X^2$ in a 6-membered ring A). The presence of $R^2$ may result in a chiral center at the atom to which $R^2$ is attached. In some embodiments of any of Formulae (I), (I-i), (I-i-a), (I-i-b), (I-i-c), (a-I), (B), (B-i), (C), (D), and (E) (and subformulae thereof), the compound has a R-configuration at the atom to which $R^2$ is attached. In some embodiments of any of Formulae (I), (I-i), (I-i-a), (I-i-b), (I-i-c), (a-I), (B), (B-i), (C), (D), and (E) (and subformulae thereof), the compound has a S-configuration at the atom to which $R^2$ is attached. In some embodiments of any of Formulae (I), (I-i), (I-i-a), (I-i-b), (I-i-c), (a-I), (B), (B-i), (C), (D), and (E) (and subformulae thereof), the compound is a racemic mixture at the atom to which $R^2$ is attached.

In some embodiments of any of Formulae (I), (I-i), (I-i-a), (I-i-b), (I-i-c), (a-I), (B), (B-i), (C), (D), and (E) (and subformulae thereof), m is 0 or an integer from 1 to 2, inclusive, as permitted by valence. In some embodiments of any of Formulae (I), (I-i), (I-i-a), (I-i-b), (I-i-c), (a-I), (B), (B-i), (C), (D), and (E) (and subformulae thereof), m is 0. In some embodiments of any of Formulae (I), (I-i), (I-i-a), (I-i-b), (I-i-c), (a-I), (B), (B-i), (C), (D), and (E) (and subformulae thereof), m is 1. In other embodiments, m is 2.

In one embodiment, ring A (including any substituent $R^2$) is

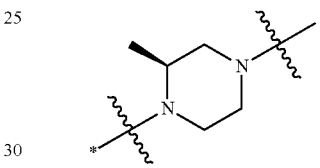

In one embodiment, ring A (including any substituent $R^2$) is

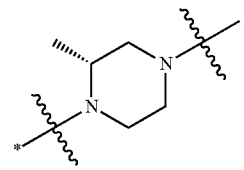

In one embodiment, ring A (including any substituent $R^2$) is

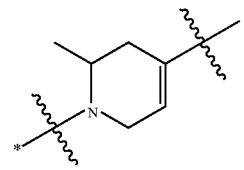

In one embodiment, ring A (including any substitutent $R^2$) is

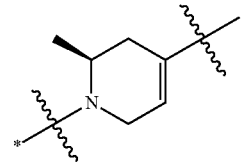

In one embodiment, ring A (including any substituent $R^2$) is

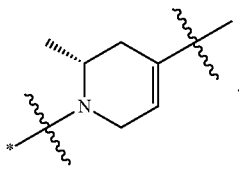

In one embodiment, ring A (including any substituent $R^2$) is

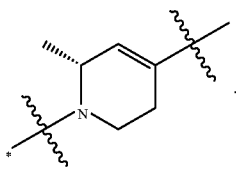

In one embodiment, ring A (including any substituent $R^2$) is

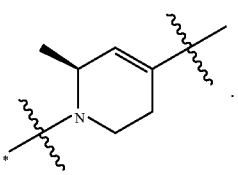

In one embodiment, ring A (including any substituent $R^2$) is

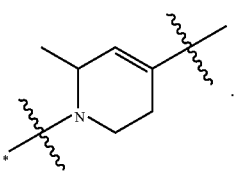

As used herein, * refers to the attachment point to —C(=O)—$R^1$, and J is a bond.

In certain aspects, the compounds of Formula (II) are compounds of Formula (III), or a pharmaceutically acceptable salt, a stereoisomer, or a tautomer thereof:

wherein:
$R^{11}$, $R^{12}$, $R^{13}$, and $R^{14}$ are each independently hydrogen or optionally substituted $C_{1-5}$ alkyl; or two non-geminal occurrences of $R^{11}$, $R^{12}$, $R^{13}$, and $R^{14}$ taken together form a $C_1$-$C_4$ (e.g., $C_1$-$C_2$) alkylene bridge.

In some embodiments, at least one of $R^{11}$ and $R^{12}$ is optionally substituted $C_{1-5}$ alkyl. In certain such embodiments, at least one of $R^{11}$ and $R^{12}$ is methyl. In some embodiments, at least one of $R^{13}$ and $R^{14}$ is optionally substituted $C_{1-5}$ alkyl. In certain embodiments, at least one of $R^{13}$ and $R^{14}$ is methyl. In some embodiments, $R^d$ and one of $R^{13}$ and $R^{14}$, taken together with the intervening atoms, form a heterocyclic ring. In further embodiments, $R^{11}$, $R^{12}$, $R^{13}$, and $R^{14}$ are hydrogen.

In one embodiment, none of $R^{11}$, $R^{12}$, $R^{13}$, and $R^{14}$ is hydrogen. In one embodiment, one of R, $R^{12}$, $R^{13}$, and $R^{14}$ is hydrogen, and the other three of $R^{11}$, $R^{12}$, $R^{13}$, and $R^{14}$ are not hydrogen.

In one embodiment, two of $R^{11}$, $R^{12}$, $R^{13}$, and $R^{14}$ are hydrogen, and the other two of $R^{11}$, $R^{12}$, $R^{13}$, and $R^{14}$ are not hydrogen.

In one embodiment, three of $R^{11}$, $R^{12}$, $R^{13}$, and $R^{14}$ are hydrogen, and the other one of $R^{11}$, $R^{12}$, $R^{13}$, and $R^{14}$ is not hydrogen. In one embodiment, $R^{12}$, $R^{13}$, and $R^{14}$ are hydrogen, and $R^{n1}$ is not hydrogen. In one embodiment, $R^{11}$, $R^{13}$, and $R^{14}$ are hydrogen, and $R^{12}$ is not hydrogen. In one embodiment, $R^{11}$, $R^{12}$, and $R^{14}$ are hydrogen, and $R^{13}$ is not hydrogen. In one embodiment, $R^{11}$, $R^{12}$, and $R^{13}$ are hydrogen, and $R^{14}$ is not hydrogen. In one embodiment, the non-hydrogen group is optionally substituted alkyl. In one embodiment, the non-hydrogen group is methyl.

The presence of non-hydrogen $R^{11}$, $R^{12}$, $R^{13}$, or $R^{14}$ may result in a chiral center at the atom to which the non-hydrogen $R^{11}$, $R^{12}$, $R^{13}$, or $R^{14}$ is attached. In one embodiment, the compound has a R-configuration at the atom to which the non-hydrogen $R^{11}$, $R^{12}$, $R^{13}$, or $R^{14}$ is attached. In one embodiment, the compound has a S-configuration at the atom to which the non-hydrogen $R^{11}$, $R^{12}$, $R^{13}$, or $R^{14}$ is attached. In one embodiment, the compound is a racemic mixture at the atom to which the non-hydrogen $R^{11}$, $R^{12}$, $R^{13}$, or $R^{14}$ is attached.

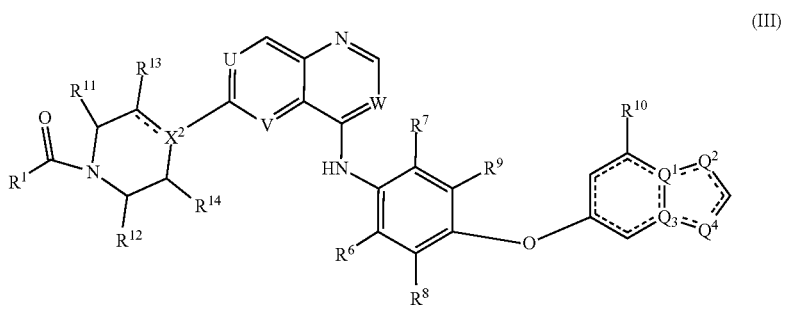

(III)

In one embodiment, the ring

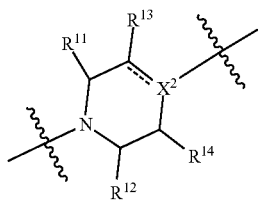

is

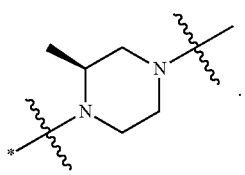

In one embodiment, the ring is

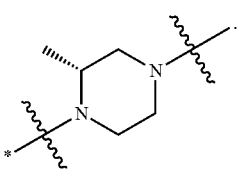

In one embodiment, the ring is

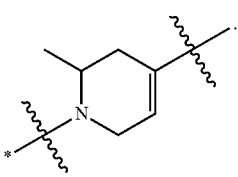

In one embodiment, the ring is

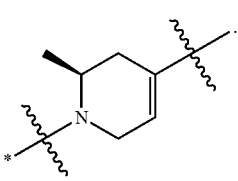

In one embodiment, the ring is

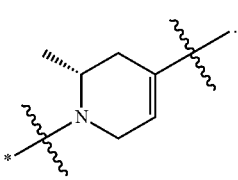

In one embodiment, the ring is

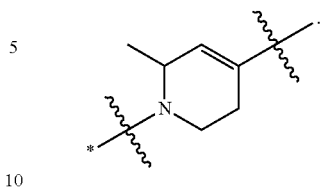

In one embodiment, the ring is

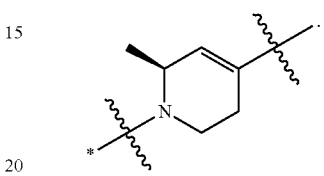

In one embodiment, the ring is

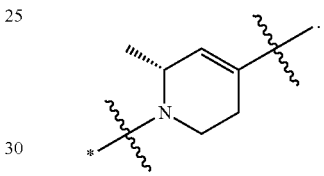

As used herein, * refers to the attachment point to —C(=O)—R$^1$.

In certain embodiments, the bond between X$^2$ and the carbon attached to R$^{13}$ is a double bond. In other embodiments, the bond between X$^2$ and the carbon attached to R$^{13}$ is a single bond.

In some embodiments, R$^1$ is

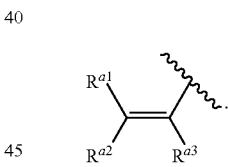

In further embodiments, R$^1$ is

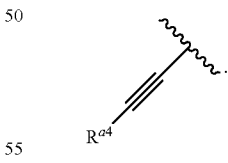

As used herein, R$^{a1}$ is independently hydrogen, halo, CN, N(R$^{n1}$)$_2$, optionally substituted C$_{1-5}$ alkyl, optionally substituted —CH$_2$O—C$_{1-5}$ alkyl, optionally substituted —CH$_2$O—(CH$_2$)$_{1-2}$—O—C$_{1-5}$ alkyl, optionally substituted —CO$_2$—C$_{1-5}$ alkyl, or optionally substituted 3- to 6-membered heterocyclyl; each instance of R$^{n1}$ is independently hydrogen or C$_{1-5}$ alkyl. In certain such embodiments, R$^{a1}$ is hydrogen. In certain embodiments, R$^{a1}$ is CN. In certain embodiments, R$^{a1}$ is CN. In certain embodiments, R$^{a1}$ is —CH$_2$O—C$_{1-5}$ alkyl. In certain embodiments, R$^{a1}$ is —CH$_2$OCH$_3$. In certain embodiments, R$^{a1}$ is optionally substituted —CH$_2$O—(CH$_2$)$_{1-2}$—O—C$_{1-5}$ alkyl. In certain embodiments, $R^{a1}$ is —$CH_2O$—$(CH_2)_{1-2}$—O—$C_{1-5}$ alkyl. In certain embodiments, $R^{a1}$ is —$CH_2O$—$(CH_2)_2$—O—$CH_3$. In certain embodiments, $R^{a1}$ is optionally substituted —$CO_2$—$C_{1-5}$ alkyl. In certain embodiments, $R^{a1}$ is —$CO_2CH_3$.

As used herein, $R^{a2}$ is independently hydrogen, halo, CN, $N(R^{n1})_2$, optionally substituted $C_{1-5}$ alkyl, optionally substituted —$CH_2O$—$C_{1-5}$ alkyl, optionally substituted —$CH_2O$—$(CH_2)_{1-2}$—O—$C_{1-5}$ alkyl, optionally substituted —$CO_2$—$C_{1-5}$ alkyl, or optionally substituted 3- to 6-membered heterocyclyl; each instance of $R^{n1}$ is independently hydrogen or $C_{1-5}$ alkyl. In certain such embodiments, $R^{a2}$ is hydrogen. In some embodiments, $R^{a2}$ is optionally substituted $C_{1-5}$ alkyl or optionally substituted 3- to 6-membered heterocyclyl. In some embodiments, $R^{a2}$ is methyl, —$CH_2$—$N(CH_3)_2$, —$CO_2CH_3$, —$CH_2OCH_3$, —$CH_2O(CH_2)_2CH_3$, morpholinomethyl, or pyrrolidinyl. In some embodiments, $R^{a2}$ is optionally substituted $C_{1-5}$ alkyl. In certain embodiments, $R^{a2}$ is optionally substituted by an amine or a 3- to 6-membered heterocyclic ring, and the amine or the heterocyclic ring is optionally substituted by $C_{1-5}$ alkyl. In some embodiments, $R^{a2}$ is dialkylaminomethyl. In certain embodiments, $R^{a2}$ is dimethylaminomethyl. In other embodiments, $R^{a2}$ is hydrogen. In certain embodiments, $R^{a2}$ is CN. In certain embodiments, $R^{a2}$ is CN. In certain embodiments, $R^{a2}$ is —$CH_2O$—$C_{1-5}$ alkyl. In certain embodiments, $R^{a2}$ is —$CH_2OCH_3$. In certain embodiments, $R^{a2}$ is optionally substituted —$CH_2O$—$(CH_2)_{1-2}$—O—$C_{1-5}$ alkyl. In certain embodiments, $R^{a2}$ is —$CH_2O$—$(CH_2)_{1-2}$—O—$C_{1-5}$ alkyl. In certain embodiments, $R^{a2}$ is —$CH_2O$—$(CH_2)_2$—O—$CH_3$. In certain embodiments, $R^{a2}$ is optionally substituted —$CO_2$—$C_{1-5}$ alkyl. In certain embodiments, $R^{a2}$ is —$CO_2CH_3$.

As used herein, $R^{a3}$ is independently hydrogen, halo, CN, $N(R^{n1})_2$, optionally substituted $C_{1-5}$ alkyl, optionally substituted —$CH_2O$—$C_{1-5}$ alkyl, optionally substituted —$CH_2O$—$(CH_2)_{1-2}$—O—$C_{1-5}$ alkyl, optionally substituted —$CO_2$—$C_{1-5}$ alkyl, or optionally substituted 3- to 6-membered heterocyclyl; each instance of $R^{n1}$ is independently hydrogen or $C_{1-5}$ alkyl. In certain such embodiments, $R^{a3}$ is hydrogen. In some embodiments, $R^{a4}$ is optionally substituted $C_{1-5}$ alkyl. In certain such embodiments, $R^{a3}$ is methyl. In certain such embodiments, $R^{a3}$ is CN. In certain such embodiments, $R^{a3}$ is F.

In some embodiments, $R^{a1}$ is independently hydrogen or $C_{1-5}$ alkyl; $R^{a2}$ is independently hydrogen, halo, CN, $N(R^{n1})_2$, optionally substituted $C_{1-5}$ alkyl, optionally substituted —$CH_2O$—$C_{1-5}$ alkyl, optionally substituted —$CH_2O$—$(CH_2)_{1-2}$—O—$C_{1-5}$ alkyl, optionally substituted —$CO_2$—$C_{1-5}$ alkyl, or optionally substituted 3- to 6-membered heterocyclyl; each instance of $R^{n1}$ is independently hydrogen or $C_{1-5}$ alkyl; and $R^{a3}$ is independently hydrogen, halo, CN, optionally substituted $C_{1-5}$ alkyl.

In some embodiments, $R^{a1}$ and $R^{a2}$ are joined together to form an alkenyl group.

In some embodiments, $R^{a1}$ and $R^{a2}$ are hydrogen. In some embodiments, $R^{a1}$, $R^{a3}$, and $R^{a3}$ are hydrogen.

In certain embodiments, $X^2$ is —C=. In other embodiments, $X^2$ is N. In other embodiments, $X^2$ is —CH—.

In some embodiments, wherein U is $CR^c$. In certain such embodiments, $R^c$ is fluoro. In some embodiments, $R^c$ is hydrogen. In other embodiments, U is N.

In certain embodiments, V is $CR^d$. In some embodiments, $R^d$ is hydrogen, fluoro, methyl, or methoxy. In certain embodiments, $R^d$ is methoxy. In certain embodiments, $R^d$ is fluoro. In other embodiments, V is N.

In some embodiments, W is N. In some embodiments, W is $CR^e$. In some embodiments, W is CH or CF.

In some embodiments, $Y^1$ and $Y^2$ are $CR^4$. In some embodiments, $Y^1$ is $CR^4$; and $Y^2$ is N.

In some embodiments, $R^4$, independently for each occurrence, is fluoro, chloro, methyl, methoxy, or difluoromethyl.

In certain embodiments, $R^6$ and $R^7$ are each independently hydrogen, halo, optionally substituted alkoxy, or optionally substituted alkyl. In some embodiments, $R^6$ and $R^7$ are each independently hydrogen, fluoro, methoxy, or difluoromethyl. In certain embodiments, $R^6$ and $R^7$ are hydrogen. In some embodiments, $R^8$ and $R^9$ are each independently hydrogen, halo, or optionally substituted alkyl. In certain embodiments, $R^8$ and $R^9$ are each independently hydrogen, chloro, or methyl. In some embodiments, $R^8$ is methyl. In other embodiments, $R^9$ is hydrogen.

In some embodiments, $R^{10}$ is hydrogen, fluoro, chloro, methyl, ethyl, or methoxy. In some embodiments, $R^{10}$ is hydrogen.

In one embodiment, none of $R^6$, $R^7$, $R^8$, and $R^9$ is hydrogen.

In one embodiment, one of $R^6$, $R^7$, $R^8$, and $R^9$ is hydrogen, and the other three of $R^6$, $R^7$, $R^8$, and $R^9$ are not hydrogen. In one embodiment, $R^7$ is hydrogen, and $R^6$, $R^8$, and $R^9$ are not hydrogen. In one embodiment, $R^9$ is hydrogen, and $R^6$, $R^7$, and $R^8$ are not hydrogen.

In one embodiment, two of $R^6$, $R^7$, $R^8$, and $R^9$ are hydrogen, and the other two of $R^6$, $R^7$, $R^8$, and $R^9$ are not hydrogen. In one embodiment, $R^7$ and $R^9$ are hydrogen, and $R^6$ and $R^8$ are not hydrogen. In one embodiment, $R^6$ and $R^9$ are hydrogen, and $R^7$ and $R^8$ are not hydrogen.

In one embodiment, three of $R^6$, $R^7$, $R^8$, and $R^9$ are hydrogen, and the other one of $R^6$, $R^7$, $R^8$, and $R^9$ is not hydrogen. In one embodiment, $R^6$, $R^7$, and $R^9$ are hydrogen, and $R^8$ is not hydrogen. In one embodiment, $R^7$, $R^8$, and $R^9$ are hydrogen, and $R^6$ is not hydrogen.

In one embodiment, $R^7$ and $R^9$ are hydrogen, one of $R^6$ and $R^8$ is optionally substituted alkyl, and the other one of $R^6$ and $R^8$ is halo. In one embodiment, $R^7$ and $R^9$ are hydrogen, $R^6$ is optionally substituted alkyl, and $R^8$ is halo. In one embodiment, $R^7$ and $R^9$ are hydrogen, $R^8$ is optionally substituted alkyl, and $R^6$ is halo. In one embodiment, the optionally substituted alkyl is methyl. In one embodiment, the halo is fluoro. In one embodiment, $R^7$ and $R^9$ are hydrogen, $R^8$ is methyl, and $R^6$ is fluoro.

In some embodiments, $Q^1$ is $CR^g$, $Q^2$ is $CR^g$, $Q^3$ is $CR^g$, and $Q^4$ is $NR^f$. In other embodiments, $Q^1$ is $NR^f$, $Q^2$ is $CR^g$, $Q^3$ is $CR^g$, and $Q^4$ is $NR^f$. In further embodiments, $Q^1$ is $CR^g$, $Q^2$ is $CR^g$, $Q^3$ is NRC, and $Q^4$ is $NR^f$. In some embodiments, $Q^1$ is NW, $Q^2$ is $NR^{11}$, $Q^3$ is $CR^g$, and $Q^4$ is $NR^f$. In still other embodiments, $Q^1$ is $NR^f$, $Q^2$ is $NR^f$, $Q^3$ is NR, and $Q^4$ is $CR^g$. In still other embodiments, $Q^1$ is $CR^g$, $Q^2$ is $NR^f$, $Q^3$ is $CR^g$, and $Q^4$ is $NR^f$. In still other embodiments, $Q^1$ is $CR^g$, $Q^2$ is $NR^f$, $Q^3$ is $NR^f$, and $Q^4$ is $CR^g$. In some embodiments, $R^f$ is hydrogen, methyl, or absent. In certain embodiments, $R^f$ is hydrogen or absent. In some embodiments, $R^g$ is hydrogen.

In some embodiments, $R^g$ is absent.

In one embodiment,

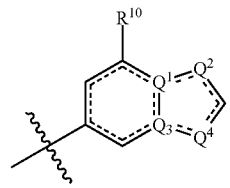

is
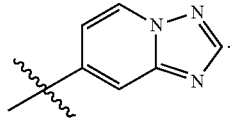
In one embodiment,
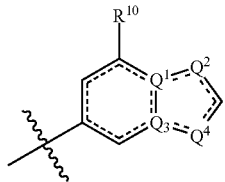
is
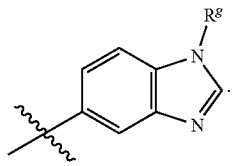
In one embodiment,
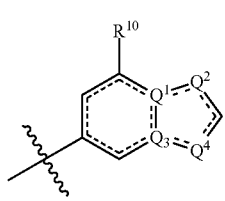
is
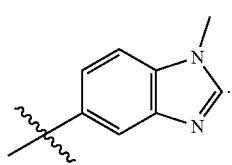 [SMILES: *c1ccc2c(c1)ncn2C]
In one embodiment, the compound is a compound of any one of following formulas:
(I-A)
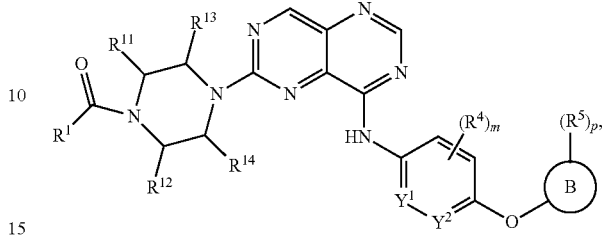
(I-B)
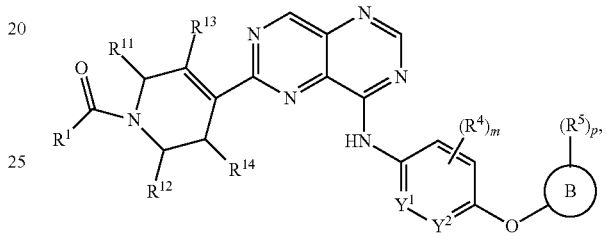
(I-C)
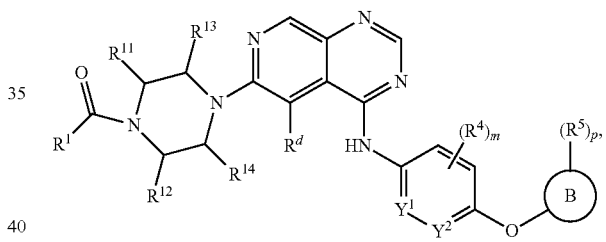
(I-D)
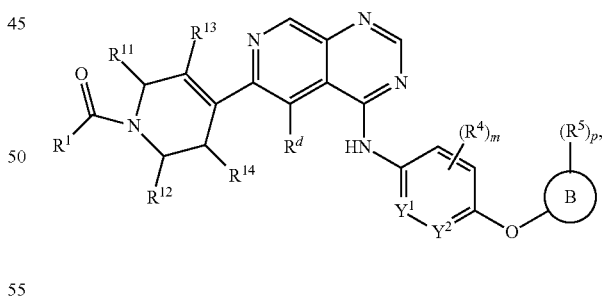
(I-E)
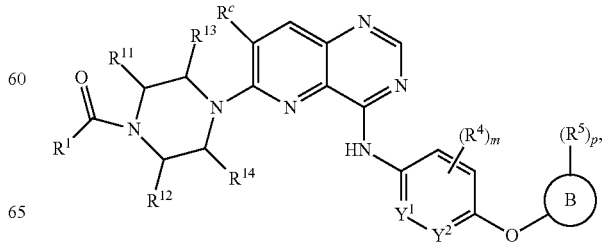

(I-F)
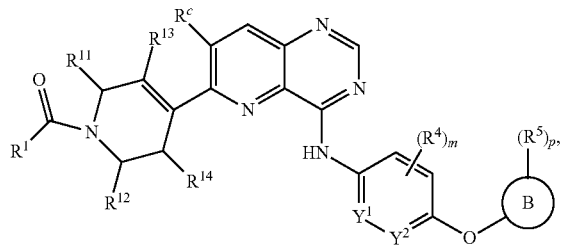
(III-C)
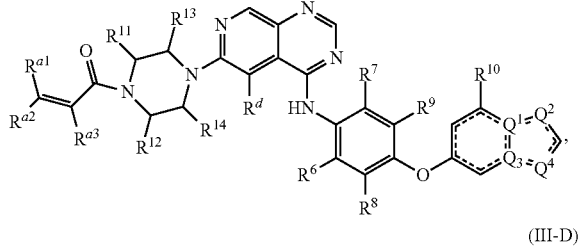
(I-G)
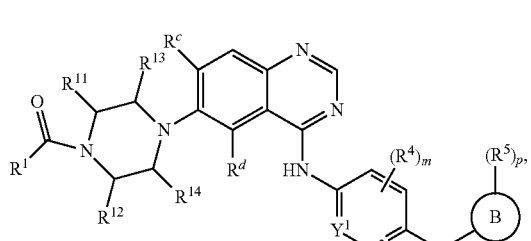
(III-D)
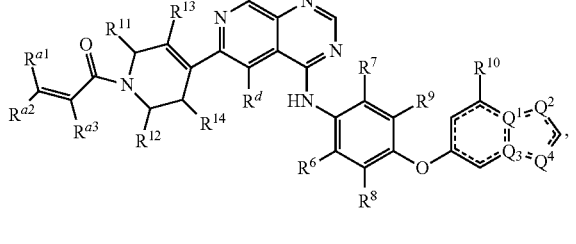
(I-H)
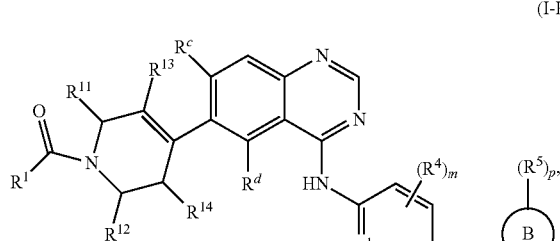
(III-E)
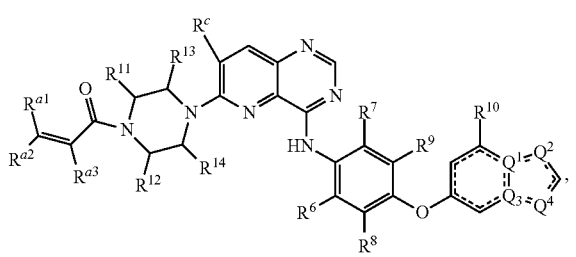
or an enantiomer, a mixture of enantiomers, or a mixture diastereomers thereof, or a pharmaceutically acceptable salt thereof,
wherein $R^1$, $R^4$, $R^5$, $R^{11}$, $R^{12}$, $R^{13}$, $R^{14}$, $R^c$, $R^d$, $Y^1$, $Y^2$, ring B, m, and p are as defined herein or elsewhere.
In one embodiment, the compound is a compound of any one of following formulas:
(III-F)
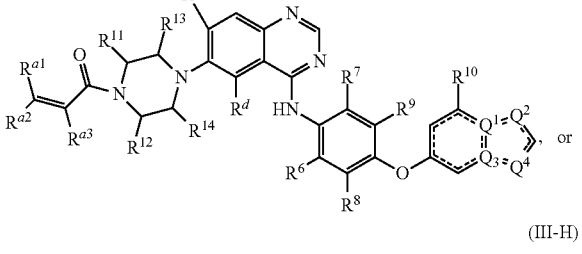
(III-A)
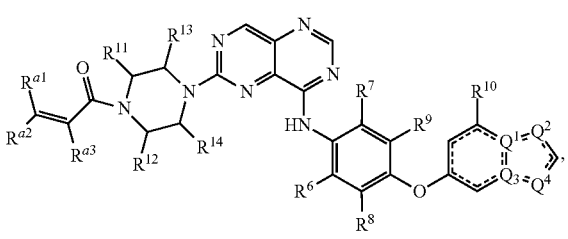
(III-G)
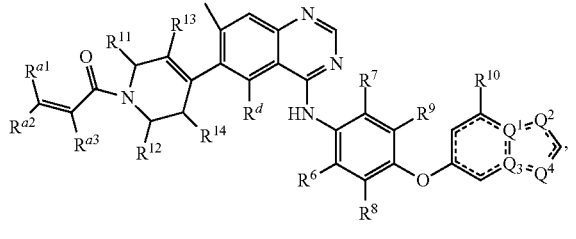
(III-B)
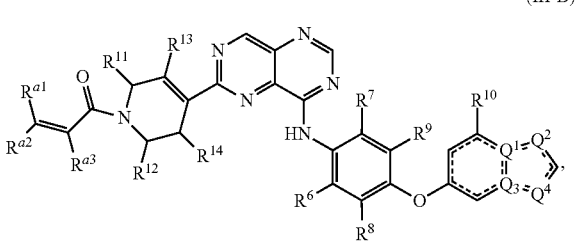
(III-H)

or an enantiomer, a mixture of enantiomers, or a mixture of diastereomers thereof, or a pharmaceutically acceptable salt thereof, wherein $R^{a1}$, $R^{a2}$, $R^{a3}$, $R^6$, $R^7$, $R^8$, $R^9$, $R^{10}$, $R^{11}$, $R^{12}$, $R^{13}$, $R^{14}$, $R^c$, $R^d$, $Q^1$, $Q^2$, $Q^3$, and $Q^4$ are as defined herein or elsewhere.

In one embodiment, the compound is a compound of any one of following formulas:

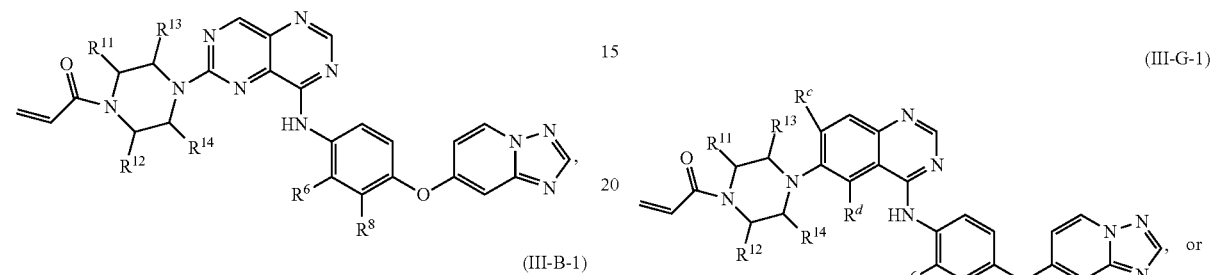
(III-A-1)

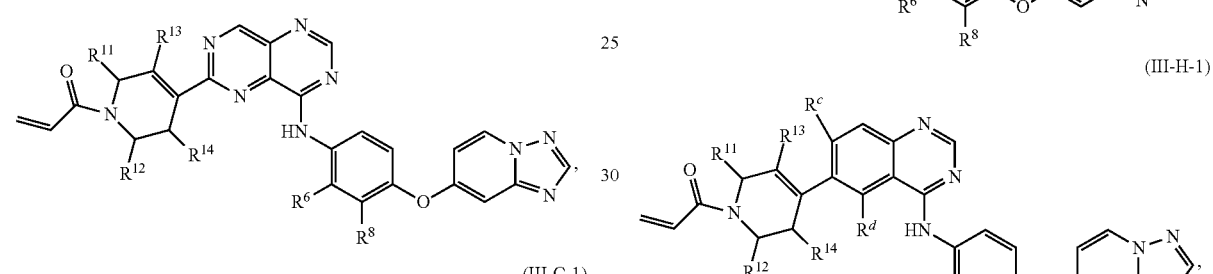
(III-B-1)

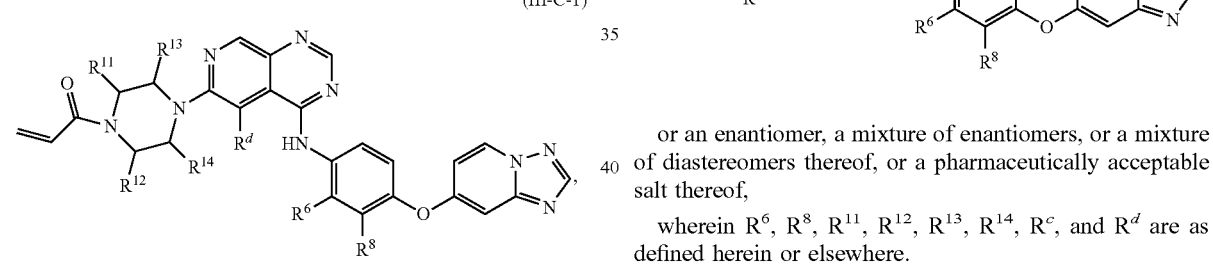
(III-C-1)

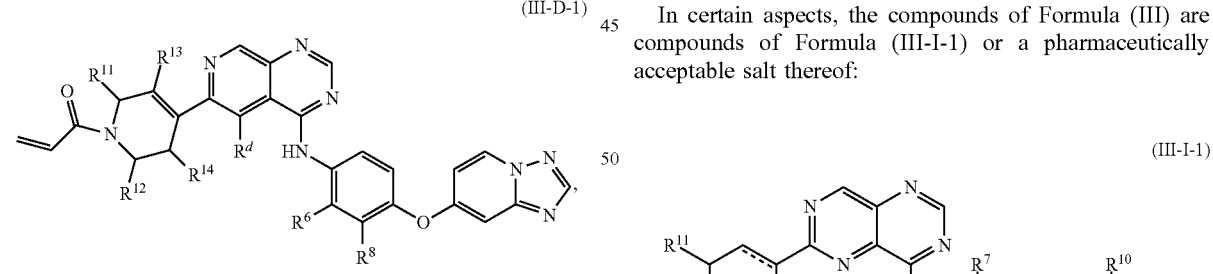
(III-D-1)

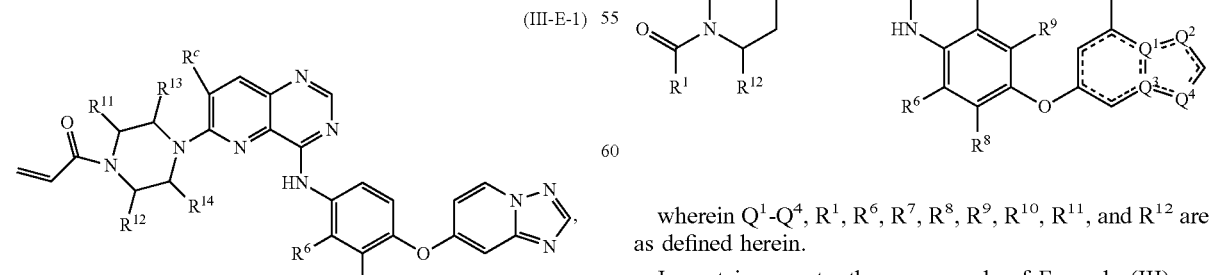
(III-E-1)

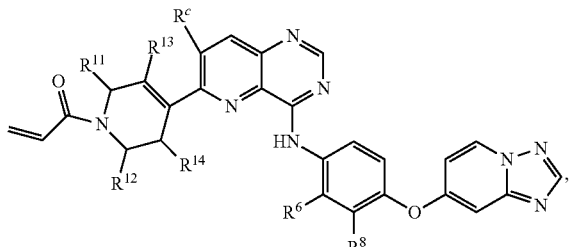
(III-F-1)

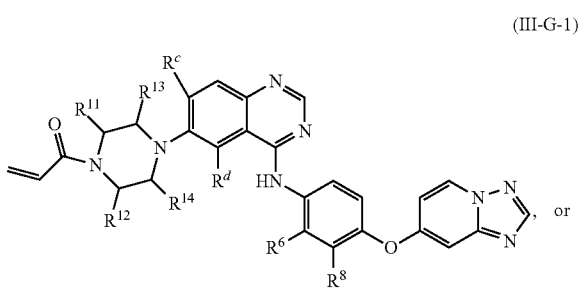
(III-G-1), or

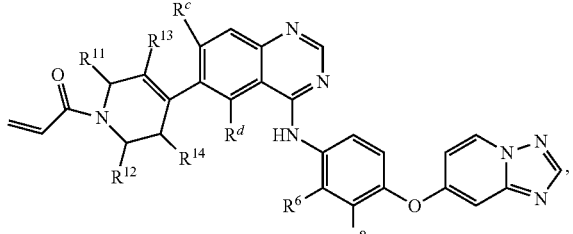
(III-H-1)

or an enantiomer, a mixture of enantiomers, or a mixture of diastereomers thereof, or a pharmaceutically acceptable salt thereof, wherein $R^6$, $R^8$, $R^{11}$, $R^{12}$, $R^{13}$, $R^{14}$, $R^c$, and $R^d$ are as defined herein or elsewhere.

In certain aspects, the compounds of Formula (III) are compounds of Formula (III-I-1) or a pharmaceutically acceptable salt thereof:

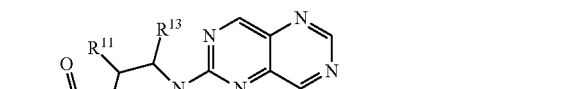
(III-I-1)

wherein $Q^1$-$Q^4$, $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-2) or a pharmaceutically acceptable salt thereof:

(III-I-2)

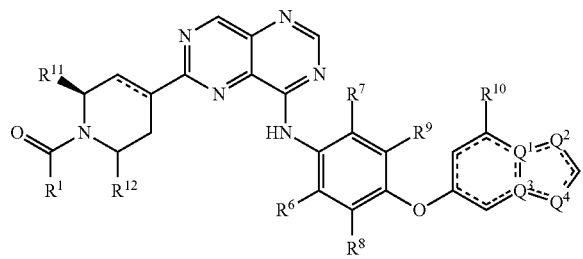

wherein $Q^1$-$Q^4$, $R^1$, $R^6$, $R^7$, $R^8$, $R^9$, $R^{10}$, $R^{11}$, and $R^{n1}$ are as defined herein.

In certain aspects, the compounds of Formula (III) are compounds of Formula (III-I-3) or a pharmaceutically acceptable salt thereof:

(III-I-3)

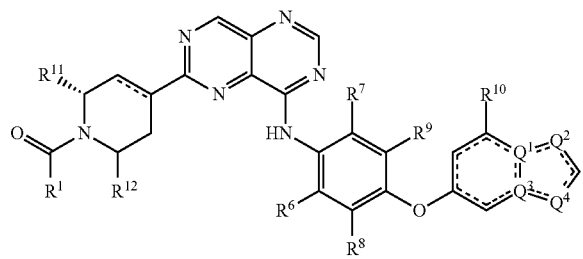

wherein $Q^1$-$Q^4$, $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-4) or a pharmaceutically acceptable salt thereof:

(III-I-4)

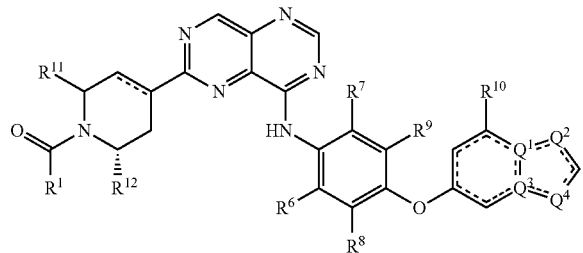

wherein $Q^1$-$Q^4$, $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-5) or a pharmaceutically acceptable salt thereof:

(III-I-5)

wherein $Q^1$-$Q^4$, $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-6) or a pharmaceutically acceptable salt thereof:

(III-I-6)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-7) or a pharmaceutically acceptable salt thereof:

(III-I-7)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-8) or a pharmaceutically acceptable salt thereof:

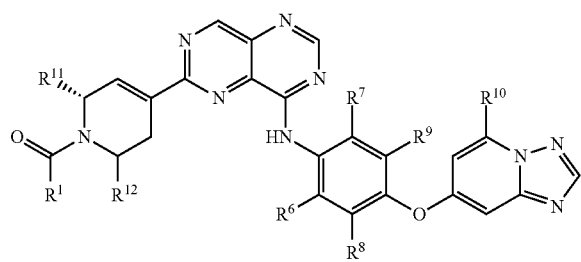

(III-I-8)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-9) or a pharmaceutically acceptable salt thereof:

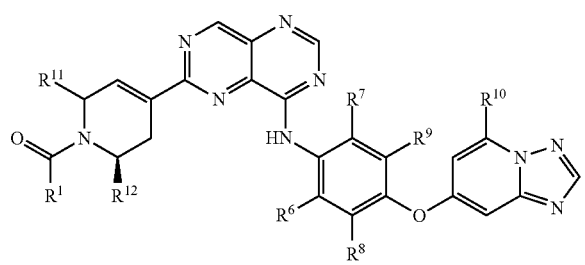

(III-I-9)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-10) or a pharmaceutically acceptable salt thereof:

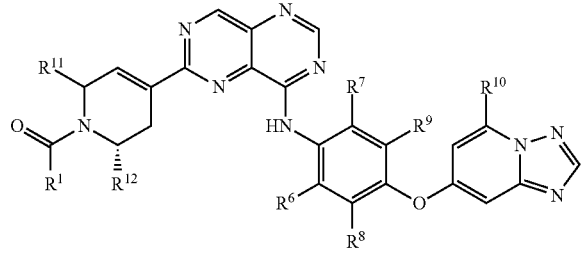

(III-I-10)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-11) or a pharmaceutically acceptable salt thereof:

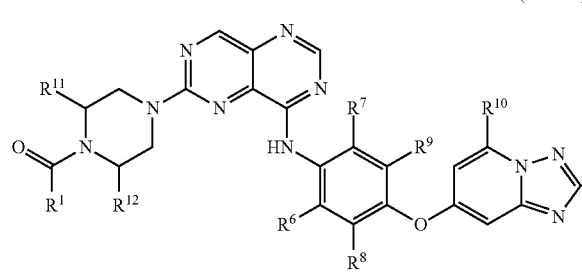

(III-I-11)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-12) or a pharmaceutically acceptable salt thereof:

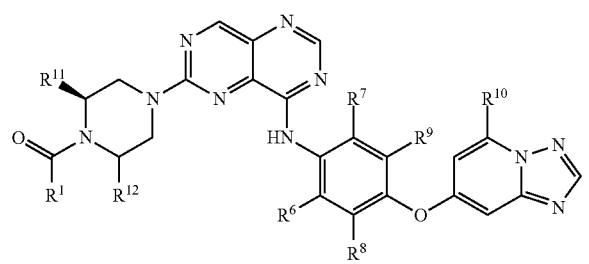

(III-I-12)

wherein $R^1$, $R^6$, $R^7$, $R^8$, $R^9$, $R^{10}$, $R^{11}$, and $R^{12}$ are as defined herein.

In certain aspects, the compounds of Formula (III) are compounds of Formula (III-I-13) or a pharmaceutically acceptable salt thereof:

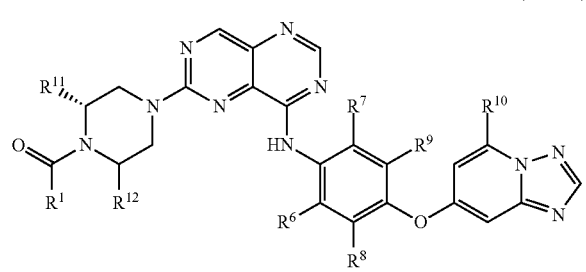

(III-I-13)

wherein $R^1$, $R^6$, $R^7$, $R^8$, $R^9$, $R^{10}$, $R^{11}$, and $R^{12}$ are as defined herein.

In one embodiment of any one of Formulae (III-I-1) to (III-I-13), $R^1$ is

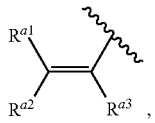

wherein $R^{a1}$, $R^{a2}$, and $R^{a3}$ are as defined herein. In certain embodiments, Rai, $R^{a2}$, and $R^{a3}$ are H.

In one embodiment of any one of Formulae (III-I-1) to (III-I-13), each of $R^6$, $R^7$, $R^8$, and $R^9$ is independently H, halogen, $C_{1-4}$ alkyl, or $C_{1-4}$ haloalkyl. In certain embodiments, $R^7$ and $R^9$ are H; and $R^6$ and $R^8$ are each independently halogen or $C_{1-4}$ alkyl.

In one embodiment of any one of Formulae (III-I-1) to (III-I-13), each of $R^{11}$ and $R^{12}$ is independently H or $C_{1-4}$ alkyl. In certain embodiments, $R^{11}$ is H and $R^{12}$ is C1-C4 alkyl. In certain embodiments, $R^{12}$ is H and $R^{n1}$ is $C_{1-4}$ alkyl.

In one embodiment of any one of Formulae (III-I-1) to (III-I-13), $R^{10}$ is H, halogen or C1-C4 alkyl.

In one embodiment of any one of Formulae (III-I-1) to (III-I-13), $R^1$ is

each of $R^6$, $R^7$, $R^8$, and $R^9$ is independently H, halogen, or $C_{1-4}$ alkyl; each of $R^{11}$ and $R^{12}$ is independently H or $C_{1-4}$ alkyl; and $R^{10}$ is H, halogen, or $C_{1-4}$ alkyl.

In one embodiment of any one of Formulae (III-A-1), (III-B-1), (III-C-1), (III-D-1), (III-E-1), (III-F-1), (III-G-1), (III-H-1), and (III-I-1) to (III-I-13), $R^8$ is optionally substituted $C_{1-4}$ alkyl, and $R^6$ is halo. In one embodiment, the optionally substituted $C_{1-4}$ alkyl is methyl. In one embodiment, the halo is fluoro. In one embodiment, $R^8$ is methyl, and $R^6$ is fluoro.

In some embodiments, disclosed herein are compounds of the following structures:

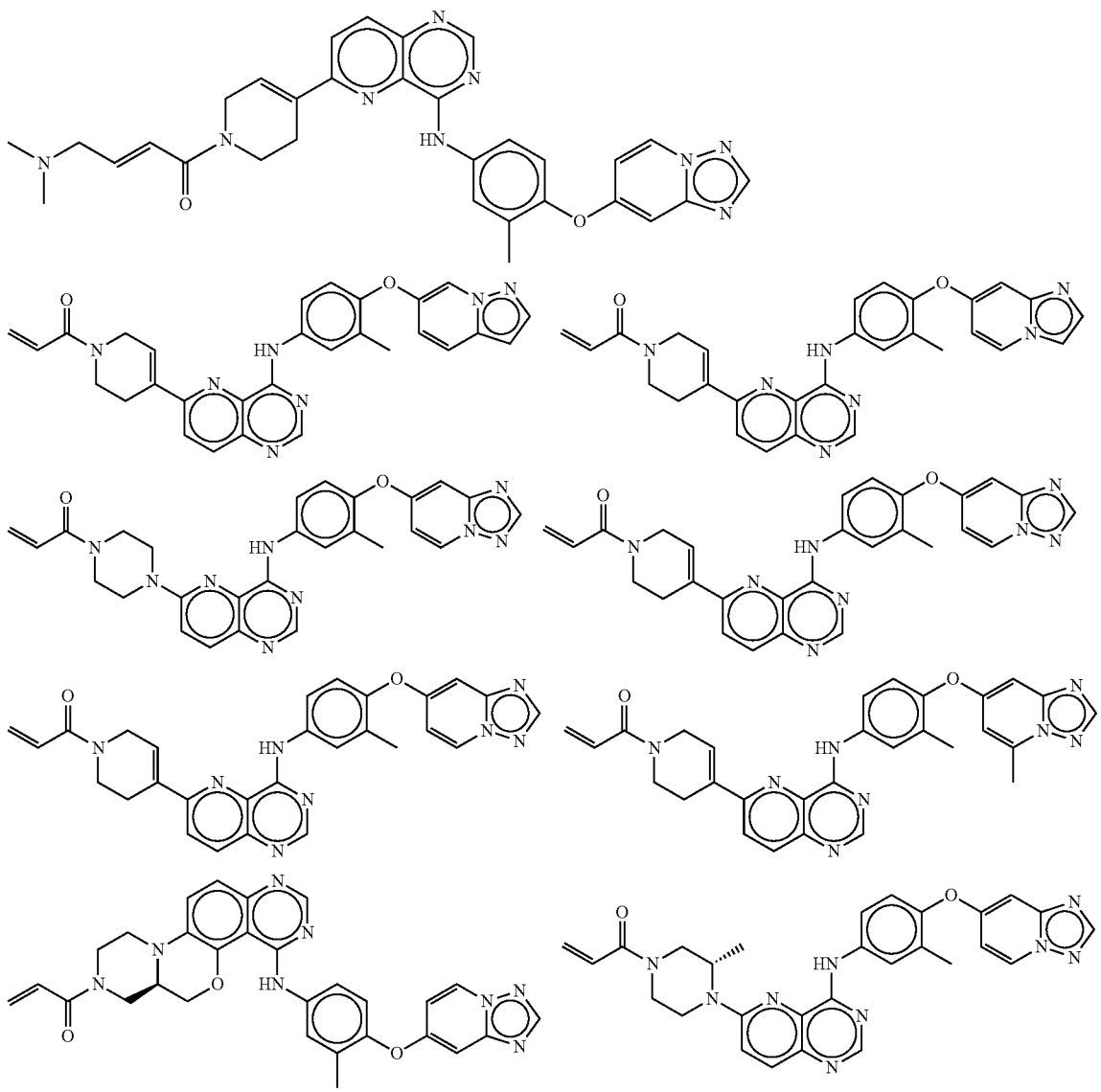

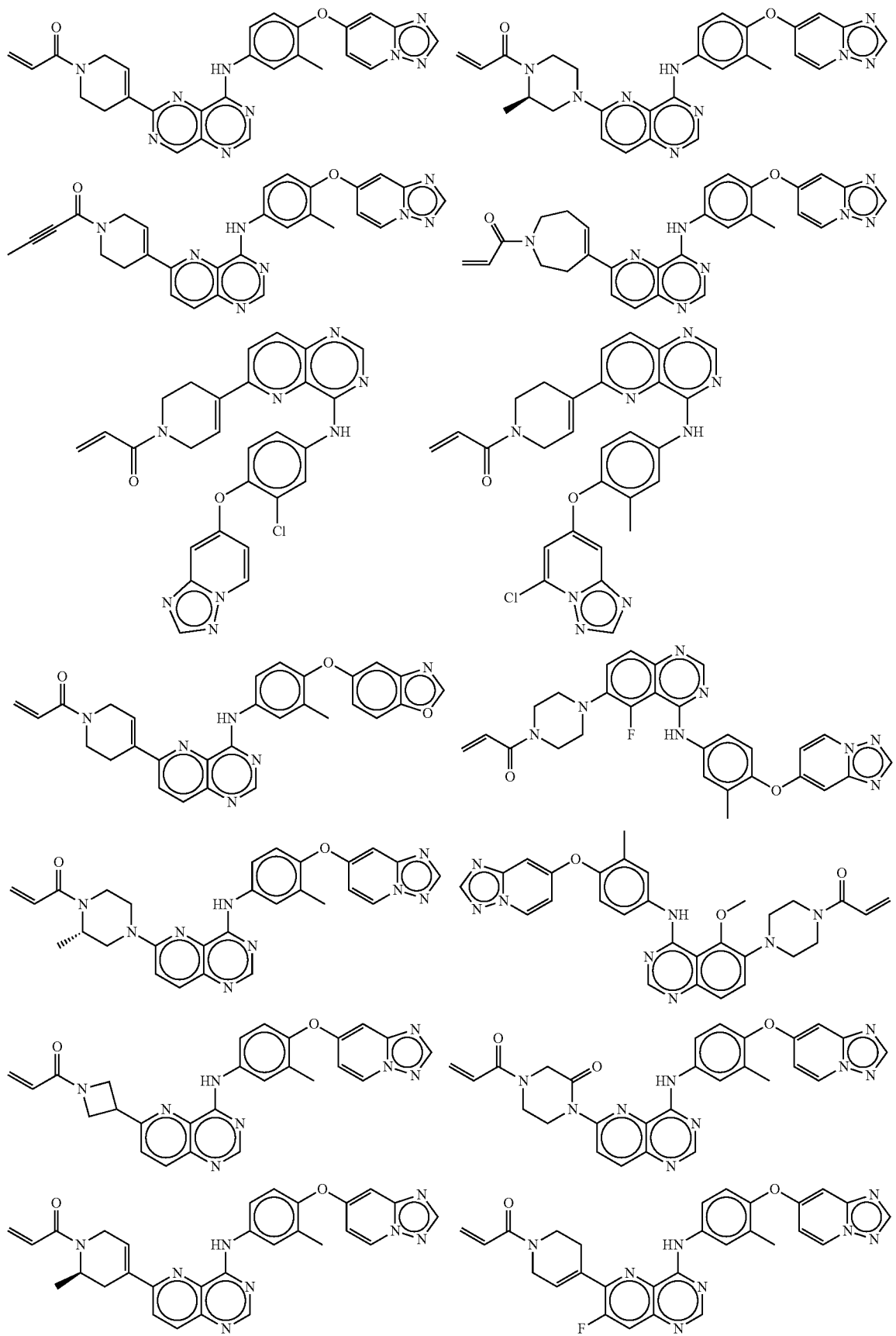

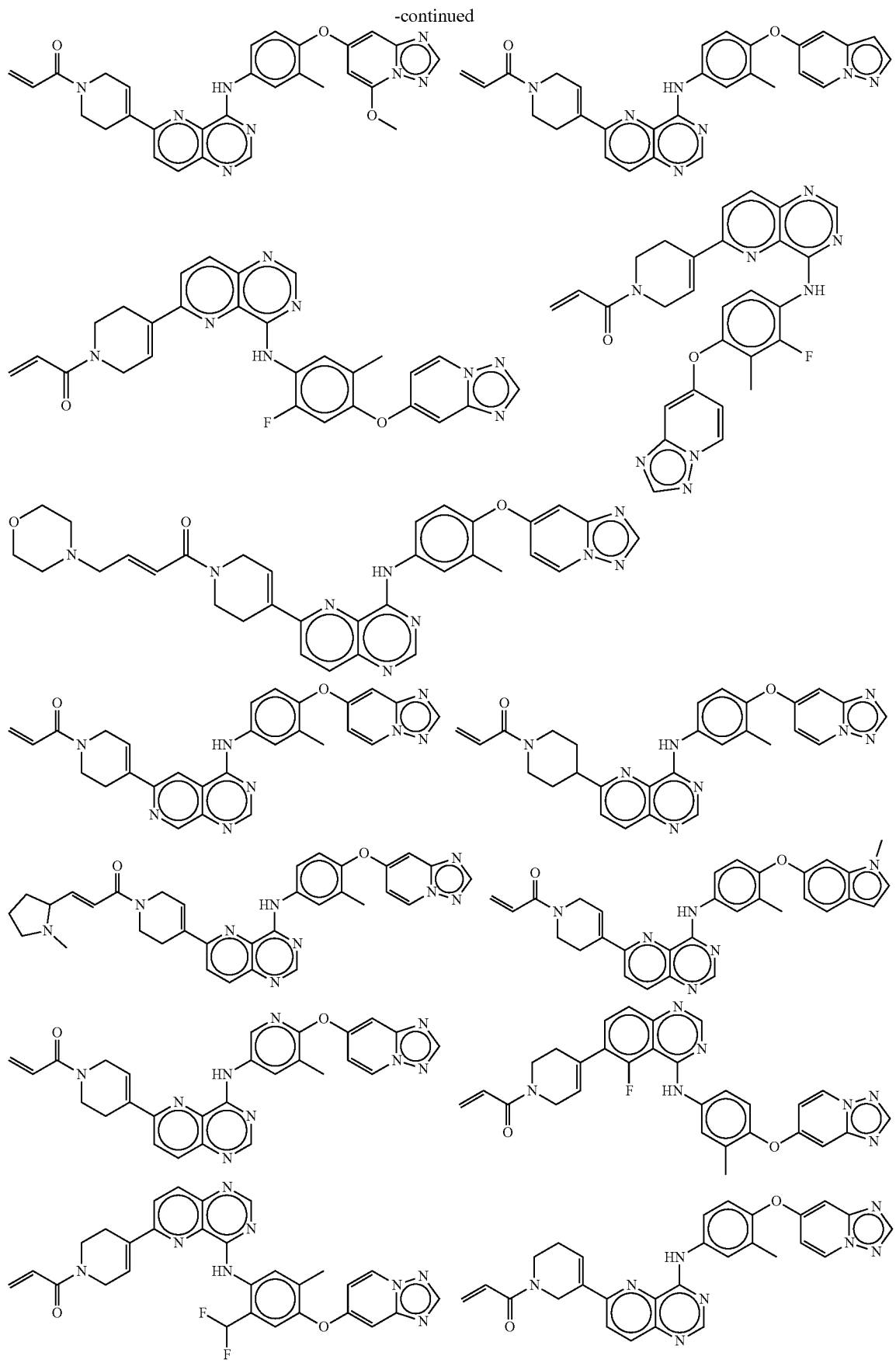

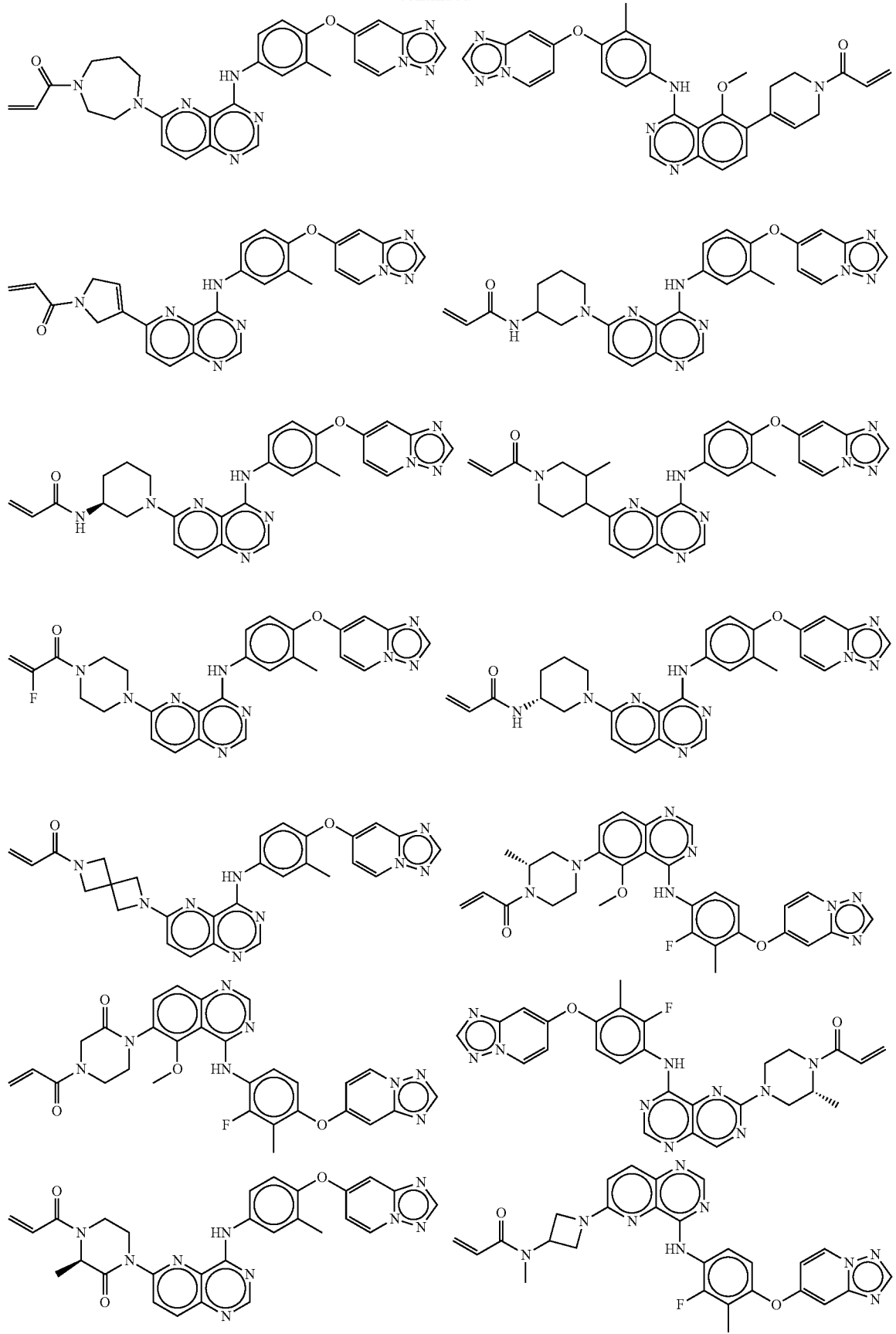

-continued
| 75 | 76 |
|---|---|
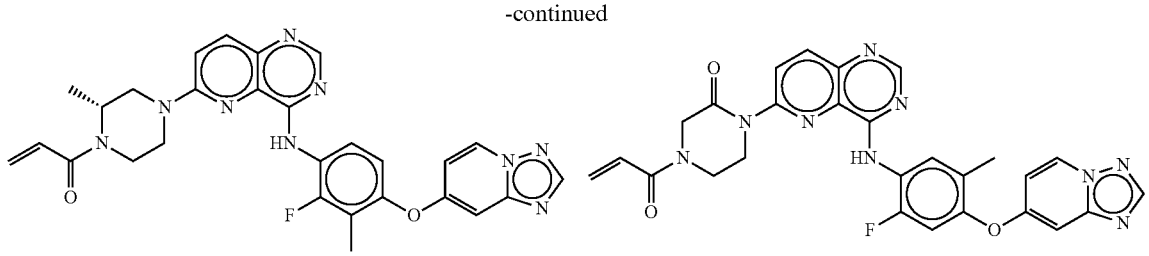
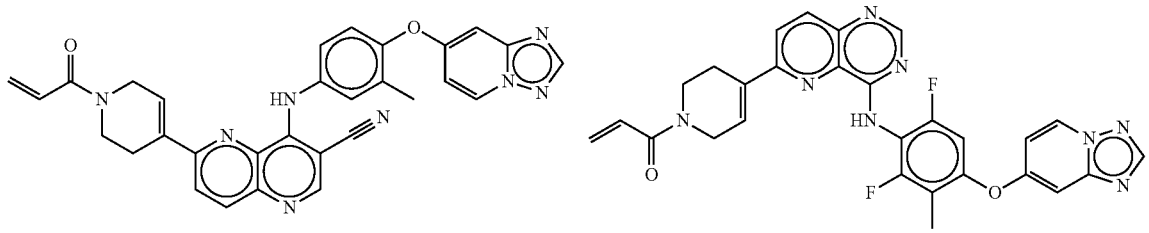
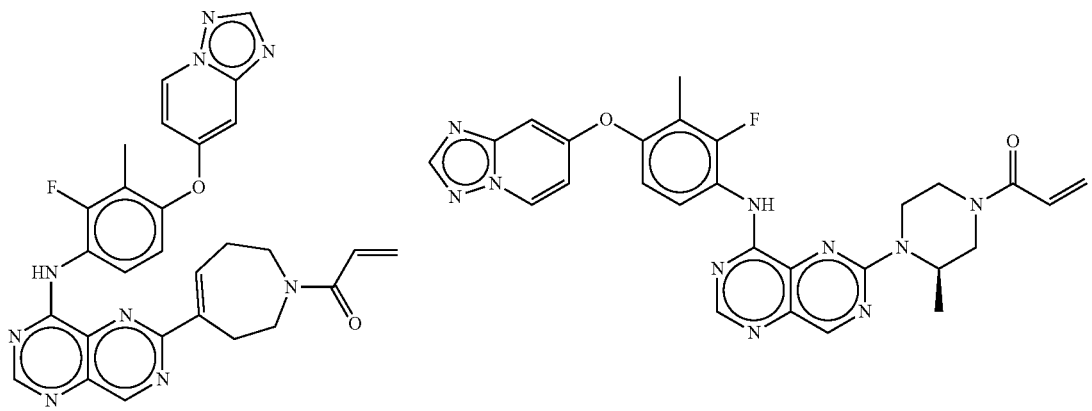
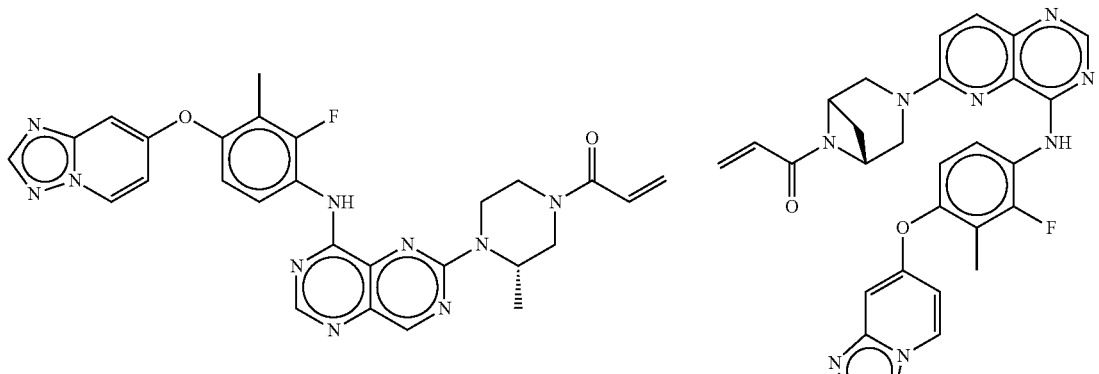
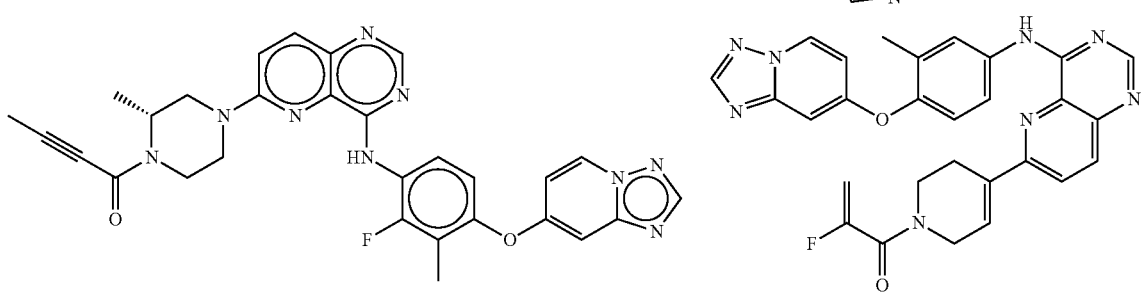

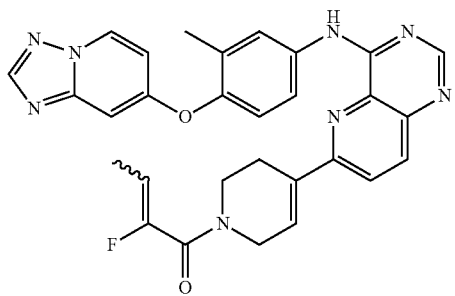
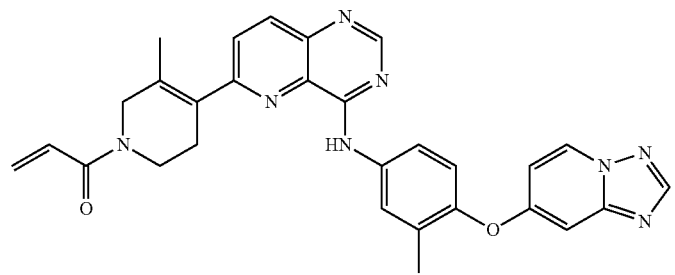
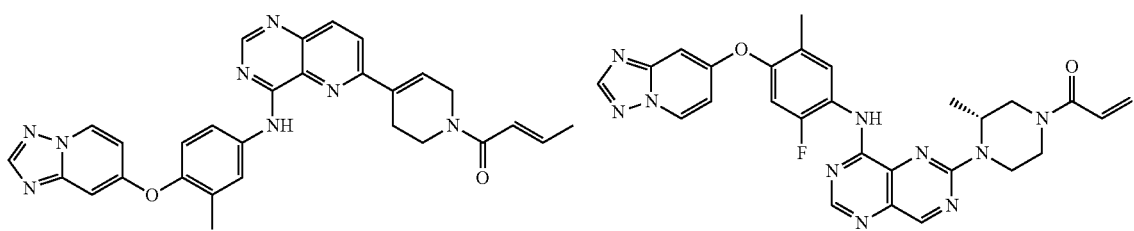
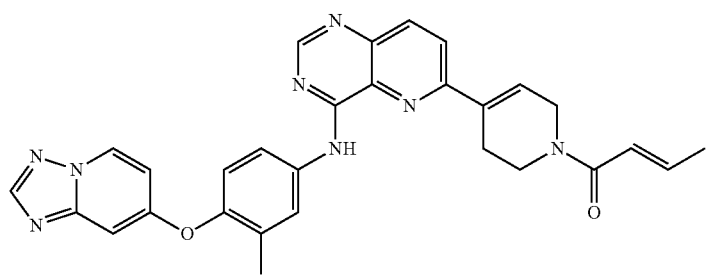
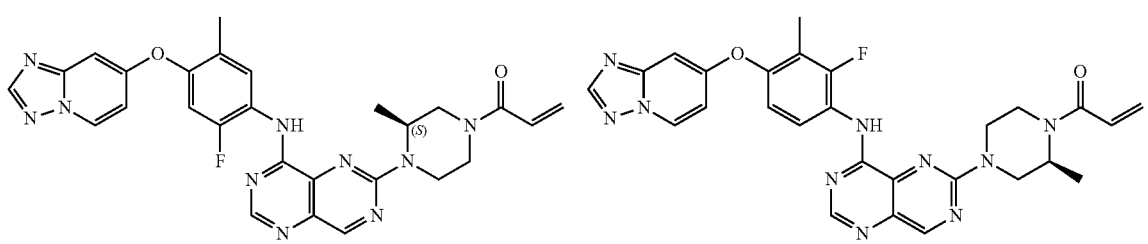
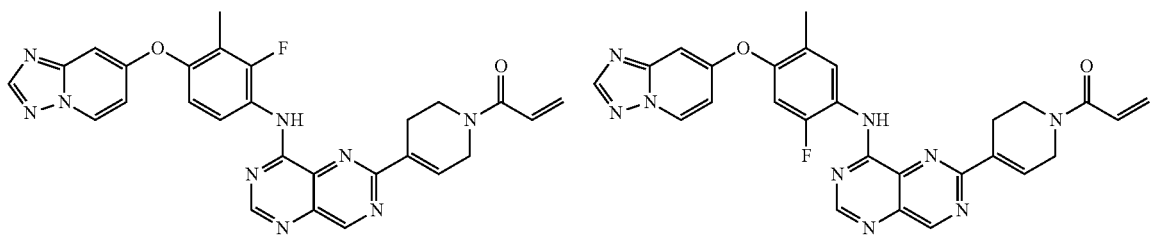
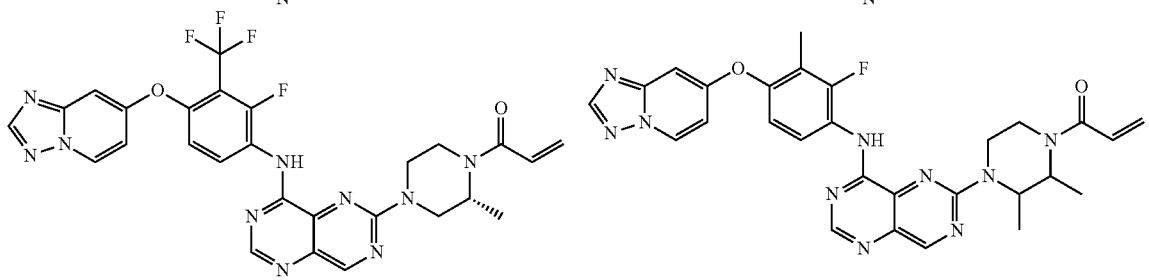

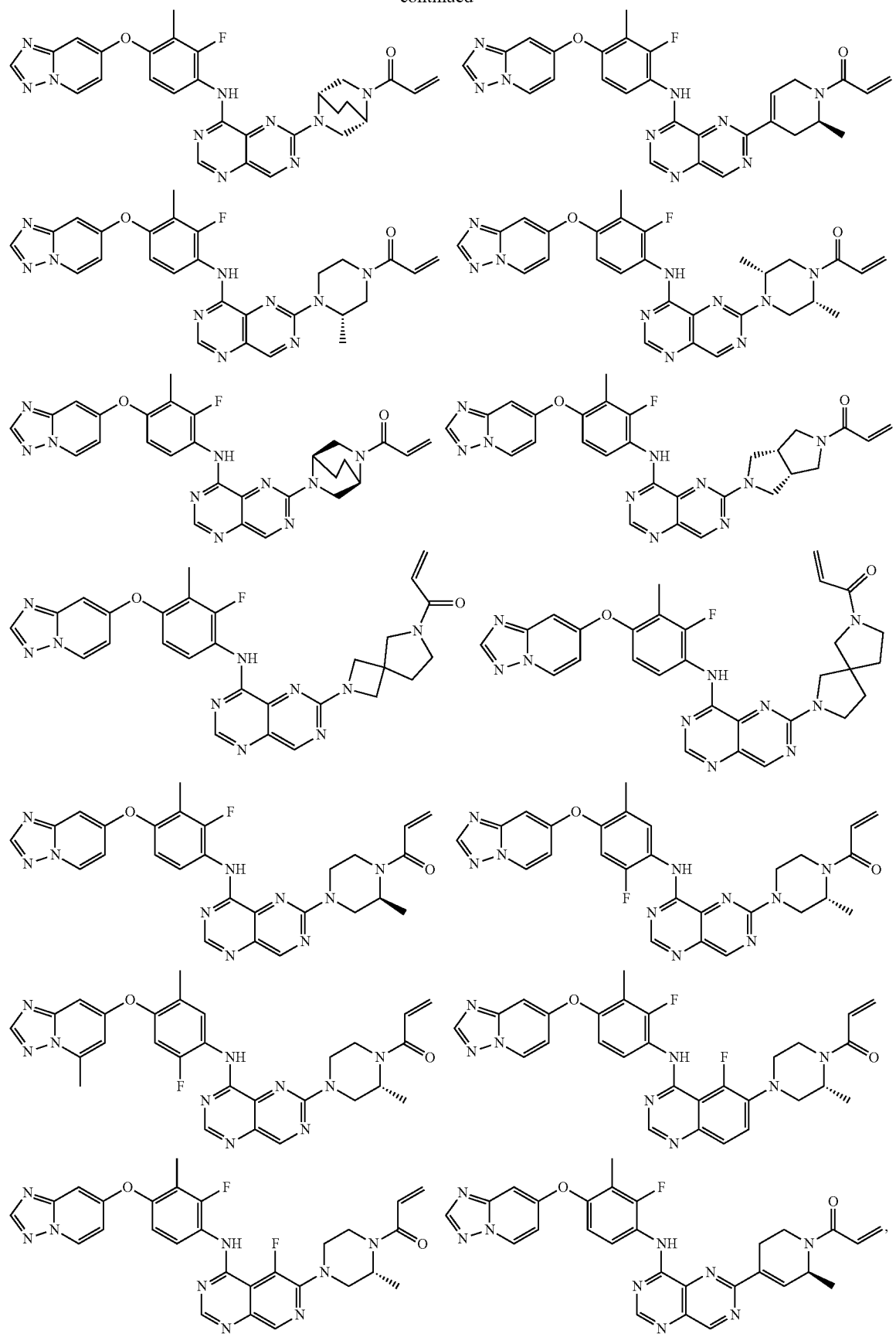

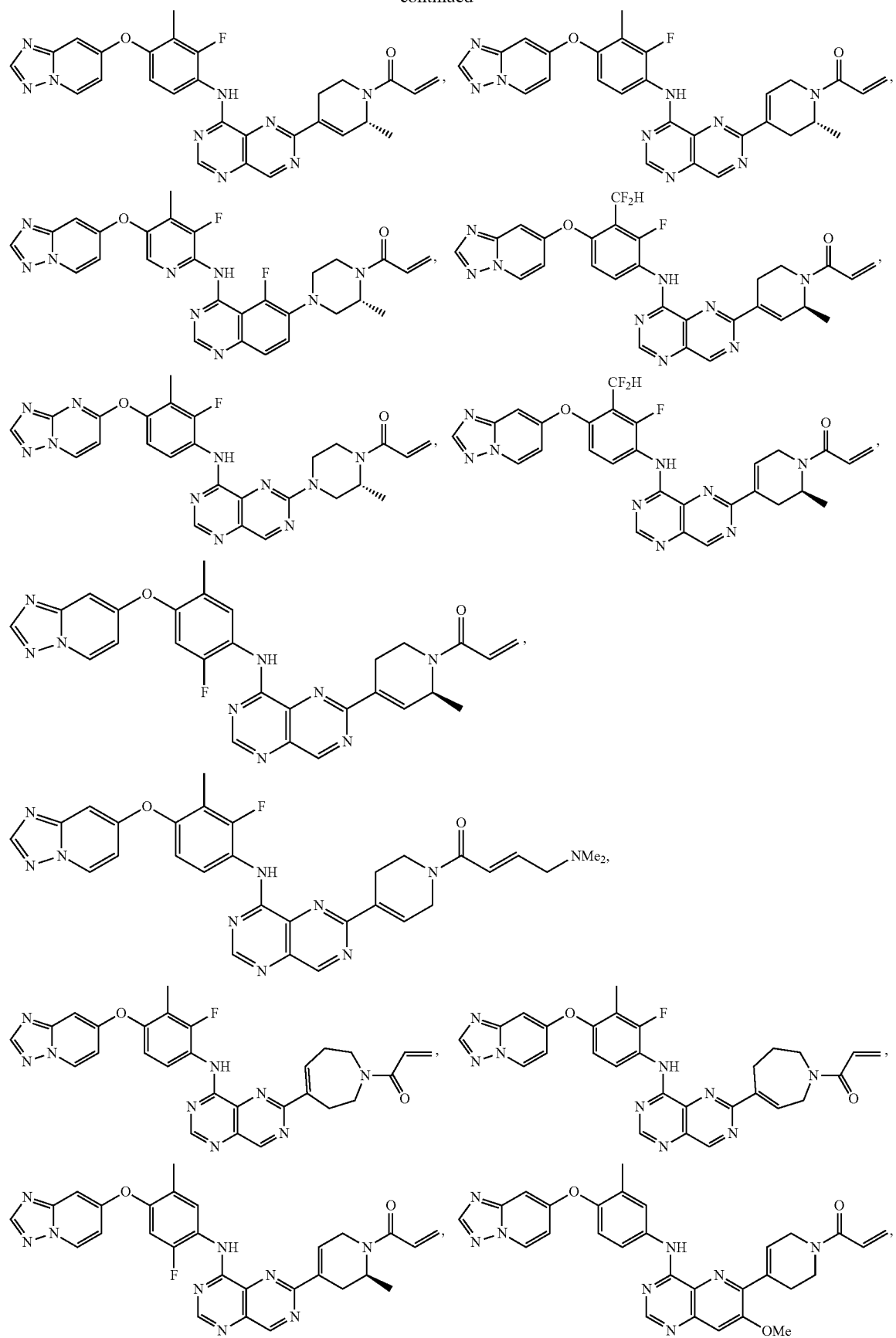

-continued
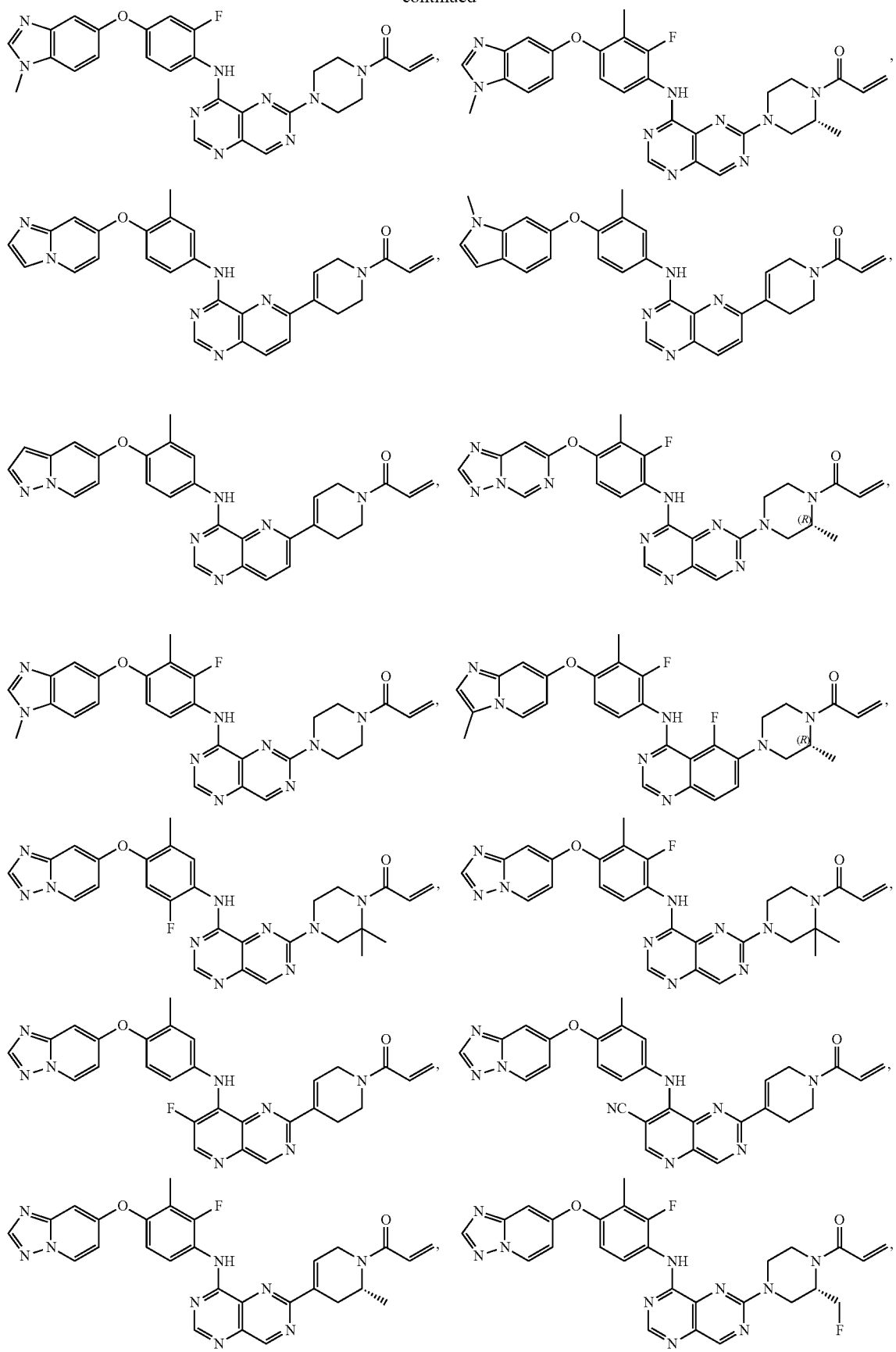

-continued
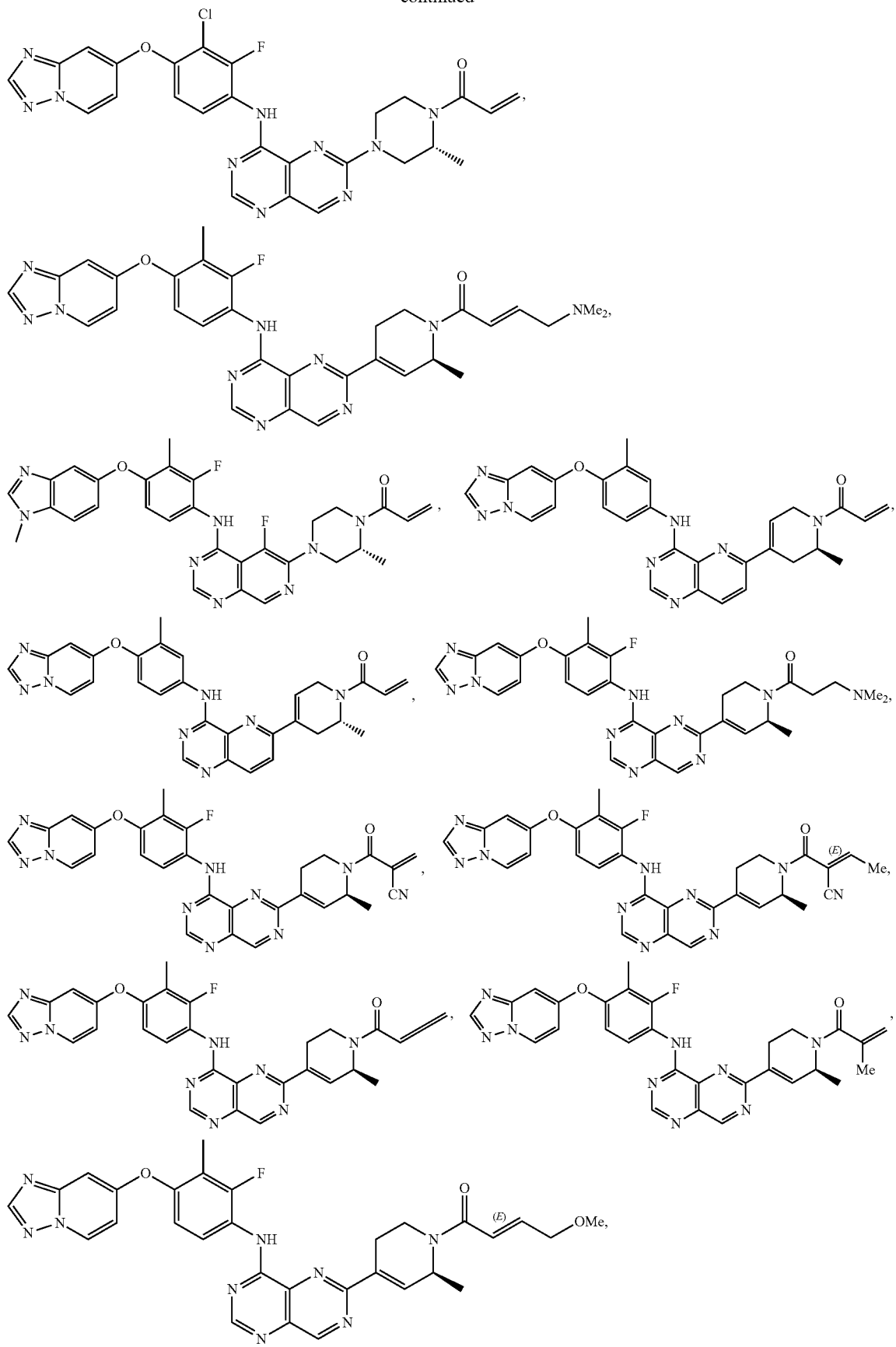

-continued
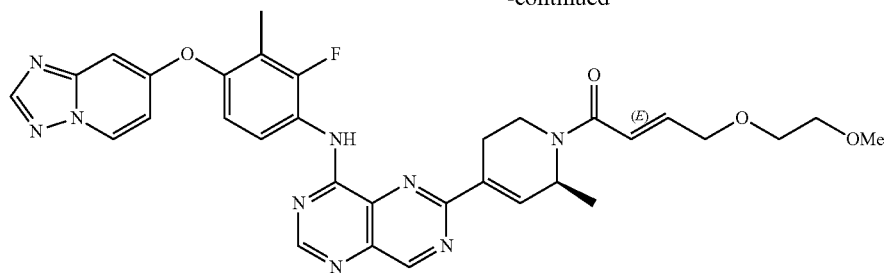
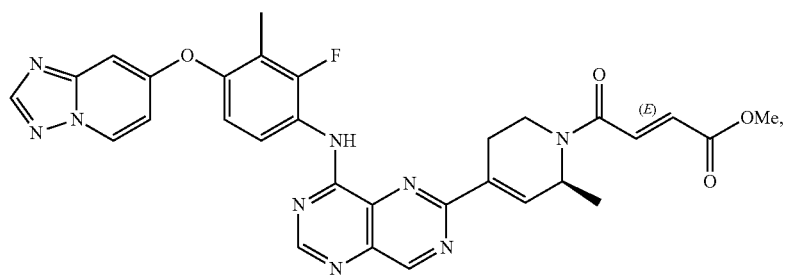
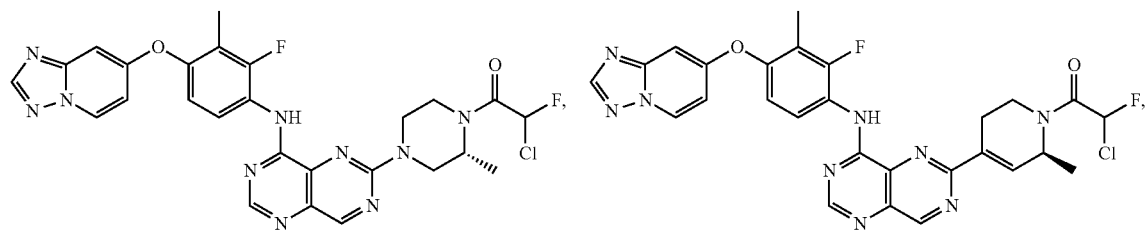
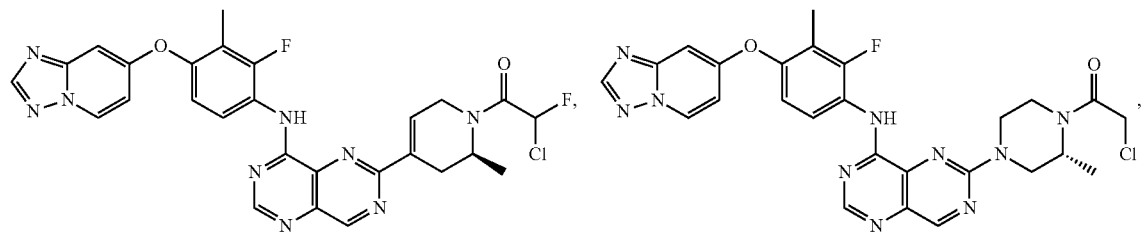
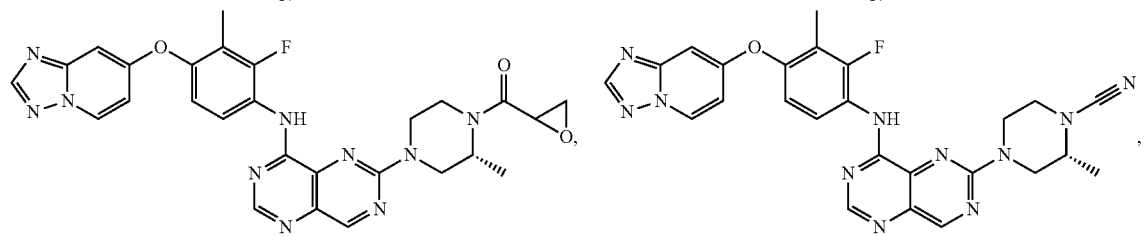
and 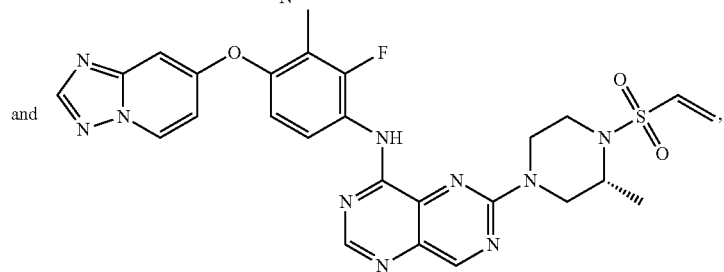
or a pharmaceutically acceptable salt, a stereoisomer, or a tautomer thereof.

In some embodiments, disclosed herein are compounds of the following structures:
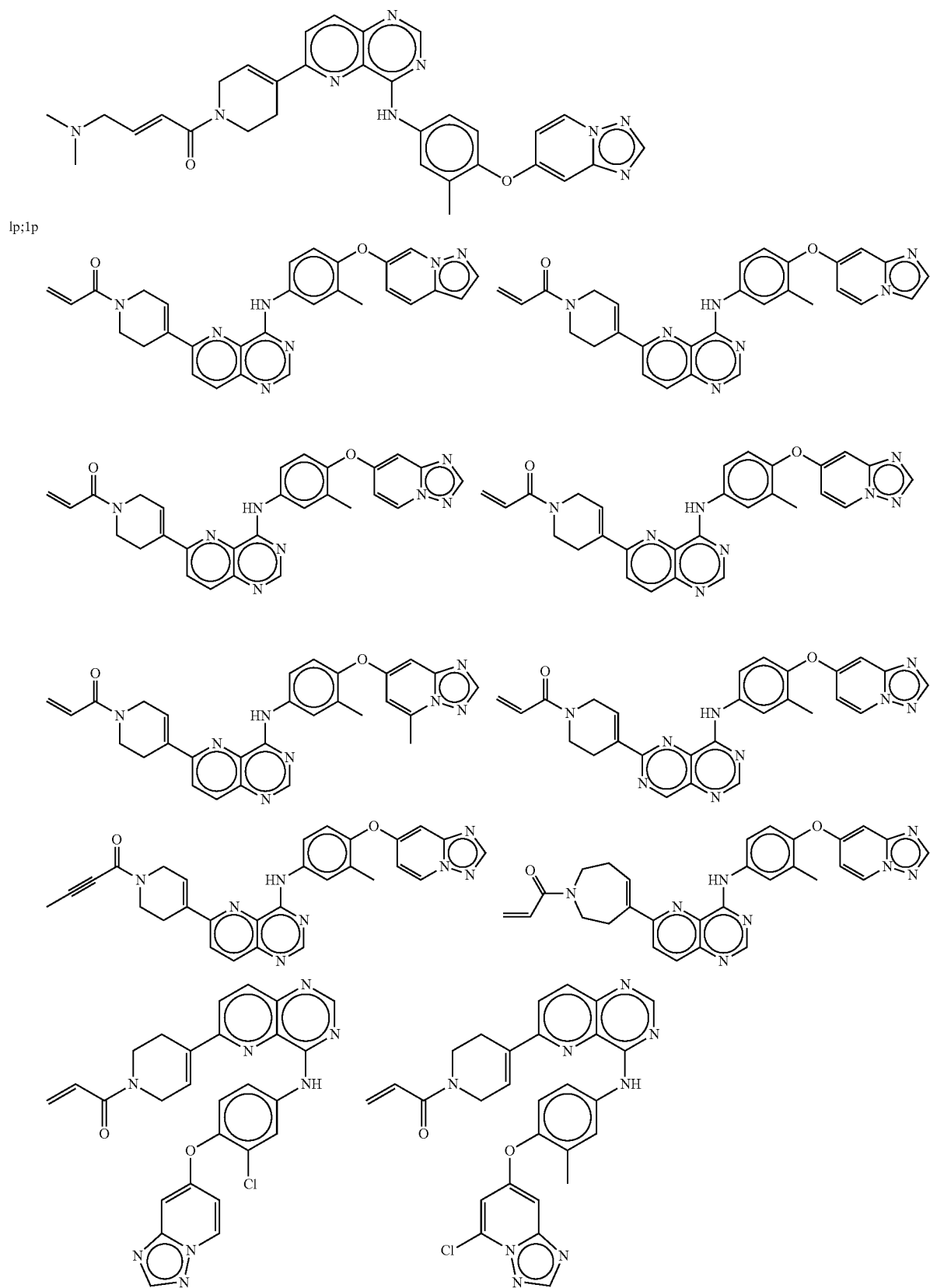
lp;1p

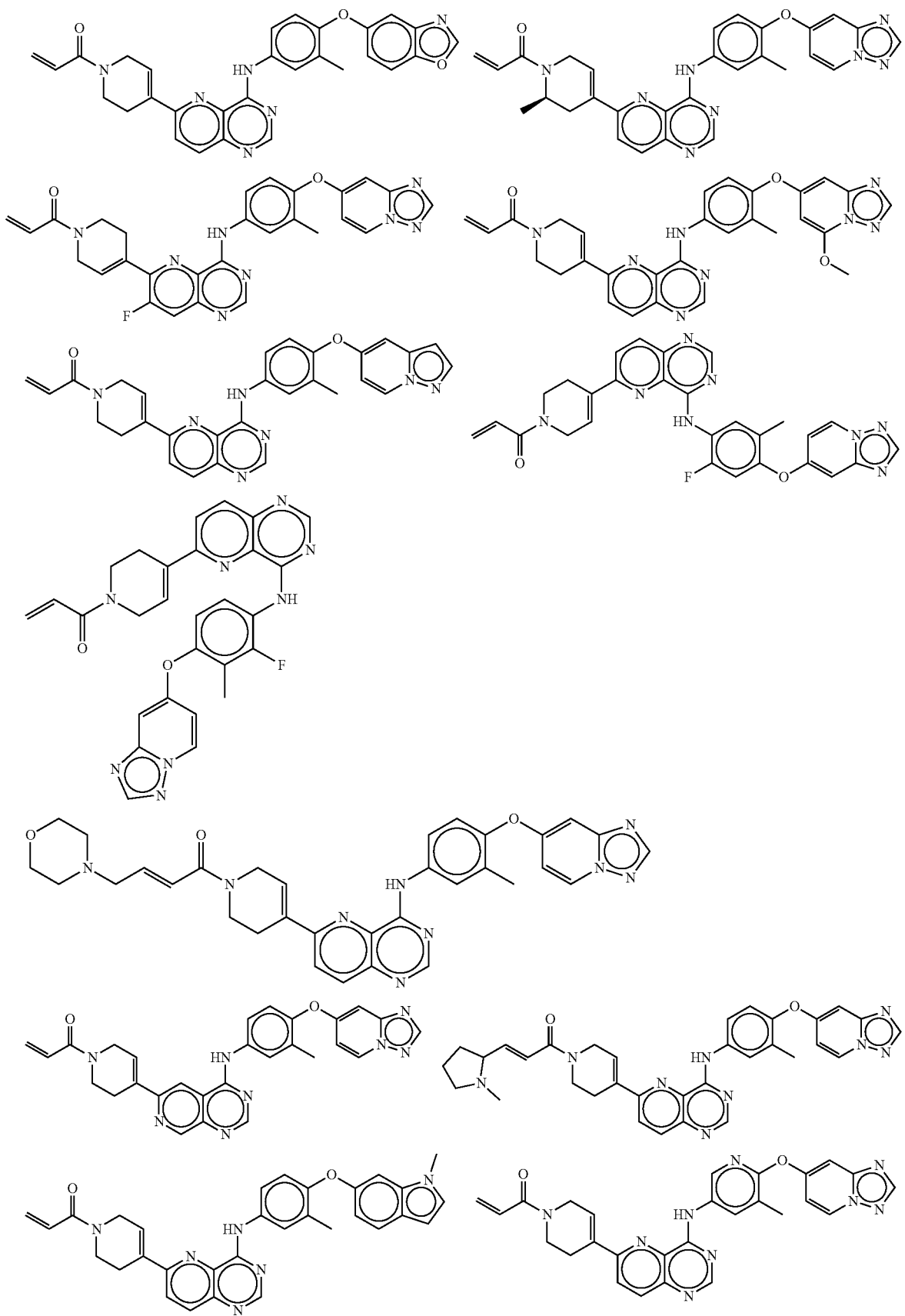

-continued
| 93 | 94 |
|---|---|
| 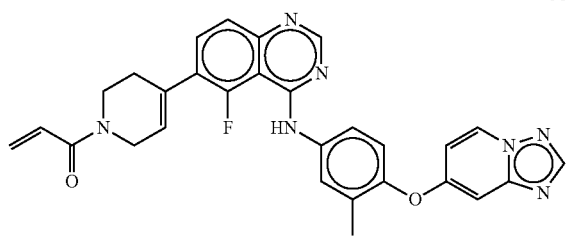 | 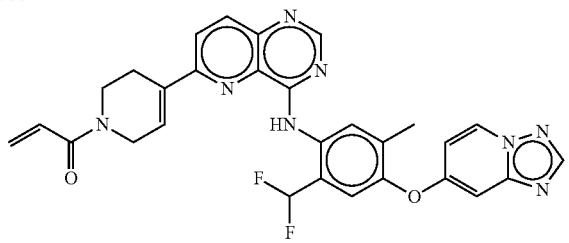 |
| 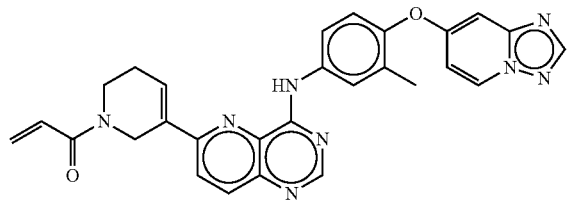 | 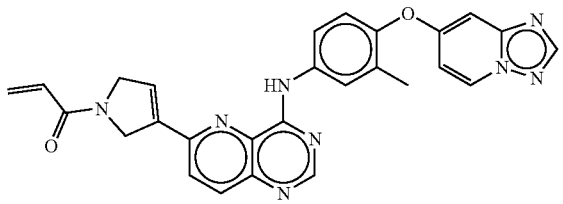 |
| 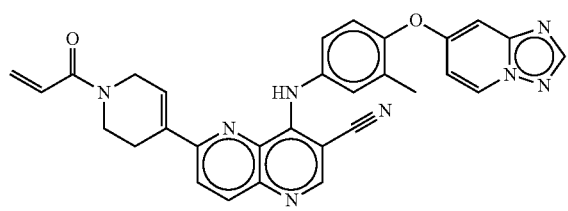 | 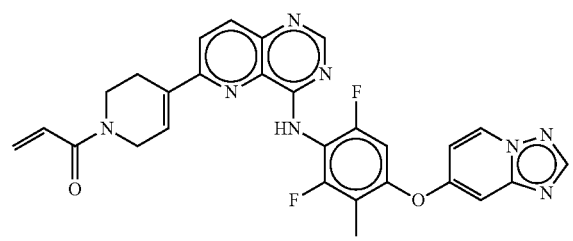 |
| 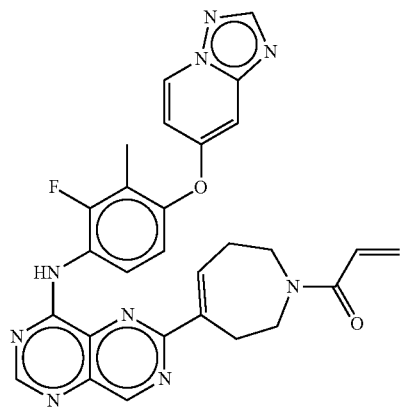 | 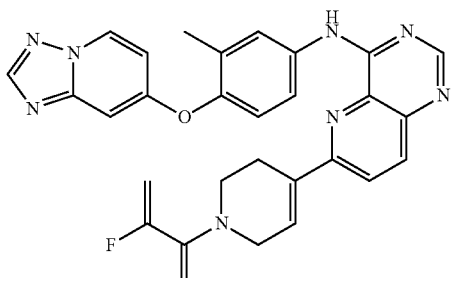 |
| 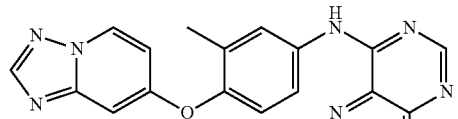 | 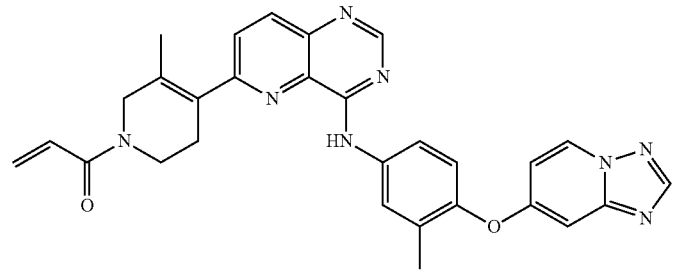 |
| 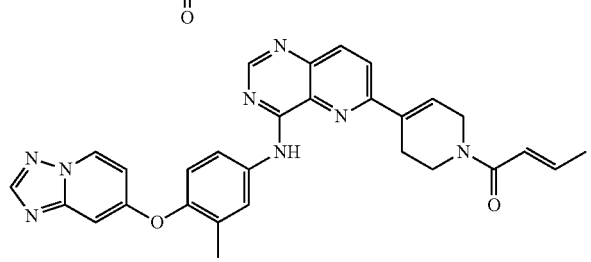 | 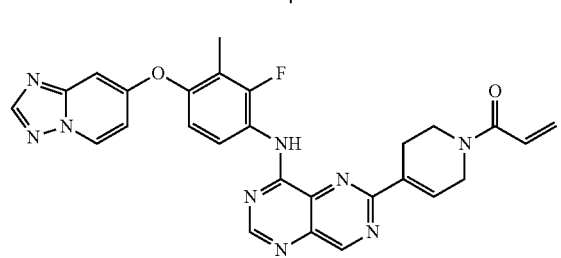 |

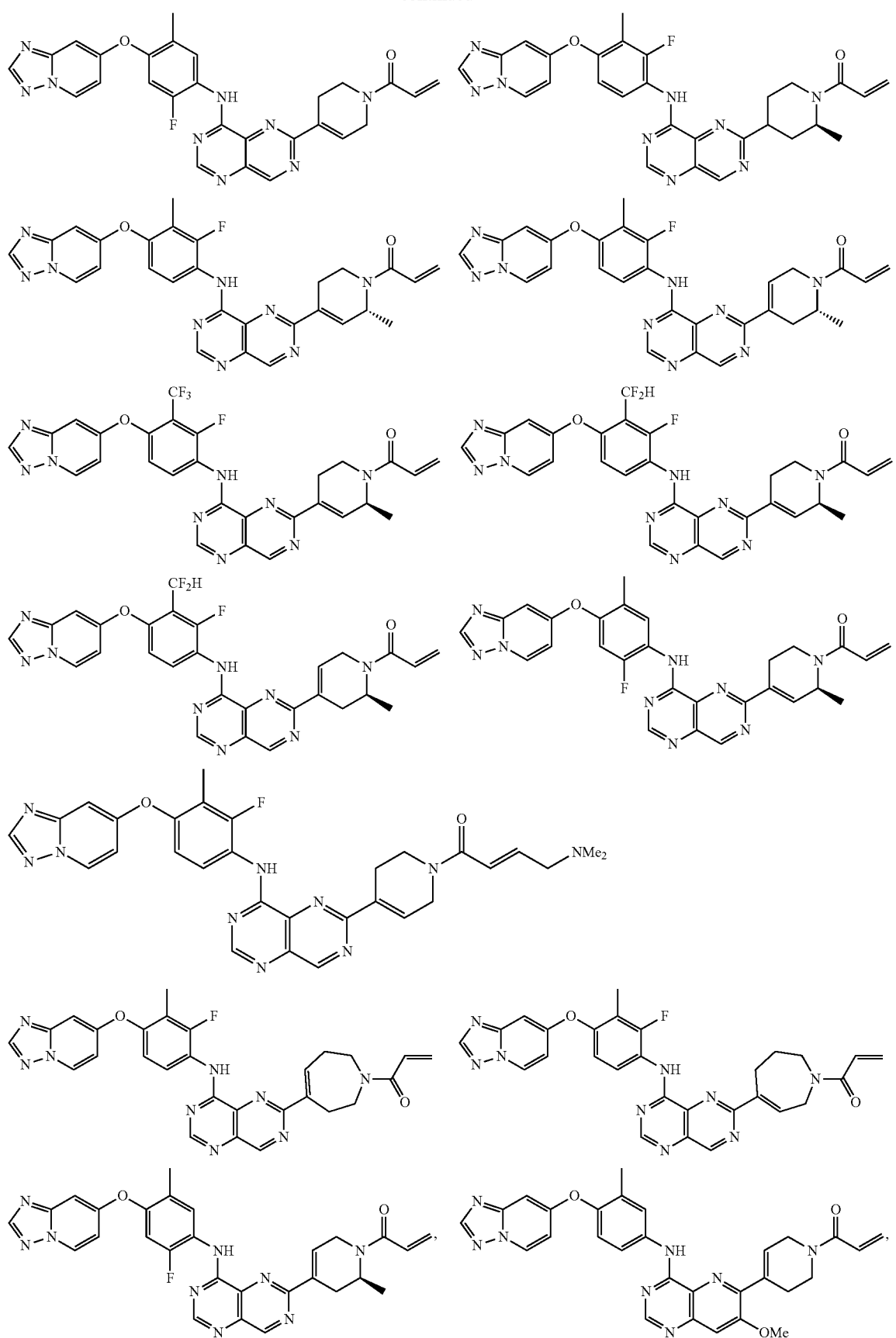

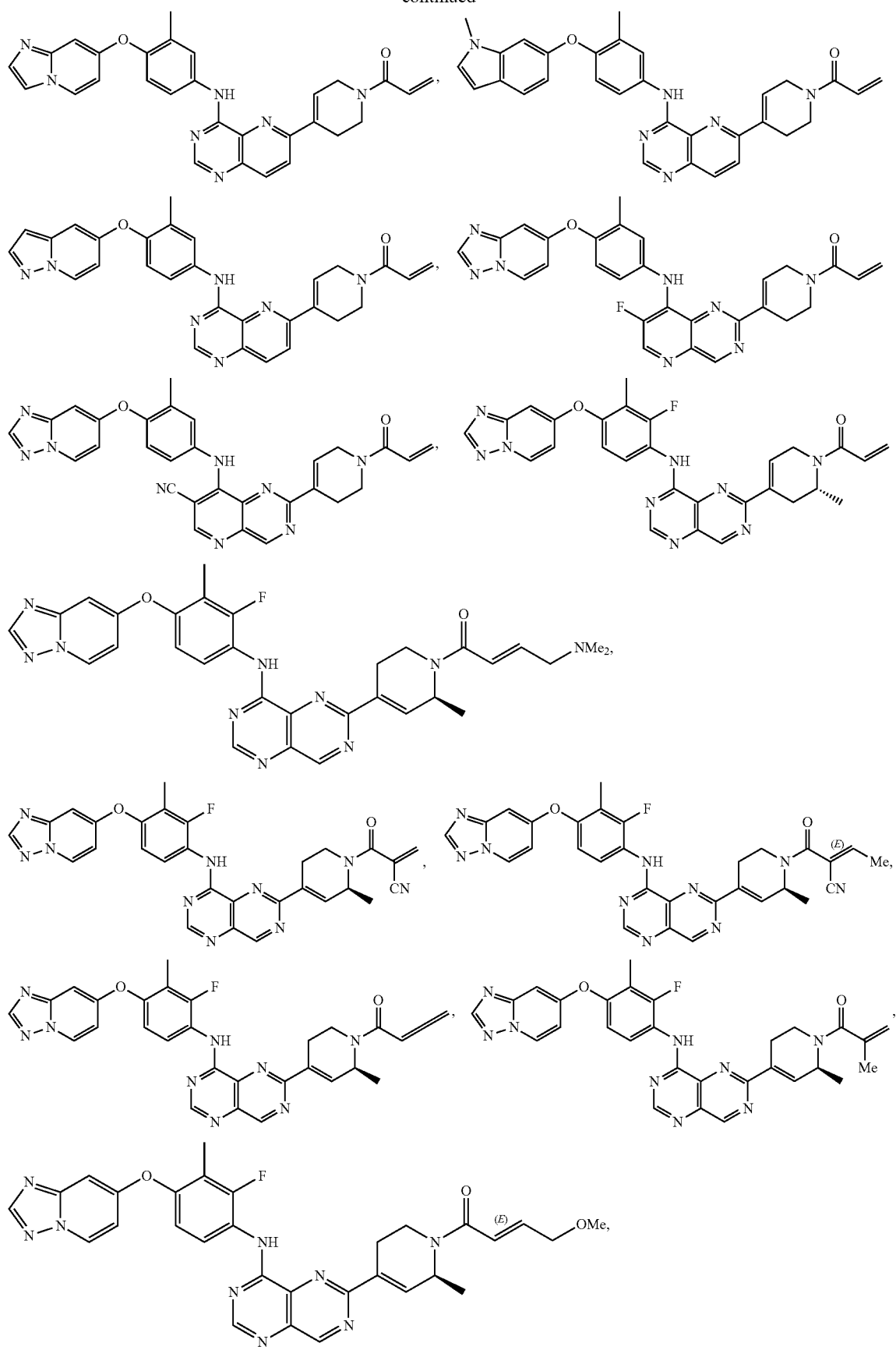

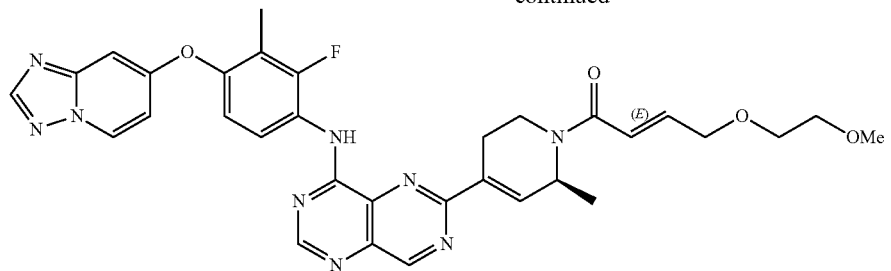
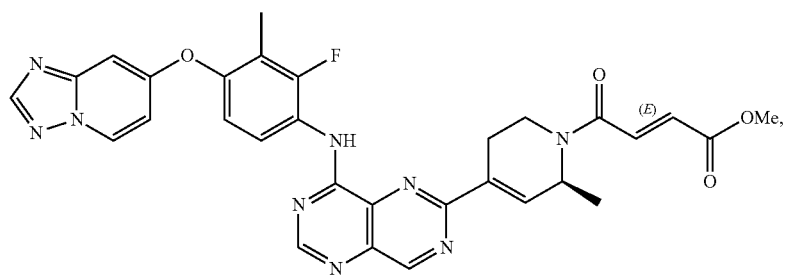
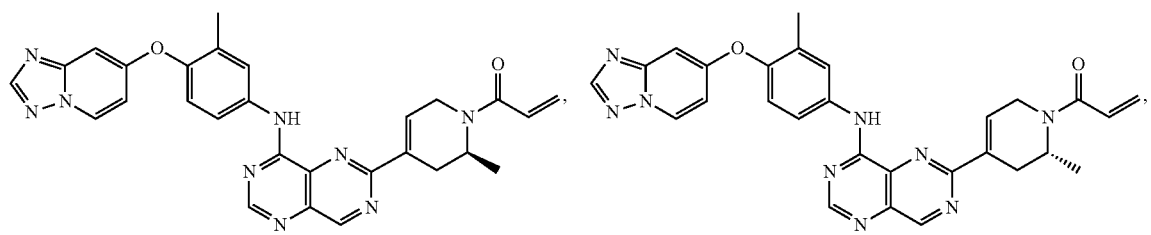
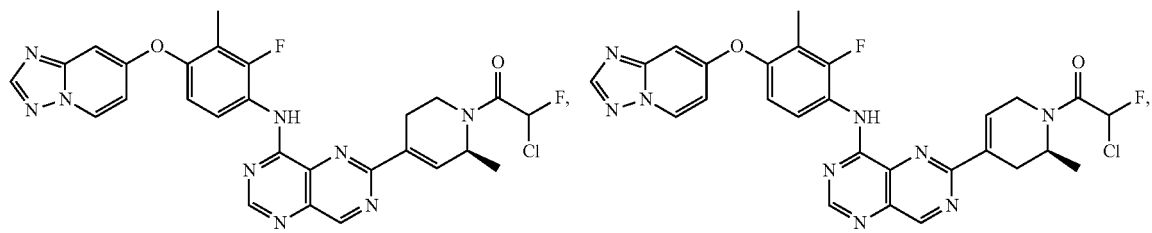
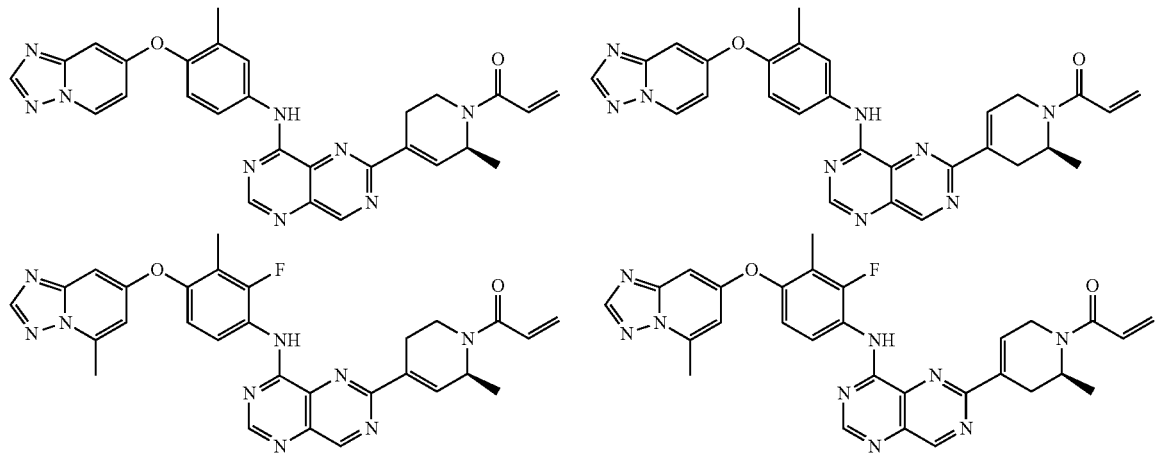
or a pharmaceutically acceptable salt, a stereoisomer, or a tautomer thereof.

In some embodiments, disclosed herein are compounds of the following structures:
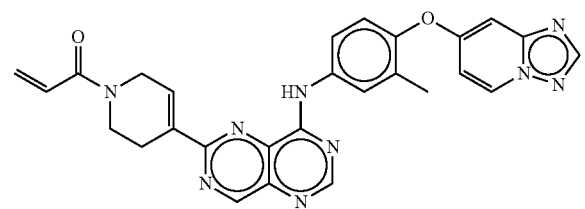
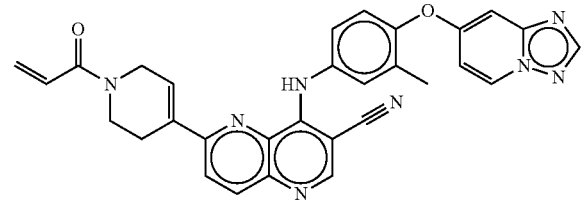
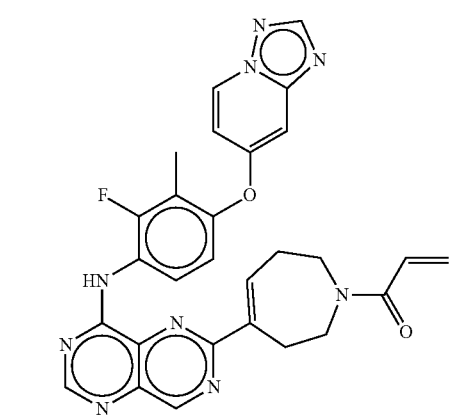
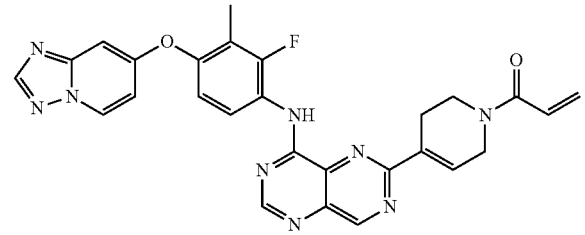
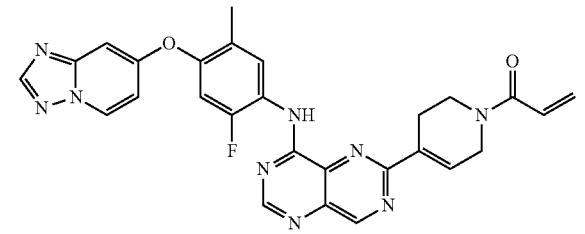
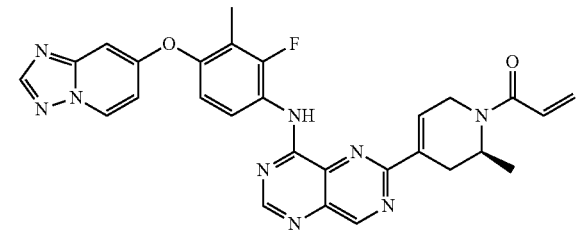
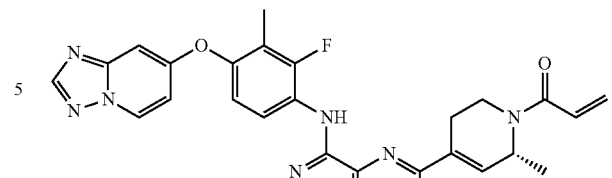
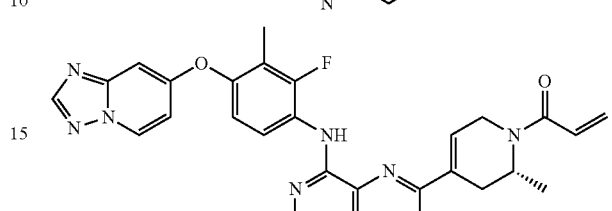
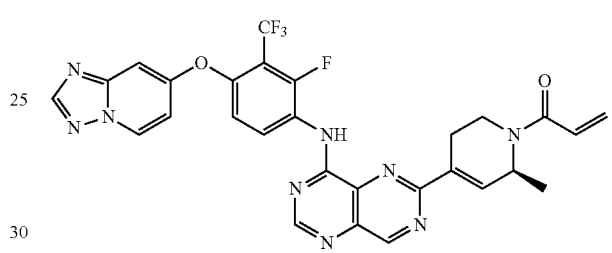
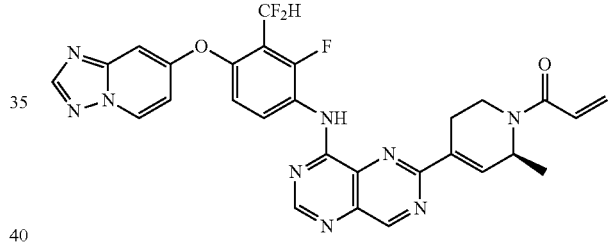
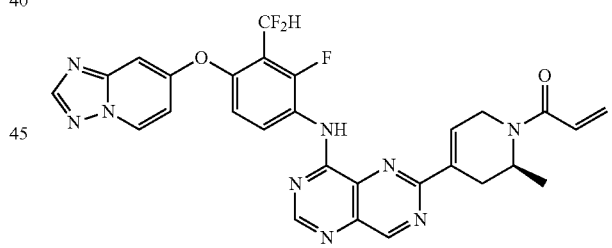
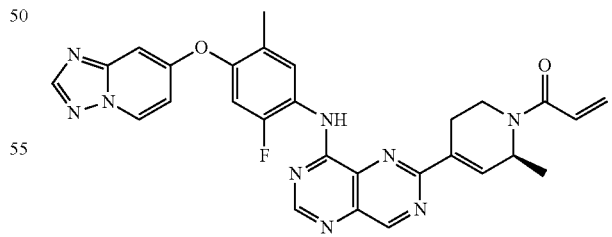
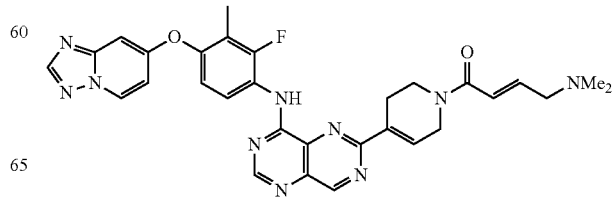

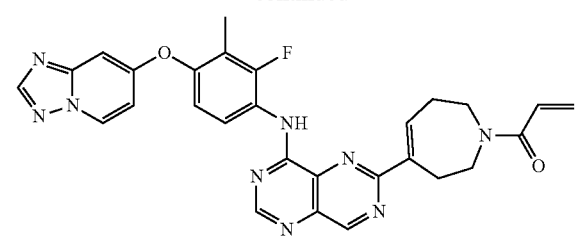
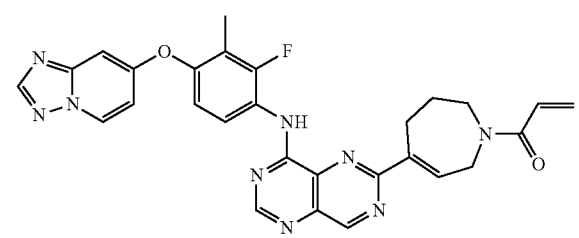
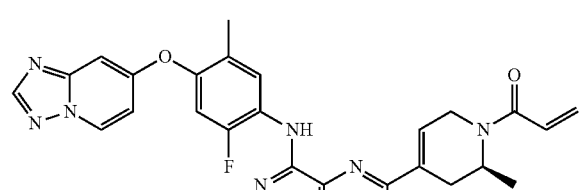
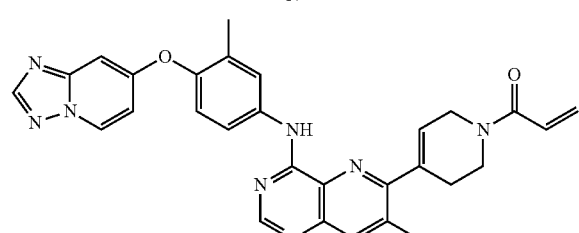
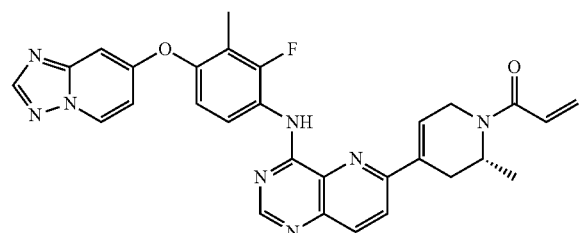
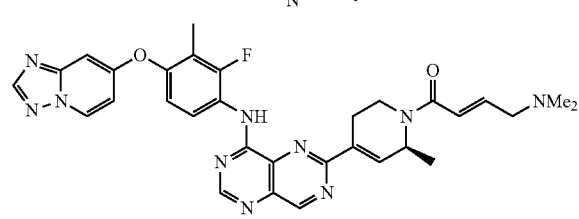
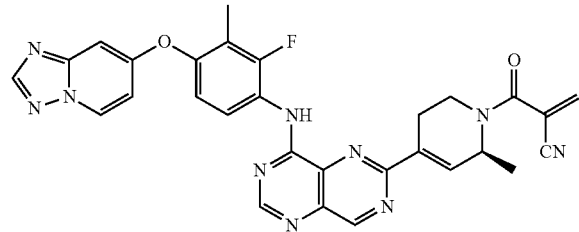
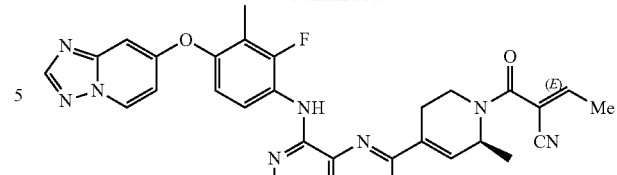
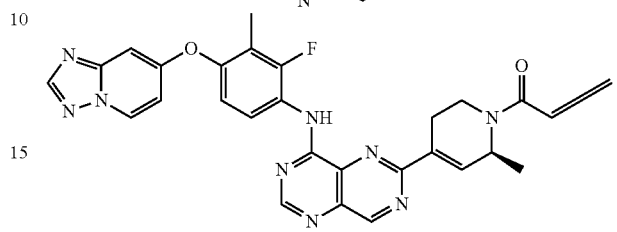
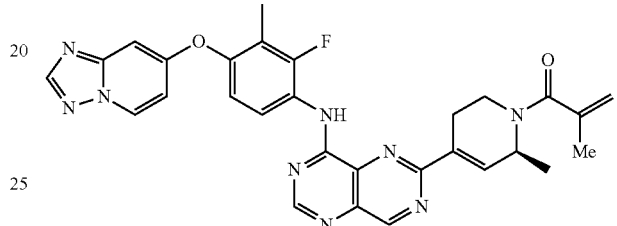
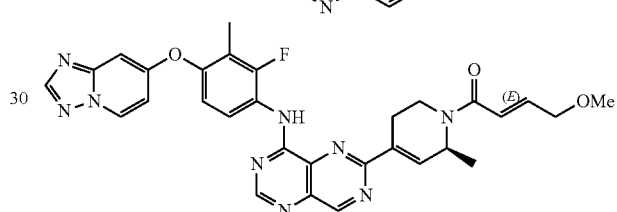
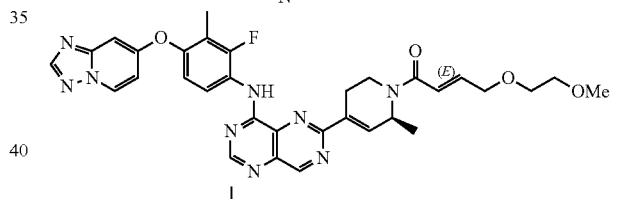
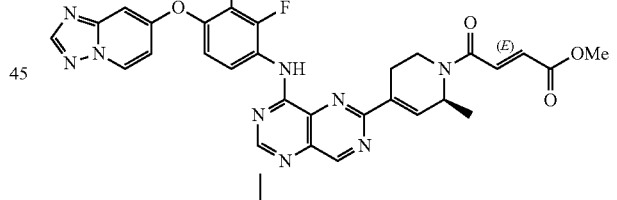
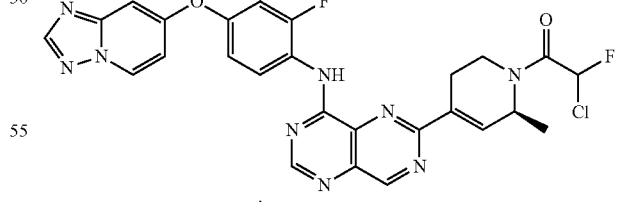
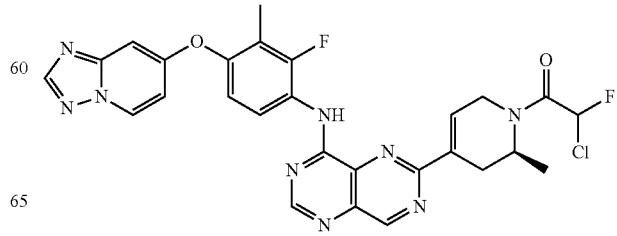

-continued

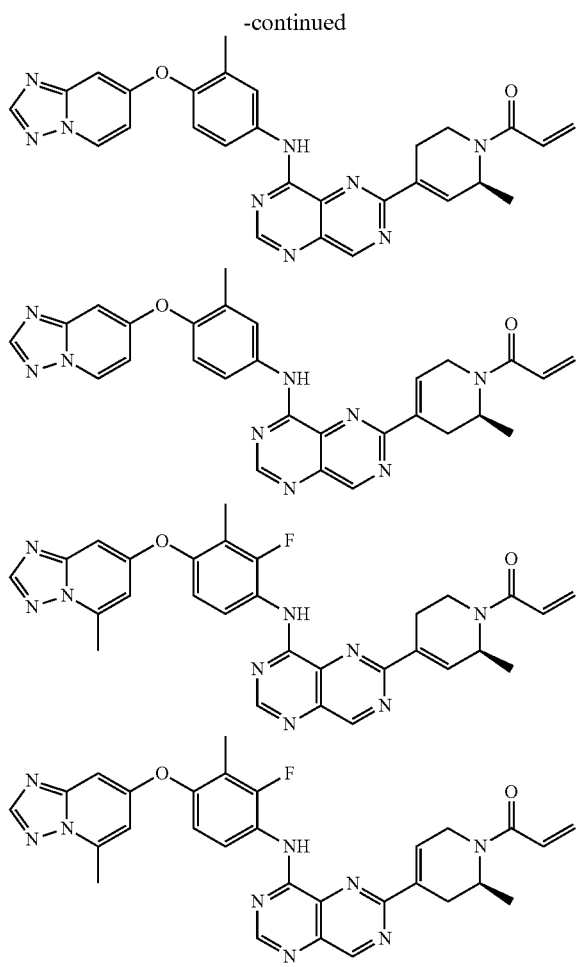

or a pharmaceutically acceptable salt, a stereoisomer, or a tautomer thereof.

Provided herein are methods of treating cancer, comprising administering to a mammal in need thereof a therapeutically effective amount of a compound disclosed herein. In some embodiments, the cancer is non-small cell lung cancer. In other embodiments the cancer is squamous head and neck cancer. In certain embodiments, the non-small cell lung cancer has one or more ErbB family mutations. In other embodiments, the non-small cell lung cancer has one or more EGFR ex20 insertion mutations. In some embodiments, the non-small cell lung cancer has one or more HER2 ex20 insertion mutations. In certain embodiments, the mammal is a human. In some embodiments, the compound is administered orally or intravenously.

Methods of Use

In one aspect, provided herein are methods of preventing and/or treating a proliferative disease such as cancer in a subject (e.g., a subject in need thereof). The methods comprise administering to the subject a compound of the present disclosure (e.g., an effective amount, such as a therapeutically effective amount).

Cancer is a disease of uncontrolled cell proliferation that results from alterations in certain genes. Some of these alterations occur in genes that encode receptor tyrosine kinases (RTKs), a family of membrane-bound proteins that transmit signals from outside the cell to promote cell survival, growth, and proliferation. Aberrant RTK activation can lead to excessive cell proliferation and hence cancer. Generally, RTKs contain an N-terminal domain that binds extracellular ligands, a transmembrane domain, and a C-terminal kinase domain that catalyzes intracellular signal transduction.

The human EGFR, also known as ErbB1 or HER1, is an RTK encoded by the EGFR gene on chromosome 7. Multiple ligands of EGFR have been identified including epidermal growth factor (EGF), transforming growth factor α (TGF-α), amphiregulin (AREG), heparin-binding EGFR-like growth factor (HB-EGF), betacellulin (BTC), epiregulin (EPR), and epigen (EPGN). EGFR is believed to play essential roles in development, proliferation, differentiation, and migration of mammalian cells. EGFR-deficient mice do not survive the first few weeks of life and show improper development of various organs including, but not limited to, the skin, the gut, and the nervous system. In humans, EGFR overexpression and activating mutations are a well-documented cause of cancer. EGFR overexpression is found in many solid tumors at high frequency and can be targeted with FDA-approved monoclonal antibodies: cetuximab, panitumumab, and necitumumab.

In some embodiments, the compound of the present disclosure is a regulator of HER2. The human HER2, also known as ErbB2, is an RTK encoded by the ERBB2 gene on chromosome 17. There are no known ligands for HER2, but it can modulate downstream signaling by heterodimerizing with other HER2-family RTKs, including EGFR. Mouse studies have demonstrated the essential roles of HER2 in mammalian development and cell differentiation, particularly in the cardiac and the nervous systems. HER2 deficiency is embryonically lethal in mice due to abnormal cardiac development, and conditional HER2 deletion causes defects in neuronal cell maturation, myelination, and migration. In humans, HER2 overexpression and activating mutations are known causes of cancer. HER2 overexpression is found in many solid tumors, most notably in 15-25% breast cancer. HER2 amplification is observed in cancers including esophagogastric cancer, breast cancer, peritoneal cancer, salivary gland cancer, bladder cancer, endometrial cancer, ampullary cancer, small bowel cancer, vaginal cancer, cervical cancer, hepatobillary cancer, ovarian cancer, colorectal cancer, NSCLC, head and neck cancer, pancreatic cancer, skin cancer, appendiceal cancer, B-lymphoblastic leukemia/lymphoma, melanoma, germ cell tumor, small cell lung cancer, mature B-cell neoplasms, prostate cancer, soft tissue sarcoma, and glioma. Many targeted therapies have been developed for the treatment of HER2-positive breast cancer including monoclonal antibodies (trastuzumab and pertuzumab), antibody-drug conjugates (ado-trastuzumab emtansine and fam-trastuzumab deruxtecan), and small-molecule kinase inhibitors (lapatinib, neratinib, and tucatinib). Tucatinib, the most recent FDA-approved HER2 inhibitor, extended the objective response rate from 23% to 41%, the median progression free survival from 5.6 to 7.8 months, and the median overall survival from 17.4 to 21.9 months compared to placebo. In contrast, HER2 exon 20 insertions are found in about 2% of NSCLC, but no targeted therapies have been approved for these mutations.

Many existing HER2 therapies including erlotinib, gefitinib, afatinib, dacomitinib, lapatinib, and neratinib are also potent inhibitors of wild-type EGFR. This presents a substantial drawback because native EGFR plays important roles in epithelial biology, including the integrity of the skin and the gut lining. Inhibition of wild-type EGFR is associated with common adverse reactions including skin rash, diarrhea, and stomatitis. New therapies that spare wild-type EGFR while selectively targeting mutant HER2 are a need in the art.

In one aspect, provided herein are methods of treating and/or preventing a proliferative disease, wherein the inhibition of wild type HER2 and/or mutant HER2 provides therapeutic benefit. In certain embodiments, provided herein are methods of treating and/or preventing a proliferative disease, wherein the inhibition of HER2 exon 20 mutant protein provides therapeutic benefit.

In another aspect, provided herein are methods of inhibiting wild type and/or mutant HER2, in a subject in need thereof, comprising administering to the subject a therapeutically effective amount of a compound as described herein, or a pharmaceutically acceptable salt thereof. In another embodiments, provided herein are methods of inhibiting a HER2 exon 20 mutant, in a subject in need thereof, comprising administering to the subject a therapeutically effective amount of a compound as described herein, or a pharmaceutically acceptable salt thereof.

In another aspect, provided herein are methods of treating cancer comprising administering to a mammal (e.g., human subject) in need thereof a therapeutically effective amount of a compound as described herein, or a pharmaceutically acceptable salt thereof, or a pharmaceutical composition as disclosed herein. In some embodiments, the cancer is HER2-associated cancer. In some embodiments, the HER2-associated cancer is associated with HER2 overexpression and/or HER2 amplification and/or HER2 mutation(s).

In some embodiments, "associated with" indicates the cause of the cancer. In some embodiments, "associated with" indicates the characteristics of the cancer.

In another aspect, provided herein are methods of treating cancer comprising administering to a mammal (e.g., human subject) in need thereof a therapeutically effective amount of a compound as described herein, or a pharmaceutically acceptable salt thereof, or a pharmaceutical composition as disclosed herein, wherein the cancer is associated with HER2 exon 20 mutation.

In some embodiments, HER2 exon 20 mutation is one or more from the group consisting of YVMA insertion, VC insertion, and GSP insertion. In some embodiments, HER2 exon 20 mutation is one or more from the group consisting of YVMA insertion and VC insertion.

In certain embodiments, the HER2 exon 20 insertion mutation is one or more selected from A775_G776insYVMA, P780_Y781insGSP, G776>VC, G776>IC, G776>LC, G778_S779insCPG, G780_P781dupGSP, Y772_A775dup, G778_P780dup, E770_A771insGIRD, G778_S779insLPS, M774_A775insAYVM, G778_S779insLPG, G778dup, G776delinsVC, M774delinsWLV, A775_G776insSVMA, and A775_G776insI. In certain embodiments, the HER2 exon 20 insertion mutation is one or more selected from A775_G776insYVMA, P780_Y781insGSP, G776>VC, G776>IC, G776>LC, G778_S779insCPG, and G780_P781dupGSP. In certain embodiments, the HER2 exon 20 insertion mutation is one or more selected from A775_G776insYVMA, P780_Y781insGSP, G776>VC, G776>IC, G776>LC, and G778_S779insCPG.

In another aspect, provided herein are methods of treating cancer comprising administering to a subject in need thereof a therapeutically effective amount of a compound as described herein, or a pharmaceutically acceptable salt thereof, wherein the cancer is characterized by HER2 overexpression, HER2 amplification, and/or HER2 exon 20 mutation(s).

In some embodiments, the cancer is a solid cancer. In some embodiments, the cancer is selected from brain cancer, breast cancer, biliary cancer, bladder cancer, cervical cancer, colorectal cancer, endometrial cancer, skin cancer, esophagus tumor, head and neck tumor, gastrointestinal cancer, gallbladder tumor, kidney cancer, liver cancer, lung cancer, and prostate cancer. In some embodiments, the cancer is lung cancer. In some embodiments, the cancer is NSCLC. In some embodiments, the cancer is small cell lung cancer. In some embodiments, the cancer is breast cancer. In some embodiments, the cancer is a metastatic cancer.

In certain embodiment, a compound provided herein is a CNS-penetrating compound. In one embodiment, after the administration of a therapeutic effective amount of a compound provided herein, the compound is able to penetrate CNS (e.g., blood-brain barrier) and achieve a concentration in CNS (e.g., brain) that is still sufficient to inhibit (e.g., selectively inhibit) HER2 overexpression and/or HER2 amplification and/or HER2 mutation(s).

In one embodiment, provided herein is a method for treating CNS metastases of a cancer, comprising administering to mammal (e.g., human subject) in need thereof a therapeutic effective amount of a compound provided herein, e.g., a compound of Formula (I), or an enantiomer, a mixture of enantiomers, or a tautomer thereof, or a pharmaceutically acceptable salt thereof. In one embodiment, the CNS metastases is brain metastases. In one embodiment, the cancer is a HER-associated cancer (e.g., associated with HER2 overexpression, and/or HER2 amplification, and/or HER2 exon 20 mutation(s)).

In another embodiments, provided herein are methods of inhibiting a HER2 exon 20 mutant(s) in a subject in need thereof, comprising administering to a mammal (e.g. human subject) a therapeutically effective amount of a compound as described herein (e.g., Formula (I) or any subformula), or a pharmaceutically acceptable salt thereof.

In certain embodiments, the compounds of the present disclosure selectively inhibit wild type HER2 over EGFR wild type. In certain embodiments, the compounds of the present disclosure selectively inhibit wild type HER2 over EGFR wild type by about 10 to about 100 folds. In certain embodiments, the compounds of the present disclosure selectively inhibit wild type HER2 over EGFR wild type by about 20 to about 80 folds. In certain embodiments, the compounds of the present disclosure selectively inhibit wild type HER2 over EGFR wild type by about 30 to about 80 folds. In certain embodiments, the compounds of the present disclosure selectively inhibit wild type HER2 over EGFR mutant(s) (e.g., EGFR exon 20). In certain embodiments, the compounds of the present disclosure selectively inhibit wild type HER2 over EGFR mutant(s) (e.g., EGFR exon 20) by about 10 to about 100 folds. In certain embodiments, the compounds of the present disclosure selectively inhibit wild type HER2 over EGFR mutant(s) (e.g., EGFR exon 20) by about 20 to about 80 folds. In certain embodiments, the compounds of the present disclosure selectively inhibit HER2 mutant(s) over EGFR wild type. In certain embodiments, the compounds of the present disclosure selectively inhibit HER2 mutant(s) over EGFR wild type by about 10 to about 100 folds. In certain embodiments, the compounds of the present disclosure selectively inhibit HER2 mutant(s) over EGFR wild type by about 20 to about 100 folds. In certain embodiments, the compounds of the present disclosure selectively inhibit HER2 exon 20 mutant(s) over EGFR wild type. In certain embodiments, the compounds of the present disclosure selectively inhibit HER2 exon 20 mutant(s) over EGFR wild type by about 10 to about 100 folds. In certain embodiments, the compounds of the present disclosure selectively inhibit HER2 exon 20 mutant(s) over EGFR wild type by about 20 to about 80 folds. In certain embodiments, the compounds of the present disclosure selectively inhibit HER2 exon 30 mutant(s) over EGFR wild type by about 20 to about 80 folds. In certain embodiments, the compounds of the present disclosure selectively inhibit HER2 mutant(s) (e.g., HER2 exon 20) over EGFR mutant(s) (e.g. EGFR exon 20). In certain embodiments, the compounds of the present disclosure selectively inhibit HER2 mutant(s) (e.g., HER2 exon 20) over EGFR mutant(s) (e.g. EGFR exon 20) by about 10 to about 100 folds. In certain embodiments, the compounds of the present disclosure selectively inhibit HER2 mutant(s) (e.g., HER2 exon 20) over EGFR mutant(s) (e.g. EGFR exon 20) by about 20 to about 80 folds. In some embodiments, the compounds of the present disclosure selectively inhibit HER2 exon 20 mutant(s) over EGFR wild type and/or EGFR exon 20 mutant(s). In some embodiments, the compounds of the present disclosure show an improved wild type EGFR sparing efficacy profile in addition to high selectivity over EGFR wild type, compared to the existing therapies. Furthermore, some compounds of the present invention show an improved pharmacokinetic and pharmacological profile. In some embodiments, the compounds as described herein have minimal activities against related kinase (e.g., wt EGFR). Inhibition of wt EGFR causes undesirable side effects (e.g., diarrhea and skin rashes) that can impact quality of life and compliance of treatments.

In some embodiments, the human subject has been identified or diagnosed as having a cancer associated with HER2 overexpression, and/or HER2 amplification, and/or HER2 exon 20 mutation(s) (a HER2-associated cancer) (e.g., as determined using a regulatory agency-approved, e.g., FDA-approved, assay or kit). In some embodiments, the subject has a tumor that is positive for HER2 overexpression, and/or HER2 amplification, and/or HER2 exon 20 mutation(s) (e.g., as determined using a regulatory agency-approved assay or kit). The subject can be a subject whose tumors have HER2 overexpression, and/or HER2 amplification, and/or HER2 exon 20 mutation(s) (e.g., where the tumor is identified as such using a regulatory agency-approved, e.g., FDA-approved, kit or assay). In some embodiments, the subject is suspected of having a HER2-associated cancer. In some embodiments, the subject has a clinical record indicating that the subject has a tumor that has HER2 overexpression, and/or HER2 amplification, and/or HER2 exon 20 mutation(s).

In some embodiments of any of the methods or uses described herein, an assay used to determine whether the subject has HER2 overexpression, and/or HER2 amplification, and/or HER2 exon 20 mutation(s), using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting HER2 overexpression, and/or HER2 amplification, and/or HER2 exon 20 mutation(s) (see, e.g., the references cited herein). In some embodiments, the sample is a biological sample or a biopsy sample (e.g., a paraffin-embedded biopsy sample) from the subject. In some embodiments, the subject is a subject suspected of having a HER2-associated cancer, a subject having one or more symptoms of a HER2-associated cancer, and/or a subject that has an increased risk of developing a HER2-associated cancer.

In some embodiments, HER2 overexpression, and/or HER2 amplification, and/or HER2 exon 20 mutation(s) can be identified using a liquid biopsy (variously referred to as a fluid biopsy or fluid phase biopsy). See, e.g., Karachialiou et al., "Real-time liquid biopsies become a reality in cancer treatment", Ann. Transl. Med., 3(3):36, 2016. Liquid biopsy methods can be used to detect total tumor burden and/or the dysregulation of a HER2 gene, a HER2 kinasev, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a HER2 gene, a HER2 kinase, or the expression or activity or level of any of the same. In some embodiments, liquid biopsies can be used to detect the presence of HER2 overexpression, and/or HER2 amplification, and/or HER2 exon 20 mutation(s) at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify HER2 overexpression, and/or HER2 amplification, and/or HER2 exon 20 mutation(s).

In some embodiments, the compounds of the present disclosure inhibit a HER2 exon 20 mutant in a subject with NSCLC. In some embodiments, HER2 exon 20 mutant is one or more from the group consisting of YVMA insertion, VC insertion, and GSP insertion. In some embodiments, the compounds of the present disclosure inhibit a HER2 non-exon 20 mutant. In some embodiments, the compounds of the present disclosure selectively inhibit HER2 non-exon 20 mutant(s) over EGFR wild type and/or mutants (e.g., exon 20). In some embodiments, the HER2 non-exon 20 mutant is one or more from the group consisting of S310X (e.g., S310F and S310Y), R678Q, V842I, L755S, G776V, and V777X. In some embodiments, the non-exon 20 mutation is one or more selected from L755S, S310F, R678Q, V842I, and V777X.

In some embodiments, provided herein are methods of inhibiting wild type HER2 and/or mutant HER2 in a cell, comprising contacting the cell with a compound of the present disclosure. In some embodiments, the mutant HER2 carries one or more exon 20 mutations.

In some embodiments, provided herein are methods of increasing the level of HER2 (wild type HER2 and/or mutant(s)) in a cell, comprising contacting the cell with the compound of the present disclosure, or a pharmaceutically acceptable salt, a stereoisomer, or a tautomer thereof.

In some embodiments, provided herein are methods of decreasing phosphorylation of HER2 (wild type HER2 and/or mutant(s)) in a cell, comprising contacting the cell with the compound of the present disclosure, or a pharmaceutically acceptable salt, a stereoisomer, or a tautomer thereof. In another embodiment, provided herein are methods of inhibiting HER2 carrying exon 20 mutations in a cell, comprising contacting the cell with the compound of the present disclosure, or a pharmaceutically acceptable salt, a stereoisomer, or a tautomer thereof.

In some embodiments, provided herein are methods of inhibiting phosphorylation of wild type HER2 and/or mutant HER2 in a cell, comprising contacting the cell with the compound of the present disclosure, or a pharmaceutically acceptable salt, a stereoisomer, or a tautomer thereof. In some embodiments, the mutant HER2 carries one or more exon 20 mutations.

In some embodiments, provided herein are methods of treating and/or prevention of a disease and/or condition, wherein the inhibition of wild type and/or mutant HER2 is of therapeutic benefit. In another embodiment, provided herein are methods of treating or preventing a disease and/or condition, wherein the inhibition of HER2 exon 20 mutant protein is of therapeutic benefit.

In some embodiments, provided herein are methods of inhibiting wild type and/or mutant HER2, in a human subject in need thereof, comprising administering to the subject a therapeutically effective amount of a compound of the present disclosure, or a pharmaceutically acceptable salt, a stereoisomer, or a tautomer thereof.

The compounds of the present disclosure are useful for inhibiting HER2 in vitro or in vivo. Accordingly, provided herein are methods of inhibiting HER2 in a cell (e.g., a cell expressing HER2), comprising contacting the cell with a compound of the present disclosure (e.g., a compound a compound of the disclosure, such as a compound of Formula (I), (I-i), (I-i-a), (I-i-a1), (I-i-a2), (a-I), (II), or (III), or a pharmaceutically acceptable salt, a stereoisomer, or a tautomer thereof). In some embodiments, the cell is in a subject, such as a human (e.g., a subject having a disease, disorder or condition described herein). Also provided herein are methods of inhibiting HER2 in a subject in need thereof (e.g., a subject having a disease, disorder or condition described herein), comprising administering to the subject a therapeutically effective amount of a compound of the present disclosure (e.g., a compound of the disclosure, such as a compound of Formula (I), (I-i), (I-i-a), (I-i-a1), (I-i-a2), (a-I), (II), or (III), or a pharmaceutically acceptable salt, a stereoisomer, or a tautomer thereof).

In some embodiments, the cell is in a mammal. In some embodiments, the cell is in a human subject. In some embodiments, the cell is in a human subject having cancer. In some embodiments, the cell is in a human subject having cancer associated with HER2 overexpression and/or HER2 amplification and/or HER2 mutation(s). In some embodiments, the cell is isolated from a mammal (e.g., a human subject having cancer).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: (1) the pathological proliferation of normally quiescent cells; (2) the pathological migration of cells from their normal location (e.g., metastasis of neoplastic cells); (3) the pathological expression of proteolytic enzymes such as the matrix metalloproteinases (e.g., collagenases, gelatinases, and elastases); and/or (4) pathological angiogenesis, as in proliferative retinopathy and tumor metastasis. Non-limiting examples of proliferative diseases include cancer (i.e., "malignant neoplasms"), benign neoplasms, angiogenesis, inflammatory diseases and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending, for example, on the following characteristics: degree of cellular differentiation (including morphology and functionality), rate of growth, local invasion, and metastasis.

A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Non-limiting examples of benign neoplasms include, but are not limited to, lipomas, chondromas, adenomas, acrochordons, senile angiomas, seborrheic keratoses, lentigos, and sebaceous hyperplasias.

In some cases, benign tumors may later give rise to malignant neoplasms, which may result from additional genetic changes in a subpopulation of the tumor's neoplastic cells. Such tumors are referred to as "pre-malignant neoplasms." An exemplary pre-malignant neoplasm is a teratoma.

A "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue, and is typically identifiable by the presence of a "secondary tumor" or "secondary cell mass" of the tissue type of the primary or original tumor and not of that of the organ or tissue in which the secondary (metastatic) tumor is located.

In certain embodiments, the proliferative disease is cancer. Accordingly, provided herein are methods for treating a cancer in a subject (e.g., a subject in need thereof), comprising administering to the subject a therapeutically effective amount of a compound of the present disclosure.

The term "cancer" refers to a class of diseases characterized by the development of abnormal cells that proliferate uncontrollably and have the ability to infiltrate and destroy normal body tissues.

A wide variety of cancers, including solid tumors, leukemias, lymphomas, and myelomas are amenable to the methods disclosed herein. In some embodiments, the cancer is a solid tumor cancer. In some embodiments, the cancer comprises a solid tumor (e.g., a colorectal, breast, prostate, lung, pancreatic, renal or ovarian tumor). Accordingly, in some embodiments, the cancer is a solid tumor cancer. In some embodiments, the cancer is selected from one or more of a cancer of the pulmonary system, a brain cancer (e.g., neuroblastoma, glioblastoma, anaplastic astrocytoma), a cancer of the gastrointestinal tract, a skin cancer, a genitourinary cancer, head and neck cancer, a sarcoma, a carcinoma, and a neuroendocrine cancer. In various embodiments, the solid tumor cancer is breast cancer, bladder cancer, endometrial cancer, esophageal cancer, liver cancer, pancreatic cancer, lung cancer, cervical cancer, colon cancer, colorectal cancer, gastric cancer, kidney cancer, ovarian cancer, prostate cancer, testicular cancer, uterine cancer, a viral-induced cancer, melanoma or sarcoma. In some embodiments, the cancer is bladder cancer. In some embodiments, the cancer is lung cancer (e.g., non-small cell lung cancer). In other embodiments, the cancer is liver cancer. In some embodiments, the cancer is a sarcoma, bladder cancer or renal cancer. In some embodiments, the cancer is prostate cancer (e.g., castration-resistant prostate cancer, castration-sensitive prostate cancer). In other embodiments, the cancer is bladder cancer, pancreatic cancer, colorectal cancer, glioblastoma, kidney cancer, non-small cell lung carcinoma, prostate cancer, sarcoma, skin cancer, thyroid cancer (e.g., anaplastic thyroid cancer), testicular cancer or vulvar cancer. In some embodiments, the cancer is endometrial cancer, pancreatic cancer, testicular cancer, renal cancer, melanoma, colorectal cancer, thyroid cancer, bladder cancer, pancreatic cancer, vulvar cancer, sarcoma, prostate cancer, lung cancer or anal cancer. In some embodiments, the cancer is a sarcoma. In some embodiments, the cancer is a renal cell carcinoma.

In some embodiments, the cancer is a non-solid tumor cancer. In some embodiments, the cancer is a hematologic cancer. Hematologic cancers that can be treated according to the methods described herein include leukemias (e.g., acute leukemias, chronic leukemias), lymphomas (e.g., B-cell lymphoma, T-cell lymphoma) and multiple myeloma. Non-limiting examples of hematologic cancers include leukemia (e.g., acute lymphocytic leukemia (ALL) (e.g., B-cell ALL, T-cell ALL), acute myelocytic leukemia (AML) (e.g., B-cell AML, T-cell AML), early T-cell precursor (ETP)-acute lymphoblastic leukemia, chronic myelocytic leukemia (CML) (e.g., B-cell CML, T-cell CML), chronic lymphocytic leukemia (CLL) (e.g., B-cell CLL, T-cell CLL)); lymphoma (e.g., Hodgkin lymphoma (HL) (e.g., B-cell HL, T-cell HL)), non-Hodgkin lymphoma (NHL) (e.g., B-cell NHL such as diffuse large cell lymphoma (DLCL) (e.g., diffuse large B-cell lymphoma)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomads, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome)), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); heavy chain disease (e.g., alpha chain disease, gamma chain disease, mu chain disease); a myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CMIL), chronic neutrophilic leukemia (CNL), hypereosinophilic syndrome (HES)); multiple myeloma (MM); plasma cell neoplasia; familiar hypereosinophilia; inflammatory myofibroblastic tumors; and immunocytic amyloidosis. In some embodiments, the hematologic cancer is selected from multiple myeloma, myelodysplastic syndrome (MDS), acute myeloid leukemia (AML), acute lymphoblastic leukemia (ALL), acute lymphocytic leukemia, lymphocytic lymphoma, mycosis fungoides, chronic lymphogenous leukemia, chronic lymphocytic leukemia (CLL), mantle cell lymphoma, diffuse large B-cell lymphoma, follicular lymphoma, Hodgkin's lymphoma, non-Hodgkin's lymphoma or myelofibrosis.

Examples of cancer treatable according to the methods described herein include, but are not limited to, adenocarcinoma of the breast, prostate, and colon; all forms of bronchogenic carcinoma of the lung; myeloid; melanoma (e.g., metastatic melanoma); astrocytoma (e.g., anaplastic astrocytoma); hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, lung cancer (e.g., large cell lung cancer, such as squamous cell carcinoma, non-small cell lung cancer (NSCLC)), oat cell, papillary, scirrhous, bronchiolar, bronchogenic, squamous cell, and transitional cell). Additional examples of cancer treatable according to the methods described herein include, but are not limited to, histiocytic disorders; leukemia; histiocytosis malignant; Hodgkin's disease; hypereosinophilia, immunoproliferative small; non-Hodgkin's lymphoma; plasmacytoma; reticuloendotheliosis; melanoma (e.g., metastatic melanoma); chondroblastoma; chondroma; chondrosarcoma; fibrotic cancer (e.g., myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans); hepatocellular carcinoma; fibroma; fibrosarcoma; giant cell tumors; histiocytoma; lipoma; liposarcoma; mesothelioma; myxoma; myxosarcoma; osteoma; osteosarcoma; pediatric malignancy, chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatocellular cancer, hepatoma; hidradenoma; islet cell tumor; Leydig cell tumor; papilloma; sertoli cell tumor; theca cell tumor; leiomyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. Yet more examples of cancer treatable according to the methods described herein include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In certain embodiments, provided herein are methods of treating cancer comprising administering to a subject in need thereof a therapeutically effective amount of a compound as described herein. In certain embodiments, provided herein are methods of treating esophagogastric cancer, breast cancer, peritoneal cancer, salivary gland cancer, bladder cancer, endometrial cancer, ampullary cancer, small bowel cancer, vaginal cancer, cervical cancer, hepatobillary cancer, ovarian cancer, colorectal cancer, NSCLC, head and neck cancer, pancreatic cancer, skin cancer, appendiceal cancer, B-lymphoblastic leukemia/lymphoma, melanoma, germ cell tumor, small cell lung cancer, mature B-cell neoplasms, prostate cancer, soft tissue sarcoma, or glioma, comprising administering to a subject in need thereof a therapeutically effective amount of a compound as described herein. In certain embodiments, the cancer is breast cancer. In certain embodiments, the cancer is lung cancer. In certain embodiments, the cancer is NSCLC.

HPV-associated cancers are also treatable according to the methods described herein. Non-limiting examples of HPV-associated cancers include cervical cancer, oropharyngeal cancer, anal cancer, vulvar/vaginal cancer, and penile cancer.

Liver cancers, such as hepatocellular cancer (HCC) (e.g., hepatocellular carcinoma, hepatoblastoma, hepatocellular adenoma), malignant hepatoma, hemangiomas and biliary cancer (e.g., cholangiocarcinoma), are also treatable according to the methods described herein.

Musculoskeletal cancers are also treatable according to the methods described herein. Non-limiting examples of musculoskeletal cancers include bone cancer (e.g., osteosarcoma, osteoid osteoma, malignant fibrous histiocytoma, Ewing's sarcoma, chordoma, malignant giant cell tumor chordoma, chondrosarcoma osteochondroma, benign chondroma, chondroblastoma chondromyxofibroma, myelodysplastic syndrome (MDS)), muscle cancer (e.g., rhabdomyosarcoma, rhabdomyoma), connective tissue cancer and synovioma.

Nervous system cancers are also treatable according to the methods described herein. Non-limiting examples of nervous system cancers include brain cancer (e.g., astrocytoma, medulloblastoma, glioma (e.g., astrocytoma, oligodendroglioma), glioblastomas, glioblastoma multiform, medulloblastoma, ependymoma, germinoma (i.e., pinealoma), oligodendroglioma, schwannoma, retinoblastoma, congenital tumors, craniopharyngioma), spinal cord cancer, neurofibroma (e.g., neurofibromatosis (NF) type 1 or type 2, schwannomatosis), neuroblastoma, primitive neuroectodermal tumors (PNT), meningeal cancer (e.g., meningioma, meningiosarcoma, gliomatosis), skull cancer, acoustic neuroma, ependymoma, hemangioblastoma, ocular cancer (e.g., intraocular melanoma, retinoblastoma), pleomorphic xenoanthrocytoma (PXA) and pediatric PXA.

Endocrine/exocrine cancers are also treatable according to the methods described herein. Non-limiting examples of endocrine/exocrine cancers include thyroid cancer (e.g., papillary thyroid carcinoma, follicular thyroid carcinoma, medullary thyroid carcinoma, multiple endocrine neoplasia type 2A, multiple endocrine neoplasia type 2B, familial medullary thyroid cancer, pheochromocytoma, paraganglioma), pancreatic cancer (e.g., pancreatic adenocarcinoma, intraductal papillary mucinous neoplasm (IPMN), islet cell tumors, ductal adenocarcinoma, insulinoma, glucagonoma, vipoma), adrenal gland cancer, neuroendocrine cancer (e.g., gastroenteropancreatic neuroendoctrine tumor (GEP-NET), carcinoid tumor), sebaceous gland carcinoma and sweat gland cancer (e.g., sweat gland carcinoma).

Head and neck cancers, such as squamous cell carcinoma of the head and neck (SCCHN) and adenoid cystic carcinoma, are also treatable according to the methods described herein.

Oral cancers, such as buccal cavity cancer, lip cancer, tongue cancer, mouth cancer, pharynx cancer, hypopharynx cancer (e.g., hypopharyngeal carcinoma), throat cancer (e.g., laryngeal cancer, pharyngeal cancer, nasopharyngeal cancer, oropharyngeal cancer) and salivary gland cancer, are also treatable according to the methods described herein.

Esophageal cancers, such as esophageal squamous cell carcinoma, esophageal adenocarcinoma, Barrett's adenocarcinoma and esophageal leiomyosarcoma, are also treatable according to the methods described herein.

Gastrointestinal cancers are also treatable according to the methods described herein.

Non-limiting examples of gastrointestinal cancers include anal cancer, colorectal cancer (e.g., colon cancer, rectal cancer, colorectal adenocarcinoma), gall bladder cancer, gastric cancer (e.g., stomach cancer (e.g., stomach adenocarcinoma)), gastrointestinal stromal tumor (GIST), small bowel cancer (e.g., appendix cancer, small bowel carcinoma, e.g., small bowel adenocarcinoma), small intestine cancer, large bowel cancer and large intestine cancer.

Cardiovascular cancers are also treatable according to the methods described herein. Non-limiting examples of cardiovascular cancers include primary cardiac tumors, angiosarcoma (e.g., lymphangiosarcoma, lymphangioendotheliosarcoma, hemangiosarcoma), endotheliosarcoma (e.g., Kaposi's sarcoma, multiple idiopathic hemorrhagic sarcoma), cardiac myxoma and cardiac rhabdomyoma.

Lung cancers are also treatable according to the methods described herein. Non-limiting examples of lung cancers include bronchus cancer (e.g., bronchogenic carcinoma, bronchial adenoma), alveolar carcinoma, mesothelioma, small cell lung cancer (SCLC), non-small cell lung cancer (NSCLC), lung adenocarcinoma, chondromatous hamartoma and papillary adenocarcinoma.

Genitourinary cancers are also treatable according to the methods described herein. Non-limiting examples of genitourinary cancers include bladder cancer (e.g., urothelial carcinoma), urethral cancer, kidney cancer (e.g., nephroblastoma a.k.a. Wilms' tumor, renal cell carcinoma), testicular cancer (e.g., seminoma, testicular embryonal carcinoma), germ cell cancer, prostate cancer (e.g., prostate adenocarcinoma) and penile cancer (e.g., Paget's disease of the penis and scrotum).

Gynecological cancers are also treatable according to the methods described herein. Non-limiting examples of gynecological cancers include breast cancer (e.g., adenocarcinoma of the breast, papillary carcinoma of the breast, mammary cancer, medullary carcinoma of the breast, triple negative breast cancer, HER-2 positive breast cancer, HER2-negative breast cancer), endometrial cancer (e.g., uterine cancer (e.g., uterine sarcoma, choriocarcinoma), endometrial carcinoma), cervical cancer (e.g., cervical adenocarcinoma), ovarian cancer (e.g., cystadenocarcinoma, ovarian embryonal carcinoma, ovarian adenocarcinoma), germ cell cancer and vulvar cancer (e.g., Paget's disease of the vulva), vaginal cancer and fallopian tube cancer.

Skin cancers are also treatable according to the methods described herein. Non-limiting examples of skin cancers include squamous cell carcinoma (SCC), keratoacanthoma (KA), melanoma, basal cell carcinoma (BCC) and dermatofibroma.

Soft tissue cancers, such as intraepithelial neoplasms, epithelial carcinomas, epithelial sarcomas, adenocarcinomas, adenomas, fibrosarcomas, fibromas, liposarcomas, lipomas, myxomas and teratomas, are also treatable according to the methods described herein.

Myeloproliferative neoplasms are also treatable according to the methods described herein. Non-limiting examples of myeloproliferative neoplasms include myelofibrosis, polycythemia vera and essential thrombocythemia.

Fibrotic cancers are also treatable according to the methods described herein. As used herein, a "fibrotic cancer" is a cancer associated with fibrosis. Fibrosis may precede (e.g., be causative of) or follow (e.g., be caused by) the cancer or treatment of the cancer in fibrotic cancers. Fibrosis may also or alternatively be present with the cancer in fibrotic cancers. Non-limiting examples of fibrotic cancers include myelofibrosis, pancreatic cancer (e.g., pancreatic ductal adenocarcinoma), kidney cancer, liver cancer, lung cancer (e.g., large cell lung cancer, such as squamous cell carcinoma), breast cancer (e.g., inflammatory breast cancer), ovarian cancer (e.g., high grade serious ovarian carcinoma), endometrial cancer, uterine cancer, uterine sarcoma (e.g., uterine leiomyosarcoma), renal cell cancer, sarcoma (e.g., soft tissue sarcoma), malignant fibrous histiocytoma, fibrosarcoma (e.g., dermatofibrosarcoma protuberans), gastric cancer, esophageal cancer, head and neck cancer, cervical cancer, vulvar cancer and hepatocellular cancer (e.g., hepatocellular carcinoma). In some embodiments, the fibrotic cancer is a solid tumor cancer (e.g., kidney, liver, lung, breast, ovarian, endometrial, uterine, and/or pancreatic cancer). In some embodiments, the fibrotic cancer is carcinoma of an internal organ (e.g., pancreas, lung, kidney, liver).

Further examples of cancers treatable according to the methods described herein include, but are not limited to, Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Cancer of the anal region; Anal Cancer; Appendix Cancer; Astrocytomas, Childhood; Atypical Teratoid/Rhabdoid Tumor, Childhood, Central Nervous System (CNS); Neoplasms of the CNS (e.g., primary CNS lymphoma, spinal axis tumors, medulloblastoma, brain stem gliomas or pituitary adenomas), Barrett's esophagus (e.g., pre-malignant syndrome), and mycoses fungoides, Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Cancer of the Endocrine system (e.g., cancer of the thyroid, pancreas, parathyroid or adrenal glands), Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Gynecologic Tumors ((e.g., uterine sarcomas, carcinoma of the fallopian tubes, carcinoma of the endometrium, carcinoma of the cervix, carcinoma of the vagina or carcinoma of the vulva), Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Cutaneous or Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis (e.g., renal cell carcinoma, carcinoma of the renal pelvis), benign prostatic hypertrophy, parathyroid cancer, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. Accordingly, in some embodiments, the cancer is a metastatic cancer. In other embodiments, the cancer is a pre-metastatic cancer.

In certain embodiments, the cancer is a rare cancer. The term "rare cancer" refers to cancers that occur in a relatively small number of patients.

In some embodiments, a proliferative disease, such as cancer (e.g., a fibrotic cancer), is treated by targeting a tumor stromal cell (e.g., in a tumor microenvironment), such as a cancer-associated fibroblast (CAF), stellate cell or myofibroblast, and/or an immune cell, such as a tumor-associated immune cell (e.g., in the tumor-immune microenvironment), for example, to thereby modulate the tumor-stroma microenvironment and/or the tumor-immune microenvironment.

Also provided herein are methods for targeting a tumor stromal cell or immune cell (e.g., tumor-associated immune cell), and/or (e.g., and thereby) modulating (e.g., normalizing) tumor microenvironment (e.g., tumor-stroma microenvironment and/or tumor-immune microenvironment) in vivo or in vitro, the methods comprising contacting a tumor stromal cell or an immune cell (e.g., a tumor-associated immune cell) with a compound of the present disclosure. In certain embodiments, the inhibition occurs in vivo in a subject. In certain embodiments, the inhibition occurs in vitro (e.g., in a cell line, tissue or biological sample). In certain embodiments, the tumor stromal cell is a cancer-associated fibroblast (CAF), a stellate cell or a myofibroblast.

Without wishing to be bound by any particular theory, it is believed that certain compounds can normalize the tumor microenvironment and thereby improve blood vessel perfusion and drug delivery. Enhanced drug delivery is expected, in turn, to enhance the efficacy of a drug, such as an immunomodulator (e.g., immunooncology agent), including any immunomodulator described herein. Accordingly, also provided herein are methods for modulating (e.g., normalizing) tumor microenvironment (e.g., tumor-stroma microenvironment and/or tumor-immune microenvironment) in vivo or in vitro, the methods comprising contacting a tumor with a compound of the present disclosure.

Also provided herein are methods of inhibiting viral infection and/or viral replication in a subject in need thereof, comprising administering to the subject an effective amount (e.g., a therapeutically effective amount, prophylactically effective amount) of a compound of the present disclosure.

The compounds of the present disclosure can be administered as a monotherapy, or can be administered as part of a combination therapy, as described herein, with other therapeutic agents and/or treatment modalities. Accordingly, in some embodiments, the methods described herein further comprise administering to the subject one or more additional therapies (e.g., one or more additional therapeutic agents). The compound of the present disclosure and the additional therapy(ies) can be co-administered, e.g., in a simultaneous or substantially simultaneous manner. The compound of the present disclosure and the additional therapy(ies) can also or alternatively be administered sequentially, either at approximately the same time or at different times. For example, the compound of the present disclosure can be administered before the additional therapy(ies). Or, the compound of the present disclosure can be administered after the additional therapy(ies). Suitable additional therapies for use in the methods disclosed herein include those discussed herein in the context of combinations.

Therapeutic agents (e.g., compounds of the present disclosure) and pharmaceutical compositions thereof can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen. In some embodiments, a therapeutic agent (e.g., a compound of the present disclosure) is administered orally. In some embodiments, a therapeutic agent (e.g., compound of the present disclosure) is administered intravenously.

Combination Therapies

The term "combination therapy" refers to the administration of two or more therapeutic agents to treat a disease, disorder or condition described herein. Such administration encompasses co-administration of the therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Such administration also encompasses use of each type of therapeutic agent in a sequential manner, either at approximately the same time or at different times. The therapeutic agents in a combination therapy can be administered via the same administration route or via different administration routes. Powders and/or liquids may be reconstituted or diluted to a desired dose prior to administration. Typically, the treatment regimen will provide beneficial effects of the drug combination in treating the diseases, conditions or disorders described herein.

A therapy for use in combination with a compound of the present disclosure can comprise an agent known to modulate other pathway(s) than is(are) modulated by the compound of the present disclosure, other component(s) (e.g., enzymes) of the same pathway(s) as is(are) modulated by the compound of the present disclosure or even one or more of the same targets (e.g., target enzyme(s)) as is(are) modulated by the compound of the present disclosure. In one aspect, a combination therapy comprises a compound of the present disclosure and a chemotherapeutic agent, immunomodulator and/or radiation therapy, for example, to provide a synergistic or additive therapeutic effect.

Examples of therapies for use in combination with a compound of the present disclosure (e.g., in combination therapy, in a pharmaceutical combination) include standard of care therapies and/or regimens (e.g., standard of care agents), such as first-line standard of care therapies (e.g., chemotherapies), intermediate-line standard of care therapies (e.g., chemotherapies) or last-line standard of care therapies (e.g., chemotherapies). Standard of care therapies are therapies that a clinician should use for a certain type of patient, illness and/or clinical circumstance. Often, organizations such as National Comprehensive Cancer Network (NCCN) publish guidelines and/or treatment algorithms setting forth best practices for treatment of certain patients, illnesses and/or clinical circumstances. See nccn.org. These guidelines often establish, set forth and/or summarize standard of care therapies.

In some embodiments, the method of treating or preventing cancer may comprise administering a compound of Formula (I), (I-i), (I-i-a), (I-i-a1), (I-i-a2), (a-I), (II), or (III), or any of the embodiments thereof disclosed herein with one or more other chemotherapeutic agent(s).

In some embodiments, one or more immunomodulators can be used in combination with compounds of the present disclosure. Non-limiting examples of immunomodulators (e.g., immunooncology agents) include afutuzumab (available from ROCHE®); pegfilgrastim (NEULASTA®); lenalidomide (CC-5013, REVLIMID®); thalidomide (THALOMID®); actimid (CC4047); and IRX-2 (mixture of human cytokines including interleukin 1, interleukin 2, and interferon γ, CAS 951209-71-5, available from IRX Therapeutics).

In certain embodiments, the immunomodulators are chimeric antigen receptor T-cell (CAR-T) therapies, such as tisagenlecleucel (Novartis), axicabtagene ciloleucel (Kite), and tocilizumab (atlizumab; Roche).

In certain embodiments, the immunomodulators are immune checkpoint inhibitors, such as PD-1 inhibitors, PD-L1 inhibitors, cytotoxic T-lymphocyte-associated modulators (e.g., CTLA-4 inhibitors), LAG-3 inhibitors, TIM-3 inhibitors.

In certain embodiments, the immunomodulators are PD-1 inhibitors, such as pembrolizumab (also known as Lambrolizumab, MK-3475, MK03475, SCH-900475, or KEYTRUDA®) and other anti-PD-1 antibodies (as disclosed in Hamid, O. et al. (2013) New England Journal of Medicine 369 (2): 134-44, U.S. Pat. No. 8,354,509, and WO 2009/114335, incorporated by reference in their entirety), nivolumab (also known as MDX-1106, MDX-1106-04, ONO-4538, BMS-936558, or OPDIVO®) and other anti-PD-1 antibodies (as disclosed in U.S. Pat. No. 8,008,449 and WO 2006/121168, incorporated by reference in their entirety), cemiplimab (LIBTAYO®), sintilimab, spartalizumab (PDR001), pidilizumab (CureTech), MEDI0680 (Medimmune), dostarlimab (TSR-042), PF-06801591 (Pfizer), sintilimab, toripalimab, tislelizumab (BGB-A317), camrelizumab (INCSHR1210, SHR-1210), AMP-224 (Amplimmune), CBT-501 (CBT Pharmaceuticals), CBT-502 (CBT Pharmaceuticals), JS001 (Junshi Biosciences), IBI308 (Innovent Biologics), INCSHR1210 (Incyte), also known as SHR-1210 (Hengrui Medicine), BGBA317 (Beigene), BGB-108 (Beigene), BAT-I306 (Bio-Thera Solutions), GLS-010 (Gloria Pharmaceuticals; WuXi Biologics), AK103, AK104, AK105 (Akesio Biopharma; Hangzhou Hansi Biologics; Hanzhong Biologics), LZM009 (Livzon), HLX-10 (Henlius Biotech), MEDI0680 (Medimmune), PDF001 (Novartis), PF-06801591 (Pfizer), pidilizumab (CureTech) also known as CT-011 and other anti-PD-1 antibodies (as disclosed in Rosenblatt, J. et al. (2011) J Immunotherapy 34(5): 409-18, U.S. Pat. Nos. 7,695,715, 7,332,582, and 8,686,119, incorporated by reference in their entirety), REGN2810 (Regeneron) and TSR-042 (Tesaro), also known as ANB011, or CS1003 (CStone Pharmaceuticals). MEDI0680 (Medimmune), is also known as AMP-514. MEDI0680 and other anti-PD-1 antibodies are disclosed in U.S. Pat. No. 9,205,148 and WO 2012/145493, incorporated by reference in their entireties. Further known anti-PD-1 antibody molecules include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entireties. In one embodiment, the PD-1 inhibitor is an anti-PD-1 antibody molecule, as described in US 2015/0210769, published on Jul. 30, 2015, entitled "Antibody Molecules to PD-1 and Uses Thereof," incorporated by reference in its entirety. In one embodiment, the anti-PD-1 antibody molecule comprises the CDRs, variable regions, heavy chains and/or light chains of BAP049-Clone-E or BAP049-Clone-B disclosed in US 2015/0210769. The antibody molecules described herein can be made by vectors, host cells, and methods described in US 2015/0210769, incorporated by reference in its entirety. In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)). In one embodiment, the PD-1 inhibitor is AMP-224 (B7-DCIg (Amplimmune), e.g., disclosed in WO 2010/027827 and WO 2011/066342, incorporated by reference in their entireties).

In certain embodiments, the immunomodulators are PD-L1 inhibitors, such as atezolizumab (also known as MPDL3280A, RG7446, RO5541267, YW243.55.570, or TECENTRIQ®) and other anti-PD-L1 antibodies as disclosed in U.S. Pat. No. 8,217,149, incorporated by reference in its entirety, avelumab (BAVENCIO® also known as MSB0010718C) and other anti-PD-L1 antibodies as disclosed in WO 2013/079174, incorporated by reference in its entirety, durvalumab (IMIINZI® or MEDI4736) and other anti-PD-L1 antibodies as disclosed in U.S. Pat. No. 8,779,108, incorporated by reference in its entirety), FAZ053 (Novartis), and BMS-936559 (Bristol-Myers Squibb). In certain embodiments, the PD-L1 inhibitor is KN035 (Alphamab; 3DMed; Ascletis Pharma), Envafolimab (TRACON Pharmaceuticals), BMS 936559 (Bristol-Myers Squibb), CS1001 (CStone Pharmaceuticals, Ligand Pharmaceuticals), CX-072 (CytomX Therapeutics), FAZ053 (Novartis), SHR-1316 (Hengrui Medicine), TQB2450 (Chiatai Tianqing), STI-A1014 (Zhaoke Pharm; Lee's Pharm, Lonza, Sorrento Therapeutics, NantWorks), LYN00102 (Lynkcell), A167 (Harbour BioMed, Kelun Group), BGB-A333 (Beigene), MSB2311 (Mabspace Biosciences), or HLX-20 (Henlius Biotech). In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entireties. In certain embodiments, the PD-L1 inhibitor is cosibelimab (Fortress Biotech), LY3300054 or iodapolimab (Eli Lilly), GS-4224 (Gilead Sciences), STI-A1015 (Yuhan, Sorrento Therapeutics), BCD-135 (BIOCAD), cosibelimab (Dana-Farber Cancer Institute, TG Therapeutics), APL-502 (Apollomics), AK106 (Akeso Biopharma), MSB2311 (Transcenta Holding), TG-1501 (TG Therapeutics) or FAZ053 (Novartis). In certain embodiments, the PD-L1 inhibitor is MT-6035 (Molecular Templates), icaritin or ZKAB001 (Lonza, Lee's Pharmaceutical Holdings, Sorrento Therapeutics, Shenogen Pharma Group), TRIDENT Antibody (MacroGenics, Zai Lab), YBL-007 (Anh-Gook Pharmaceutical, Y-Biologics), HTI-1316 (Hengrui Therapeutics), PD-L1 Oncology Project (Weizmann Institute of Sciences), JS003 (Shanghai Junshi Biosciences), ND021 (Numab Therapeutics, CStone Pharmaceuticals), Toca 521 (Tocagen) or STTO1 (STCube). In certain embodiments, the PD-L1 inhibitor is DB004 (DotBio), MT-5050 (Molecular Templates), KD036 (Kadmon). In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety. In one embodiment, the anti-PD-L1 antibody molecule comprises the CDRs, variable regions, heavy chains and/or light chains of BAP058-Clone O or BAP058-Clone N disclosed in US 2016/0108123, incorporated by reference in its entirety. Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, incorporated by reference in their entireties.

In certain embodiments, the immunomodulators are CTLA-4 inhibitors, such as ipilimumab (YERVOY®), tremelimumab, ALPN-202 (Alpine Immune Sciences), RP2 (Replimune), BMS-986249 (Bristol-Myers Squibb), BMS-986218 (Bristol-Myers Squibb), zalifrelimab (Agenus, Ludwig Institute for Cancer Research, UroGen Pharma, Recepta Biopharma), BCD-217 (BIOCAD), Onc-392 (Pfizer, OncoImmune), IBI310 (Innovent Biologics), KN046 (Alphamab), MK-1308 (Merck & Co), REGN4659 (Regeneron Pharmaceuticals), XmAb20717 (Xencor), XmAb22841 (Xencor), Anti-CTLA-4 NF (Bristol-Myers Squibb), MEDI5752 (AstraZeneca), AGEN1181 (Agenus), MGD019 (MacroGenics), ATOR-1015 (Alligator Bioscience), BCD-145 (BIOCAD), PSB205 (Sound Biologics), CS1002 (CStone Pharmaceuticals), ADU-1604 (Aduro Biotech), PF-06753512 (Pfizer), BioInvent-Transgene Research Program (Transgene), AGEN2041 (Agenus, Recepta Biopharam), ATOR-1144 (Alligator Bioscience), CTLA-4 Research Project (Sorrento Therapeutics), PD-L1/CTLA-4 Research Project (Sorrento Therapeutics), HLX13 (Shanghai Henlius Biotech), ISA203 (ISA Pharmaceuticals), PRS-300 Series A (*Pieris* Pharmaceuticals), BA3071 (BioAtla), CTLA4 Cancer Research Program (Biosortia Pharmaceuticals), RP3 (Replimune), CGO161 (Cold Genesys), APL-509 (Apollomics, JSR), AGEN2041 (Ludwig Institute for Cancer Research), APC 101 (Advanced Proteome), CTLA-4 Inhibitor (Advanced Proteome), BA3071 (BeiGene), BPI-002 (BeyondSpring Pharmaceuticals), CTLA-4 Antibody (Tikcro Technologies), Immuno-Oncology Research Program II (OliPass), PBP1701 (Prestige BioPharma), DB002 (DotBio), DB003 (DotBio), OR-2299 (OncoResponse) and NK044 (Alphamab).

In some embodiments, the immunodulators are LAG-3 inhibitors, such as LAG525 (Novartis), BMS-986016 (Bristol-Myers Squibb), and TSR-033 (Tesaro). In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety. In one embodiment, the anti-LAG-3 antibody molecule comprises the CDRs, variable regions, heavy chains and/or light chains of BAP050-Clone I or BAP050-Clone J disclosed in US 2015/0259420. In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entireties. In one embodiment, the anti-LAG-3 antibody molecule is TSR-033 (Tesaro). In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entireties. In one embodiment, the anti-LAG-3 antibody molecule is IMP761 (Prima BioMed). Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entireties. In one embodiment, the anti-LAG-3 inhibitor is a soluble LAG-3 protein, e.g., IMP321 (Prima BioMed), e.g., as disclosed in WO 2009/044273, incorporated by reference in its entirety.

In some embodiments, the immunodulators are TIM-3 inhibitors, such as MGB453 (Novartis) and TSR-022 (Tesaro). In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety. In one embodiment, the anti-TIM-3 antibody molecule comprises the CDRs, variable regions, heavy chains and/or light chains of ABTIM3-hum11 or ABTIM3-hum03 disclosed in US 2015/0218274, incorporated by reference in its entirety. In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121. APE5137, APE5121, and other anti-TIM-3 antibodies are disclosed in WO 2016/161270, incorporated by reference in its entirety. In one embodiment, the anti-TIM-3 antibody molecule is the antibody clone F38-2E2. Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entireties.

In some embodiments, a platinum analogue can be used in combination with compounds of the present disclosure. In certain embodiments, a platinum analogue (e.g., cisplatin, paclitaxel, carboplatin) and combination therapy comprising a platinum analogue (e.g., docetaxel and carboplatin; paclitaxel and carboplatin; carboplatin and liposomal doxorubicin (dox) can be used in combination with compounds of the present disclosure.

In some embodiments, exemplified chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9,10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9,10-dioxo-9,10-dihydroanthracene-2-sulfonate, 1-amino-4-[2-anthracenylamino]-9,10-dioxo-9,10-dihydroanthracene-2-sulfonate, ABT-263, ado-trastuzumab emtansine, afatinib dimaleate, axitinib, aminoglutethimide, amsacrine, anastrozole, APCP, asparaginase, AZD5363, Bacillus Calmette-Guerin vaccine (bcg), bicalutamide, bleomycin, bortezomib, β-methylene-ADP (AOPCP), buserelin, busulfan, cabazitaxel, cabozantinib, campothecin, capecitabine, carboplatin, carfilzomib, carmustine, ceritinib, chlorambucil, chloroquine, cisplatin, cladribine, clodronate, cobimetinib, colchicine, crizotinib, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, eribulin, erlotinib, estradiol, estramustine, etoposide, everolimus, exemestane, fam-trastuzumab deruxtecan, filgrastim, fludarabine, fludrocortisone, fluorouracil, fluoxymesterone, flutamide, gefitinib, gemcitabine, genistein, goserelin, GSK1120212, hydroxyurea, idarubicin, ifosfamide, imatinib, interferon, irinotecan, ixabepilone, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, mutamycin, N-(4-sulfamoylphenylcarbamothioyl) pivalamide, NF279, NF449, nilutamide, nocodazole, octreotide, olaparib, oxaliplatin, paclitaxel, pamidronate, pazopanib, pemexetred, pentostatin, perifosine, PF-04691502, plicamycin, pomalidomide, porfimer, PPADS, procarbazine, quercetin, raltitrexed, ramucirumab, reactive blue 2, rituximab, rolofylline, romidepsin, rucaparib, selumetinib, sirolimus, sodium 2,4-dinitrobenzenesulfonate, sorafenib, streptozocin, sunitinib, suramin, talazoparib, tamoxifen, temozolomide, temsirolimus, teniposide, testosterone, thalidomide, thioguanine, thiotepa, titanocene dichloride, tonapofylline, topotecan, trametinib, trastuzumab, tretinoin, veliparib, vinblastine, vincristine, vindesine, vinorelbine, and vorinostat (SAHA). In other embodiments, chemotherapeutic agents that may be conjointly administered with compounds of the disclosure include: ABT-263, dexamethasone, 5-fluorouracil, PF-04691502, romidepsin, and vorinostat (SAHA). In other embodiments, chemotherapeutic agents that may be conjointly administered with compounds of the disclosure include: 1-amino-4-phenylamino-9,10-dioxo-9,10-dihydroanthracene-2-sulfonate (acid blue 25), 1-amino-4-[4-hydroxyphenyl-amino]-9,10-dioxo-9,10-dihydroanthracene-2-sulfonate, 1-amino-4-[4-aminophenylamino]-9,10-dioxo-9, 10-dihydroanthracene-2-sulfonate, 1-amino-4-[1-naphthylamino]-9,10-dioxo-9,10-dihydroanthracene-2-sulfonate, 1-amino-4-[4-fluoro-2-carboxyphenylamino]-9, 10-dioxo-9,10-dihydroanthracene-2-sulfonate, 1-amino-4-[2-anthracenylamino]-9,10-dioxo-9,10-dihydroanthracene-2-sulfonate, APCP, P-methylene-ADP (AOPCP), capecitabine, cladribine, cytarabine, fludarabine, doxorubicin, gemcitabine, N-(4-sulfamoylphenylcarbamothioyl) pivalamide, NF279, NF449, PPADS, quercetin, reactive blue 2, rolofylline sodium 2,4-dinitrobenzenesulfonate, sumarin, and tonapofylline.

Many combination therapies have been developed for the treatment of cancer. In certain embodiments, compounds of the disclosure (e.g., compounds of Formula (I)) or (II) or (III) may be conjointly administered with one or more combination therapies. Examples of combination therapies with which compounds of the disclosure may be conjointly administered are included in

TABLE 1

| \multicolumn{2}{c}{Exemplary combinatorial therapies for the treatment of cancer} | |
|---|---|
| Name | Therapeutic agents |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |

TABLE 1-continued

Exemplary combinatorial therapies for the treatment of cancer

| Name | Therapeutic agents |
|---|---|
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |

TABLE 1-continued

Exemplary combinatorial therapies for the treatment of cancer

| Name | Therapeutic agents |
| --- | --- |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PCV | Lomustine, Procarbazine, Vincristine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, the conjoint therapies of the disclosure comprise conjoint administration with other types of chemotherapeutic agents, such as immuno-oncology agents. Cancer cells often have specific cell surface antigens that can be recognized by the immune system. Thus, immuno-oncology agents, such as monoclonal antibodies, can selectively bind to cancer cell antigens and effect cell death. Other immuno-oncology agents can suppress tumor-mediated inhibition of the native immune response or otherwise activate the immune response and thus facilitate recognition of the tumor by the immune system. Exemplary antibody immuno-oncology agents, include, but are not limited to, abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab. In some embodiments, the antibody immuno-oncology agents are selected from anti-CD73 monoclonal antibody (mAb), anti-CD39 mAb, anti-PD-1 mAb, and anti-CTLA4 mAb. Thus, in some embodiments, the methods of the disclosure comprise conjoint administration of one or more immuno-oncology agents, such as the agents mentioned above.

In some embodiments, the combination therapy comprises conjoint administration of a compound of the disclosure, such as a compound of Formula (I) or (II) or (III), with SH2 inhibitors, such as CGP78850, CPG85793, C90, C126, G7-18NATE, G7-B1, and NSC642056.

In some embodiments, the combination therapy comprises conjoint administration of a compound of the disclosure, such as a compound of Formula (I) or (II) or (III), with MEK inhibitors, such as trametinib, cobimetinib, binimetinib, selumetinib, PD-325901, CI-1040, and TAK-733.

In some embodiments, the combination therapy comprises conjoint administration of a compound of the disclosure, such as a compound of Formula (I) or (II) or (III), with a MET inhibitor selected from JNJ-38877605, PF-04217903, foretinib, AMG 458, tivantinib, cabozantinib, capmatinib hydrochloride, tepotinib hydrochloride, savolitinib, and crizotinib.

In some embodiments, the combination therapy comprises conjoint administration of a compound of the disclosure, such as Formula (I) or (II) or (III), with a SHP2 inhibitor selected from TNO-155, RMC-4630, JAB-3068, or RLY-1971.

In some embodiments, an ataxia-telangiectasia mutated (ATM) kinase inhibitor can be used in combination with compounds of the present disclosure. Non-limiting examples of ATM inhibitors include M-4076 and AZD-1390.

In some embodiments, the combination therapy comprises conjoint administration of a compound of the disclosure with an EGFR inhibitor selected from osimertinib, gefitinib, erlotinib, afatinib or dacomitinib.

In some embodiments, the combination therapy comprises conjoint administration of a compound of the disclosure with a RAS inhibitor selected from aliskiren, captopril, losartan, irbesartan, olmesartan, candesartan, valsartan, fimasartan, azilsartan, telmisartan, eprosartan, benazepril, enalapril, lisinopril, perindopril, quinapril, ramipril, and trandolapril.

In some embodiments, the combination therapy comprises conjoint administration of a compound of the disclosure with anti-PD-1 therapy. In certain embodiments, the combination therapy comprises conjoint administration of a compound of the disclosure with oxaliplatin. In other embodiments, the combination therapy comprises conjoint administration of a compound of the disclosure with doxorubicin.

In certain embodiments, a compound of the disclosure may be conjointly administered with non-chemical methods of cancer treatment. In certain embodiments, a compound of the disclosure may be conjointly administered with radiation therapy. In certain embodiments, a compound of the disclosure may be conjointly administered with surgery, with thermoablation, with focused ultrasound therapy, with cryotherapy, or with any combination of these.

In certain instances, it may be advantageous to administer a compound of the present disclosure in combination with one or more additional therapeutic agent(s). For example, it may be advantageous to administer a compound of the present disclosure (e.g., a compound of Formula I, or a subformula thereof, or a pharmaceutically acceptable salt of the foregoing) in combination with one or more additional therapeutic agents, e.g., independently selected from an anti-cancer agent (e.g., chemotherapeutic agent), anti-allergic agent, anti-emetic, pain reliever, immunomodulator and cytoprotective agent, to treat cancer.

In some embodiments, a compound of the present disclosure is administered in combination with radiation therapy. Non-limiting examples of radiation therapy include external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At211, I131, I125, Y90, Re186, Re188, Sm153, Bi212, P32, and radioactive isotopes of Lu). Suitable radiation sources for use as a cell conditioner include both solids and liquids. By way of non-limiting example, the radiation source can be a radionuclide, such as I125, I131, Yb169, Ir192 as a solid source, I125 as a solid source, or other radionuclides that emit photons, beta particles, gamma radiation, or other therapeutic rays. The radioactive material can also be a fluid made from any solution of radionuclide(s), e.g., a solution of I125 or I131, or a radioactive fluid can be produced using a slurry of a suitable fluid containing small particles of solid radionuclides, such as Au198, Y90. Moreover, the radionuclide(s) can be embodied in a gel or radioactive microspheres.

Compounds of the present disclosure may be effective in sensitizing abnormal cells to radiation therapy. Thus, also provided herein is a method for sensitizing abnormal cells in a subject (e.g., subject in need thereof) to treatment with radiation, comprising administering to the subject an amount of a compound of the present disclosure effective to sensitize abnormal cells to treatment with radiation. The amount of a compound of the present disclosure effective to sensitize abnormal cells to treatment with radiation can be determined by a person of ordinary skill in the art, for example, according to the means for ascertaining effective amounts described herein.

In some embodiments, standard of care therapy includes radiation therapy. DNA damaging agents can also be used in combination with a compound of the present disclosure. As used herein, "DNA damaging agent" refers to any agent that directly or indirectly damages DNA in such a way that homologous recombination could repair the damage. Non-limiting examples of DNA damaging agents are DNA damaging chemicals, chemotherapeutic agents, radiochemotherapy and ionizing or ultraviolet radiation. Non-limiting examples of DNA damaging chemotherapeutic agents include alkylating agents, nitrosoureas, anti-metabolites, plant alkaloids, plant extracts and radioisotopes. Non-limiting examples of DNA damaging chemotherapeutic agents also include DNA-damaging drugs, for example, 5-fluorouracil (5-FU), capecitabine, gemcitabine, temozolomide, S-1 (Tegafur, 5-chloro-2,4-dihydroxypyridine and oxonic acid), 5-ethynyluracil, arabinosylcytosine (ara-C), 5-azacytidine (5-AC), 2',2'-difluoro-2'-deoxycytidine (dFdC), purine antimetabolites (e.g., mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, rebeccamycin, anthracyclins such as doxorubicin (adriamycin; ADR), daunorubicin (Cerubicine), idarubicin (Idamycin) and epirubicin (Ellence), anthracyclin analogs such as mitoxantrone, actinomycin D, topoisomerase inhibitors (e.g., non-intercalating topoisomerase inhibitors such as epipodophyllotoxins (etoposide or VP16, teniposide or VM-26)), PARP inhibitors, podophylotoxin, bleomycin (Blea), pepleomycin, compounds that form adducts with nucleic acid including platinum derivatives, e.g., cisplatin (CDDP), trans analog of cisplatin, carboplatin, iproplatin, tetraplatin and oxaliplatin, as well as camptothecin, topotecan, irinotecan (CPT-11), and SN-38. Radiation, e.g., ultraviolet (UV), infrared (IR), or $\alpha$-, $\beta$-, or $\gamma$-radiation, is also a DNA damaging agent. In some embodiments, standard of care therapy includes a DNA damaging agent, such as a DNA crosslinking agent.

Agents that induce endoplasmic reticulum (ER) stress can also be used in combination with a compound of the present disclosure. Non-limiting examples of agents that induce ER stress include agents that increase levels of reactive oxygen species (ROS) (e.g., napabucasin), chaperone inhibitors, HSP90 inhibitors, HSP70 inhibitors, PDI inhibitors and proteasome inhibitors. Further non-limiting examples of agents that induce ER stress include GSK2606414, GSK2656157, STF-083010, TKI (e.g., sorafenib), phosphor-eif2a phosphatase (e.g., Sal003), diindolylmethane derivatives, proteasome inhibitors (e.g., bortezomib), levistolide A, andrographolide, tolfenamic acid, cantharidin, carnosic acid, casticin, cryptotanshinone, curcumin, flavokawain B, fucoidan, 2-3,4-dihydroxyphenylethanol, 7-dimethoxyflavone, SMIP004 (N-(4-butyl-2-methyl-phenylacetamide), licochalcone A, neferine, paeonol, pardaxin, parthenolide, piperine, polyphenon E, polyphyllin D, resveratrol, dehydrocostuslactone, $\gamma$-tocotrienol, $\Omega$-hydroxyundec-9-enoic acid, ampelopsin, ardisianone, genistein, guttiferone H, guggulsterone, marchantin M, sarsasapogenin, saxifragifolin, prodigiosin, quercetin, honokiol, brefeldin A, A-tocopheryl succinate, verrucarin A, vitamin E succinate, ultrafine and zerumbone. See, for example, Walczak, A., et al. *Oxidative Medicine and Cellular Longevity* Volume 2019, Article ID 5729710, the entire content of which is incorporated herein by reference.

Anti-cancer agents of particular interest for use in combination with the compounds of the present disclosure include:

Topoisomerase inhibitors, including Type I topoisomerase inhibitors, such as irinotecan, topotecan, and camptothecin, and Type 2 topoisomerase inhibitors, such as etoposide, doxorubicin, and epirubicin.

Poly(ADP-ribose) polymerase (PARP) inhibitors, such as olaparib, rucaparib, niraparib, talazoparib, veliparib, pamiparib and iniparib.

In some embodiments, a compound of the present disclosure is administered in combination with DNA crosslinking agents, such as cisplatin, carboplatin and oxaliplatin. Agents that increase levels of reactive oxygen species (ROS), such as napabucasin. PARP inhibitors, such as olaparib, rucaparib, niraparib, veliparib and talazoparib. Purine antimetabolites and/or inhibitors of de novo purine synthesis, such as pemetrexed (Alimta®), gemcitabine (Gemzar®), 5-fluorouracil (Adrucil®, Carac® and Efudex®), methotrexate (Trexall®), capecitabine (Xeloda®), floxuridine (FUDR®), decitabine (Dacogen®), azacitidine (Vidaza® and Azadine®), 6-mercaptopurine (Purinethol®), cladribine (Leustatin®, Litak® and Movectro®), fludarabine (Fludara®), pentostatin (Nipent®), nelarabine (Arranon®), clofarabine (Clolar® and Evoltra®), and cytarabine (Cytosar®). Anti-angiogenesis agents, such as matrix metalloproteinase (MMP) inhibitors (e.g., MMP-2 inhibitors, MMP-9 inhibitors), rapamycin, temsirolimus (CCI-779), everolimus (RAD001), sorafenib, sunitinib and bevacizumab, as well as COX-II inhibitors, such as CELEBREX™ (alecoxib), valdecoxib and rofecoxib. Examples of useful matrix metalloproteinase inhibitors are described in WO 96/33172 (published October 24,1996), WO 96/27583 (published March 7,1996), European Patent Application No. 97304971.1 (filed Jul. 8,1997), European Patent Application No. 99308617.2 (filed Oct. 29, 1999), WO 98/07697 (published February 26,1998), WO 98/03516 (published January 29,1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published July 13,1994), European Patent Publication 931, 788 (published July 28,1999), WO 90/05719 (published May 31,1990), WO 99/52910 (published October 21,1999), WO 99/52889 (published Oct. 21, 1999), WO 99/29667 (published June 17,1999), PCT International Application No. PCT/IB98/01113 (filed Jul. 21,1998), European Patent Application No. 99302232.1 (filed Mar. 25,1999), Great Britain Patent Application No. 9912961.1 (filed Jun. 3, 1999), U.S. Provisional Application No. 60/148,464 (filed Aug. 12,1999), United States Patent 5,863, 949 (issued Jan. 26,1999), United States Patent 5,861, 510 (issued Jan. 19,1999), and European Patent Publication 780,386 (published Jun. 25, 1997), all of which are incorporated herein in their entireties by reference. Embodiments of MMP-2 and/or MMP-9 inhibitors include those that have little or no activity inhibiting MMP-1. Other embodiments include MMP inhibitors that selectively inhibit MMP-2 and/or MMP-9 relative to other matrix metalloproteinases (e.g., MMP-1, MMP-3, MMP-4, MMP-5, MMP-6, MMP-7, MMP-8, MMP-10, MMP-11, MMP-12 and/or MMP-13). Specific examples of MMP inhibitors useful in some embodiments include AG-3340, RO 323555 and RS 13-0830.

In some embodiments, a compound of the present disclosure is administered in combination with autophagy inhibitors, such as chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside and vinblastine, as well as antisense or siRNA that inhibits expression of proteins including but not limited to ATG5 (which are implicated in autophagy).

In some embodiments, a compound of the present disclosure is administered in combination with B-cell lymphoma 2 (BCL-2) inhibitors, such as venetoclax.

In some embodiments, a compound of the present disclosure is administered in combination with B-cell receptor signaling antagonists, such as a Bruton's tyrosine kinase (BTK) inhibitor (e.g., ibrutinib).

In some embodiments, a compound of the present disclosure is administered in combination with Bromodomain inhibitors. A bromodomain inhibitor inhibits at least one bromodomain protein, such as Brd2, Brd3, Brd4 and/or BrdT, for example, Brd4. Non-limiting examples of bromodomain inhibitors include JQ-1 (Nature 2010 Dec. 23; 468(7327):1067-73), BI2536 (ACS Chem. Biol. 2014 May 16; 9(5):1160-71; Boehringer Ingelheim), TG101209 (ACS Chem. Biol. 2014 May 16; 9(5):1160-71), OTX015 (Mol. Cancer Ther. November 201312; C244; Oncoethix), IBET762 (J Med Chem. 2013 Oct. 10; 56(19):7498-500; GlaxoSmithKline), IBET151 (Bioorg. Med. Chem. Lett. 2012 Apr. 15; 22(8):2968-72; GlaxoSmithKline), PFI-1 (J. Med. Chem. 2012 Nov. 26; 55(22):9831-7; Cancer Res. 2013 Jun. 1; 73(11):3336-46; Structural Genomics Consortium), CPI-0610 (Constellation Pharmaceuticals). In some embodiments, the bromodomain inhibitor is TG101209, BI2536, OTX015, C244, IBET762, IBET151, or PFI-1. Histone deacetylase (HDAC) inhibitors. HDAC proteins may be grouped into classes based on homology to yeast HDAC proteins with Class I made up of HDAC1, HDAC2, HDAC3 and HDAC 8; Class IIa made up of HDAC4, HDAC5, HDAC7 and HDAC 9; Class IIb made up of HDAC6 and HDAC10; and Class IV made up of HDAC11. Non-limiting examples of HDAC inhibitors include trichostatin A, vorinostat (Proc. Natl. Acad. Sci. U.S.A. 1998 Mar. 17; 95(6):3003-7), givinostat, abexinostat (Mol. Cancer Ther. 2006 May; 5(5):1309-17), belinostat (Mol. Cancer Ther. 2003 August; 2(8):721-8), panobinostat (Clin. Cancer Res. 2006 Aug. 1; 12(15):4628-35), resminostat (Clin. Cancer Res. 2013 Oct. 1; 19(19):5494-504), quisinostat (Clin. Cancer Res. 2013 Aug. 1; 19(15):4262-72), depsipeptide (Blood. 2001 Nov. 1; 98(9):2865-8), entinostat (Proc. Natl. Acad. Sci. U.S.A. 1999 Apr. 13; 96(8):4592-7), mocetinostat (Bioorg. Med. Chem. Lett. 2008 Feb. 1; 18(3):106771) and valproic acid (EMBO J. 2001 Dec. 17; 20(24):6969-78). In some embodiments, the HDAC inhibitor is panobinostat, vorinostat, MS275, belinostat, SAHA or LBH589.

In some embodiments, a compound of the present disclosure is administered in combination with epidermal growth factor receptor tyrosine kinase (EGFR) inhibitors, such as erlotinib, osimertinib, cetuximab, gefitinib, necitumumab, lapatinib, neratinib, panitumumab, vandetanib, and necitumumab. A combination of a compound as described herein and an EGFR inhibitor may be useful, for example, in the treatment of cancers that are related to EGFR dysregulation, such as non-small-cell lung cancer (NSCLC), pancreatic cancer, breast cancer, and colon cancer. EGFR may be dysregulated, for example, due to activating mutations in exons 18, 19, 20, or 21. In particular embodiments, the EGFR inhibitor is erlotinib or osimertinib. In particular embodiments, the combination of a compound of the present disclosure and an EGFR inhibitor is used to treat EGFR-mutated NSCLC. In particular embodiments, the combination of a compound of the present disclosure and an EGFR inhibitor is used to treat an EGFR inhibitor-resistant cancer, for example, and the compound of the present disclosure sensitizes the cancer to the EGFR inhibitor.

EGFR antibodies, such as cetuximab (Erbitux®).

Methylthioadenosine phosphorylase (MTAP) inhibitors, such as (3R,4S)-1-((4-amino-5H-pyrrolo[3,2-d]pyrimidin-7-yl)methyl)-4-((methylthio)methyl)pyrrolidin-3-ol (MT-DADMe-Immucillin-A, CAS 653592-04-2).

Methylthioadenosine ((2R,3R,4S,5S)-2-(6-amino-9H-purin-9-yl)-5-((methylthio)methyl)tetrahydrofuran-3,4-diol, CAS 2457-80-9).

Epidermal growth factor receptor (EGFR) inhibitors, such as erlotinib hydrochloride (Tarceva®) and gefitinib (Iressa®).

Mesenchymal-epithelial transition (MET) inhibitors, such as capmatinib (INC280, CAS 1029712-80-8).

In some embodiments, a compound of the present disclosure is administered in combination with platelet-derived growth factor (PDGF) receptor inhibitors, such as imatinib (Gleevec®); linifanib (N-[4-(3-amino-1H-indazol-4-yl)phenyl]-N'-(2-fluoro-5-methylphenyl)urea, also known as ABT 869, available from Genentech); sunitinib malate (Sutent®); quizartinib (AC220, CAS 950769-58-1); pazopanib (Votrient®); axitinib (Inlyta®); sorafenib (Nexavar®); vargatef (BIBF1120, CAS 928326-83-4); telatinib (BAY57-9352, CAS 332012-40-5); vatalanib dihydrochloride (PTK787, CAS 212141-51-0); and motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470).

In some embodiments, a HER2 (Receptor tyrosine-protein kinase erbB-2) antibody can be used in combination with the compounds as described herein. In some embodiments, the HER2 antibody or biologics is fam-trastuzumab deruxtecan-nxki, trastuzumab, pertuzumab, ado-trastuzumab emtansine, or margetuximab-cmkb.

In some embodiments, a compound of the present disclosure is administered in combination with phosphoinositide 3-kinase (PI3K) inhibitors, such as 4-[2-(1H-indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 4-(trifluoromethyl)-5-(2,6-dimorpholinopyrimidin-4-yl)pyridin-2-amine (also known as BKM120 or NVP-BKM120, and described in PCT Publication No. WO 2007/084786); alpelisib (BYL719); (5Z)-5-[[4-(4-pyridinyl)-6-quinolinyl]methylene]-2,4-thiazolidinedione (GSK1059615, CAS 958852-01-2); 5-[8-methyl-9-(1-methylethyl)-2-(4-morpholinyl)-9H-purin-6-yl]-2-pyrimidinamine (VS-5584, CAS 1246560-33-7); and everolimus (AFINITOR®). Cyclin-dependent kinase (CDK) inhibitors, such as ribociclib (LEE011, CAS 1211441-98-3); aloisine A; alvocidib (also known as flavopiridol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); crizotinib (PF-02341066, CAS 877399-52-5); 2-(2-chlorophenyl)-5,7-dihydroxy-8-[(2R,3S)-2-(hydroxymethyl)-1-methyl-3-pyrrolidinyl]-4H-1-benzopyran-4-one, hydrochloride (P276-00, CAS 920113-03-7); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265, CAS 927880-90-8); indisulam (E7070); roscovitine (CYC202); 6-acetyl-8-cyclopentyl-5-methyl-2-(5-piperazin-1-yl-pyridin-2-ylamino)-8H-pyrido [2,3-d]pyrimidin-7-one, hydrochloride (PD0332991); dinaciclib (SCH727965); N-[5-[[(5-tert-butyloxazol-2-yl) methyl]thio]thiazol-2-yl]piperidine-4-carboxamide (BMS 387032, CAS 345627-80-7); 4-[[9-chloro-7-(2,6-difluorophenyl)-5H-pyrimido[5,4-d][2]benzazepin-2-yl]amino]-benzoic acid (MLN8054, CAS 869363-13-3); 5-[3-(4,6-difluoro-1H-benzimidazol-2-yl)-1H-indazol-5-yl]-N-ethyl-4-methyl-3-pyridinemethanamine (AG-024322, CAS 837364-57-5); 4-(2,6-dichlorobenzoylamino)-1H-pyrazole-3-carboxylic acid N-(piperidin-4-yl)amide (AT7519, CAS 844442-38-2); 4-[2-methyl-1-(1-methylethyl)-1H-imidazol-5-yl]-N-[4-(methylsulfonyl)phenyl]-2-pyrimidinamine (AZD5438, CAS 602306-29-6); palbociclib (PD-0332991); and (2R,3R)-3-[[2-[[3-[[S(R)]—S-cyclopropylsulfonimidoyl]-phenyl]amino]-5-(trifluoromethyl)-4-pyrimidinyl] oxy]-2-butanol (BAY 10000394).

In some embodiments, a compound of the present disclosure is administered in combination with p53-MDM2 inhibitors, such as (S)-1-(4-chloro-phenyl)-7-isopropoxy-6- methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, (S)-5-(5-chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RG7112), 4-[[(2R,3S,4R,5S)-3-(3-chloro-2-fluorophenyl)-4-(4-chloro-2-fluorophenyl)-4-cyano-5-(2,2-dimethylpropyl)pyrrolidine-2-carbonyl]amino]-3-methoxybenzoic acid (RG7388), SAR299155, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (AMG232), {(3R,5R,6S)-5-(3-chlorophenyl)-6-(4-chlorophenyl)-1-[(2S,3S)-2-hydroxy-3-pentanyl]-3-methyl-2-oxo-3-piperidinyl}acetic acid (AM-8553), (+)-4-[4,5-bis(4-chlorophenyl)-2-(2-isopropoxy-4-methoxy-phenyl)-4,5-dihydro-imidazole-1-carbonyl]-piperazin-2-one (Nutlin-3), 2-methyl-7-[phenyl(phenylamino)methyl]-8-quinolinol (NSC 66811), 1-N-[2-(1H-indol-3-yl)ethyl]-4-N-pyridin-4-ylbenzene-1,4-diamine (JNJ-26854165), 4-[4,5-bis(3,4-chlorophenyl)-2-(2-isopropoxy-4-methoxy-phenyl)-4,5-dihydro-imidazole-1-carboxyl]-piperazin-2-one (Caylin-1), 4-[4,5-bis(4-trifluoromethyl-phenyl)-2-(2-isopropoxy-4-methoxy-phenyl)-4,5-dihydro-imidazole-1-carboxyl]-piperazin-2-one (Caylin-2), 5-[[3-dimethylamino)propyl]amino]-3,10-dimethylpyrimido[4,5-b]quinoline-2,4(3H,10H)-dione dihydrochloride (HLI373) and trans-4-iodo-4'-boranyl-chalcone (SC204072).

In some embodiments, a compound of the present disclosure is administered in combination with mitogen-activated protein kinase (MEK) inhibitors, such as XL-518 (also known as GDC-0973, CAS No. 1029872-29-4, available from ACC Corp.); selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO 2003/077914); 2-[(2-chloro-4-iodophenyl)amino]-N-(cyclopropylmethoxy)-3,4-difluoro-benzamide (also known as CI-1040 or PD184352 and described in PCT Publication No. WO 2000/035436); N-[(2R)-2,3-dihydroxypropoxy]-3,4-difluoro-2-[(2-fluoro-4-iodophenyl)amino]-benzamide (also known as PD0325901 and described in PCT Publication No. WO 2002/006213); 2,3-bis[amino[(2-aminophenyl)thio]methylene]-butanedinitrile (also known as U0126 and described in U.S. Pat. No. 2,779,780); N-[3,4-difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO 2007/014011); (3S,4R,5Z,8S,9S,11E)-14-(ethylamino)-8,9,16-trihydroxy-3,4-dimethyl-3,4,9;19-tetrahydro-1H-2-benzoxacyclotetradecine-1,7(8H)-dione] (also known as E6201 and described in PCT Publication No. WO 2003/076424); 2'-amino-3'-methoxyflavone (also known as PD98059 available from Biaffin GmbH & Co., KG, Germany); (R)-3-(2,3-dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); pimasertib (AS-703026, CAS 1204531-26-9); trametinib dimethyl sulfoxide (GSK-1120212, CAS 1204531-25-80); 2-(2-fluoro-4-iodophenylamino)-N-(2-hydroxyethoxy)-1,5-dimethyl-6-oxo-1,6-dihydropyridine-3-carboxamide (AZD 8330); 3,4-difluoro-2-[(2-fluoro-4-iodophenyl)amino]-N-(2-hydroxyethoxy)-5-[(3-oxo-[1,2]oxazinan-2-yl)methyl]benzamide (CH 4987655 or Ro 4987655); and 5-[(4-bromo-2-fluorophenyl)amino]-4-fluoro-N-(2-hydroxyethoxy)-1-methyl-1H-benzimidazole-6-carboxamide (MEK162). B-RAF inhibitors, such as regorafenib (BAY73-4506, CAS 755037-03-7); tuvizanib (AV951, CAS 475108-18-0); vemurafenib (ZELBORAF®, PLX-4032, CAS 918504-65-1); encorafenib (also known as LGX818); 1-methyl-5-[[2-[5-(trifluoromethyl)-1H-imidazol-2-yl]-4-pyridinyl]oxy]-N-[4-(trifluoromethyl)phenyl-1H-benzimidazol-2-amine (RAF265, CAS 927880-90-8); 5-[1-(2-hydroxyethyl)-3-(pyridin-4-yl)-1H-pyrazol-4-yl]-2,3-dihydroinden-1-one oxime (GDC-0879, CAS 905281-76-7); 5-[2-[4-[2-(dimethylamino)ethoxy]phenyl]-5-(4-pyridinyl)-1H-imidazol-4-yl]-2,3-dihydro-1H-inden-1-one oxime (GSK2118436 or SB590885); (+/-)-methyl (5-(2-(5-chloro-2-methylphenyl)-1-hydroxy-3-oxo-2,3-dihydro-1H-isoindol-1-yl)-1H-benzimidazol-2-yl)carbamate (also known as XL-281 and BMS908662); dabrafenib (TAFINLAR®); and N-(3-(5-chloro-1H-pyrrolo[2,3-b]pyridine-3-carbonyl)-2,4-difluorophenyl)propane-1-sulfonamide (also known as PLX4720).

In some embodiments, a compound of the present disclosure is administered in combination with proteasome inhibitors, such as bortezomib (VELCADE®), N-5-benzyloxycarbonyl-Ile-Glu(O-tert-butyl)-Ala-leucinal (PSI), carfilzomib and ixazomib, marizomib (NPI-0052), delanzomib (CEP-18770), and O-methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (oprozomib, ONX-0912, PR-047) (e.g., bortezomib), e.g., for the treatment of multiple myeloma.

A host of chemotherapeutic agents can be used in combination with the compound of the present disclosure. In some embodiments, the chemotherapeutic agent is selected from the group consisting of mitotic inhibitors (e.g., paclitaxel, nab-paclitaxel), alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, a compound of the present disclosure is administered in combination with a secondary chemotherapeutic agent selected from alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.), docetaxel (TAXOTERE™, Rhone-Poulenc Rorer, Antony, France) and cabazitaxel (JEVTANA, Sanofi Genzyme); retinoic acid; esperamicins; capecitabine; and pharmaceutically acceptable salts, acids or derivatives of any of the above. Further non-limiting examples of chemotherapeutic agents for use in combination with a compound of the present disclosure (e.g., in combination therapy, in a pharmaceutical combination) include bortezomib, capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), erlotinib, fludarabine phosphate (Fludara®), 5-fluorouracil (Adrucil®, Efudex®), FOLFIRINOX, gemcitabine (difluorodeoxycitidine), irinotecan (Camptosar®), L-asparaginase (ELSPAR®), 6-mercaptopurine (Purinethol®), methotrexate (Folex®), nabpaclitaxel, pentostatin, 6-thioguanine, thiotepa, and topotecan hydrochloride for injection (Hycamptin®). Yet further non-limiting examples of chemotherapeutic agents for use in combination with a compound of the present disclosure (e.g., in combination therapy, in a pharmaceutical combination) include erlotinib, afatinib, gefitinib, GDC0941, MLN1117, BYL719 (alpelisib), BKM120 (buparlisib), CYT387, GLPG0634, baricitinib, lestaurtinib, momelotinib, pacritinib, ruxolitinib, TG101348, crizotinib, tivantinib, AMG337, cabozantinib, foretinib, onartuzumab, NVP-AEW541, dasatinib, ponatinib, saracatinib, bosutinib, trametinib, selumetinib, cobimetinib, PD0325901, RO5126766, axitinib, bevacizumab, cetuximab, fostamatinib, imatinib, lapatinib, lenvatinib, ibrutinib, nilotinib, panitumumab, pazopanib, pegaptanib, ranibizumab, sorafenib, sunitinib, SU6656, trastuzumab, tofacitinib, vandetanib, vemurafenib, irinotecan, Taxol, docetaxel, rapamycin and M-LN0128. More non-limiting examples of chemotherapeutic agents for use in combination with a compound of the present disclosure (e.g., in combination therapy, in a pharmaceutical combination) include capecitabine (Xeloda®), N4-pentoxycarbonyl-5-deoxy-5-fluorocytidine, carboplatin (Paraplatin®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), doxorubicin hydrochloride (Adriamycin®, Rubex®), fludarabine phosphate (Fludara®), 5-fluorouracil (Adrucil®, Efudex®), gemcitabine (difluorodeoxycitidine), irinotecan (Camptosar®), L-asparaginase (ELSPAR®), 6-mercaptopurine (Purinethol®), methotrexate (Folex®), pentostatin, 6-thioguanine, thiotepa, and topotecan hydrochloride for injection (Hycamptin®).

Commonly prescribed anti-cancer drugs can also be used in combination with a compound of the present disclosure. Non-limiting examples of commonly prescribed anti-cancer drugs include Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Chemotherapeutic cell conditioners can also be used in combination with compound of the present disclosure. Non-limiting examples of chemotherapeutic cell conditioners include anti-hormonal agents that act to regulate or inhibit hormone action on tumors, such as anti-estrogens, including, for example, tamoxifen, (Nolvadex™), raloxifene, aromatase inhibiting 4(5)-imidazoles, 4-hydroxytamoxifen, trioxifene, keoxifene, LY 117018, onapristone and toremifene (Fareston); and anti-androgens, such as flutamide, nilutamide, bicalutamide, leuprolide and goserelin; chlorambucil; gemcitabine; 6-thioguanine; mercaptopurine; methotrexate; platinum analogs, such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; and difluoromethylornithine (DMFO). mTOR inhibitors can also be used in combination with a compound of the present disclosure. Non-limiting examples of mTOR inhibitors include, e.g., temsirolimus; ridaforolimus (formally known as deferolimus, (1R,2R,4S)-4-[(2R)-2 [(1R,9S, 12S,15R,16E,18R,19R,21R, 23S,24E,26E,28Z,30S,32S, 35R)-1,18-dihydroxy-19,30-dimethoxy-15,17,21,23, 29,35-hexamethyl-2,3,10,14,20-pentaoxo-11,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and $N^2$-[1,4-dioxo-4-[[4-(4-oxo-8-phenyl-4H-1-benzopyran-2-yl)morpholinium-4-yl]

methoxy]butyl]-L-arginylglycyl-L-α-aspartylL-serine-inner salt (SEQ ID NO: 1482) (SF1126, CAS 936487-67-1) and XL765.

Some patients may experience allergic reactions to compounds of the present disclosure and/or other therapeutic agent(s) (e.g., anti-cancer agent(s)) during or after administration. Therefore, anti-allergic agents can be administered in combination with compounds of the present disclosure and/or other therapeutic agent(s) (e.g., anti-cancer agent(s)) to minimize the risk of an allergic reaction. Suitable anti-allergic agents include corticosteroids (Knutson, S., et al., *PLoS One*, DOI:10.1371/journal.pone.0111840 (2014)), such as dexamethasone (e.g., DECADRON®), beclomethasone (e.g., BECLOVENT®), hydrocortisone (also known as cortisone, hydrocortisone sodium succinate, hydrocortisone sodium phosphate, sold under the tradenames ALA-CORT®, hydrocortisone phosphate, SOLU-CORTEF®, HYDROCORT ACETATE® and LANACORT®), prednisolone (sold under the tradenames DELTA-CORTEL®, ORAPRED®, PEDIAPRED® and PRELONE®), prednisone (sold under the tradenames DELTASONE®, LIQUID RED®, METICORTEN® and ORASONE®), methylprednisolone (also known as 6-methylprednisolone, methylprednisolone acetate, methylprednisolone sodium succinate, sold under the tradenames DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

Some patients may experience nausea during and after administration of the compounds described herein and/or other therapeutic agent(s) (e.g., anti-cancer agent(s)). Therefore, anti-emetics can be used in combination with compounds of the present disclosure and/or other therapeutic agent(s) (e.g., anti-cancer agent(s)) to prevent nausea (upper stomach) and vomiting. Suitable anti-emetics include aprepitant (EMEND®), ondansetron (ZOFRAN®), granisetron HCl (KYTRIL®), lorazepam (ATIVAN®, dexamethasone (DECADRON®), prochlorperazine (COMPAZINE®), casopitant (REZONIC® and ZUNRISA®), and combinations thereof.

Medication to alleviate the pain experienced during the treatment period is often prescribed to make the patient more comfortable. Common over-the-counter analgesics, such TYLENOL®, can also be used in combination with compounds of the present disclosure and/or other therapeutic agent(s) (e.g., anti-cancer agent(s)). Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) can be useful for moderate or severe pain, and can be used in combination with compounds of the present disclosure and/or other therapeutic agent(s) (e.g., anti-cancer agent(s)).

In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid). In an effort to protect normal cells from treatment toxicity and to limit organ toxicities, cytoprotective agents (such as neuroprotectants, free-radical scavengers, cardioprotectors, anthracycline extravasation neutralizers, nutrients and the like) may be used as an adjunct therapy in combination with compounds of the present disclosure. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In the combination therapies of the present disclosure, the compound of the present disclosure and the other therapeutic agent may be manufactured and/or formulated by the same or different manufacturers. Moreover, the compound of the present disclosure and the other therapeutic agent may be brought together into a combination therapy: (i) prior to release of the combination product to physicians (e.g., in the case of a kit comprising the compound of the present disclosure and the other therapeutic agent); (ii) by the physician (or under the guidance of a physician) shortly before administration; (iii) in the patient themselves, e.g., during sequential administration of the compound of the present disclosure and the other therapeutic agent.

Pharmaceutical Compositions

In certain embodiments, the present disclosure provides a pharmaceutical preparation suitable for use in a human patient, comprising any of the compounds shown above (e.g., a compound of the disclosure, such as a compound of Formula (I) or (II) or (III), and one or more pharmaceutically acceptable excipients. In certain embodiments, the pharmaceutical preparations may be for use in treating or preventing a condition or disease as described herein. Any of the disclosed compounds may be used in the manufacture of medicaments for the treatment of any diseases or conditions disclosed herein.

The compositions and methods of the present disclosure may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, suspension, cream, gel, ointment, aerosol infusion, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound or to enable manufacturing such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams, or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure. Exemplary ophthalmic formulations are described in U.S. Publication Nos. 2005/0080056, 2005/0059744, 2005/0031697 and 2005/004074 and U.S. Pat. No. 6,583,124, the contents of each of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In certain embodiments, the active compound will be administered once daily.

In certain embodiments, compounds of the disclosure may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the disclosure with one or more additional therapeutic agent(s) (e.g., one or more additional chemotherapeutic agent(s)) provides improved efficacy relative to each individual administration of the compound of the disclosure (e.g., compound of Formula (I) or (II) or (III)) or the one or more additional therapeutic agent(s). In certain such embodiments, the conjoint administration provides an additive effect, wherein an additive effect refers to the sum of each of the effects of individual administration of the compound of the disclosure and the one or more additional therapeutic agent(s).

This disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Pharmaceutically acceptable anionic salts include acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, acetate, succinate, sulfate, tartrate, teoclate, and tosylate.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The disclosure now being generally described, it will be more readily understood by reference to the following examples which are included merely for purposes of illustration of certain aspects and embodiments of the present disclosure, and are not intended to limit the disclosure.

EXAMPLES

General Synthetic Procedures

The starting materials and reagents used in preparing these compounds are either available from commercial supplier such as Aldrich Chemical Co., Bachem, etc., or can be made by methods well known in the art. The schemes are merely illustrative of some methods by which the compounds disclosed herein can be synthesized and various modifications to these schemes can be made and will be suggested to one of skill in the art having referred to this disclosure. The starting materials and the intermediates and the final products of the reaction may be isolated and purified if desired using conventional techniques, including but not limited to filtration, distillation, crystallization, chromatography, and the like and may be characterized using conventional means, including physical constants and spectral data.

Unless specified otherwise, the reactions described herein take place at atmospheric pressure over a temperature range from about −78° C. to about 150° C.

| Abbreviations | Definition |
|---|---|
| EA, EtOAc | Ethyl acetate |
| PE | Petroleum ether |
| SFC | Supercritical fluid chromatography |
| DIAD | Diethyl azodicarboxylate |
| THF | Tetrahydrofuran |
| DCM | Dichloromethane |
| DMF | N,N-dimethylformamide |
| V/V | Volume/volume |
| LC/MS, LC-MS, LCMS | Liquid chromatography-mass spectrometry |
| MeOH | Methanol |
| EtOH | Ethanol |
| MS | Mass spectrometry |
| DIPEA | N,N-diisopropylethylamine |
| DMSO | Dimethyl sulfoxide |
| IPA | Isopropyl alcohol |
| NMP | N-methyl pyrrolidinone |
| NMR | Nuclear magnetic resonance |
| TEA | Triethylamine |
| ppm | Parts per million |
| ATP | Adenosine triphosphate |
| TFA | Trifluoroacetic acid |
| FA | Formic acid |
| ESI | Electrospray ionization |
| sat. | saturated |
| TLC | Thin layer chromatography |

-continued

| Abbreviations | Definition |
| --- | --- |
| DIBAL, DIBAL-H | Diisobutylaluminium hydride |
| AcOH, HOAc | Acetic acid |
| TES | Triethylsilane |
| BuLi | Butyllithium |
| LDA | Lithium diisopropylamide |
| NBS | N-Bromosuccinimide |
| NIS | N-Iodosuccinimide |
| NCS | N-Chlorosuccinimide |
| DME | Dimethoxyethane |
| DMP | Dess-Martin periodinane |
| DEA | Diethylamine |
| DMF-DMA | Dimethylformamide dimethylacetal |
| NMO | N-Methylmorpholine N-oxide |
| TBSCl | tert-Butyldimethylsilyl chloride |
| HPLC | High-pressure liquid chromatography |
| KOAc | Potassiuma acetate |
| Prep | Preperative |
| SM | Starting material |
| wt | Wild-type |
| rt, r.t. | Room-temperature |
| TMSOK | Potassium trimethylsilanolate |
| $Pd(dppf)Cl_2$ | [1,1'-Bis(diphenylphosphino)ferrocene]dichloropalladium(II) |
| $Pd(PPh_3)_4$ | Tetrakis(triphenylphosphine)-palladium(0) |
| $K_2CO_3$ | Potassium Carbonate |
| CuI | Copper Iodine |
| $[Ir(OMe)(cod)_2]$ | Cyclooctadiene iridium methoxide dimer |
| MBTE | tert-Butyl methyl ether |
| $Na_2SO_4$ | Sodium Sulfate |
| $Na_2CO_3$ | Sodium carbonate |
| $LiAlH_4$ | Lithium Aluminium hydride |
| Pd/C | Palladium on Carbon |
| $N_2$ | Nitrogen |
| dtbpy | 4,4'-Di-tert-butyl-2,2'-dipyridyl |
| TsCl | Tosyl Chloride |
| $HNO_3$ | Nitric acid |
| BrCN | Cyanogen Bromide |
| tBuONa | Sodium tertbutoxide |
| $NH_4CO_3$ | Ammonium carbonate |
| NaH | Sodium hydride |
| Zn | Zinc |
| HOBt | Hydroxybenzotriazole |
| DIC | N,N'-Diisopropylcarbodiimide |
| $NaBH_4$ | Sodium borohydride |
| $NaBH(OAc)_3$ | Triacetoxy borohydride |
| $NH_4Cl$ | Ammonium chloride |
| HATU | (1-[Bis(dimethylamino)methylene]-1H-1,2,3-triazolo [4,5-b]pyridinium 3-oxide hexafluorophosphate |
| C18 | octadecane |
| HCHO | Formaldehyde |
| $NH_4Cl$ | Ammonium Chloride |
| HCl | Hydrochloric acid |
| NaOH | Sodium hydroxide |
| $PtO_2$ | Platinium oxide |
| $Cs_2CO_3$ | Cesium Carbonate |
| TMEDA | Tetramethylethylenediamine |
| HMDS | Hexamethyldisilazane |
| PTSA | p-Toluenesulfonic Acid |
| ACN | Acetonitrile |
| PMBCl | para-methoxybenzyl chloride |
| DAST | Diethylaminosulfur trifluoride |
| TMSOTf | Trimethylsilyl trifluoromethanesulfonate |
| mCPBA | meta-Chloroperoxybenzoic acid |
| TMSOTf | Trimethylsilyl trifluoromethanesulfonate |
| DiMeIHeptCl)Pd(cinnamyl)Cl | 1H-Imidazolium, 1,3-bis[2,6-bis[3-methyl-1-(2-methylpropyl)butyl]phenyl]-4,5-dichloro-Palladium(π-cinnamyl) chloride |

The compounds of the invention can be prepared by a variety of synthetic methods, as further described and illustrated herein. It will be understood by those with skill in the art that the following general synthetic methods are representative and not intended to be limiting.

Those having skill in the art will recognize that the starting materials and reaction conditions may be varied, the sequence of the reactions altered, and additional steps employed to produce compounds encompassed by the present disclosure, as demonstrated by the following examples. In some cases, protection of certain reactive functionalities may be necessary to achieve some of the above transformations. In general, the need for such protecting groups as well as the conditions necessary to attach and remove such groups will be apparent to experienced organic chemists. The disclosures of all articles and references mentioned in this application, including patents, are incorporated herein by reference.

The preparation of the compounds of the present disclosure is illustrated further by the following examples, which are not to be construed as limiting the disclosure in scope or spirit to the specific procedures and compounds described in them.

Analytical Methods

LCMS data was collected using one of the following methods:

| Method | Method Details |
|---|---|
| A | Instrument: SHIMADZU 2020 |
| | Column: Poroshell HPH C-18, 50 × 3.0 mm I.D., 2.7 μm |
| | Mobile phase: A is $H_2O$/5 mM $NH_4CO_3$ and B is CH3CN |
| | Run Time: 10% B (0.01 min); 95% B (2.0 min); 95% B (2.7 min); 10% B (2.75 min); stop (3.0 min) |
| | Flow rate: 1.2 mL/min |
| | Column temperature: 40° C. |
| | Wavelength: 220 nm/254 nm |
| B | Instrument: SHIMADZU 2020 |
| | Column: SHIM-Pack Scepter Cl 8, 33 * 3.0 mm, 3.0 μm |
| | Mobile phase: A is HO (+0.1% TFA) and B is $CH_3CN$ |
| | Run Time: 10% B (0.01 min); 95% B (1.2 min); 95% B (1.8 min); 95% B (1.82 min); stop (2.0 min) |
| | Flow rate: 1.5 mL/min |
| | Column temperature: 40° C. |
| | Wavelength: 220 nm/254 nm |
| C | Instrument: SHIMADZU 2020 |
| | Column: Halo C18, 30 * 3.0 mm, 2.0 μm |
| | Mobile phase: A is $H_2O$ (+0.05% TFA) and B is $CH_3CN$ (+0.05% TFA) |
| | Run Time: 5% B (0.01 min); 100% B (1.2 min); 100% B (1.8 min); 5% B (1.82 min); stop (2.0 min) |
| | Flow rate: 1.3 mL/min |
| | Column temperature: 40° C. |
| | Wavelength: 220 nm/254 nm |
| D | Instrument: SHIMADZU 2020 |
| | Column: Halo C18, 30 * 3.0 mm, 2.0 μm |
| | Mobile phase: A is HO (+0.05% TFA) and B is $CH_3CN$ (+0.05% TFA) |
| | Run Time: 20% B (0.01 min); 60% B (1.7 min); 95% B (2.3 min); 95% B (2.8 min); 5% (2.83 min); stop (3.0 min) |
| | Flow rate: 1.3 mL/min |
| | Column temperature: 40° C. |
| | Wavelength: 220 nm/254 nm |
| E | Instrument: SHIMADZU 2020 |
| | Column: Shim-pack GIST C18 50 *4.6 mm, 5 μm |
| | Mobile phase: A is $H_2O$ (+0.1% FA) and B is $CH_3CN$ |
| | Run Time: 20% B (0. 1 min); 95% B (1.7 min); 95% B (2.4 min); 20% B (2.8 min); stop (3.0 min) |
| | Flow rate: 2.5 mL/min |
| | Column temperature: 40° C. |
| | Wavelength: 220 nm/254 nm |
| F | Instrument: SHIMADZU 2020 |
| | Column: Halo C18, 30 * 3.0 mm, 2.0 μm |
| | Mobile phase: A is $H_2O$ (+0.1 %FA) and B is $CH_3CN$ (+ 0.1% FA) |
| | Run Time: 20% B (0.01 min); 60% B (1.7 min); 95% B (2.3 min); 95% B (2.8 min); 5% (2.83 min); stop (3.0 min) |
| | Flow rate: 1.3 mL/min |
| | Column temperature: 40° C. |
| | Wavelength: 220 nm/254 nm |
| G | Instrument: SHIMADZU 2020 |
| | Column: YMC Triart C18, 50 * 4.6 mm, 5.0 μm |
| | Mobile phase: A is $H_2O$/$CH_3CN$/TFA (90/10/0.1) and B is $H_2O$/$CH_3CN$/TFA (10/90/0.1) |
| | Run Time: 20% B (0.4 min); 95% B (3.4 min); 95% B (4.2 min) |
| | Flow rate: 2.5 mL/min |
| | Column temperature: 40° C. |
| | Wavelength: 220 nm/254 nm |

| Method | Method Details |
|---|---|
| H | Instrument: SHIMADZU 2020<br>Column: YMC Triart C18, 50 * 4.6 mm, 5.0 μm<br>Mobile phase: A is $H_2O/CH_3CN/NH_3$ (90/10/0.1) and B is $H_2O/CH_3CN/TFA$ (10/90/0.1)<br>Run Time: 20% B (0.4 min); 95% B (3.4 min); 95% B (4.2 min)<br>Flow rate: 2.5 mL/min<br>Column temperature: 40° C.<br>Wavelength: 220 nm/254 nm |
| I | Instrument: SHIMADZU 2020<br>Column: Halo C18, 30 * 3.0 mm, 2.0 μm<br>Mobile phase: A is $H_2O$ (+0.05% TFA) and B is $CH_3CN$ (+0.05% TFA)<br>Run Time: 20% B (0.01 min); 70% B (1.7 min); 100% B (2.3 min); 100% B (2.8 min); 5% (2.83 min); stop (3.0 min)<br>Flow rate: 1.3 mL/min<br>Column temperature: 40° C.<br>Wavelength: 220 nm/254 nm |
| J | Instrument: SHIMADZU 2020<br>Column: Shim-Pack Scepter, 33 * 3.0 mm, 3.0 μm<br>Mobile phase: A is $H_2O$ (+5 mM $NH_4CO_3$) and B is $CH_3CN$<br>Run Time: 10% B (0.01 min); 95% B (1.2 min); 95% B (1.8 min); 10% B (1.82 min); stop (2.0 min)<br>Flow rate: 1.5 mL/min<br>Column temperature: 40° C.<br>Wavelength: 220 nm/254 nm |
| K | Instrument: SHIMADZU 2020<br>Column: YMC Triart C18, 50 * 4.6 mm, 5.0 μm<br>Mobile phase: A is $H_2O/CH_3CN/FA$ (90/10/0.05) and B is $CH_3CN$<br>Run Time: 20% B (0.01 min); 95% B (1.79 min); 95% B (2.49 min)<br>Flow rate: 2.3 mL/min<br>Column temperature: 40° C.<br>Wavelength: 220 nm/254 nm |
| L | Instrument: SHIMADZU 2020<br>Column: L-column3 C18, 30 * 3.0 mm, 3.0 μm<br>Mobile phase: A is $H_2O$ (+5 mM $NH_4CO_3$) and B is $CH_3CN$<br>Run Time: 20% B (0.01 min); 95% B (1.20 min); 95% B (1.80 min), 10% B (1.82 min), stop (2 min)<br>Flow rate: 1.5 mL/min<br>Column temperature: 40° C.<br>Wavelength: 220 nm/254 nm |
| M | Instrument: SHIMADZU 2020<br>Column: Shim-Pack Scepter, 33 * 3.0 mm, 3.0 μm<br>Mobile phase: A is $H_2O$ (+5 mM $NH_4CO_3$) and B is $CH_3CN$<br>Run Time: 30% B (0.01 min); 70% B (1.7 min); 95% B (2.3 min); 95% B (2.80 min); 10% B (2.83 min); stop (3.00 min)<br>Flow rate: 1.5 mL/min<br>Column temperature: 40° C.<br>Wavelength: 220 nm/254 nm |

Exemplified Synthesis

Several variables are used in the exemplified synthesis, e.g., the exemplified general synthetic schemes. As used herein, each occurrence of X is independently $CR_5$, or N as valency permits; $R_{1a}$ is hydrogen, halogen, or optionally substituted alkyl; $R_{2a}$ is hydrogen, halogen, optionally substituted alkyl, or optionally substituted alkoxy; $R_5$ is independently halo, optionally substituted alkyl, or optionally substituted alkoxy; $R_{2b}$ is hydrogen or optionally substituted alkyl; $R_{1a}$ is hydrogen, halo, or optionally substituted alkyl; $R_{3a}$ is halo, optionally substituted alkyl, or optionally substituted heterocyclyl; $R_{4a}$ is hydrogen, halo, or optionally substituted alkoxy; $R_{5a}$ is hydrogen, optionally substituted alkyl or heterocyclyl; $R^{6a}$ is hydrogen or halo; alkenyl or alkynyl, each of which is optionally substituted by ne or more occurrences of $R^a$ ($R^a$ is as defined in this application); each occurrence of A is C or N as valency permits; PG is a nitrogen protecting group when attached to nitrogen or an oxygen protecting group when attached to oxygen.

Figure 2:
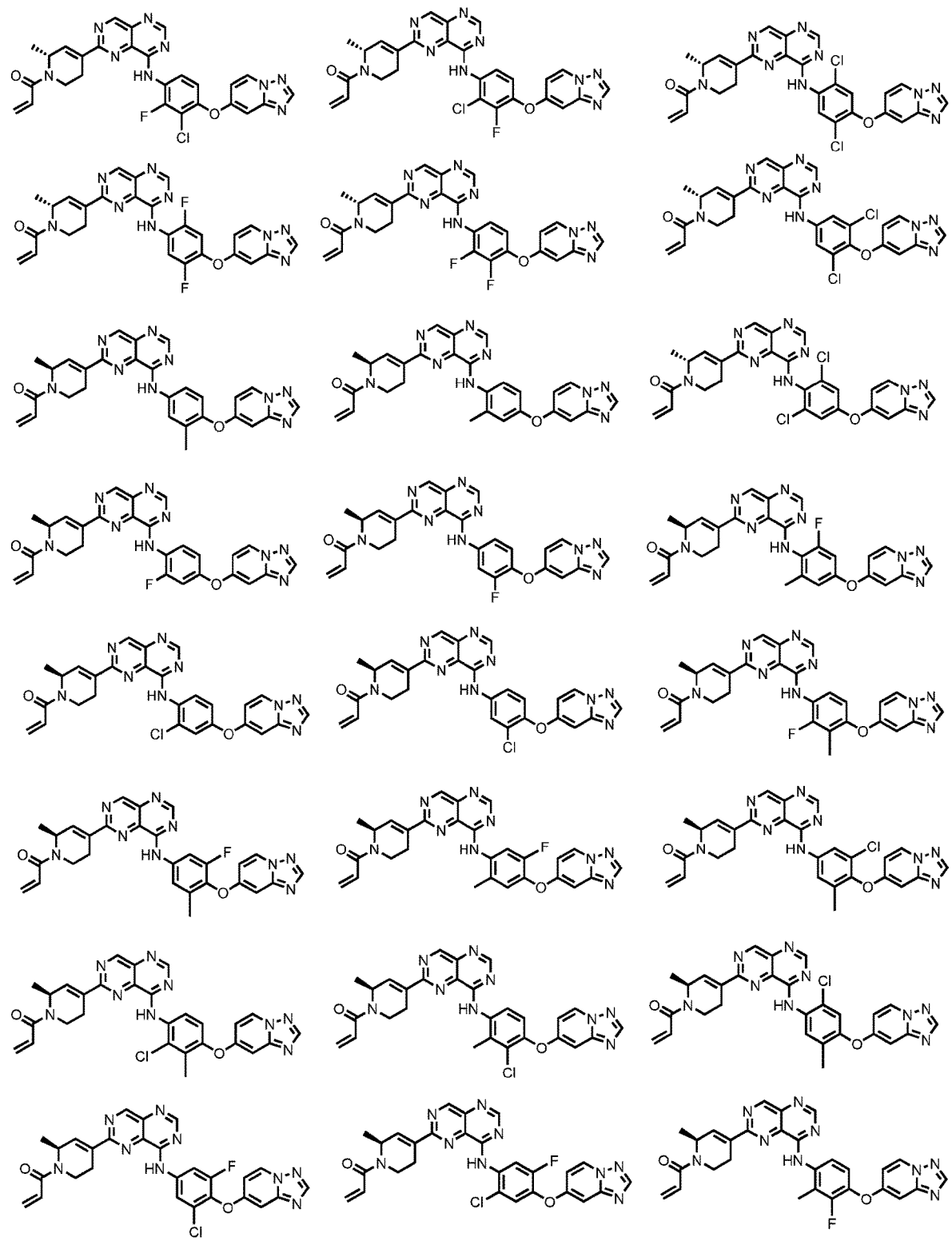
Figure 3:
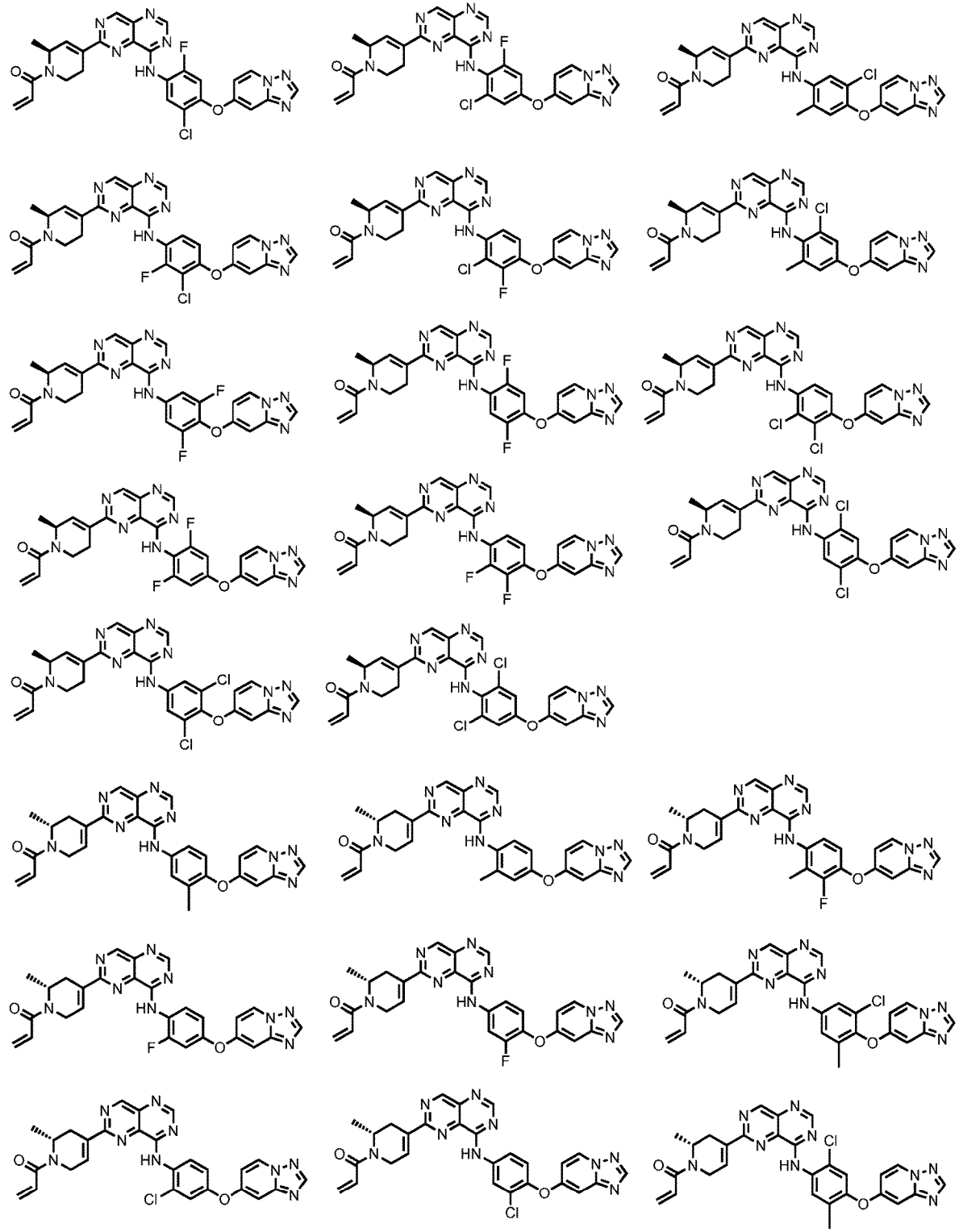
Figure 4:
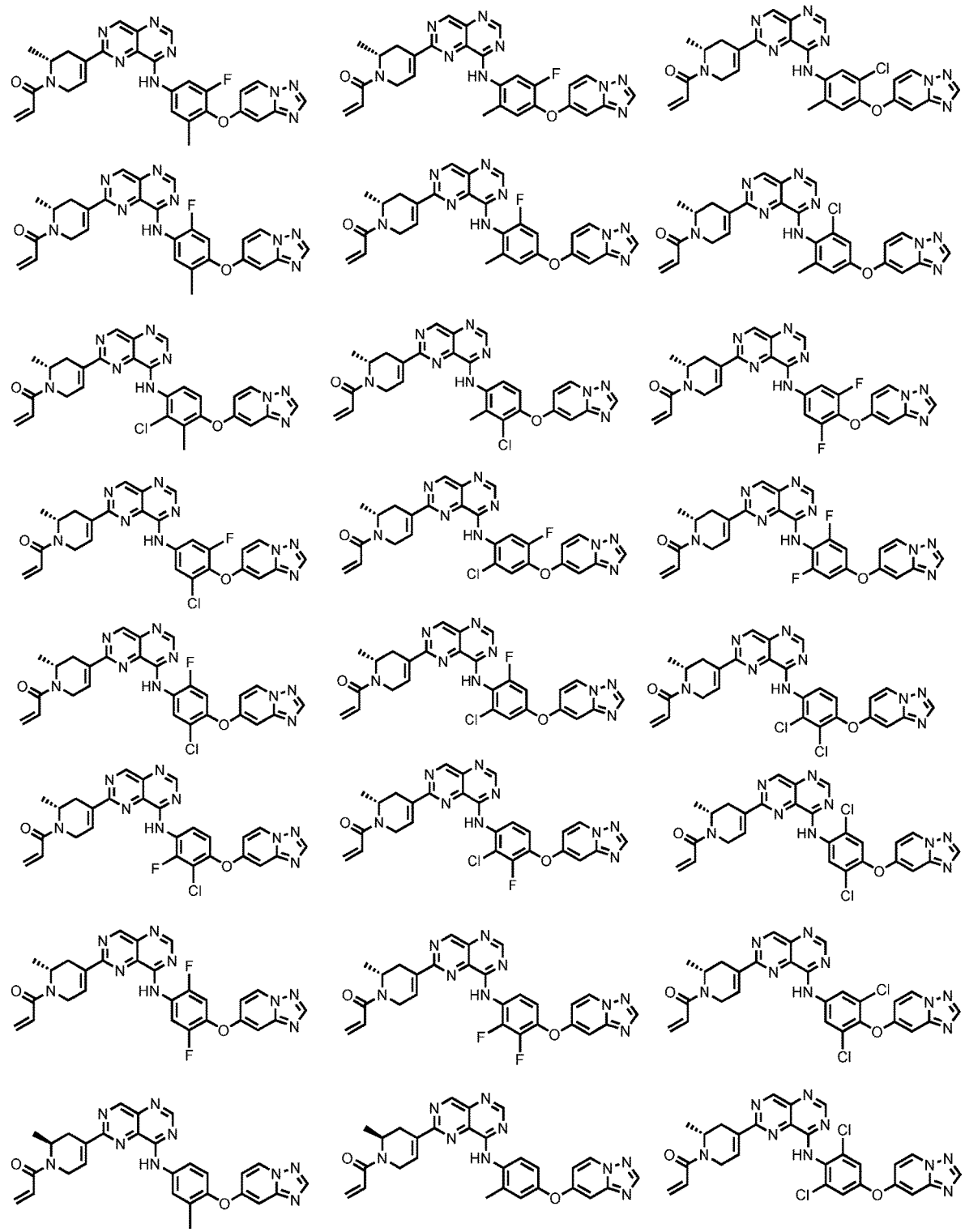
Figure 5:
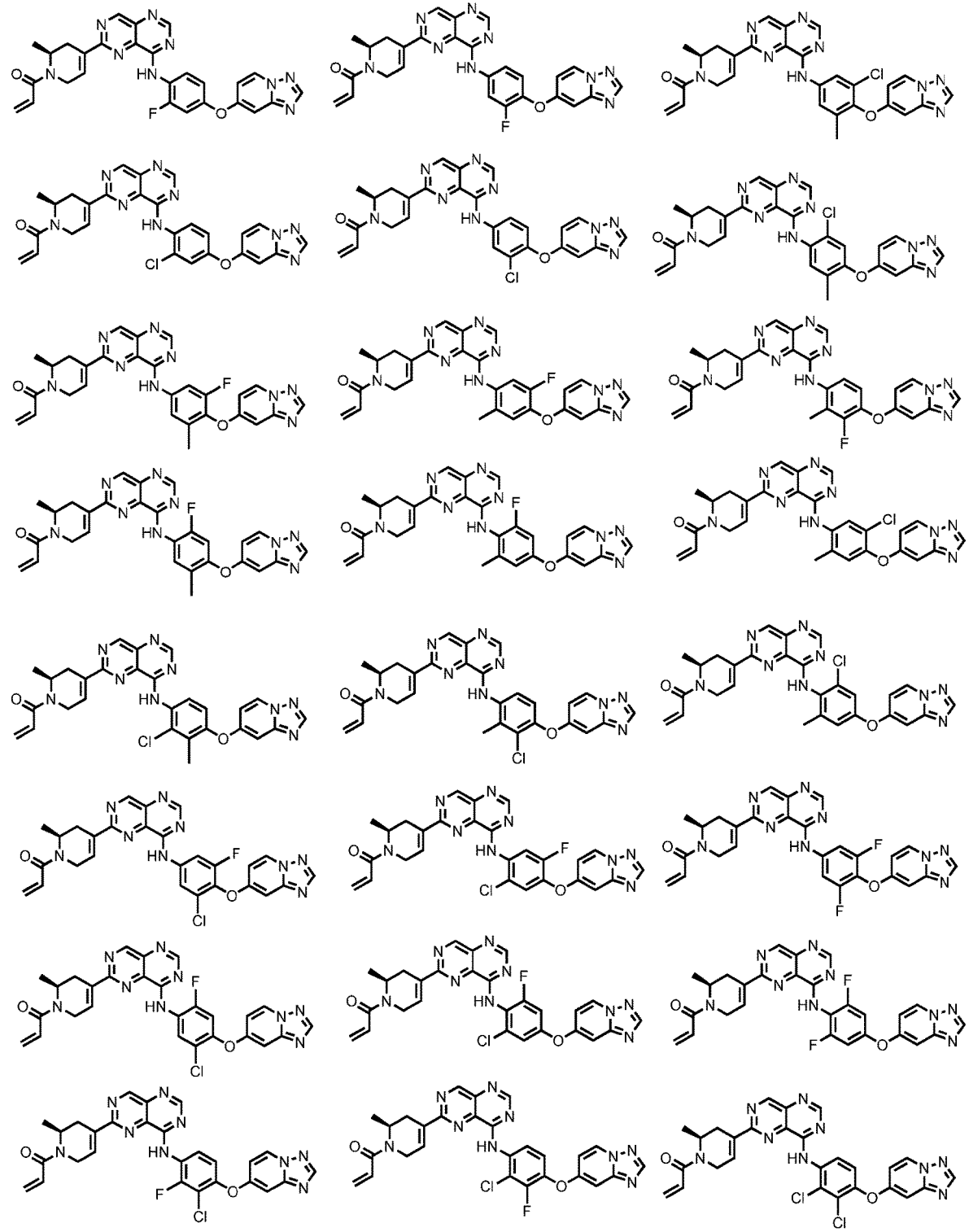
Figure 6:
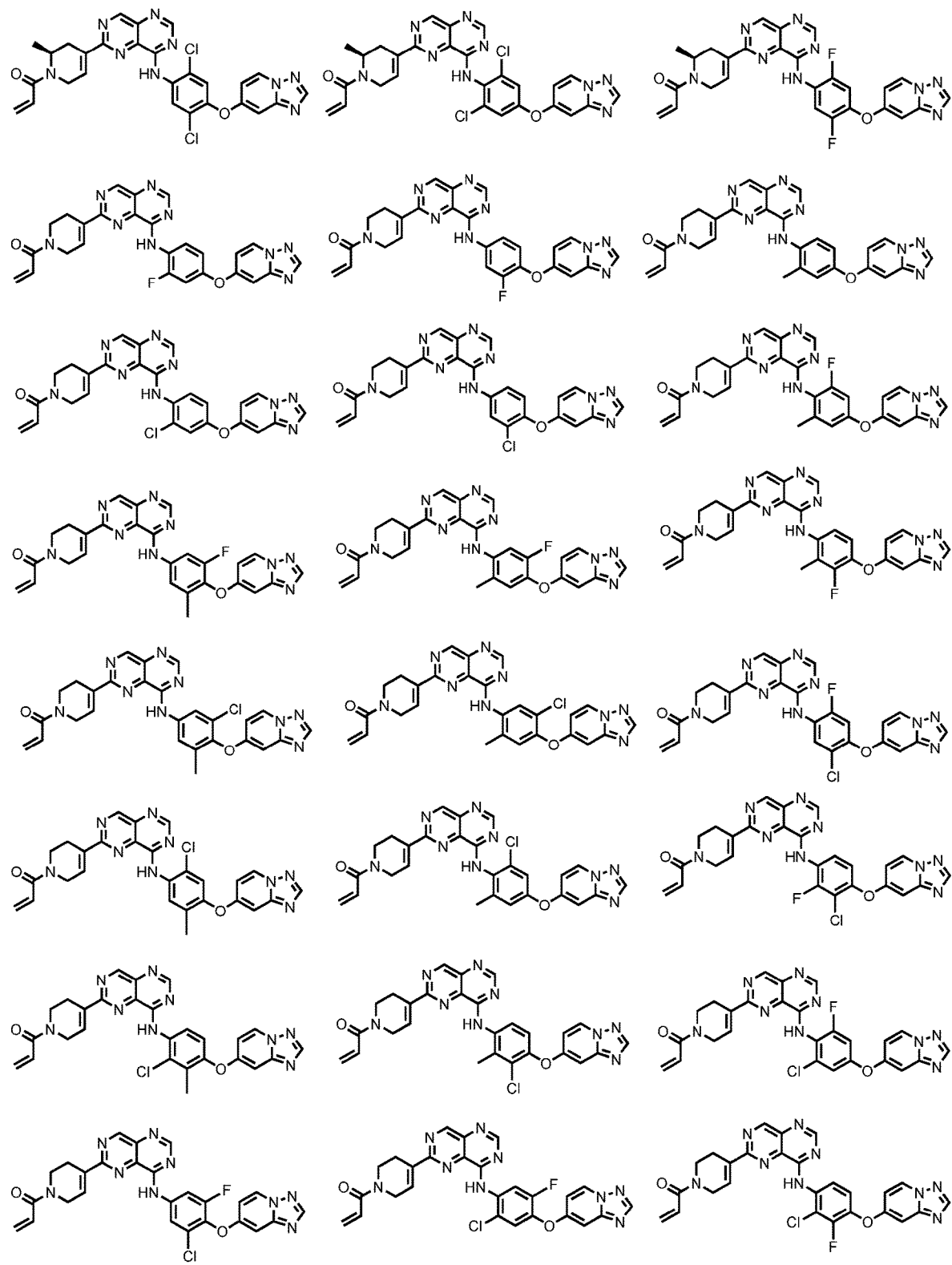
Figure 7:
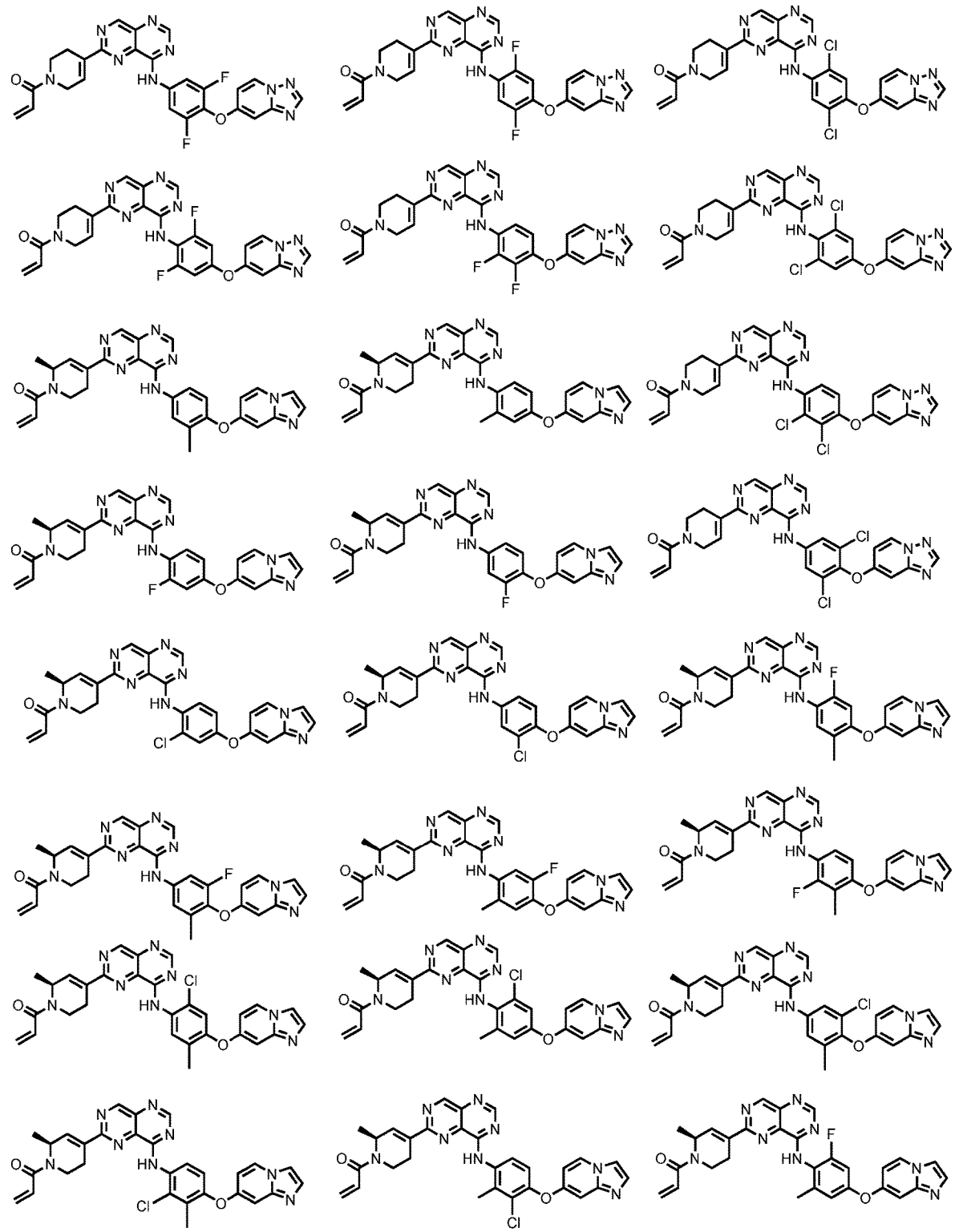
Figure 8:
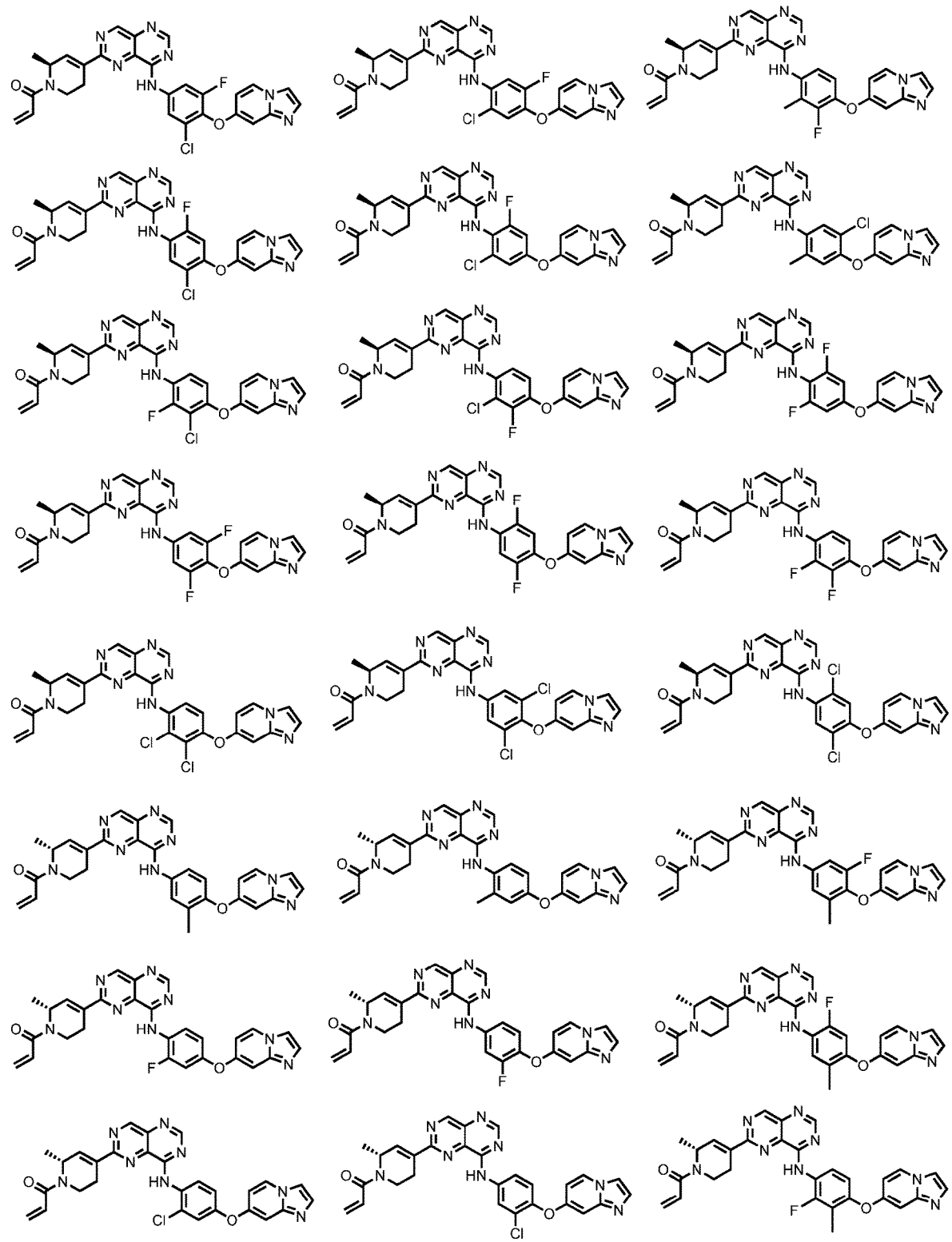
Figure 9:
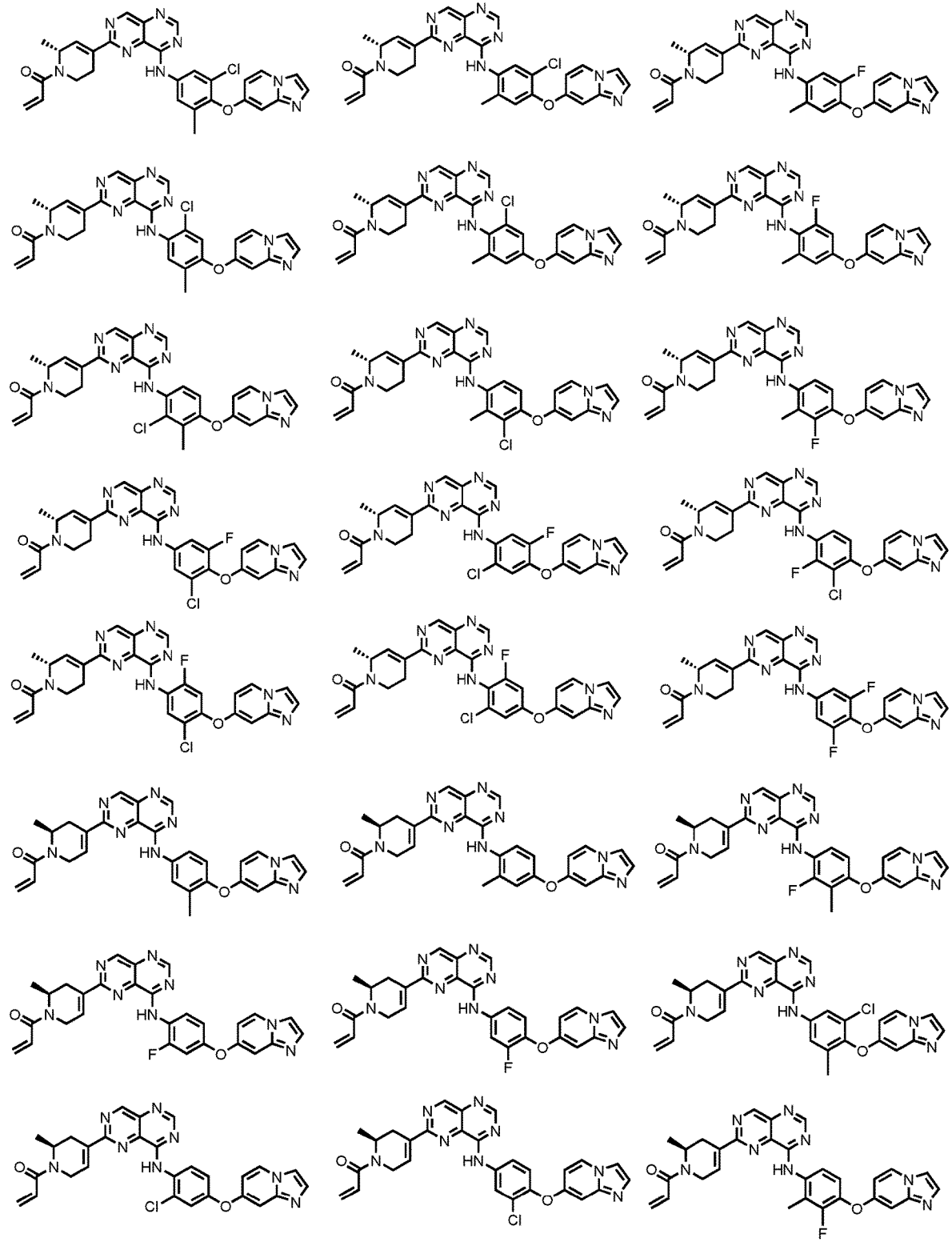
Figure 10:
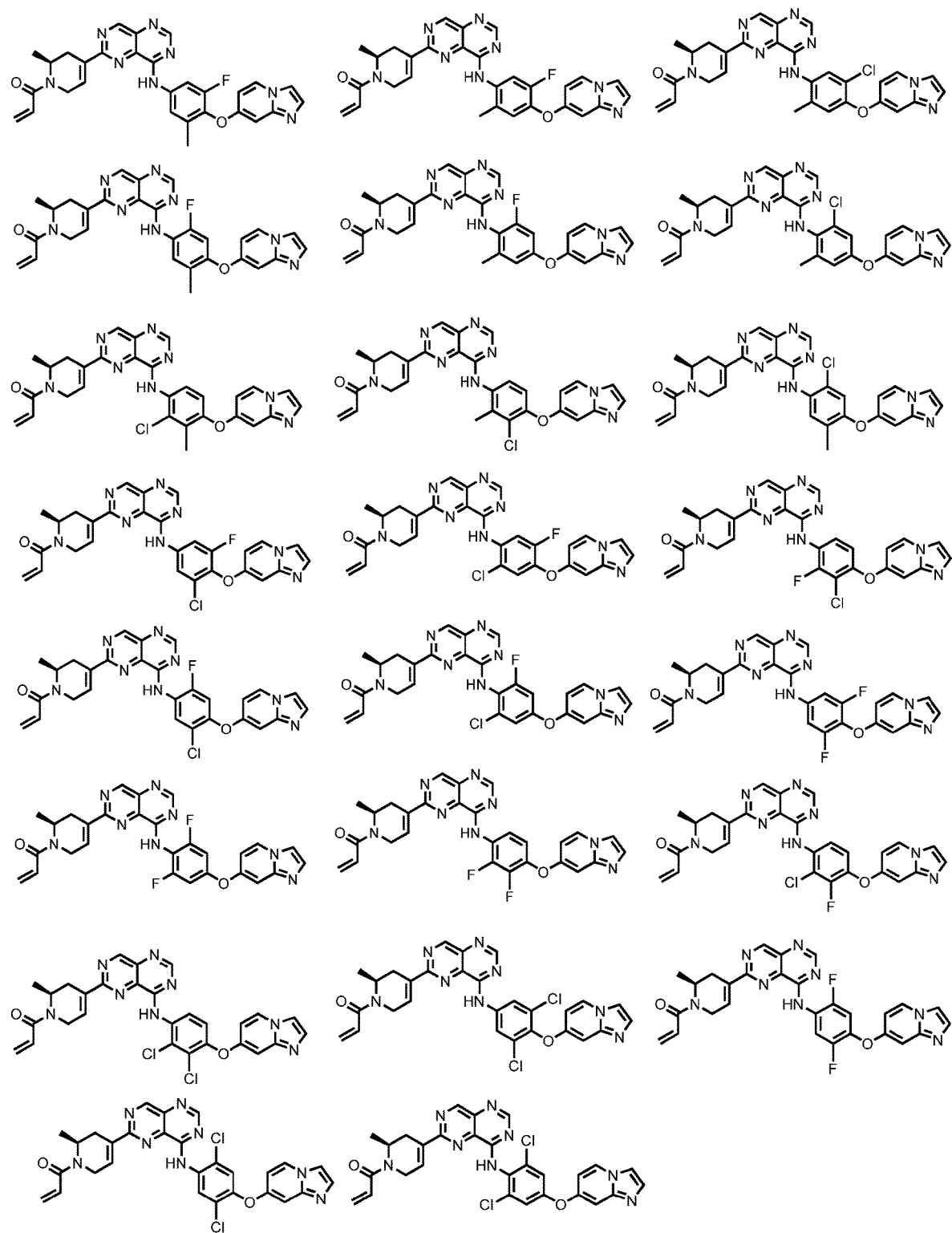
Figure 11:
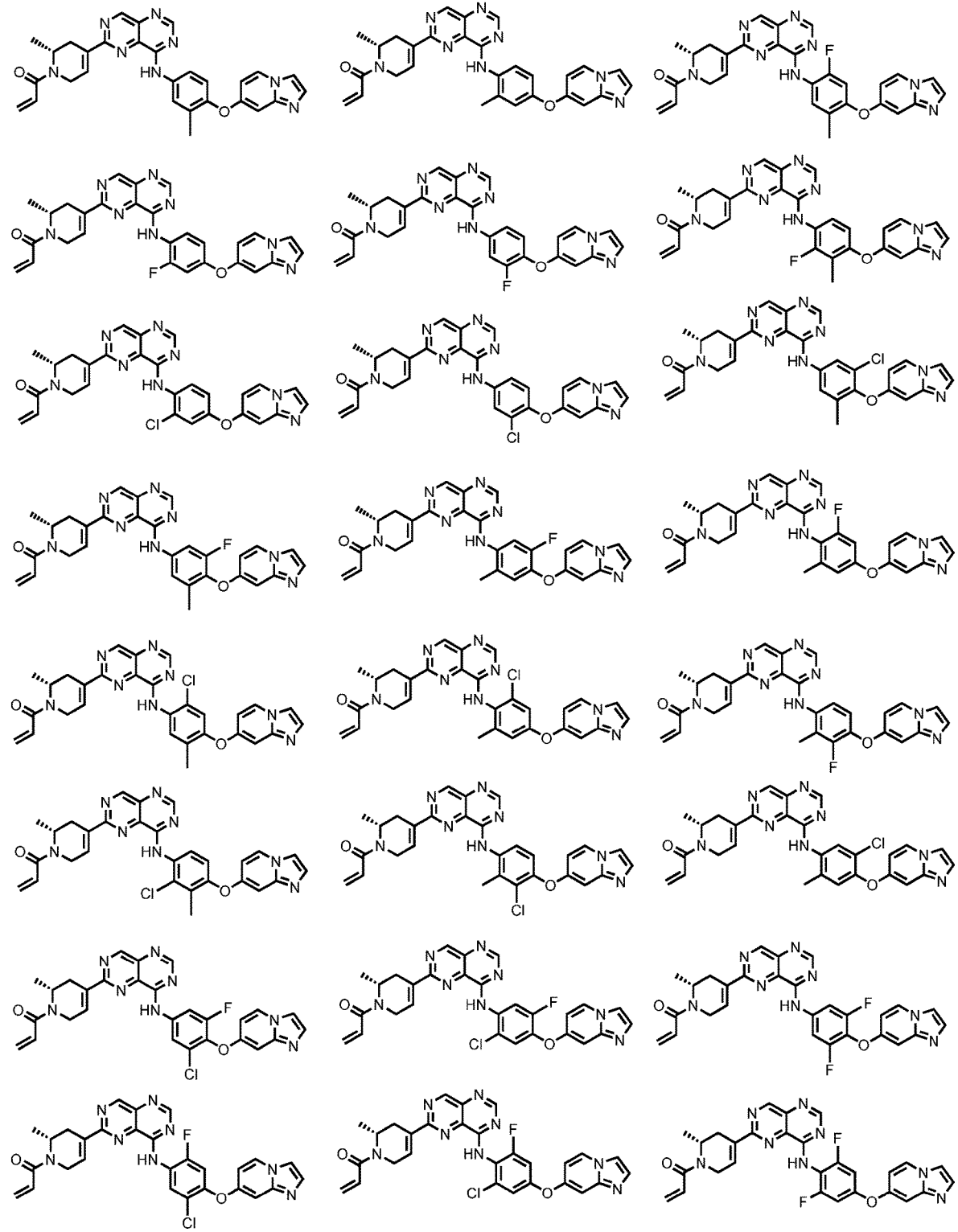
Figure 12:
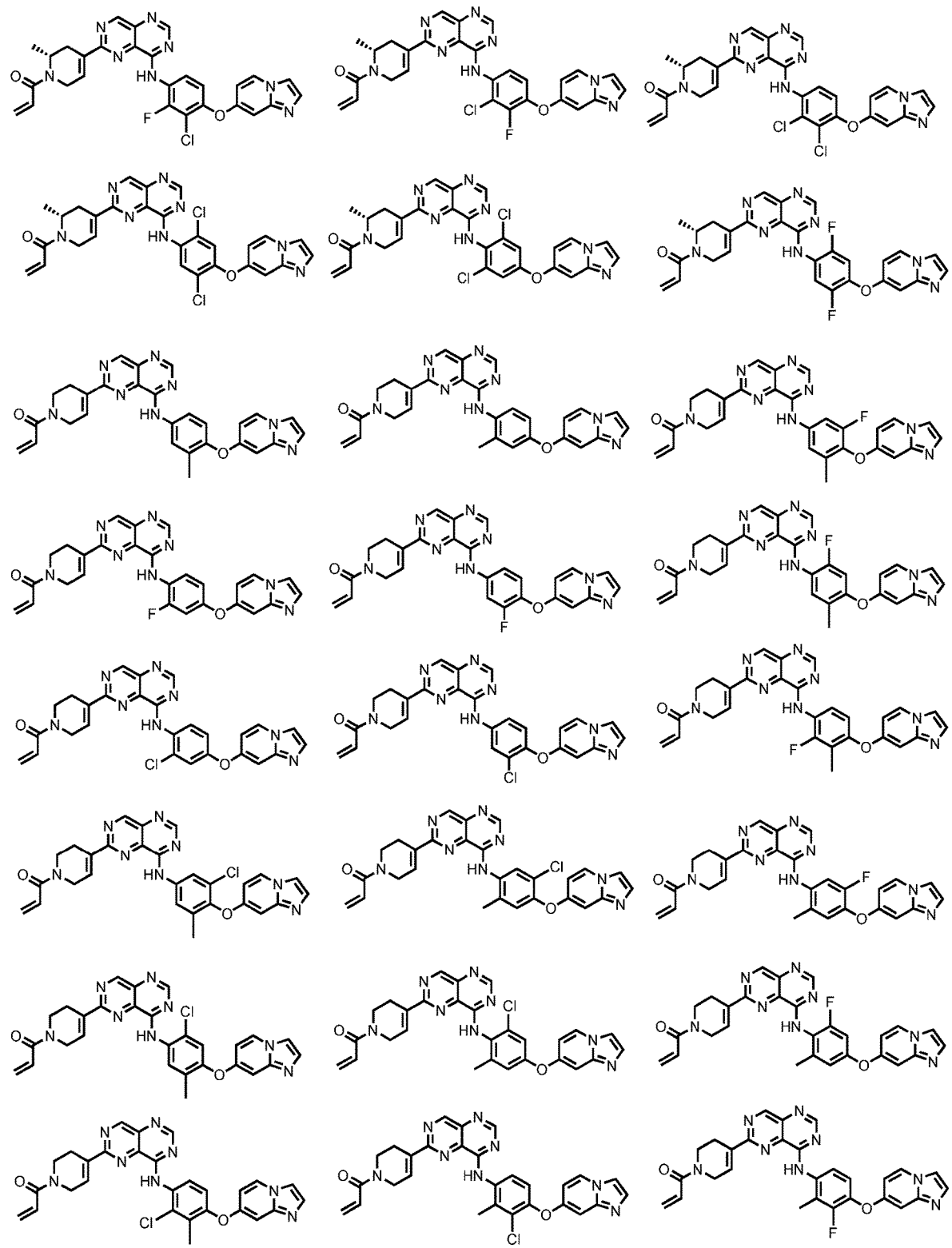
Figure 13:
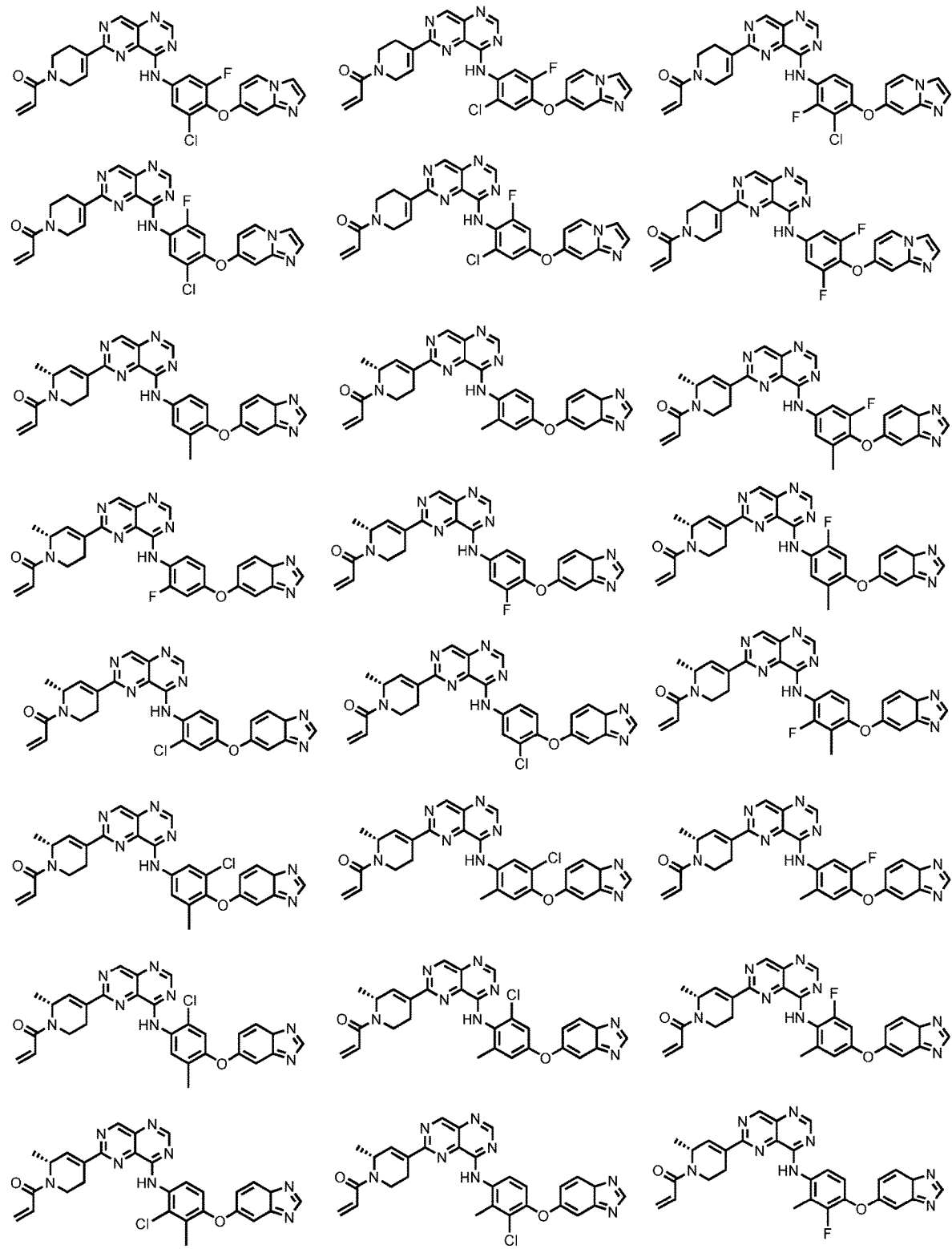
Figure 14:
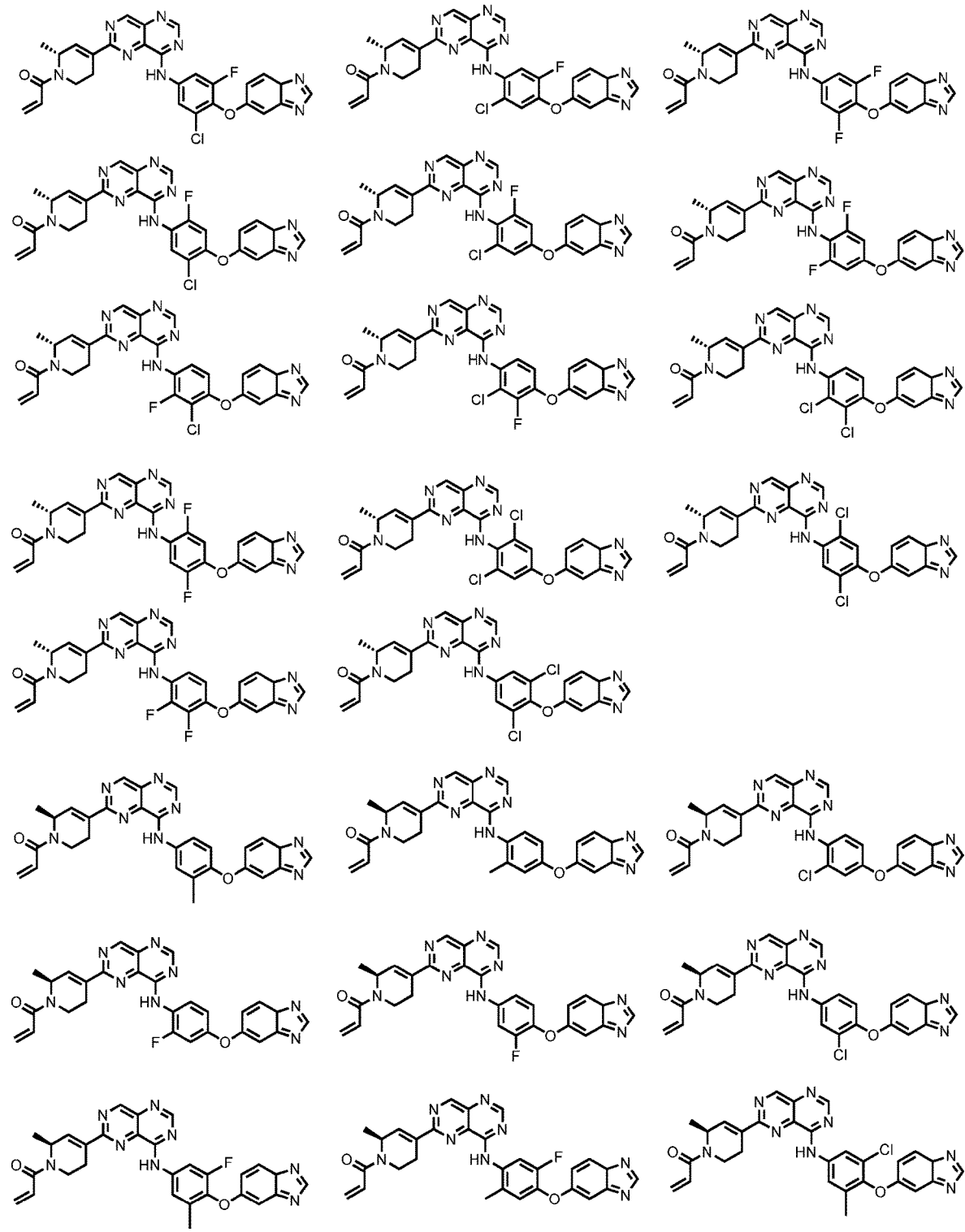
Figure 15:
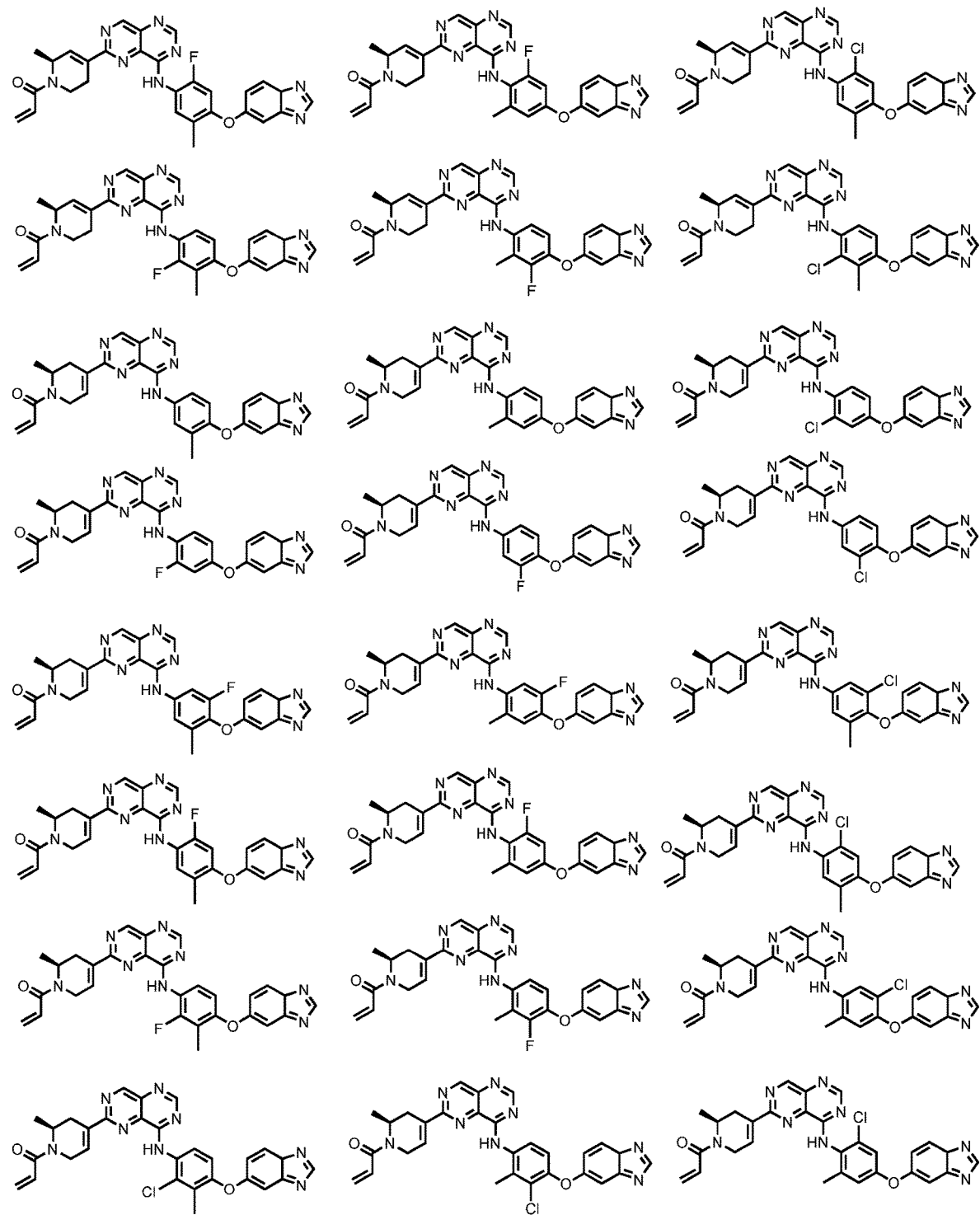
Figure 16:
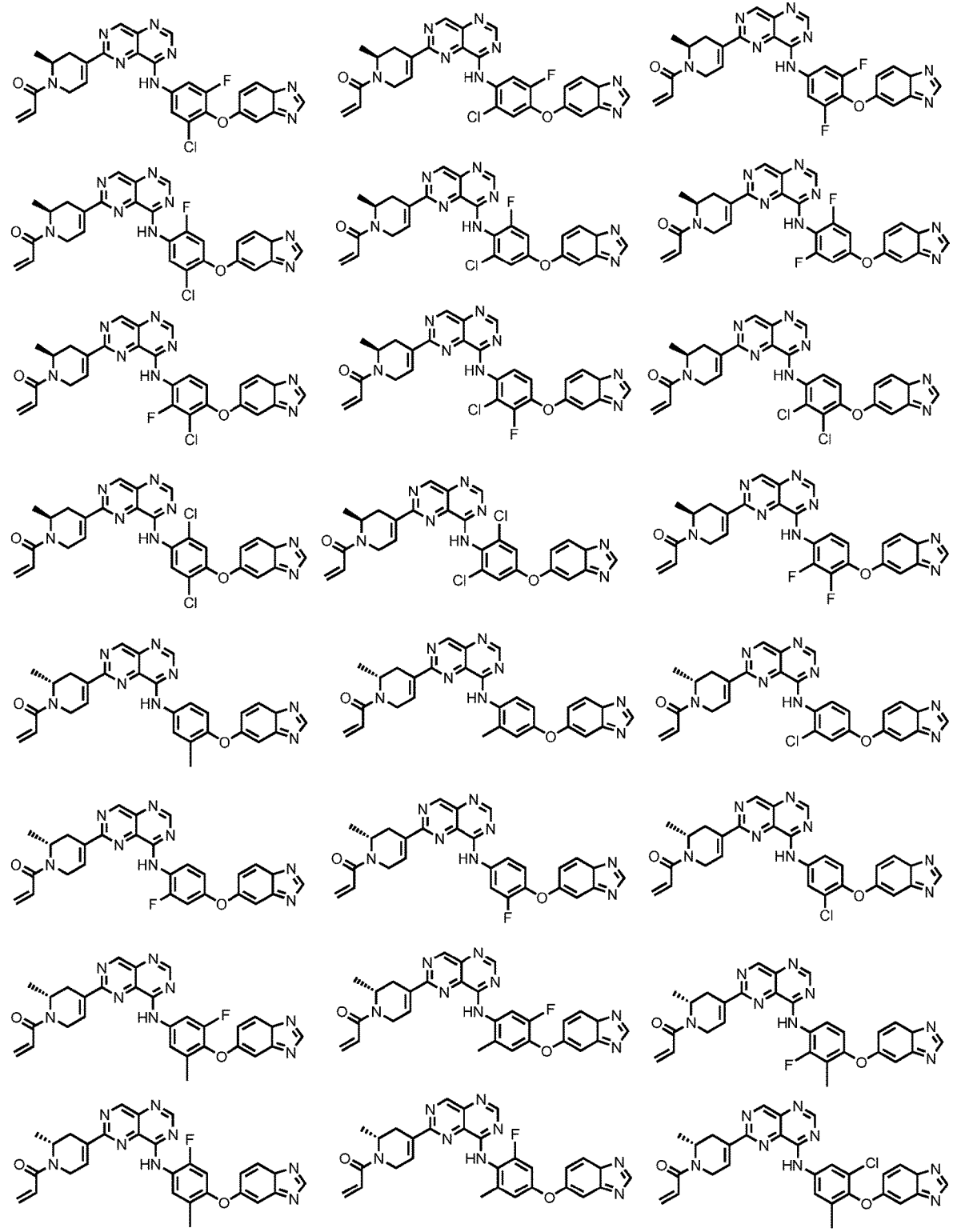
Figure 17:
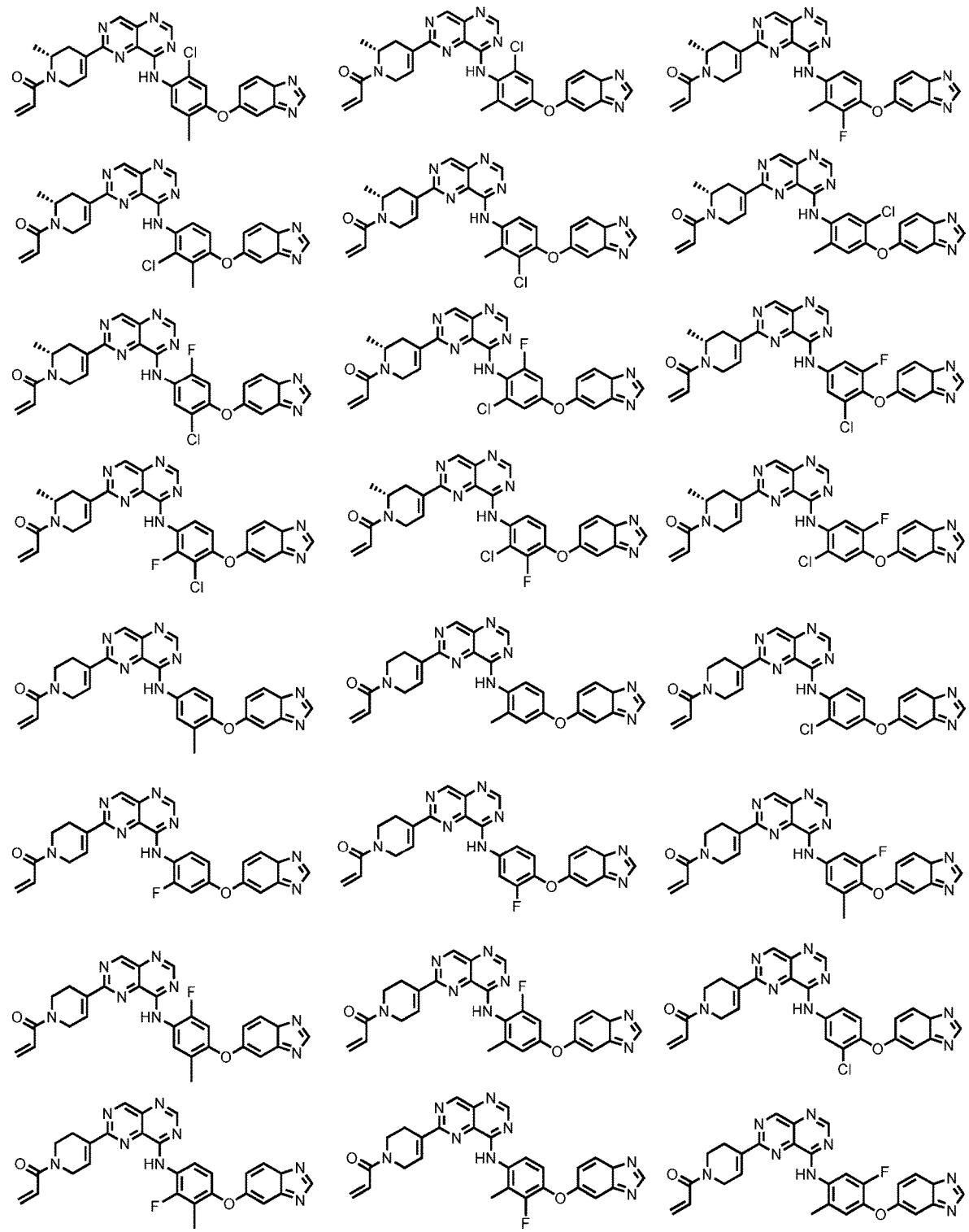
Figure 17:
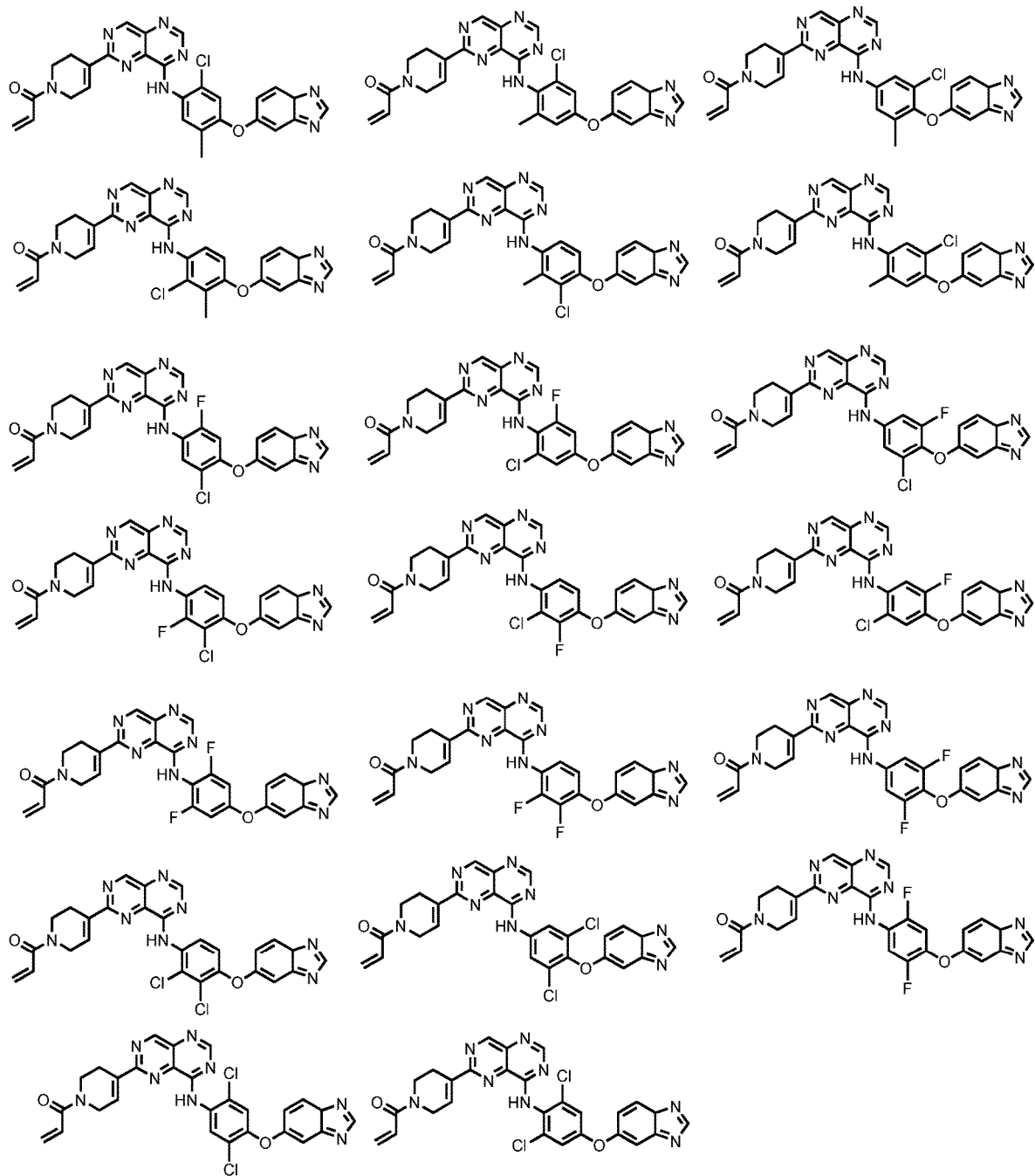

Exemplified compounds in FIGS. 1-17 can be synthesized using the following procedures from the corresponding starting materials and commercially available reagents.

Synthesis of Intermediates

Synthesis of 4-(benzo[d]oxazol-5-yloxy)-3-methyl-aniline 7

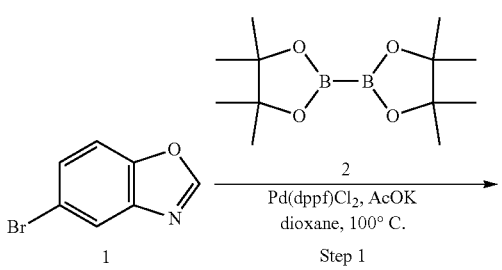

Step 1

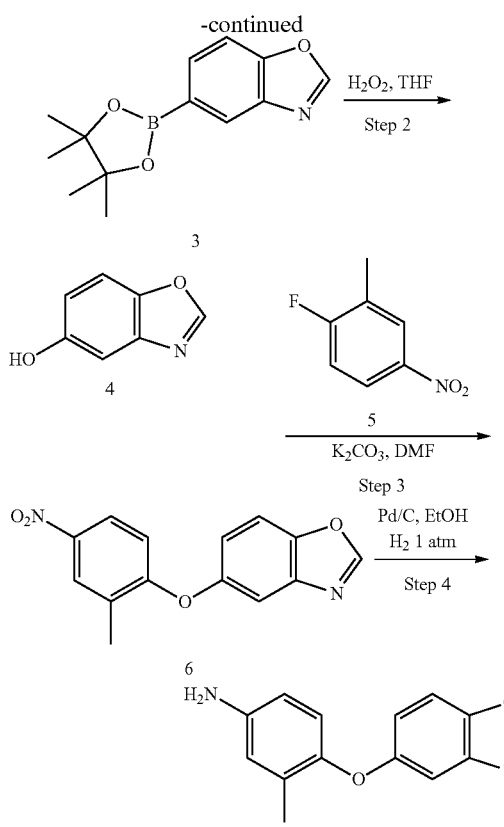

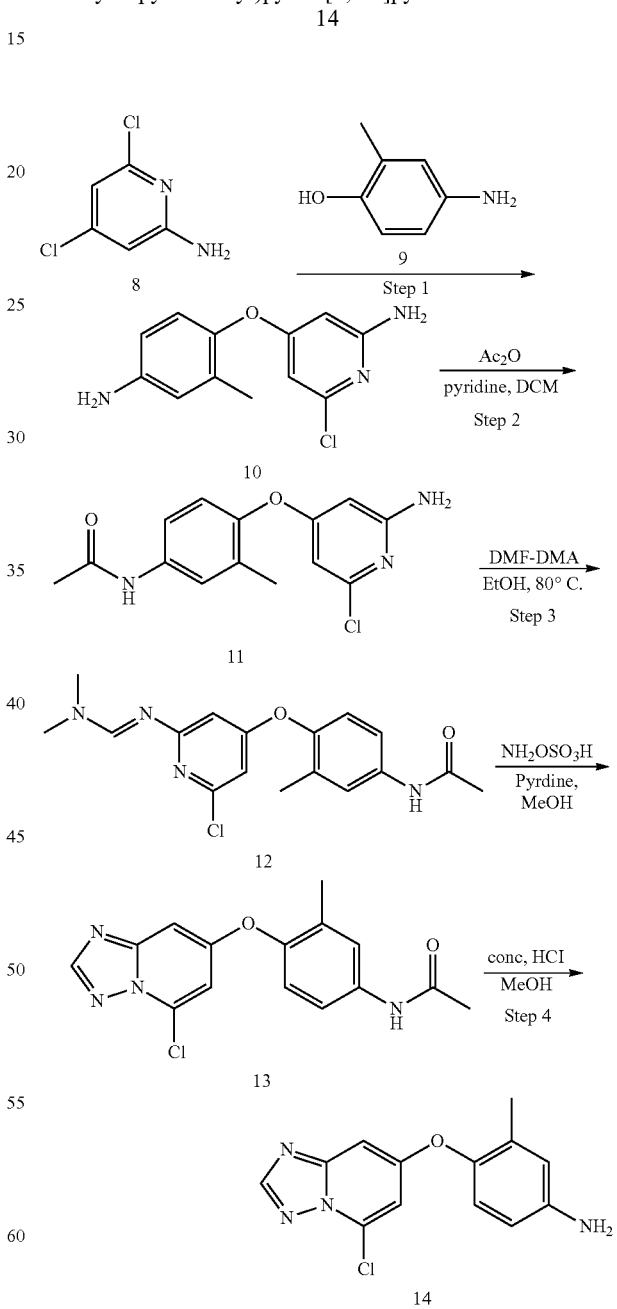

Step 4: A mixture of 5-(2-methyl-4-nitrophenoxy)benzo[d]oxazole 6 (250.0 mg, 0.92 mmol, 1.00 equiv.) and Pd/C (wet, 10%, 25.0 mg, 1/10 w/w) in EtOH (5.00 mL) was stirred at ambient temperature for 2 h under $H_2$ atmosphere and then filtered. The filtrate was concentrated under vacuum to afford 4-(benzo[d]oxazol-5-yloxy)-3-methylaniline 7 (crude, 210.0 mg) as a yellow solid, which was used for the next step without further purification. LCMS (ESI, m z): 241 [M+H]$^+$.

Synthesis of N-(4-(5-methoxy-[1,2,4]triazolo[1,5-a]pyridin-7-yloxy)-3-methylphenyl)-6-(1,2,3,6-tetrahydropyridin-4-yl)pyrido[3,2-d]pyrimidin-4-amine 14

Step 1: A mixture of 5-bromobenzo[d]oxazole 1 (2.00 g, 10.10 mmol, 1.00 equiv.), Pd(dppf)Cl$_2$ (1.65 g, 2.02 mmol, 0.20 equiv.), AcOK (2.97 g, 30.30 mmol, 3.00 equiv.) and bis(pinacolato)diboron 2 (3.85 g, 15.15 mmol, 1.50 equiv.) in dioxane (50.00 mL) was stirred at 100° C. for 6 h under $N_2$ atmosphere. The resulting mixture was concentrated under vacuum. The residue was purified by flash chromatography on silica gel (0-20% MeOH in DCM) to afford 5-(4,4,5,5-tetramethyl-1,3,2-dioxaborolan-2-yl)benzo[d]oxazole 3 (2.10 g, 85%) as a yellow solid. LCMS (ESI, m z): 246 {[M+H]$^+$.

Step 2: A mixture of 5-(4,4,5,5-tetramethyl-1,3,2-dioxaborolan-2-yl)benzo[d]oxazole 3 (2.00 g, 8.16 mmol, 1.00 equiv.) and $H_2O_2$ (30%, 50.00 mL, 2.00 equiv.) in THF (60.00 mL) was stirred at 0° C. for 1 h and then concentrated under vacuum to afford benzo[d]oxazol-5-ol 4 (crude, 2.30 g) as a black oil, which was used for the next step without further purification. LCMS (ESI, m z): 136 [M+H]$^+$.

Step 3: A mixture of benzo[d]oxazol-5-ol 4 (1.28 g, 8.16 mmol, 1.00 equiv.), 1-fluoro-2-methyl-4-nitrobenzene 5 (1.39 g, 8.98 mmol, 1.10 equiv.) and $K_2CO_3$ (3.38 g, 24.48 mmol, 3.00 equiv.) in DMF (30.00 mL) was stirred at 50° C. for 16 h. The resulting mixture was diluted with water and extracted with EtOAc 3 times. The organic layers were combined, washed with brine, dried over $Na_2SO_4$ and concentrated under vacuum. The residue was purified by flash chromatography on silica gel (0-20% MeOH in DCM) to afford 5-(2-methyl-4-nitrophenoxy)benzo[d]oxazole 6 (610.0 mg, 28%) as a yellow solid. $^1$H NMR (400 MHz, DMSO-d6) δ 8.84 (s, 1H), 8.26 (s, 1H), 8.04 (d, J=9.2 Hz, 1H), 7.89 (d, J=8.8 Hz, 1H), 7.63 (s, 1H), 7.27 (d, J=8.8 Hz, 1H), 6.81 (d, J=9.2 Hz, 1H), 2.43 (s, 3H). LCMS (ESI, m z): 271 [M+H]$^+$.

Step 1: To a stirred solution of 4-amino-2-methylphenol 8 (3.2 g, 25.9 mmol) in DMSO (50 mL) was added potassium tert-butoxide (7.0 g, 61.3 mmol). After stirring at r.t for 0.5 h, 4,6-dichloropyridin-2-amine 9 (5.0 g, 30.7 mmol) was added. The reaction was stirred at 80° C. under N₂ for 18 hrs. After cooling to r.t., the reaction mixture was poured into water (150 mL) and extracted with EtOAc (50 mL×3). The combined organic layers were washed with brine (100 mL), dried over Na₂SO₄ and concentrated to dryness. The residue was purified by flash chromatography (0-100% of EtOAc in PE) to give 4-(4-amino-2-methylphenoxy)-6-chloropyridin-2-amine 10 (4.9 g, 52.2% yield) as a yellow solid. LCMS (ESI) (m/z): 250 [M+H]⁺.

Step 2: To a stirred solution of 4-(4-amino-2-methylphenoxy)-6-chloropyridin-2-amine 10 (3.0 g, 12.0 mmol) in DCM (20 mL) were added pyridine (1.4 g, 18.0 mmol) and acetic anhydride (1.2 g, 12.0 mmol) at 0° C. The reaction was stirred at r.t for 1 h, and then concentrated to dryness. The residue was purified by flash chromatography (0-33% of EtOAc in PE) to give N-(4-((2-amino-6-chloropyridin-4-yl)oxy)-3-methylphenyl)acetamide 11 (2.5 g, 71.3% yield) as a yellow oil. LCMS (ESI) m/z: 292 [M+H]⁺.

Step 3: To a solution of N-(4-((2-amino-6-chloropyridin-4-yl)oxy)-3-methylphenyl)acetamide 11 (2.5 g, 8.6 mmol) in EtOH (20 mL) was added DMF-DMA (3.1 g, 25.7 mmol). The reaction was degassed with N₂ and stirred at 80° C. for 36 hrs. The reaction was concentrated to dryness. The residue was purified by flash chromatography (0-66% of EtOAc in PE) to give (E)-N-(4-((2-chloro-6-(((dimethylamino)methylene)amino)pyridin-4-yl)oxy)-3-methylphenyl)acetamide 12 (2.5 g, 84.1% yield) as a yellow solid. LCMS ESI (m/z): 347 [M+H]⁺.

Step 4: To a stirred solution of (E)-N-(4-((2-chloro-6-(((dimethylamino)methylene)amino)pyridin-4-yl)oxy)-3-methylphenyl)acetamide 12 (1.0 g, 2.9 mmol) in MeOH (20 mL) were added hydroxylamine-O-sulfonic acid (0.3 g, 3.0 mmol) and pyridine (0.3 g, 4.3 mmol) at 0° C. The mixture was degassed with N₂ and stirred at r.t for 18 hrs. The reaction was concentrated to dryness. The residue was dissolved in THF (20 mL) and trifluoroacetic anhydride (0.7 g, 3.5 mmol) was added. The reaction was stirred at 40° C. overnight, then quenched with ice water (0.5 mL) and concentrated to dryness. The residue was purified by flash chromatography (0-100% of EtOAc in PE) to give N-(4-((5-chloro-[1,2,4]triazolo[1,5-a]pyridin-7-yl)oxy)-3-methylphenyl)acetamide 13 (150 mg, 12.3% yield) as a yellow oil. LCMS ESI (m/z): 317 [M+H]⁺.

Step 5: To a stirred solution of N-(4-((5-chloro-[1,2,4]triazolo[1,5-a]pyridin-7-yl)oxy)-3-methylphenyl)acetamide 13 (150 mg, 0.5 mmol) in MeOH (2 mL) was added conc. HCl (0.2 mL, 12 N). The reaction was stirred at 80° C. for 18 hrs. The reaction was concentrated and purified by prep-TLC (DCM:MeOH=10:1) to give 4-((5-chloro-[1,2,4]triazolo[1,5-a]pyridin-7-yl)oxy)-3-methylaniline 14 (80 mg, 61.5% yield) as a yellow solid. LCMS ESI (m/z): 275 [M+H]⁺.

Synthesis of 4-((5-methoxy-[1,2,4]triazolo[1,5-a]pyridin-7-yl)oxy)-3-methylaniline 16

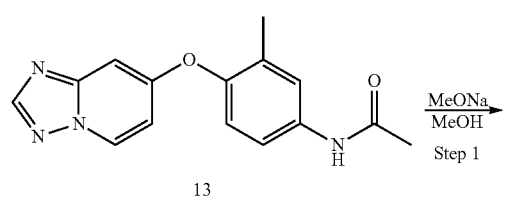

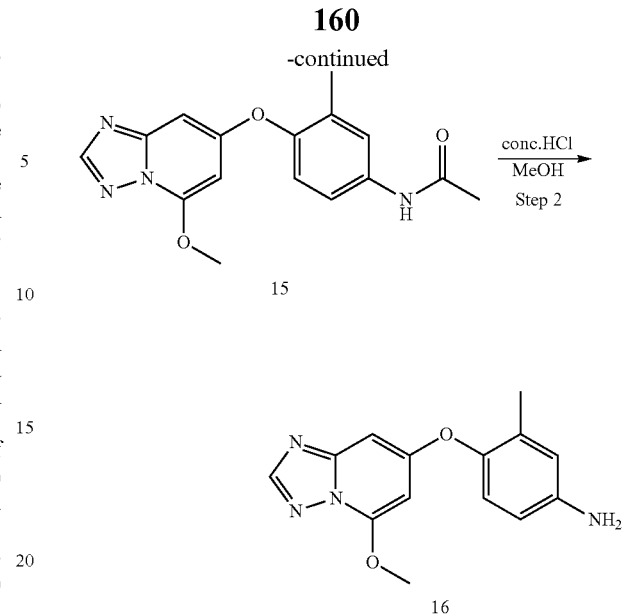

Step 1: To a solution of N-[4-({5-chloro-[1,2,4]triazolo[1,5-a]pyridin-7-yl}oxy)-3-methylphenyl]acetamide 13 (150 mg, 0.5 mmol) in MeOH (5.0 mL) was added sodium methoxide (256 mg, 1.4 mmol). The reaction was stirred at 70° C. for 4 hours. After cooling to r.t., the reaction was quenched by the addition of saturated aqueous NH₄Cl. The reaction mixture was extracted with EA (2×10 mL). The combined extracts were washed with water (5 mL), brine (5 mL), dried over anhydrous Na₂SO₄, filtered and concentrated to give crude N-[4-({5-methoxy-[1,2,4]triazolo[1,5-a]pyridin-7-yl}oxy)-3-methylphenyl]acetamide 15 (148 mg, 100%) as a brown solid. The residue was used directly in the next step. LCMS ESI (m/z): 313 [M+H]⁺.

Step 2: To a solution of N-[4-({5-methoxy-[1,2,4]triazolo[1,5-a]pyridin-7-yl}oxy)-3-methylphenyl]acetamide 15 (140 mg, 0.5 mmol) in MeOH (5.0 mL) was added conc. HCl (1.0 mL). The reaction was stirred at 70° C. overnight. After cooling to 0° C., the reaction mixture was neutralized with aq. NH₃ and then concentrated in vacuo. The residue was purified by prep-TLC (6% of MeOH in DCM) to give 4-((5-methoxy-[1,2,4]triazolo[1,5-a]pyridin-7-yl)oxy)-3-methylaniline 16 (42 mg, 34.7%) as a light yellow solid. LCMS (ESI) m/z: 271[M+H]⁺.

Synthesis of 3-methyl-4-({5-methyl-[1,2,4]triazolo[1,5-a]pyridin-7-yl}oxy)aniline 26

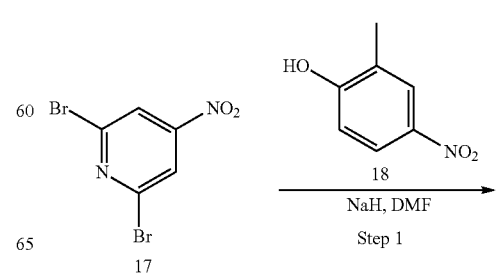

-continued

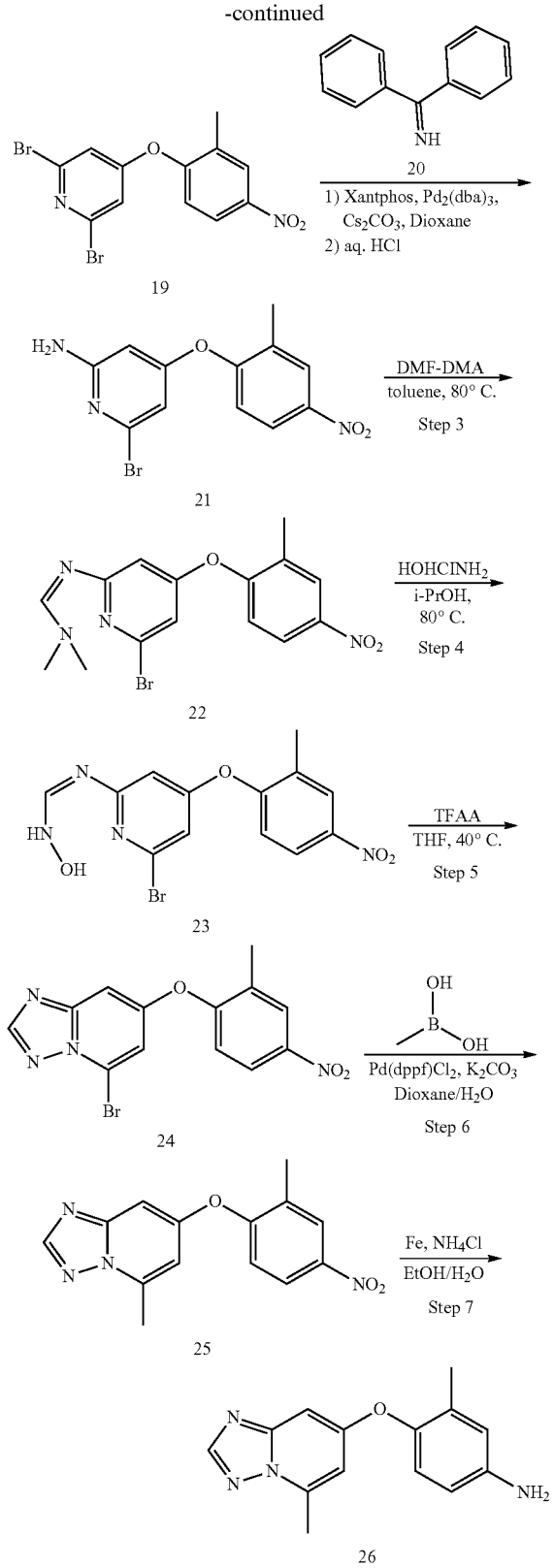

Step 1: To a stirred solution of 2-methyl-4-nitrophenol 17 (2.70 g, 17.7 mmol) in DMF (50 mL) was added NaH (0.71 g, 17.7 mmol, 60% in mineral oil) at 0° C. under N₂. After stirring at 0° C. for 30 min, a solution of 2,6-dibromo-4-nitropyridine 18 (5.0 g, 17.7 mmol) in DMF (30 mL) was added at 0° C. The reaction was stirred at 70° C. overnight, then quenched with sat. NH₄Cl (10 mL) and extracted with EtOAc (100 mL×2). The combined organic solution was dried over Na₂SO₄ and concentrated to dryness. The residue was purified by chromatography on silica gel (PE:EtOAc=5:1) to give 2,6-dibromo-4-(2-methyl-4-nitrophenoxy)pyridine 19 (4.4 g, 48.6% yield) as a yellow solid. LCMS (ESI) m/z: 387/389/391 [M+H]⁺.

Step 2: To a stirred solution of 2,6-dibromo-4-(2-methyl-4-nitrophenoxy)pyridine 19 (4.40 g, 8.66 mmol) and diphenylmethanimine 20 (1.5 mL, 8.66 mmol) in dioxane (100 mL), were added Xantphos (1.0 g, 1.73 mmol), Pd₂(dba)₃ (0.79 g, 0.87 mmol) and Cs₂CO₃ (5.64 g, 17.3 mmol) at 25° C. After stirring at 80° C. for 4 h under N₂, LCMS showed the reaction worked well. HCl (26 mL, 1M) was then added to this solution at 25° C. This reaction was stirred at 25° C. for 1 h. Then NaHCO₃ solution was added to adjust the PH>7. Then the mixture was extracted with EtOAc (100 mL×2). The combined organic solution was dried over Na₂SO₄ and concentrated to dryness. The residue was purified by chromatography on silica gel (PE:EtOAc=3:1) to give 6-bromo-4-(2-methyl-4-nitrophenoxy)pyridin-2-amine 21 (1.21 g, 43.1% yield) as a yellow solid. LCMS (ESI) m/z: 324/326 [M+H]⁺.

Step 3: To a stirred solution of 6-bromo-4-(2-methyl-4-nitrophenoxy)pyridin-2-amine 21 (1.21 g, 3.74 mmol) in toluene (20 mL) was added DMF-DMA (0.58 g, 4.86 mmol) at 25° C. The reaction was stirred at 80° C. overnight. LCMS showed the reaction worked well. Then the reaction mixture was concentrated to give crude product (Z)—N'-[6-bromo-4-(2-methyl-4-nitrophenoxy)pyridin-2-yl]-N,N-dimethylmethanimidamide 22 (1.42 g, 80.2% yield) as a brown oil. LCMS (ESI) m/z: 379/381 [M+H]⁺.

Step 4: To a stirred solution of (Z)—N'-[6-bromo-4-(2-methyl-4-nitrophenoxy)pyridin-2-yl]-N,N-dimethylmethanimidamide 22 (1.42 g, 3.75 mmol) in i-PrOH (20 mL) was added hydroxylamine.HCl salt (0.29 g, 4.12 mmol) at 25° C. After stirring at 80° C. for 1 h, LCMS showed the reaction worked well. The mixture was diluted by DCM (60 mL) and washed by water (20 mL). This separated organic solution was dried over Na₂SO₄ and concentrated to give crude product (Z)—N'-[6-bromo-4-(2-methyl-4-nitrophenoxy)pyridin-2-yl]-N-hydroxymethanimidamide 23 (1.38 g, 70.5% yield) as a yellow solid. LCMS (ESI) m/z: 367/369 [M+H]⁺.

Step 5: To a stirred solution of (Z)—N'-[6-bromo-4-(2-methyl-4-nitrophenoxy)pyridin-2-yl]-N-hydroxymethanimidamide 23 (1.38 g, 3.759 mmol) in THF (20 mL) was added trifluoroacetic anhydride (0.87 g, 4.13 mmol) at 25° C. After stirring at 40° C. overnight under N₂, LCMS showed the reaction worked well. The reaction mixture was added NaHCO₃ solution to adjust the PH to greater than 7. And then the mixture was extracted with EtOAc (20 mL×2), dried over Na₂SO₄ and concentrated to dryness. The residue was purified by chromatography on silica gel (PE:EtOAc=2:1) to give 5-bromo-7-(2-methyl-4-nitrophenoxy)-[1,2,4]triazolo[1,5-a]pyridine 24 (300 mg, 22.9% yield) as a yellow solid. LCMS (ESI) m/z: 349/351 [M+H]⁺.

Step 6: To a stirred solution of 5-bromo-7-(2-methyl-4-nitrophenoxy)-[1,2,4]triazolo[1,5-a]pyridine 24 (300 mg, 0.86 mmol) and methylboronic acid (61.7 mg, 1.03 mmol) in 1,4-dioxane (5 mL) and water (1 mL) was added Pd(dppf)Cl₂ (126 mg, 0.17 mmol) and K₂CO₃ (238 mg, 1.72 mmol) at r.t. The reaction was degassed under N₂ atmosphere for three times and stirred at 80° C. overnight. The reaction was cooled to r.t, diluted with EtOAc (25 mL). This organic solution was washed with brine (25 mL), dried over Na$_2$SO$_4$ and concentrated to give crude product 5-methyl-7-(2-methyl-4-nitrophenoxy)-[1,2,4]triazolo[1,5-a]pyridine 25 (244 mg, 80.0% yield) as a black solid. LCMS (ESI) m/z: 285 [M+H]$^+$.

Step 7: To a mixture of 5-methyl-7-(2-methyl-4-nitrophenoxy)-[1,2,4]triazolo[1,5-a]pyridine 25 (244 mg, 0.86 mmol) in EtOH (5 mL) and water (1 mL) were added iron powder (479 mg, 8.58 mmol) and NH$_4$Cl (459 mg, 8.58 mmol). This mixture was stirred at 80° C. for 2 hours. Then this mixture was filtered immediately and concentrated. The residue was purified by column chromatography on silica gel (PE:EA=0:1) to give 3-methyl-4-({5-methyl-[1,2,4]triazolo[1,5-a]pyridin-7-yl}oxy)aniline 26 (133 mg, 61.0% yield) as a yellow solid. LCMS (ESI) m/z: 255 [M+H]$^+$.

Synthesis of 4-([1,2,4]triazolo[1,5-a]pyridin-7-yloxy)-2-fluoro-3-(trifluoromethyl)aniline 31

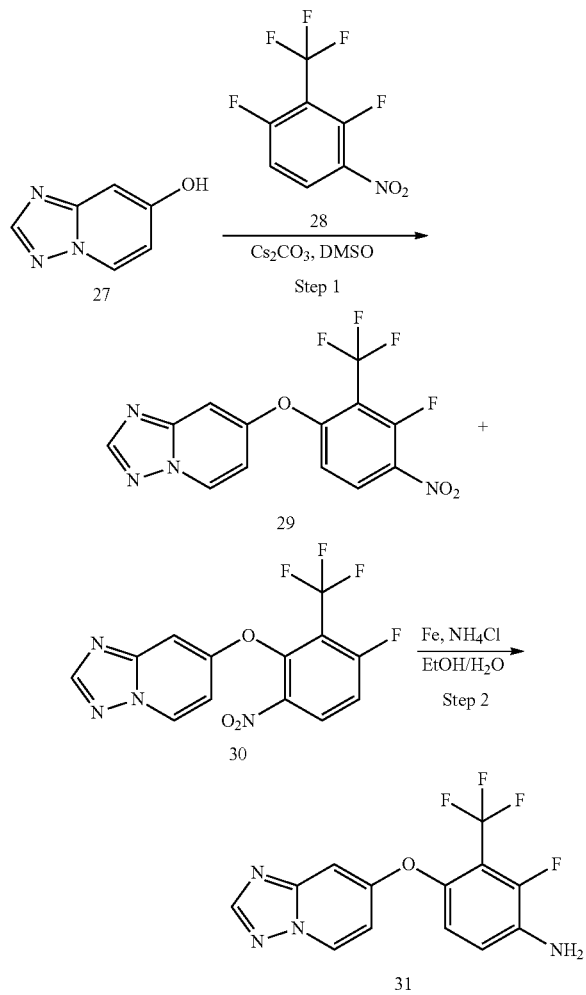

pleted. The reaction mixture was quenched by adding ice-water (100 mL) and extracted with EtOAc (3×50 mL). The combined organic phases were washed with brine (100 mL), dried over anhydrous Na$_2$SO$_4$, filtered and concentrated in vacuo to dryness to give a mixture of 7-(3-fluoro-4-nitro-2-(trifluoromethyl)phenoxy)-[1,2,4]triazolo[1,5-a]pyridine 29 and 7-(3-fluoro-6-nitro-2-(trifluoromethyl)phenoxy)-[1,2,4]triazolo[1,5-a]pyridine 30 (1.10 g, crude) as a yellow solid. The crude product was directly used in the next step without any further purification. LCMS ESI (m/z): 343 [M+H]$^+$.

Step 2: To a solution of 7-(3-fluoro-4-nitro-2-(trifluoromethyl)phenoxy)-[1,2,4]triazolo[1,5-a]pyridine and 7-(3-fluoro-6-nitro-2-(trifluoromethyl)phenoxy)-[1,2,4]triazolo[1,5-a]pyridine (1.10 g, crude) in EtOH (30 mL) and H$_2$O (10 mL), were added Fe (0.90 g, 16.02 mmol) and NH$_4$Cl (1.72 g, 32.11 mmol). Then the resulting mixture was stirred at 75° C. for 1 h. LCMS showed the reaction was completed. The reaction mixture was concentrated in vacuo to give the residue. The residue was purified by flash chromatography with EtOAc in PE (0-10%, V/V) to give 4-([1,2,4]triazolo[1,5-a]pyridin-7-yloxy)-2-fluoro-3-(trifluoromethyl)aniline 31 (320 mg, 27.6%, yield over two steps) as a yellow solid. LCMS ESI (m/z): 313 [M+H]$^+$.

Synthesis of 4-([1,2,4]triazolo[1,5-a]pyridin-7-yloxy)-2-fluoro-3-methylaniline 35

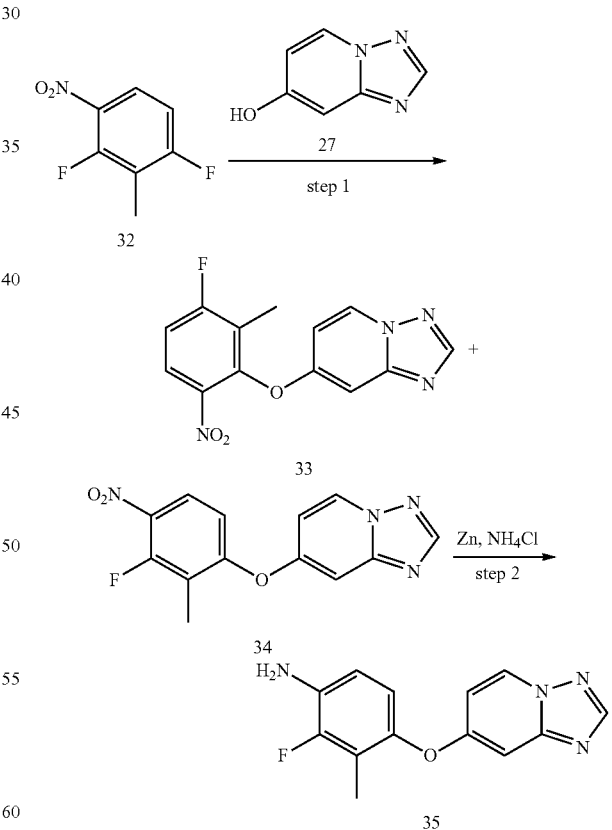

Step 1: To a stirred mixture of Cs$_2$CO$_3$ (1.44 g, 4.44 mmol) in DMSO (10 mL), was added a solution of [1,2,4]triazolo[4,3-a]pyridin-7-ol 27 (500 mg, 3.70 mmol) and 1,3-difluoro-4-nitro-2-(trifluoromethyl)benzene 28 (1.68 g, 7.40 mmol) in DMSO (10 mL) dropwise at room temperature. Then the resulting mixture was stirred at room temperature for 15 min. LCMS showed the reaction was com- Step 1: To a stirred mixture of Cs$_2$CO$_3$ (21.7 g, 66.6 mmol) in DMSO (150 mL), were added a solution of 1,3-difluoro-2-methyl-4-nitrobenzene 32 (23.1 g, 133.5 mmol) and [1,2,4]triazolo[1,5-a]pyridin-7-ol 27 (9.0 g, 66.7 mmol) in DMSO (300 mL) dropwise at 80° C. in a period of 1 h. Then the resulting mixture was stirred at 80° C. for another 0.5 h. LCMS showed the reaction was completed. The reaction mixture was cooled down to room temperature, diluted with water (800 mL) and extracted with EtOAc (3×600 mL). The combined organic phases were washed with brine (600 mL), dried over anhydrous Na$_2$SO$_4$, filtered and concentrated in vacuo to give a mixture of 7-(3-fluoro-2-methyl-4-nitrophenoxy)-[1,2,4]triazolo[1,5-a]pyridine 33 and 7-(3-fluoro-2-methyl-6-nitrophenoxy)-[1,2,4]triazolo[1,5-a]pyridine 34 (21.1 g, crude) as a yellow oil. The crude product was directly used in the next step without further purification. LCMS ESI (m/z): 289 [M+H]$^+$ Step 2: To a mixture of 7-(3-fluoro-2-methyl-4-nitrophenoxy)-[1,2,4]triazolo[1,5-a]pyridine and 7-(3-fluoro-2-methyl-6-nitrophenoxy)-[1,2,4]triazolo[1,5-a]pyridine (21.1 g, crude) in EtOH (200 mL), were added Fe (18.7 g, 333.7 mmol), NH$_4$Cl (35.4 g, 667.4 mmol) and water (60 mL). Then the resulting mixture was stirred at 80° C. for 1 h. LCMS showed the reaction was completed. The reaction mixture was cooled down to room temperature, diluted with EtOAc (600 mL) and filtered. The filtrate was washed with brine (500 mL), dried over anhydrous Na$_2$SO$_4$, filtered and concentrated in vacuo to give the crude product. The crude product was purified by flash column chromatography on silica gel with EtOAc in PE (30-70%, V/V) to give pure 4-([1,2,4]triazolo[1,5-a]pyridin-7-yloxy)-2-fluoro-3-methylaniline 35 (3.91 g, 22.7%, yield over two steps) as a light yellow solid and some crude product as a gray solid. LCMS ESI (m/z): 259 [M+H]$^+$ Synthesis of 2-fluoro-3-methyl-4-((1-methyl-1lH-benzo[d]imidazol-5-yl)oxy)aniline 38

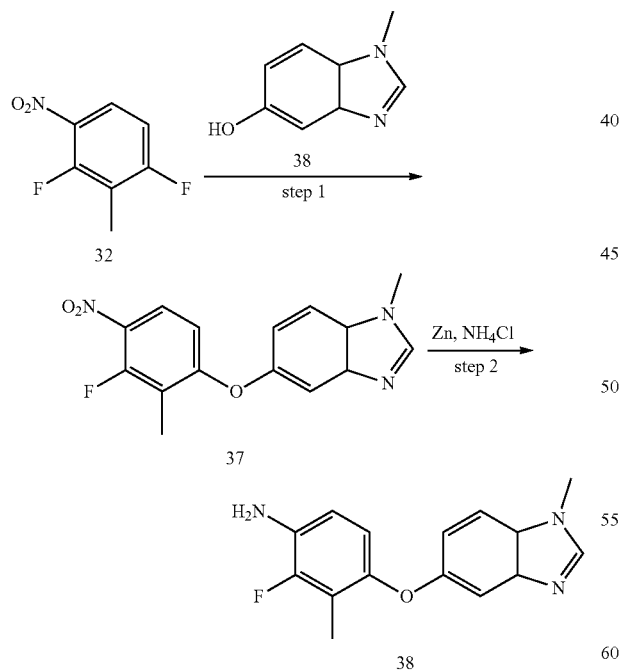

Step 1: A mixture of 1-methyl-1H-benzo[d]imidazol-5-ol 36 (5.5 g, 37.16 mol, 1.00 equiv), 1,3-difluoro-2-methyl-4-nitrobenzene (12.8 g, 74.32 mol, 2.00 equiv) 32 and K$_2$CO$_3$ (15.4 g, 111.48 mol, 3.00 equiv) in DMF (50.0 mL) was stirred at ambient temperature for 16 h and then filtered through a pad of celite. The filtrate was concentrated under vacuum. The residue was purified by reverse phase flash chromatography on C18 silica gel (0-70% acetonitrile in water (containing 0.05% NH$_4$HCO$_3$)) to afford 5-(3-fluoro-2-methyl-4-nitrophenoxy)-1-methyl-1H-benzo[d]imidazole 37 (1.4 g, 12%) as a yellow solid. LCMS (ESI, m/z): 304 [M+H]$^+$.

Step 2: A mixture of 5-(3-fluoro-2-methyl-4-nitrophenoxy)-1-methyl-1H-benzo[d]imidazole 37 (1.4 g, 4.65 mol, 1.00 equiv) and zinc powder (1.5 g, 23 mol, 5.00 equiv) in MeOH (22.4 mL) and water (5.6 mL) was stirred at 70° C. for 3 h and then filtered through a pad of celite. The filtrate was diluted with water and the mixture was extracted with DCM 3 times. The organic layers were dried over Na$_2$SO$_4$ and concentrated under vacuum to afford 2-fluoro-3-methyl-4-((1-methyl-1H-benzo[d]imidazol-5-yl)oxy)aniline 38 (crude, 3.0 g) as a yellow solid, which was used for the next step without further purification. 1H NMR (300 MHz, DMSO-d6) δ 8.36 (s, 1H), 7.59 (d, J=9.0 Hz, 1H), 7.00-6.96 (m, 2H), 6.60 (t, J=9.0 Hz, 1H), 6.51 (d, J=8.7 Hz, 1H), 4.96 (s, 2H), 3.88 (s, 3H), 1.95 (d, J=5.4 Hz, 3H). LCMS (ESI, m/z): 274 [M+H]$^+$.

Synthesis of 4-([1,2,4]triazolo[1,5-a]pyridin-7-yloxy)-2-fluoro-3-(difluoromethyl)aniline 42

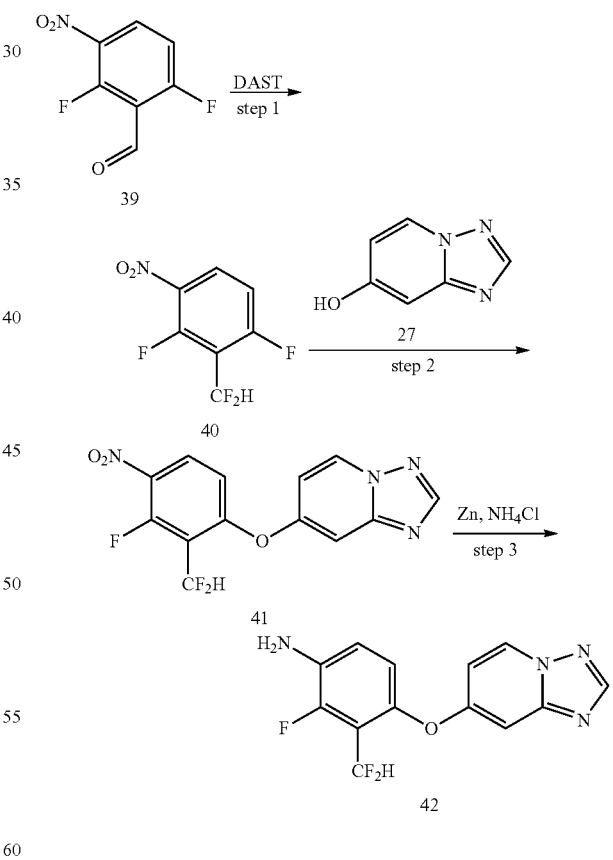

Step 1: To a stirred solution of 2,6-difluoro-3-nitrobenzaldehyde 49 g, 24.05 mmol, 1.00 equiv) in DCM (30.0 mL) was added dropwise a solution of DAST (11.6 g, 72.15 mmol, 3.0 equiv) in DCM (10 mL) at −78° C. under N$_2$ atmosphere. The resulting mixture was stirred at this temperature for 4 h and then quenched at 0° C. with water/ice and extracted with DCM 3 times. The combined organic layers were concentrated under vacuum to afford 2-(difluoromethyl)-1,3-difluoro-4-nitrobenzene 40 (crude, 4.70 g), which was used in the next step directly without further purification.

Step 2: To a stirred mixture of 2-(difluoromethyl)-1,3-difluoro-4-nitrobenzene 40 (3.60 g, 17.21 mmol, 1.00 equiv) and [1,2,4]triazolo[1,5-a]pyridin-7-ol 27 (2.56 g, 18.93 mmol, 1.10 equiv) in acetonitrile (20.0 mL) at ambient temperature was added DIEA (6.68 g, 51.65 mmol, 3.00 equiv). The resulting mixture was stirred at this temperature for 4 h and then diluted with water and extracted with EtOAc 3 times. The combined organic layers were washed with brine, dried over $Na_2SO_4$ and concentrated under vacuum. The residue was purified by flash chromatography on silica gel (0-60% EtOAc in petroleum ether) to afford 7-[2-(difluoromethyl)-3-fluoro-4-nitrophenoxy]-[1,2,4]triazolo[1,5-a]pyridine 41 (850 mg, 14%) as a yellow solid. LCMS (ESI, m z): 325 $[M+H]^+$.

Step 3: To a stirred mixture of 7-[2-(difluoromethyl)-3-fluoro-4-nitrophenoxy]-[1,2,4]triazolo[1,5-a]pyridine 41 (500.0 mg, 1.54 mmol, 1.00 equiv) in THF (10 mL) and water (2 mL) was added Zn powder (806.6 mg, 12.33 mmol, 8.00 equiv) and $NH_4Cl$ (659.9 mg, 12.33 mmol, 8.00 equiv). The resulting mixture was stirred at 70° C. for 3 h and filtered. The filtrate was concentrated under vacuum. The residue was diluted with water and extracted with EtOAc 3 times.

The combined organic layers were dried over $Na_2SO_4$ and concentrated under vacuum to afford 3-(difluoromethyl)-2-fluoro-4-{[1,2,4]triazolo[1,5-a]pyridin-7-yloxy}aniline 42 (crude, 420 mg) as a yellow solid, which was used for the next step without further purification. LCMS (ESI, m z): 295 $[M+H]^+$.

Synthesis of 5-([1,2,4]triazolo[1,5-a]pyridin-7-yloxy)-3-fluoro-4-methylpyridin-2-amine 49

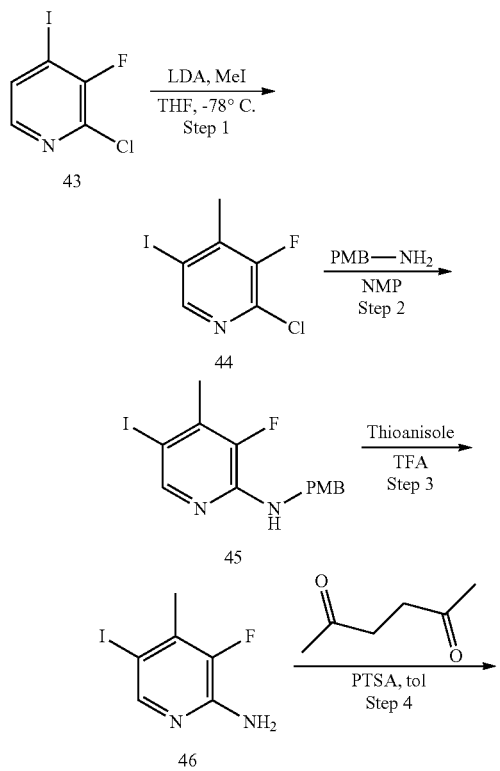

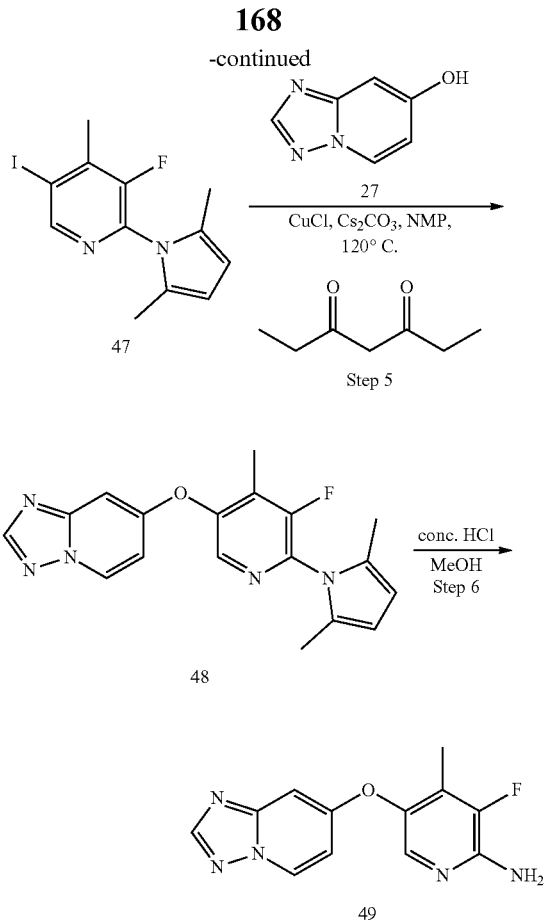

Step 1: To a solution of LDA (21.3 mL, 42.73 mmol, 2.0 M in toluene) in THF (60 mL) was added a solution of 2-chloro-3-fluoro-4-iodopyridine 43 (10.0 g, 38.84 mmol) in THF (20 mL). Then the resulting mixture was stirred under $N_2$ at −78° C. for 4 h, iodomethane (2.7 mL, 42.73 mmol) was added and the reaction mixture was stirred at −78° C. for additional 1 h. After additional 1 h, the reaction was quenched with sat. aqueous $NH_4Cl$ solution (50 mL), warmed to room temperature and extracted EtOAc (2×80 mL). The organic phases were washed with brine (50 mL), dried over anhydrous $Na_2SO_4$, filtered and concentrated in vacuo to give the crude product. The crude product was purified by flash chromatography with EtOAc in PE (0-3%, V/V) to give 2-chloro-3-fluoro-5-iodo-4-methylpyridine 44 (6.10 g, 57.8% yield) as a yellow oil. LC/MS ESI (m/z): 272/274 $[M+H]^+$.

Step 2: To a solution of 2-chloro-3-fluoro-5-iodo-4-methylpyridine 44 (2.50 g, 9.20 mmol) in NMP (10 mL) was added (4-methoxyphenyl)methanamine (1.80 mL, 13.81 mmol). Then the resulting mixture was stirred at 120° C. for 16 h. LCMS showed the reaction was completed. The reaction mixture was cooled down to room temperature, diluted with water (30 mL) and extracted with EtOAc (3×30 mL). The combined organic phases were washed with brine (2×25 mL), dried over anhydrous $Na_2SO_4$, filtered and concentrated in vacuo to give the crude product. The crude product was purified by flash chromatography with EtOAc in PE (0-5%, V/V) to give 3-fluoro-5-iodo-N-(4-methoxybenzyl)-4-methylpyridin-2-amine 45 (1.40 g, 40.8% yield) as a yellow oil. LCMS ESI (m/z): 373 $[M+H]^+$.

Step 3: To a solution of 3-fluoro-5-iodo-N-(4-methoxybenzyl)-4-methylpyridin-2-amine 45 (650 mg, 1.74 mmol) in TFA (10 mL), was added thioanisole (10 mg, 0.087 mmol). Then the resulting mixture was degassed under $N_2$ for twice and stirred at room temperature for 16 h. LCMS showed the reaction was completed. The reaction mixture was concentrated in vacuo to give the residue, the residue was basified by adding sat. aqueous $NaHCO_3$ solution to pH~ 8 and extracted with DCM (3×20 mL). The organic phases were washed with brine (20 mL), dried over anhydrous $Na_2SO_4$, filtered and concentrated in vacuo to give the crude product. The crude product was purified by flash chromatography with EtOAc in PE (0-10%, V/V) to give 3-fluoro-5-iodo-4-methylpyridin-2-amine 46 (410 mg, 93.1% yield) as a white solid. LCMS ESI (m/z): 253 [M+H]$^+$.

Step 4: To a solution of 3-fluoro-5-iodo-4-methylpyridin-2-amine 46 (410 mg, 1.62 mmol) in toluene (10 mL), were added hexane-2,5-dione (557 mg, 4.88 mmol) and PTSA (14 mg, 0.081 mmol). Then the resulting mixture was stirred at 120° C. for 16 h. LCMS showed the reaction was completed. The reaction mixture was cooled down to room temperature and concentrated in vacuo to give the residue. The residue was diluted with water (10 mL) and extracted with EtOAc (3×15 mL). The combined organic phases were washed with brine (2×15 mL), dried over anhydrous $Na_2SO_4$, filtered and concentrated in vacuo to give the crude product. The crude product was purified by flash chromatography with EtOAc in PE (0-5%, V/V) to give 2-(2,5-dimethyl-1H-pyrrol-1-yl)-3-fluoro-5-iodo-4-methylpyridine 47 (440 mg, 81.9% yield) as a yellow oil. LCMS ESI (m/z): 331[M+H]$^+$.

Step 5: To the solution of 2-(2,5-dimethyl-1H-pyrrol-1-yl)-3-fluoro-5-iodo-4-methylpyridine 47 (296 mg, 0.89 mmol) in NMP (15 mL), were added [1,2,4]triazolo[1,5-a]pyridin-7-ol (242 mg, 1.79 mmol), CuCl (27 mg, 0.26 mmol), 2,2,6,6-tetramethylheptane-3,5-dione (64 mg, 0.44 mmol) and $Cs_2CO_3$ (584 mg, 1.79 mmol). The reaction mixture was degassed under $N_2$ for three times and stirred at 120° C. for 16 h. LCMS showed the reaction was completed. The reaction mixture was cooled down to room temperature, diluted with water (20 mL) and extracted with EtOAc (3×20 mL). The combined organic phases were washed with brine (2×20 mL), dried over anhydrous $Na_2SO_4$, filtered and concentrated in vacuo to give the crude product. The crude product was purified by flash chromatography with EtOAc in PE (0-30%, V/V) to give 7-((6-(2,5-dimethyl-1H-pyrrol-1-yl)-5-fluoro-4-methylpyridin-3-yl)oxy)-[1,2,4]triazolo[1,5-a]pyridine 48 (54 mg, 17.8% yield) as a yellow solid. LCMS ESI (m/z): 338 [M+H]$^+$.

Step 6: To a solution of 7-((6-(2,5-dimethyl-1H-pyrrol-1-yl)-5-fluoro-4-methylpyridin-3-yl)oxy)-[1,2,4]triazolo[1,5-a]pyridine 48 (54 mg, 0.16 mmol) in MeOH (3 mL) was added conc. HCl (3 mL). Then the resulting mixture was stirred at 60° C. for 16 h. LCMS showed the reaction was completed. The reaction mixture was cooled down to room temperature and concentrated in vacuo to give the residue. The residue was basified by adding sat. aqueous $NaHCO_3$ solution to pH~8 and extracted with DCM (3×15 mL). The combined organic phases were washed with brine (2×15 mL), dried over anhydrous $Na_2SO_4$, filtered and concentrated in vacuo to give the crude product. The crude product was purified by flash chromatography with MeOH in DCM (0-7%, V/V) to give 5-([1,2,4]triazolo[1,5-a]pyridin-7-yloxy)-3-fluoro-4-methylpyridin-2-amine 49 (38 mg, 91.6% yield) as a yellow solid. LCMS ESI (m/z): 260 [M+H]$^+$.

Synthesis of 4-([1,2,4]triazolo[1,5-a]pyrimidin-5-yloxy)-2-fluoro-3-methylaniline 52

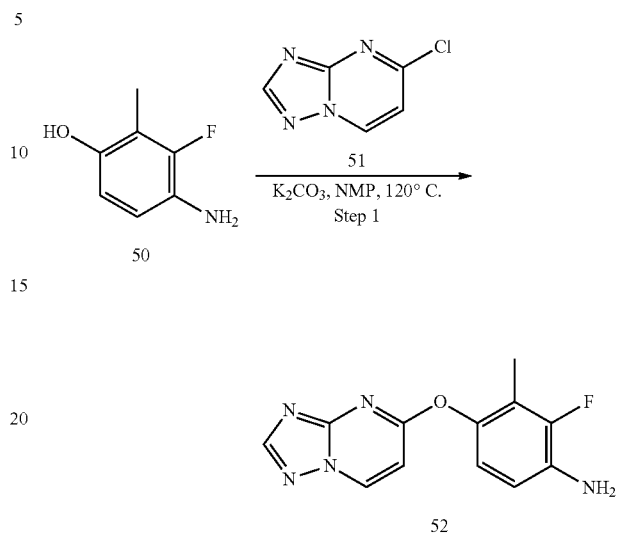

Step 1: To a stirred solution of 4-amino-3-fluoro-2-methylphenol 50 (92 mg, 0.65 mmol, synthesized based on the preparation disclosed in WO2010051373) and 5-chloro-[1,2,4]triazolo[1,5-a]pyrimidine 51 (120 mg, 0.78 mmol) in NMP (4 mL), was added $K_2CO_3$ (270 mg, 1.96 mmol). Then the resulting mixture was stirred at 120° C. for 2 h. LCMS showed the reaction was completed. The reaction mixture was cooled down to room temperature, diluted with sat. aqueous $NH_4Cl$ solution (20 mL) and extracted with EtOAc (3×10 mL). The combined organic phases were washed with sat. aqueous $NH_4Cl$ solution (10 mL) and brine (10 mL), dried over anhydrous $Na_2SO_4$, filtered and concentrated in vacuo to give the crude product. The crude product was triturated with MeOH/DCM (1/30, V/V) to give 4-([1,2,4]triazolo[1,5-a]pyrimidin-5-yloxy)-2-fluoro-3-methylaniline 52 (111 mg, 65.7% yield) as a brown solid. LCMS ESI (m/z): 260 [M+H]$^+$ Synthesis of 2-fluoro-4-[(1-methyl-1,3-benzodiazol-5-yl)oxy]aniline 56

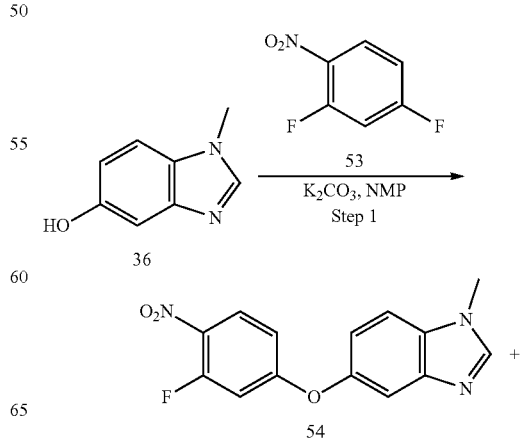

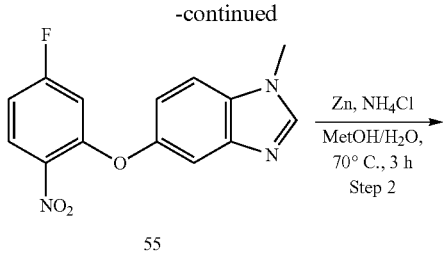

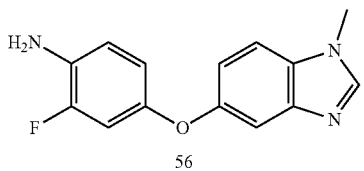

Step 1: A mixture of 1-methyl-1,3-benzodiazol-5-ol 36 (500 mg, 3.38 mmol, 1 equiv), 2,4-difluoro-1-nitrobenzene 53 (644.25 mg, 4.05 mmol, 1.2 equiv) and K$_2$CO$_3$ (1.40 g, 10.14 mmol, 3 equiv) in NMP (6 mL) was stirred at ambient temperature for 3 h and then filtered. The filtrate was diluted with EtOAc. The organic solution was washed with water twice and brine, dried over Na$_2$SO$_4$ and concentrated under vacuum. The residue was purified by flash chromatography on silica gel (0-10% MeOH in DCM) to afford a mixture of 54 and 55 (900 mg, 92%) as a yellow solid. LCMS (ESI, m z): 288 [M+H]$^+$.

Step 2: A mixture of 5-(3-fluoro-4-nitrophenoxy)-1-methyl-1,3-benzodiazole (980 mg, 3.41 mmol, 1 equiv), Zn (2.23 g, 34.12 mmol, 10 equiv) and NH$_4$Cl (1.82 g, 34.12 mmol, 10 equiv) in MeOH (5 mL) and H$_2$O (5 mL) was stirred at 70° C. for 3 h under N$_2$ atmosphere and then filtered. The filtrate was concentrated under vacuum. The residue was purified by flash chromatography on silica gel (0-10% MeOH in DCM) to afford 2-fluoro-4-[(1-methyl-1,3-benzodiazol-5-yl)oxy]aniline (470 mg, 53%) 56 as a yellow solid. LCMS (ESI, m z): 258 [M+H]$^+$.

Synthesis of 4-(imidazo[1,2-a]pyridin-7-yloxy)-3-methylaniline 59

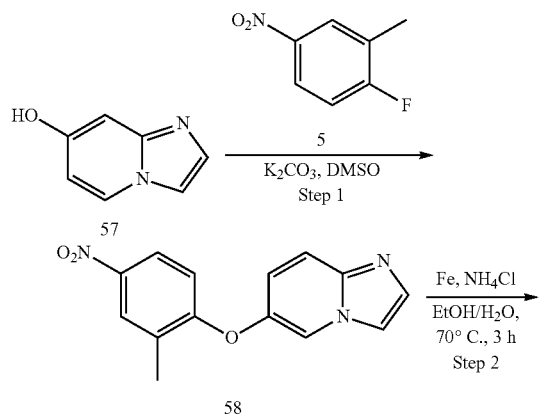

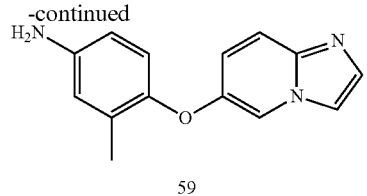

Step 1: To a solution of imidazo[1,2-a]pyridin-7-ol 57 (300 mg, 2.24 mmol) in DMSO (5 mL), were added 1-fluoro-2-methyl-4-nitrobenzene 5 (347 mg, 2.27 mmol) and K$_2$CO$_3$ (927 mg, 6.69 mmol). Then the resulting mixture was stirred at 100° C. for 16 h. LCMS showed the reaction was completed. The reaction mixture was cooled down to room temperature, diluted with sat. aqueous NH$_4$Cl solution (20 mL) and extracted with EtOAc (3×20 mL). The combined organic phases were washed with brine (20 mL), dried over anhydrous Na$_2$SO$_4$, filtered and concentrated in vacuo to give the crude product. The crude product was purified by column chromatography on silica gel with EtOAc in PE (0-50%, V/V) to give 7-(2-methyl-4-nitrophenoxy)imidazo[1,2-a]pyridine 58 (380 mg, 63.1% yield) as a yellow solid. LCMS ESI (m/z): 270 [M+H]$^+$.

Step 2: To a solution of 7-(2-methyl-4-nitrophenoxy) imidazo[1,2-a]pyridine 58 (380 mg, 1.41 mmol) in EtOH (10 mL) and water (2 mL), were added iron powder (788 mg, 14.11 mmol) and ammonium chloride (755 mg, 14.11 mmol). Then the resulting mixture was stirred at 80° C. for 3 h. LCMS showed the reaction was completed. The reaction mixture was cooled down to room temperature and concentrated in vacuo to give the crude product. The crude product was purified by flash chromatography with EtOAc in PE (0-90%, V/V) to give 4-(imidazo[1,2-a]pyridin-7-yloxy)-3-methylaniline 59 (180 mg, 53.30% yield) as a yellow solid. LCMS ESI (m/z): 240 [M+H]$^+$.

Synthesis of 3-methyl-4-((1-methyl-1H-indol-6-yl)oxy)aniline 63

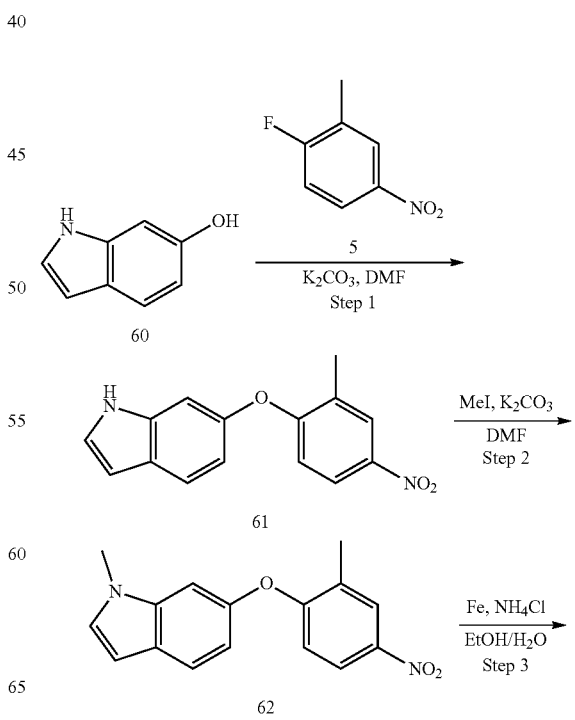

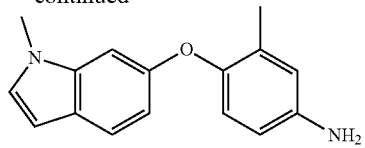

63

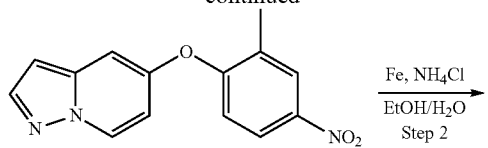

65

Step 1: To a solution of 1H-indol-6-ol 60 (940 mg, 7.1 mmol) in DMF (10 mL), were added 1-fluoro-2-methyl-4-nitrobenzene 5 (1.0 g, 6.45 mmol) and $K_2CO_3$ (1.49 g, 10.76 mmol). Then the resulting mixture was stirred at 80° C. for 16 h. LCMS showed the reaction was completed. The reaction mixture was cooled down to room temperature, diluted with sat. aqueous $NH_4Cl$ solution (20 mL) and extracted with EtOAc (3×20 mL). The combined organic phases were washed with sat. aqueous $NH_4Cl$ solution (20 mL) and brine (20 mL), dried over anhydrous $Na_2SO_4$, filtered and concentrated in vacuo to give the crude product. The crude product was purified by column chromatography on silica gel with EtOAc in PE (0-50%, V/V) to give 6-(2-methyl-4-nitrophenoxy)-1H-indole 61 (1.00 g, 57.8%) as a yellow gum. LCMS ESI (m/z): 269 $[M+H]^+$.

Step 2: To a solution of 6-(2-methyl-4-nitrophenoxy)-1H-indole 61 (686 mg, 2.56 mmol) in DMF (10 mL), were added $K_2CO_3$ (707 mg, 5.10 mmol) and iodomethane (545 mg, 3.84 mmol) was added in sequence. Then the resulting mixture was stirred at 80° C. for 16 h. LCMS showed the reaction was completed. The reaction mixture was diluted with sat. aqueous $NH_4Cl$ solution (20 mL) and extracted with EtOAc (3×20 mL). The combined organic phases were washed with sat. aqueous $NH_4Cl$ solution (20 mL) and brine (20 mL), dried over anhydrous $Na_2SO_4$, filtered and concentrated in vacuo to give the crude product. The crude product was purified by column chromatography on silica gel with EtOAc in PE (0-50%, V/V) to give 1-methyl-6-(2-methyl-4-nitrophenoxy)-1H-indole 62 (650 mg, 90.0% yield) as a yellow gum. LCMS ESI (m/z): 283 $[M+H]^+$.

Step 3: To a solution of 1-methyl-6-(2-methyl-4-nitrophenoxy)-1H-indole 62 (200 mg, 0.71 mmol) in EtOH (8 mL) and water (3 mL), were added iron powder (198 mg, 3.54 mmol) and ammonium chloride (379 mg, 7.08 mmol). Then the resulting mixture was stirred at 75° C. for 0.5 h. LCMS showed the reaction was completed. The reaction mixture was cooled down to room temperature and concentrated in vacuo to give the crude product. The crude product was purified by flash chromatography with EtOAc in PE (0-90%, V/V) to give 3-methyl-4-((1-methyl-1H-indol-6-yl)oxy)aniline 63 (135 mg, 75.5% yield) as a light-yellow gum. LCMS ESI (m/z): 253 $[M+H]^+$.

Synthesis of 3-methyl-4-(pyrazolo[1,5-a]pyridin-5-yloxy)aniline 66

Step 1: To a solution of pyrazolo[1,5-a]pyridin-5-ol 64 (150 mg, 1.12 mmol) in DMSO (5 mL), were added 1-fluoro-2-methyl-4-nitrobenzene 5 (173 mg, 1.12 mmol) and $K_2CO_3$ (464 mg, 3.36 mmol). Then the resulting mixture was stirred at 100° C. for 16 h. LCMS showed the reaction was completed. The reaction mixture was cooled down to room temperature, diluted with sat. aqueous $NH_4Cl$ solution (20 mL) and extracted with EtOAc (3×20 mL). The combined organic phases were washed with brine (20 mL), dried over anhydrous $Na_2SO_4$, filtered and concentrated in vacuo to give the crude product. The crude product was purified by column chromatography on silica gel with EtOAc in PE (0-50%, V/V) to give 5-(2-methyl-4-nitrophenoxy)pyrazolo[1,5-a]pyridine 65 (250 mg, 83.0% yield) as a yellow solid. LCMS ESI (m/z):270 $[M+H]^+$.

Step 2: To a solution of 5-(2-methyl-4-nitrophenoxy)pyrazolo[1,5-a]pyridine 65 (250 mg, 0.93 mmol) in EtOH (10 mL) and water (2 mL), were added iron powder (518 mg, 9.28 mmol) and ammonium chloride (496 mg, 9.28 mmol). Then the resulting mixture was stirred at 80° C. for 3 h. LCMS showed the reaction was completed. The reaction mixture was cooled down to room temperature and concentrated in vacuo to give the crude product. The crude product was purified by flash chromatography with EtOAc in PE (0-90%, V/V) to give 3-methyl-4-(pyrazolo[1,5-a]pyridin-5-yloxy)aniline 66 (200 mg, 90.0% yield) as a yellow solid. LCMS ESI (m/z): 240 $[M+H]^+$.

Synthesis of 2-fluoro-3-methyl-4-((3-methylimidazo[1,2-a]pyridin-7-yl)oxy)aniline 75

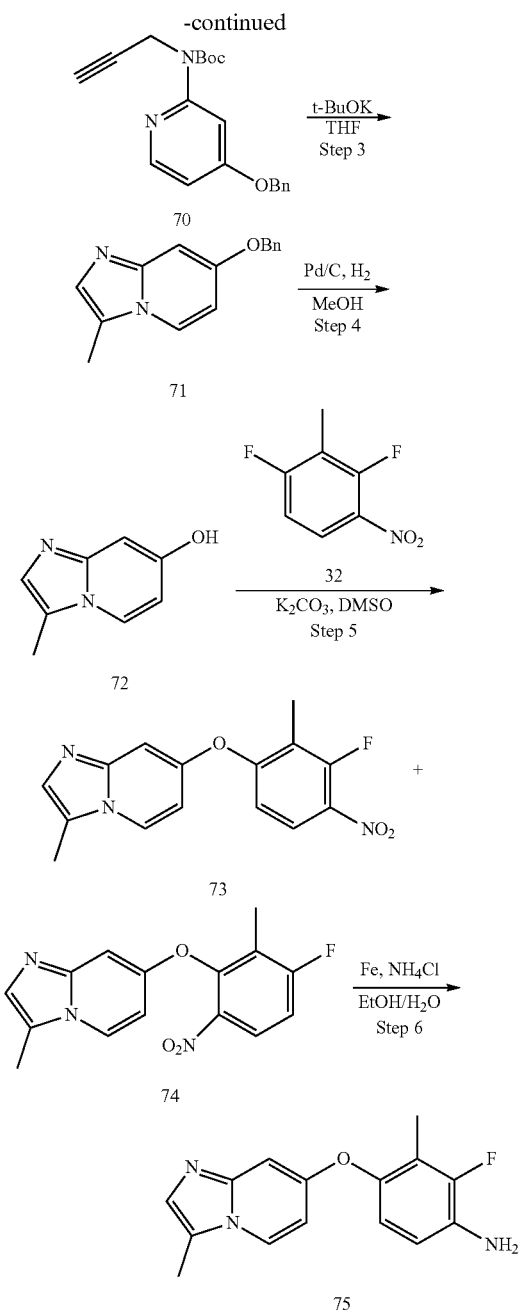

Step 1: To a solution of 4-(benzyloxy)pyridin-2-amine 67 (5.00 g, 0.025 mol) in t-BuOH (75 mL) was added Boc₂O (6.00 g, 0.027 mmol) dropwise at room temperature. Then the resulting mixture was stirred at 50° C. for 1 h. LCMS showed the reaction was completed. The reaction mixture was cooled down to room temperature and concentrated in vacuo to give the crude product. The crude product was purified by flash chromatography with EtOAc in PE (0-50%, V/V) to give tert-butyl (4-(benzyloxy)pyridin-2-yl)carbamate 68 (6.63 g, 88.5% yield) as a white solid. LCMS ESI (m/z): 301 [M+H]⁺.

Step 2: To a stirred solution of tert-butyl (4-(benzyloxy) pyridin-2-yl)carbamate 68 (6.50 g, 21.6 mmol) in DMF (50 mL), was added NaH (1.30 g, 32.5 mmol, 60% in mineral oil) at 0° C. After stirring at 0° C. for 1 h, a solution of 3-bromoprop-1-yne 69 (2.78 mL, 32.5 moml) in DMF (15 mL) was added dropwise. Then the resulting mixture was stirred at room temperature for 1 hour. LCMS showed the reaction was completed. The reaction mixture was quenched with sat. aqueous NH₄Cl solution (100 mL) and extracted with EtOAc (3×100 mL). The combined organic phases were washed with brine (100 mL), dried over anhydrous Na₂SO₄, filtered and concentrated in vacuo to give the crude product. The crude product was purified by flash chromatography with EtOAc in PE (0-50%, V/V) to give tert-butyl (4-(benzyloxy)pyridin-2-yl)(prop-2-yn-1-yl)carbamate 70 (6.08 g, 83.1% yield) as a yellow oil. LCMS ESI (m/z): 339 [M+H]⁺.

Step 3: To a solution of tert-butyl (4-(benzyloxy)pyridin-2-yl)(prop-2-yn-1-yl)carbamate 70 (6.07 g, 17.96 mmol) in THF (60 mL) was added a solution of t-BuOK (2.42 g, 21.56 mmol) in THF (10 mL) dropwise at room temperature. Then the resulting mixture was stirred at room temperature for 1 h. LCMS showed the reaction was completed. The reaction mixture was quenched with sat. aqueous NH₄Cl solution (60 mL) and extracted with EtOAc (3×60 mL). The combined organic phases were dried over anhydrous Na₂SO₄ and concentrated in vacuo to give the residue. The residue was purified by flash chromatography with EtOAc in PE (0-60%, V/V) to give 7-(benzyloxy)-3-methylimidazo[1,2-a]pyridine 71 (3.34 g, 78.2% yield) as a yellow solid. LCMS ESI (m/z): 239 [M+H]⁺.

Step 4: To a solution of 7-(benzyloxy)-3-methylimidazo [1,2-a]pyridine 71 (3.34 g, 14.05 mmol) in MeOH (30 mL) was added Pd/C (1.67 g, 10% wt). Then the resulting mixture was degassed with H₂ for three times and stirred at room temperature for overnight. LCMS showed the reaction was completed. The reaction mixture was filtered and concentrated in vacuo to give 3-methylimidazo[1,2-a]pyridin-7-ol 72 (1.44 g, 69.6% yield) as a yellow solid. LCMS ESI (m/z): 149 [M+H]⁺.

Step 5: To a stirred mixture of K₂CO₃ (4.04 g, 29.25 mmol) in DMSO (30 mL) was added a solution of 3-methylimidazo[1,2-a]pyridin-7-ol 72 (1.44 g, 9.75 mmol) and 1,3-difluoro-2-methyl-4-nitrobenzene 32 (2.02 g, 11.70 mmol) in DMSO (5 mL) dropwise at room temperature. Then the resulting mixture was stirred at room temperature for 3 h. LCMS showed the reaction was completed. The reaction mixture was quenched by adding water (60 mL) and extracted with EtOAc (3×60 mL). The combined organic phases were washed with brine (60 mL), dried over anhydrous Na₂SO₄, filtered and concentrated in vacuo to give a mixture of 7-(3-fluoro-2-methyl-4-nitrophenoxy)-3-methylimidazo[1,2-a]pyridine 73 and 7-(3-fluoro-2-methyl-6-nitrophenoxy)-3-methylimidazo[1,2-a]pyridine 74 (1.30 g, crude) as a yellow oil. The crude product was directly used in the next step without any further purification. LCMS ESI (m/z): 302 [M+H]⁺.

Step 6: To a solution of 7-(3-fluoro-2-methyl-4-nitrophenoxy)-3-methylimidazo[1,2-a]pyridine and 7-(3-fluoro-2-methyl-6-nitrophenoxy)-3-methylimidazo[1,2-a]pyridine (1.30 g, crude) in EtOH (15 mL) and water (3 mL), were added iron power (1.21 g, 21.59 mmol) and NH₄Cl (2.31 g, 43.18 mmol). Then the resulting mixture was stirred at 80° C. for 1 h. LCMS showed the reaction was completed. The reaction mixture was cooled down to room temperature and concentrated in vacuo to give the crude product. The crude product was purified by flash chromatography with EtOAc in PE (0-70%, V/V) to give 2-fluoro-3-methyl-4-((3-methylimidazo[1,2-a]pyridin-7-yl)oxy)aniline 75 (134 mg, 5.1% yield over two steps) as a white solid. LCMS ESI (m/z): 272 [M+H]⁺.

Synthesis of tert-butyl (S)-2-methyl-4-(4,4,5,5-tetramethyl-1,3,2-dioxaborolan-2-yl)-3,6-dihydropyridine-1(2H)-carboxylate 80

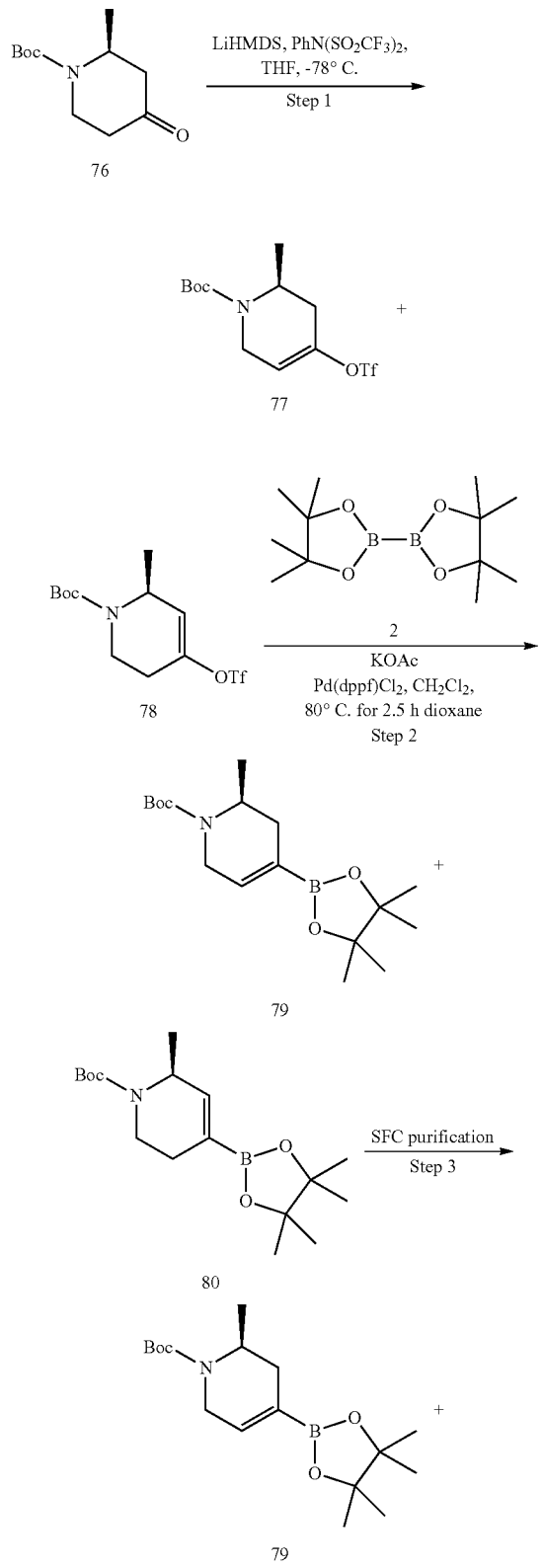

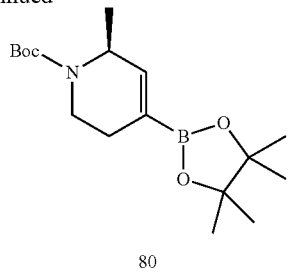

The synthesis was based on the procedures from WO2019163865. Step 1: To a stirred solution of tert-butyl (S)-2-methyl-4-oxopiperidine-1-carboxylate 76 (50.00 g, 234.7 mmol, 1.00 equiv) in THF (500 mL) at −78° C. was added dropwise LiHMDS (1 M in THF, 305 mL, 305 mmol, 1.3 equiv) under $N_2$ atmosphere. The resulting mixture was stirred at −60° C. for 1.5 h. To this at −78° C. was added dropwise a solution of 1,1,1-trifluoro-N-phenyl-N-trifluoromethanesulfonylmethanesulfonamide (100.56 g, 281.6 mmol, 1.2 equiv) in THF (400 mL). The resulting mixture was allowed to warm up to ambient temperature and stirred for another 2.5 h. The reaction was quenched with saturated $NH_4Cl$ solution and extracted with DCM 3 times.

The combined organic layers were washed with water 3 times, dried over $Na_2SO_4$ and concentrated under vacuum. The residue was purified by flash chromatography on silica gel (Petroleum ether:EtOAc=20:1) to afford a mixture of isomers of tert-butyl (S)-2-methyl-4-(((trifluoromethyl)sulfonyl)oxy)-3,6-dihydropyridine-1(2H)-carboxylate (77 and 78) (62.5 g, 77%) as yellow oil. LCMS ESI (m/z): 346 $[M+H]^+$.

Step 2: To a stirred mixture of tert-butyl $(S)_2$-methyl-4-(trifluoromethanesulfonyloxy)-3,6-dihydro-2H-pyridine-1-carboxylate 77 and 78 (62.4 g, 180.8 mmol, 1.00 equiv) and bis(pinacolato)diboron (55.1 g, 217.0 mmol, 1.2 equiv) in 1,4-dioxane at ambient temperature was added KOAc (35.4 g, 361.6 mmol, 2 equiv) and Pd(dppf)$Cl_2$·$CH_2Cl_2$ (22.1 g, 27.1 mmol, 0.15 equiv) under $N_2$ atmosphere. The resulting mixture was stirred at 80° C. for 2.5 h and then concentrated under vacuum. The residue was re-dissolved in DCM. The organic solution was washed with water 3 times, dried over $Na_2SO_4$ and concentrated under vacuum. The residue was purified by flash chromatography on silica gel (Petroleum ether:EtOAc=20:1) to afford a mixture of isomers of tert-butyl (S)-2-methyl-4-(4,4,5,5-tetramethyl-1,3,2-dioxaborolan-2-yl)-3,6-dihydropyridine-1(2H)-carboxylate (79 and 80) (67.1 g, >100%) as yellow oil. LCMS ESI (m/z): 324 $[M+H]^+$.

Step 3: The mixture of 79 and 80 was purified under SFC conditions using Water Thar 80 preparative SFC (ChiralPaK C-IG, 250×21.2 mm I.D., 5 m, mobile phase A for $CO_2$ and B for MeOH, gradient B: 20%, flow rate 40 mL/min, back pressure 100 bar, column temperature 35° C., cycle time 4 min, eluted time 3h).

Compound 79: $^1$H NMR (400 MHz, DMSO-d6) δ 6.39 (s, 1H), 4.32 (s, 1H), 4.08 (dt, J=20.2, 3.4 Hz, 1H), 3.54 (d, J=19.8 Hz, 1H), 2.31-2.16 (m, 1H), 1.97 (d, J=17.2 Hz, 1H), 1.40 (s, 9H), 1.20 (s, 12H), 0.96 (d, J=6.8 Hz, 3H). LCMS: Method G; Retention Time: 2.16 min; ESI (m/z): 324 $[M+H]^+$.

Compound 80: $^1$H NMR (400 MHz, DMSO-d6) δ 6.33 (s, 1H), 4.32 (s, 1H), 3.90 (s, 1H), 2.68 (s, 1H), 2.14-1.88 (m, 2H), 1.40 (s, 9H), 1.20 (s, 12H), 1.12 (d, J=6.6 Hz, 3H).

LCMS ESI (m/z): 324 [M+H]+. LCMS: Method G; Retention Time: 2.18 min; ESI (m/z): 324 [M+H]+.

Synthesis of (2S)-2-(fluoromethyl)-1-[(4-methoxyphenyl)methyl]piperazine 85

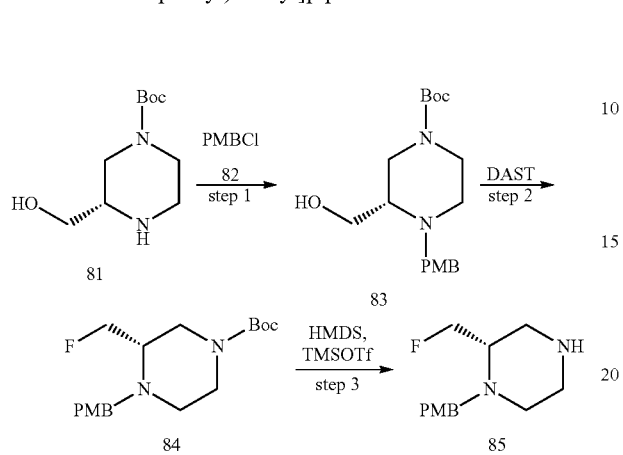

Step 1: To a stirred solution of tert-butyl (3S)-3-(hydroxymethyl)piperazine-1-carboxylate 81 (3.00 g, 13.87 mmol, 1.00 equiv) in acetonitrile (30.0 mL) at ambient temperature was added PMBCl 82 (2.60 g, 16.64 mmol, 1.20 equiv) and TEA (4.21 g, 41.61 mmol, 3.00 equiv). The resulting mixture was stirred at 60° C. for 16 h and then diluted with water and extracted with EtOAc 3 times. The combined organic layers were washed with brine, dried over Na$_2$SO$_4$ and then concentrated under vacuum. The residue was purified by flash chromatography on silica gel (0-80% EtOAc in petroleum ether) to afford tert-butyl (3S)-3-(hydroxymethyl)-4-[(4-methoxyphenyl)methyl]piperazine-1-carboxylate 83 (3.1 g, 63%) as colorless oil. MS (ESI, m z): 337 [M+H]+.

Step 2: To a stirred solution of tert-butyl (3S)-3-(hydroxymethyl)-4-[(4-methoxyphenyl)methyl]piperazine-1-carboxylate 83 (2.00 g, 5.94 mmol, 1.00 equiv) in DCM (20.0 mL) was added dropwise a solution of DAST (2.87 g, 17.83 mmol, 3.00 equiv) in DCM (10.0 mL) at −78° C. under N$_2$ atmosphere. The resulting mixture was stirred at this temperature for 4 h and then quenched at 0° C. with water/ice and extracted with DCM 3 times. The combined organic layers were washed with brine, dried over Na$_2$SO$_4$ and concentrated under vacuum. The residue was purified by flash chromatography on silica gel (0-40% EtOAc in petroleum ether) to afford tert-butyl (3S)-3-(fluoromethyl)-4-[(4-methoxyphenyl)methyl]piperazine-1-carboxylate 84 (1.5 g, 67%) as colorless oil. MS (ESI, m z): 339 [M+H]+.

Step 3: To a stirred solution of tert-butyl (3S)-3-(fluoromethyl)-4-[(4-methoxyphenyl)methyl]piperazine-1-carboxylate 84 (200 mg, 0.591 mmol, 1 equiv) in EtOAc (5.0 mL) at 0° C. was added HMDS (476.9 mg, 2.95 mmol, 5.00 equiv) and TMSOTf (525.3 mg, 2.36 mmol, 4.00 equiv). The resulting mixture was stirred at ambient temperature for 1 h and then diluted with water and extracted with EtOAc 3 times. The combined organic layers were washed with brine, dried over Na$_2$SO$_4$ and concentrated under vacuum to afford (2S)-2-(fluoromethyl)-1-[(4-methoxyphenyl)methyl]piperazine 85 (crude, 155 mg) as a yellow solid, which was used for the next step without further purification. MS (ESI, m z): 239 [M+H]+.

Synthesis of (S)-2-(difluoromethyl)piperazine 92

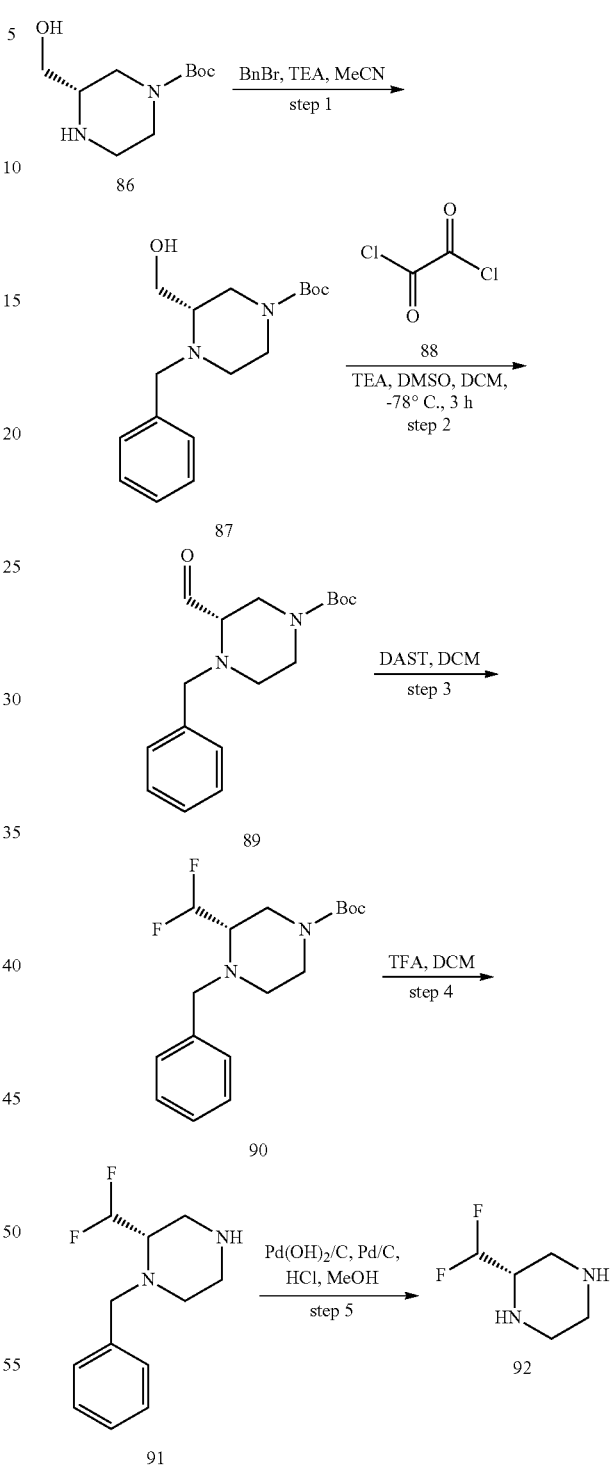

Step 1: A mixture of tert-butyl (S)-3-(hydroxymethyl)piperazine-1-carboxylate 86 (800.0 mg, 3.70 mmol, 1.00 equiv), benzyl bromide (1.26 g, 7.40 mmol, 2.00 equiv) and TEA (747.4 mg, 7.40 mmol, 2.00 equiv) in acetonitrile (20.00 mL) was stirred at 60° C. for 2 h. The resulting mixture was concentrated under vacuum. The residue was purified by flash chromatography on silica gel (0-70%

EtOAc in petroleum ether) to afford tert-butyl (S)-4-benzyl-3-(hydroxymethyl)piperazine-1-carboxylate 87 (510.0 mg, 45%) as yellow oil. MS (ESI, m z): 307 (M+H)+.

Step 2: To a stirred solution of oxalyl chloride 88 (621.3 mg, 4.896 mmol, 3.00 equiv) in DCM (10.00 mL) was added DMSO (509.9 mg, 6.53 mmol, 4.00 equiv) dropwise at −78° C. under N$_2$ atmosphere. The resulting mixture was stirred at this temperature for 0.5 h and to this was added tert-butyl (S)-4-benzyl-3-(hydroxymethyl)piperazine-1-carboxylate 87 (500.0 mg, 1.63 mmol, 1.00 equiv) and TEA (495.3 mg, 4.89 mmol, 3.00 equiv). The resulting mixture was stirred at ambient temperature for additional 1 h and then diluted with water and extracted with DCM 3 times. The organic layers were combined and concentrated under vacuum to afford tert-butyl (S)-4-benzyl-3-formylpiperazine-1-carboxylate 89 (crude, 450.0 mg) as yellow oil, which was used for the next step without further purification. MS (ESI, m z): 305 (M+H)+.

Step 3: To a stirred solution of tert-butyl (S)-4-benzyl-3-formylpiperazine-1-carboxylate 89 (350.0 mg, 1.15 mmol, 1.00 equiv) in DCM (5.00 mL) at −78° C. was added DAST (463.3 mg, 2.87 mmol, 2.50 equiv) under N$_2$ atmosphere. The resulting mixture was stirred at ambient temperature for 2 h and then quenched with NaHCO$_3$ solution and extracted with EtOAc 3 times. The organic layers were combined, washed with brine, dried over Na$_2$SO$_4$ and concentrated under vacuum. The residue was purified by reverse phase flash chromatography on C18 silica gel (5-85% acetonitrile in water (containing 0.05% NH$_4$HCO$_3$)) to afford tert-butyl (S)-4-benzyl-3-(difluoromethyl)piperazine-1-carboxylate 90 (210.0 mg, 56%) as yellow oil. MS (ESI, m z): 327 (M+H)+.

Step 4: To a stirred solution of tert-butyl (S)-4-benzyl-3-(difluoromethyl)piperazine-1-carboxylate 90 (200.0 mg, 0.61 mmol, 1.00 equiv) in DCM (8.00 mL) at 0° C. was added TFA (695.4 mg, 6.10 mmol, 10.00 equiv). The resulting mixture was stirred at ambient temperature for 1 h and then concentrated under vacuum to afford (S)-1-benzyl-2-(difluoromethyl)piperazine trifluoroacetate 91 (crude, 150.0 mg) as yellow oil, which was used for the next step without further purification. MS (ESI, m z): 227 (M+H)+.

Step 5: A mixture of (S)-1-benzyl-2-(difluoromethyl)piperazine trifluoroacetate 91 (150.0 mg, 0.44 mmol, 1.00 equiv), Pd(OH)$_2$/C (15.0 mg, 10% w/w), Pd/C (wet, 10%, 15.0 mg, 10% w/w) and HCl (0.60 mL, 19.81 mmol, 148.94 equiv) in MeOH (5.00 mL) was stirred at ambient temperature for 16 h under H$_2$ atmosphere and then filtered. The filtrate was concentrated under vacuum to afford (S)-2-(difluoromethyl)piperazine hydrochloride 92 (crude, 80.0 mg) as yellow oil, which was used for the next step without further purification. MS (ESI, m z): 137 (M+H)+.

Synthesis of 4-([1,2,4]triazolo[1,5-a]pyridin-7-yloxy)-3-chloro-2-fluoroaniline 95

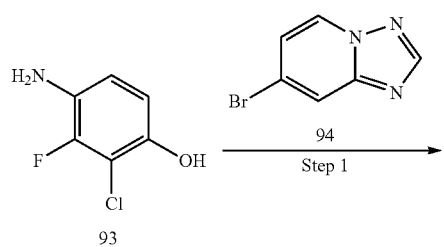

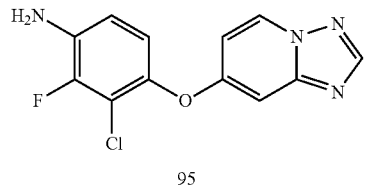

Step 1: A mixture of 4-amino-2-chloro-3-fluorophenol 93 (1.0 g, 6.21 mmol, 1.00 equiv), 7-bromo-[1,2,4]triazolo[1,5-a]pyridine 94 (1.8 g, 9.32 mmol, 1.50 equiv) and K$_2$CO$_3$ (1.7 g, 12.42 mmol, 2.00 equiv) in NMP (10.0 mL) was stirred at 80° C. for 4 h under N$_2$ atmosphere and then filtered through a pad of celite. The filtrate was diluted with H$_2$O and extracted with EtOAc 3 times. The combined organic layers were washed with brine, dried over Na$_2$SO$_4$ and then concentrated under vacuum. The residue was purified by flash chromatography on silica gel (0-80% EtOAc in petroleum ether) to afford 4-([1,2,4]triazolo[1,5-a]pyridin-7-yloxy)-3-chloro-2-fluoroaniline 95 (950.0 mg, 55%) as a brown solid. MS (ESI, m z): 279, 281 [M+H]+.

General Synthetic Method for Intermediate IM-III

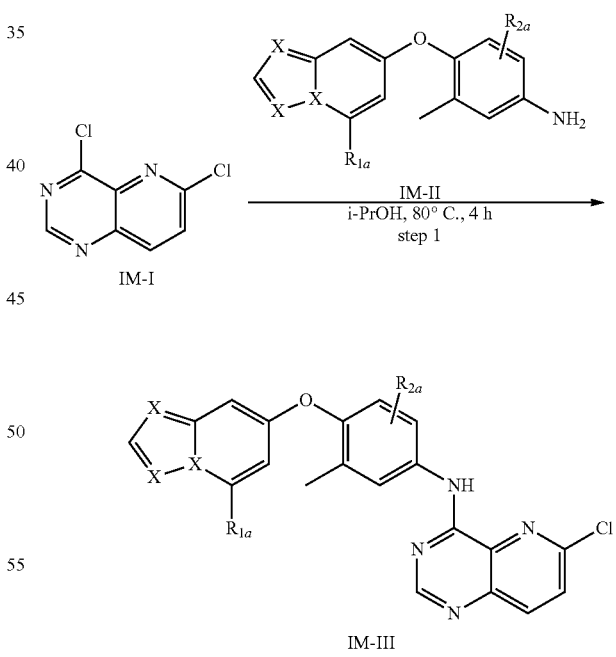

Step 1: A mixture of 4,6-dichloropyrido[3,2-d]pyrimidine IM-I (1.00 equiv.) and intermediate IM-II (1.00 equiv.) in i-PrOH (4.00 mL) was stirred at 80° C. for 4 h and then concentrated under vacuum to intermediate IM-III (crude) which was used for the next step without further purification.

Synthesis of N-(4-([1,2,4]triazolo[1,5-a]pyridin-7-yloxy)-3-methylphenyl)-6-chloropyrido[3,2-d]pyrimidin-4-amine 98

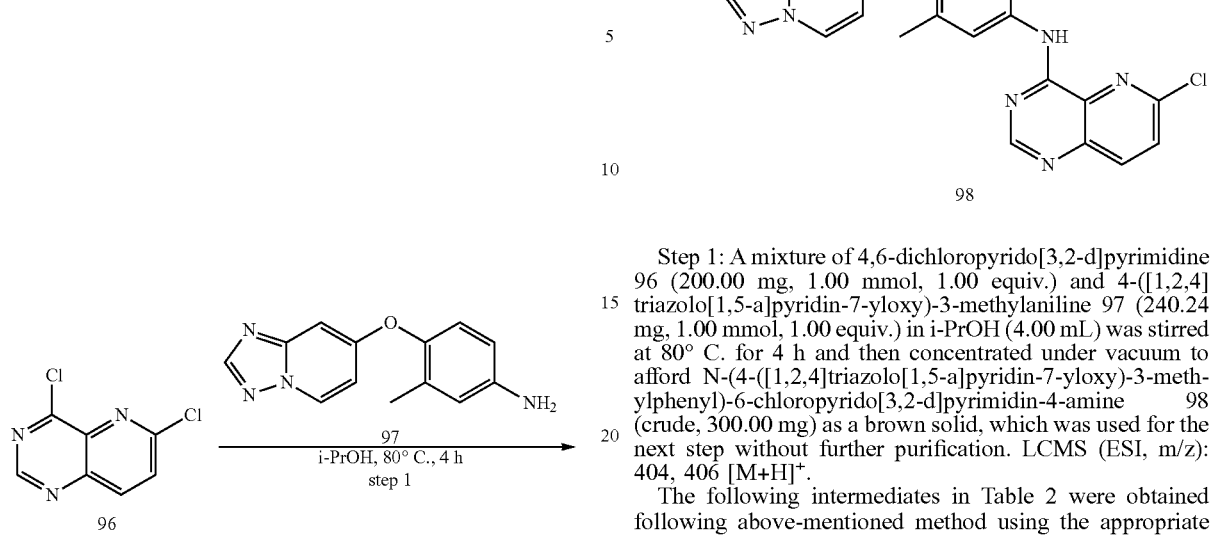

Step 1: A mixture of 4,6-dichloropyrido[3,2-d]pyrimidine 96 (200.00 mg, 1.00 mmol, 1.00 equiv.) and 4-([1,2,4]triazolo[1,5-a]pyridin-7-yloxy)-3-methylaniline 97 (240.24 mg, 1.00 mmol, 1.00 equiv.) in i-PrOH (4.00 mL) was stirred at 80° C. for 4 h and then concentrated under vacuum to afford N-(4-([1,2,4]triazolo[1,5-a]pyridin-7-yloxy)-3-methylphenyl)-6-chloropyrido[3,2-d]pyrimidin-4-amine 98 (crude, 300.00 mg) as a brown solid, which was used for the next step without further purification. LCMS (ESI, m/z): 404, 406 [M+H]$^+$.

The following intermediates in Table 2 were obtained following above-mentioned method using the appropriate starting materials.

TABLE 2

| Intermediate # | Compound Structure | Physical Data MS [ESI, m/z] |
|---|---|---|
| 99 | N-(4-([1,2,4]triazolo[1,5-a]pyridin-7-yloxy)-2-fluoro-3-methylphenyl)-6-chloropyrido[3,2-d]pyrimidin-4-amine | 422 [M + H]$^+$ |
| 100 | N-(4-([1,2,4]triazolo[1,5-a]pyridin-7-yloxy)-2-fluoro-5-methylphenyl)-6-chloropyrido[3,2-d]pyrimidin-4-amine | 422 [M + H]$^+$ |

TABLE 2-continued

Intermediates

| Intermediate # | Compound Structure | Physical Data MS [ESI, m/z] |
|---|---|---|
| 101 | 6-chloro-N-(4-(5-methoxy-[1,2,4]triazolo[1,5-a]pyridin-7-yloxy)-3-methylphenyl)pyrido[3,2-d]pyrimidin-4-amine | 434 [M + H]$^+$ |
| 102 | 6-chloro-N-(4-((5-chloro-[1,2,4]triazolo[1,5-a]pyridin-7-yl)oxy)-3-methylphenyl)pyrido[3,2-d]pyrimidin-4-amine | 438 [M + H]$^+$ |
| 103 | 6-chloro-N-[3-methyl-4-({5-methyl-[1,2,4]triazolo[1,5-a]pyridin-7-yl}oxy)phenyl]pyrido[3,2-d]pyrimidin-4-amine | 418 [M + H]$^+$ |
| 104 | 6-chloro-N-(4-(imidazo[1,2-a]pyridin-7-yloxy)-3-methylphenyl)pyrido[3,2-d]pyrimidin-4-amine | 403 [M + H]$^+$ |

TABLE 2-continued

Intermediates

| Intermediate # | Compound Structure | Physical Data MS [ESI, m/z] |
|---|---|---|
| 105 | 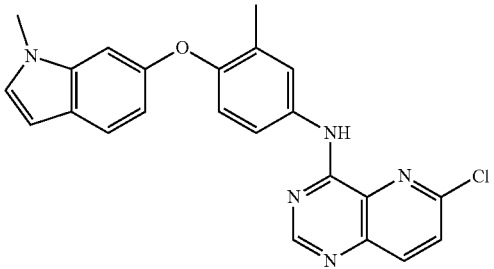 [SMILES: Cc1cc(Nc2ncnc3ccc(Cl)nc23)ccc1Oc1ccc2ccn(C)c2c1]<br>6-chloro-N-(3-methyl-4-((1-methyl-3a,7a-dihydro-1H-indol-6-yl)oxy)phenyl)pyrido[3,2-d]pyrimidin-4-amine | 418 [M + H]⁺ |
| 106 | 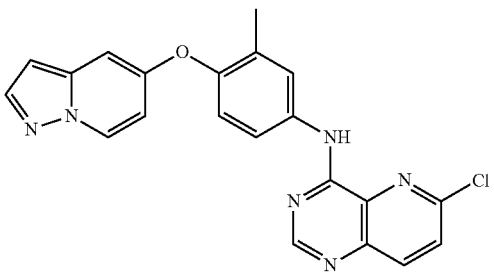 [SMILES: Cc1cc(Nc2ncnc3ccc(Cl)nc23)ccc1Oc1ccn2nccc2c1]<br>6-chloro-N-(3-methyl-4-(pyrazolo[1,5-a]pyridin-5-yloxy)phenyl)pyrido[3,2-d]pyrimidin-4-amine | 403 [M + H]⁺ |

Method A: General Method for Intermediate IM-VI

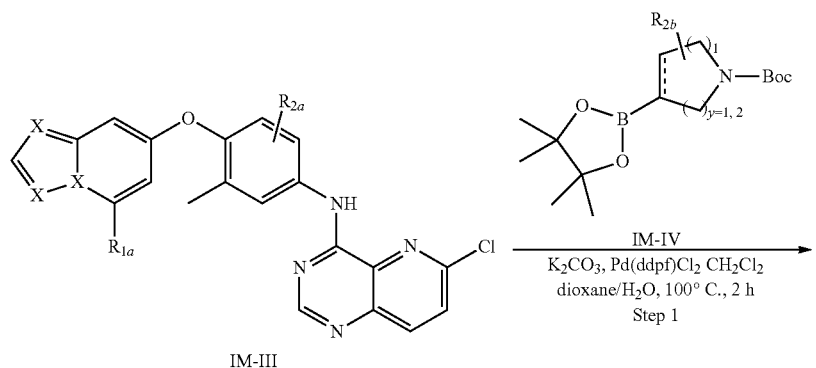

IM-III

IM-IV
K₂CO₃, Pd(ddpf)Cl₂ CH₂Cl₂
dioxane/H₂O, 100° C., 2 h
Step 1

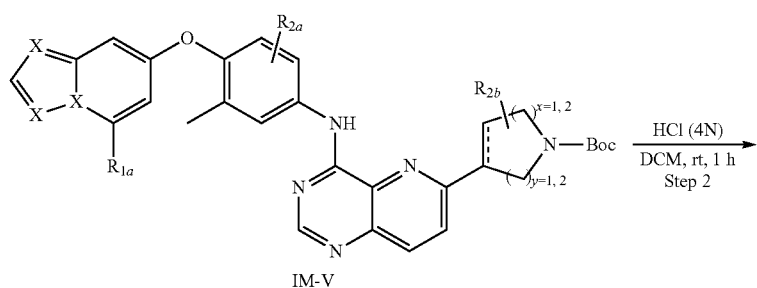

IM-V

HCl (4N)
DCM, rt, 1 h
Step 2

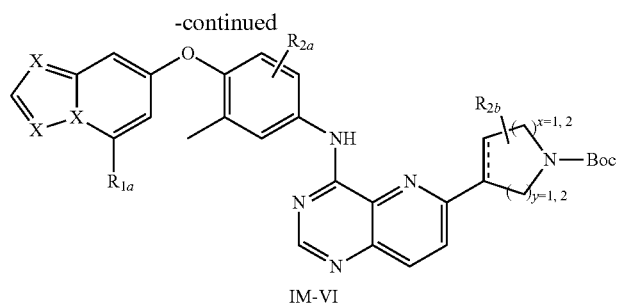

IM-VI

Step 1: A mixture of N-(4-([1,2,4]triazolo[1,5-a]pyridin-7-yloxy)-3-methylphenyl)-6-chloropyrido[3,2-d]pyrimidin-4-amine IM-III (1.00 equiv.), boronic ester IM-IV (1.20 equiv.), $K_2CO_3$ (3.00 equiv.) and Pd(dppf)$Cl_2$·$CH_2Cl_2$ (0.10 equiv.) in dioxane and $H_2O$ was stirred at 100° C. under $N_2$ atmosphere until the reaction was complete and then quenched with brine and extracted with EtOAc 3 times. The organic layers were combined, dried over $Na_2SO_4$ and concentrated under vacuum. The residue was purified by flash chromatography on silica gel (0-20% MeOH in DCM) to afford intermediate IM-V.

Step 2: A mixture of intermediate IM-V (1.00 equiv.) and HCl (4 N in 1,4-dioxane, 1.00 mL) in DCM (4.00 mL) was stirred at ambient temperature until the reaction was complete and then concentrated under vacuum to afford intermediate IM-VI (crude) as a yellow solid, which was used for the next step without further purification.

Synthesis of N-(3-methyl-4-[[1,2,4]triazolo[1,5-a]pyridin-7-yloxy]phenyl)-6-(2,3,6,7-tetrahydro-1H-azepin-4-yl)pyrido[3,2-d]pyrimidin-4-amine 109

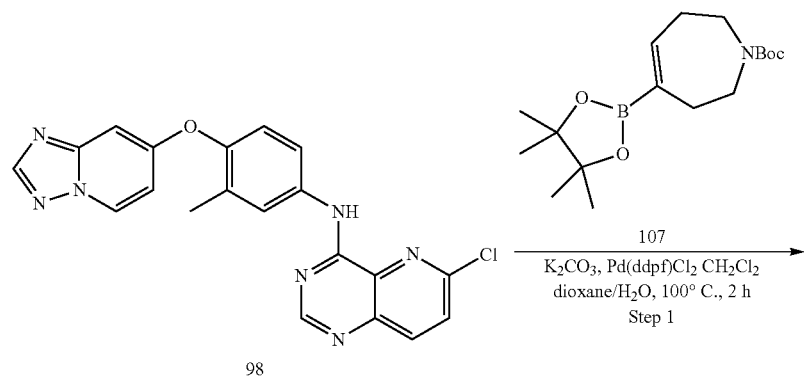

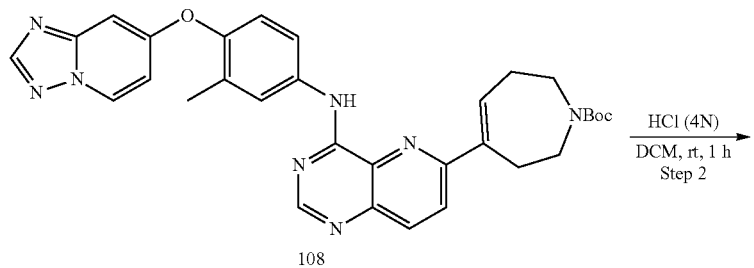

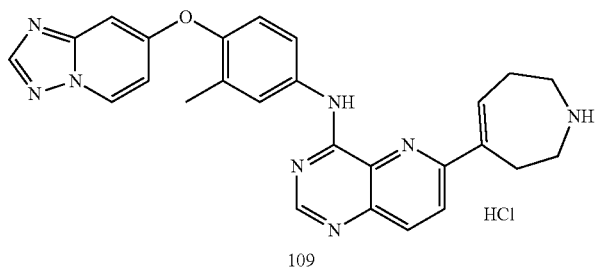

Step 1: To a stirred mixture of 6-chloro-N-(3-methyl-4-[[1,2,4] triazolo[1,5-a] pyridin-7-yloxy] phenyl) pyrido[3,2-d]pyrimidin-4-amine 98 (300.00 mg, 0.74 mmol, 1.00 equiv.), tert-butyl 4-(4,4,5,5-tetramethyl-1,3,2-dioxaborolan-2-yl)-2,3,6,7-tetrahydroazepine-1-carboxylate 107 (288.16 mg, 0.89 mmol, 1.20 equiv.) and $K_2CO_3$ (308.01 mg, 2.23 mmol, 3.00 equiv.) in dioxane (15.00 mL) and $H_2O$ (3.00 mL) at ambient temperature was added Pd(dppf) $Cl_2CH_2C_2$ (60.52 mg, 0.07 mmol, 0.10 equiv.) under $N_2$ atmosphere. The resulting mixture was stirred at 100° C. for 2 h and then diluted with $H_2O$ and extracted with EtOAc 3 times. The combined organic layers were washed with brine, dried over $Na_2SO_4$ and concentrated under vacuum. The residue was purified by reverse phase flash chromatography on C18 silica gel (5-95% acetonitrile in $H_2O$ (containing 0.05% $NH_4HCO_3$)) to afford tert-butyl 4-[4-[(3-methyl-4-[[1,2,4] triazolo[1,5-a]pyridin-7-yloxy]phenyl)amino] pyrido[3,2-d]pyrimidin-6-yl]-2,3,6,7-tetrahydroazepine-1-carboxylate 108 (100 mg, 24%) as a brown solid. LCMS (ESI, m z): 565 $[M+H]^+$.

Step 2: To a stirred mixture of tert-butyl 4-[4-[(3-methyl-4-[[1,2,4] triazolo[1,5-a]pyridin-7-yloxy]phenyl)amino] pyrido[3,2-d]pyrimidin-6-yl]-2,3,6,7-tetrahydroazepine-1-carboxylate 108 (100.00 mg, 0.18 mmol, 1.00 equiv.) in DCM (4.00 mL) at ambient temperature was added HCl (4 N in 1,4-dioxane, 1.00 mL, 4.00 mmol). The resulting mixture was stirred at this temperature for 1 h and concentrated under vacuum to afford N-(3-methyl-4-[[1,2,4] triazolo[1,5-a]pyridine-7-yloxy]phenyl)-6-(2,3,6,7-tetrahydro-1H-azepin-4-yl)pyrido[3,2-d]pyrimidin-4-amine hydrochloride 109 (crude, 110 mg) as a yellow solid, which was used for the next step without further purification. LCMS (ESI, m z): 465 $[M+H]^+$.

Intermediates in Table 3 were obtained following above-mentioned method using the appropriate starting materials.

TABLE 3

Intermediates

| Intermediate # | Compound Structure | Physical Data MS [ESI, m/z] |
|---|---|---|
| 110 | 6-(2,5-dihydro-1H-pyrrol-3-yl)-N-(3-methyl-4-[[1,2,4]triazolo-[1,5-a]pyridin-7-yloxy]phenyl)pyrido[3,2-d]pyrimidin-4-amine hydrochloride | 437 $[M + H]^+$ |
| 111 | N-(4-([1,2,4]triazolo[1,5-a]pyridin-7-yloxy)-3-methylphenyl)-6-(1,2,3,6-tetrahydropyridin-4-yl)pyrido[3,2-d]pyrimidin-4-amine hydrochloride | 451 $[M + H]^+$ |
| 112 | N-(4-([1,2,4]triazolo[1,5-a]pyridin-7-yloxy)-2-fluoro-3-methylphenyl)-6-(1,2,3,6-tetrahydropyridin-4-yl)pyrido[3,2-d]pyrimidin-4-amine hydrochloride | 469 $[M + H]^+$ |

TABLE 3-continued

| Intermediate # | Compound Structure | Physical Data MS [ESI, m/z] |
|---|---|---|
| 113 | 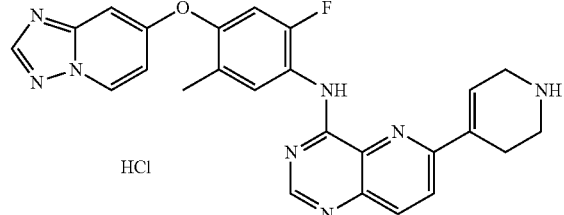<br>N-(4-([1,2,4]triazolo[1,5-a]pyridin-7-yloxy)-2-fluoro-5-methyl-phenyl)-6-(1,2,3,6-tetrahydropyridin-4-yl)pyrido[3,2-d]-pyrimidin-4-amine hydrochloride | 469 [M + H]+ |
| 114 | 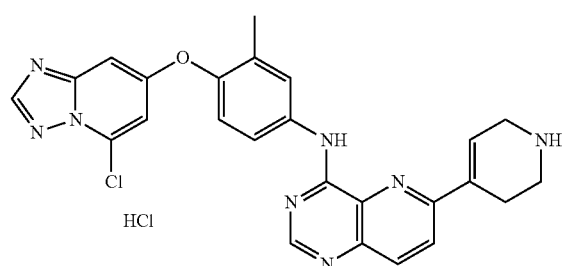<br>N-(4-((5-chloro-[1,2,4]triazolo[1,5-a]pyridin-7-yl)oxy)-3-methyl-phenyl)-6-(1,2,3,6-tetrahydropyridin-4-yl)pyrido[3,2-d]-pyrimidin-4-amine hydrochloride | 485 [M + H]+ |
| 115 | 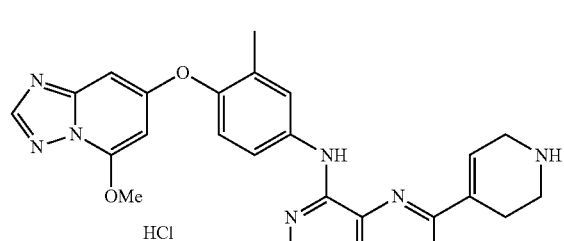<br>N-(4-(5-methoxy-[1,2,4]triazolo[1,5-a]pyridin-7-yloxy)-3-methyl-phenyl)-6-(1,2,3,6-tetrahydropyridin-4-yl)pyrido[3,2-d]pyrimidin-4-amine hydrochloride | 481 [M + H]+ |
| 116 | 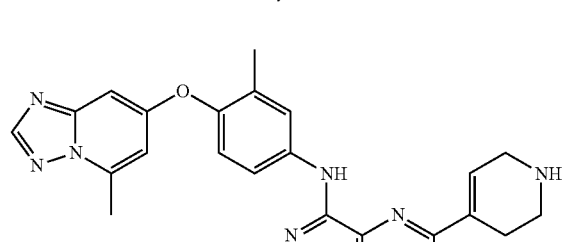<br>N-[3-methyl-4-({5-methyl-[1,2,4]triazolo[1,5-a]pyridin-7-yl}oxy)-phenyl]-6-(1,2,3,6-tetrahydropyridin-4-yl)pyrido[3,2-d]pyrimidin-4-amine hydrochloride | 465 [M + H]+ |

TABLE 3-continued

Intermediates

| Intermediate # | Compound Structure | Physical Data MS [ESI, m/z] |
|---|---|---|
| 117 | 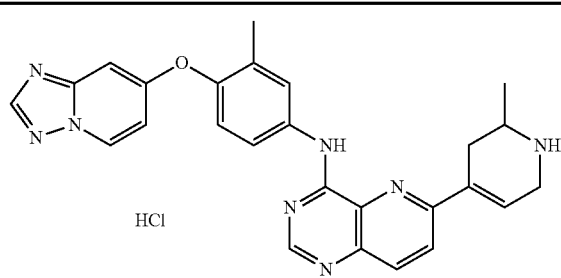<br>N-(4-([1,2,4]triazolo[1,5-a]pyridin-7-yloxy)-3-methylphenyl)-6-(2-methyl-1,2,3,6-tetrahydropyridin-4-yl)pyrido[3,2-d]pyrimidin-4-amine hydrochloride | 465 [M + H]⁺ |
| 118 | 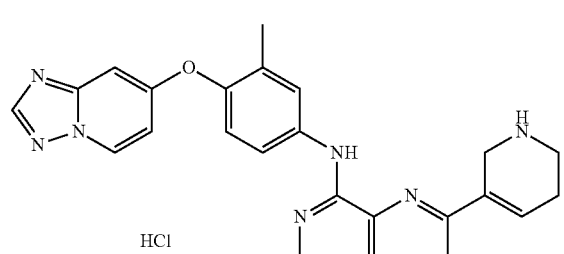<br>N-(3-methyl-4-{[1,2,4]triazolo[1,5-a]pyridin-7-yloxy}phenyl)-6-(1,2,5,6-tetrahydropyridin-3-yl)pyrido[3,2-d]pyrimidin-4-amine hydrochloride | 451 [M + H]⁺ |
| 119 | 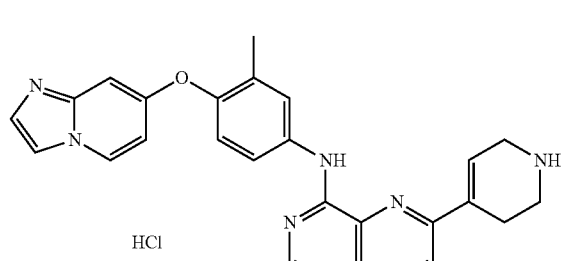<br>N-(4-(imidazo[1,2-a]pyridin-7-yloxy)-3-methylphenyl)-6-(1,2,3,6-tetrahydropyridin-4-yl)pyrido[3,2-d]pyrimidin-4-amine hydrochloride | 450 [M + H]⁺ |
| 120 | 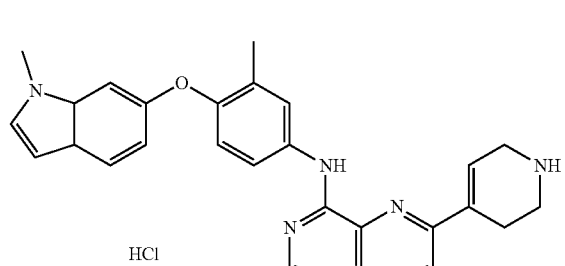<br>N-(3-methyl-4-((1-methyl-3a,7a-dihydro-1H-indol-6-yl)oxy)phenyl)-6-(1,2,3,6-tetrahydropyridin-4-yl)pyrido[3,2-d]-pyrimidin-4-amine hydrochloride | 465 [M + H]⁺ |

TABLE 3-continued

Intermediates

| Intermediate # | Compound Structure | Physical Data MS [ESI, m/z] |
|---|---|---|
| 121 | N-(3-methyl-4-(pyrazolo[1,5-a]pyridin-5-yloxy)phenyl)-6-(1,2,3,6-tetrahydropyridin-4-yl)pyrido[3,2-d]pyrimidin-4-amine hydrochloride | 450 [M + H]+ |
| 122 | (S)-N-(4-([1,2,4]triazolo[1,5-a]pyridin-7-yloxy)-3-methylphenyl)-6-(6-methyl-1,2,3,6-tetrahydropyridin-4-yl)pyrido[3,2-d]-pyrimidin-4-amine hydrochloride | 465 [M + H]+ |
| 123 | (R)-N-(4-([1,2,4]triazolo[1,5-a]pyridin-7-yloxy)-3-methylphenyl)-6-(6-methyl-1,2,3,6-tetrahydropyridin-4-yl)pyrido[3,2-d]-pyrimidin-4-amine hydrochloride | 465 [M + H]+ |

Method B: General Method for Intermediate IM-VIII

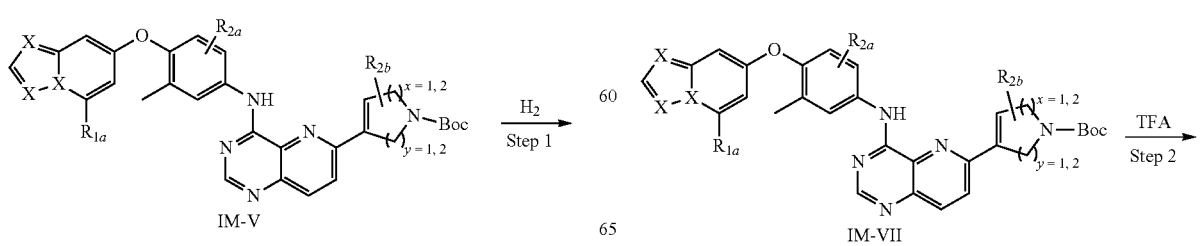

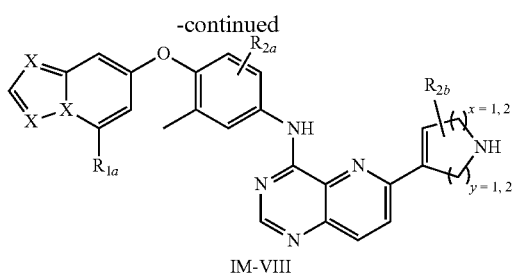

Step 1: A mixture of intermediate IM-V (1.00 equiv.) and Pd/C (wet, 10%, 0.2 equiv.) in MeOH was stirred at ambient temperature until the reaction was complete under $H_2$ atmosphere and then filtered through a pad of celite. The filtrate was concentrated under vacuum to afford intermediate IM-VII (crude) as a brown solid, which was used for the next step without further purification.

Step 2: To a stirred mixture of intermediate IM-VII (1.00 equiv.) in DCM at ambient temperature was added TFA. The reaction mixture was stirred at this temperature until the reaction was complete h and then concentrated under vacuum to afford intermediate IM-VIII (crude) as brown oil, which was used for the next step without further purification.

Synthesis of tert-butyl 4-(4-((4-([1,2,4]triazolo[1,5-a]pyridin-7-yloxy)-3-methylphenyl)amino)pyrido[3,2-d]pyrimidin-6-yl)-3-methylpiperidine-1-carboxylate 126

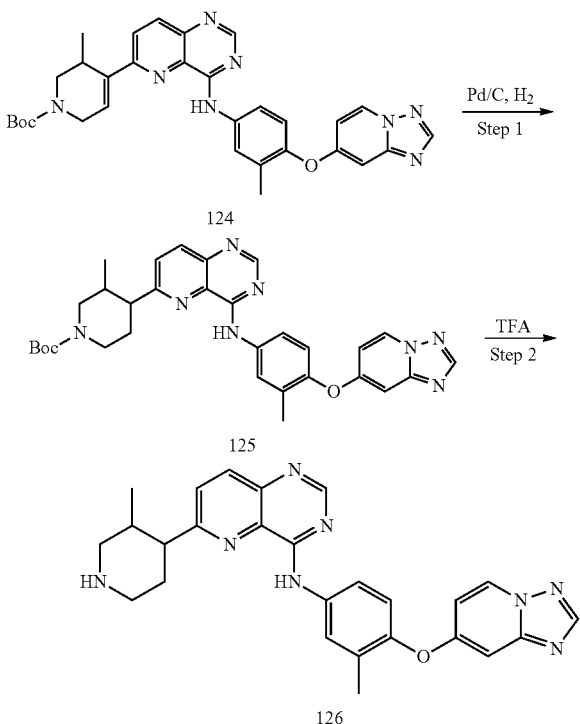

Step 1: A mixture of 3-methyl-4-{4-[(3-methyl-4-{[1,2,4]triazolo[1,5-a]pyridin-7-yloxy}phenyl)amino]pyrido[3,2-d]pyrimidin-6-yl}-3,6-dihydro-2H-pyridine-1-carboxylate 124 (150.0 mg, 0.27 mmol, 1.00 equiv.) and Pd/C (wet, 10%, 30.0 mg) in MeOH (5.0 mL) was stirred at ambient temperature for 96 h under $H_2$ atmosphere and then filtered through a pad of celite. The filtrate was concentrated under vacuum to afford tert-butyl 4-(4-((4-([1,2,4]triazolo[1,5-a]pyridin-7-yloxy)-3-methylphenyl)amino)pyrido[3,2-d]pyrimidin-6-yl)-3-methylpiperidine-1-carboxylate 125 (crude, 190.5 mg) as a brown solid, which was used for the next step without further purification. LCMS (ESI, m z): 567 [M+H]⁺.

Step 2: To a stirred mixture of (2R)-2-methyl-4-{4-[(3-methyl-4-{[1,2,4]triazolo[1,5-a]pyridin-7-yloxy}phenyl)amino]pyrido[3,2-d]pyrimidin-6-yl}piperazine-1-carboxylate 125 (150.0 mg, 0.27 mmol, 1.00 equiv.) in DCM (2.0 mL) at ambient temperature was added TFA (1.0 mL). The reaction mixture was stirred at this temperature for 2 h and then concentrated under vacuum to afford N-(4-([1,2,4]triazolo[1,5-a]pyridin-7-yloxy)-3-methylphenyl)-6-(3-methylpiperidin-4-yl)pyrido[3,2-d]pyrimidin-4-amine trifluoroacetate 126 (crude, 40.0 mg) as brown oil, which was used for the next step without further purification. LCMS (ESI, m z): 467 [M+H]⁺.

Method C: General Method for Intermediate IM-XI

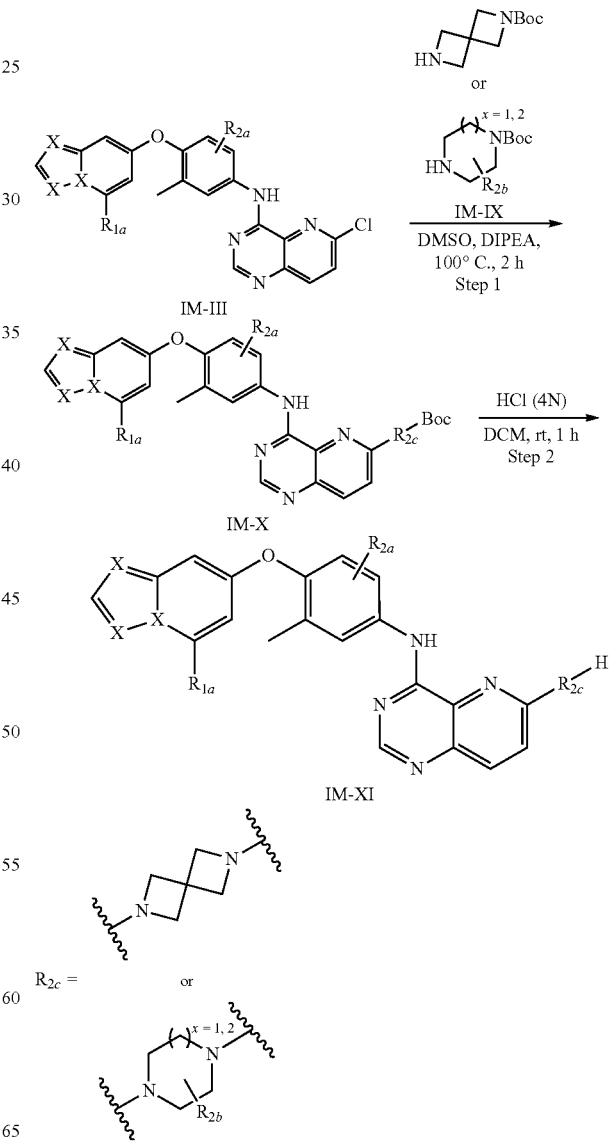

Step 1: A mixture of intermediate IM-III (1.00 equiv.), N-Boc protected intermediate IM-IX (2.00 equiv.) and TEA (3.00 equiv.) in DMSO was stirred at 100° C. for 2 h and then diluted with water and extracted with EtOAc 3 times. The combined organic layers were dried over Na₂SO₄ and concentrated under vacuum. The residue was purified by reverse phase flash chromatography on C18 silica gel (5-95% acetonitrile in water (containing 0.05% NH₄HCO₃) to afford intermediate IM-X.

Step 2: A mixture of intermediate IM-X (1.00 equiv.) and HCl (4 N in 1,4-dioxane) in DCM (4.0 mL) was stirred at ambient temperature for 1 h and then concentrated under vacuum to afford intermediate IM-XI (crude) as a yellow solid, which was used for the next step without further purification.

Synthesis of N-(4-([1,2,4]triazolo[1,5-a]pyridin-7-yloxy)-3-methylphenyl)-6-(1,4-diazepan-1-yl)pyrido[3,2-d]pyrimidin-4-amine 52

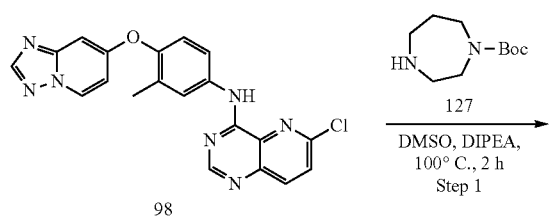

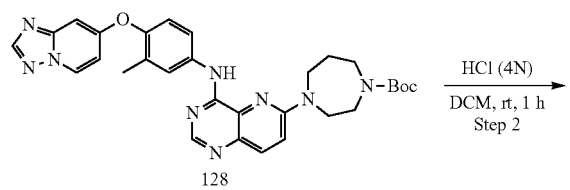

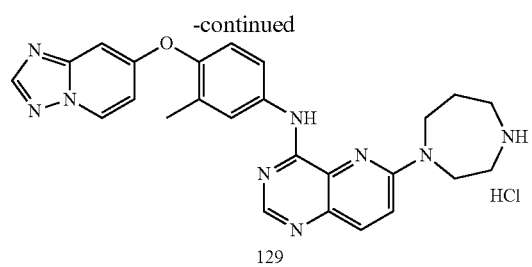

129

Step 1: A mixture of N-(4-([1,2,4]triazolo[1,5-a]pyridin-7-yloxy)-3-methylphenyl)-6-chloropyrido[3,2-d]pyrimidin-4-amine 98 (250.0 mg, 0.62 mmol, 1.00 equiv.), tert-butyl 1,4-diazepane-1-carboxylate 127 (248.1 mg, 1.24 mmol, 2.00 equiv.) and TEA (187.9 mg, 1.86 mmol, 3.00 equiv.) in DMSO (7.5 mL) was stirred at 100° C. for 2 h and then diluted with water and extracted with EtOAc 3 times. The combined organic layers were dried over Na₂SO₄ and concentrated under vacuum. The residue was purified by reverse phase flash chromatography on C18 silica gel (5-95% acetonitrile in water (containing 0.05% NH₄HCO₃) to afford tert-butyl 4-(4-((4-([1,2,4]triazolo[1,5-a]pyridin-7-yloxy)-3-methylphenyl)amino)pyrido[3,2-d]pyrimidin-6-yl)-1,4-diazepane-1-carboxylate 128 (100.0 mg, 28%) as brown oil. LCMS (ESI, m z): 568 [M+H]⁺.

Step 2: A mixture of tert-butyl 4-(4-((4-([1,2,4]triazolo[1,5-a]pyridin-7-yloxy)-3-methylphenyl)amino)pyrido[3,2-d]pyrimidin-6-yl)-1,4-diazepane-1-carboxylate 128 (130.0 mg, 0.23 mmol, 1.00 equiv.) and HCl (4 N in 1,4-dioxane, 4.0 mL) in DCM (4.0 mL) was stirred at ambient temperature for 1 h and then concentrated under vacuum to afford N-(4-([1,2,4]triazolo[1,5-a]pyridin-7-yloxy)-3-methylphenyl)-6-(1,4-diazepan-1-yl)pyrido[3,2-d]pyrimidin-4-amine hydrochloride 129 (crude, 160.0 mg) as a yellow solid, which was used for the next step without further purification. LCMS (ESI, m z): 468 [M+H]⁺.

Alternatively, TFA in DCM (1/1) could be used to remove floe protecting group instead of HCl (4 N in 1,4-dioxane). After completion of the reaction, the reaction mixture was concentrated under vacuum to afford the desired intermediate as TFA salt.

The following intermediates in Table 4 were obtained following above-mentioned method using the appropriate starting materials.

TABLE 4

| | Intermediates | |
|---|---|---|
| Example | Compound Structure | Physical Data MS [ESI, m/z] |
| 130 | N-(4-([1,2,4]triazolo[1,5-a]pyridin-7-yloxy)-3-methylphenyl)-6-(piperazin-1-yl)pyrido[3,2-d]pyrimidin-4-amine hydrochloride | 454 [M + H]⁺ |

TABLE 4-continued

Intermediates

| Example | Compound Structure | Physical Data MS [ESI, m/z] |
|---|---|---|
| 131 | 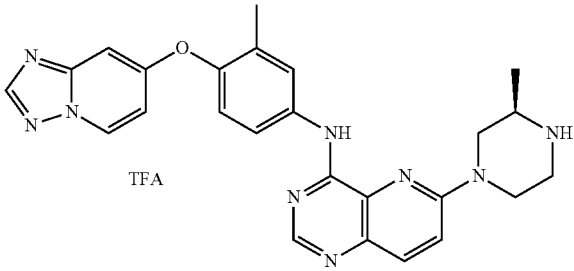 N-(3-methyl-4-{[1,2,4]triazolo[1,5-a]pyridin-7-yloxy}phenyl)-6-[(3R)-3-methylpiperazin-1-yl]pyrido[3,2-d]pyrimidin-4-amine trifluoroacetate | 468 [M + H]+ |
| 132 | 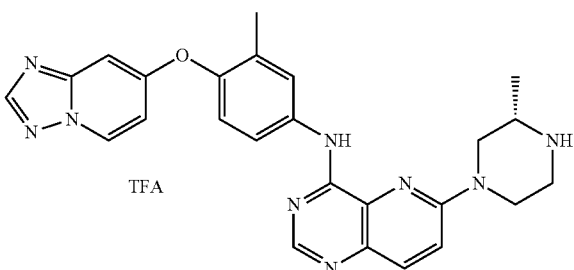 N-(3-methyl-4-{[1,2,4]triazolo[1,5-a]pyridin-7-yloxy}phenyl)-6-[(3S)-3-methylpiperazin-1-yl]pyrido[3,2-d]pyrimidin-4-amine trifluoroacetate | 468 [M + H]+ |
| 133 | 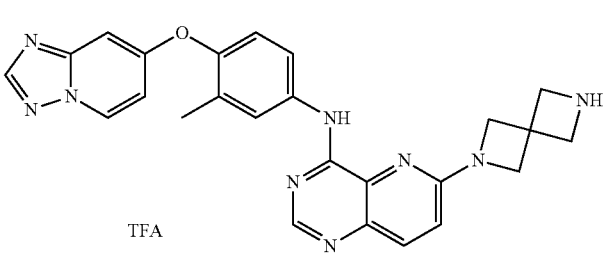 N-(4-([1,2,4]triazolo[1,5-a]pyridin-7-yloxy)-3-methylphenyl)-6-(2,6-diazaspiro[3.3]heptan-2-yl)pyrido[3,2-d]pyrimidin-4-amine 2,2,2-trifluoroacetate | 466 [M + H]+ |

Method D: General Method for Intermediate IM-XIV

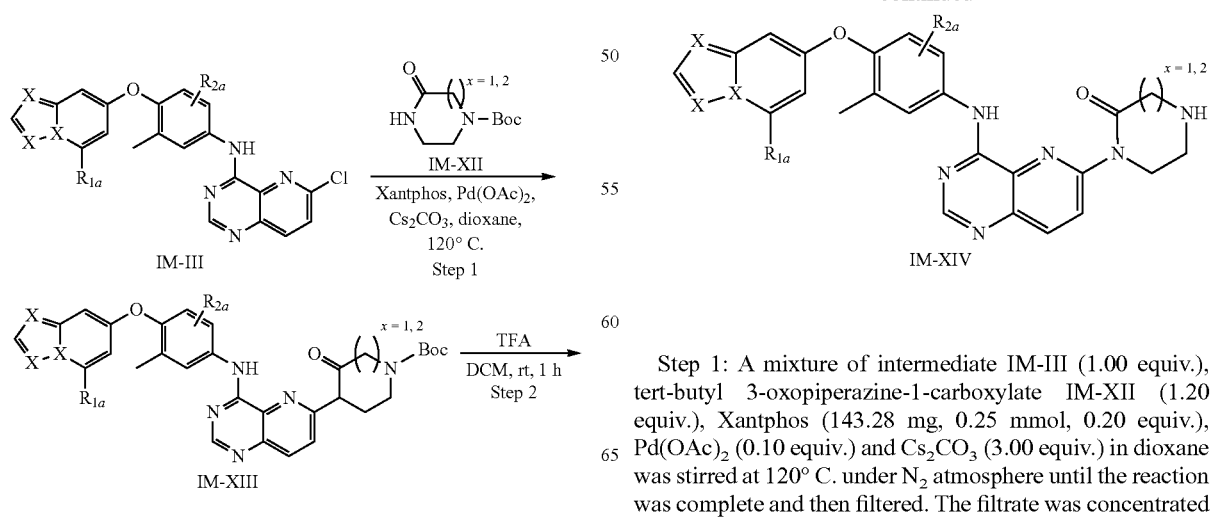

Step 1: A mixture of intermediate IM-III (1.00 equiv.), tert-butyl 3-oxopiperazine-1-carboxylate IM-XII (1.20 equiv.), Xantphos (143.28 mg, 0.25 mmol, 0.20 equiv.), Pd(OAc)$_2$ (0.10 equiv.) and Cs$_2$CO$_3$ (3.00 equiv.) in dioxane was stirred at 120° C. under N$_2$ atmosphere until the reaction was complete and then filtered. The filtrate was concentrated under vacuum to afford intermediate IM-XIII (crude) as a brown solid, which was used for the next step without further purification.

Step 2: To a stirred mixture of intermediate IM-XIII (1.00 equiv.) in DCM at ambient temperature was added TFA. The resulting mixture was stirred at this temperature until the reaction was complete and then concentrated under vacuum to afford intermediate IM-XIV (crude) as a brown solid, which was used for the next step without further purification.

Synthesis of 1-[4-[(3-methyl-4-[[1,2,4] triazolo[1,5-a]pyridin-7-yloxy]phenyl)amino]pyrido[3,2-d]pyrimidin-6-yl]piperazin-2-one 136

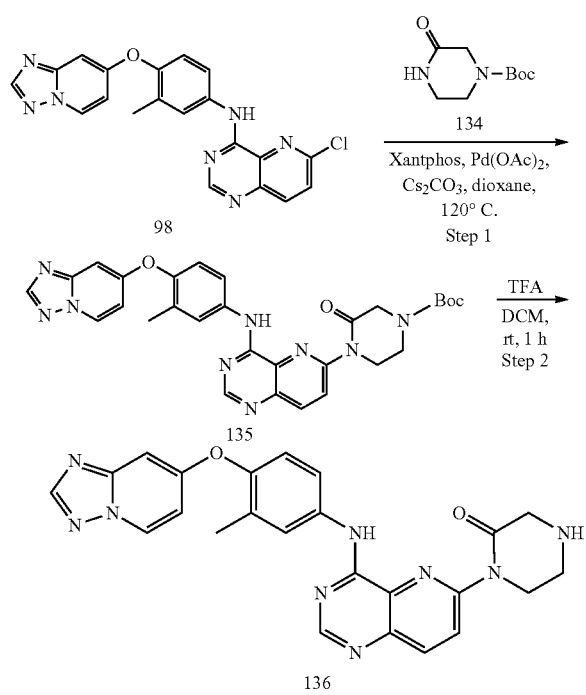

Step 1: A mixture of 6-chloro-N-(3-methyl-4-[[1,2,4]triazolo[1,5-a]pyridin-7-yloxy]phenyl)pyrido[3,2-d]pyrimidin-4-amine 98 (500.00 mg, 1.24 mmol, 1.00 equiv.), tert-butyl 3-oxopiperazine-1-carboxylate 134 (297.51 mg, 1.49 mmol, 1.20 equiv.), Xantphos (143.28 mg, 0.25 mmol, 0.20 equiv.), Pd(OAc)$_2$ (27.80 mg, 0.12 mmol, 0.10 equiv.) and Cs$_2$CO$_3$ (1.21 g, 3.71 mmol, 3.00 equiv.) in dioxane (8.00 mL) was stirred at 120° C. for 6 h under N$_2$ atmosphere and then filtered. The filtrate was concentrated under vacuum to afford tert-butyl 4-[4-[(3-methyl-4-[[1,2,4]triazolo[1,5-a]pyridin-7-yloxy]phenyl)amino]pyrido[3,2-d]pyrimidin-6-yl]-3-oxopiperazine-1-carboxylate 135 (crude, 600 mg) as a brown solid, which was used for the next step without further purification. LCMS (ESI, m z): 568 [M+H]$^+$.

Step 2: To a stirred mixture of tert-butyl 4-[4-[(3-methyl-4-[[1,2,4] triazolo[1,5-a]pyridin-7-yloxy]phenyl)amino] pyrido[3,2-d]pyrimidin-6-yl]-3-oxopiperazine-1-carboxylate 135 (600.00 mg, 1.06 mmol, 1.00 equiv.) in DCM (6.00 mL) at ambient temperature was added TFA (6 mL). The resulting mixture was stirred at this temperature for 2 h and then concentrated under vacuum to afford 1-[4-[(3-methyl-4-[[1,2,4] triazolo[1,5-a]pyridin-7-yloxy]phenyl)amino] pyrido[3,2-d]pyrimidin-6-yl]piperazin-2-one trifluoroacetate 136 (crude, 120 mg) as a brown solid, which was used for the next step without further purification. LCMS (ESI, m z): 468 [M+H]$^+$.

Method E: General Method for Intermediate IM-XVIII

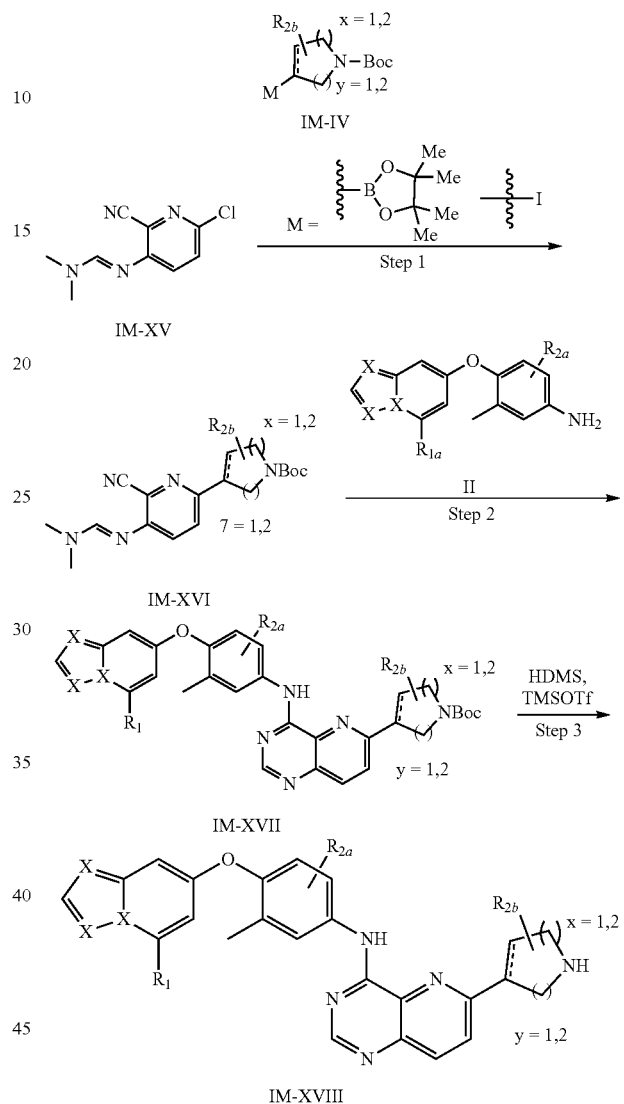

Step 1: A mixture of (E)-N'-(6-chloro-2-cyanopyridin-3-yl)-N,N-dimethylformimidamide IM-XV (1.00 equiv.), boronic ester IM-IV (1.50 equiv.), Pd(PPh$_3$)$_2$Cl$_2$ (0.10 equiv.) and K$_2$CO$_3$ (3.00 equiv.) in DME/H$_2$O/EtOH (2/2/1) was stirred at 95° C. under N$_2$ atmosphere until the reaction was complete. The resulting mixture was diluted with water and extracted with EtOAc 3 times. The organic layers were combined, washed with brine, dried over Na$_2$SO$_4$ and concentrated under vacuum. The residue was purified by flash chromatography on silica gel (0-20% MeOH in DCM) to afford desired intermediate IM-XVI.

Step 2: A mixture of aniline IM-II (1.00 equiv.) and intermediate IM-XVI (1.10 equiv.) in AcOH was stirred at 80° C. until the reaction was complete and then concentrated under vacuum. The residue was purified by reverse phase flash chromatography on C18 silica gel (5-70% acetonitrile in water (containing 0.05% NH$_4$HCO$_3$)) to afford desired intermediate IM-XVII.

Step 3: To a stirred mixture of intermediate IM-XVII (1.00 equiv.) and HMDS (2.50 equiv.) in EtOAc at ambient temperature was added TMSOTf (2.00 equiv.). The resulting mixture was stirred at this temperature until the reaction was complete and then diluted with water and extracted with EtOAc 3 times. The organic layers were combined, washed with brine, dried over $Na_2SO_4$ and concentrated under vacuum to afford intermediate IM-XVIII which was used for the next step without further purification.

Synthesis of N-(4-(benzo[d]oxazol-5-yloxy)-3-methylphenyl)-6-(1,2,3,6-tetrahydropyridin-4-yl)pyrido[3,2-d]pyrimidin-4-amine 65

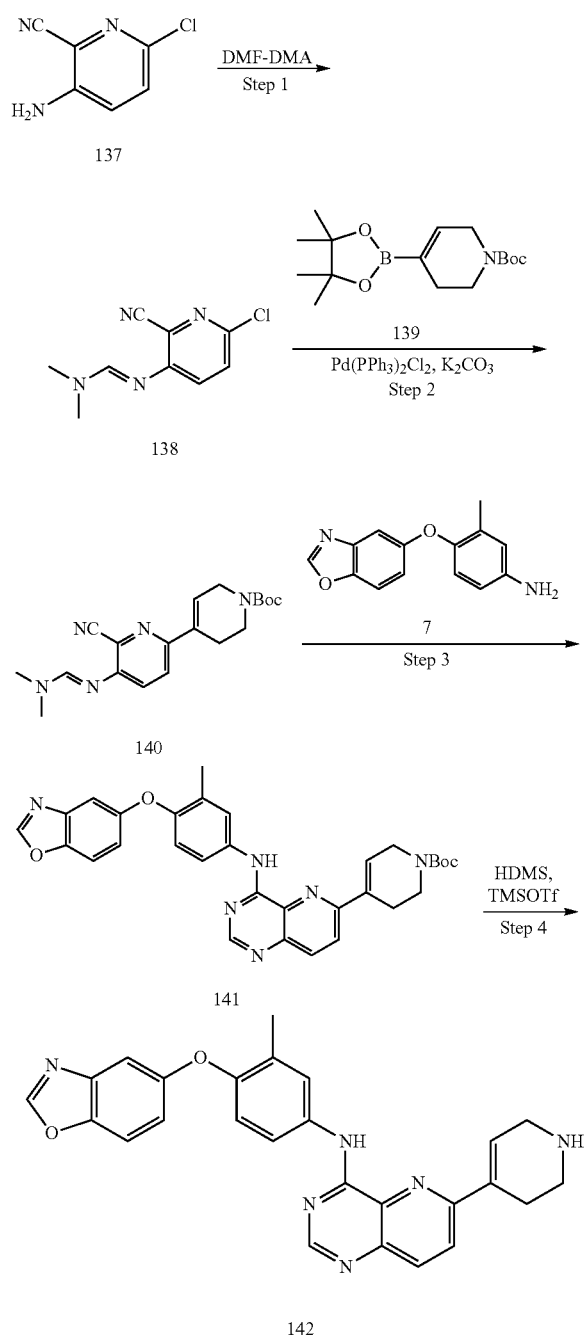

Step 1: A mixture of 3-amino-6-chloropicolinonitrile 137 (750.0 mg, 4.90 mmol, 1.00 equiv.) and DMF-DMA (1.75 g, 14.70 mmol, 3.00 equiv.) in toluene (15.00 mL) was stirred at 80° C. for 2 h under $N_2$ atmosphere. The mixture was concentrated under vacuum to afford (E)-N'-(6-chloro-2-cyanopyridin-3-yl)-N,N-dimethylformimidamide 138 (crude, 950.0 mg) as a yellow solid, which was used for the next step without further purification. LCMS (ESI, m z): 209, 211 $[M+H]^+$.

Step 2: A mixture of (E)-N'-(6-chloro-2-cyanopyridin-3-yl)-N,N-dimethylformimidamide 138 (950.0 mg, 4.56 mmol, 1.00 equiv.), tert-butyl 4-(4,4,5,5-tetramethyl-1,3,2-dioxaborolan-2-yl)-3,6-dihydropyridine-1(2H)-carboxylate 139 (2.12 g, 6.85 mmol, 1.50 equiv.), $Pd(PPh_3)_2Cl_2$ (320.0 mg, 0.45 mmol, 0.10 equiv.) and $K_2CO_3$ (1.88 g, 13.68 mmol, 3.00 equiv.) in DME (10.00 mL), $H_2O$ (10.00 mL) and EtOH (5.00 mL) was stirred at 95° C. for 2 h under $N_2$ atmosphere. The resulting mixture was diluted with water and extracted with EtOAc 3 times. The organic layers were combined, washed with brine, dried over $Na_2SO_4$ and concentrated under vacuum. The residue was purified by flash chromatography on silica gel (0-20% MeOH in DCM) to afford tert-butyl (E)-6-cyano-5-(((dimethylamino)methylene)amino)-3',6'-dihydro-[2,4'-bipyridine]-1'(2'H)-carboxylate 140 (810.0 mg, 50%) as a yellow solid. $^1$H NMR (400 MHz, DMSO-d6) δ 8.12 (s, 1H), 7.77-7.66 (m, 2H), 6.58 (s, 1H), 4.03 (d, J=3.2 Hz, 2H), 3.55-3.48 (m, 2H), 3.10 (s, 3H), 3.02 (s, 3H), 2.54-2.51 (m, 2H), 1.42 (s, 9H). LCMS (ESI, m z): 356 $[M+H]^+$.

Step 3: A mixture of 4-(benzo[d]oxazol-5-yloxy)-3-methylaniline 7 (210.0 mg, 0.87 mmol, 1.00 equiv.) and tert-butyl (E)-6-cyano-5-(((dimethylamino)methylene)amino)-3',6'-dihydro-[2,4'-bipyridine]-1'(2'H)-carboxylate 140 (341.0 mg, 0.96 mmol, 1.10 equiv.) in AcOH (6.00 mL) was stirred at 80° C. for 2 h and then concentrated under vacuum. The residue was purified by reverse phase flash chromatography on C18 silica gel (5-70% acetonitrile in water (containing 0.05% $NH_4HCO_3$)) to afford tert-butyl 4-(4-((4-(benzo[d]oxazol-5-yloxy)-3-methylphenyl)amino)pyrido[3,2-d]pyrimidin-6-yl)-3,6-dihydropyridine-1(2H)-carboxylate 141 (140.0 mg, 29%) as a yellow solid. LCMS (ESI, m z): 551 $[M+H]^+$.

Step 4: To a stirred mixture of tert-butyl 4-(4-((4-(benzo[d]oxazol-5-yloxy)-3-methylphenyl)amino)pyrido[3,2-d]pyrimidin-6-yl)-3,6-dihydropyridine-1(2H)-carboxylate 141 (140.0 mg, 0.25 mmol, 1.00 equiv.) and HMDS (102.5 mg, 0.64 mmol, 2.50 equiv.) in EtOAc (5.00 mL) at ambient temperature was added TMSOTf (111.0 mg, 0.50 mmol, 2.00 equiv.). The resulting mixture was stirred at this temperature for 1 h and then diluted with water and extracted with EtOAc 3 times. The organic layers were combined, washed with brine, dried over $Na_2SO_4$ and concentrated under vacuum to afford N-(4-(benzo[d]oxazol-5-yloxy)-3-methylphenyl)-6-(1,2,3,6-tetrahydropyridin-4-yl)pyrido[3,2-d]pyrimidin-4-amine 142 (crude, 120.0 mg) as a yellow solid, which was used for the next step without further purification. LCMS (ESI, m z): 451 $[M+H]^+$.

The following intermediates in Table 5 were obtained following above-mentioned method using the appropriate starting materials.

TABLE 5

Intermediates

| Example | Compound Structure | Physical Data MS [ESI, m/z] |
|---|---|---|
| 143 | 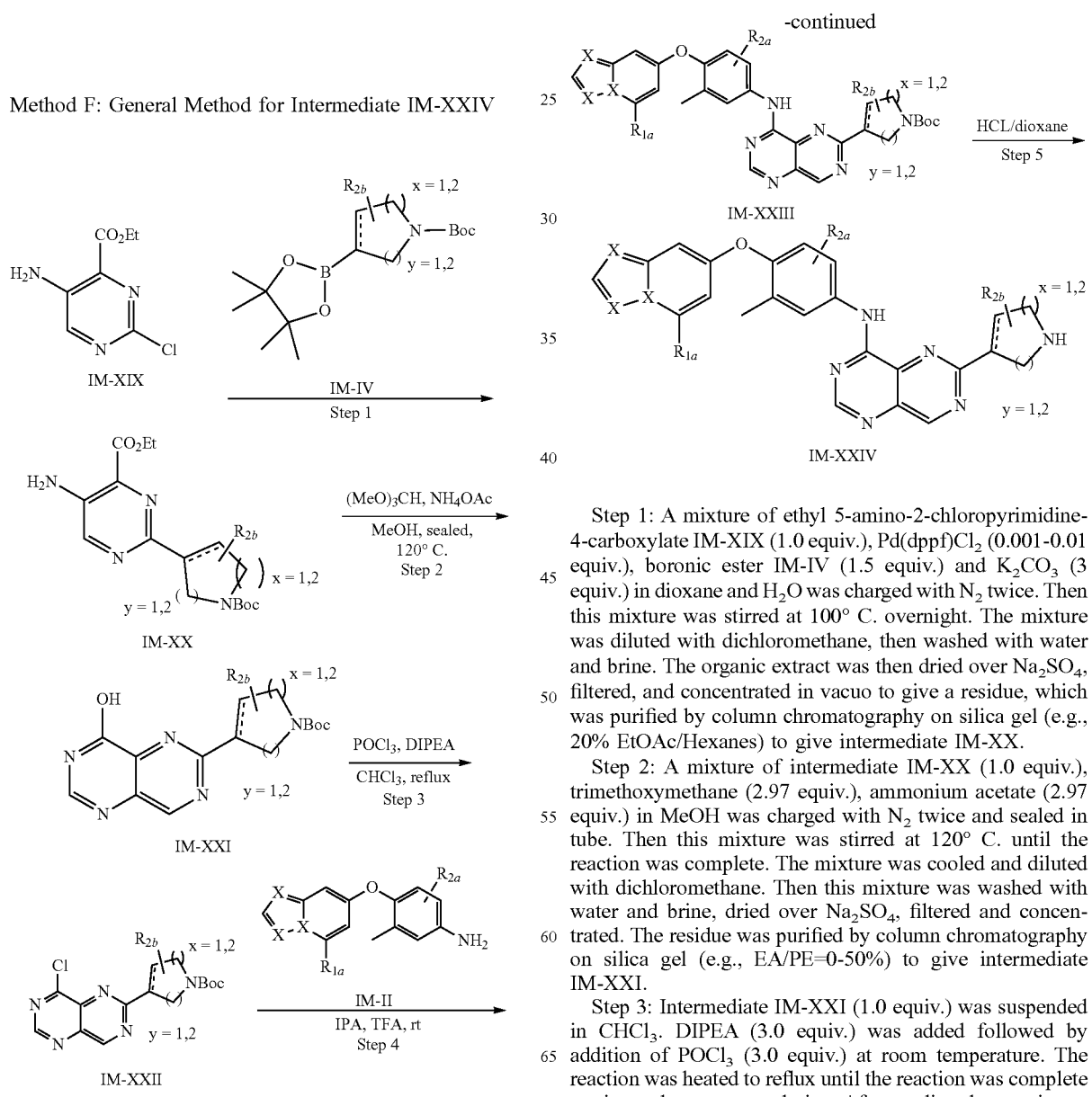 N-(4-([1,2,4]triazolo[1,5-a]pyridin-7-yloxy)-3-methylphenyl)-6-(azetidin-3-yl)pyrido[3,2-d]pyrimidin-4-amine | 425 [M + H]+ |

Method F: General Method for Intermediate IM-XXIV

Step 1: A mixture of ethyl 5-amino-2-chloropyrimidine-4-carboxylate IM-XIX (1.0 equiv.), Pd(dppf)Cl$_2$ (0.001-0.01 equiv.), boronic ester IM-IV (1.5 equiv.) and K$_2$CO$_3$ (3 equiv.) in dioxane and H$_2$O was charged with N$_2$ twice. Then this mixture was stirred at 100° C. overnight. The mixture was diluted with dichloromethane, then washed with water and brine. The organic extract was then dried over Na$_2$SO$_4$, filtered, and concentrated in vacuo to give a residue, which was purified by column chromatography on silica gel (e.g., 20% EtOAc/Hexanes) to give intermediate IM-XX.

Step 2: A mixture of intermediate IM-XX (1.0 equiv.), trimethoxymethane (2.97 equiv.), ammonium acetate (2.97 equiv.) in MeOH was charged with N$_2$ twice and sealed in tube. Then this mixture was stirred at 120° C. until the reaction was complete. The mixture was cooled and diluted with dichloromethane. Then this mixture was washed with water and brine, dried over Na$_2$SO$_4$, filtered and concentrated. The residue was purified by column chromatography on silica gel (e.g., EA/PE=0-50%) to give intermediate IM-XXI.

Step 3: Intermediate IM-XXI (1.0 equiv.) was suspended in CHCl$_3$. DIPEA (3.0 equiv.) was added followed by addition of POCl$_3$ (3.0 equiv.) at room temperature. The reaction was heated to reflux until the reaction was complete to give a clear orange solution. After cooling the reaction to room temperature, it was concentrated under reduced pressure followed by adding water. Then this mixture was extracted with dichloromethane. The combined organic solution was washed with water and brine, dried over anhydrous $Na_2SO_4$, concentrated in vacuo to give the crude intermediate IM-XXII which was used for next reaction step immediately within a few minutes without any further purification.

Step 4: To a solution of intermediate IM-XXII (1.0 equiv.) in i-PrOH, was added aniline IM-II (1.0 equiv.) at 25° C. TFA was added, and stirred at 20° C. until the reaction was complete. The reaction was quenched by adding water, then extracted with dichloromethane. The combined organic solution was washed with sat. $NaHCO_3$ and brine, dried over anhydrous $Na_2SO_4$, concentrated in vacuo to give the crude product. This crude was purified by flash (EA/PE=0-50%) to give intermediate IM-XXIII.

Step 5: The solution of intermediate IM-XXIII (1.0 equiv.) was treated with HCl (4N in dioxane), and then the reaction mixture was stirred at 20° C. until the reaction was complete. The reaction mixture was concentrated in vacuo to remove solvent to give intermediate IM-XXIV which was used directly for next reaction step without purification.

Synthesis of N-(4-([1,2,4]triazolo[1,5-a]pyridin-7-yloxy)-3-methylphenyl)-6-(1,2,3,6-tetrahydropyridin-4-yl)pyrimido[5,4-d]pyrimidin-4-amine 72

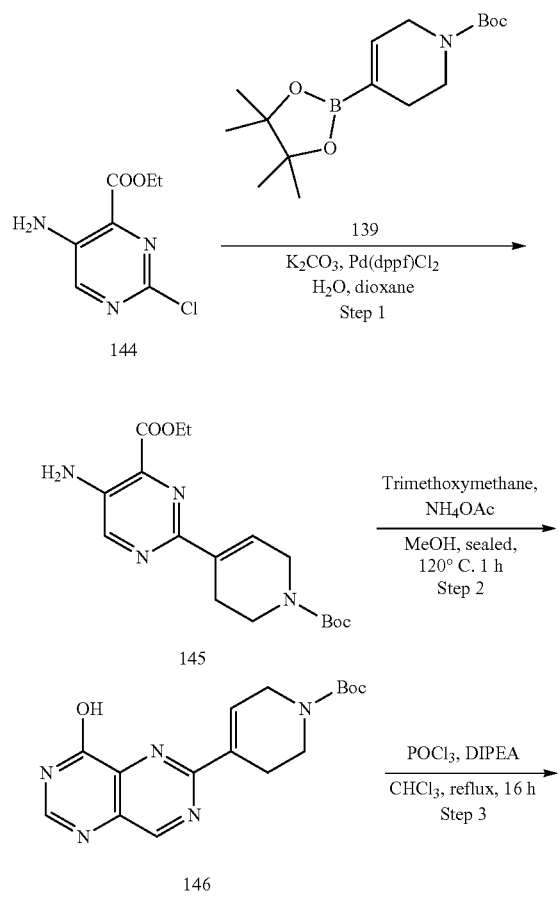

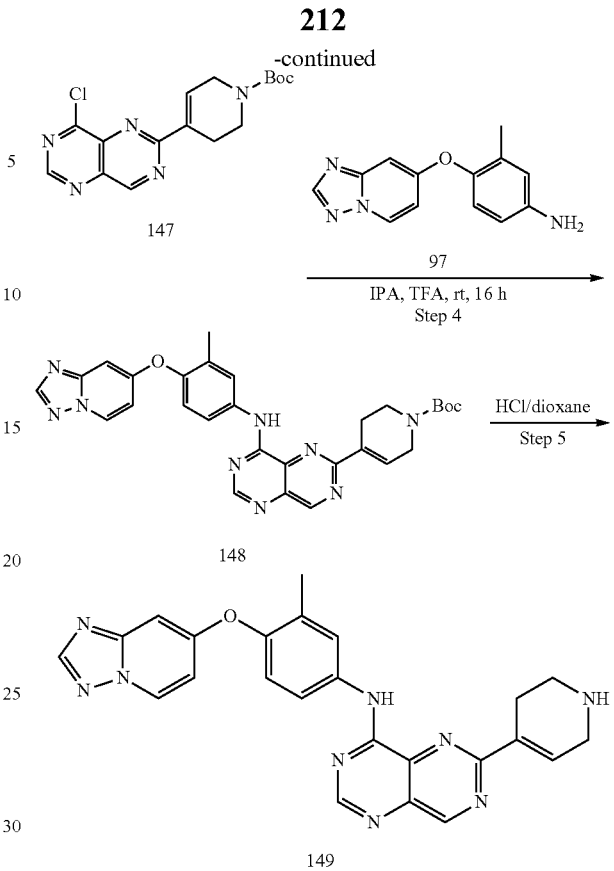

Step 1: A mixture of ethyl 5-amino-2-chloropyrimidine-4-carboxylate 144 (1.0 g, 4.96 mmol), $Pd(dppf)Cl_2$ (5.12 mg, 0.007 mmol), tert-butyl 4-(tetramethyl-1,3,2-dioxaborolan-2-yl)-1,2,3,6-tetrahydropyridine-1-carboxylate 139 (1.99 g, 6.45 mmol) and $K_2CO_3$ (2.06 g, 14.9 mmol) in dioxane (30 mL) and $H_2O$ (2 mL) was charged with $N_2$ twice. Then this mixture was stirred at 100° C. overnight. The mixture was diluted with dichloromethane (50 mL), then washed with water and brine. The organic extract was then dried over $Na_2SO_4$, filtered, and concentrated in vacuo to give a residue, which was purified by column chromatography on silica gel (20% EtOAc/Hexanes) to give ethyl 5-amino-2-(1-(tert-butoxycarbonyl)-1,2,3,6-tetrahydropyridin-4-yl)pyrimidine-4-carboxylate 145 (850 mg, 49.1% yield). LCMS ESI (m/z): 349 [M+H]$^+$.

Step 2: A mixture of ethyl 5-amino-2-{1-[(tert-butoxy)carbonyl]-1,2,3,6-tetrahydropyridin-4-yl}pyrimidine-4-carboxylate 145 (600 mg, 1.72 mmol), trimethoxymethane (0.56 mL, 5.12 mmol), ammonium acetate (398 mg, 5.12 mmol) in MeOH (10 mL) was charged with $N_2$ twice and sealed in tube. Then this mixture was stirred at 120° C. for 16 hours. The mixture was cooled and diluted with dichloromethane (50 mL). Then this mixture was washed with water and brine, dried over $Na_2SO_4$, filtered and concentrated. The residue was purified by column chromatography on silica gel (EA/PE=0-50%) to give tert-butyl 4-{8-hydroxy-[1,3]diazino[5,4-d]pyrimidin-2-yl}-1,2,3,6-tetrahydropyridine-1-carboxylate 146 (200 mg, 35.3% yield). LCMS ESI (m/z): 330 [M+H]$^+$.

Step 3: tert-butyl 4-{8-hydroxy-[1,3]diazino[5,4-d]pyrimidin-2-yl}-1,2,3,6-tetrahydropyridine-1-carboxylate 146 (100 mg, 0.30 mmol) was suspended in 10 mL of $CHCl_3$. Ethylbis(propan-2-yl) amine (DIPEA, 0.15 mL, 0.90 mmol) was added followed by addition of $POCl_3$ (137.8 mg, 0.90 mmol) at room temperature. The reaction was heated to reflux for 24 hours to give a clear orange solution. After cooling the reaction to room temperature, it was concentrated under reduced pressure followed by adding water (10 mL). Then this mixture was extracted with dichloromethane (3×10 mL). The combined organic solution was washed with water (5 mL) and brine (5 mL), dried over anhydrous Na$_2$SO$_4$, concentrated in vacuo to give the crude tert-butyl 4-{8-chloro-[1,3]diazino[5,4-d]pyrimidin-2-yl}-1,2,3,6-tetrahydropyridine-1-carboxylate 147 (200 mg, purity: 50%) as a brown gum which was used for next reaction step immediately within a few minutes without any further purification. LCMS ESI (m/z): 348 [M+H]$^+$.

Step 4: To a solution of tert-butyl 4-{8-chloro-[1,3]diazino[5,4-d]pyrimidin-2-yl}-1,2,3,6-tetrahydropyridine-1-carboxylate 147 (200 mg, purity: 50%, 0.288 mmol) in i-PrOH (5 mL), was added 3-methyl-4-{[1,2,4]triazolo[1,5-a]pyridin-7-yloxy}aniline 97 (69 mg, 0.29 mmol) at 25° C. TFA (0.1 mL) was added, and stirred at 20° C. for another 16 hours. The reaction was quenched by adding water (5 mL), then extracted with dichloromethane (3×10 mL). The combined organic solution was washed with sat. NaHCO$_3$ (5 mL) and brine (5 mL), dried over anhydrous Na$_2$SO$_4$, concentrated in vacuo to give the crude product. This crude was purified by flash (EA/PE=0-50%) to give tert-butyl 4-{8-[(3-methyl-4-{[1,2,4]triazolo[1,5-a]pyridin-7-yloxy}phenyl)amino]pyrimido[5,4-d][1,3] diazin-2-yl}-1,2,3,6-tetrahydropyridine-1-carboxylate 148 (95 mg, 72% yield) as a yellow gum. LCMS (ESI): m/z 552 [M+H]$^+$.

Step 5: The solution of tert-butyl 4-{8-[(3-methyl-4-{[1,2,4]triazolo[1,5-a]pyridin-7-yloxy}phenyl)amino]pyrimido[5,4-d][1,3]diazin-2-yl}-1,2,3,6-tetrahydropyridine-1-carboxylate 148 (95 mg, 0.172 mmol) was treated with HCl (2 mL, 4N in dioxane), and then the reaction mixture was stirred at 20° C. for 1 hour. After 1 hour, the reaction mixture was concentrated in vacuo to remove solvent to give N-(3-methyl-4-{[1,2,4]triazolo[1,5-a]pyridin-7-yloxy}phenyl)-6-(1,2,3,6-tetrahydropyridin-4-yl)pyrimido[5,4-d][1,3]diazin-4-amine hydrochloride 149 (70 mg, 90% yield) as a brown gum which was used directly for next reaction step without purification. LCMS (ESI): m/z 452 [M+H]$^+$.

The following intermediates in Table 6 were obtained following above-mentioned method using the appropriate starting materials.

TABLE 6

Intermediates

| Example | Compound Structure | Physical Data MS [ESI, m/z] |
|---|---|---|
| 150 | N-(4-([1,2,4]triazolo[1,5-a]pyridin-7-yloxy)-2-fluoro-3-methylphenyl)-6-(1,2,3,6-tetrahydropyridin-4-yl)pyrimido[5,4-d]pyrimidin-4-amine hydrochloride | 470 [M + H]$^+$ |
| 151 | N-(4-([1,2,4]triazolo[1,5-a]pyridin-7-yloxy)-2-fluoro-5-methylphenyl)-6-(1,2,3,6-tetrahydropyridin-4-yl)pyrimido[5,4-d]pyrimidin-4-amine hydrochloride | 470 [M + H]$^+$ |

TABLE 6-continued

| | Intermediates | |
|---|---|---|
| Example | Compound Structure | Physical Data MS [ESI, m/z] |
| 152 | 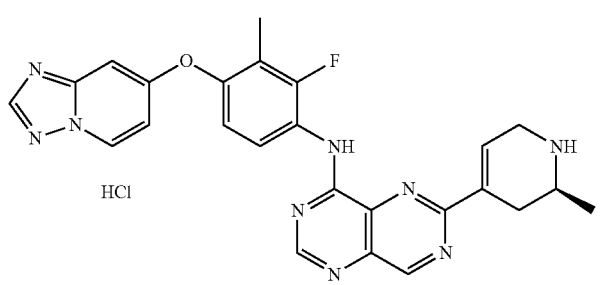 (S)-N-(4-([1,2,4]triazolo[1,5-a]pyridin-7-yloxy)-2-fluoro-3-methylphenyl)-6-(2-methyl-1,2,3,6-tetrahydropyridin-4-yl)pyrimido[5,4-d]pyrimidin-4-amine hydrochloride | 484 [M + H]$^+$ |
| 153 | 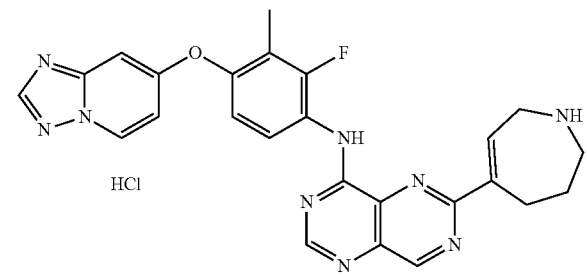 [SMILES: Cc1c(Oc2ccn3ncnc3c2)ccc(Nc2ncnc3cnc(C4=CCNCCC4)nc23)c1F ; Cl] N-(4-([1,2,4]triazolo[1,5-a]pyridin-7-yloxy)-2-fluoro-3-methylphenyl)-6-(2,3,6,7-tetrahydro-1H-azepin-4-yl)pyrimido[5,4-d]pyrimidin-4-amine hydrochloride | 484 [M + H]$^+$ |
| 154 | 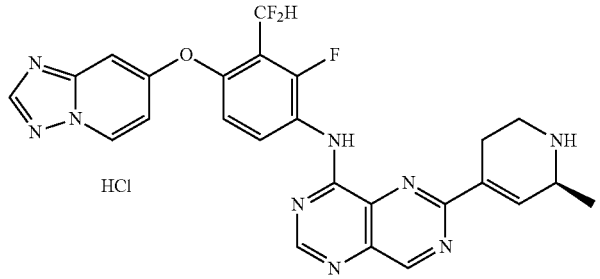 [SMILES: C[C@H]1C=C(c2ncc3ncnc(Nc4ccc(Oc5ccn6ncnc6c5)c(C(F)(F)F)c4F)c3n2)CCN1 ; Cl] N-[3-(difluoromethyl)-2-fluoro-4-{[1,2,4]triazolo[l,5-a]pyridin-7-yloxy}phenyl]-6-[(2S)-2-methyl-1,2,3,6-tetrahydropyridin-4-yl]-[1,3]diazino[5,4-d]pyrimidin-4-amine hydrochloride | 520 [M + H]$^+$ |

TABLE 6-continued

Intermediates

| Example | Compound Structure | Physical Data MS [ESI, m/z] |
|---|---|---|
| 155 | | 538 [M + H]⁺ |

(S)-N-(4-([1,2,4]triazolo[1,5-a]pyridin-7-yloxy)-2-fluoro-3-(trifluoromethyl)phenyl)-6-(2-methyl-1,2,3,6-tetrahydropyridin-4-yl)pyrimido[5,4-d]pyrimidin-4-amine hydrochloride

| 156 | | 484 [M + H]⁺ |

N-(2-fluoro-5-methyl-4-{[1,2,4]triazolo[1,5-a]pyridin-7-yloxy}phenyl)-6-[(2S)-2-methyl-1,2,3,6-tetrahydropyridin-4-yl]-[1,3]diazino[5,4-d]pyrimidin-4-amine hydrochloride

TABLE 6-continued
Intermediates
| Example | Compound Structure | Physical Data MS [ESI, m/z] |
|---|---|---|
| 157 | 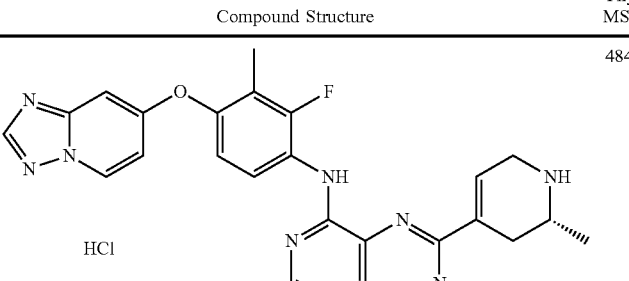<br>HCl<br><br>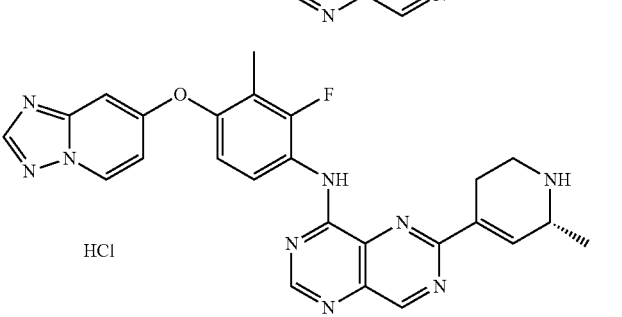<br>HCl<br><br>(R)-N-(4-([1,2,4]triazolo[1,5-a]pyridin-7-yloxy)-2-fluoro-3-methylphenyl)-6-(2-methyl-1,2,3,6-tetrahydropyridin-4-yl)pyrimido[5,4-d]pyrimidin-4-amine hydrochloride | 484 [M + H]$^+$ |
Method G: General Method for Intermediate IM-XXIX
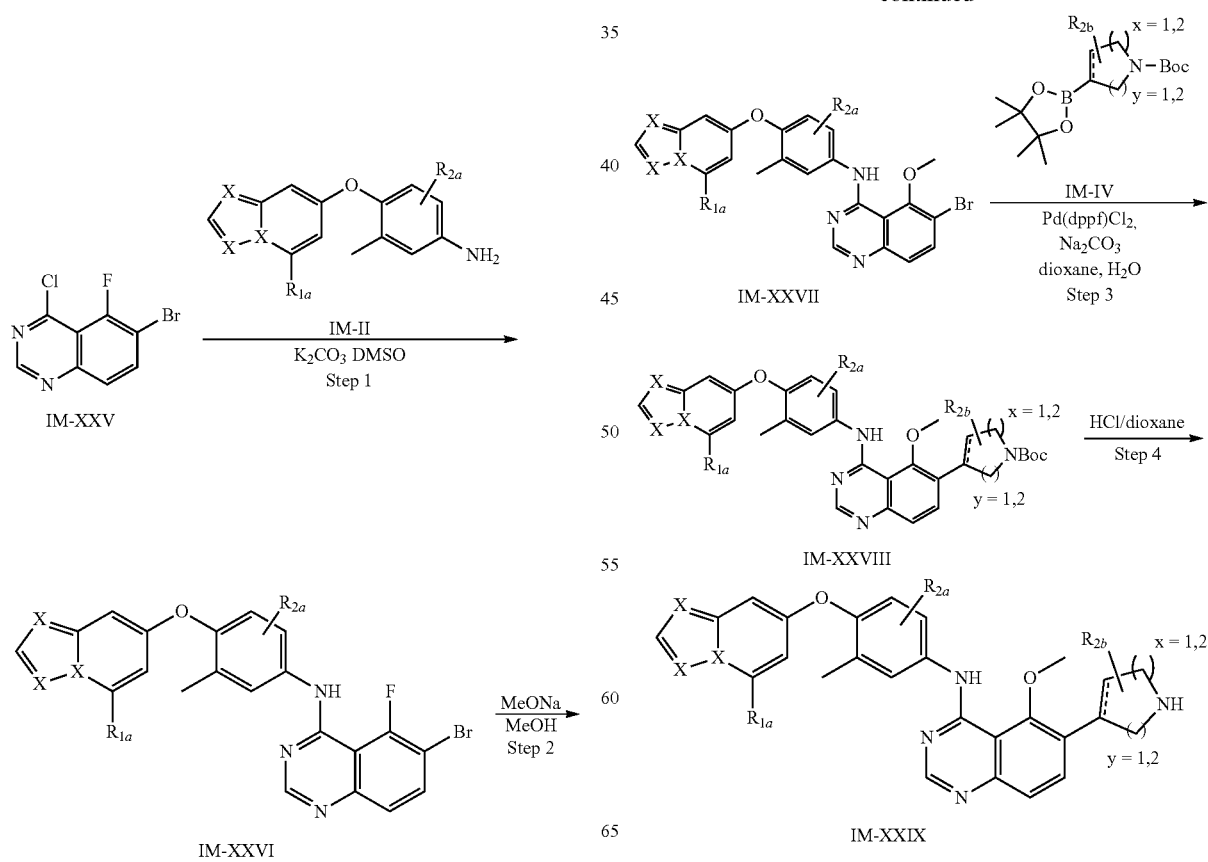

Step 1: To a solution of aniline IM-II (1.0 equiv.) in DMSO were added K$_2$CO$_3$ (2.9 equiv,) and 6-bromo-4-chloro-5-fluoroquinazoline IM-XXV (1.0 equiv.) at room temperature. After stirring at 100° C. until the reaction was complete, TLC showed the reaction was completed. The reaction mixture was diluted by EtOAc (20 mL). The organic layer was washed by sat. NH$_4$Cl and brine, dried over anhydrous Na$_2$SO$_4$, filtered and concentrated. The residue was purified by column chromatography on silica gel (e.g., PE:EtOAc=1:2) to afford intermediate IM-XXVI.

Step 2: To a mixture of intermediate IM-XXVI (1.0 equiv.) in MeOH was added a solution of MeONa (3.0 equiv., 30% wt) in MeOH at room temperature. The reaction was stirred at 50° C. until the reaction was complete, then concentrated directly. The residue was diluted with EtOAc (10 mL), washed with water and brine. The organic phase was dried over anhydrous Na$_2$SO$_4$, filtered and concentrated to dryness to give intermediate IM-XXVII.

Step 3: To a stirred solution of intermediate IM-XXVII (1.0 equiv.) and boronic ester IM-IV (1.2 equiv.) in 1,4-dioxane and water, were added Na$_2$CO$_3$ (3.0 equiv.) and Pd(dppf)Cl$_2$ (0.1 equiv.) at room temperature. The reaction was degassed under N$_2$ atmosphere for three times and stirred at 100° C. until the reaction was complete. The reaction was cooled to r.t, filtered and the solid was washed with EtOAc. The filtrate was washed with water and brine, dried over Na$_2$SO$_4$ and concentrated to dryness. The residue was purified by chromatography on silica gel (DCM:MeOH=15:1) to give intermediate IM-XXVIII.

Step 4: To a stirred solution of intermediate IM-XXVIII (1.0 equiv.) in ethyl acetate was added HCl-dioxane at 0° C. under N$_2$. After stirring at 0° C. until the reaction was complete, the reaction was concentrated to give intermediate IM-XXIX.

Synthesis of N-(4-([1,2,4]triazolo[1,5-a]pyridin-7-yloxy)-3-methylphenyl)-5-methoxy-6-(1,2,3,6-tetrahydropyridin-4-yl)quinazolin-4-amine hydrochloride 164

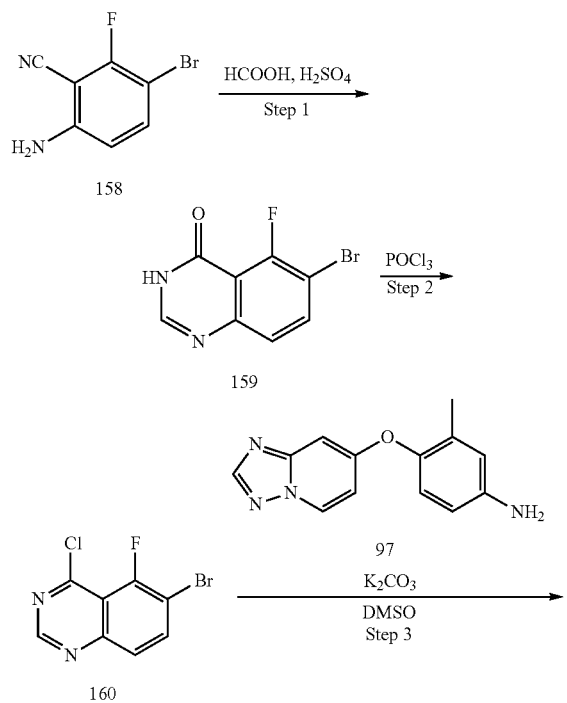

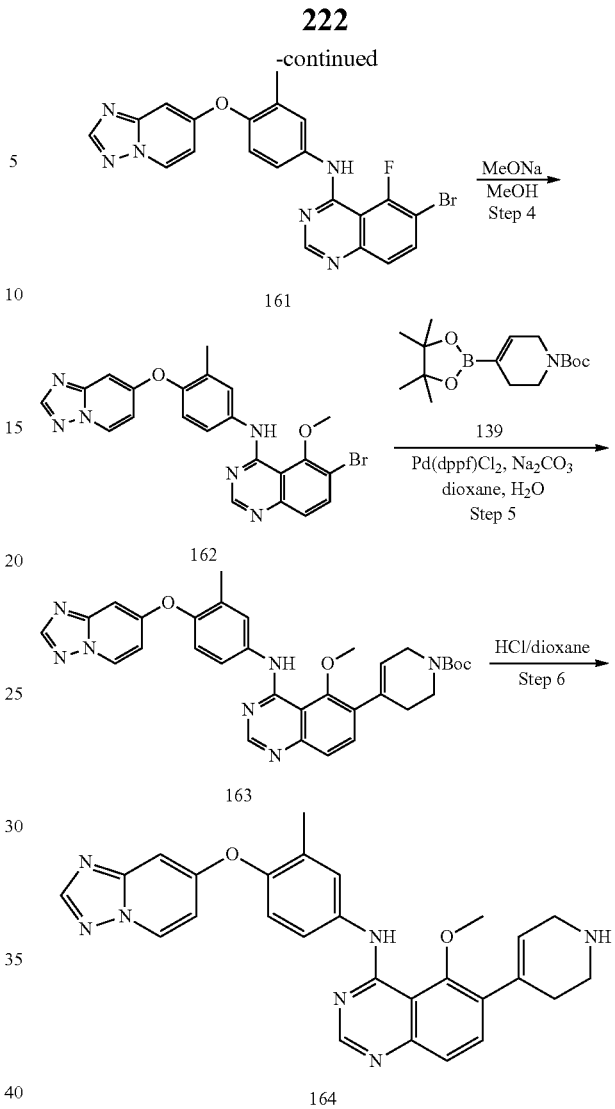

Step 1: To a suspension of 6-amino-3-bromo-2-fluorobenzonitrile 158 (5.0 g, 23 mmol) in formic acid (30 mL) was added a mixture of conc. H$_2$SO$_4$ (2 mL) and formic acid (5 mL). The mixture was stirred at 115° C. for 1 hr. LCMS showed that the reaction was completed. The mixture was cooled down to r.t. and poured into ice water (100 mL). This mixture was stirred at r.t for 15 minutes and filtered. The filtered cake was washed with water (5 mL) and ethanol (100 mL) to give 6-bromo-5-fluoro-3, 4-dihydroquinazolin-4-one 159 (5.0 g, 89%) as a white solid. $^1$H NMR (400 MHz, DMSO-d6) δ 8.16 (s, 1H), 8.06 (dd, J=8.8, 7.1 Hz, 1H), 7.46 (dd, J=8.8, 1.2 Hz, 1H). LCMS ESI (m/z):242 [M+H]$^+$.

Step 2: A suspension of 6-bromo-5-fluoro-3,4-dihydroquinazolin-4-one 159 (1.0 g, 4.1 mmol) in POCl$_3$ (10 mL) was stirred and refluxed for 18 hours. TLC showed that 30% of desired product. The mixture was concentrated to give the crude product, which was purified by column chromatography on silica gel (PE:EtOAc=10:1-2:1) to afford 6-bromo-4-chloro-5-fluoroquinazoline 160 (0.24 g, 22%) as a yellow solid. LCMS ESI (m/z):262 [M+H]$^+$.

Step 3: To a solution of 4-([1,2,4]triazolo[1,5-a]pyridin-7-yloxy)-3-methylaniline 97 (400 mg, 1.70 mmol) in DMSO (5 mL) were added K$_2$CO$_3$ (690 mg, 5.00 mmol) and 6-bromo-4-chloro-5-fluoroquinazoline 160 (435 mg, 1.70 mmol) at room temperature. After stirring at 100° C. for 16 h, TLC showed the reaction was completed. The reaction mixture was diluted by EtOAc (20 mL). The organic layer was washed by sat. NH₄Cl (30 mL) and brine (15 mL), dried over anhydrous Na₂SO₄, filtered and concentrated. The residue was purified by column chromatography on silica gel (PE:EtOAc=1:2) to afford N-(4-([1,2,4]triazolo[1,5-a]pyridin-7-yloxy)-3-methylphenyl)-6-bromo-5-fluoroquinazolin-4-amine 161 (300 mg, 38.7%) as a white solid. LCMS ESI (m/z):465/467 [M+H]⁺.

Step 4: To a mixture of N-(4-([1,2,4]triazolo[1,5-a]pyridin-7-yloxy)-3-methylphenyl)-6-bromo-5-fluoroquinazolin-4-amine 161 (100 mg, 0.22 mmol) in MeOH (2 mL) was added a solution of MeONa (116 mg, 0.65 mmol, 30% wt) in MeOH at room temperature. The reaction was stirred at 50° C. for 12 hours, then concentrated directly. The residue was diluted with EtOAc (10 mL), washed with water and brine. The organic phase was dried over anhydrous Na₂SO₄, filtered and concentrated to dryness to give N-(4-([1,2,4]triazolo[1,5-a]pyridin-7-yloxy)-3-methylphenyl)-6-bromo-5-methoxyquinazolin-4-amine 162 (97 mg, 95% yield) as a white solid. LCMS (ESI) (m/z): 477/479 [M+H]⁺.

Step 5: To a stirred solution of N-(4-([1,2,4]triazolo[1,5-a]pyridin-7-yloxy)-3-methylphenyl)-6-bromo-5-methoxyquinazolin-4-amine 162 (90 mg, 0.19 mmol) and tert-butyl 4-(4,4,5,5-tetramethyl-1,3,2-dioxaborolan-2-yl)-3,6-dihydropyridine-1(2H)-carboxylate 139 (64 mg, 0.21 mmol) in 1,4-dioxane (1 mL) and water (0.2 mL), were added Na₂CO₃ (60 mg, 0.57 mmol) and Pd(dppf)Cl₂ (14 mg, 0.02 mmol) at room temperature. The reaction was degassed under N₂ atmosphere for three times and stirred at 100° C. for 4 hours. The reaction was cooled to r.t, filtered and the solid was washed with EtOAc (15 mL). The filtrate was washed with water (15 mL) and brine (15 mL), dried over Na₂SO₄ and concentrated to dryness. The residue was purified by chromatography on silica gel (DCM:MeOH=15:1) to give tert-butyl 4-(4-((4-([1,2,4]triazolo[1,5-a]pyridin-7-yloxy)-3-methylphenyl)amino)-5-methoxyquinazolin-6-yl)-3,6-dihydropyridine-1(2H)-carboxylate 163 (108 mg, 98.8% yield) as a yellow oil. LCMS (ESI) (m/z): 580 [M+H]⁺.

Step 6: To a stirred solution of tert-butyl 4-(4-((4-([1,2,4]triazolo[1,5-a]pyridin-7-yloxy)-3-methylphenyl)amino)-5-methoxyquinazolin-6-yl)-3,6-dihydropyridine-1(2H)-carboxylate 163 (108 mg, 0.19 mmol) in EA (2 mL) was added HCl-dioxane (2 mL, 4 M) at 0° C. under N₂. After stirring at 0° C. for 1 h, the reaction was concentrated to give N-(4-([1,2,4]triazolo[1,5-a]pyridin-7-yloxy)-3-methylphenyl)-5-methoxy-6-(1,2,3,6-tetrahydropyridin-4-yl)quinazolin-4-amine hydrochloride 164 (95 mg, 99% yield) as a white solid. LCMS (ESI) (m/z): 480 [M+H]⁺.

Method H: General Method for Intermediate IM-XXXI

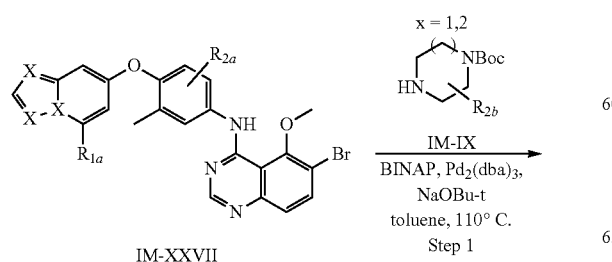

IM-XXVII

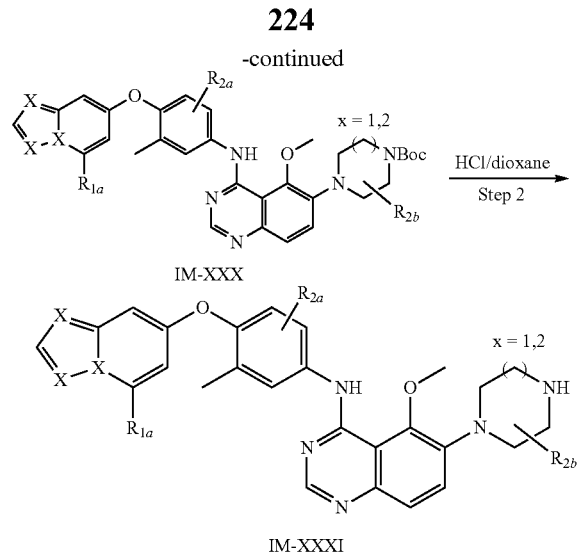

IM-XXX

IM-XXXI

Step 1: To a solution of intermediate IM-XXVII (1.0 equiv.) in toluene were added BINAP (0.2 equiv.), and Pd₂(dba)₃ (0.05 equiv.) and ᵗ-BuONa (2.0 equiv.) and tert-butyl piperazine-1-carboxylate IM-IX (1.3 equiv.), then the mixture was stirred at 110° C. overnight. After overnight, the reaction mixture was quenched by NH₄Cl aq. This mixture was extracted with ethyl acetate. The combined organic solution was washed with sat NH₄Cl aq and brine, dried over anhydrous Na₂SO₄, concentrated in vacuo to give the residue. The residue was purified by prep-TLC to give intermediate IM-XXX.

Step 2: To a solution of intermediate IM-XXX (1.0 equiv.) in DCM was added TFA. Then the mixture was stirred at r.t. until the reaction was complete. The mixture was concentrated in vacuo to give the residue. The reaction mixture was partitioned between ethyl acetate and saturated aqueous NaHCO₃ solution. This organic solution was separated, dried over anhydrous Na₂SO₄, concentrated in vacuo to give the residue. The residue was purified by flash to give intermediate IM-XXXI.

Synthesis of 5-methoxy-N-(3-methyl-4-{[1,2,4]triazolo[1,5-a]pyridin-7-yloxy}phenyl)-6-(piperazin-1-yl)quinazolin-4-amine 167

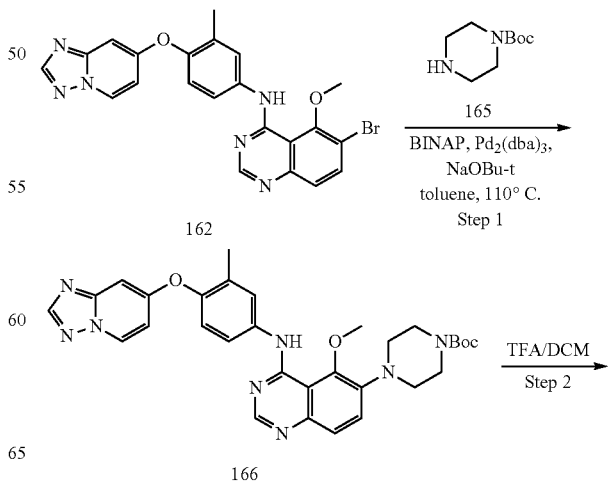

162

166

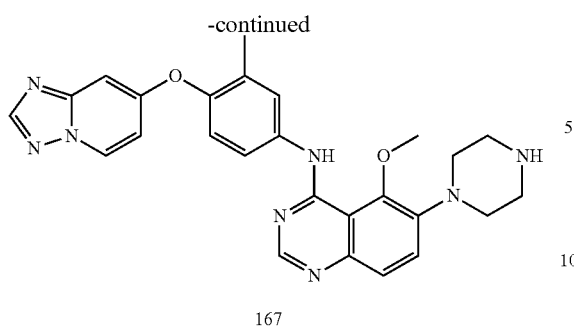

167

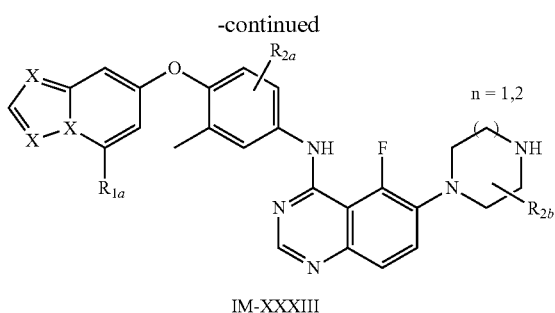

IM-XXXIII

Step 1: To a solution of 6-bromo-5-methoxy-N-(3-methyl-4-{[1,2,4]triazolo[1,5-a]pyridin-7-yloxy}phenyl) quinazolin-4-amine 162 (20 mg, 0.042 mmol) in toluene (0.5 mL) were added BINAP (5.2 mg, 0.008 mmol), and Pd$_2$(dba)$_3$ (1.9 mg, 0.002 mmol) and $^t$-BuONa (8 mg, 0.084 mmol) and tert-butyl piperazine-1-carboxylate 165 (9.36 mg, 0.050 mmol), then the mixture was stirred at 110° C. overnight. After overnight, the reaction mixture was quenched by NH$_4$Cl aq. This mixture was extracted with EA (3×10 mL). The combined organic solution was washed with sat NH$_4$Cl aq (10 mL) and brine (10 mL), dried over anhydrous Na$_2$SO$_4$, concentrated in vacuo to give the residue. The residue was purified by prep-TLC (MeOH/DCM=0-20%) to give tert-butyl 4-{5-methoxy-4-[(3-methyl-4-{[1,2,4]triazolo[1,5-a]pyridin-7-yloxy}phenyl) amino]quinazolin-6-yl}piperazine-1-carboxylate 166 (18 mg, 73.7% yield) as a yellow solid. LCMS ESI (m/z): 583 [M+H]$^+$.

Step 2: To a solution of tert-butyl 4-{5-methoxy-4-[(3-methyl-4-{[1,2,4]triazolo[1,5-a]pyridin-7-yloxy}phenyl) amino]quinazolin-6-yl}piperazine-1-carboxylate 166 (86 mg, 0.148 mmol) in DCM (1 mL) was added TFA (0.8 mL). Then the mixture was stirred at r.t. for 2 hours. After 2 hours, this mixture was concentrated in vacuo to give the residue. The reaction mixture was partitioned between EA and saturated aqueous NaHCO$_3$ solution. This organic solution was separated, dried over anhydrous Na$_2$SO$_4$, concentrated in vacuo to give the residue. The residue was purified by flash (MeOH/DCM=0-20%) to give 5-methoxy-N-(3-methyl-4-{[1,2,4]triazolo[1,5-a]pyridin-7-yloxy}phenyl)-6-(piperazin-1-yl)quinazolin-4-amine 167 (60 mg, 84.2% yield) as a yellow oil. LCMS ESI (m/z): 483 [M+H]$^+$.

Method I: General method for intermediate IM-XXXIII

Step 1: To a solution of intermediate IM-XXVI (1.0 equiv.) in toluene were added Boc protected amine IM-IX (1.2 equiv.), NaOtBu (2.0 equiv.), BINAP (0.2 equiv.) and Pd$_2$(dba)$_3$ (0.04 equiv.) under N$_2$. Then this mixture was stirred at 120° C. until the reaction was complete. The reaction mixture was quenched with saturated NaHCO$_3$ and extracted with DCM. The combined organic layers were washed with brine (5 mL), dried over anhydrous Na$_2$SO$_4$, and concentrated. The residue was purified by column chromatography on silica gel (DCM:MeOH) to intermediate IM-XXXII as a yellow solid.

Step 2: To a solution of IM-XXXII (1.0 equiv.) in DCM was added TFA. The resulting mixture was stirred at room temperature until the reaction was complete. The reaction mixture was quenched with saturated NaHCO$_3$ and extracted with DCM. The combined organic layers were washed with brine (5 mL), dried over anhydrous Na$_2$SO$_4$, and concentrated. The residue was purified by column chromatography on silica gel (DCM:MeOH) to give intermediate IM-XXXIII.

Synthesis of N-(4-([1,2,4]triazolo[1,5-a]pyridin-7-yloxy)-3-methylphenyl)-5-fluoro-6-(piperazin-1-yl)quinazolin-4-amine 169

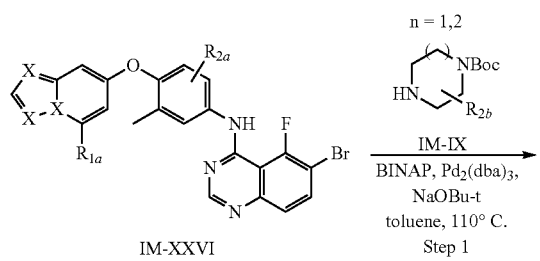

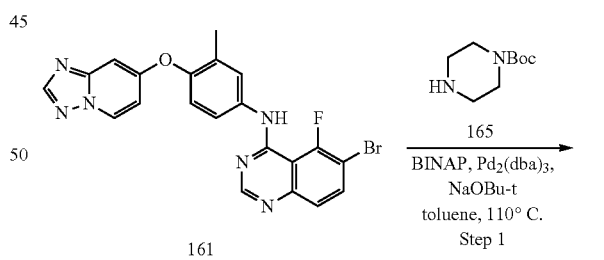

161

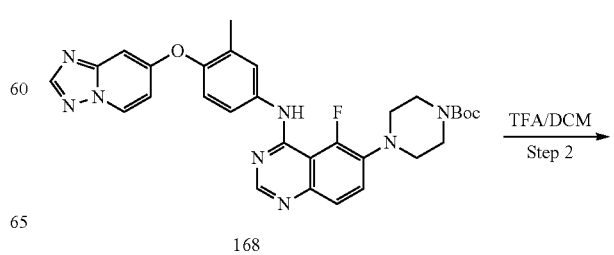

168

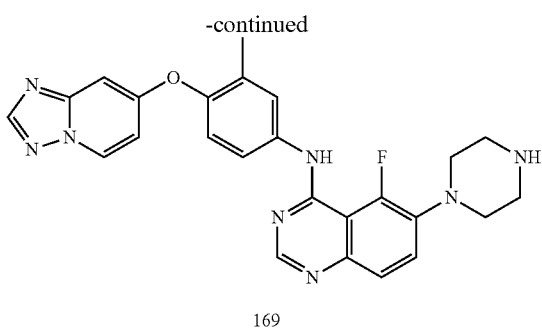

169

Step 1: To a solution of N-(4-([1,2,4]triazolo[1,5-a]pyridin-7-yloxy)-3-methylphenyl)-6-bromo-5-fluoroquinazolin-4-amine 161 (200 mg, 0.43 mmol) in toluene (10 mL) were added tert-butyl piperazine-1-carboxylate 165 (96 mg, 0.52 mmol), NaO$^t$Bu (82 mg, 0.86 mmol), BINAP (53 mg, 0.086 mmol) and Pd$_2$(dba)$_3$ (17 mg, 0.021 mmol) under N$_2$. Then this mixture was stirred at 120° C. for 24 hours. The reaction mixture was quenched with saturated NaHCO$_3$ and extracted with DCM (5 mL×2). The combined organic layers were washed with brine (5 mL), dried over anhydrous Na$_2$SO$_4$, and concentrated. The residue was purified by column chromatography on silica gel (DCM:MeOH=20:1, V/V) to give tert-butyl 4-(4-((4-([1,2,4]triazolo[1,5-a]pyridin-7-yloxy)-3-methylphenyl)amino)-5-fluoroquinazolin-6-yl)piperazine-1-carboxylate 168 (90 mg, 36.7% yield) as a yellow solid. LCMS ESI (m/z):571 [M+H]$^+$.

Step 2: To a solution of tert-butyl 4-(4-((4-([1,2,4]triazolo[1,5-a]pyridin-7-yloxy)-3-methylphenyl)amino)-5-fluoroquinazolin-6-yl)piperazine-1-carboxylate 168 (90 mg, 0.16 mmol) in DCM (1 mL) was added TFA (0.5 mL, 6.7 mmol). The resulting mixture was stirred at room temperature for 2 hours. The reaction mixture was quenched with saturated NaHCO$_3$ and extracted with DCM (5 mL×2). The combined organic layers were washed with brine (5 mL), dried over anhydrous Na$_2$SO$_4$, and concentrated. The residue was purified by column chromatography on silica gel (DCM:MeOH=15:1, V/V) to give N-(4-([1,2,4]triazolo[1,5-a]pyridin-7-yloxy)-3-methylphenyl)-5-fluoro-6-(piperazin-1-yl)quinazolin-4-amine 169 (66 mg, 88.9% yield) as a yellow oil. LCMS ESI (m/z):471 [M+H]$^+$.

The following intermediates in Table 7 were obtained following above-mentioned method using the appropriate starting materials.

TABLE 7

| Example | Compound Structure | Physical Data MS [ESI, m/z] |
|---|---|---|
| 170 | N-(5-([1,2,4]triazolo[1,5-a]pyridin-7-yloxy)-3-fluoro-4-methylpyridin-2-yl)-5-fluoro-6-(piperazin-1-yl)quinazolin-4-amine | 490 [M + H]$^+$ |
| 171 | (R)-N-(5-([1,2,4]triazolo[1,5-a]pyridin-7-yloxy)-3-fluoro-4-methylpyridin-2-yl)-5-fluoro-6-(3-methylpiperazin-1-yl)quinazolin-4-amine | 504 [M + H]$^+$ |

TABLE 7-continued

| | Intermediate | |
|---|---|---|
| Example | Compound Structure | Physical Data MS [ESI, m/z] |
| 172 | 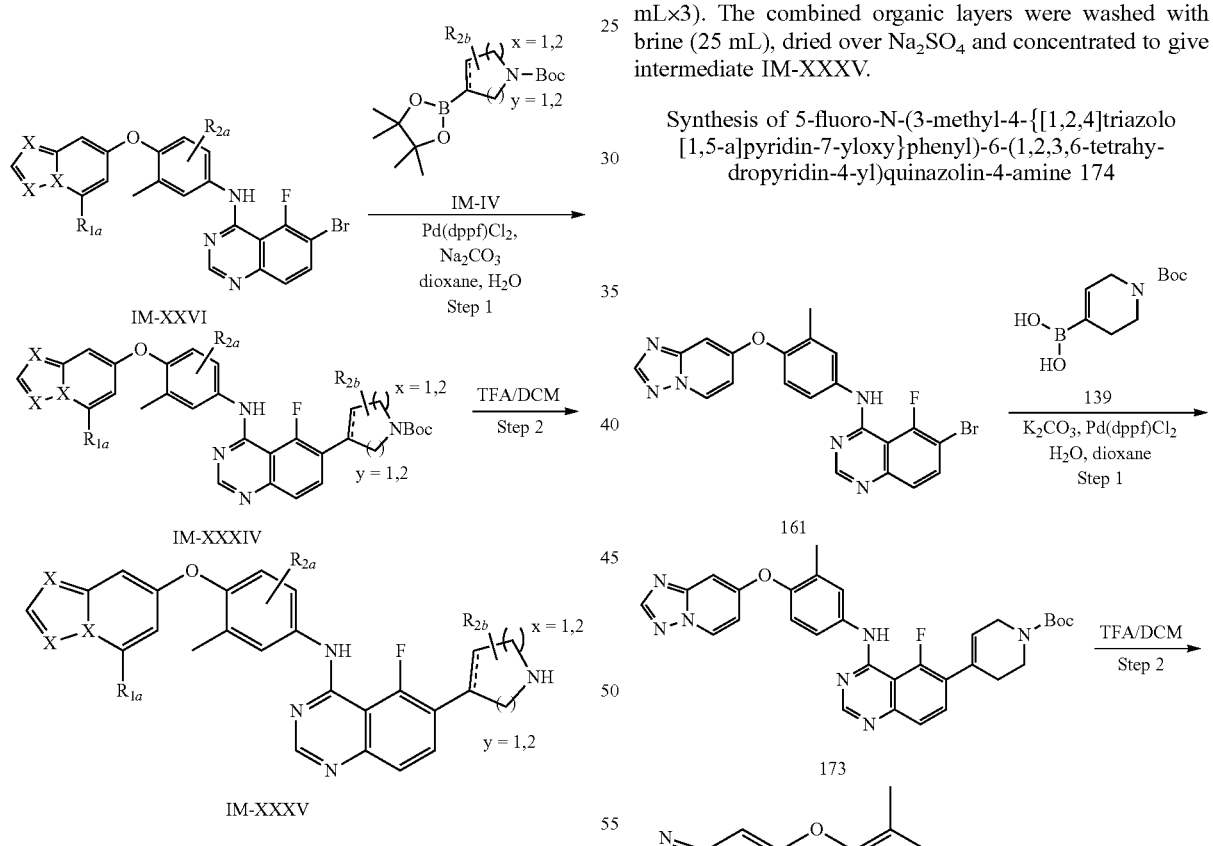  tert-butyl (R)-4-(5-fluoro-4-((2-fluoro-3-methyl-4-((3-methylimidazo[1,2-a]pyridin-7-yl)oxy)phenyl)amino)quinazolin-6-yl)-2-methylpiperazine-1-carboxylate | 616 [M + H]+ |

Method J: General Method for Intermediate IM-XXXV

Step 1: To a solution of intermediate IM-XXVI (1 equiv.) in dioxane and water were added boronic ester IM-IV (1.2 equiv.), Pd(dppf)Cl₂ (0.1 equiv.) and K₂CO₃ (2.0 equiv.). Then this mixture was stirred at 100° C. until the reaction was complete. After cooling to r.t., this mixture was concentrated, diluted with H₂O, and then extracted with EtOAc. The combined organic solutions were dried over Na₂SO₄ and concentrated. The residue was purified by prep-TLC (PE:EA=0:1) to give intermediate IM-XXXIV.

Step 2: A solution of intermediate IM-XXXIV (1.0 equiv.) in TFA and DCM was stirred at r.t. until the reaction was complete. Then this mixture was concentrated, basified with saturated aqueous NaHCO₃ and extracted with EtOAc (25 mL×3). The combined organic layers were washed with brine (25 mL), dried over Na₂SO₄ and concentrated to give intermediate IM-XXXV.

Synthesis of 5-fluoro-N-(3-methyl-4-{[1,2,4]triazolo[1,5-a]pyridin-7-yloxy}phenyl)-6-(1,2,3,6-tetrahydropyridin-4-yl)quinazolin-4-amine 174

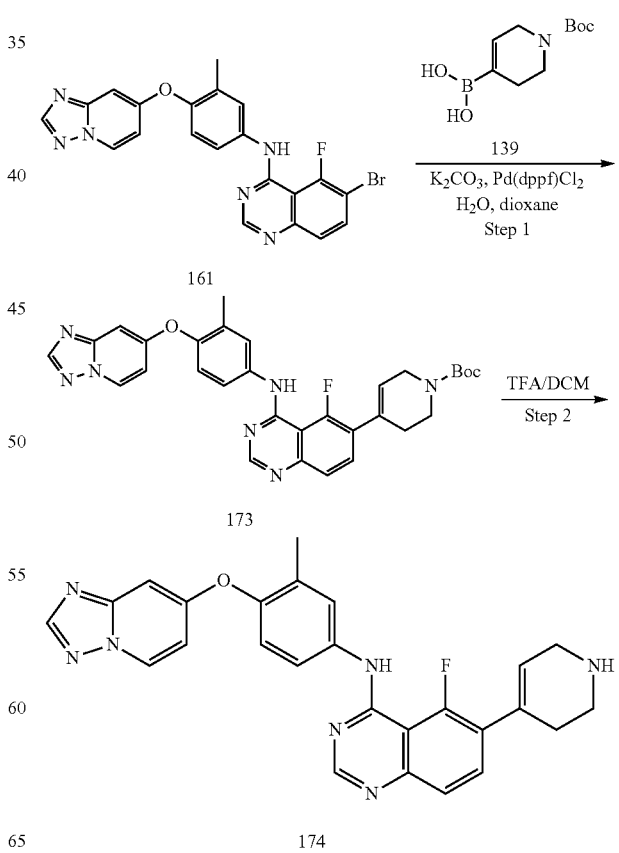

Step 1: To a solution of 6-bromo-5-fluoro-N-(3-methyl-4-{[1,2,4]triazolo[1,5-a]pyridin-7-yloxy}phenyl)quinazolin-4-amine 161 (200 mg, 0.430 mmol) in dioxane (4 mL) and water (1 mL) were added {1-[(tert-butoxy)carbonyl]-1,2,3,6-tetrahydropyridin-4-yl}boronic acid 139 (107 mg, 0.473 mmol), Pd(dppf)Cl$_2$ (31.4 mg, 0.043 mmol) and K$_2$CO$_3$ (119 mg, 0.860 mmol). Then this mixture was stirred at 100° C. for 16 hours. After cooling to r.t., this mixture was concentrated, diluted with H$_2$O, and then extracted with EtOAc (10 mL×3). The combined organic solutions were dried over Na$_2$SO$_4$ and concentrated. The residue was purified by prep-TLC (PE:EA=0:1) to give tert-butyl4-{5-fluoro-4-[(3-methyl-4-{[1,2,4]triazolo[1,5-a]pyridin-7-yloxy}phenyl)amino]quinazolin-6-yl}-1,2,3,6-tetrahydropyridine-1-carboxylate 173 (88 mg, yield: 37%) as a yellow solid. LCMS (ESI) m/z: 568.1[M+H]$^+$.

Step 2: A solution of tert-butyl 4-{5-fluoro-4-[(3-methyl-4-{[1,2,4]triazolo[1,5-a]pyridin-7-yloxy}phenyl)amino]quinazolin-6-yl}-1,2,3,6-tetrahydropyridine-1-carboxylate 173 (88 mg, 0.155 mmol) in TFA (2 mL) and DCM (2 mL) was stirred at r.t. for 1 hour. Then this mixture was concentrated, basified with saturated aqueous NaHCO$_3$and extracted with EtOAc (25 mL×3). The combined organic layers were washed with brine (25 mL), dried over Na$_2$SO$_4$ and concentrated to give 5-fluoro-N-(3-methyl-4-{[1,2,4]triazolo[1,5-a]pyridin-7-yloxy}phenyl)-6-(1,2,3,6-tetrahydropyridin-4-yl)quinazolin-4-amine 174 (135 mg, yield: 82.8%) as a white solid. LCMS (ESI) m/z: 466.1[M−H]$^+$.

Method K: General Method for Intermediate IM-XL

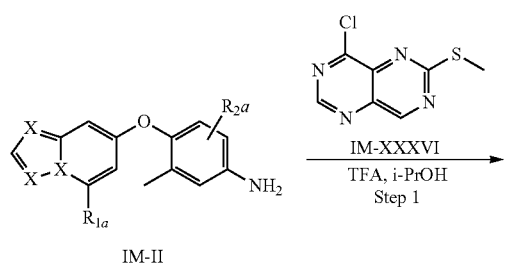

IM-II

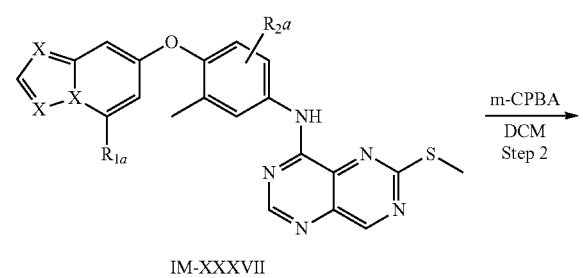

IM-XXXVII

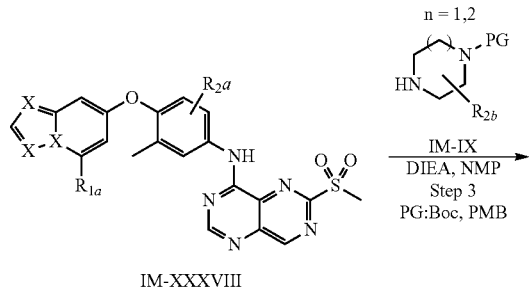

IM-XXXVIII

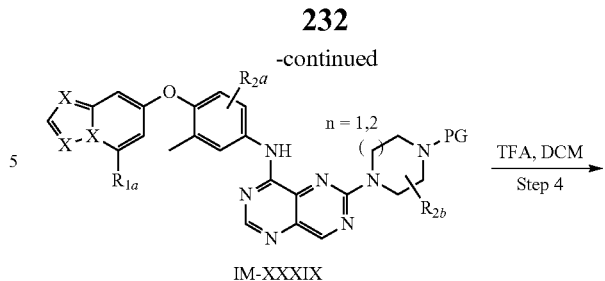

IM-XXXIX

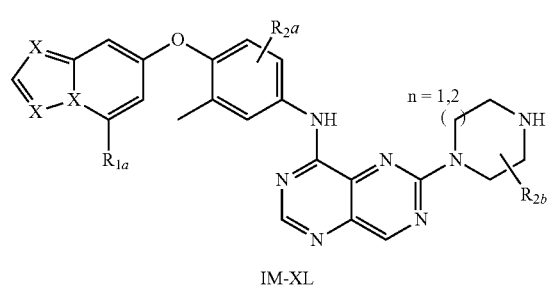

IM-XL

Step 1: To intermediate IM-II (1.0 equiv.) in i-PrOH was added 8-chloro-2-(methylsulfanyl)[1,3]diazino[5,4-d]pyrimidine IM-XXXVI (1.0 equiv.) and TFA, then the mixture was stirred at room temperature until the reaction was complete. LCMS showed the reaction was completed. The reaction mixture was concentrated, basified by saturated NaHCO$_3$and filtered. The filter cake was washed with water twice and dried under vacuum to give intermediate IM-XXXVII.

Step 2: To the intermediate IM-XXXVII (1.0 equiv.) in DCM was added m-CPBA (2.0 equiv.) at 0° C., then the mixture was stirred at room temperature until the reaction was complete. LCMS showed the consumption of starting material. The reaction mixture was quenched by saturated NaHCO$_3$and extracted with DCM. The organic solution was washed with brine, dried over anhydrous Na$_2$SO$_4$, filtered and concentrated to dryness to give intermediate IM-XXXVIII which was used directly in the next step.

Step 3: To intermediate IM-XXXVIII (1.0 equiv.) in NMP were added DIPEA (4.0 equiv.) and intermediate IM-IX (2 equiv.), then the mixture was stirred at 50° C. until the reaction was complete. LCMS showed the reaction was completed. The reaction mixture was quenched by ice water and extracted with EtOAc. The organic solution was washed with brine, dried over anhydrous Na$_2$SO$_4$, filtered and concentrated to dryness. The residue was purified by flash chromatography (DCM 95%-MeOH 5%) to give intermediate IM-XXXLX.

Step 4: To intermediate IM-XXXIX (1 equiv.) in DCM was added TFA, then the mixture was stirred at room temperature until the reaction was complete. LCMS showed the reaction was completed. The reaction mixture was concentrated to dryness to give intermediate IM-XL which was used directly in the next step.

233

Synthesis of (R)—N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine 181

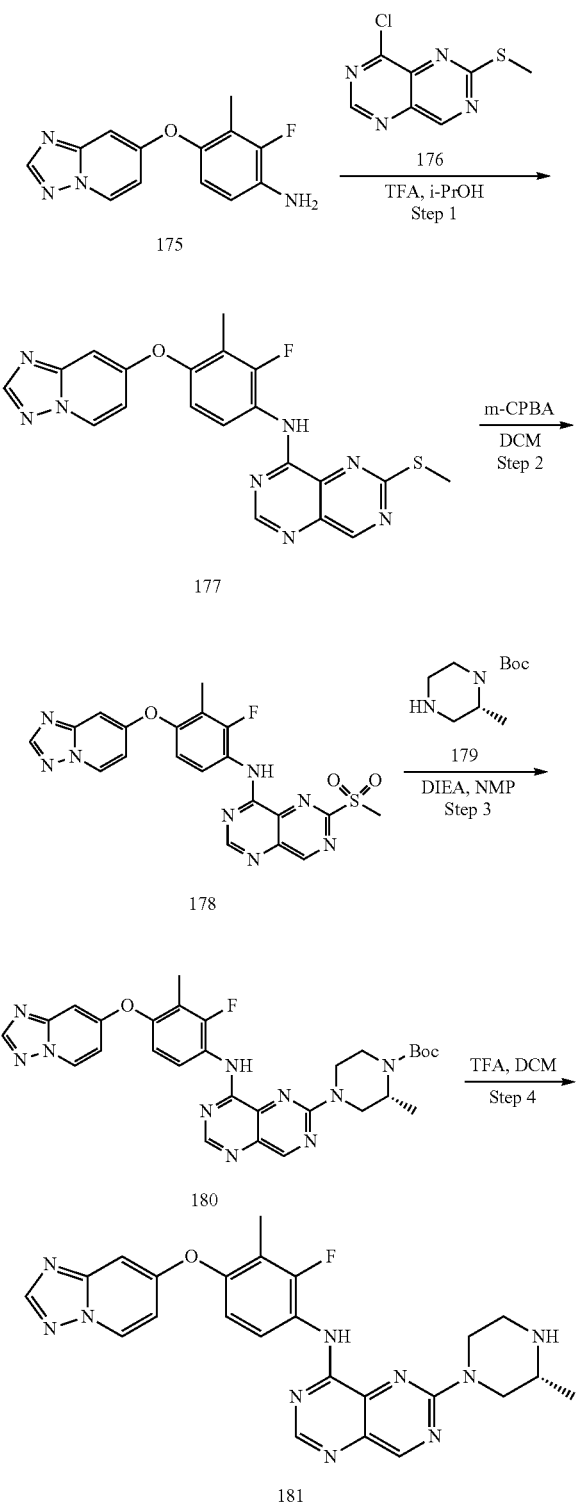

Step 1: To 4-([1,2,4]triazolo[1,5-a]pyridin-7-yloxy)-2-fluoro-3-methylaniline 175 (200 mg, 0.77 mmol) in i-PrOH (10 mL) was added 8-chloro-2-(methylsulfanyl)[1,3]diazino[5,4-d]pyrimidine 176 (164 mg, 0.77 mmol) and TFA (0.3 mL), then the mixture was stirred at room temperature for 16 hours. LCMS showed the reaction was completed. The reaction mixture was concentrated, basified by saturated NaHCO$_3$ and filtered. The filter cake was washed with water twice and dried under vacuum to give N-(4-([1,2,4]triazolo[1,5-a]pyridin-7-yloxy)-2-fluoro-3-methylphenyl)-6-(methylthio)pyrimido[5,4-d]pyrimidin-4-amine 177 (310 mg, yield: 92.1%) as a yellow solid. LCMS ESI (m/z): 435[M+H]$^+$.

Step 2: To the mixture of N-(4-([1,2,4]triazolo[1,5-a]pyridin-7-yloxy)-2-fluoro-3-methylphenyl)-6-(methylthio)pyrimido[5,4-d]pyrimidin-4-amine 177 (100 mg, 0.23 mmol) in DCM (5 mL) was added m-CPBA (93.5 mg, 0.46 mmol, 85% wt) at 0° C., then the mixture was stirred at room temperature for 2 hours. LCMS showed the consumption of starting material. The reaction mixture was quenched by saturated NaHCO$_3$ and extracted with DCM. The organic solution was washed with brine, dried over anhydrous Na$_2$SO$_4$, filtered and concentrated to dryness to give N-(4-([1,2,4]triazolo[1,5-a]pyridin-7-yloxy)-2-fluoro-3-methylphenyl)-6-(methylsulfonyl)pyrimido[5,4-d]pyrimidin-4-amine 178 (105 mg, yield: 97.8%) as a yellow solid which was used directly in the next step. LCMS ESI (m/z): 467 [M+H]+ and 451 (sulfone) [M+H]$^+$.

Step 3: To the mixture of N-(4-([1,2,4]triazolo[1,5-a]pyridin-7-yloxy)-2-fluoro-3-methylphenyl)-6-(methylsulfonyl)pyrimido[5,4-d]pyrimidin-4-amine 178 (105 mg, 0.22 mmol) in NMP (3 mL) were added DIPEA (116 mg, 0.90 mmol) and tert-butyl (R)-2-methylpiperazine-1-carboxylate 179 (90 mg, 0.45 mmol), then the mixture was stirred at 50° C. for 16 hours. LCMS showed the reaction was completed. The reaction mixture was quenched by ice water and extracted with EtOAc. The organic solution was washed with brine, dried over anhydrous Na$_2$SO$_4$, filtered and concentrated to dryness. The residue was purified by flash chromatography (DCM 95%-MeOH 5%) to give (R)-tert-butyl 4-(8-(4-([1,2,4]triazolo[1,5-a]pyridin-7-yloxy)-2-fluoro-3-methylphenylamino)pyrimido[5,4-d]pyrimidin-2-yl)-2-methylpiperazine-1-carboxylate 180 (120 mg, yield: 90.8%) as yellow solid. LCMS ESI (m/z): 587 [M+H]$^+$.

Step 4: To the mixture of tert-butyl (R)-4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazine-1-carboxylate 180 (120 mg, 0.21 mmol) in DCM (4 mL) was added TFA (2 mL), then the mixture was stirred at room temperature for 2 hours. LCMS showed the reaction was completed. The reaction mixture was concentrated to dryness to give the mixture of (R)—N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine 181 (90 mg, yield: 90.4%) as a yellow oil which was used directly in the next step. LCMS ESI (m/z): 487 [M+H]$^+$.

Alternatively, HCl (4N in 1,4-dioxane) in DCM could be used to remove the Boc protecting group instead of TFA in DCM. After completion of the reaction, the reaction mixture was concentrated under vacuum to afford the desired intermediate as HCl salt.

The following intermediates in Table 8 were obtained following above-mentioned method using the appropriate starting materials.

TABLE 8

Intermediates

| Example | Compound Structure | Physical Data MS [ESI, m/z] |
|---|---|---|
| 182 | (R)-N-(4-([1,2,4]triazolo[1,5-a]pyridin-7-yloxy)-2-fluoro-5-methylphenyl)-6-(2-methylpiperazin-1-yl)pyrimido[5,4-d]pyrimidin-4-amine hydrochloride | 487 [M + H]+ |
| 183 | (S)-N-(4-([1,2,4]triazolo[1,5-a]pyridin-7-yloxy)-2-fluoro-5-methylphenyl)-6-(2-methylpiperazin-1-yl)pyrimido[5,4-d]pyrimidin-4-amine hydrochloride | 487 [M + H]+ |
| 184 | (S)-N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine hydrochloride | 487 [M + H]+ |
| 185 | (R)-N-(4-([1,2,4]triazolo[1,5-a]pyridin-7-yloxy)-2-fluoro-3-(trifluoromethyl)phenyl)-6-(3-methylpiperazin-1-yl)pyrimido[5,4-d]pyrimidin-4-amine trifluoroacetate | 541 [M + H]+ |

TABLE 8-continued

Intermediates

| Example | Compound Structure | Physical Data MS [ESI, m/z] |
|---|---|---|
| 186 | 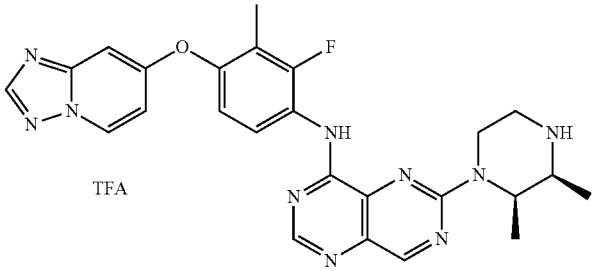<br>TFA<br>relative stereochemistry<br>6-(2,3-dimethylpiperazin-1-yl)-N-(2-fluoro-3-methyl-4-{[1,2,4]triazolo[1,5-a]pyridin-7-yloxy}phenyl)-[1,3]diazino[5,4-d]pyrimidin-4-amine trifluoroacetate | 501 [M + H]$^+$ |
| 187 | 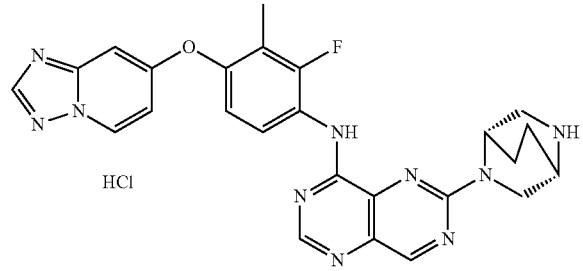<br>HCl<br>N-(4-([1,2,4]triazolo[1,5-a]pyridin-7-yloxy)-2-fluoro-3-methylphenyl)-6-((1S,4S)-2,5-diazabicyclo[2.2.2]octan-2-yl)pyrimido[5,4-d]pyrimidin-4-amine hydrochloride | 499 [M + H]$^+$ |
| 188 | 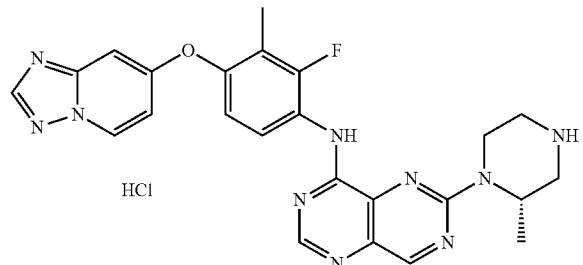<br>HCl<br>(S)-N-(4-([1,2,4]triazolo[1,5-a]pyridin-7-yloxy)-2-fluoro-3-methylphenyl)-6-(2-methylpiperazin-1-yl)pyrimido[5,4-d]pyrimidin-4-amine hydrochloride | 487 [M + H]$^+$ |
| 189 | 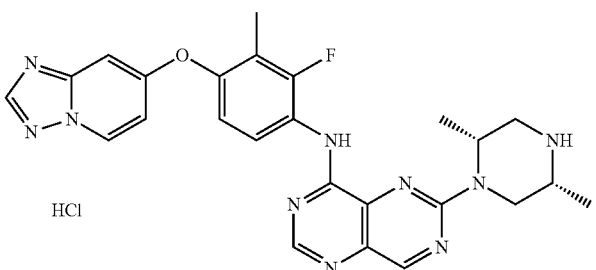<br>HCl<br>6-[(2R,5R)-2,5-dimethylpiperazin-1-yl]-N-(2-fluoro-3-methyl-4-{[1,2,4]triazolo[1,5-a]pyridin-7-yloxy}phenyl)pyrimido[5,4-d][1,3]diazin-4-amine hydrochloride | 501 [M + H]$^+$ |

TABLE 8-continued

Intermediates

| Example | Compound Structure | Physical Data MS [ESI, m/z] |
|---|---|---|
| 190 | 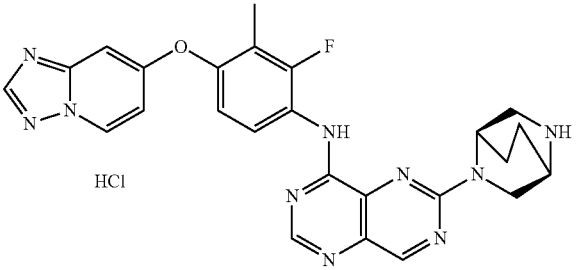 HCl<br>N-(4-([1,2,4]triazolo[1,5-a]pyridin-7-yloxy)-2-fluoro-3-methylphenyl)-6-((1R,4R)-2,5-diazabicyclo[2.2.2]octan-2-yl)pyrimido[5,4-d]pyrimidin-4-amine hydrochloride | 499 [M + H]+ |
| 191 | 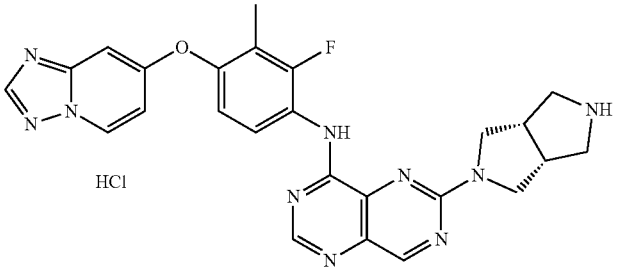 HCl<br>N-(4-([1,2,4]triazolo[1,5-a]pyridin-7-yloxy)-2-fluoro-3-methylphenyl)-6-((3aR,6aS)-hexahydropyrrolo[3,4-c]pyrrol-2(1H)-yl)pyrimido[5,4-d]pyrimidin-4-amine | 499 [M + H]+ |
| 192 | 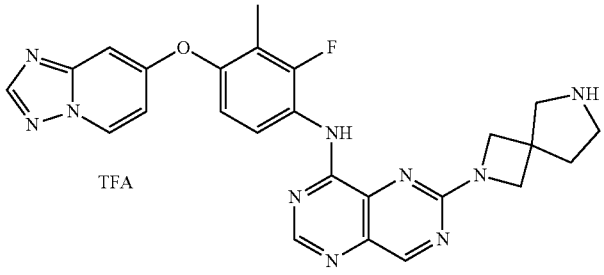 TFA<br>N-(4-([1,2,4]triazolo[1,5-a]pyridin-7-yloxy)-2-fluoro-3-methylphenyl)-6-(2,6-diazaspiro[3.4]octan-2-yl)pyrimido[5,4-d]pyrimidin-4-amine trifluoroacetate | 499 [M + H]+ |
| 193 | 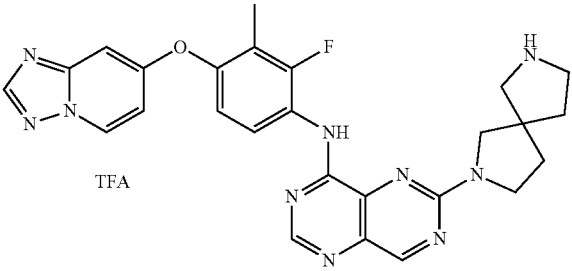 TFA<br>N-(4-([1,2,4]triazolo[1,5-a]pyridin-7-yloxy)-2-fluoro-3-methylphenyl)-6-(2,7-diazaspiro[4.4]nonan-2-yl)pyrimido[5,4-d]pyrimidin-4-amine trifluoroacetate | 513 [M + H]+ |

TABLE 8-continued

Intermediates

| Example | Compound Structure | Physical Data MS [ESI, m/z] |
|---|---|---|
| 194 | 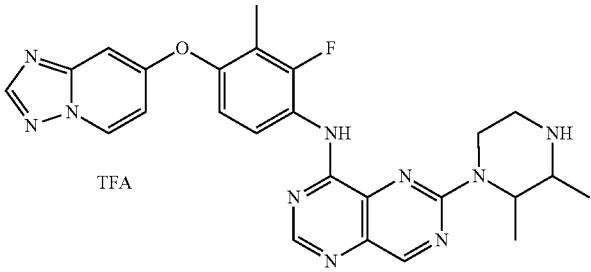<br>TFA<br>6-(2,3-dimethylpiperazin-1-yl)-N-(2-fluoro-3-methyl-4-{[1,2,4]triazolo[1,5-a]pyridin-7-yloxy}phenyl)-[1,3]diazino[5,4-d]pyrimidin-4-amine trifluoroacetate | 501 [M + H]⁺ |
| 195 | 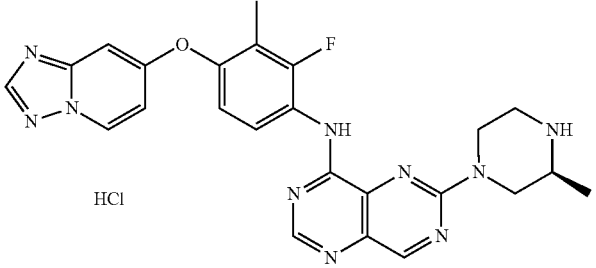<br>HCl<br>(S)-N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine hydrochloride | 487 [M + H]⁺ |
| 196 | 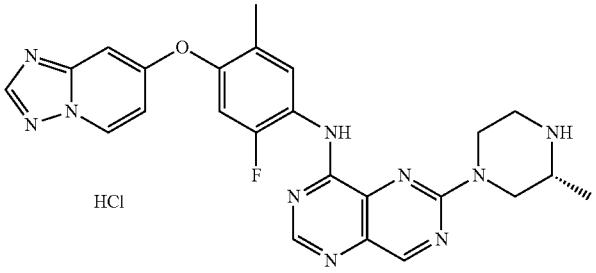<br>HCl<br>(R)-N-(4-([1,2,4]triazolo[1,5-a]pyridin-7-yloxy)-2-fluoro-5-methylphenyl)-6-(3-methylpiperazin-1-yl)pyrimido[5,4-d]pyrimidin-4-amine hydrochloride | 487 [M + H]⁺ |
| 197 | 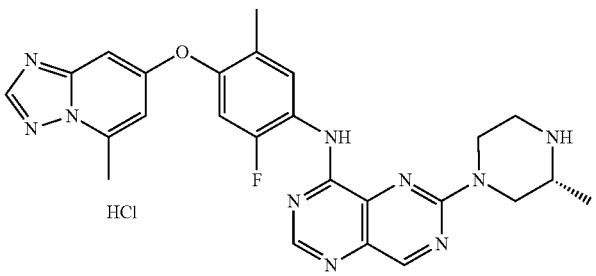<br>HCl<br>(R)-N-(2,6-difluoro-3-methyl-4-((5-methyl-[1,2,4]triazolo[1,5-a]pyridin-7-yl)oxy)phenyl)-6-(3-methylpiperazin-1-yl)pyrimido[5,4-d]pyrimidin-4-amine hydrochloride | 501 [M + H]⁺ |

TABLE 8-continued

| | Intermediates | |
|---|---|---|
| Example | Compound Structure | Physical Data MS [ESI, m/z] |
| 198 | 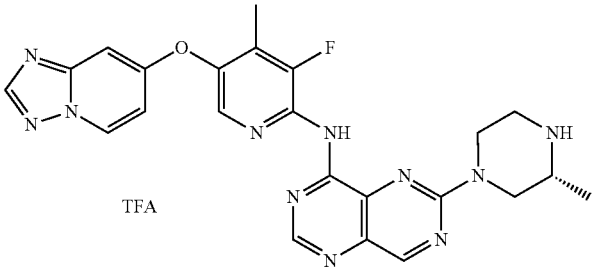<br>(R)-N-(5-([1,2,4]triazolo[1,5-a]pyridin-7-yloxy)-3-fluoro-4-methylpyridin-2-yl)-<br>6-(3-methylpiperazin-1-yl)pyrimido[5,4-d]pyrimidin-4-amine trifluoroacetate | 488 [M + H]$^+$ |
| 199 | 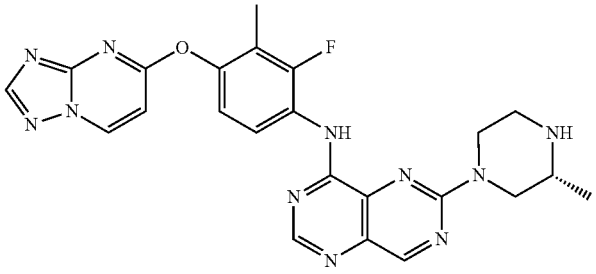<br>(R)-N-(4-([1,2,4]triazolo[1,5-a]pyrimidin-5-yloxy)-2-fluoro-3-methylphenyl)-6-<br>(3-methylpiperazin-1-yl)pyrimido[5,4-d]pyrimidin-4-amine | 488 [M + H]$^+$ |
| 200 | 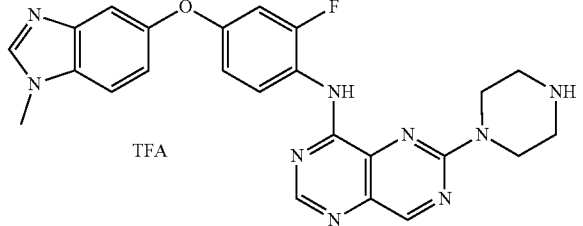<br>N-(2-fluoro-4-((1-methyl-1H-benzo[d]imidazol-5-yl)oxy)phenyl)-6-(piperazin-<br>1-yl)pyrimido[5,4-d]pyrimidin-4-amine trifluoroacetate | 472 [M + H]$^+$ |
| 201 | 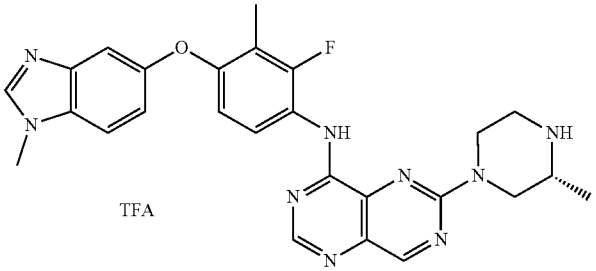<br>N-{2-fluoro-3-methyl-4-[(1-methyl-1,3-benzodiazol-5-yl)oxy]phenyl}-6-[(3R)-<br>3-methylpiperazin-1-yl]pyrimido[5,4-d][1,3]diazin-4-amine trifluoroacetate | 500 [M + H]$^+$ |

TABLE 8-continued

| | Intermediates | |
|---|---|---|
| Example | Compound Structure | Physical Data MS [ESI, m/z] |
| 202 | TFA<br>(R)-N-(4-([1,2,4]triazolo[1,5-c]pyrimidin-7-yloxy)-2-fluoro-3-methylphenyl)-6-(3-methylpiperazin-1-yl)pyrimido[5,4-d]pyrimidin-4-amine trifluoroacetate | 488 [M + H]⁺ |
| 203 | TFA<br>N-(2-fluoro-3-methyl-4-((1-methyl-1H-benzo[d]imidazol-5-yl)oxy)phenyl)-6-(piperazin-1-yl)pyrimido[5,4-d]pyrimidin-4-amine trifluoroacetate | 486 [M + H]⁺ |
| 204 | TFA<br>6-(3,3-dimethylpiperazin-1-yl)-N-(2-fluoro-5-methyl-4-{[1,2,4]triazolo[1,5-a]pyridin-7-yloxy}phenyl)-[1,3]diazino[5,4-d]pyrimidin-4-amine trifluoroacetate | 501 [M + H]⁺. |
| 205 | HCl<br>6-(3,3-dimethylpiperazin-1-yl)-N-(2-fluoro-3-methyl-4-{[1,2,4]triazolo[1,5-a]pyridin-7-yloxy}phenyl)-[1,3]diazino[5,4-d]pyrimidin-4-amine hydrochloride | 501 [M + H]⁺. |

TABLE 8-continued

Intermediates

| Example | Compound Structure | Physical Data MS [ESI, m/z] |
|---|---|---|
| 206 | TFA<br>N-(2-fluoro-3-methyl-4-{[1,2,4]triazolo[1,5-a]pyridin-7-yloxy}phenyl)-6-[(3S)-3-(fluoromethyl)piperazin-1-yl]pyrimido[5,4-d][1,3]diazin-4-amine trifluoroacetate | 505 [M + H]+. |
| 207 | HCl<br>(R)-N-(4-([1,2,4]triazolo[1,5-a]pyridin-7-yloxy)-3-chloro-2-fluorophenyl)-6-(3-methylpiperazin-1-yl)pyrimido[5,4-d]pyrimidin-4-amine hydrochloride | 507/509 [M + H]+. |

Method L: General Method for Intermediate IM-XLI

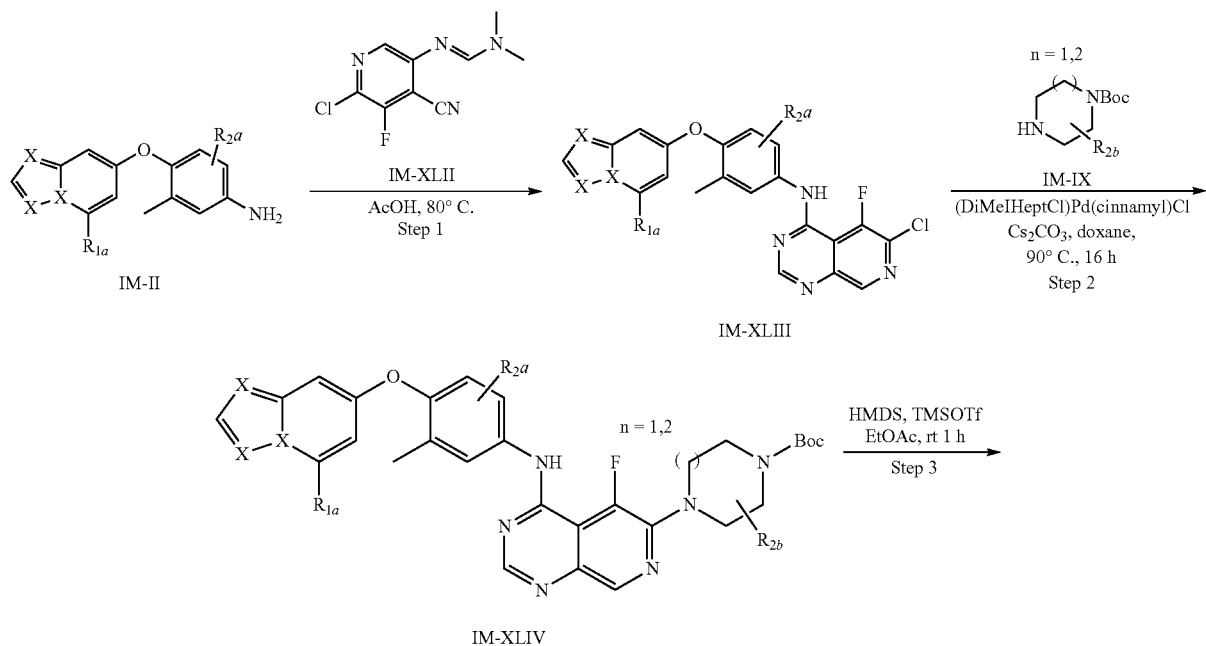

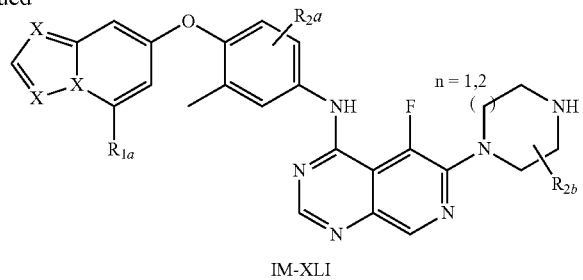

IM-XLI

Step 1: To intermediate IM-II (1.1 equiv.) in acetic acid was added (E)-N'-(6-chloro-4-cyano-5-fluoropyridin-3-yl)-N,N-dimethylformimidamide IM-XLII (1.0 equiv.) then the mixture was stirred at 80° C. until the reaction was complete. LCMS showed the reaction was completed. The reaction mixture was concentrated. The residue was purified by reverse phase flash chromatography on C18 silica gel (5-80% acetonitrile in water (containing 0.05% $NH_4HCO_3$) to afford intermediate IM-XLIII as a yellow solid.

Step 2: A mixture of intermediate IM-XLIII (1.0 equiv.) and IM-IX (1.1 equiv.), (DiMeIHeptCl)Pd(cinnamyl)Cl (0.1 equiv.) and $Cs_2CO_3$ (2.0 equiv.) in dioxane was stirred at 90° C. until the reaction was complete under $N_2$ atmosphere. LCMS showed the consumption of starting material. The resulting mixture was diluted with water and extracted with EtOAc 3 times. The organic layers were combined, washed with brine, dried over $Na_2SO_4$ and concentrated under vacuum. The residue was purified by reverse phase flash chromatography on C18 silica gel (5-70% acetonitrile in water (containing 0.05% $NH_4HCO_3$)) to afford intermediate IM-XLIV.

Step 3: To a stirred mixture intermediate IM-XLIV (1.0 equiv.) and HMDS (5.0 equiv.) in EtOAc at 0° C. was added TMSOTf (4.0 equiv.) The resulting mixture was stirred at this temperature until the reaction was complete and then quenched with $NaHCO_3$ solution and extracted with EtOAc 3 times. The organic layers were combined, washed with brine, dried over $Na_2SO_4$ and concentrated under vacuum to afford intermediate IM-XLI.

Synthesis of (R)—N-(4-([1,2,4]triazolo[1,5-a]pyridin-7-yloxy)-2-fluoro-3-methylphenyl)-5-fluoro-6-(3-methylpiperazin-1-yl)pyrido[3,4-d]pyrimidin-4-amine 217

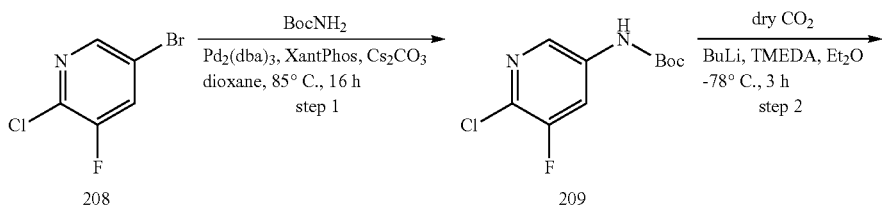

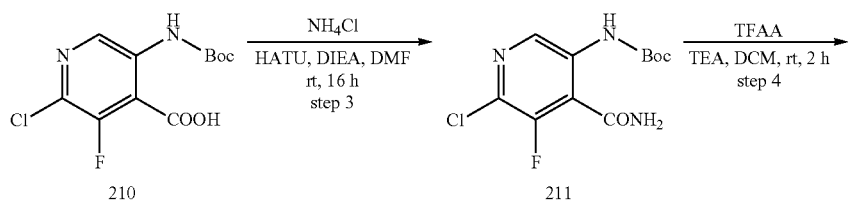

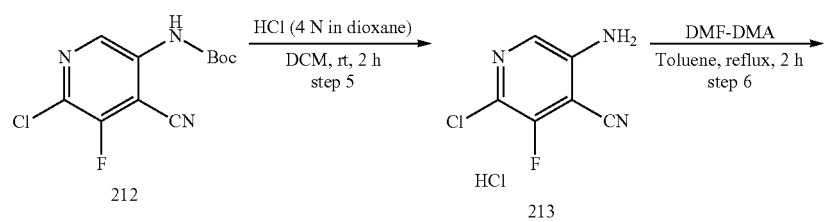

-continued
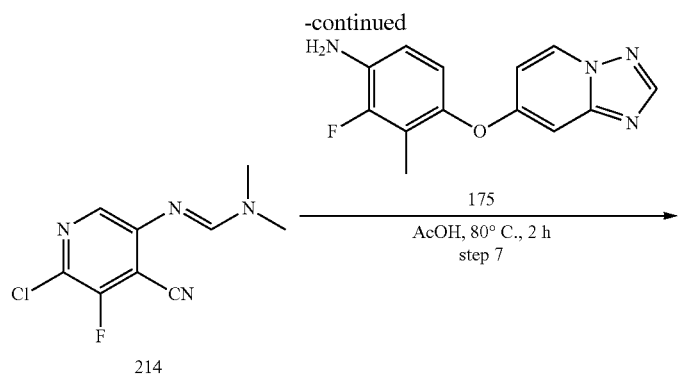
175
AcOH, 80° C., 2 h
step 7
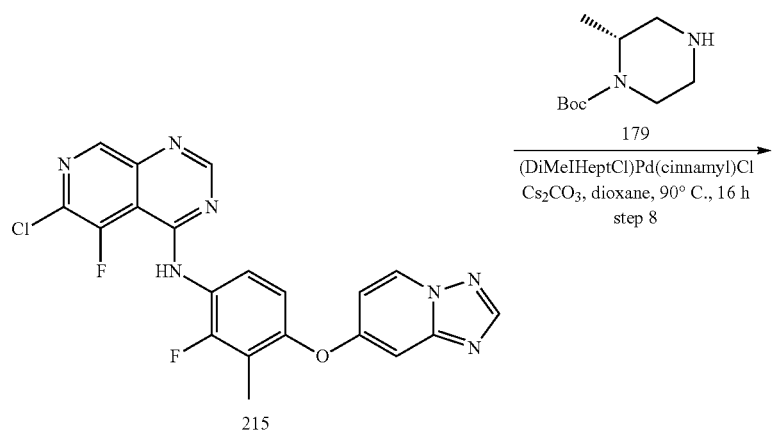
179
(DiMeIHeptCl)Pd(cinnamyl)Cl
Cs₂CO₃, dioxane, 90° C., 16 h
step 8
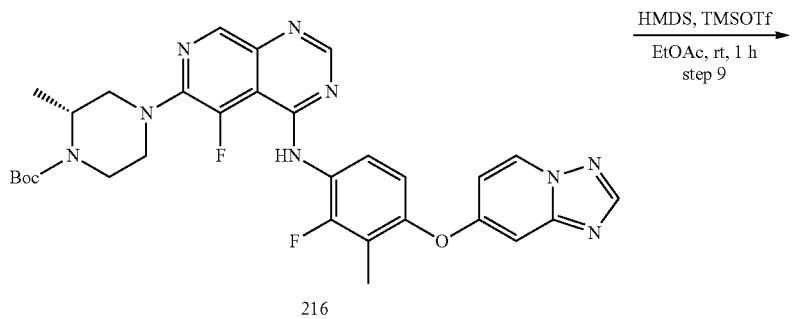
HMDS, TMSOTf
EtOAc, rt, 1 h
step 9
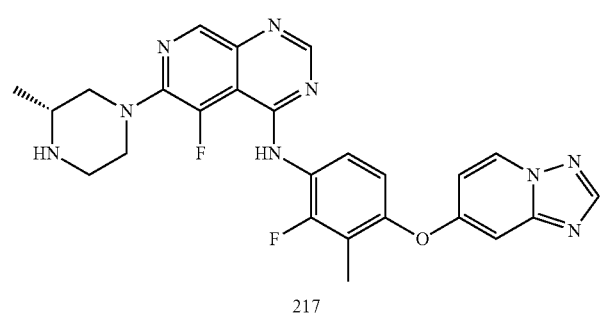

Step 1: A mixture of 5-bromo-2-chloro-3-fluoropyridine 208 (10.00 g, 47.85 mmol, 1.00 equiv.), BocNH$_2$ (5.65 g, 48.33 mmol, 1.01 equiv.), Pd$_2$(dba)$_3$ (4.39 g, 4.79 mmol, 0.10 equiv.), XantPhos (5.53 g, 9.57 mmol, 0.20 equiv.) and Cs$_2$CO$_3$ (31.20 g, 95.70 mmol, 2.00 equiv.) in dioxane (100.00 mL) was stirred at 85° C. for 16 h under N$_2$ atmosphere. The resulting mixture was diluted with water and extracted with EtOAc 3 times. The organic layers were combined, washed with brine, dried over Na$_2$SO$_4$ and concentrated under vacuum. The residue was purified by flash chromatography on silica gel (0-20% MeOH in DCM) to afford tert-butyl (6-chloro-5-fluoropyridin-3-yl)carbamate 209 (9.40 g, 80%) as a yellow solid. LCMS (ESI, m z): 247 [M+H]$^+$.

Step 2: To a stirred mixture of tert-butyl (6-chloro-5-fluoropyridin-3-yl)carbamate 209 (5.00 g, 20.32 mmol, 1.00 equiv.) and TMEDA (7.07 g, 60.96 mmol, 3.00 equiv.) in Et$_2$O (100.00 mL) at −78° C. was added dropwise nBuLi (2 M in THF, 30.48 mL, 60.96 mmol, 3.00 equiv.) under N$_2$ atmosphere. The resulting mixture was stirred at −20° C. for 1 h. To this at −78° C. was added dry ice (excess). The resulting mixture was allowed to warm up to ambient temperature and stirred for 2 h. The reaction was quenched with NH$_4$Cl solution at 0° C. and then concentrated under vacuum. The residue was purified by reverse phase flash chromatography on C18 silica gel (5-80% acetonitrile in water (containing 0.05% TFA)) to afford 5-((tert-butoxycarbonyl)amino)-2-chloro-3-fluoroisonicotinic acid 210 (4.80 g, 81%) as a white solid. LCMS (ESI, m z): 291 [M+H]$^+$.

Step 3: To a stirred mixture of 5-((tert-butoxycarbonyl)amino)-2-chloro-3-fluoroisonicotinic acid 210 (4.80 g, 16.55 mmol, 1.00 equiv.), HATU (8.18 g, 21.52 mmol, 1.30 equiv.) and DIEA (12.81 g, 99.30 mmol, 6.00 equiv.) in DMF (50.00 mL) at ambient temperature was added NH$_4$Cl (2.68 g, 49.65 mmol, 3.00 equiv.). The resulting mixture was stirred at this temperature for 16 h and then diluted with water and extracted with EtOAc 3 times. The organic layers were combined, washed with brine, dried over Na$_2$SO$_4$ and concentrated under vacuum. The residue was purified by flash chromatography on silica gel (0-20% EtOAc in petroleum ether) to afford tert-butyl (4-carbamoyl-6-chloro-5-fluoropyridin-3-yl)carbamate 211 (2.50 g, 52%) as a yellow solid. LCMS (ESI, m z): 290 [M+H]$^+$.

Step 4: To a stirred mixture of tert-butyl (4-carbamoyl-6-chloro-5-fluoropyridin-3-yl)carbamate 211 (2.00 g, 6.92 mmol, 1.00 equiv.) and TEA (2.10 g, 20.76 mmol, 3.00 equiv.) in DCM (20.00 mL) at ambient temperature was added trifluoroacetic anhydride (2.91 g, 13.84 mmol, 2.00 equiv.). The resulting mixture was stirred at this temperature for 2 h and then concentrated under vacuum. The residue was purified by reverse phase flash chromatography on C18 silica gel (5-80% acetonitrile in water (containing 0.05% NH$_4$HCO$_3$)) to afford tert-butyl (6-chloro-4-cyano-5-fluoropyridin-3-yl)carbamate 212 (850.0 mg, 45%) as a yellow solid. LCMS (ESI, m z): 272 [M+H]$^+$.

Step 5: To a stirred solution of tert-butyl (6-chloro-4-cyano-5-fluoropyridin-3-yl)carbamate 212 (850.0 mg, 3.12 mmol, 1.00 equiv.) in DCM (15.00 mL) at ambient temperature was added HCl (4 N in dioxane, 4.00 mL). The resulting mixture was stirred at this temperature for 2 h and then concentrated under vacuum to afford 5-amino-2-chloro-3-fluoroisonicotinonitrile hydrochloride 213 (crude, 900.0 mg) as a yellow solid, which was used for the next step without further purification. LCMS (ESI, m z): 172 [M+H]$^+$.

Step 6: A mixture of 5-amino-2-chloro-3-fluoroisonicotinonitrile hydrochloride 213 (900.0 mg, 5.23 mmol, 1.00 equiv.) and DMF-DMA (934.0 mg, 7.85 mmol, 1.50 equiv.) in toluene (10.00 mL) was stirred at 80° C. for 2 h and then concentrated under vacuum. The residue was purified by reverse phase flash chromatography on C18 silica gel (5-80% acetonitrile in water (containing 0.05% NH$_4$HCO$_3$)) to afford (E)-N'-(6-chloro-4-cyano-5-fluoropyridin-3-yl)-N,N-dimethylformimidamide 214 (410.0 mg, 34%) as a yellow solid. LCMS (ESI, m z): 227 [M+H]$^+$.

Step 7: A mixture of (E)-N'-(6-chloro-4-cyano-5-fluoropyridin-3-yl)-N,N-dimethylformimidamide 214 (400.0 mg, 1.77 mmol, 1.00 equiv.) and 4-([1,2,4]triazolo[1,5-a]pyridin-7-yloxy)-2-fluoro-3-methylaniline 175 (502.3 mg, 1.95 mmol, 1.10 equiv.) in AcOH (3.00 mL) was stirred at 80° C. for 2 h and then concentrated under vacuum. The residue was purified by reverse phase flash chromatography on C18 silica gel (5-80% acetonitrile in water (containing 0.05% NH$_4$HCO$_3$)) to afford N-(4-([1,2,4]triazolo[1,5-a]pyridin-7-yloxy)-2-fluoro-3-methylphenyl)-6-chloro-5-fluoropyrido[3,4-d]pyrimidin-4-amine 215 (420.0 mg, 54%) as a yellow solid. LCMS (ESI, m z): 440 (M+H)$^+$.

Step 8: A mixture of N-(4-([1,2,4]triazolo[1,5-a]pyridin-7-yloxy)-2-fluoro-3-methylphenyl)-6-chloro-5-fluoropyrido[3,4-d]pyrimidin-4-amine 215 (200.0 mg, 0.46 mmol, 1.00 equiv.), tert-butyl (R)-2-methylpiperazine-1-carboxylate 179 (100.2 mg, 0.50 mmol, 1.10 equiv.), (DiMeIHeptCl)Pd(cinnamyl)Cl (CAS: 2138491-47-9, 58.35 mg, 0.05 mmol, 0.10 equiv.) and Cs$_2$CO$_3$ (299.9 mg, 0.92 mmol, 2.00 equiv.) in dioxane (4.00 mL) was stirred at 90° C. for 16 h under N$_2$ atmosphere. The resulting mixture was diluted with water and extracted with EtOAc 3 times. The organic layers were combined, washed with brine, dried over Na$_2$SO$_4$ and concentrated under vacuum. The residue was purified by reverse phase flash chromatography on C18 silica gel (5-70% acetonitrile in water (containing 0.05% NH$_4$HCO$_3$)) to afford tert-butyl (R)-4-(4-((4-([1,2,4]triazolo[1,5-a]pyridin-7-yloxy)-2-fluoro-3-methylphenyl)amino)-5-fluoropyrido[3,4-d]pyrimidin-6-yl)-2-methylpiperazine-1-carboxylate 216 (110.0 mg, 39%) as a yellow solid. LCMS (ESI, m z): 604 [M+H]$^+$ Step 9: To a stirred mixture of tert-butyl (R)-4-(4-((4-([1,2,4]triazolo[1,5-a]pyridin-7-yloxy)-2-fluoro-3-methylphenyl)amino)-5-fluoropyrido[3,4-d]pyrimidin-6-yl)-2-methylpiperazine-1-carboxylate 216 (100.0 mg, 0.17 mmol, 1.00 equiv.) and HMDS (136.8 mg, 0.85 mmol, 5.00 equiv.) in EtOAc (3.00 mL) at 0° C. was added TMSOTf (150.9 mg, 0.68 mmol, 4.00 equiv.). The resulting mixture was stirred at this temperature for 1 h and then quenched with NaHCO$_3$ solution and extracted with EtOAc 3 times. The organic layers were combined, washed with brine, dried over Na$_2$SO$_4$ and concentrated under vacuum to afford (R)—N-(4-([1,2,4]triazolo[1,5-a]pyridin-7-yloxy)-2-fluoro-3-methylphenyl)-5-fluoro-6-(3-methylpiperazin-1-yl)pyrido[3,4-d]pyrimidin-4-amine 217 (crude, 90.0 mg) as a yellow solid, which was used for the next step without further purification. LCMS (ESI, m z): 504 [M+H]$^+$.

The following intermediates in Table 9 were obtained following above-mentioned method using the appropriate starting materials.

TABLE 9
Intermediate
| Example | Compound Structure | Physical Data MS [ESI, m/z] |
|---|---|---|
| 218 | (R)-5-fluoro-N-(2-fluoro-3-methyl-4-((1-methyl-1H-benzo[d]imidazol-5-yl)oxy)phenyl)-6-(3-methylpiperazin-1-yl)pyrido[3,4-d]pyrimidin-4-amine | 517 [M + H]+ |
Method M: General Method for Intermediate IM-XLV
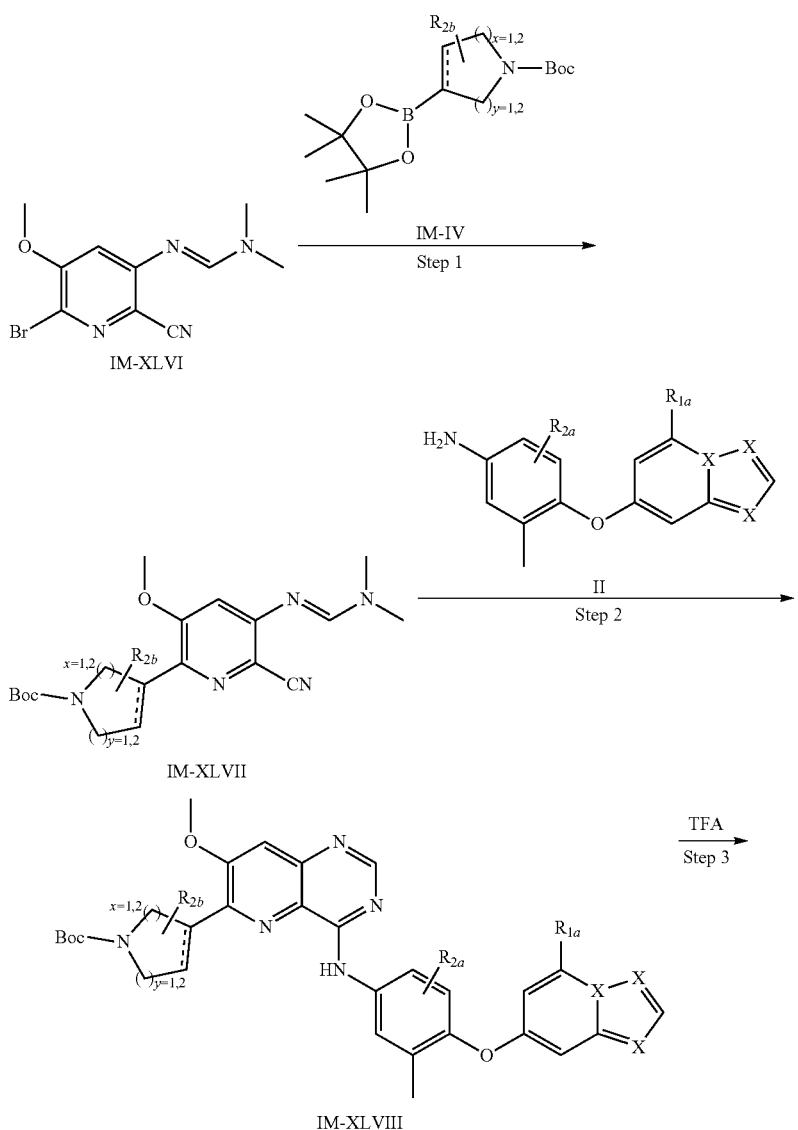

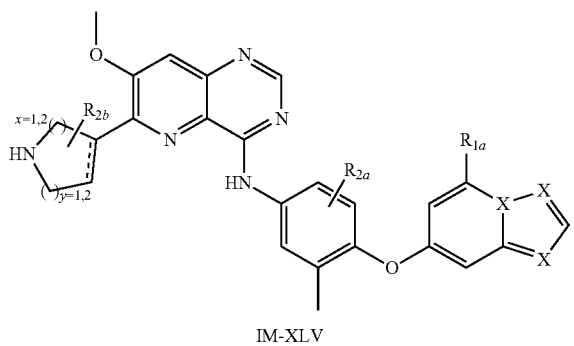

IM-XLV

Step 1: A mixture of intermediate IM-XLVI (1.00 equiv), IM-IV (1.30 equiv), K₂CO₃ (3.00 equiv) and Pd(dppf)Cl₂·CH₂Cl₂ (0.10 equiv) in dioxane and water was stirred at 80° C. until the reaction was complete under N₂ atmosphere. The resulting mixture was diluted with water and extracted with DCM 3 times. The combined organic layers were dried over Na₂SO₄ and concentrated under vacuum. The residue was purified by flash chromatography on silica gel (0 to 5% MeOH in DCM) to afford intermediate IM-XLVII as a brown oil.

Step 2: A mixture of intermediate IM-XLVII (1.00 equiv) and IM-II (1.00 equiv) in AcOH was stirred at 80° C. until the reaction was complete and then diluted with water. The mixture was neutralized with saturated NaHCO₃ to pH 8 and then extracted with EtOAc 3 times. The combined organic layers were dried over Na₂SO₄ and concentrated under vacuum. The residue was purified by reverse phase flash chromatography on C18 silica gel (5 to 60% acetonitrile in water (containing 0.05% NH₄HCO₃) to afford intermediate IM-XLVIII as a yellow solid.

Step 3: To a stirred mixture intermediate IM-XLVIII (1.0 equiv.) in DCM at ambient temperature was added TFA. The resulting mixture was stirred at ambient temperature until the reaction was complete and then concentrated under vacuum to IM-XLV as brown oil, Synthesis of 1-(4-(4-((4-([1,2,4]triazolo[1,5-a]pyridin-7-yloxy)-3-methylphenyl)amino)-7-methoxypyrido[3,2-d]pyrimidin-6-yl)-3,6-dihydropyridin-1(2H)-yl)prop-2-en-1-one 225

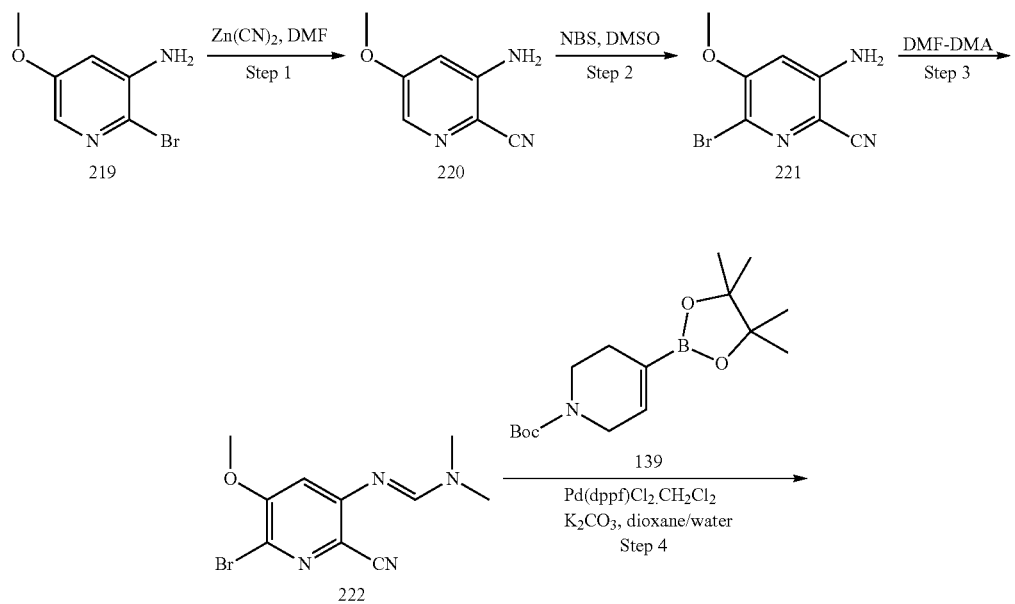

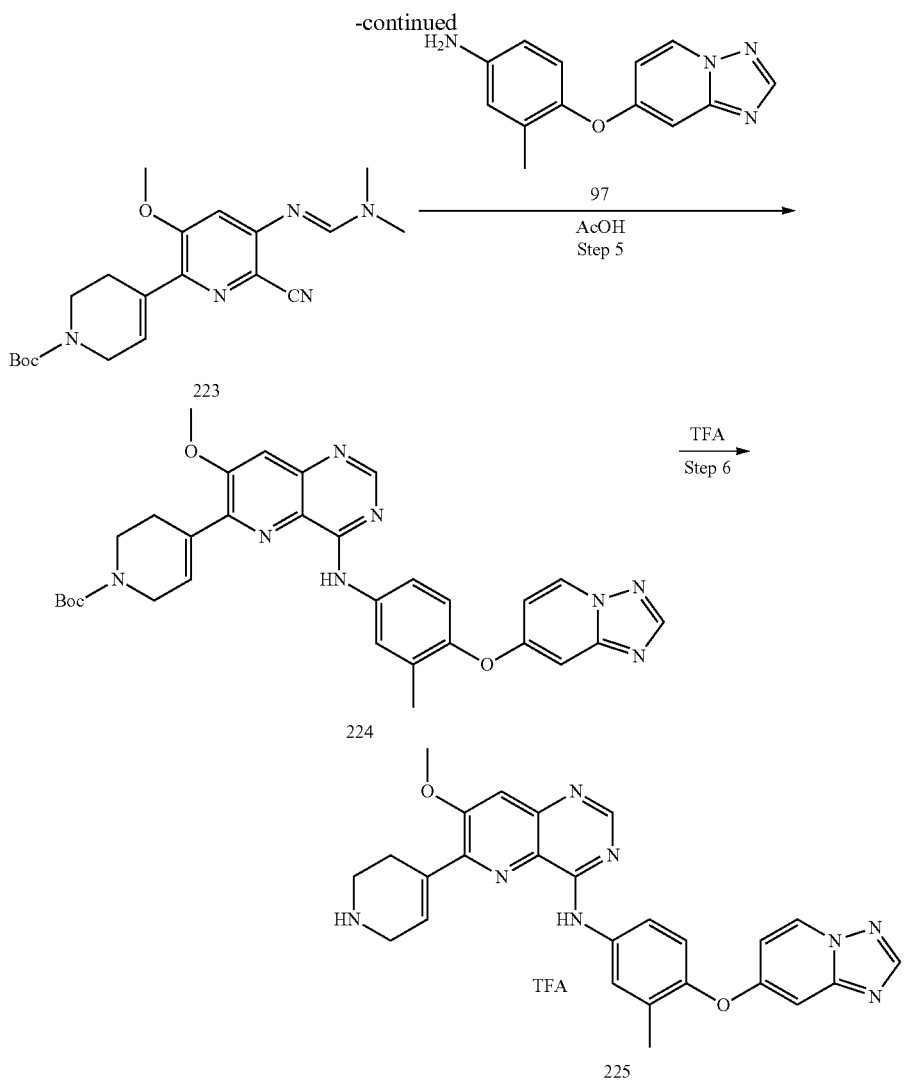

Step 1: A mixture of 2-bromo-5-methoxypyridin-3-amine 219 (2.0 g, 9.90 mmol, 1.00 equiv), Zn(CN)₂ (1.16 g, 9.90 mmol, 1.00 equiv) and Pd(PPh₃)₄ (1.14 g, 0.99 mmol, 0.10 equiv) in DMF (60.0 mL) was stirred at 120° C. for 16 h under N₂ atmosphere. The resulting mixture was diluted with water and extracted with EtOAc 3 times. The combined organic layers were dried over Na₂SO₄ and concentrated under vacuum. The residue was purified by flash chromatography on silica gel (50 to 80% EtOAc in petroleum ether) to afford 3-amino-5-methoxypicolinonitrile 220 (1.0 g, 68%) as a yellow solid. LCMS (ESI, m/z): 150 [M+H]⁺.

Step 2: To a stirred solution of 3-amino-5-methoxypicolinonitrile 220 (1.0 g, 6.71 mmol, 1.00 equiv) in DMSO (25.0 mL) and water (2.5 mL) was added NBS (3.6 g, 20.13 mmol, 3.00 equiv) at ambient temperature. The resulting mixture was stirred at ambient temperature for 16 h and then diluted with EtOAc. The organic solution was washed with water twice and brine, dried over Na₂SO₄ and concentrated under vacuum. The residue was purified by flash chromatography on silica gel (40% to 80% EtOAc in petroleum ether) to afford 3-amino-6-bromo-5-methoxypicolinonitrile 221 (930.0 mg, 61%) as a white solid. LCMS (ESI, m z): 228, 230 [M+H]⁺.

Step 3: A mixture of 3-amino-6-bromo-5-methoxypicolinonitrile 221 (930.0 mg, 4.10 mmol, 1.00 equiv) and DMF-DMA (1.5 g, 12.30 mmol, 3.00 equiv) in toluene (30.0 mL) was stirred at 80° C. for 2 h. The resulting mixture was concentrated under vacuum to afford (E)-N'-(6-bromo-2-cyano-5-methoxypyridin-3-yl)-N,N-dimethylformimidamide 222 (crude, 950.0 mg) as a white solid, which was used for the next step without further purification. LCMS (ESI, m z): 283, 285 [M+H]⁺.

Step 4: A mixture of (E)-N'-(6-bromo-2-cyano-5-methoxypyridin-3-yl)-N,N-dimethylformimidamide 222 (300.0 mg, 1.06 mmol, 1.00 equiv), tert-butyl 4-(4,4,5,5-tetramethyl-1,3,2-dioxaborolan-2-yl)-3,6-dihydropyridine-1 (2H)-carboxylate 139 (427.3 mg, 1.38 mmol, 1.30 equiv), K₂CO₃ (438.8 mg, 3.18 mmol, 3.00 equiv) and Pd(dppf) Cl₂·CH₂Cl₂ (114.2 mg, 0.14 mmol, 0.10 equiv) in dioxane (8.0 mL) and water (0.8 mL) was stirred at 80° C. for 2 h under N₂ atmosphere. The resulting mixture was diluted with water and extracted with DCM 3 times. The combined organic layers were dried over Na₂SO₄ and concentrated under vacuum. The residue was purified by flash chromatography on silica gel (0 to 5% MeOH in DCM) to afford tert-butyl (E)-6-cyano-5-(((dimethylamino)methylene)

amino)-3-methoxy-3',6'-dihydro-[2,4'-bipyridine]-1'(2'H)-carboxylate 223 (340.0 mg, 83%) as a brown oil. LCMS (ESI, m z): 386 [M+H]+.

Step 5: A mixture of tert-butyl (E)-6-cyano-5-(((dimethylamino)methylene)amino)-3-methoxy-3',6'-dihydro-[2,4'-bipyridine]-1'(2'H)-carboxylate 223 (340.0 mg, 0.88 mmol, 1.00 equiv) and 4-([1,2,4]triazolo[1,5-a]pyridin-7-yloxy)-3-methylaniline 97 (211.9 mg, 0.88 mmol, 1.00 equiv) in AcOH (14.0 mL) was stirred at 80° C. for 2 h and then diluted with water. The mixture was neutralized with saturated NaHCO$_3$ to pH 8 and then extracted with EtOAc 3 times. The combined organic layers were dried over Na$_2$SO$_4$ and concentrated under vacuum. The residue was purified by reverse phase flash chromatography on C18 silica gel (5 to 60% acetonitrile in water (containing 0.05% NH$_4$HCO$_3$) to afford tert-butyl 4-(4-((4-([1,2,4]triazolo[1,5-a]pyridin-7-yloxy)-3-methylphenyl)amino)-7-methoxypyrido[3,2-d]pyrimidin-6-yl)-3,6-dihydropyridine-1(2H)-carboxylate 224 (105.0 mg, 21%) as a yellow solid. LC/MS (ESI, m z): 581 [M+H]+.

Step 6: To a stirred mixture of tert-butyl 4-(4-((4-([1,2,4]triazolo[1,5-a]pyridin-7-yloxy)-3-methylphenyl)amino)-7-methoxypyrido[3,2-d]pyrimidin-6-yl)-3, 6-dihydropyridine-1(2H)-carboxylate 224 (100.0 mg, 0.17 mmol, 1.00 equiv) in DCM (3.0 mL) at ambient temperature was added TFA (1.0 mL). The resulting mixture was stirred at ambient temperature for 1 h and then concentrated under vacuum to afford N-(4-([1,2,4]triazolo[1,5-a]pyridin-7-yloxy)-3-methylphenyl)-7-methoxy-6-(1,2,3,6-tetrahydropyridin-4-yl)pyrido[3,2-d]pyrimidin-4-amine trifluoroacetate 225 (crude, 140.0 mg) as brown oil, which was used for the next step without further purification. LCMS (ESI, m z): 481 [M+H]+.

Method N: General Method for Intermediate IM-XLIX

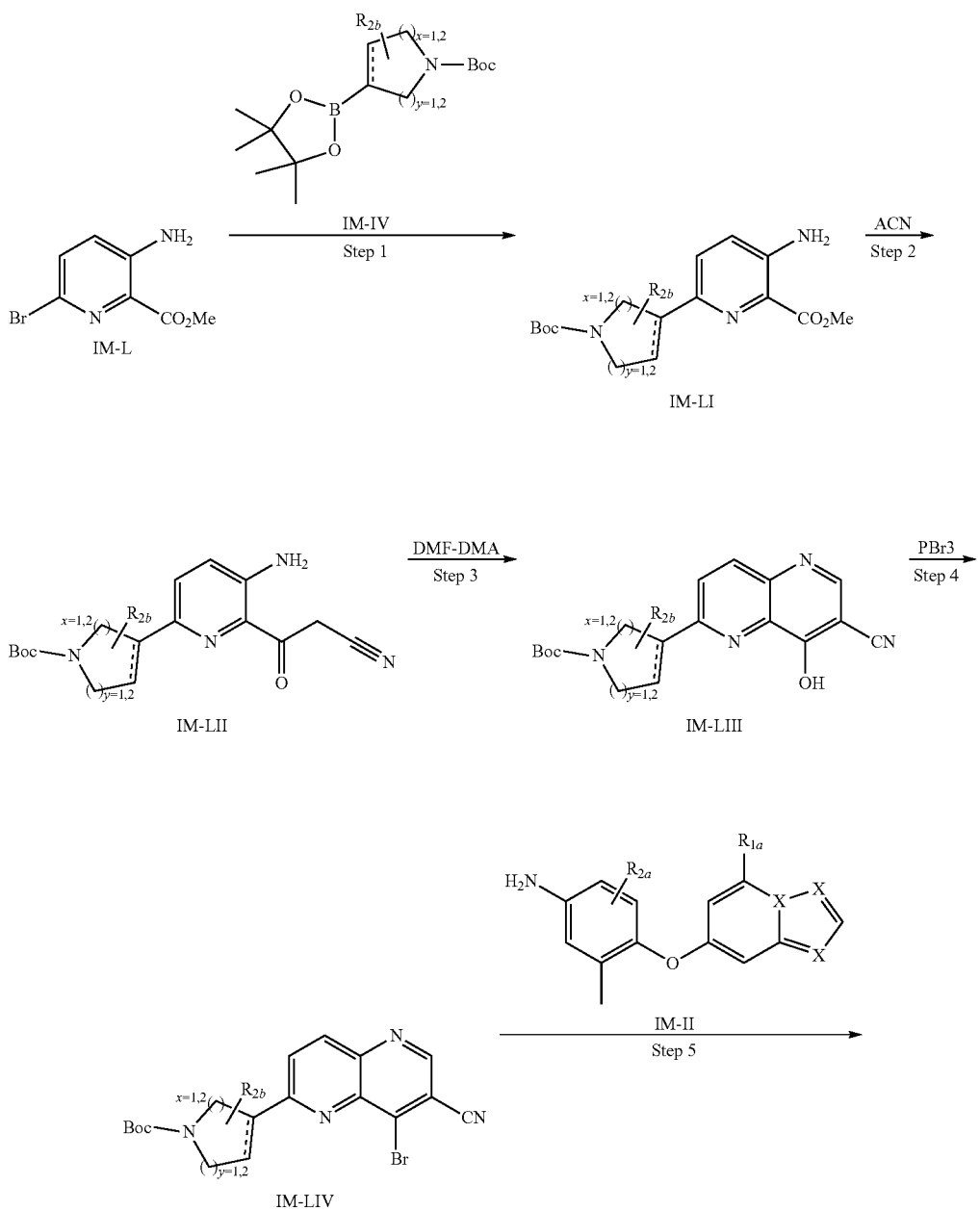

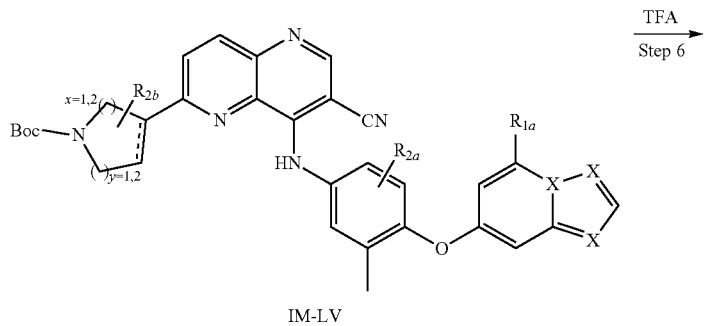

IM-LV

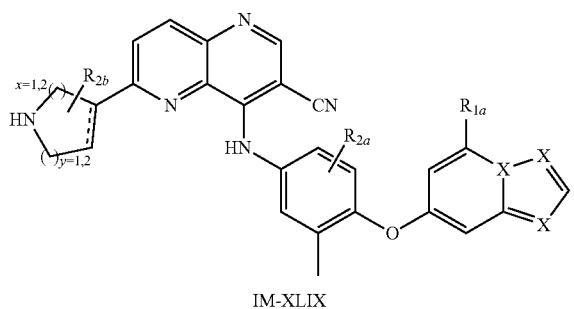

IM-XLIX

Step 1: A mixture of intermediate IM-L (1.00 equiv), IM-IV (1.20 equiv), Pd(dppf)Cl$_2$·CH$_2$Cl$_2$ (0.10 equiv) and K$_2$CO$_3$ (2.00 equiv) in dioxane and water was stirred until the reaction was complete at 80° C. under N$_2$ atmosphere and then filtered through a pad of celite. The filtrate was concentrated under vacuum. The residue was purified by flash chromatography on silica gel (0-80% EtOAc in petroleum ether) to intermediate IM-LI.

Step 2: To a stirred solution of acetonitrile (5.00 equiv) in THF at −78° C. was added dropwise n-BuLi (2.5 M in hexane, 5.50 equiv) under N$_2$ atmosphere for 30 min. To this was added a solution of intermediate IM-LI (1.00 equiv) in THF. The resulting mixture was stirred at ambient temperature until the reaction was complete and then quenched with NH$_4$Cl solution and extracted with EtOAc 3 times. The organic layers were combined, dried over Na$_2$SO$_4$ and concentrated under vacuum. The residue was purified by flash chromatography on silica gel (0-70% EtOAc in petroleum ether) to afford intermediate IM-LII.

Step 3: A mixture of intermediate IM-LI (1.00 equiv) and DMF-DMA (3.00 equiv) in toluene was stirred at 100° C. under N$_2$ atmosphere until the reaction was complete and then concentrated under vacuum. The residue is purified by flash chromatography on silica gel (0-70% EtOAc in petroleum ether) to afford intermediate IM-L-L.

Step 4: To a stirred solution of intermediate IM-LIII (1.00 equiv) in DMF at 0° C. was added phosphorus tribromide (1.50 equiv) dropwise under N$_2$ atmosphere. The resulting mixture was stirred at ambient temperature until the reaction was complete and then quenched with water and extracted with EtOAc. The organic layer was dried over Na$_2$SO$_4$ and concentrated under vacuum. The residue was purified by flash chromatography on silica gel (0-60% EtOAc in petroleum ether) to afford intermediate IM-LIV Step 5: A mixture of intermediate IM-LIV (1.00 equiv), IM-II (1.00 equi.), Pd$_2$(dba)$_3$ (0.20 equiv), XantPhos (0.20 equiv) and Cs$_2$CO$_3$ (2.00 equiv) in dixoane was stirred at 100° C. under N$_2$ atmosphere until the reaction was complete. The resulting mixture was diluted with water and extracted with EtOAc 3 times. The combined organic layers were concentrated under vacuum. The residue was purified by flash chromatography on silica gel (0-80% EtOAc in petroleum ether) to afford intermediate LV.

Step 6: To a mixture of intermediate IM-LV (1.00 equiv) in DCM at ambient temperature was added TFA (10.00 equiv). The resulting mixture was stirred at this temperature until the reaction was complete and concentrated under vacuum to intermediate IM-LVI which was used for the next step without further purification.

Synthesis of 4-((4-([1,2,4]triazolo[1,5-a]pyridin-7-yloxy)-3-methylphenyl)amino)-6-(1,2,3,6-tetrahydropyridin-4-yl)-1,5-naphthyridine-3-carbonitrile 232
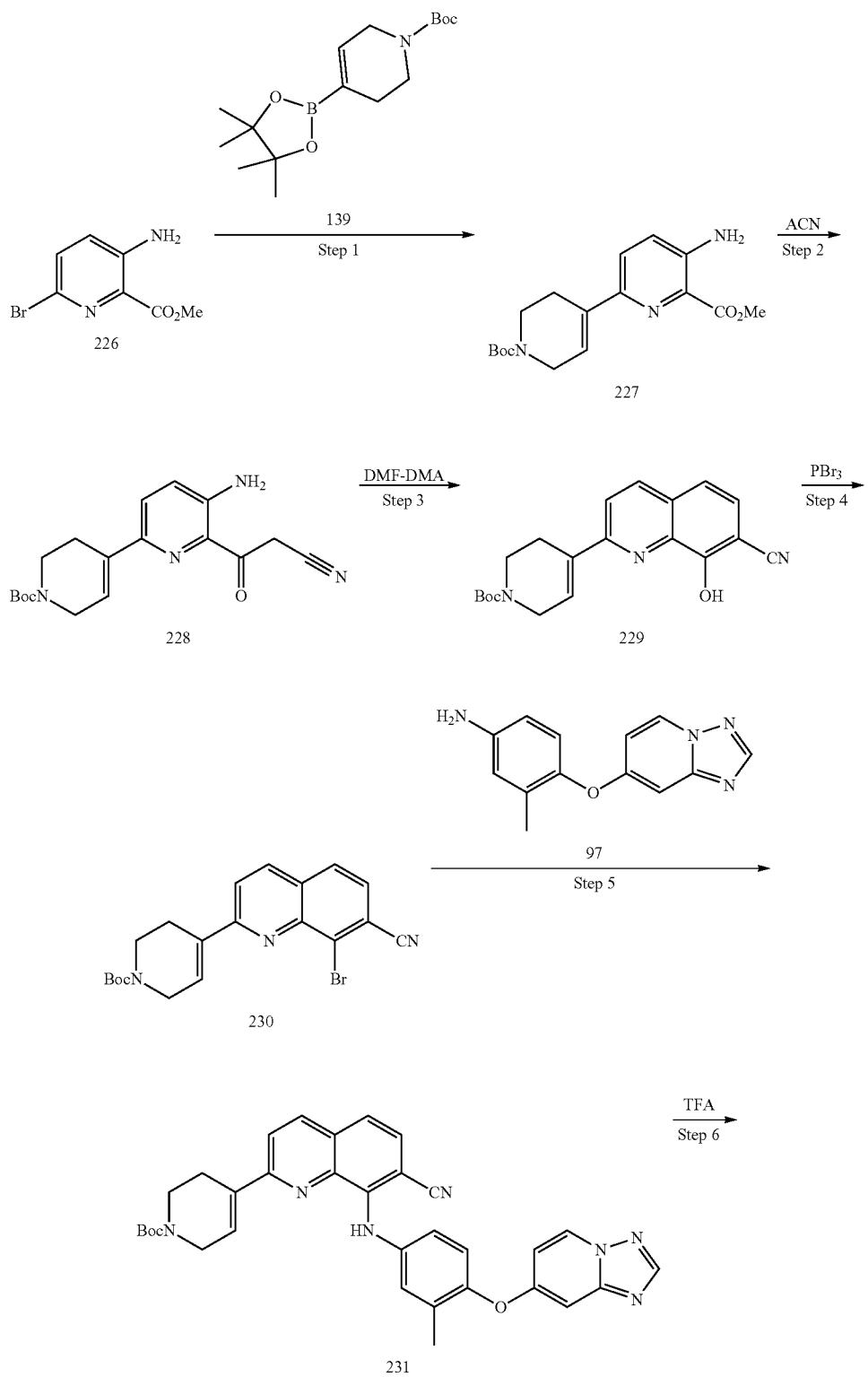

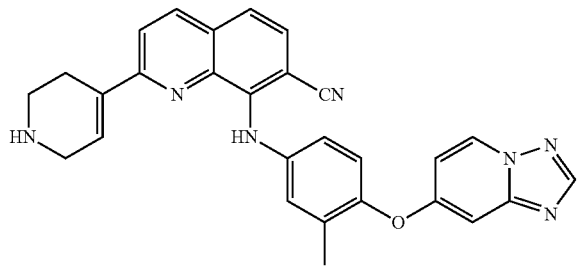

232

Step 1: A mixture of methyl 3-amino-6-bromopyridine-2-carboxylate 226 (3.7 g, 16.08 mmol, 1.00 equiv), tert-butyl 4-(4,4,5,5-tetramethyl-1,3,2-dioxaborolan-2-yl)-3,6-dihydro-2H-pyridine-1-carboxylate 139 (5.9 g, 19.30 mmol, 1.20 equiv), Pd(dppf)Cl$_2$·CH$_2$Cl$_2$ (1.3 g, 1.60 mmol, 0.10 equiv) and K$_2$CO$_3$ (4.4 g, 32.16 mmol, 2.00 equiv) in dioxane (30.0 mL) and water (3.0 mL) was stirred for 2 h at 80° C. under N$_2$ atmosphere and then filtered through a pad of celite. The filtrate was concentrated under vacuum. The residue was purified by flash chromatography on silica gel (0-80% EtOAc in petroleum ether) to afford 1'-(tert-butyl) 6-methyl 5-amino-3',6'-dihydro-[2,4'-bipyridine]-1',6(2'H)-dicarboxylate 227 (3.2 g, 59%) as yellow oil. MS (ESI, m z): 334 [M+H]$^+$.

Step 2: To a stirred solution of acetonitrile (615.7 mg, 15.00 mmol, 5.00 equiv) in THF (16.0 mL) at −78° C. was added dropwise n-BuLi (2.5 M in hexane, 6.6 mL, 16.50 mmol, 5.50 equiv) under N$_2$ atmosphere for 30 min. To this was added a solution of 1'-tert-butyl 6-methyl 5-amino-3',6'-dihydro-2'H-[2,4'-bipyridine]-1',6-dicarboxylate 227 (1.0 g, 3.00 mmol, 1.00 equiv) in THF (2.0 mL). The resulting mixture was stirred at ambient temperature for further 1 h and then quenched with NH$_4$Cl solution and extracted with EtOAc 3 times. The organic layers were combined, dried over Na$_2$SO$_4$ and concentrated under vacuum. The residue was purified by flash chromatography on silica gel (0-70% EtOAc in petroleum ether) to afford tert-butyl 5-amino-6-(2-cyanoacetyl)-3',6'-dihydro-[2,4'-bipyridine]-1'(2'H)-carboxylate 228 (790.0 mg, 76%) as a yellow oil. MS (ESI, m/z): 343 [M+H]$^+$.

Step 3: A mixture of tert-butyl 5-amino-6-(2-cyanoacetyl)-3',6'-dihydro-2'H-[2,4'-bipyridine]-1'-carboxylate 228 (580.0 mg, 1.69 mmol, 1.00 equiv) and DMF-DMA (117.0 mg, 5.08 mmol, 3.00 equiv) in toluene (10.0 mL) was stirred for 2 h at 100° C. under N$_2$ atmosphere and then concentrated under vacuum. The residue was purified by flash chromatography on silica gel (0-70% EtOAc in petroleum ether) to afford tert-butyl 4-(7-cyano-8-hydroxy-1,5-naphthyridin-2-yl)-3,6-dihydropyridine-1(2H)-carboxylate 229 (322.0 mg, 53%) as a yellow solid. MS (ESI, m/z): 353 [M+H]$^+$.

Step 4: To a stirred solution of tert-butyl 4-(7-cyano-8-hydroxy-1,5-naphthyridin-2-yl)-3,6-dihydro-2H-pyridine-1-carboxylate 229 (320.0 mg, 0.91 mmol, 1.00 equiv) in DMF (3.2 mL) at 0° C. was added phosphorus tribromide (368.7 mg, 1.36 mmol, 1.50 equiv) dropwise under N$_2$ atmosphere. The resulting mixture was stirred at ambient temperature for 2 h and then quenched with water and extracted with EtOAc. The organic layer was dried over Na$_2$SO$_4$ and concentrated under vacuum. The residue was purified by flash chromatography on silica gel (0-60% EtOAc in petroleum ether) to afford tert-butyl 4-(8-bromo-7-cyano-1,5-naphthyridin-2-yl)-3,6-dihydropyridine-1(2H)-carboxylate 230 (220.0 mg, 58%) as an off-white solid. MS (ESI, m z): 415, 417 [M+H]$^+$.

Step 5: A mixture of tert-butyl 4-(7-cyano-8-hydroxy-1,5-naphthyridin-2-yl)-3,6-dihydro-2H-pyridine-1-carboxylate 230 (220.0 mg, 0.53 mmol, 1.00 equiv), Pd(dba)$_2$ (63.25 mg, 0.11 mmol, 0.20 equiv), XantPhos (63.58 mg, 0.11 mmol, 0.20 equiv) and Cs$_2$CO$_3$ (345.5 mg, 1.06 mmol, 2.00 equiv) in dixoane (2.0 mL) was stirred at 100° C. for 4 h under N$_2$ atmosphere. The resulting mixture was diluted with water and extracted with EtOAc 3 times. The combined organic layers were concentrated under vacuum. The residue was purified by flash chromatography on silica gel (0-80% EtOAc in petroleum ether) to afford tert-butyl 4-(8-((4-([1,2,4]triazolo[1,5-a]pyridin-7-yloxy)-3-methylphenyl)amino)-7-cyano-1,5-naphthyridin-2-yl)-3,6-dihydropyridine-1(2H)-carboxylate 231 (280.0 mg, 91%) as a brown solid. MS (ESI, m z): 575 [M+H]$^+$.

Step 6: To a mixture of tert-butyl 4-(8-((4-([1,2,4]triazolo[1,5-a]pyridin-7-yloxy)-3-methylphenyl)amino)-7-cyano-1,5-naphthyridin-2-yl)-3,6-dihydropyridine-1(2H)-carboxylate 231 (210.00 mg, 0.36 mmol, 1.00 equiv) in DCM (2.0 mL) at ambient temperature was added TFA (410.4 mg, 3.60 mmol, 10.00 equiv). The resulting mixture was stirred at this temperature for 1 h and concentrated under vacuum to afford 4-((4-([1,2,4]triazolo[1,5-a]pyridin-7-yloxy)-3-methylphenyl)amino)-6-(1,2,3,6-tetrahydropyridin-4-yl)-1,5-naphthyridine-3-carbonitrile 2,2,2-trifluoroacetate 232 (crude, 200.0 mg) as a yellow oil, which was used for the next step without further purification. MS (ESI, m/z): 475 [M+H]$^+$.

Method O: General Method for Intermediate IM-LVI.
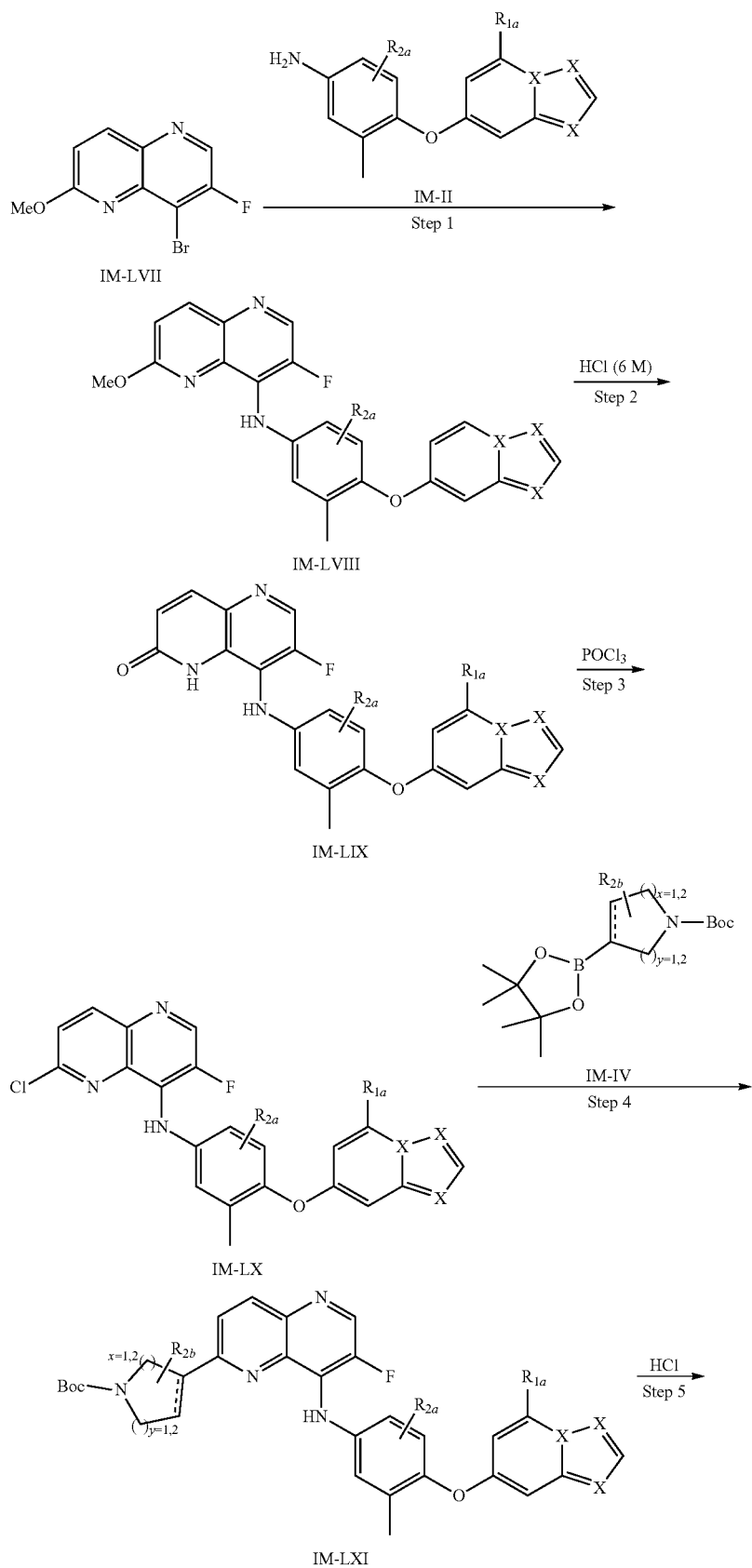

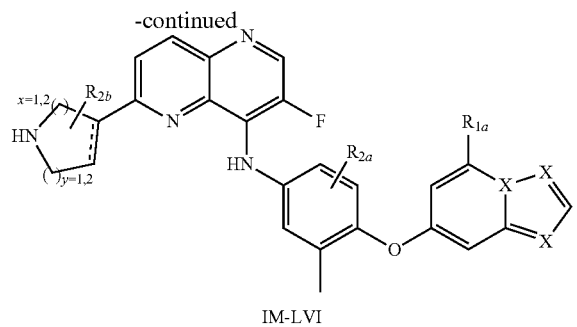

IM-LVI

Step 1: A mixture of intermediate IM-LVII (1.00 equiv), IM-I (1.50 equiv), Pd$_2$(dba)$_3$ (0.20 equiv), XantPhos (0.10 equiv) and Cs$_2$CO$_3$ (3.00 equiv) in dioxane was stirred at 120° C. until the reaction was complete under N$_2$ atmosphere. The resulting mixture was quenched with brine and extracted with EtOAc 3 times. The organic layers were combined, dried over Na$_2$SO$_4$ and concentrated under vacuum. The residue was purified by reverse phase flash chromatography on C18 silica gel (e.g., 0-70% acetonitrile in water (containing 0.05% NH$_4$HCO$_3$)) to afford intermediate IM-LVIII.

Step 2: A mixture of intermediate IM-LVIII (1.00 equiv) in HCl (6 M) was stirred at 90° C. until the reaction was complete and then concentrated under vacuum to afford intermediate IM-LIX (crude) which was used for the next step without further purification.

Step 3: A mixture of intermediate IM-LIX (1.00 equiv), POCl$_3$ (3.00 equiv) and DIEA (2.00 equiv) in DCE was stirred at 80° C. until the reaction was complete. The resulting mixture was concentrated under vacuum to afford intermediate IM-LX (crude) which was used for the next step without further purification.

Step 4: A mixture of intermediate IM-LX (1.00 equiv), TM-IV (2.00 equiv), Na$_2$CO$_3$ (3.00 equiv) and Pd(dppf)Cl$_2$ (0.20 equiv) in dioxane and water was stirred at 100° C. for 4 h under N$_2$ atmosphere. The reaction was quenched with brine and extracted with EtOAc 3 times. The organic layers were combined, dried over Na$_2$SO$_4$ and concentrated under vacuum. The residue was purified by flash chromatography on silica gel (e.g., 0-20% MeOH in DCM) to afford intermediate IM-LXI.

Step 5: A mixture of intermediate IM-LXI (1.00 equiv) and HCl (1.00 mL) in DCM (3.00 mL) was stirred at ambient temperature until the reaction was complete. The resulting mixture was concentrated under vacuum to afford intermediate IM-LXII hydrochloride (crude) which was used for the next step without further purification.

Synthesis of N-(4-([1,2,4]triazolo[1,5-a]pyridin-7-yloxy)-3-methylphenyl)-3-fluoro-6-(1,2,3,6-tetrahydropyridin-4-yl)-1,5-naphthyridin-4-amine 238

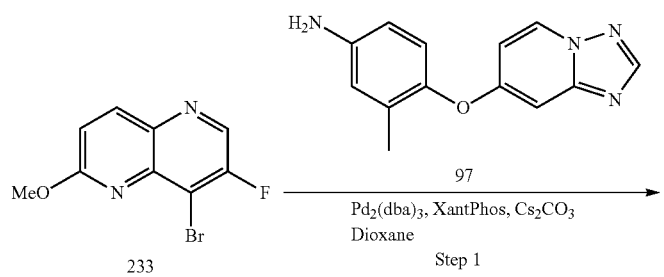

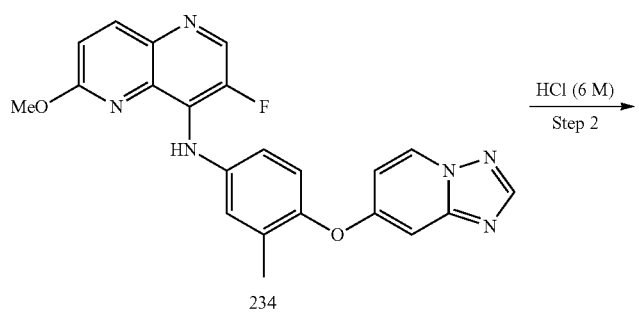

-continued

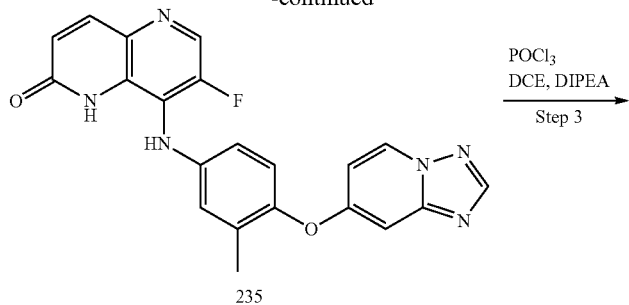

235

POCl₃
DCE, DIPEA
———————→
Step 3

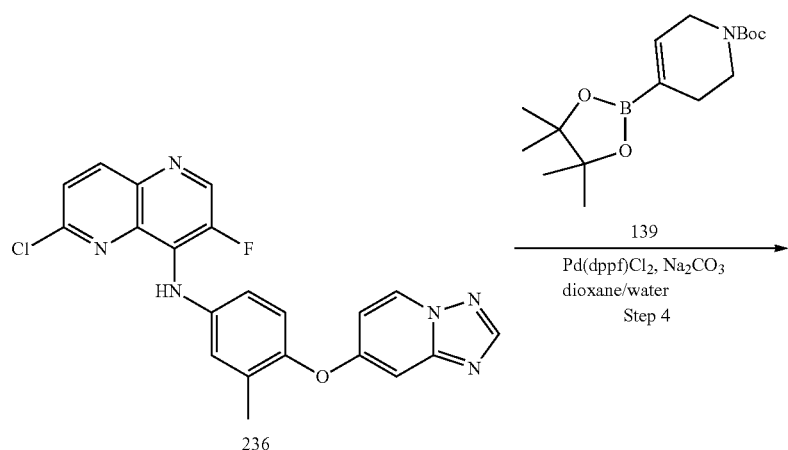

236

139
Pd(dppf)Cl₂, Na₂CO₃
dioxane/water
———————→
Step 4

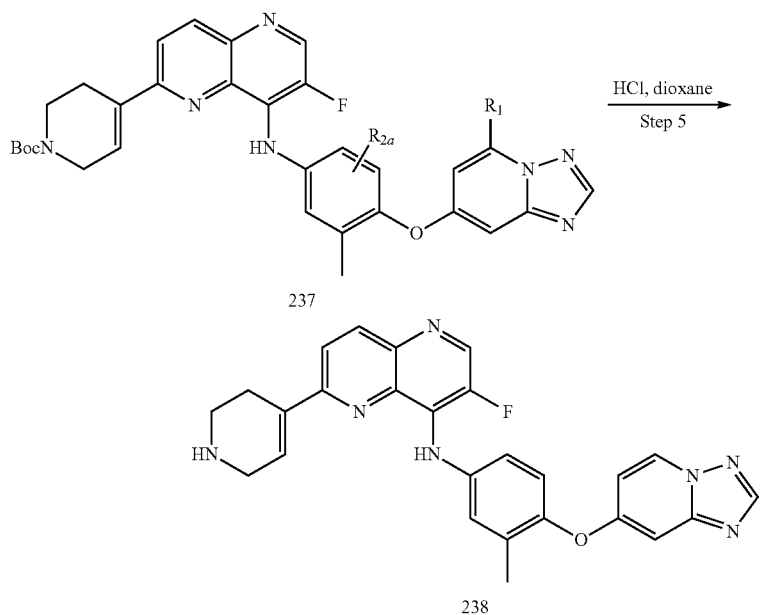

237

HCl, dioxane
———————→
Step 5

238

Step 1: A mixture of 8-bromo-7-fluoro-2-methoxy-1,5-naphthyridine 233 (400 mg, 1.56 mmol, 1.00 equiv), 4-([1,2,4]triazolo[1,5-a]pyridin-7-yloxy)-3-methylaniline 97 (560.8 mg, 2.33 mmol, 1.50 equiv), Pd₂(dba)₃ (285.0 mg, 0.31 mmol, 0.20 equiv), XantPhos (90.1 mg, 0.16 mmol, 0.10 equiv) and Cs₂CO₃ (1.52 g, 4.67 mmol, 3.00 equiv) in dioxane (8.00 mL) was stirred at 120° C. for 16 h under N₂ atmosphere. The resulting mixture was quenched with brine and extracted with EtOAc 3 times. The organic layers were combined, dried over Na₂SO₄ and concentrated under vacuum. The residue was purified by reverse phase flash chromatography on C18 silica gel (0-70% acetonitrile in water (containing 0.05% NH$_4$HCO$_3$)) to afford N-(4-([1,2,4]triazolo[1,5-a]pyridin-7-yloxy)-3-methylphenyl)-3-fluoro-6-methoxy-1,5-naphthyridin-4-amine 234 (560 mg, 73%) as a light-yellow solid. MS (ESI, m z): 417 [M+H]$^+$.

Step 2: A mixture of N-(4-([1,2,4]triazolo[1,5-a]pyridin-7-yloxy)-3-methylphenyl)-3-fluoro-6-methoxy-1,5-naphthyridin-4-amine 234 (560 mg, 1.35 mmol, 1.00 equiv) in HCl (6 M, 10.00 mL) was stirred at 90° C. for 16 h and then concentrated under vacuum to afford 8-((4-([1,2,4]triazolo[1,5-a]pyridin-7-yloxy)-3-methylphenyl)amino)-7-fluoro-1,5-naphthyridin-2(1H)-one 235 (crude, 500.00 mg) as a yellow solid, which was used for the next step without further purification. MS (ESI, m z): 403 [M+H]$^+$.

Step 3: A mixture of 8-((4-([1,2,4]triazolo[1,5-a]pyridin-7-yloxy)-3-methylphenyl)amino)-7-fluoro-1,5-naphthyridin-2(1H)-one 235 (200.00 mg, 0.50 mmol, 1.00 equiv), POCl$_3$ (228.6 mg, 1.49 mmol, 3.00 equiv) and DIEA (128.50 mg, 0.99 mmol, 2.00 equiv) in DCE (4.00 mL) was stirred at 80° C. for 4 h. The resulting mixture was concentrated under vacuum to afford N-(4-([1,2,4]triazolo[1,5-a]pyridin-7-yloxy)-3-methylphenyl)-6-chloro-3-fluoro-1,5-naphthyridin-4-amine 236 (crude, 180 mg) as a yellow solid, which was used for the next step without further purification. MS (ESI, m z): 421, 423 [M+H]$^+$.

Step 4: A mixture of N-(4-([1,2,4]triazolo[1,5-a]pyridin-7-yloxy)-3-methylphenyl)-6-chloro-3-fluoro-1,5-naphthyridin-4-amine 236 (160.00 mg, 0.38 mmol, 1.00 equiv), tert-butyl 4-(4,4,5,5-tetramethyl-1,3,2-dioxaborolan-2-yl)-3,6-dihydropyridine-1(2H)-carboxylate 139 (235.12 mg, 0.76 mmol, 2.00 equiv), Na$_2$CO$_3$ (120.89 mg, 1.14 mmol, 3.00 equiv) and Pd(dppf)Cl$_2$ (61.94 mg, 0.076 mmol, 0.20 equiv) in dioxane (3.00 mL) and water (0.60 mL) was stirred at 100° C. for 4 h under N$_2$ atmosphere. The reaction was quenched with brine and extracted with EtOAc 3 times. The organic layers were combined, dried over Na$_2$SO$_4$ and concentrated under vacuum. The residue was purified by flash chromatography on silica gel (0-20% MeOH in DCM) to afford tert-butyl 4-(8-((4-([1,2,4]triazolo[1,5-a]pyridin-7-yloxy)-3-methylphenyl)amino)-7-fluoro-1,5-naphthyridin-2-yl)-3,6-dihydropyridine-1(2H)-carboxylate 237 (230 mg, 93%) as a yellow solid. MS (ESI, m z):568 [M+H]$^+$.

Step 5: A mixture of tert-butyl 4-(8-((4-([1,2,4]triazolo[1,5-a]pyridin-7-yloxy)-3-methylphenyl)amino)-7-fluoro-1,5-naphthyridin-2-yl)-3,6-dihydropyridine-1(2H)-carboxylate 237 (130.00 mg, 0.229 mmol, 1.00 equiv) and HCl (4 N in 1,4-dioxane, 1.00 mL) in DCM (3.00 mL) was stirred at ambient temperature for 1 h. The resulting mixture was concentrated under vacuum to afford N-(4-([1,2,4]triazolo[1,5-a]pyridin-7-yloxy)-3-methylphenyl)-3-fluoro-6-(1,2,3,6-tetrahydropyridin-4-yl)-1,5-naphthyridin-4-amine hydrochloride 238 (crude, 130.00 mg) as a yellow solid, which was used for the next step without further purification. MS (ESI, m z): 469 [M+H]$^+$.

General Method for Final Analog IM-LXIII
Coupling Condition A:

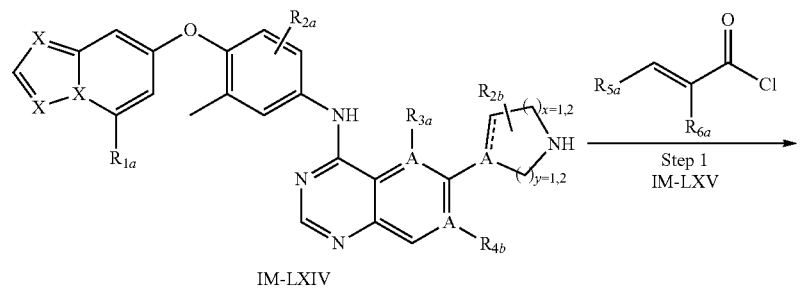

IM-LXIV

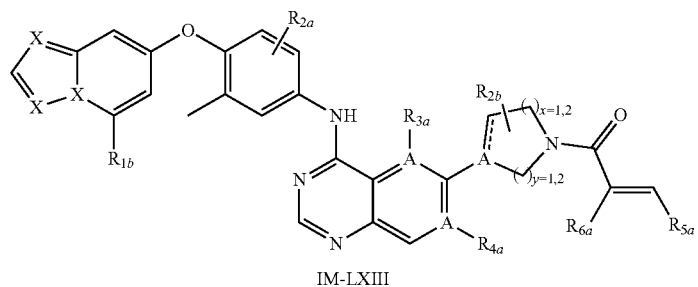

IM-LXIII

Step 1: To a stirred mixture of intermediate IM-LXIV (1.00 equiv.) and TEA (3.00 equiv.) in DCM at 0° C. was added dropwise acryloyl chloride IM-LXV (1.00 equiv.). The resulting mixture was stirred at ambient temperature until the reaction was complete and then diluted with H$_2$O and extracted with EtOAc 3 times. The combined organic layers were washed with brine, dried over Na$_2$SO$_4$ and concentrated under vacuum. The residue was purified by reverse phase flash chromatography on C18 silica gel (5-65% acetonitrile in H$_2$O (containing 0.05% TFA)) to afford desired final product IM-LXIII.

Synthesis of 1-(4-[4-[(3-methyl-4-[[1,2,4] triazolo[1,5-a]pyridin-7-yloxy]phenyl)amino]pyrido[3,2-d]pyrimidin-6-yl]-2,3,6,7-tetrahydroazepin-1-yl)prop-2-en-1-one Example 1

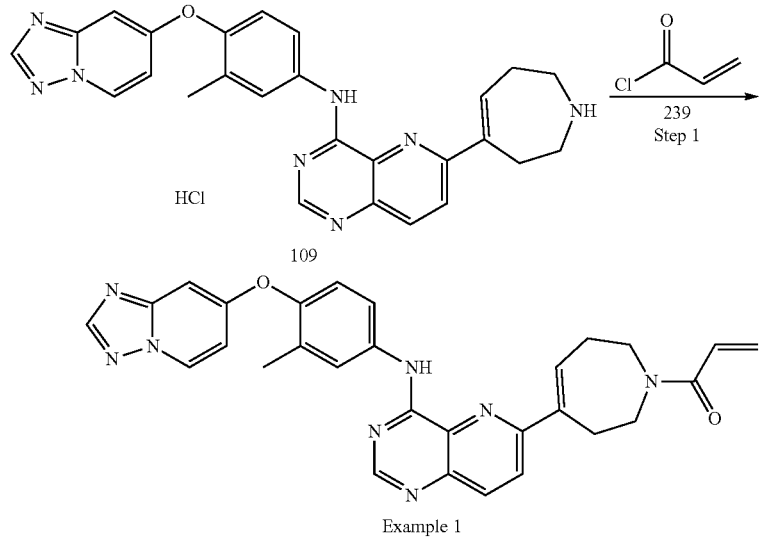

Step 1: To a stirred mixture of N-(3-methyl-4-[[1,2,4]triazolo[1,5-a]pyridin-7-yloxy]phenyl)-6-(2,3,6,7-tetrahydro-1H-azepin-4-yl)pyrido[3,2-d]pyrimidin-4-amine hydrochloride 109 (110.00 mg, 0.22 mmol, 1.00 equiv.) and TEA (66.66 mg, 0.66 mmol, 3.00 equiv.) in DCM (4.00 mL) at 0° C. was added dropwise acryloyl chloride 239 (19.80 mg, 0.22 mmol, 1.00 equiv.). The resulting mixture was stirred at this temperature for 2 h and then diluted with H₂O and extracted with EtOAc 3 times. The combined organic layers were washed with brine, dried over Na₂SO₄ and concentrated under vacuum. The residue was purified by flash chromatography on silica gel (0-20% MeOH in DCM) and further purified by Prep-HPLC (NH₄HCO₃ system) to afford 1-(4-[4-[(3-methyl-4-[[1,2,4] triazolo[1,5-a]pyridin-7-yloxy]phenyl)amino]pyrido[3,2-d]pyrimidin-6-yl]-2,3,6,7-tetrahydroazepin-1-yl)prop-2-en-1-one Example 1 (20.9 mg, 18%) as a yellow solid. $^1$H NMR (300 MHz, DMSO-d6) δ 9.82 (brs, 1H), 8.92 (d, J=9.0 Hz 1H), 8.62 (s, 1H), 8.37 (s, 1H), 8.19-8.08 (m, 2H), 7.98-7.90 (m, 2H), 7.27-7.18 (m, 1H), 7.06-6.92 (m, 2H), 6.92-6.74 (m, 2H), 6.17-6.08 (m, 1H), 5.72-5.64 (m, 1H), 4.34 (dd, J=9.6, 5.1 Hz, 2H), 3.88-3.67 (m, 2H), 3.26-2.96 (m, 2H), 2.20 (s, 3H), 2.06-1.89 (m, 2H). MS (ESI, m z): 519 (M+H)+, LCMS: Method A; Retention Time: 1.45 min; MS (ESI, m z): 519.15 [M+H]$^+$.

Coupling Condition B:

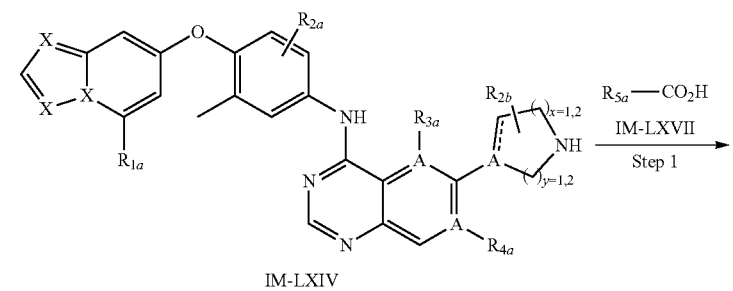

IM-LXIV

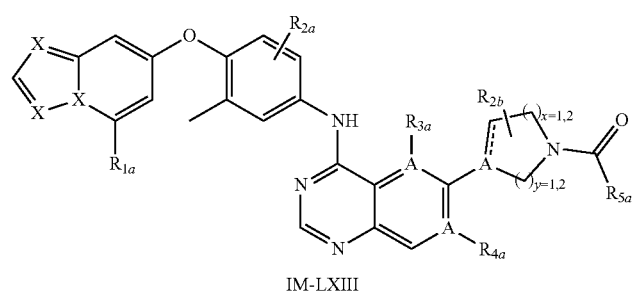

IM-LXIII

Step 1: A mixture of intermediate IM-LXIV (1.00 equiv.), carboxylic acid IM-LXVI (1.20 equiv.), HATU (1.50 equiv.) and DIEA (3.00 equiv.) in DMF was stirred at ambient temperature until the reaction was complete. The reaction was diluted with brine and extracted with EtOAc 3 times. The organic layers were combined, dried over $Na_2SO_4$ and concentrated under vacuum. The residue was purified by Prep-HPLC ($NH_4HCO_3$ system) to desired final product IM-LXIII.

Synthesis of 1-(4-(4-((4-([1,2,4]triazolo[1,5-a]pyridin-7-yloxy)-3-methylphenyl)amino)pyrido[3,2-d]pyrimidin-6-yl)-3,6-dihydropyridin-1(2H)-yl)but-2-yn-1-one Example 2

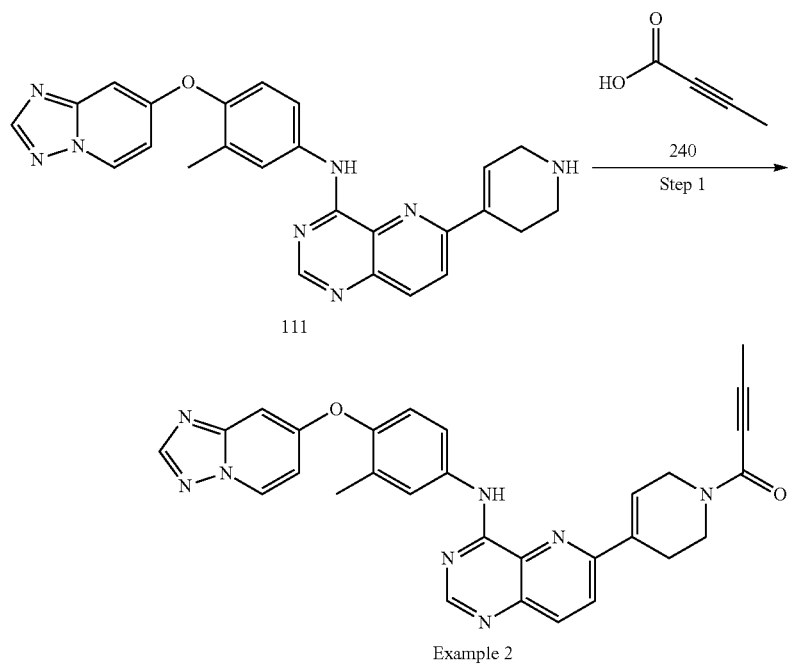

A mixture of N-(4-([1,2,4]triazolo[1,5-a]pyridin-7-yloxy)-3-methylphenyl)-6-(1,2,3,6-tetrahydropyridin-4-yl)pyrido[3,2-d]pyrimidin-4-amine hydrochloride 111 (107.89 mg, 0.222 mmol, 1.00 equiv.), but-2-ynoic acid 240 (22.39 mg, 0.266 mmol, 1.20 equiv.), HATU (126.60 mg, 0.333 mmol, 1.50 equiv.) and DIEA (86.07 mg, 0.666 mmol, 3.00 equiv.) in DMF (2.00 mL) was stirred at ambient temperature for 1 h. The reaction was diluted with brine and extracted with EtOAc 3 times. The organic layers were combined, dried over $Na_2SO_4$ and concentrated under vacuum. The residue was purified by Prep-HPLC ($NH_4HCO_3$ system) to afford 1-(4-(4-((4-([1,2,4]triazolo[1,5-a]-248-pyridine-7-yloxy)-3-methylphenyl)amino)pyrido[3,2-d]pyrimidin-6-yl)-3,6-dihydropyridin-1(2H)-yl)but-2-yn-1-one Example 2 (45.5 mg, 39%) as a white solid. $^1$H NMR (400 MHz, DMSO-d6) δ9.84 (s, 1H), 8.95 (d, J=7.6 Hz, 1H), 8.65 (s, 1H), 8.38 (s, 1H), 8.21-8.14 (m, 2H), 8.04-7.95 (m, 2H), 7.29-7.22 (m, 1H), 7.09-7.00 (m, 2H), 6.80 (d, J=2.8 Hz, 1H), 4.56-4.25 (m, 2H), 4.02-3.74 (m, 2H), 3.02-2.84 (m, 2H), 2.22 (s, 3H), 2.10-2.02 (m, 3H). LCMS: Method A; Retention Time: 1.49 min; LCMS (ESI, m/z): 517 [M+H]$^+$, Coupling Condition C:

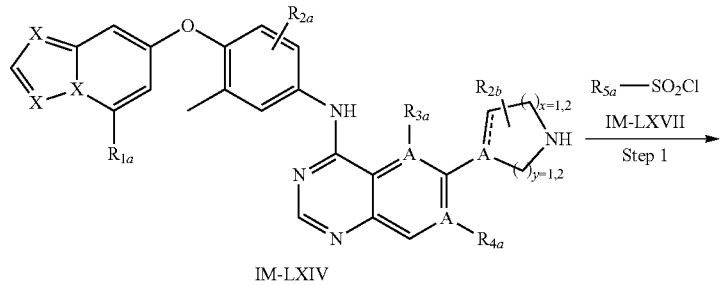

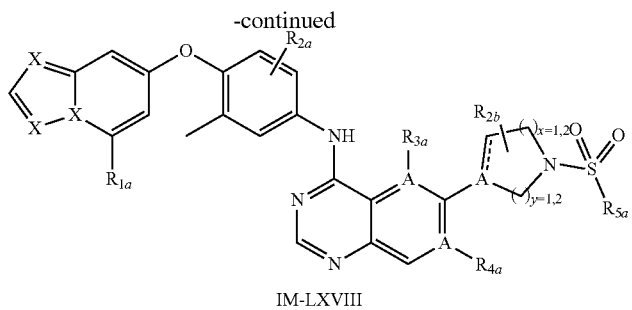

IM-LXVIII

Step 1: A mixture of intermediate IM-LXIV (1.00 equiv.), Sulfonyl chloride IM-LXVII (1.20 equiv.), and DIEA (3.00 equiv.) in DCM was stirred at −10° C. until the reaction was complete. The reaction was diluted with brine and extracted with EtOAc 3 times. The organic layers were combined, dried over Na$_2$SO$_4$ and concentrated under vacuum. The residue was purified by Prep-HPLC to desired final product IM-LXVIII.

Synthesis of (R)—N-(4-([1,2,4]triazolo[1,5-a]-249-yridine-7-yloxy)-2-fluoro-3-methylphenyl)-6-(3-methyl-4-(vinylsulfonyl)piperazin-1-yl)pyrimido[5,4-d]pyrimidin-4-amine, example 3 prep-TLC (MeOH/DCM=1/15, V/V) and prep-HPLC (Column: AZZOTA C18 GEMINI 250*20 mm 10 um, MeCN in H$_2$O with 0.1% HCOOH) to give the desired product (8.1 mg, 10.3% yield over two steps) as a yellow solid. $^1$H NMR (400 MHz, DMSO-d$_6$) δ 9.64 (s, 1H), 9.15 (s, 1H), 8.98 (d, J=7.4 Hz, 1H), 8.42 (s, 1H), 8.40 (s, 1H), 7.83 (t, J=8.7 Hz, 1H), 7.19-7.12 (m, 1H), 7.07 (dd, J=7.5, 2.6 Hz, 1H), 6.95-6.86 (m, 2H), 6.14 (d, J=16.4 Hz, 1H), 6.07 (d, J=9.9 Hz, 1H), 4.82 (d, J=39.2 Hz, 2H), 4.08 (dt, J=6.4, 3.0 Hz, 1H), 3.59-3.50 (m, 1H), 3.41-3.36 (m, 1H), 3.30-3.18 (m, 2H), 2.17 (d, J=1.9 Hz, 3H), 1.19 (d, J=6.7 Hz, 3H). LC/MS: Method K; Retention Time: 1.63 min MS (ESI, m/z): 577 [M+H]$^+$. Coupling Condition D:

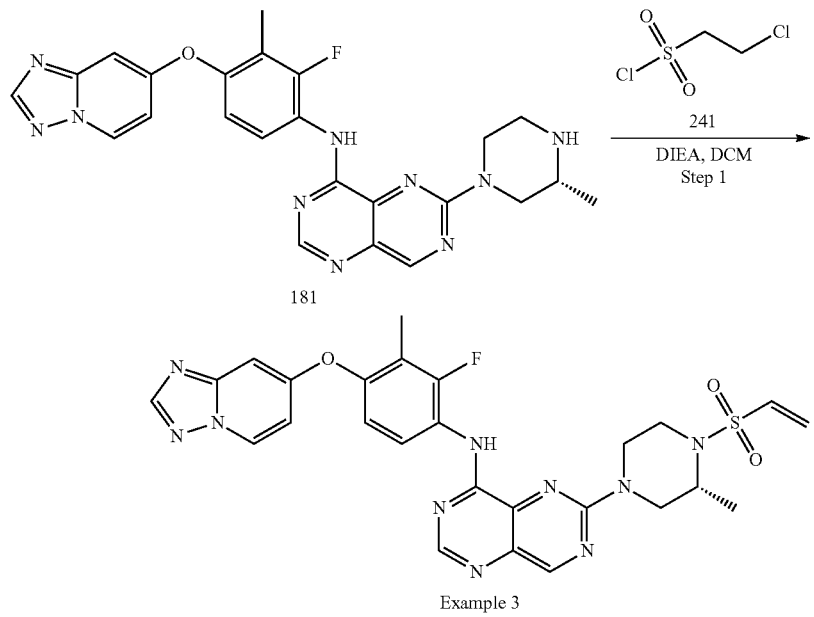

Step 1: To a stirred mixture of (R)—N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine (79 mg, crude) in DCM (5 mL), were added DIEA (0.2 mL) and 2-chloroacetyl chloride 241 (23 mg, 0.14 mmol) in sequence at −10° C. Then the resulting mixture was stirred at −10° C. for 1 h. LCMS showed the reaction was completed. The reaction mixture was quenched by adding water (5 mL) and extracted with DCM (3×5 mL). The combined organic phases were washed with brine (5 mL), dried over anhydrous Na$_2$SO$_4$, filtered and concentrated in vacuo to give the crude product. The crude product was purified by

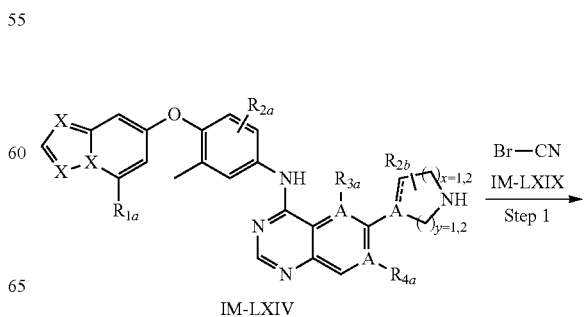

IM-LXIV

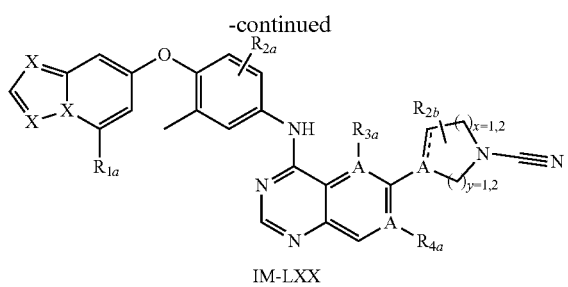

IM-LXX

Step 1: A mixture of intermediate IM-LXIV (1.00 equiv.), and NaHCO$_3$ (5.00 equiv.) in DCM and water was stirred at 0° C. Cyanic bromide (1.0 equiv.) was added dropwise at 0° C. and stirred for 10 min. The reaction mixture was stirred overnight. Upon completion, the mixture was diluted with brine and extracted with DCM 3 times. The organic layers were combined, dried over Na$_2$SO$_4$ and concentrated under vacuum. The residue was purified by Prep-HPLC to desired final product IM-LXX.

Synthesis of (R)-4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazine-1-carbonitrile, Example 4

Step 1: To a stirred mixture of (R)—N-(4-([1,2,4]triazolo[1,5-a]pyridin-7-yloxy)-2-fluoro-3-methylphenyl)-6-(3-methylpiperazin-1-yl)pyrimido[5,4-d]pyrimidin-4-amine (65 mg, crude) and NaHCO$_3$ (50 mg, 0.6 mmol) in H$_2$O (3.6 mL) and DCM (1 mL), was added cyanic bromide 242 (14 mg, 0.13 mmol) in DCM (1 mL) dropwise at 0° C. Then the resulting mixture was stirred at 0° C. for 10 min. After 10 min, the reaction mixture was warmed to room temperature and stirred overnight. LCMS showed the reaction was completed. The reaction mixture was quenched by adding water (5 mL) and extracted with DCM (3×5 mL). The combined organic phases were washed with brine (5 mL), dried over anhydrous Na$_2$SO$_4$, filtered and concentrated in vacuo to give the crude product. The crude product was purified by prep-TLC (MeOH/DCM=1/15, V/V) and prep-HPLC (Column: AZZOTA C18 GEMINI 250*20 mm 10 um, MeCN in H$_2$O with 0.1% HCOOH) to give the desired product (15.7 mg, 26.17% yield over two steps) as a yellow solid. $^1$H NMR (400 MHz, DMSO-d6) δ 9.68 (s, 1H), 9.16 (s, 1H), 8.98 (d, J=7.4 Hz, 1H), 8.41 (d, J=6.0 Hz, 2H), 7.77 (t, J=8.7 Hz, 1H), 7.15 (d, J=8.7 Hz, 1H), 7.07 (dd, J=7.5, 2.5 Hz, 1H), 6.93 (d, J=2.4 Hz, 1H), 4.77 (t, J=14.5 Hz, 2H), 3.56 (d, J=12.0 Hz, 1H), 3.44-3.33 (m, 3H), 3.07 (dd, J=13.4, 9.7 Hz, 1H), 2.17 (s, 3H), 1.31 (d, J=6.4 Hz, 3H). LC/MS: Method G; Retention Time: 1.28 min MS (ESI, m/z): 512 [M+H]+

The following compounds in Table 10 were obtained following above-mentioned method using the appropriate starting materials.

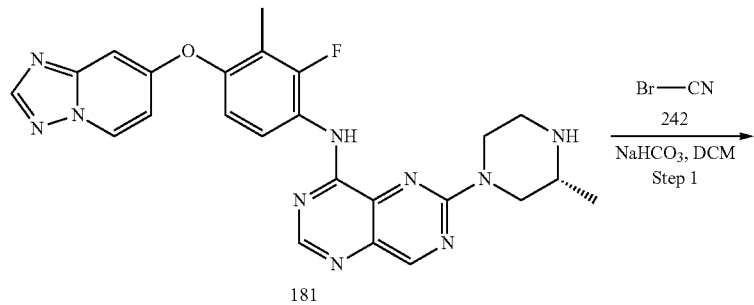

181

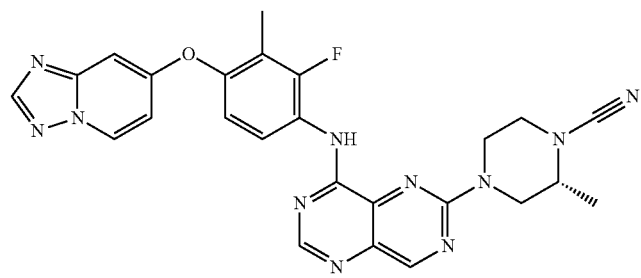

Example 4

TABLE 10

| Example | Synthetic Method | Coupling Method | Compound Structure | Physical Data (¹H NMR and MS) |
|---|---|---|---|---|
| 5 | A | A | 1-(4-(4-((4-([1,2,4]triazolo[1,5-a]pyridin-7-yloxy)-2-fluoro-3-methylphenyl)amino)pyrido[3,2-d]pyrimidin-6-yl)-3,6-dihydropyridin-1(2H)-yl)prop-2-en-1-one | ¹H NMR (400 MHz, DMSO-d6) δ 9.81-9.70 (m, 1H), 8.97 (d, J = 7.6 Hz, 1H), 8.63 (s, 1H), 8.41 (s, 1H), 8.26-8.17 (m, 2H), 8.16-8.01 (m, 1H), 7.19-7.13 (m, 1H), 7.10-7.01 (m, 2H), 6.97-6.80 (m, 2H), 6.22-6.11 (m, 1H), 5.77-5.69 (m, 1H), 4.51-4.28 (m, 2H), 3.94-3.73 (m, 2H), 2.95-2.79 (m, 2H), 2.22-2.14 (m, 3H). LCMS: Method A; Retention Time: 1.28 min; MS (ESI, m/z): 523 [M + H]⁺ |
| 6 | C | A | 1-[(2R)-2-methyl-4-{4-[(3-methyl-4-{[1,2,4]triazolo[1,5-a]pyridin-7-yloxy}phenyl)amino]pyrido[3,2-d]pyrimidin-6-yl}piperazin-1-yl]prop-2-en-1-one | ¹H NMR (300 MHz, DMSO-d6) δ 9.37 (s, 1H), 8.94 (d, J = 7.5 Hz, 1H), 8.44 (s, 1H), 8.38 (s, 1H), 8.02-7.92 (m, 3H), 7.58 (d, J = 9.3 Hz, 1H), 7.23 (d, J = 8.4 Hz, 1H), 7.03 (dd, J = 7.5, 2.7 Hz, 1H), 6.92-6.78 (m, 2H), 6.17 (dd, J = 16.5, 2.4 Hz, 1H), 5.73 (dd, J = 10.5, 2.4 Hz, 1H), 4.81-4.56 (m, 2H), 4.53-4.37 (m, 2H), 4.34-4.03 (m, 1H), 3.44 (d, J = 12.3 Hz, 1H), 3.25-3.07 (m, 1H), 2.21 (s, 3H), 1.20 (d, J = 6.6 Hz, 3H). LCMS: Method B; Retention Time: 0.98 min; MS (ESI, m/z): 522 [M + H]⁺ |
| 7 | C | A | (E)-1-(4-(4-((4-([1,2,4]triazolo[1,5-a]pyridin-7-yloxy)-3-methylphenyl)amino)pyrido[3,2-d]pyrimidin-6-yl)piperazin-1-yl)-4-(dimethylamino)but-2-en-1-one | 1H NMR (300 MHz, DMSO-d6) δ 9.39 (brs, 1H), 8.94 (d, J = 7.2 Hz, 1H), 8.46 (s, 1H), 8.38 (s, 1H), 8.06-7.93 (m, 3H), 7.60 (d, J = 9.3 Hz, 1H), 7.23 (d, J = 8.7 Hz, 1H), 7.03 (dd, J = 7.5, 2.7 Hz, 1H), 6.79 (d, J = 2.7 Hz, 1H), 6.71-6.63 (m, 2H), 3.92-3.82 (m, 4H), 3.80-3.68 (m, 4H), 3.09-3.04 (m, 2H), 2.33-2.14 (m, 9H). LCMS: Method B; Retention Time: 0.92 min; MS (ESI, m/z): 5652 [M + H]⁺ |
| 8 | D | A | 1-[4-[(3-methyl-4-[[1,2,4]triazolo[1,5-a]pyridin-7-yloxy]phenyl)amino]pyrido[3,2-d]pyrimidin-6-yl]-4-(prop-2-enoyl)piperazin-2-one; trifluoroacetate | ¹H NMR (400 MHz, DMSO-d6) δ 10.07 (brs, 1H), 8.96 (brs, 1H), 8.71 (s, 1H), 8.51-8.44 (m, 1H), 8.39 (s, 1H), 8.29-8.22 (m, 1H), 7.97-7.83 (m, 2H), 7.30-7.25 (m, 1H), 7.24-7.09 (m, 1H), 7.04 (dd, J = 7.6, 2.4 Hz, 1H), 6.98 (s, 1H), 6.81 (d, J = 2.4 Hz, 1H), 6.28-6.18 (m, 1H), 5.84-5.74 (m, 1H), 4.63-4.53 (m, 2H), 3.97-3.91 (m, 2H), 2.22 (s, 3H), 1.52 (d, J = 7.2 Hz, 2H). LCMS: Method C; Retention Time: 0.78 min; MS (ESI, m/z): 522 [M + H]⁺, 262 ([M + 2H] / 2)⁺. |

TABLE 10-continued

Compounds

| Example | Synthetic Method | Coupling Method | Compound Structure | Physical Data ($^1$H NMR and MS) |
|---|---|---|---|---|
| 9 | C | A | 1-(4-(4-((4-([1,2,4]triazolo[1,5-a]pyridin-7-yloxy)-3-methylphenyl)amino)pyrido[3,2-d]pyrimidin-6-yl)piperazin-1-yl)prop-2-en-1-one | $^1$H NMR (300 MHz, DMSO-$d_6$) δ 9.41 (s, 1H), 8.95 (d, J = 7.5 Hz, 1H), 8.46 (s, 1H), 8.39 (s, 1H), 8.06-7.92 (m, 3H), 7.60 (d, J = 9.6 Hz, 1H), 7.24 (d, J = 8.4 Hz, 1H), 7.04 (dd, J = 7.5, 2.7 Hz, 1H), 6.95-6.86 (m, 1H), 6.79 (d, J = 2.7 Hz, 1H), 6.21-6.14 (m, 1H), 5.77-5.72 (m, 1H), 3.95-3.81 (m, 4H), 3.79-373. (m, 4H), 2.21 (s, 3H). LCMS: Method A; Retention Time: 1.35 min; MS (ESI, m/z): 508 [M + H]$^+$ |
| 10 | E | A | 1-(4-(4-((4-(benzo[d]oxazol-5-yloxy)-3-methylphenyl)amino)pyrido[3,2-d]pyrimidin-6-yl)-3,6-dihydropyridin-1(2H)-yl)prop-2-en-1-one | $^1$H NMR (300 MHz, DMSO-d6) δ 9.79 (s, 1H), 8.76 (s, 1H), 8.62 (s, 1H), 8.16-8.13 (m, 2H), 7.92-7.84 (m, 2H), 7.78 (d, J = 9.0 Hz, 1H), 7.26 (d, J = 2.4 Hz, 1H), 7.13-6.87 (m, 4H), 6.22-6.12 (m, 1H), 5.78-5.70 (m, 1H), 4.34-4.43 (m, 2H), 3.83-3.85 (m, 2H), 2.94-2.90 (m, 2H), 2.26 (s, 3H). LCMS: Method D; Retention Time: 1.20 min; MS (ESI, m/z): 505 [M + H]$^+$. |
| 11 | A | A | 1-(4-(4-((4-([1,2,4]triazolo[1,5-a]pyridin-7-yloxy)-2-fluoro-5-methylphenyl)amino)pyrido[3,2-d]pyrimidin-6-yl)-3,6-dihydropyridin-1(2H)-yl)prop-2-en-1-one | $^1$H NMR (400 MHz, DMSO-$d_6$) δ 9.86-9.77 (m, 1H), 8.98 (d, J = 7.6 Hz, 1H), 8.61 (d, J = 2.0 Hz, 1H), 8.42 (s, 1H), 8.26-8.15 (m, 2H), 8.06-7.93 (m, 1H), 7.36 (d, J = 10.8 Hz, 1H), 7.12-6.99 (m, 2H), 7.08-6.92 (m, 2H), 6.22-6.12 (m, 1H), 5.77-5.68 (m, 1H), 4.48-4.26 (m, 2H), 3.89-3.73 (m, 2H), 2.95-2.80 (m, 2H), 2.21 (s, 3H). LCMS: Method B; Retention Time: 1.02 min; MS (ESI, m/z): 523 [M + H]$^+$ |
| 12 | A | A | 1-(4-[4-[(3-methyl-4-[[1,2,4]triazolo[1,5-a]pyridin-7-yloxy]phenyl)amino]pyrido[3,2-d]pyrimidin-6-yl]-3,6-dihydro-2H-pyridin-1-yl)prop-2-en-1-one | $^1$H NMR (400 MHz, DMSO-d6) δ 9.86 (brs, 1H), 8.95 (d, J = 7.6 Hz, 1H), 8.65 (s, 1H), 8.39 (s, 1H), 8.19 (s, 2H), 8.00 (d, J = 7.6 Hz, 2H), 7.28-7.23 (m, 1H), 7.12-7.02 (m, 2H), 6.96-6.82 (m, 1H), 6.81 (d, J = 2.4 Hz, 1H), 6.22-6.10 (m, 1H), 5.76-5.69 (m, 1H), 4.44 (s, 1H), 4.35 (s, 1H), 3.93-3.76 (m, 2H), 2.93 (d, J = 20.8 Hz, 2H), 2.22 (s, 3H). LCMS: Method C; Retention Time: 0.68 min; MS (ESI, m/z): 505 [M + H]$^+$ |

TABLE 10-continued

| Example | Synthetic Method | Coupling Method | Compound Structure | Physical Data (¹H NMR and MS) |
|---|---|---|---|---|
| 13 | A | A | (E)-1-(4-(4-((4-([1,2,4]triazolo[1,5-a]pyridin-7-yloxy)-3-methylphenyl)amino)pyrido[3,2-d]pyrimidin-6-yl)-3,6-dihydropyridin-1(2H)-yl)-4-(dimethylamino)but-2-en-1-one | 1H NMR (400 MHz, DMSO-d6) δ 9.86 (s, 1H), 8.96-8.92 (m, 1H), 8.65 (s, 1H), 8.39 (s, 1H), 8.21-8.15 (m, 2H), 8.00-7.96 (m, 2H), 7.28-7.23 (m, 1H), 7.11-7.02 (m, 2H), 6.80 (d, J = 2.4 Hz, 1H), 6.73-6.61 (m, 2H), 4.44-4.31 (m, 2H), 3.87-3.78 (m, 2H), 3.08-3.03 (m, 2H), 2.97-2.86 (m, 2H), 2.22 (s, 3H), 2.17 (s, 6H). LCMS: Method A; Retention Time: 1.35 min; MS (ESI, m/z): 562 [M + H]⁺, 281 ([M + 2H] / 2)⁺, 302 ([M + acetonitrile + 2H] / 2)⁺. |
| 14 | C | A | 1-(4-[4-[(3-methyl-4-[[1,2,4]triazolo[1,5-a]pyridin-7-yloxy]phenyl)amino]pyrido[3,2-d]pyrimidin-6-yl]-1,4-diazepan-1-yl)prop-2-en-1-one | ¹H NMR (300 MHz, DMSO-d₆) δ 9.38 (brs, 1H), 8.94 (d, ] = 7.5 Hz, 1H), 8.44 (d, J = 4.2 Hz, 1H), 8.39 (s, 1H), 8.02-7.85 (m, 3H), 7.52-7.42 (m, 1H), 7.29-7.19 (m, 1H), 7.07-6.99 (m, 1H), 6.83-6.64 (m, 2H), 6.16-5.80 (m, 1H), 5.71-5.41 (m, 1H), 4.11-4.04 (m, 2H), 3.93-3.74 (m, 4H), 3.60-3.45 (m, 2H), 2.22 (s, 3H), 1.98-1.83 (m, 2H). LCMS: Method A; Retention Time: 1.36 min; MS (ESI, m/z): 522 [M + H]⁺, 262 ([M + 2H] / 2)⁺. |
| 15 | A | A | 1-(4-(4-(4-(5-methoxy-[1,2,4]triazolo[1,5-a]pyridin-7-yloxy)-3-methylphenylamino)pyrido[3,2-d]pyrimidin-6-yl)-5,6-dihydropyridin-1(2H)-yl)prop-2-en-1-one | ¹H NMR (400 MHz, MeOD) δ 8.82 (s, 1H), 8.41-8.26 (m, 2H), 8.20 (d, J = 9.0 Hz, 1H), 7.98-7.78 (m, 2H), 7.29 (d, J = 8.6 Hz, 1H), 7.11 (d, J = 25.1 Hz, 1H), 6.96-6.76 (m, 1H), 6.64 (d, J = 2.1 Hz, 1H), 6.41 (s, 1H), 6.28 (d, J = 15.5 Hz, 1H), 5.82 (d, J = 10.9 Hz, 1H), 4.48 (d, J = 14.8 Hz, 2H), 4.24 (s, 3H), 4.23 (m, 1H), 3.95 (s, 2H), 3.08-2.95 (m, 2H), 2.31 (s, 3H) LCMS: Method G; Retention Time: 2.22 min MS (ESI, m/z): 535 [M + H]⁺ |
| 16 | A | A | 1-(4-(4-((4-((5-chloro-[1,2,4]triazolo[1,5-a]pyridin-7-yl)oxy)-3-methylphenyl)amino)pyrido[3,2-d]pyrimidin-6-yl)-3,6-dihydropyridin-1(2H)-yl)prop-2-en-1-one | ¹H NMR (400 MHz, MeOD) δ 8.62 (s, 1H), 8.38 (s, 1H), 8.20 (d, J = 8.9 Hz, 1H), 8.12 (d, J = 8.9 Hz, 1H), 7.97-7.93 (m, 2H), 7.31 (d, J = 2.4 Hz, 1H), 7.23 (d, J = 8.3 Hz, 1H), 6.99 (d, J = 21.7 Hz, 1H), 6.92-6.78 (m, 3H), 6.28 (d, J = 16.6 Hz, 1H), 5.81 (d, J = 10.6 Hz, 1H), 4.46 (d, J = 14.2 Hz, 2H), 3.96 (d, J = 5.5 Hz, 2H), 3.01 (d, J = 18.8 Hz, 2H), 2.28 (s, 3H). LCMS: Method G; Retention Time: 2.22 min MS (ESI, m/z): 539 [M + H]⁺ |

TABLE 10-continued

| Example | Synthetic Method | Coupling Method | Compound Structure | Physical Data (¹H NMR and MS) |
|---|---|---|---|---|
| 17 | A | A | 1-(4-(4-((4-((5-Methyl-[1,2,4]triazolo[1,5-a]pyridin-7-yl)oxy)-3-methylphenyl)amino)pyrido[3,2-d]pyrimidin-6-yl)-3,6-dihydropyridin-1(2H)-yl)prop-2-en-1-one | ¹H NMR (400 MHz, DMSO) δ 9.85 (s, 1H), 8.65 (s, 1H), 8.39 (s, 1H), 8.22-8.13 (m, 2H), 8.03-7.95 (m, 2H), 7.23 (d, J = 8.8 Hz, 1H), 7.08 (d, J = 16.8 Hz, 1H), 6.99 (s, 1H), 6.96-6.81 (m, 1H), 6.69 (d, J = 2.0 Hz, 1H), 6.18 (d, J = 16.8 Hz, 1H), 5.75 (d, J = 10.8 Hz, 1H), 4.39 (d, J = 34.8 Hz, 2H), 3.91-3.79 (m, 2H), 2.93 (d, J = 20.8 Hz, 2H), 2.73 (s, 3H), 2.22 (s, 3H). LCMS: Method E; Retention Time: 1.25 min MS (ESI, m/z): 519 [M + H]⁺ |
| 18 | F | A | 1-(4-(8-((4-([1,2,4]triazolo[1,5-a]pyridin-7-yloxy)-3-methylphenyl)amino)pyrimido[5,4-d]pyrimidin-2-yl)-3,6-dihydropyridin-1(2H)-yl)prop-2-en-1-one | ¹H NMR (400 MHz, DMSO-d₆) δ 10.13 (s, 1H), 9.43 (s, 1H), 8.94 (d, J = 7.5 Hz, 1H), 8.73 (s, 1H), 8.39 (s, 1H), 7.97 (d, J = 4.0 Hz, 2H), 7.54 (d, J = 21.6 Hz, 1H), 7.29-7.24 (m, 1H), 7.05 (dd, J = 7.5, 2.6 Hz, 1H), 7.00-6.83 (m, 1H), 6.81 (d, J = 2.6 Hz, 1H), 6.18 (d, J = 16.6 Hz, 1H), 5.75 (dd, J = 10.5, 2.3 Hz, 1H), 4.43 (d, J = 40.3 Hz, 2H), 3.85 (d, J = 7.2 Hz, 2H), 2.92 (d, J = 17.2 Hz, 2H), 2.23 (s, 3H). LCMS: Method E; Retention Time: 1.28 min MS (ESI, m/z): 506 [M + H]⁺ |
| 19 | G | A | 1-(4-(4-((4-([1,2,4]triazolo[1,5-a]pyridin-7-yloxy)-3-methylphenyl)amino)-5-methoxyquinazolin-6-yl)-3,6-dihydropyridin-1(2H)-yl)prop-2-en-1-one | ¹H NMR (400 MHz, DMSO) δ 10.24 (s, 1H), 8.94 (d, J = 7.6 Hz, 1H), 8.58 (s, 1H), 8.38 (s, 1H), 7.95 (dd, J = 8.8, 2.8 Hz, 1H), 7.87 (d, J = 2.8 Hz, 1H), 7.71 (d, J = 8.8 Hz, 1H), 7.57 (d, J = 8.8 Hz, 1H), 7.23 (d, J = 8.8 Hz, 1H), 7.03 (dd, J = 7.6, 2.8 Hz, 1H), 6.98-6.82 (m, 1H), 6.80 (d, J = 2.4 Hz, 1H), 6.18 (d, J = 16.4 Hz, 1H), 6.11-6.04 (m, 1H), 5.77-5.71 (m, 1H), 4.29 (d, J = 38.8 Hz, 2H), 3.92 (s, 3H), 3.88-3.78 (m, 2H), 2.69-2.53 (m, 2H), 2.21 (s, 3H). LCMS: Method E; Retention Time: 1.01 min MS (ESI, m/z): 534 [M + H]⁺ |
| 20 | H | A | 1-(4-(4-((4-([1,2,4]triazolo[1,5-a]pyridin-7-yloxy)-3-methylphenyl)amino)-5-methoxyquinazolin-6-yl)piperazin-1-yl)prop-2-en-1-one | ¹H NMR (400 MHz, DMSO) δ 10.36 (s, 1H), 8.92 (d, J = 7.5 Hz, 1H), 8.48 (s, 1H), 8.37 (s, 1H), 7.97 (dd, J = 8.7, 2.5 Hz, 1H), 7.87 (d, J = 2.4 Hz, 1H), 7.65 (d, J = 9.1 Hz, 1H), 7.56 (d, J = 9.0 Hz, 1H), 7.21 (d, J = 8.7 Hz, 1H), 7.02 (dd, J = 7.5, 2.6 Hz, 1H), 6.88 (dd, J = 16.7, 10.4 Hz, 1H), 6.78 (d, J = 2.5 Hz, 1H), 6.16 (dd, J = 16.6, 2.3 Hz, 1H), 5.73 (dd, J = 10.4, 2.3 Hz, 1H), 4.15 (s, 3H), 3.80 (s, 4H), 3.15 (s, 4H), 2.20 (s, 3H). LCMS: Method E; Retention Time: 0.80 min MS (ESI, m/z): 537 [M + H]⁺ |

TABLE 10-continued

| Example | Synthetic Method | Coupling Method | Compound Structure | Physical Data (¹H NMR and MS) |
|---|---|---|---|---|
| 21 | A | A | 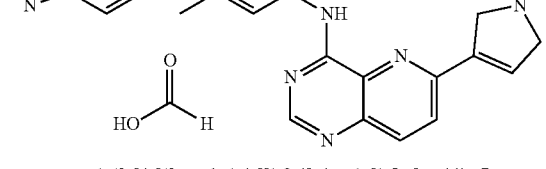<br>1-(3-[4-[(3-methyl-4-[[1,2,4]triazolo[1,5-a]pyridin-7-yloxy]phenyl)amino]pyrido[3,2-d]pyrimidin-6-yl]-2,5-dihydropyrrol-1-yl)prop-2-en-1-one formate | $^1$H NMR (300 MHz, DMSO-$d_6$) δ 9.90 (brs, 1H), 8.94 (dd, J = 7.8, 1.8 Hz, 1H), 8.63 (d, J = 5.1 Hz, 1H), 8.37 (s, 1H), 8.35-8.23 (m, 1H), 8.22-8.14 (m, 1H), 8.06-7.86 (m, 2H), 7.31-7.20 (m, 1H), 7.12 (s, 1H), 7.03 (dd, J = 7.5, 2.7 Hz, 1H), 6.92-6.60 (m, 2H), 6.33-6.17 (m, 1H), 5.86-5.69 (m, 1H), 5.07 (s, 1H), 4.85 (s, 1H), 4.72 (s, 1H), 4.48 (s, J = 3.2 Hz, 1H), 2.21 (s, 3H). LCMS: Method F; Retention Time: 1.16 min. MS (ESI, m/z): 491 [M + H]$^+$ 246 ([M + 2H] / 2)$^+$, 267 ([M + H + acetonitrile] / 2)$^+$. |
| 22 | C | A | 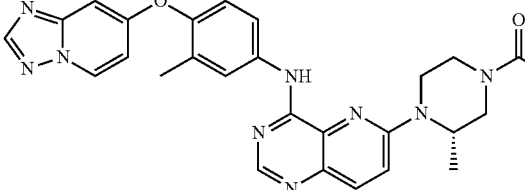<br>(S)-1-(4-(4-((4-([1,2,4]triazolo[1,5-a]pyridin-7-yloxy)-3-methylphenyl)amino)pyrido[3,2-d]pyrimidin-6-yl)-3-methylpiperazin-1-yl)prop-2-en-1-one | $^1$H NMR (300 MHz, DMSO-$d_6$) δ 9.35 (s, 1H), 8.94 (dd, J = 7.5, 0.6 Hz, 1H), 8.44 (s, 1H), 8.37 (s, 1H), 8.01-7.94 (m, 3H), 7.53 (d, J = 9.0 Hz, 1H), 7.21 (d, J = 9.0 Hz, 1H), 7.02 (dd, J = 7.5, 2.7 Hz, 1H), 6.90-6.85 (m 1H), 6.79-6.78 (m, 1H), 6.16 (d, J = 18.0 Hz, 1H), 5.76 (dd, J = 12.0, 2.4 Hz, 1H), 4.95-4.86 (m, 1H), 4.59-4.01 (m, 3H), 3.64-3.34 (m, 1H), 3.31-2.87 (m, 2H), 2.21 (s, 3H), 1.11 (d, J = 6.0 Hz, 3H). LCMS: Method B; Retention Time: 0.99 min. MS (ESI, m/z): 522 [M + H]$^+$ |
| 23 | C | A | 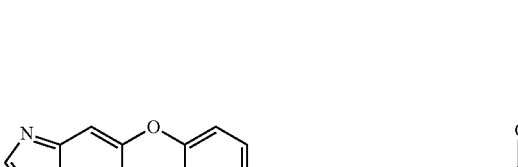<br>1-(6-(4-((4-([1,2,4]triazolo[1,5-a]pyridin-7-yloxy)-3-methylphenyl)amino)pyrido[3,2-d]pyrimidin-6-yl)-2,6-diazaspiro[3.3]heptan-2-yl)prop-2-en-1-one | $^1$H NMR (300 MHz, DMSO-$d_6$) δ 9.16 (s, 1H), 8.81 (d, J = 7.5 Hz, 1H), 8.35 (s, 1H), 8.26 (s, 1H), 7.92-7.77 (m, 3H), 7.11 (d, J = 9.0 Hz, 1H), 6.96 (d, J = 9.0 Hz, 1H), 6.92-6.89 (m, 1H), 6.67 (d, J = 3.0 Hz, 1H), 6.25-6.16 (m, 1H), 6.02-5.96 (m, 1H), 5.59-5.54 (m, 1H), 4.36 (s, 2H), 4.26 (s, 4H), 4.06 (s, 2H), 2.08 (s, 3H). LCMS: Method B; Retention Time: 0.93 min. MS (ESI, m/z): 520 [M + H]$^+$ 260 ([M + 2H] / 2)$^+$. |
| 24 | C | B | 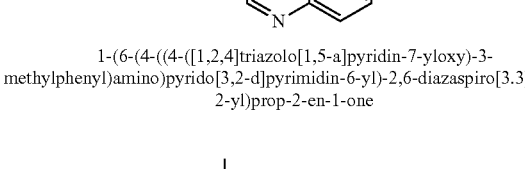<br>1-(4-(4-((4-([1,2,4]triazolo[1,5-a]pyridin-7-yloxy)-3-methylphenyl)amino)pyrido[3,2-d]pyrimidin-6-yl)piperazin-1-yl)-2-fluoroprop-2-en-1-one | $^1$H NMR (300 MHz, DMSO-d6) δ 9.37 (s, 1H), 8.92 (d, J = 7.5 Hz, 1H), 8.44 (s, 1H), 8.36 (s, 1H), 8.02-7.89 (m, 3H), 7.56 (d, J = 9.0 Hz, 1H), 7.21 (d, J = 9.0 Hz, 1H), 7.01 (dd, J = 7.5, 2.7 Hz, 1H), 6.76 (d, J = 3.0 Hz, 1H), 5.38-5.17 (d, J = 6.0 Hz, 2H), 3.92-3.89 (m, 4H), 3.71-3.69 (m, 4H), 2.18 (s, 3H). LCMS: Method B; Retention Time: 1.03 min. MS (ESI, m/z): 526 [M + H]$^+$ |

TABLE 10-continued

Compounds

| Example | Synthetic Method | Coupling Method | Compound Structure | Physical Data (¹H NMR and MS) |
|---|---|---|---|---|
| 25 | A | A | (E)-1-(4-(4-((4-([1,2,4]triazolo[1,5-a]pyridin-7-yloxy)-3-methylphenyl)amino)pyrido[3,2-d]pyrimidin-6-yl)-3,6-dihydropyridin-1(2H)-yl)-3-(1-methylpyrrolidin-2-yl)prop-2-en-1-one | $^1$H NMR (300 MHz, DMSO-$d_6$) δ 9.73 (s, 1H), 8.88-8.79 (m, 1H), 8.53 (s, 1H), 8.26 (s, 1H), 8.07 (s, 2H), 7.89-7.87 (m, 2H), 7.14 (d, J = 9.0 Hz, 1H), 7.02-6.88 (m, 2H), 6.69 (d, J = 3.0 Hz, 1H), 6.63-6.33 (m, 2H), 4.30-4.21 (m, 2H), 3.90-3.75 (m, 2H), 2.93-2.82 (m, 3H), 2.66-2.63 (m, 1H), 2.10-2.02 (m, 7H), 1.93-1.78 (m, 1H), 1.61-1.58 (m, 2H), 1.45-1.42 (m, 1H). LCMS: Method B; Retention Time: 0.99 min. MS (ESI, m/z): 588 [M + H]$^+$, 294 ([M + 2H] / 2)$^+$, 315 ([M + 2H + acetonitrile] / 2)$^+$. |
| 26 | A | A | 1-(4-(4-((4-([1,2,4]triazolo[1,5-a]pyridin-7-yloxy)-3-methylphenyl)amino)pyrido[3,2-d]pyrimidin-6-yl)-2-methyl-3,6-dihydropyridin-1(2H)-yl)prop-2-en-1-one | $^1$H NMR (300 MHz, DMSO-$d_6$) δ 9.72 (d, J = 6.0 Hz, 1H), 8.83 (d, J = 7.5 Hz, 1H), 8.53 (s, 1H), 8.27 (s, 1H), 8.14-8.00 (m, 2H), 8.02-7.95 (m, 2H), 7.14 (d, J = 9.0 Hz, 1H), 7.00-6.75 (m, 3H), 6.69 (d, J = 3.0 Hz, 1H), 6.06-6.01 (m, 1H), 5.63-5.89 (m, 1H), 5.25-4.10 (m, 3H), 3.11-2.61 (m, 2H), 2.10 (s, 3H), 1.35-0.96 (m, 3H). LCMS: Method B; Retention Time: 1.03 min. MS (ESI, m/z): 519 [M + H]$^+$ |
| 27 | A | A | 1-(3-{4-[(3-methyl-4-{[1,2,4]triazolo[1,5-a]pyridin-7-yloxy}phenyl)amino]pyrido[3,2-d]pyrimidin-6-yl}-5,6-dihydro-2H-pyridin-1-yl)prop-2-en-1-one trifluoroacetate | $^1$H NMR (400 MHz, DMSO-$d_6$) δ 11.01 (brs, 1H), 9.01-8.88 (m, 2H), 8.48-8.32 (m, 2H), 8.25 (d, J = 8.8 Hz, 1H), 7.89-7.75 (m, 2H), 7.31 (d, J = 17.6 Hz, 2H), 7.22-7.01 (m, 2H), 7.00-6.79 (m, 2H), 6.26-6.14 (m, 1H), 5.82-5.71 (m, 1H), 4.83 (d, J = 20.4 Hz, 2H), 3.83-3.72 (m, 2H), 2.50-2.46 (m, 1H), 2.26 (s, 3H). LCMS: Method D; Retention Time: 1.32 min. MS (ESI, m/z): 505 [M + H]$^+$ |
| 28 | B | A | 1-(4-(4-((4-([1,2,4]triazolo[1,5-a]pyridin-7-yloxy)-3-methylphenyl)amino)pyrido[3,2-d]pyrimidin-6-yl)-3-methylpiperidin-1-yl)prop-2-en-1-one | $^1$H NMR (300 MHz, DMSO-d6) δ 9.79 (s, 1H), 8.95 (d, J = 7.5 Hz, 1H), 8.67 (s, 1H), 8.39 (s, 1H), 8.18 (d, J = 8.4 Hz, 1H), 8.08-7.95 (m, 2H), 7.87 (d, J = 8.7 Hz, 1H), 7.25 (d, J = 8.7 Hz, 1H), 7.04 (dd, J = 7.5, 2.7 Hz, 1H), 6.95-6.83 (m, 1H), 6.80 (d, J = 2.7 Hz, 1H), 6.20-6.09 (m, 1H), 5.76-5.63 (m, 1H), 4.82-4.49 (m, 1H), 4.33-4.05 (m, 1H), 3.53-3.41 (m, 2H), 3.17-3.00 (m, 1H), 2.86-2.69 (m, 1H), 2.43-2.33 (m, 1H), 2.22 (s, 3H), 2.00-1.89 (m, 1H), 0.59 (d, J = 6.9 Hz, 3H). LCMS: Method D; Retention Time: 1.09 min. MS (ESI, m/z): 521 [M + H]$^+$ |

TABLE 10-continued

Compounds

| Example | Synthetic Method | Coupling Method | Compound Structure | Physical Data (¹H NMR and MS) |
|---|---|---|---|---|
| 29 | I | A | 1-(4-(4-((4-([1,2,4]triazolo[1,5-a]pyridin-7-yloxy)-3-methylphenyl)amino)-5-fluoroquinazolin-6-yl)piperazin-1-yl)prop-2-en-1-one | ¹H NMR (400 MHz, DMSO-d$_6$) δ 9.19 (d, J = 13.6 Hz, 1H), 8.94 (d, J = 1.6 Hz, 1H), 8.51 (s, 1H), 8.39 (s, 1H), 7.83-7.79 (m, 2H), 7.74 (t, J = 9.2 Hz, 1H), 7.63 (d, J = 9.2 Hz, 1H), 7.27-7.16 (m, 1H), 7.04 (dd, J = 7.6, 2.8 Hz, 1H), 6.90 (dd, J = 16.8, 10.4 Hz, 1H), 6.80 (d, J = 2.8 Hz, 1H), 6.18 (dd, J = 16.8, 2.4 Hz, 1H), 5.74 (dd, J = 10.4, 2.4 Hz, 1H), 3.83-3.72 (m, 4H), 3.21-3.16 (m, 4H), 2.20 (s, 3H). LCMS: Method H; Retention Time: 2.64 min. MS (ESI, m/z): 525 [M + H]⁺ |
| 30 | J | A | 1-(4-(4-((4-([1,2,4]triazolo[1,5-a]pyridin-7-yloxy)-3-methylphenyl)amino)-5-fluoroquinazolin-6-yl)-3,6-dihydropyridin-1(2H)-yl)prop-2-en-1-one | ¹H NMR (400 MHz, DMSO-d$_6$) δ 9.24 (d, J = 13.6 Hz, 1H), 8.94 (d, J = 7.6 Hz, 1H), 8.59 (s, 1H), 8.38 (s, 1H), 7.84 (d, J = 8.6 Hz, 1H), 7.76 (dd, J = 11.2, 2.4 Hz, 2H), 7.63 (d, J = 8.8 Hz, 1H), 7.21 (d, J = 8.8 Hz, 1H), 7.03 (dd, J = 7.6, 2.6 Hz, 1H), 6.18 (d, J = 16.4 Hz, 2H), 5.74 (dd, J = 10.4, 2.4 Hz, 1H), 4.30 (d, J = 38.6 Hz, 2H), 3.87-3.76 (m, 2H), 3.32 (s, 2H), 2.60 (d, J = 20.0 Hz, 2H), 2.19 (s, 3H). LCMS: Method G; Retention Time: 3.26 min. MS (ESI, m/z): 522 [M + H]⁺ |
| 31 | A | B | 1-(4-(4-((4-([1,2,4]triazolo[1,5-a]pyridin-7-yloxy)-3-methylphenyl)amino)pyrido[3,2-d]pyrimidin-6-yl)-3,6-dihydropyridin-1(2H)-yl)-2-fluoroprop-2-en-1-one | ¹H NMR (300 MHz, DMSO-d6) δ 9.86 (brs, 1H), 8.95 (s, 1H), 8.65 (s, 1H), 8.39 (s, 1H), 8.19 (s, 2H), 8.04-7.97 (m, 2H), 7.30-7.21 (m, 1H), 7.13-7.01 (m, 2H), 6.81 (d, J = 2.7 Hz, 1H), 5.44-5.16 (m, 2H), 4.33-4.30 (m, 2H), 3.82 (t, J = 5.7 Hz, 2H), 3.11-2.98 (m, 2H), 2.22 (s, 3H). LCMS: Method C; Retention Time: 0.90 min MS (ESI, m/z): 523 [M + H]⁺ |
| 32 | K | A | (R)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazin-1-yl)prop-2-en-1-one | ¹H NMR (400 MHz, DMSO-d6) δ 9.64 (s, 1H), 9.16 (s, 1H), 8.98 (d, J = 7.6 Hz, 1H), 8.42 (d, J = 4.3 Hz, 2H), 7.95-7.83 (m, 1H), 7.16 (d, J = 8.1 Hz, 1H), 7.10-7.05 (m, 1H), 6.97-6.93 (m, 1H), 6.92-6.83 (m, 1H), 6.21-6.11 (m, 1H), 5.79-5.69 (m, 1H), 4.96-4.46 (m, 4H), 3.67-3.61 (m, 2H), 3.20-3.15 (m, 1H), 2.18 (s, 3H), 1.21-1.13 (m, 3H). LCMS: Method H; Retention Time: 1.31 min MS (ESI, m/z): 541 [M + H]⁺ |

TABLE 10-continued

Compounds

| Example | Synthetic Method | Coupling Method | Compound Structure | Physical Data (¹H NMR and MS) |
|---|---|---|---|---|
| 33 | E | A | 1-(3-(4-((4-([1,2,4]triazolo[1,5-a]pyridin-7-yloxy)-3-methylphenyl)amino)pyrido[3,2-d]pyrimidin-6-yl)azetidin-1-yl)prop-2-en-1-one | $^1$H NMR (400 MHz, DMSO-$d_6$) δ 9.96 (brs, 1H), 8.95 (d, J = 7.6 Hz, 1H), 8.68 (s, 1H), 8.39 (s, 1H), 8.22 (d, J = 8.8 Hz, 1H), 8.00-7.88 (m, 3H), 7.26 (d, J = 8.4 Hz, 1H), 7.04 (dd, J = 7.6, 2.8 Hz, 1H), 6.80 (d, J = 2.8 Hz, 1H), 6.47-6.38 (m, 1H), 6.16 (dd, J = 16.0, 2.8 Hz, 1H), 5.71 (dd, J = 10.8, 2.4 Hz, 1H), 4.76-4.64 (m, 2H), 4.47-4.28 (m, 3H), 2.22 (s, 3H). MS (ESI, m/z): 479 (M + H)⁺. LCMS: Method B; Retention Time: 0.86 min MS (ESI, m/z): 479 [M + H]⁺ |
| 34 | K | A | (R)-1-(4-(8-((4-([1,2,4]triazolo[1,5-a]pyridin-7-yloxy)-2-fluoro-5-methylphenyl)amino)pyrimido[5,4-d]pyrimidin-2-yl)-3-methylpiperazin-1-yl)prop-2-en-1-one | $^1$H NMR (400 MHz, DMSO) δ 9.69 (s, 1H), 9.19 (d, J = 8.3 Hz, 1H), 9.02 (d, J = 7.5 Hz, 1H), 8.45 (d, J = 4.6 Hz, 2H), 7.92 (d, J = 8.1 Hz, 1H), 7.38 (d, J = 10.8 Hz, 1H), 7.10 (dd, J = 7.5, 2.5 Hz, 1H), 7.03-6.87 (m, 2H), 6.24 (d, J = 16.5 Hz, 1H), 5.79 (dd, J = 10.5, 2.1 Hz, 1H), 5.37-5.06 (m, 1H), 4.94-4.72 (m, 1H), 4.45 (dd, J = 50.1, 13.0 Hz, 1H), 4.28-4.02 (m, 1H), 3.68-3.40 (m, 1H), 3.31-2.92 (m, 2H), 2.24 (s, 3H), 1.20 (d, J = 4.8 Hz, 3H). LCMS: Method H; Retention Time: 2.92 min MS (ESI, m/z): 541 [M + H]⁺ |
| 35 | K | A | (S)-1-(4-(8-((4-([1,2,4]triazolo[1,5-a]pyridin-7-yloxy)-2-fluoro-5-methylphenyl)amino)pyrimido[5,4-d]pyrimidin-2-yl)-3-methylpiperazin-1-yl)prop-2-en-1-one | $^1$H NMR (400 MHz, DMSO) δ 9.66 (s, 1H), 9.17 (s, 1H), 8.98 (d, J = 7.5 Hz, 1H), 8.42 (d, J = 4.8 Hz, 2H), 7.88 (d, J = 9.1 Hz, 1H), 7.34 (d, J = 10.7 Hz, 1H), 7.07 (dd, J = 7.5, 2.5 Hz, 1H), 6.98-6.85 (m, 2H), 6.25-6.14 (m, 1H), 5.80-5.71 (m, 1H), 5.25-5.02 (m, 1H), 4.89-4.68 (m, 1H), 4.42 (dd, J = 49.7, 12.8 Hz, 1H), 4.27-3.99 (m, 1H), 3.58-3.41 (m, 1H), 3.22-2.84 (m, 2H), 2.21 (s, 3H), 1.16 (s, 3H). LCMS: Method H; Retention Time: 2.97 min MS (ESI, m/z): 541 [M + H]⁺ |
| 36 | K | A | (S)-1-(4-(8-((4-([1,2,4]triazolo[1,5-a]pyridin-7-yloxy)-2-fluoro-5-methylphenyl)amino)pyrimido[5,4-d]pyrimidin-2-yl)-2-methylpiperazin-1-yl)prop-2-en-1-one | $^1$H NMR (400 MHz, DMSO) δ 9.68 (s, 1H), 9.15 (s, 1H), 8.98 (d, J = 7.5 Hz, 1H), 8.41 (d, J = 10.6 Hz, 2H), 7.86 (d, J = 8.5 Hz, 1H), 7.34 (d, J = 10.7 Hz, 1H), 7.06 (dd, J = 7.5, 2.6 Hz, 1H), 6.93 (d, J = 2.5 Hz, 1H), 6.88 (dd, J = 16.6, 10.5 Hz, 1H), 6.21-6.11 (m, 1H), 5.77-5.70 (m, 1H), 5.00-4.72 (m, 2H), 4.70-3.87 (m, 2H), 3.44-3.38 (m, 1H), 3.27-2.92 (m, 2H), 2.20 (s, 3H), 1.17 (m, 3H). LCMS: Method H; Retention Time: 1.31 min MS (ESI, m/z): 541 [M + H]⁺ |

TABLE 10-continued

| Example | Synthetic Method | Coupling Method | Compound Structure | Physical Data (¹H NMR and MS) |
|---|---|---|---|---|
| 37 | F | A | 1-(4-(8-((4-([1,2,4]triazolo[1,5-a]pyridin-7-yloxy)-2-fluoro-3-methylphenyl)amino)pyrimido[5,4-d]pyrimidin-2-yl)-3,6-dihydropyridin-1(2H)-yl)prop-2-en-1-one | ¹H NMR (400 MHz, DMSO) δ 10.07 (d, J = 13.0 Hz, 1H), 9.47 (s, 1H), 8.98 (d, J = 7.5 Hz, 1H), 8.69 (s, 1H), 8.41 (s, 1H), 7.90-7.78 (m, 1H), 7.49 (d, J = 19.3 Hz, 1H), 7.16 (d, J = 8.8 Hz, 1H), 7.07 (dd, J = 7.5, 2.6 Hz, 1H), 7.00-6.81 (m, 2H), 6.16 (d, J = 16.7 Hz, 1H), 5.73 (dd, J = 10.5, 2.3 Hz, 1H), 4.39 (d, J = 24.8 Hz, 2H), 3.89-3.79 (m, 2H), 2.87 (d, J = 17.0 Hz, 2H), 2.18 (d, J = 1.5 Hz, 3H). LCMS: Method H; Retention Time: 2.63 min MS (ESI, m/z): 524 [M + H]⁺ |
| 38 | F | A | 1-(4-(8-((4-([1,2,4]triazolo[1,5-a]pyridin-7-yloxy)-2-fluoro-5-methylphenyl)amino)pyrimido[5,4-d]pyrimidin-2-yl)-3,6-dihydropyridin-1(2H)-yl)prop-2-en-1-one | ¹H NMR (400 MHz, DMSO) δ 10.11 (s, 1H), 9.46 (s, 1H), 8.98 (d, J = 7.5 Hz, 1H), 8.68 (s, 1H), 8.43 (s, 1H), 7.85 (t, J = 10.3 Hz, 1H), 7.50 (d, J = 19.6 Hz, 1H), 7.36 (d, J = 10.7 Hz, 1H), 7.07 (dd, J = 7.4, 2.5 Hz, 1H), 6.99-6.82 (m, 2H), 6.18 (d, J = 16.6 Hz, 1H), 5.74 (dd, J = 10.5, 2.1 Hz, 1H), 4.43 (d, J = 42.0 Hz, 2H), 3.89-3.81 (m, 2H), 2.93-2.83 (m, 2H), 2.21 (s, 3H). LCMS: Method H; Retention Time: 2.81 min MS (ESI, m/z): 524 [M + H]⁺ |
| 39 | K | A | (R)-1-(4-(8-((4-([1,2,4]triazolo[1,5-a]pyridin-7-yloxy)-2-fluoro-3-(trifluoromethyl)phenyl)amino)pyrimido[5,4-d]pyrimidin-2-yl)-2-methylpiperazin-1-yl)prop-2-en-1-one | ¹H NMR (400 MHz, DMSO) δ 9.76 (s, 1H), 9.17 (s, 1H), 9.02 (d, J = 7.5 Hz, 1H), 8.47 (s, 1H), 8.42 (s, 1H), 8.27 (t, J = 8.6 Hz, 1H), 7.37 (d, J = 9.1 Hz, 1H), 7.30 (d, J = 2.5 Hz, 1H), 7.13 (dd, J = 7.5, 2.7 Hz, 1H), 6.87 (dd, J = 16.5, 10.3 Hz, 1H), 6.21-6.13 (m, 1H), 5.76-5.70 (m, 1H), 4.90-4.15 (m, 4H), 3.44-3.35 (m, 2H), 3.22-3.14 (m, 1H), 1.20-1.11 (m, 3H) LCMS: Method H; Retention Time: XX min MS (ESI, m/z): 595 [M + H]⁺ |
| 40 | K | A | 1-(4-{8-[(2-fluoro-3-methyl-4-{[1,2,4]triazolo[1,5-a]pyridin-7-yloxy}phenyl)amino]-[1,3]diazino[5,4-d]pyrimidin-2-yl}-2,3-dimethylpiperazin-1-yl)prop-2-en-1-one Relative stereochemistry | ¹H NMR (400 MHz, DMSO-d6) δ 9.50 (s, 1H), 9.15 (s, 1H), 8.98 (d, J = 7.6 Hz, 1H), 8.42 (d, J = 2.4 Hz, 2H), 8.03-7.94 (m, 1H), 7.15 (d, J = 8.8 Hz, 1H), 7.07 (dd, J = 7.6, 2.8 Hz, 1H), 6.93 (d, J = 2.8 Hz, 1H), 6.85-6.75 (m, 1H), 6.12 (dd, J = 16.8, 2.4 Hz, 1H), 5.68 (dd, J = 10.4, 2.4 Hz, 1H), 5.06-4.96 (m, 1H), 4.61-4.49 (m, 2H), 4.06-3.98 (m, 1H), 3.66-3.56 (m, 2H), 2.17 (d, J = 2.0 Hz, 3H), 1.37-1.32 (m, 6H) LCMS: Method 1; Retention Time: 1.15 min MS (ESI, m/z): 555 [M + H]⁺ |

TABLE 10-continued

Compounds

| Example | Synthetic Method | Coupling Method | Compound Structure | Physical Data (¹H NMR and MS) |
|---|---|---|---|---|
| 41 | K | A | 1-((1S,4S)-5-(8-((4-([1,2,4]triazolo[1,5-a]pyridin-7-yloxy)-2-fluoro-3-methylphenyl)amino)pyrimido[5,4-d]pyrimidin-2-yl)-2,5diazabicyclo[2.2.2]octan-2-yl)prop-2-en-1-one | ¹H NMR (400 MHz, DMSO-d$_6$) δ 9.69-9.27 (m, 1H), 9.19-9.09 (m, 1H), 9.03-8.92 (m, 1H), 8.46-8.35 (m, 2H), 8.18-7.79 (m, 1H), 7.17-7.04 (m, 2H), 6.95-6.91 (m, 1H), 6.90-6.55 (m, 1H), 6.25-6.12 (m, 1H), 5.76-5.66 (m, 1H), 5.43-5.11 (m, 1H), 4.86-4.54 (m, 1H), 3.90-3.77 (m, 3H), 3.69-3.60 (m, 1H), 2.17 (s, 3H), 2.02-1.81 (m, 4H) LCMS: Method A; Retention Time: 1.01 min MS (ESI, m/z): 553 [M + H]$^+$ |
| 42 | F | A | (S)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-methyl-3,6-dihydropyridin-1(2H)-yl)prop-2-en-1-one | 1H NMR (300 MHz, DMSO-d6) δ 10.00 (brs, 1H), 9.44 (s, 1H), 8.99 (d, J = 7.5 Hz, 1H), 8.69 (s, 1H), 8.43 (s, 1H), 7.93-7.84 (m, 1H), 7.56-7.46 (m, 1H), 7.16 (dd, J = 1.5, 9.0 Hz, 1H), 7.09 (dd, J = 2.7, 7.5 Hz, 1H), 7.18-6.85 (m, 2H), 6.18 (dd, J = 2.1, 16.5 Hz, 1H), 5.74 (dd, J = 2.4, 10.5 Hz, 1H), 5.17-4.69 (m, 2H), 4.22-3.81 (m, 1H), 3.13 (d, J = 17.7 Hz, 1H), 2.80-2.64 (m, 1H), 2.19 (d, J = 2.1 Hz, 3H), 1.26-1.10 (m, 3H). LCMS: Method A; Retention Time: 1.04 min MS (ESI, m/z): 538 [M + H]$^+$ |
| 43 | K | A | (S)-1-(4-(8-((4-([1,2,4]triazolo[1,5-a]pyridin-7-yloxy)-2-fluoro-3-methylphenyl)amino)pyrimido[5,4-d]pyrimidin-2-yl)-3-methylpiperazin-1-yl)prop-2-en-1-one | ¹H NMR (300 MHz, DMSO-d$_6$) δ 9.58 (s, 1H), 9.17 (s, 1H), 8.98 (d, J = 7.5, 1H), 8.42 (s, 2H), 7.99-7.84 (m, 1H), 7.15 (dd, J = 9.0, 1.5 Hz, 1H), 7.08 (dd, J = 7.5, 2.7 Hz, 1H), 7.01-6.83 (m, 2H), 6.21 (d, J = 16.5 Hz, 1H), 5.76 (dd, J = 10.5, 2.4 Hz, 1H), 5.23-5.03 (m, 1H), 4.86-4.62 (m, 1H), 4.55-4.30 (m, 1H), 4.25-4.02 (m, 1H), 3.60-2.89 (m, 3H), 2.17 (d, J = 2.1 Hz, 3H), 1.17 (d, J = 6.6 Hz, 3H) LCMS: Method J; Retention Time: 1.05 min MS (ESI, m/z): 541 [M + H]$^+$ |
| 44 | K | A | 1-[(2R,5R)-4-{8-[(2-fluoro-3-methyl-4-{[1,2,4]triazolo[1,5-a]pyridin-7-yloxy}phenyl)amino]pyrimido[5,4-d][1,3]diazin-2-yl}-2,5-dimethylpiperazin-1-yl]prop-2-en-1-one | ¹H NMR (400 MHz, DMSO-d6) δ 9.49 (s, 1H), 9.12 (s, 1H), 8.98 (d, J = 7.2 Hz, 1H), 8.40 (d, J = 6.4 Hz, 2H), 7.97 (s, 1H), 7.21-7.12 (m, 1H), 7.07 (dd, J = 7.6, 2.8 Hz, 1H), 6.93 (d, J = 2.4 Hz, 1H), 6.81 (s, 1H), 6.12 (d, J = 16.4 Hz, 1H), 5.67 (dd, J = 10.4, 2.4 Hz, 1H), 4.99 (s, 1H), 4.60-4.16 (m, 3H), 3.24 (d, J = 12.4 Hz, 2H), 2.17 (d, J = 2.0 Hz, 3H), 1.26 (d, J = 6.0 Hz, 3H), 1.21 (s, 3H) LCMS: Method J; Retention Time: 1.08 min MS (ESI, m/z): 555 [M + H]$^+$ |

TABLE 10-continued

Compounds

| Example | Synthetic Method | Coupling Method | Compound Structure | Physical Data (¹H NMR and MS) |
|---|---|---|---|---|
| 45 | K | A | 1-(1R,4R)-5-(8-((4-([1,2,4]triazolo[1,5-a]pyridin-7-yloxy)-2-fluoro-3-methylphenyl)amino)pyrimido[5,4-d]pyrimidin-2-yl)-2,5diazabicyclo[2.2.2]octan-2-yl)prop-2-en-1-one | ¹H NMR (400 MHz, DMSO-d6) δ 9.70-9.32 (m, 1H), 9.18-9.12 (m, 1H), 8.98 (d, J = 7.6 Hz, 1H), 8.50-8.36 (m, 2H), 8.21-7.78 (m, 1H), 7.15 (d, J = 8.8 Hz, 1H), 7.07 (dd, J = 7.6, 2.8 Hz, 1H), 6.94 (d, J = 2.4 Hz, 1H), 6.91-6.56 (m, 1H), 6.25-6.11 (m, 1H), 5.78-5.66 (m, 1H), 5.43-5.10 (m, 1H), 4.87-4.54 (m, 1H), 4.01-3.71 (m, 3H), 3.69-3.60 (m, 1H), 2.17 (s, 3H), 2.10-1.78 (m, 4H). LCMS: Method A; Retention Time: 1.04 min MS (ESI, m/z): 553 [M + H]⁺ |
| 46 | K | A | 1-((3aR,6aS)-5-(8-((4-([1,2,4]triazolo[1,5-a]pyridin-7-yloxy)-2-fluoro-3-methylphenyl)amino)pyrimido[5,4-d]pyrimidin-2-yl)hexahydropyrrolo[3,4-c]pyrrol-2(1H)-yl)prop-2-en-1-one | ¹H NMR (300 MHz, DMSO-d₆) δ 9.21 (s, 1H), 9.01 (s, 1H), 8.85 (d, J = 7.2 Hz, 1H), 8.30 (d, J = 6.9 Hz, 2H), 8.03 (s, 1H), 7.11-6.87 (m, 2H), 6.81 (d, J = 2.4 Hz, 1H), 6.51-6.42 (m, 1H), 6.01 (d, J = 16.8 Hz, 1H), 5.63-5.45 (m, 1H), 3.80-3.74 (m, 3H), 3.63-3.56 (m, 1H), 3.53-3.40 (m, 3H), 3.33-3.28 (m, 1H), 3.05-2.96 (m, 2H), 2.04 (s, 3H). LCMS: Method J; Retention Time: 0.97 min MS (ESI, m/z): 553 [M + H]⁺ |
| 47 | K | A | 1-(2-(8-((4-([1,2,4]triazolo[1,5-a]pyridin-7-yloxy)-2-fluoro-3-methylphenyl)amino)pyrimido[5,4-d]pyrimidin-2-yl)-2,6-diazaspiro[3.4]octan-6-yl)prop-2-en-1-one | ¹H NMR (400 MHz, DMSO-d₆) δ 9.31 (d, J = 8.8 Hz, 1H), 9.15 (d, J = 2.4 Hz, 1H), 8.98 (d, J = 7.6 Hz, 1H), 8.50-8.39 (m, 2H), 8.24-8.14 (m, 1H), 7.15 (d, J = 8.8 Hz, 1H), 7.12-7.05 (m, 1H), 6.94 (s, 1H), 6.66-6.51 (m, 1H), 6.16 (d, J = 16.8 Hz, 1H), 5.69 (d, J = 10.4 Hz, 1H), 4.25-4.14 (m, 4H), 3.90-3.84 (m, 1H), 3.72-3.63 (m, 2H), 3.50-3.46 (m, 1H), 2.30-2.23 (m, 1H), 2.20-2.12 (m, 4H) LCMS: Method J; Retention Time: 0.96 min MS (ESI, m/z): 553 [M + H]⁺ |
| 48 | K | A | 1-(7-(8-((4-([1,2,4]triazolo[1,5-a]pyridin-7-yloxy)-2-fluoro-3-methylphenyl)amino)pyrimido[5,4-d]pyrimidin-2-yl)-2,7-diazaspiro[4.4]nonan-2-yl)prop-2-en-1-one | ¹H NMR (300 MHz, DMSO-d₆) δ 9.33 (d, J = 14.4 Hz, 1H), 9.12 (s, 1H), 8.97 (d, J = 7.5 Hz, 1H), 8.41 (s, 2H), 8.20-8.02 (m, 1H), 7.14 (d, J = 8.7 Hz, 1H), 7.10-7.02 (m, 1H), 6.93 (d, J = 2.7 Hz, 1H), 6.68-6.53 (m, 1H), 6.21-6.10 (m, 1H), 5.73-5.61 (m, 1H), 3.84-3.60 (m, 6H), 3.56-3.48 (m, 2H), 2.16 (d, J = 2.1 Hz, 3H), 2.11-1.90 (m, 4H). LCMS: Method J; Retention Time: 1.01 min MS (ESI, m/z): 567 [M + H]⁺ |

TABLE 10-continued

| Example | Synthetic Method | Coupling Method | Compound Structure | Physical Data (¹H NMR and MS) |
|---|---|---|---|---|
| 49 | K | A | (S)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazin-1-yl)prop-2-en-1-one | ¹H NMR (400 MHz, DMSO) δ 9.63 (s, 1H), 9.16 (s, 1H), 8.98 (d, J = 7.5 Hz, 1H), 8.42 (d, J = 4.2 Hz, 2H), 7.88 (t, J = 8.8 Hz, 1H), 7.16 (d, J = 8.5 Hz, 1H), 7.10-7.06 (m, 1H), 6.94 (d, J = 2.5 Hz, 1H), 6.92-6.84 (m, 1H), 6.20-6.13 (m, 1H), 5.76-5.71 (m, 1H), 4.94-4.43 (m, 4H), 3.51-3.48 (m, 2H), 3.22-3.16 (m, 1H), 2.18 (s, 3H), 1.21-1.13 (m, 3H). LCMS: Method H; Retention Time: 2.39 min MS (ESI, m/z): 541 [M + H]⁺ |
| 50 | K | A | (R)-1-(4-(8-((4-([1,2,4]triazolo[1,5-a]pyridin-7-yloxy)-2-fluoro-5-methylphenyl)amino)pyrimido[5,4-d]pyrimidin-2-yl)-2-methylpiperazin-1-yl)prop-2-en-1-one | ¹H NMR (400 MHz, DMSO) δ 9.66 (s, 1H), 9.14 (s, 1H), 8.97 (d, J = 7.4 Hz, 1H), 8.40 (d, J = 8.8 Hz, 2H), 7.86 (d, J = 8.7 Hz, 1H), 7.33 (d, J = 10.7 Hz, 1H), 7.05 (dd, J = 7.5, 2.6 Hz, 1H), 6.93 (d, J = 2.5 Hz, 1H), 6.87 (dd, J = 16.7, 10.5 Hz, 1H), 6.15 (dd, J = 16.6, 2.0 Hz, 1H), 5.72 (dd, J = 10.4, 2.2 Hz, 1H), 4.77 (s, 2H), 4.71-3.98 (m, 2H), 3.37 (d, J = 12.4 Hz, 1H), 3.17 (s, 2H), 2.20 (s, 3H), 1.16 (s, 3H). LCMS: Method H; Retention Time: 2.75 min MS (ESI, m/z): 541 [M + H]⁺ |
| 51 | K | A | (R)-1-(4-(8-((2-fluoro-5-methyl-4-((5-methyl-[1,2,4]triazolo[1,5-a]pyridin-7-yl)oxy)phenyl)amino)pyrimido[5,4-d]pyrimidin-2-yl)-2-methylpiperazin-1-yl)prop-2-en-1-one | ¹H NMR (400 MHz, DMSO) δ 9.66 (s, 1H), 9.14 (s, 1H), 8.41 (d, J = 9.8 Hz, 2H), 7.86 (d, J = 8.6 Hz, 1H), 7.30 (d, J = 10.7 Hz, 1H), 7.02 (s, 1H), 6.93-6.76 (m, 2H), 6.16 (d, J = 16.3 Hz, 1H), 5.73 (d, J = 12.6 Hz, 1H), 4.90-3.53 (m, 6H), 3.23-3.08 (m, 1H), 2.74 (s, 3H), 2.20 (s, 3H), 1.26-1.08 (m, 3H). LCMS: Method H; Retention Time: 2.70 min MS (ESI, m/z): 555 [M + H]⁺ |
| 52 | J | A | (R)-1-(4-(4-((4-([1,2,4]triazolo[1,5-a]pyridin-7-yloxy)-2-fluoro-3-methylphenyl)amino)-5-fluoropyrido[3,4-d]pyrimidin-6-yl)-2-methylpiperazin-1-yl)prop-2-en-1-one | ¹H NMR (400 MHz, DMSO-d6) δ 9.28 (s, 1H), 8.99 (d, J = 7.6 Hz, 1H), 8.81 (s, 1H), 8.49 (s, 1H), 8.43 (s, 1H), 7.80 (s, 1H), 7.17-7.05 (m, 2H), 6.95 (d, J = 2.8 Hz, 1H), 6.92-6.81 (m, 1H), 6.17 (d, J = 17.2 Hz, 1H), 5.78-5.69 (m, 1H), 4.77-4.38 (m, 2H), 4.02-3.99 (m, 1H), 3.88-3.84 (m, 1H), 3.62-3.44 (m, 1H), 3.21-3.19 (m, 1H), 3.07-2.96 (m, 1H), 2.16 (s, 3H), 1.33-1.25 (m, 3H). LCMS: Method D; Retention Time: 1.18 min MS (ESI, m/z): 558 [M + H]⁺ |

TABLE 10-continued

Compounds

| Example | Synthetic Method | Coupling Method | Compound Structure | Physical Data (¹H NMR and MS) |
|---|---|---|---|---|
| 53 | I | A | (R)-1-(4-(4-((4-([1,2,4]triazolo[1,5-a]pyridin-7-yloxy)-2-fluoro-3-methylphenyl)amino)-5-fluoroquinazolin-6-yl)2-methylpiperazin-1-yl)prop-2-en-1-one | ¹H NMR (400 MHz, DMSO-d₆) δ 9.14 (d, J = 10.2 Hz, 1H), 8.98 (d, J = 7.5 Hz, 1H), 8.47 (s, 1H), 8.42 (s, 1H), 7.86 (t, J = 8.7 Hz, 1H), 7.73 (t, J = 9.1 Hz, 1H), 7.64 (d, J = 9.1 Hz, 1H), 7.12 (d, J = 8.8 Hz, 1H), 7.08 (dd, J = 7.4, 2.4 Hz, 1H), 6.94 (d, J = 2.3 Hz, 1H), 6.86 (dd, J = 16.4, 10.5 Hz, 1H), 6.17 (d, J = 16.7 Hz, 1H), 5.73 (d, J = 10.4 Hz, 1H), 4.87-4.05 (m, 2H), 3.49-3.43 (m, 3H), 3.09-2.86 (m, 2H), 2.16 (s, 3H), 1.39 (s, 3H). LCMS: Method H; Retention Time: 1.10 min MS (ESI, m/z): 557 [M + H]⁺ |
| 54 | F | A | (S)-1-(4-(8-((4-([1,2,4]triazolo[1,5-a]pyridin-7-yloxy)-2-fluoro-3-methylphenyl)amino)pyrimido[5,4-d]pyrimidin-2-yl)-6-methyl-3,6-dihydropyridin-1(2H)-yl)prop-2-en-1-one | ¹H NMR (300 MHz, DMSO-d6) δ 10.00 (br.s, 1H), 9.45 (s, 1H), 8.99 (dd, J = 0.6, 7.5 Hz, 1H), 8.69 (s, 1H), 8.42 (s, 1H), 7.92-7.82 (m, 1H), 7.45 (s, 1H), 7.17 (dd, J = 1.5, 8.7 Hz, 1H), 7.08 (dd, J = 2.7, 7.5 Hz, 1H), 6.97-6.83 (m, 2H), 6.24-6.14 (m, 1H), 5.74 (d, J = 10.2 Hz, 1H), 5.14-4.94 (m, 1H), 4.72-4.25 (m, 1H), 3.39-2.87 (m, 1H, overlapped with H2O), 3.17-3.11 (m, 1H), 2.61-2.40 (m, 1H, overlapped with DMSO), 2.19 (s, 3H), 1.39-1.31 (m, 3H). LCMS: Method A; Retention Time: 1.065 min MS (ESI, m/z): 538 [M + H]⁺ |
| 55 | F | A | (R)-1-(4-(8-((4-([1,2,4]triazolo[1,5-a]pyridin-7-yloxy)-2-fluoro-3-methylphenyl)amino)pyrimido[5,4-d]pyrimidin-2-yl)-6-methyl-3,6-dihydropyridin-1(2H)-yl)prop-2-en-1-one | ¹H NMR (300 MHz, DMSO-d6) δ 10.00 (br.s, 1H), 9.45 (s, 1H), 8.99 (dd, J = 0.6, 7.5 Hz, 1H), 8.69 (s, 1H), 8.42 (s, 1H), 7.92-7.82 (m, 1H), 7.45 (s, 1H), 7.17 (dd, J = 1.5, 8.7 Hz, 1H), 7.08 (dd, J = 2.7, 7.5 Hz, 1H), 6.97-6.83 (m, 2H), 6.24-6.14 (m, 1H), 5.74 (d, J = 10.2 Hz, 1H), 5.14-4.94 (m, 1H), 4.72-4.25 (m, 1H), 3.39-2.87 (m, 1H, overlapped with H2O), 3.17-3.11 (m, 1H), 2.61-2.40 (m, 1H, overlapped with DMSO), 2.19 (s, 3H), 1.39-1.31 (m, 3H). LCMS: Method A; Retention Time: 1.065 min MS (ESI, m/z): 538 [M + H]⁺ |
| 56 | F | A | 1-(4-(8-((4-([1,2,4]triazolo[1,5-a]pyridin-7-yloxy)-2-fluoro-3-methylphenyl)amino)pyrimido[5,4-d]pyrimidin-2-yl)-2,3,6,7-tetrahydro-1H-azepin-1-yl)prop-2-en-1-one | ¹H NMR (400 MHz, DMSO) δ 10.10 (d, J = 14.9 Hz, 1H), 9.42 (s, 1H), 8.99 (d, J = 7.5 Hz, 1H), 8.66 (s, 1H), 8.42 (s, 1H), 7.80-7.66 (m, 2H), 7.16 (d, J = 8.8 Hz, 1H), 7.08 (d, J = 7.5 Hz, 1H), 6.96 (s, 1H), 6.90-6.82 (m, 1H), 6.15 (d, J = 16.5 Hz, 1H), 5.70 (d, J = 12.2 Hz, 1H), 3.85-3.73 (m, 4H), 3.28 (d, J = 3.8 Hz, 2H), 2.67 (d, J = 5.3 Hz, 2H), 2.18 (s, 3H). LCMS: Method J; Retention Time: 1.08 min MS (ESI, m/z): 538 [M + H]⁺ |

TABLE 10-continued

Compounds

| Example | Synthetic Method | Coupling Method | Compound Structure | Physical Data (¹H NMR and MS) |
|---|---|---|---|---|
| 57 | F | A | 1-(5-(8-((4-([1,2,4]triazolo[1,5-a]pyridin-7-yloxy)-2-fluoro-3-methylphenyl)amino)pyrimido[5,4-d]pyrimidin-2-yl)-2,3,4,7-tetrahydro-1H-azepin-1-yl)prop-2-en-1-one | ¹H NMR (400 MHz, DMSO) δ 10.08 (d, J = 11.9 Hz, 1H), 9.42 (s, 1H), 8.98 (d, J = 7.5 Hz, 1H), 8.67 (s, 1H), 8.42 (s, 1H), 7.80 (t, J = 8.6 Hz, 1H), 7.66 (s, 1H), 7.16 (d, J = 8.4 Hz, 1H), 7.08 (dd, J = 7.5, 2.3 Hz, 1H), 6.96 (d, J = 2.4 Hz, 1H), 6.84 (dd, J = 16.6, 10.4 Hz, 1H), 6.13 (d, J = 14.9 Hz, 1H), 5.69 (d, J = 10.5 Hz, 1H), 4.41 (dd, J = 25.0, 5.1 Hz, 2H), 3.93-3.69 (m, 2H), 3.14-3.00 (m, 2H), 2.18 (s, 3H), 2.01-1.91 (m, 2H). LCMS: Method J; Retention Time: 1.07 min MS (ESI, m/z): 538 [M + H]⁺ |
| 58 | F | A | (S)-1-(4-(8-((4-([1,2,4]triazolo[1,5-a]pyridin-7-yloxy)-2-fluoro-5-methylphenyl)amino)pyrimido[5,4-d]pyrimidin-2-yl)-6-methyl-3,6-dihydropyridin-1(2H)-yl)prop-2-en-1-one | ¹H NMR (400 MHz, DMSO-d6) δ 10.14 (s, 1H), 9.47 (s, 1H), 8.99 (d, J = 7.4 Hz, 1H), 8.68 (s, 1H), 8.43 (s, 1H), 7.89-7.79 (m, 1H), 7.62-7.48 (m, 1H), 7.37 (d, J = 10.7 Hz, 1H), 7.08 (dd, J = 7.5, 2.7 Hz, 1H), 6.96 (d, J = 2.6 Hz, 1H), 6.95-6.74 (m, 1H), 6.17 (d, J = 16.7 Hz, 1H), 5.73 (d, J = 11.1 Hz, 1H), 5.22-4.62 (m, 2H), 4.29-3.72 (m, 1H), 3.17 (d, J = 17.5 Hz, 1H), 2.86-2.65 (m, 1H), 2.22 (s, 3H), 1.15 (d, J = 13.2 Hz, 3H). LCMS: Method J; Retention Time: 0.94 min MS (ESI, m/z): 538 [M + H]⁺ |
| 59 | F | A | (S)-1-(4-(8-((4-([1,2,4]triazolo[1,5-a]pyridin-7-yloxy)-2-fluoro-5-methylphenyl)amino)pyrimido[5,4-d]pyrimidin-2-yl)-2-methyl-3,6-dihydropyridin-1(2H)-yl)prop-2-en-1-one | ¹H NMR (400 MHz, DMSO-d6) δ 10.12 (s, 1H), 9.46 (s, 1H), 8.99 (d, J = 7.4 Hz, 1H), 8.68 (s, 1H), 8.43 (s, 1H), 7.84 (t, J = 9.3 Hz, 1H), 7.47 (s, 1H), 7.36 (d, J = 10.7 Hz, 1H), 7.07 (dd, J = 7.5, 2.6 Hz, 1H), 6.96 (d, J = 2.5 Hz, 1H), 6.90 (dd, J = 24.3, 14.3 Hz, 1H), 6.19 (t, J = 17.4 Hz, 1H), 5.74 (d, J = 9.4 Hz, 1H), 5.04 (d, J = 77.0 Hz, 1H), 4.49 (dd, J = 179.2, 8.6 Hz, 1H), 3.20-2.88 (m, 2H), 2.21 (s, 3H), 1.36 (dd, J = 27.2, 5.7 Hz, 3H), 1.27-1.10 (m, 1H). LCMS: Method G; Retention Time: .132 min MS (ESI, m/z): 538 [M + H]⁺ |
| 60 | F | A | 1-[(2S)-4-(8-{[3-(difluoromethyl)-2-fluoro-4-{[1,2,4]triazolo[1,5-a]pyridin-7-yloxy}phenyl]amino}-[1,3]diazino[5,4-d]pyrimidin-2-yl)-2-methyl-5,6-dihydro-2H-pyridin-1-yl]prop-2-en-1-one | ¹H NMR (300 MHz, DMSO-d6) δ 10.02 (s, 1H), 9.48 (s, 1H), 9.09-8.98 (m, 1H), 8.70 (s, 1H), 8.48 (s, 1H), 8.16-8.01 (m, 1H), 7.64-7.32 (m, 2H), 7.32-7.19 (m, 2H), 7.16-7.10 (m, 1H), 7.01-6.83 (m, 1H), 6.27-6.11 (m, 1H), 5.81-5.67 (m, 1H), 4.76-4.20 (m, 1H), 3.82-3.71 (m, 1H), 3.26-3.13 (m, 2H), 2.71-2.65 (m, 1H), 1.46-1.22 (m, 3H). LCMS: Method J; Retention Time: 1.00 min MS (ESI, m/z): 574 [M + H]⁺ |

TABLE 10-continued

Compounds

| Example | Synthetic Method | Coupling Method | Compound Structure | Physical Data (¹H NMR and MS) |
|---|---|---|---|---|
| 61 | F | A | 1-[(2S)-4-(8-{[3-(difluoromethyl)-2-fluoro-4-{[1,2,4]triazolo[1,5-a]pyridin-7-yloxy}phenyl]amino}-[1,3]diazino[5,4-d]pyrimidin-2-yl)-2-methyl-3,6-dihydro-2H-pyridin-1-yl]prop-2-en-1-one | ¹H NMR (300 MHz, DMSO-d6) δ 10.09 (s, 1H), 9.36 (s, 1H), 8.95-8.87 (m, 1H), 8.57 (s, 1H), 8.36 (s, 1H), 8.02-7.90 (m, 1H), 7.46-7.24 (m, 2H), 7.19-7.05 (m, 2H), 7.03-6.76 (m, 2H), 6.06-6.01 (m, 1H), 5.66-5.58 (m, 1H), 4.67-4.58 (m, 1H), 3.82-3.71 (m, 1H), 3.08-2.97 (m, 2H), 2.69-2.61 (m, 1H), 1.14-0.99 (m, 3H). LCMS: Method J; Retention Time: 0.936 min MS (ESI, m/z): 574 [M + H]⁺ |
| 62 | F | A | (S)-1-(4-(8-((4-([1,2,4]triazolo[1,5-a]pyridin-7-yloxy)-2-fluoro-3-(trifluoromethyl)phenyl)amino)pyrimido[5,4-d]pyrimidin-2-yl)-2-methyl-3,6-dihydropyridin-1(2H)-yl)prop-2-en-1-one | ¹H NMR (300 MHz, DMSO-d6) δ 10.22 (s, 1H), 9.49 (s, 1H), 9.04 (d, J = 7.5 Hz, 1H), 8.72 (s, 1H), 8.49 (s, 1H), 8.31-8.14 (m, 1H), 7.47 (s, 1H), 7.42-7.29 (m, 1H), 7.19-7.11 (m, 1H), 7.00-6.78 (m, 1H), 6.29-6.09 (m, 1H), 5.81-5.63 (m, 1H), 5.21-4.90 (m, 1H), 4.76-4.23 (m, 1H), 3.26-3.10 (m, 1H), 3.09-2.78 (m, 1H), 2.76-2.56 (m, 1H), 1.49-1.27 (m, 3H). LCMS: Method J; Retention Time: 1.11 min MS (ESI, m/z): 592 [M + H]⁺ |
| 63 | K | A | (R)-1-(4-(8-((5-([1,2,4]triazolo[1,5-a]pyridin-7-yloxy)-3-fluoro-4-methylpyridin-2-yl)amino)pyrimido[5,4-d]pyrimidin-2-yl)-2-methylpiperazin-1-yl)prop-2-en-1-one | ¹H NMR (400 MHz, DMSO) δ 10.31 (s, 1H), 9.16 (s, 1H), 9.01 (d, J = 7.4 Hz, 1H), 8.45 (s, 1H), 8.38 (s, 1H), 8.31 (s, 1H), 7.17-7.14 (m, 1H), 7.12 (d, J = 2.4 Hz, 1H), 6.91-6.82 (m, 1H), 6.16 (d, J = 14.8 Hz, 1H), 5.75-5.71 (m, 1H), 4.83-4.36 (m, 4H), 3.19-3.11 (m, 3H), 2.26-2.24 (m, 3H), 1.25-1.22 (m, 3H). LCMS: Method K; Retention Time: 1.26 min MS (ESI, m/z): 542 [M + H]⁺ |
| 64 | K | A | (R)-1-(4-(4-((5-([1,2,4]triazolo[1,5-a]pyridin-7-yloxy)-3-fluoro-4-methylpyridin-2-yl)amino)-5-fluoroquinazolin-6-yl)-2-methylpiperazin-1-yl)prop-2-en-1-one | ¹H NMR (400 MHz, DMSO) δ 9.56 (s, 1H), 9.01 (d, J = 7.5 Hz, 1H), 8.64-8.28 (m, 2H), 8.23 (s, 1H), 7.89-7.43 (m, 2H), 7.17-7.13 (m, 1H), 7.12-7.06 (m, 1H), 6.91-6.81 (m, 1H), 6.20-6.11 (m, 1H), 5.76-5.69 (m, 1H), 4.94-3.83 (m, 3H), 3.47-3.42 (m, 2H), 3.05-2.83 (m, 2H), 2.22 (s, 3H), 1.37 (s, 3H). LCMS: Method K; Retention Time: 0.79 min MS (ESI, m/z): 558 [M + H]⁺ |

TABLE 10-continued

Compounds

| Example | Synthetic Method | Coupling Method | Compound Structure | Physical Data (¹H NMR and MS) |
|---|---|---|---|---|
| 65 | K | A | (R)-1-(4-(8-((4-([1,2,4]triazolo[1,5-a]pyrimidin-5-yloxy)-2-fluoro-3-methylphenyl)amino)pyrimido[5,4-d]pyrimidin-2-yl)-2-methylpiperazin-1-yl)prop-2-en-1-one | ¹H NMR (400 MHz, DMSO-d6) δ 9.68 (s, 1H), 9.38 (d, J = 7.3 Hz, 1H), 9.15 (s, 1H), 8.49 (s, 1H), 8.41 (s, 1H), 7.80 (t, J = 8.7 Hz, 1H), 7.26-7.18 (m, 2H), 6.88 (dd, J = 16.7, 10.5 Hz, 1H), 6.16 (dd, J = 16.8, 2.3 Hz, 1H), 5.73 (dd, J = 10.2, 2.2 Hz, 1H), 4.92-3.92 (m, 4H), 3.44-3.38 (m, 1H), 3.23-3.09 (m, 2H), 2.11 (d, J = 1.9 Hz, 3H), 1.17 (s, 3H). LCMS: Method K; Retention Time: 0.76 min MS (ESI, m/z): 542 [M + H]⁺ |
| 66 | M | A | 1-(4-(4-((4-([1,2,4]triazolo[1,5-a]pyridin-7-yloxy)-3-methylphenyl)amino)-7-methoxypyrido[3,2-d]pyrimidin-6-yl)-3,6-dihydropyridin-1(2H)-yl)prop-2-en-1-one | ¹H NMR (400 MHz, DMSO-d6) δ 9.66 (brs, 1H), 8.93 (dd, J = 7.6, 2.4 Hz, 1H), 8.59 (d, J = 6.0 Hz, 1H), 8.37 (s, 1H), 7.97-7.95 (m, 2H), 7.61 (d, J = 6.0 Hz, 1H), 7.25-7.18 (m, 1H), 7.06-6.97 (m, 1H), 6.87-6.81 (m, 2H), 6.79 (d, J = 2.4 Hz, 1H), 6.17 (d, J = 2.4 Hz, 1H), 5.78-5.70 (m, 1H), 4.43-4.26 (m, 2H), 4.05-3.97 (m, 3H), 3.87-3.75 (m, 2H), 2.93-2.80 (m, 2H), 2.22-2.17 (m, 3H). LCMS: Method J; Retention Time: 0.71 min MS (ESI, m/z): 535 [M + H]⁺ |
| 67 | K | A | 1-{4-[8-({2-fluoro-4-[(1-methyl-1,3-benzodiazol-5-yl)oxy]phenyl}amino)pyrimido[5,4-d][1,3]diazin-2-yl]piperazin-1-yl}prop-2-en-1-one | ¹H NMR (300 MHz, DMSO-d6) δ 9.64 (s, 1H), 9.12 (s, 1H), 8.32 (s, 1H), 8.24 (s, 1H), 7.67 (t, J = 8.4 Hz, 2H), 7.39 (d, J = 2.1 Hz, 1H), 7.12 (t, J = 6.6 Hz, 1H), 6.98-6.82 (m, 3H), 6.20 (dd, J = 16.8 Hz, 2.4 Hz, 1H), 5.75 (dd, J = 10.5 Hz, 2.4 Hz, 1H), 4.03-3.95 (m, 4H), 3.87 (s, 3H), 3.71-3.68 (m, 4H). LCMS: Method F; Retention Time: 1.17 min MS (ESI, m/z): 526 [M + H]⁺ |
| 68 | K | A | 1-[(2R)-4-[8-({2-fluoro-3-methyl-4-[(1-methyl-1,3-benzodiazol-5-yl)oxy]phenyl}amino)pyrimido[5,4-d][1,3]diazin-2-yl]-2-methylpiperazin-1-yl]prop-2-en-1-one | ¹H NMR (300 MHz, DMSO-d6) δ 9.59 (s, 1H), 9.12 (s, 1H), 8.35 (s, 1H), 8.22 (s, 1H), 7.66-7.54 (m, 2H), 7.23 (d, J = 2.4 Hz, 1H), 7.06 (dd, J = 8.4 Hz, 2.4 Hz, 1H), 6.95-6.80 (m, 1H), 6.74-6.65 (m, 1H), 6.16 (dd, J = 16.5 Hz, 2.4 Hz, 1H), 5.73 (dd, J = 10.2 Hz, 2.4 Hz, 1H), 4.89-4.12 (m, 5H), 3.86 (s, 3H), 3.44-3.36 (m, 1H), 3.21-3.13 (m, 1H), 2.24 (d, J = 2.1 Hz, 3H), 1.17 (s, 3H). LCMS: Method F; Retention Time: 1.33 min MS (ESI, m/z): 554 [M + H]⁺ |

TABLE 10-continued

| Example | Synthetic Method | Coupling Method | Compound Structure | Physical Data (¹H NMR and MS) |
|---|---|---|---|---|
| 69 | F | B | (E)-1-(4-(8-((4-([1,2,4]triazolo[1,5-a]pyridin-7-yloxy)-2-fluoro-3-methylphenyl)amino)pyrimido[5,4-d]pyrimidin-2-yl)-3,6-dihydropyridin-1(2H)-yl)-4-(dimethylamino)but-2-en-1-one | ¹H NMR (400 MHz, DMSO) δ 10.06 (s, 1H), 9.47 (s, 1H), 8.98 (d, J = 7.4 Hz, 1H), 8.69 (s, 1H), 8.41 (s, 1H), 7.89-7.78 (m, 1H), 7.49 (d, J = 20.3 Hz, 1H), 7.16 (d, J = 8.6 Hz, 1H), 7.08 (dd, J = 7.5, 2.6 Hz, 1H), 6.96 (d, J = 2.5 Hz, 1H), 6.73-6.61 (m, 2H), 4.41 (d, J = 42.1 Hz, 2H), 3.82 (s, 2H), 3.06 (s, 2H), 2.89 (s, 2H), 2.18 (d, 3H), 2.16 (s, 6H). LCMS: Method K; Retention Time: 0.67 min MS (ESI, m/z): 581 [M + H]⁺ |
| 70 | A | A | 1-(4-(4-((4-(imidazo[1,2-a]pyridin-7-yloxy)-3-methylphenyl)amino)pyrido[3,2-d]pyrimidin-6-yl)-3,6-dihydropyridin-1(2H)-yl)prop-2-en-1-one | ¹H NMR (400 MHz, DMSO-d6) δ 9.85 (s, 1H), 8.64 (s, 1H), 8.55 (d, J = 7.4 Hz, 1H), 8.21-8.16 (m, 2H), 7.98-7.91 (m, 2H), 7.84 (s, 1H), 7.44 (d, J = 1.2 Hz, 1H), 7.21-7.15 (m, 1H), 7.08 (d, J = 16.2 Hz, 1H), 7.03-6.83 (m, 1H), 6.81 (dd, J = 7.4, 2.5 Hz, 1H), 6.55 (d, J = 2.5 Hz, 1H), 6.17 (dd, J = 16.7, 2.1 Hz, 1H), 5.74 (d, J = 12.4 Hz, 1H), 4.39 (d, J = 34.4 Hz, 2H), 3.93-3.76 (m, 2H), 2.93 (d, J = 20.4 Hz, 2H), 2.23 (s, 3H). LCMS: Method K; Retention Time: 0.53 min MS (ESI, m/z): 504 [M + H]⁺ |
| 71 | A | A | 1-(4-(4-((3-methyl-4-((1-methyl-1H-indol-6-yl)oxy)phenyl)amino)pyrido[3,2-d]pyrimidin-6-yl)-3,6-dihydropyridin-1(2H)-yl)prop-2-en-1-one | ¹H NMR (400 MHz, MeOH-d4) δ 8.53 (s, 1H), 8.19-8.11 (m, 1H), 8.07 (d, J = 8.9 Hz, 1H), 7.77 (d, J = 2.6 Hz, 1H), 7.67 (dd, J = 8.7, 2.6 Hz, 1H), 7.49 (d, J = 8.6 Hz, 1H), 7.09 (d, J = 3.1 Hz, 1H), 6.95 (d, J = 18.0 Hz, 1H), 6.91 (d, J = 2.2 Hz, 1H), 6.90-6.79 (m, 2H), 6.76 (dd, J = 8.6, 2.2 Hz, 1H), 6.40 (dd, J = 3.2, 0.9 Hz, 1H), 6.27 (dd, J = 16.8, 1.9 Hz, 1H), 5.80 (dd, J = 10.5, 1.9 Hz, 1H), 4.44 (dd, J = 15.8, 3.3 Hz, 2H), 3.93 (q, J = 6.3, 5.9 Hz, 2H), 3.70 (s, 3H), 2.97 (d, J = 18.0 Hz, 2H), 2.34 (s, 3H). LCMS: Method K; Retention Time: 1.42 min MS (ESI, m/z): 517 [M + H]⁺ |
| 72 | A | A | 1-(4-(4-((3-methyl-4-(pyrazolo[1,5-a]pyridin-5-yloxy)phenyl)amino)pyrido[3,2-d]pyrimidin-6-yl)-3,6-dihydropyridin-1(2H)-yl)prop-2-en-1-one | ¹H NMR (400 MHz, DMSO-d6) δ 9.83 (s, 1H), 8.68 (d, J = 7.3 Hz, 1H), 8.64 (s, 1H), 8.18 (s, 2H), 7.98-7.94 (m, 2H), 7.91 (d, J = 2.2 Hz, 1H), 7.19 (d, J = 9.2 Hz, 1H), 7.08 (d, J = 16.5 Hz, 1H), 6.98-6.81 (m, 1H), 6.76-6.72 (m, 2H), 6.41 (d, J = 2.1 Hz, 1H), 6.17 (dd, J = 16.7, 2.2 Hz, 1H), 5.78-5.72 (m, 1H), 4.39 (d, J = 34.7 Hz, 2H), 3.88-3.80 (m, 2H), 2.97-2.88 (m, 2H), 2.22 (s, 3H). LCMS: Method K; Retention Time: 1.58 min MS (ESI, m/z): 504 [M + H]⁺ |

TABLE 10-continued

Compounds

| Example | Synthetic Method | Coupling Method | Compound Structure | Physical Data ($^1$H NMR and MS) |
|---|---|---|---|---|
| 73 | K | A | (R)-1-(4-(8-((4-([1,2,4]triazolo[1,5-c]pyrimidin-7-yloxy)-2-fluoro-3-methylphenyl)amino)pyrimido[5,4-d]pyrimidin-2-yl)-2-methylpiperazin-1-yl)prop-2-en-1-one | $^1$H NMR (400 MHz, DMSO-d6) δ 9.69 (d, J = 1.2 Hz, 1H), 9.64 (s, 1H), 9.15 (s, 1H), 8.62 (s, 1H), 8.39 (s, 1H), 7.78 (t, J = 8.6 Hz, 1H), 7.34 (d, J = 1.2 Hz, 1H), 7.14 (dd, J = 9.0, 1.3 Hz, 1H), 6.88 (dd, J = 16.6, 10.5 Hz, 1H), 6.16 (dd, J = 16.8, 1.9 Hz, 1H), 5.73 (dd, J = 10.5, 2.1 Hz, 1H), 4.88-3.97 (m, 4H), 3.52-3.38 (m, 1H), 3.18 (d, J = 12.1 Hz, 2H), 2.15 (d, J = 1.9 Hz, 3H), 1.17 (s, 3H). LCMS: Method K; Retention Time: 0.97 min MS (ESI, m/z): 542 [M + H]$^+$ |
| 74 | K | A | 1-{4-[8-({2-fluoro-3-methyl-4-[(1-methyl-1,3-benzodiazol-5-yl)oxy]phenyl}amino)pyrimido[5,4-d][1,3]diazin-2-yl]piperazin-1-yl}prop-2-en-1-one | $^1$H NMR (400 MHz, DMSO-d$_6$) δ 9.62 (s, 1H), 9.13 (s, 1H), 8.35 (s, 1H), 8.21 (s, 1H), 7.62 (d, J = 8.7 Hz, 1H), 7.57 (t, J = 8.9 Hz, 1H), 7.25-7.21 (m, 1H), 7.08-7.04 (m, 1H), 6.94-6.85 (m, 1H), 6.69 (d, J = 8.9 Hz, 1H), 6.21-6.14 (m, 1H), 5.77-5.72 (m, 1H), 4.06-3.96 (m, 4H), 3.86 (s, 3H), 3.76-3.68 (m, 4H), 2.26-2.22 (m, 3H). LCMS: Method K; Retention Time: 1.14 min MS (ESI, m/z): 540 [M + H]$^+$ |
| 75 | I | A | (R)-1-(4-(5-fluoro-4-((2-fluoro-3-methyl-4-((3-methylimidazo[1,2-a]pyridin-7-yl)oxy)phenyl)amino)quinazolin-6-yl)-2-methylpiperazin-1-yl)prop-2-en-1-one | $^1$H NMR (400 MHz, DMSO-d6) δ 9.12 (d, J = 13.7 Hz, 1H), 8.45 (s, 1H), 8.30 (d, J = 7.4 Hz, 1H), 7.78-7.69 (m, 2H), 7.63 (d, J = 9.0 Hz, 1H), 7.26 (s, 1H), 6.99 (d, J = 8.6 Hz, 1H), 6.90-6.82 (m, 2H), 6.69 (d, J = 2.3 Hz, 1H), 6.16 (dd, J = 16.6, 2.1 Hz, 1H), 5.72 (dd, J = 10.4, 2.3 Hz, 1H), 4.93-4.20 (m, 2H), 4.19-3.82 (m, 1H), 3.47-3.45 (m, 2H), 3.04-2.86 (m, 2H), 2.44 (s, 3H), 2.17 (d, J = 1.5 Hz, 3H), 1.38 (s, 3H). LCMS: Method K; Retention Time: 0.774 min MS (ESI, m/z): 570 [M + H]$^+$ |
| 76 | K | A | 1-(4-(8-((4-([1,2,4]triazolo[1,5-a]pyridin-7-yloxy)-2-fluoro-5-methylphenyl)amino)pyrimido[5,4-d]pyrimidin-2-yl)-2,2-dimethylpiperazin-1-yl)prop-2-en-1-one | $^1$H NMR (400 MHz, DMSO-d6) δ 9.65-9.38 (m, 1H), 9.16 (s, 1H), 8.98 (d, J = 7.2 Hz, 1H), 8.42 (s, 2H), 8.15-7.80 (m, 1H), 7.35 (d, J = 10.8 Hz, 1H), 7.06 (dd, J = 7.6, 2.4 Hz, 1H), 6.93 (d, J = 2.8 Hz, 1H), 6.82-6.71 (m, 1H), 6.04 (dd, J = 16.8, 2.4 Hz, 1H), 5.63 (dd, J = 10.4, 2.4 Hz, 1H), 4.15-4.08 (m, 2H), 3.96-3.90 (m, 2H), 3.85-3.78 (m, 2H), 2.20 (s, 3H), 1.49 (s, 6H). MS (ESI, m/z): 555 (M + H)$^+$. LCMS: Method D; Retention Time: 1.119 min MS (ESI, m/z): 555 [M + H]$^+$ |

TABLE 10-continued

Compounds

| Example | Synthetic Method | Coupling Method | Compound Structure | Physical Data (¹H NMR and MS) |
|---|---|---|---|---|
| 77 | K | A | 1-(4-(8-((4-([1,2,4]triazolo[1,5-a]pyridin-7-yloxy)-2-fluoro-3-methylphenyl)amino)pyrimido[5,4-d]pyrimidin-2-yl)-2,2-dimethylpiperazin-1-yl)prop-2-en-1-one | ¹H NMR (300 MHz, DMSO-d$_6$) δ 9.47 (brs, 1H), 9.16 (s, 1H), 8.98 (d, J = 7.5 Hz, 1H), 8.45-8.41 (m, 2H), 8.25-7.78 (m, 1H), 7.21-7.12 (m, 1H), 7.10-7.02 (m, 1H), 6.97-6.90 (m, 1H), 6.85-6.70 (m, 1H), 6.12-5.97 (m, 1H), 5.70-5.59 (m, 1H), 4.12 (s, 2H), 4.03-3.77 (m, 4H), 2.17 (s, 3H), 1.49 (s, 6H). LCMS: Method J; Retention Time: 1.09 min MS (ESI, m/z): 555 [M + H]⁺ |
| 78 | O | A | 1-(4-(8-((4-([1,2,4]triazolo[1,5-a]pyridin-7-yloxy)-3-methylphenyl)amino)-7-fluoropyrido[3,2-d]pyrimidin-2-yl)-3,6-dihydropyridin-1(2H)-yl)prop-2-en-1-one | ¹H NMR (400 MHz, DMSO-d6) δ 8.94 (d, J = 7.6 Hz, 1H), 8.89 (s, 1H), 8.73 (d, J = 4.0 Hz, 1H), 8.38 (s, 1H), 8.31 (d, J = 8.8 Hz, 1H), 8.06 (d, J = 8.8 Hz, 1H), 7.29 (s, 1H), 7.21-7.11 (m, 2H), 7.08-6.98 (m, 1H), 6.96-6.82 (m, 1H), 6.76 (s, 1H), 6.16 (d, J = 16.8 Hz, 1H), 5.77-5.67 (m, 1H), 4.45-4.38 (m, 1H), 4.36-4.29 (m, 1H), 3.86-3.75 (m, 2H), 2.95-2.82 (m, 2H), 2.16 (s, 3H). LCMS: Method J; Retention Time: 1.119 min MS (ESI, m/z): 522 [M + H]⁺ |
| 79 | N | A | 8-((4-([1,2,4]triazolo[1,5-a]pyridin-7-yloxy)-3-methylphenyl)amino)-2-(1-acryloyl-1,2,3,6-tetrahydropyridin-4-yl)pyrido[3,2-d]pyrimidine-7-carbonitrile | ¹H NMR (400 MHz, DMSO-d6) δ 10.08 (brs, 1H), 8.95 (d, J = 7.6 Hz, 1H), 8.55 (s, 1H), 8.37 (s, 1H), 8.28 (d, J = 8.8 Hz, 1H), 8.16-8.15 (m, 1H), 7.52 (d, J = 2.8 Hz, 1H), 7.43 (dd, J = 8.4, 2.8 Hz, 1H), 7.30 (d, J = 8.4 Hz, 1H), 7.15-7.05 (m, 2H), 6.98-6.79 (m, 1H), 6.17 (d, J = 16.8 Hz, 1H), 5.74 (dd, J = 10.4, 2.4 Hz, 1H), 4.42 (s, 1H), 4.36-4.31 (m, 1H), 3.85-3.78 (m, 2H), 2.94-2.89 (m, 2H), 2.20 (s, 3H). LCMS: Method J; Retention Time: 1.119 min MS (ESI, m/z): 529 [M + H]⁺ |
| 80 | F | A | (R)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-methyl-3,6-dihydropyridin-1(2H)-yl)prop-2-en-1-one | ¹H NMR (400 MHz, DMSO-d6) δ 10.00 (br.s, 1H), 9.47 (s, 1H), 9.00 (d, J = 7.6 Hz, 1H), 8.69 (s, 1H), 8.43 (s, 1H), 7.88-7.76 (m, 1H), 7.58-7.48 (m, 1H), 7.17 (d, J = 8.4 Hz, 1H), 7.09 (dd, J = 7.6, 2.8 Hz, 1H), 7.03-6.77 (m, 2H), 6.21-6.13 (m, 1H), 5.73 (dd, J = 10.4, 2.4 Hz, 1H), 5.25-4.37 (m, 2H), 4.25-3.75 (m, 1H), 3.17-3.12 (m, 1H), 2.85-2.58 (m, 1H), 2.19 (s, 3H), 1.23-1.14 (m, 3H). LCMS: Method L; Retention Time: 0.822 min MS (ESI, m/z): 538 (M + H)⁺. |

TABLE 10-continued

| Example | Synthetic Method | Coupling Method | Compound Structure | Physical Data ($^1$H NMR and MS) |
|---|---|---|---|---|
| 81 | K | A | 1-[(2S)-4-{8-[(2-fluoro-3-methyl-4-{[1,2,4]triazolo[1,5-a]pyridin-7-yloxy}phenyl)amino]pyrimido[5,4-d][1,3]diazin-2-yl}-2-(fluoromethyl)piperazin-1-yl]prop-2-en-1-one | $^1$H NMR (300 MHz, DMSO-d6) δ 9.64 (s, 1H), 9.15 (s, 1H), 8.99-8.94 (m, 1H), 8.41 (s, 2H), 7.91-7.82 (m, 1H), 7.18-7.12 (m, 1H), 7.09-7.04 (m, 1H), 6.95-6.84 (m, 2H), 6.23-6.12 (m, 1H), 5.78-5.70 (m, 1H), 5.02-4.86 (m, 2H), 4.75-4.60 (m, 2H), 4.57-4.38 (m, 2H), 3.53-3.36 (m, 2H), 3.11 (s, 1H), 2.20-2.12 (m, 3H). LCMS: Method J; Retention Time: 1.09 min MS (ESI, m/z): 559 [M + H]$^+$ |
| 82 | K | A | (R)-1-(4-(8-((4-([1,2,4]triazolo[1,5-a]pyridin-7-yloxy)-3-chloro-2-fluorophenyl)amino)pyrimido[5,4-d]pyrimidin-2-yl)-2-methylpiperazin-1-yl)prop-2-en-1-one | $^1$H NMR (400 MHz, DMSO-d$_6$) δ 9.80 (brs, 1H), 9.17 (s, 1H), 9.09-8.96 (m, 1H), 8.44 (d, J = 15.2 Hz, 2H), 8.01-7.89 (m, 1H), 7.38 (dd, J = 9.2, 1.6 Hz, 1H), 7.24-7.07 (m, 2H), 6.88 (dd, J = 16.4, 10.4 Hz, 1H), 6.17 (dd, J = 16.4, 2.4 Hz, 1H), 5.73 (dd, J = 10.4, 2.4 Hz, 1H), 5.05-4.43 (m, 3H), 4.42-3.93 (m, 1H), 3.53-3.01 (m, 3H), 1.17 (s, 3H). LCMS: Method J; Retention Time: 1.037 min MS (ESI, m/z): 561/563 [M + H]$^+$ |
| 83 | F | B | (2E)-4-(dimethylamino)-1-[(2S)-4-(8-[(2-fluoro-3-methyl-4-{[1,2,4]triazolo[1,5-a]pyridin-7-yloxy}phenyl) amino]-[1,3] diazino[5,4-d]pyrimidin-2-yl}-2-methyl-5,6-dihydro-2H-pyridin-1-yl]but-2-en-1-one | $^1$H NMR (300 MHz, DMSO-d$_6$) δ 10.07 (s, 1H), 9.47 (s, 1H), 9.03-8.97 (m, 1H), 8.70 (s, 1H), 8.43 (s, 1H), 7.91-7.78 (m, 1H), 7.47 (s, 1H), 7.20-7.15 (m, 1H), 7.12-7.06 (m, 1H), 7.01-6.95 (m, 1H), 6.77-6.62 (m, 2H), 5.20-4.98 (m, 1H), 4.77-4.53 (m, 1H), 3.22-3.11 (m, 1H), 3.10-3.03 (m, 2H), 2.97-2.86 (m, 1H), 2.24-2.19 (m, 3H), 2.17-2.12 (m, 6H), 1.44-1.27 (m, 4H). LCMS: Method J; Retention Time: 1.312 min MS (ESI, m/z): 595 [M + H]$^+$ |
| 84 | L | A | (R)-1-(4-(5-fluoro-4-((2-fluoro-3-methyl-4-((1-methyl-1H-benzo[d]imidazol-5-yl)oxy)phenyl)amino)pyrido[3,4-d]pyrimidin-6-yl)-2-methylpiperazin-1-yl)prop-2-en-1-one | $^1$H NMR (400 MHz, DMSO-d$_6$) δ 9.21 (d, J = 10.2 Hz, 1H), 8.79 (s, 1H), 8.43 (s, 1H), 8.22 (s, 1H), 7.62 (d, J = 8.7 Hz, 1H), 7.51 (t, J = 8.7 Hz, 1H), 7.24 (d, J = 2.1 Hz, 1H), 7.07 (dd, J = 8.7, 2.1 Hz, 1H), 6.86 (dd, J = 16.5, 10.5 Hz, 1H), 6.64 (dd, J = 9.0, 1.5 Hz, 1H), 6.16 (dd, J = 16.5, 2.4 Hz, 1H), 5.72 (dd, J = 10.5, 2.4 Hz, 1H), 4.72-4.33 (m, 1H), 3.98 (d, J = 12.6 Hz, 1H), 3.86 (s, 3H), 3.84-3.80 (m, 1H), 3.19-3.10 (m, 3H), 3.00 (t, J = 12.6 Hz, 1H), 2.24 (s, 3H), 1.29 (d, J = 6.6 Hz, 3H). LCMS: Method J; Retention Time: 0.90 min MS (ESI, m/z): 571 [M + H]$^+$ |

TABLE 10-continued

Compounds

| Example | Synthetic Method | Coupling Method | Compound Structure | Physical Data (¹H NMR and MS) |
|---|---|---|---|---|
| 85 | A | A | (S)-1-(4-(4-((4-([1,2,4]triazolo[1,5-a]pyridin-7-yloxy)-3-methylphenyl)amino)pyrido[3,2-d]pyrimidin-6-yl)-2-methyl-3,6-dihydropyridin-1(2H)-yl)prop-2-en-1-one | ¹H NMR (300 MHz, DMSO-d₆) δ 9.82 (s, 1H), 8.94 (d, J = 7.5 Hz, 1H), 8.65 (s, 1H), 8.38 (s, 1H), 8.24-8.16 (m, 2H), 8.00-7.97 (m, 2H), 7.27-7.24 (m, 1H), 7.11-7.02 (m, 2H), 6.89-6.80 (m, 2H), 6.18-6.12 (m, 1H), 5.75-5.70 (m, 1H), 5.17-4.75 (m, 2H), 4.14-3.77 (m, 1H), 3.15-3.09 (m, 1H), 2.83-2.73 (m, 1H), 2.22 (s, 3H), 1.28-1.22 (m, 3H). LCMS: Method J; Retention Time: 1.03 min MS (ESI, m/z): 519 [M + H]⁺ |
| 86 | A | A | (R)-1-(4-(4-((4-([1,2,4]triazolo[1,5-a]pyridin-7-yloxy)-3-methylphenyl)amino)pyrido[3,2-d]pyrimidin-6-yl)-2-methyl-3,6-dihydropyridin-1(2H)-yl)prop-2-en-1-one | ¹H NMR (400 MHz, DMSO-d₆) δ 9.84 (brs, 1H), 8.94 (d, ] = 7.6 Hz, 1H), 8.65 (s, 1H), 8.38 (s, 1H), 8.20 (q, J = 8.8 Hz, 2H), 8.02-7.91 (m, 2H), 7.29-7.23 (m, 2H), 7.12 (s, 1H), 7.04 (dd, J = 7.6, 2.8 Hz, 1H), 6.81 (d, J = 2.8 Hz, 1H), 6.20-6.11 (m, 1H), 5.77-5.69 (m, 1H), 5.25-4.55 (m, 2H), 4.28-3.60 (m, 1H), 3.17-3.06 (m, 1H), 2.89-2.76 (m, 1H), 2.23 (s, 3H), 1.23 (s, 3H). LCMS: Method J; Retention Time: 1.03 min MS (ESI, m/z): 519 [M + H]⁺ |
| 87 | K | B | 1-((R)-4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazin-1-yl)-2-chloro-2-fluoroethan-1-one | ¹H NMR (400 MHz, DMSO) δ 9.66 (d, J = 10.8 Hz, 1H), 9.16 (s, 1H), 8.98 (d, J = 7.5 Hz, 1H), 8.41 (d, J = 2.6 Hz, 2H), 7.89-7.79 (m, 1H), 7.55-7.21 (m, 1H), 7.15 (d, J = 8.8 Hz, 1H), 7.07 (dd, J = 7.5, 2.6 Hz, 1H), 6.94 (d, J = 2.5 Hz, 1H), 4.93-4.65 (m, 2H), 4.63-4.19 (m, 1H), 3.84-3.38 (m, 2H), 3.29-3.06 (m, 2H), 2.18 (s, 3H), 1.29-1.11 (m, 3H). LCMS: Method K; Retention Time: 1.41 min MS (ESI, m/z): 581/583 [M + H]⁺ |
| 88 | F | B | 1-((S)-4-(8-((4-([1,2,4]triazolo[1,5-a]pyridin-7-yloxy)-2-fluoro-3-methylphenyl)amino)pyrimido[5,4-d]pyrimidin-2-yl)-6-methyl-3,6-dihydropyridin-1(2H)-yl)-2-chloro-2-fluoroethan-1-one | ¹H NMR (400 MHz, DMSO-d6) δ 10.09 (d, J = 17.0 Hz, 1H), 9.47 (d, J = 4.5 Hz, 1H), 8.99 (d, J = 7.5 Hz, 1H), 8.69 (d, J = 5.9 Hz, 1H), 8.42 (s, 1H), 7.90-7.76 (m, 1H), 7.56-7.28 (m, 2H), 7.17 (d, J = 8.2 Hz, 1H), 7.08 (dd, J = 7.5, 2.6 Hz, 1H), 6.96 (d, J = 2.1 Hz, 1H), 5.10-4.77 (m, 1H), 4.63-4.39 (m, 1H), 4.28-3.85 (m, 1H), 3.13 (d, J = 17.1 Hz, 1H), 2.91-2.67 (m, 1H), 2.19 (s, 3H), 1.29-1.15 (m, 3H). LCMS: Method K; Retention Time: 1.64 min MS (ESI, m/z): 578/580 [M + H]⁺ |

TABLE 10-continued

| Example | Synthetic Method | Coupling Method | Compound Structure | Physical Data (¹H NMR and MS) |
|---|---|---|---|---|
| 89 | F | B | 1-((S)-4-(8-((4-([1,2,4]triazolo[1,5-a]pyridin-7-yloxy)-2-fluoro-3-methylphenyl)amino)pyrimido[5,4-d]pyrimidin-2-yl)-2-methyl-3,6-dihydropyridin-1(2H)-yl)-2-chloro-2-fluoroethan-1-one | ¹H NMR (400 MHz, DMSO-$d_6$) δ 10.09 (d, J = 19.0 Hz, 1H), 9.46 (d, J = 4.9 Hz, 1H), 8.99 (d, J = 7.5 Hz, 1H), 8.69 (d, J = 6.6 Hz, 1H), 8.42 (s, 1H), 7.84 (dt, J = 35.5, 8.7 Hz, 1H), 7.51-7.34 (m, 2H), 7.17 (d, J = 8.6 Hz, 1H), 7.09 (dd, J = 7.5, 2.5 Hz, 1H), 6.96 (s, 1H), 5.07-3.96 (m, 2H), 3.18 (d, J = 16.8 Hz, 1H), 2.66 (d, J = 12.0 Hz, 1H), 2.19 (s, 3H), 1.47 (d, J = 6.5 Hz, 1H), 1.33 (dd, J = 14.4, 6.8 Hz, 3H). LCMS: Method K; Retention Time: 1.45 min MS (ESI, m/z): 578/580 [M + H]⁺ |
| 90 | K | B | (R)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazin-1-yl)-2-chloroethan-1-one | ¹H NMR (400 MHz, DMSO-$d_6$) δ 9.65 (s, 1H), 9.15 (s, 1H), 8.98 (d, J = 7.6 Hz, 1H), 8.41 (d, J = 4.9 Hz, 2H), 7.86 (t, J = 8.5 Hz, 1H), 7.15 (d, J = 8.7 Hz, 1H), 7.07 (dd, J = 7.5, 2.6 Hz, 1H), 6.94 (d, J = 2.5 Hz, 1H), 5.08-4.54 (m, 3H), 4.54-4.41 (m, 2H), 4.41-4.15 (m, 1H), 3.89-3.47 (m, 2H), 2.18 (s, 3H), 1.17 (d, J = 56.6 Hz, 4H). LCMS: Method K; Retention Time: 1.27 min MS (ESI, m/z): 563/565 [M + H]⁺ |
| 91 | K | B | ((R)-4-(8-((4-([1,2,4]triazolo[1,5-a]pyridin-7-yloxy)-2-fluoro-3-methylphenyl)amino)pyrimido[5,4-d]pyrimidin-2-yl)-2-methylpiperazin-1-yl)(oxiran-2-yl)methanone | ¹H NMR (400 MHz, DMSO-$d_6$) δ 9.61 (s, 1H), 9.15 (s, 1H), 8.97 (d, J = 7.5 Hz, 1H), 8.41 (d, J = 2.9 Hz, 2H), 7.88 (t, 1H), 7.15 (d, J = 8.7 Hz, 1H), 7.07 (dd, J = 7.5, 2.6 Hz, 1H), 6.93 (d, J = 2.4 Hz, 1H), 5.00-4.70 (m, 2H), 4.67-4.55 (m, 1H), 4.32-4.11 (m, 1H), 3.99-3.89 (m, 1H), 3.57-3.44 (m, 1H), 3.26-3.17 (m, 1H), 3.13-3.04 (m, 1H), 2.95 (s, 1H), 2.86-2.75 (m, 1H), 2.17 (s, 3H), 1.29-1.10 (m, 3H). LCMS: Method K; Retention Time: 1.30 min MS (ESI, m/z): 557 [M + H]⁺ |
| 92 | C | A | 1-((2S,6R)-4-(4-((4-([1,2,4]triazolo[1,5-a]pyridin-7-yloxy)-3-methylphenyl)amino)pyrido[3,2-d]pyrimidin-6-yl)-2,6-dimethylpiperazin-1-yl)prop-2-en-1-one | ¹HNMR (400 MHz, DMSO-$d_6$) δ 9.35 (s, 1H), 8.94 (d, J = 7.6 Hz, 1H), 8.40 (d, J = 22.0 Hz, 2H), 7.99-7.90 (m, 3H), 7.67 (d, J = 9.4 Hz, 1H), 7.23 (d, J = 8.4 Hz, 1H), 7.03 (dd, J = 7.6, 2.4 Hz, 1H), 6.89-6.77 (m, 2H), 6.17 (dd, J = 16.4, 2.4 Hz, 1H), 5.72 (dd, J = 10.4, 2.4 Hz, 1H), 4.72 (d, J = 13.2 Hz, 2H), 4.53 (s, 2H), 3.27 (d, J = 13.6 Hz, 2H), 2.21 (s, 3H), 1.25 (d, J = 6.8 Hz, 6H). LCMS: Method G; Retention Time: 3.03 min MS (ESI, m/z): 536 [M + H]⁺ |

TABLE 10-continued

Compounds

| Example | Synthetic Method | Coupling Method | Compound Structure | Physical Data (¹H NMR and MS) |
|---|---|---|---|---|
| 93 | I | A | 1-(4-(4-((4-([1,2,4]triazolo[1,5-a]pyridin-7-yloxy)-2-fluoro-3-methylphenyl)amino)-5-fluoroquinazolin-6-yl)piperazin-1-yl)prop-2-en-1-one | ¹H NMR (400 MHz, DMSO) δ 9.12 (s, 1H), 8.97 (d, J = 7.5 Hz, 1H), 8.47 (s, 1H), 8.41 (s, 1H), 7.87 (t, J = 8.8 Hz, 1H), 7.75 (t, J = 9.1 Hz, 1H), 7.64 (d, J = 9.0 Hz, 1H), 7.11 (d, J = 8.5 Hz, 1H), 7.07 (dd, J = 7.5, 2.6 Hz, 1H), 6.93 (d, J = 2.5 Hz, 1H), 6.88 (dd, J = 16.7, 10.4 Hz, 1H), 6.16 (dd, J = 16.7, 2.4 Hz, 1H), 5.73 (dd, J = 10.5, 2.4 Hz, 1H), 3.77 (d, J = 12.6 Hz, 4H), 3.18 (s, 4H), 2.16 (s, 3H). LCMS: Method G; Retention Time: 1.03 min MS (ESI, m/z): 543 [M + H]⁺ |
| 94 | F | A | (S)-1-(4-(8-((4-([1,2,4]triazolo[1,5-a]pyridin-7-yloxy)-3-methylphenyl)amino)pyrimido[5,4-d]pyrimidin-2-yl)-6-methyl-3,6-dihydropyridin-1(2H)-yl)prop-2-en-1-one | ¹H NMR (400 MHz, DMSO-d₆) δ 10.13 (s, 1H), 9.45 (s, 1H), 8.96 (d, J = 7.5 Hz, 1H), 8.74 (s, 1H), 8.40 (s, 1H), 8.00-7.93 (m, 2H), 7.50 (d, J = 12.8 Hz, 1H), 7.33-7.25 (m, 1H), 7.05 (dd, J = 7.4, 2.6 Hz, 1H), 6.97-6.84 (m, 1H), 6.82 (d, J = 2.6 Hz, 1H), 6.19 (t, J = 17.0 Hz, 1H), 5.75 (d, J = 10.6 Hz, 1H), 5.05 (d, J = 80.3 Hz, 1H), 4.77-4.20 (m, 1H), 3.40-3.36 (m, 1H), 3.24 (d, J = 18.0 Hz, 1H), 2.95-2.56 (m, 1H), 2.23 (s, 3H), 1.42-1.31 (m, 3H). LCMS: Method G; Retention Time: 1.29 min MS (ESI, m/z): 520 [M + H]⁺ |
| 95 | F | A | (S)-1-(4-(8-((4-([1,2,4]triazolo[1,5-a]pyridin-7-yloxy)-3-methylphenyl)amino)pyrimido[5,4-d]pyrimidin-2-yl)-2-methyl-3,6-dihydropyridin-1(2H)-yl)prop-2-en-1-one | ¹H NMR (400 MHz, DMSO-d6) δ 10.13 (s, 1H), 9.44 (s, 1H), 8.95 (d, J = 7.5 Hz, 1H), 8.73 (s, 1H), 8.39 (s, 1H), 7.98-7.94 (m, 2H), 7.58 (d, J = 21.3 Hz, 1H), 7.28 (d, J = 9.5 Hz, 1H), 7.04 (dd, J = 7.5, 2.7 Hz, 1H), 7.01-6.82 (m, 1H), 6.82 (d, J = 2.6 Hz, 1H), 6.16 (d, J = 16.7 Hz, 1H), 5.73 (dd, J = 10.5, 2.4 Hz, 1H), 5.23-4.66 (m, 2H), 4.26-3.79 (m, 1H), 3.19 (d, J = 17.8 Hz, 1H), 2.89-2.57 (m, 1H), 2.23 (s, 3H), 1.24-1.11 (m, 3H). LCMS: Method G; Retention Time: 1.29 min MS (ESI, m/z): 520 [M + H]⁺ |
| 96 | F | A | (S)-1-(4-(8-((2-fluoro-3-methyl-4-((5-methyl-[1,2,4]triazolo[1,5-a]pyridin-7-yl)oxy)phenyl)amino)pyrimido[5,4-d]pyrimidin-2-yl)-6-methyl-3,6-dihydropyridin-1(2H)-yl)prop-2-en-1-one | ¹H NMR (400 MHz, DMSO-d₆) δ 10.09 (s, 1H), 9.47 (s, 1H), 8.69 (s, 1H), 8.43 (s, 1H), 7.83 (d, J = 10.5 Hz, 1H), 7.53 (d, J = 17.4 Hz, 1H), 7.06-7.04 (m, 1H), 7.03-6.86 (m, 1H), 6.85 (d, J = 2.4 Hz, 1H), 6.17 (d, J = 16.6 Hz, 1H), 5.74 (dd, J = 10.4, 2.4 Hz, 1H), 5.20-4.67 (m, 2H), 4.27-3.77 (m, 1H), 3.15 (d, J = 17.6 Hz, 1H), 2.84-2.64 (m, 4H), 2.19 (d, J = 1.9 Hz, 3H), 1.27-1.10 (m, 3H). LCMS: Method G; Retention Time: 1.42 min MS (ESI, m/z): 552 [M + H]⁺ |

TABLE 10-continued

Compounds

| Example | Synthetic Method | Coupling Method | Compound Structure | Physical Data (¹H NMR and MS) |
|---|---|---|---|---|
| 97 | F | A | (S)-1-(4-(8-((2-fluoro-3-methyl-4-((5-methyl-[1,2,4]triazolo[1,5-a]pyridin-7-yl)oxy)phenyl)amino)pyrimido[5,4-d]pyrimidin-2-yl)-2-methyl-3,6-dihydropyridin-1(2H)-yl)prop-2-en-1-one | ¹H NMR (400 MHz, DMSO-$d_6$) δ 10.07 (s, 1H), 9.47 (s, 1H), 8.70 (s, 1H), 8.43 (s, 1H), 7.83 (dt, J = 19.1, 9.3 Hz, 1H), 7.46 (d, 1H), 7.15 (dd, J = 8.9, 1.5 Hz, 1H), 7.04 (dd, J = 2.6, 1.2 Hz, 1H), 7.01-6.86 (m, 1H), 6.85 (d, J = 2.6 Hz, 1H), 6.19 (t, J = 17.2 Hz, 1H), 5.79-5.69 (m, 1H), 5.05 (d, J = 75.7 Hz, 1H), 4.49 (dd, J = 173.8, 13.3 Hz, 1H), 3.32-3.24 (m, 1H), 3.17 (d, J = 17.4 Hz, 1H), 2.96-2.55 (m, 4H), 2.19 (d, J = 2.1 Hz, 3H), 1.45-1.18 (m, 3H). LCMS: Method G; Retention Time: 1.40 min MS (ESI, m/z): 552 [M + H]⁺ |
| 98 | K | A | 2-(2,5-dimethylpyrazol-3-yl)-N-{7-ethoxy-1-[2-(prop-2-enoyl)-2-azaspiro[3.4]octan-6-yl]-1,3-benzodiazol-2-yl}pyridine-4-carboxamide | ¹H NMR (300 MHz, DMSO-$d_6$) δ 9.67 (s, 1H), 9.17 (s, 1H), 8.99 (d, J = 7.5 Hz, 1H), 8.42 (d, J = 2.7 Hz, 2H), 7.90-7.82 (m, 1H), 7.21-7.14 (m, 1H), 7.10-7.03 (m, 1H), 6.98-6.86 (m, 2H), 6.23-6.14 (m, 1H), 5.78-5.72 (m, 1H), 4.10-3.96 (m, 4H), 3.81-3.66 (m, 4H), 2.18 (s, 3H). LCMS: Method J; Retention Time: 0.98 min MS (ESI, m/z): 527 [M + H]⁺ |
| 99 | K | A | (S)-1-(4-(8-((4-([1,2,4]triazolo[1,5-a]pyridin-7-yloxy)-2-fluoro-3-methylphenyl)amino)pyrimido[5,4-d]pyrimidin-2-yl)-2-(difluoromethyl)piperazin-1-yl)prop-2-en-1-one | ¹H NMR (300 MHz, DMSO-d6) δ 9.61 (s, 1H), 9.17 (s, 1H), 8.99-8.94 (m, 1H), 8.41 (d, J = 5.7 Hz, 2H), 7.98-7.85 (m, 1H), 7.19-7.11 (m, 1H), 7.10-7.03 (m, 1H), 6.98-6.85 (m, 2H), 6.55-6.27 (m, 1H), 6.26-6.15 (m, 1H), 5.85-5.71 (m, 1H), 5.17-4.62 (m, 3H), 4.53-4.11 (m, 1H), 3.57-3.38 (m, 2H), 3.26-3.03 (m, 1H), 2.16 (s, 3H). LCMS: Method J; Retention Time: 1.04 min MS (ESI, m/z): 577 [M + H]⁺ |
| 100 | K | A | 1-((2R,3R)-4-(8-((4-([1,2,4]triazolo[1,5-a]pyridin-7-yloxy)-2-fluoro-3-methylphenyl)amino)pyrimido[5,4-d]pyrimidin-2-yl)-2,3-dimethylpiperazin-1-yl)prop-2-en-1-one | ¹H NMR (400 MHz, DMSO-d6) δ 9.50 (s, 1H), 9.15 (s, 1H), 8.98 (d, J = 7.6 Hz, 1H), 8.42 (d, J = 2.4 Hz, 2H), 8.03-7.94 (m, 1H), 7.15 (d, J = 8.8, 1H), 7.07 (dd, J = 7.6, 2.8 Hz, 1H), 6.93 (d, J = 2.8 Hz, 1H), 6.85-6.74 (m, 1H), 6.12 (dd, J = 16.8, 2.4 Hz, 1H), 5.68 (dd, J = 10.4, 2.4 Hz, 1H), 5.06-4.96 (m, 1H), 4.61-4.49 (m, 2H), 4.06-3.98 (m, 1H), 3.66-3.56 (m, 2H), 2.17 (d, J = 2.0 Hz, 3H), 1.39-1.31 (m, 6H). LCMS: Method M; Retention Time: 1.27 min MS (ESI, m/z): 555 [M + H]⁺ |

Biochemical Kinase Assay

Generation of Ba/F3 Stable Cell Lines

The gene encoding HER2-A775_G776insYVMA ("HER2-YVMA") was synthesized at GeneRay, cloned into the retroviral construct pMSCV-puro (Biovector), and packaged into retroviral particles. The virus was used to infect Ba/F3 cells (RIKEN) at multiplicity of infection=1 or 10 for 1 day. Infected cells were rescued in media (RPMI-1640 with 10% fetal bovine serum and 1% streptomycin and penicillin) supplemented with mouse IL-3 (10 ng/mL) for 2 days, and stable cell lines were selected by IL-3 withdrawal and puromycin (0.8 μg/mL) for 7 days. Monoclones were selected by single-cell dilution in IL-3-free medium containing puromycin (0.8 g/mL). Transformation of desired genes was confirmed by Sanger sequencing and western blot using the following antibody: HER2 (CST #2242).

Besides Ba/F3s, two commercially available cell lines were also used. NCI-H1781 is a HER2 exon20 insertion cell line bearing HER2-A775_G776insV-G776C. A431 bears amplification of the wild-type EGFR gene.

Cellular Phosphorylation Assay

Ba/F3 cells were plated at 50,000 cells/well (40 µL), or NCI-H1781 cells or A431 cells were plated at 12,500 cells/well (40 µL), in a 384-well plate for 1 day. Test compounds (40 nL) were then added in a 3-fold dilution series using the TECAN EV0200 liquid handler and incubated for 5 hours. Only for pEGFR analysis in A431, the cells were briefly stimulated with EGF (30 ng/mL) for 15 minutes. Media were removed using Apricot Designs. Phosphoproteins were analyzed using the phospho-EGFR Tyr1068 AlphaLISA kit ("pEGFR"; PerkinElmer #ALSU-PEGFR-B10K;) phospho-ERK Thr202/Tyr204 AlphaLISA kit ("pERK"; PerkinElmer #ALSU-PERK-A10K) or the phospho-ErbB2 Tyr1221/1222 AlphaLISA kit ("pHER2"; PerkinElmer #ALSU-PEB2-A10K;) according to the manufacturer's instructions. Briefly, cells were lysed with lysis buffer (10 µL) containing protease-inhibitor and phosphatase-inhibitor cocktails. The lysates were transferred into a new optical plate, incubated with the acceptor mix (5 µL) for 1.5-2 hours at room temperature in darkness, and then mixed with the donor mix (5 µL) overnight in darkness. Fluorescence was measured on a plate reader using the appropriate AlphaLISA settings. Half-maximal inhibitory concentration ($IC_{50}$) was calculated from percent inhibition and inhibitor concentration using four-parameter logistic regression. Compound potency can be interpreted by binning $IC_{50}$ values: bin A for high potency, $IC_{50}$<100 nM; bin B for medium potency, 100 nM≤$IC_{50}$<500 nM; bin C for low potency, 500 nM≤$IC_{50}$<1000 nM; and bind D for very low potency, $IC_{50}$≥1000 nM. Exemplary data is given in Table 11.

HER2 is phosphorylated when activated. Therefore, phospho-HER2 indicates HER2 activity in the cells. Compounds that potently inhibit the phosphorylation of the on-target cells (Ba/F3s and NCI-H1781) are also expected to inhibit/HER2 signaling in human cancers that express HER2, providing support for the potential clinical efficacy of such compounds. Similarly, compounds that do not potently inhibit the phosphorylation of the off-target A431 cell, which bears wild-type EGFR amplification, are expected to poorly inhibit wild-type EGFR signaling in humans and hence avoid the clinical toxicity arising from wild-type EGFR inhibition.

TABLE 11

Cellular Phosphorylation Assay $IC_{50}$ Summary
A < 100 nM ≤ B < 500 nM < C < ≤1000 nM ≤ D

| Compound # | A431 pERK | A431 pEGFR | NCI-H1781 pHER2 |
|---|---|---|---|
| 1 | B | B | A |
| 2 | C | C | A |
| 5 | D | D | A |
| 6 | B | B | |
| 7 | B | B | |
| 8 | D | D | |
| 9 | C | B | A |
| 10 | B | A | |
| 11 | | D | |
| 12 | C | C | A |
| 13 | D | B | A |
| 14 | D | D | A |
| 15 | D | D | |
| 16 | C | C | |
| 17 | D | D | |
| 18 | C | C | A |
| 19 | | D | A |
| 20 | D | D | |
| 21 | D | D | A |
| 22 | C | D | |
| 23 | | D | A |
| 24 | | D | |
| 25 | D | D | |
| 26 | D | D | |
| 27 | D | D | |
| 28 | D | D | |
| 29 | | D | |
| 30 | | D | |
| 31 | D | D | |
| 32 | C | | |
| 33 | D | D | |
| 34 | | D | |
| 35 | D | D | |
| 36 | D | D | |
| 37 | D | C | |
| 38 | | D | |
| 39 | D | D | |
| 40 | A | A | |
| 41 | A | A | |
| 42 | | D | |
| 43 | B | B | |
| 44 | | D | |
| 45 | D | D | |
| 46 | | D | |
| 47 | | D | |
| 48 | | D | |
| 49 | D | D | A |
| 50 | | D | A |
| 51 | D | D | A |
| 52 | D | D | A |
| 53 | D | D | A |
| 54 | B | C | A |
| 55 | B | D | A |
| 56 | | C | A |
| 57 | | B | |
| 58 | D | D | |
| 59 | | D | A |
| 60 | D | C | A |
| 61 | D | | |
| 62 | D | D | A |
| 63 | D | D | B |
| 64 | D | D | A |
| 65 | D | D | |
| 66 | | B | |
| 67 | C | D | |
| 68 | B | C | |
| 69 | B | C | |
| 70 | B | B | |
| 71 | B | B | |
| 72 | B | A | |
| 73 | B | B | |
| 74 | A | B | |
| 75 | B | C | |
| 76 | | D | |
| 77 | | B | |
| 78 | D | D | |
| 79 | | D | |
| 80 | C | D | |
| 81 | B | B | |
| 82 | B | A | |
| 83 | B | B | |
| 84 | B | C | |
| 85 | D | D | |
| 86 | B | B | |
| 92 | | D | |

TABLE 11-continued

Cellular Phosphorylation Assay IC$_{50}$ Summary
A < 100 nM ≤ B < 500 nM < C < ≤1000 nM ≤ D

| Compound # | A431 pERK | A431 pEGFR | NCI-H1781 pHER2 |
|---|---|---|---|
| 93 | | D | |
| 94 | D | C | |
| 95 | D | D | |
| 96 | D | D | |
| 97 | C | | |
| 98 | | C | |
| 99 | | A | |
| 100 | B | D | |

Cell Proliferation Assay

Ba/F3 cells were plated at 1,000 cells/well (40 µL), or NCI-H1781 or A431 cells were plated at 2,000 cells/well (40 µL), in a 384-well plate for 1 day. Test compounds (40 nL) were then added in a 3-fold dilution series using the TECAN EV0200 liquid handler and incubated for 48 hours ("2 days"), 72 hours ("3 days"), or 48 hours followed by renewal of compound solutions and further incubation for 72 hours ("2 days/3 days"). The 72-hour assay was necessary for NCI-H1781 cells, which are slow-growing, and the resupply of fresh compounds on day 3 obviated the potential confounding effects arising from compound degradation in cell media over 72 hours. Plates were equilibrated at room temperature for 15 minutes followed by addition of 40 µL CellTiter-Glo reagent (Promega). Luminescence was measured on a plate reader. Half-maximal inhibitory concentration (IC$_{50}$) was calculated from percent inhibition and inhibitor concentration using four-parameter logistic regression. A431 and NCI-H1781 showed a biphasic growth inhibition behavior with two inflexion points: the first is associated with on-target inhibition, whereas the second is associated with off-target toxicity. In these cases, the regression curve was drawn only for the first inflexion to accurately measure on-target growth inhibitory effect. Compound potency can be interpreted by binning IC$_{50}$ values: bin A for high potency, IC$_{50}$<100 nM; bin B for medium potency, 100 nM≤IC$_{50}$<500 nM; bin C for low potency, 500 nM≤IC$_{50}$<1,000 nM; and bind D for very low potency, IC$_{50}$≥1,000 nM. Exemplary data is given in Table 12.

Ba/F3, NCI-H1781, and A431 proliferation is driven by the oncogenes in the same way that cancer cell proliferation in humans is driven by the expression of equivalent oncogenes. Hence, compounds that potently inhibit the proliferation of the on-target cells (Ba/F3s and NCI-H1781) are also expected to inhibit human cancers that express equivalent oncogenes, providing support for the potential clinical efficacy of such compounds. Similarly, compounds that do not potently inhibit the off-target A431 cell, which bears wild-type EGFR amplification, are expected to poorly inhibit wild-type EGFR in humans and hence avoid the clinical toxicity arising from wild-type EGFR inhibition.

TABLE 12

Cell Proliferation Assay IC$_{50}$ Summary
A < 100 nM ≤ B < 500 nM ≤ C < 1000 nM ≤ D

| Compound # | Ba/F3 HER2-YVMA | NCI-H1781 |
|---|---|---|
| 1 | A | A |
| 2 | A | A |
| 5 | A | B |
| 6 | A | A |
| 7 | A | A |
| 8 | A | A |
| 9 | A | A |
| 10 | A | |
| 11 | A | B |
| 12 | A | A |
| 13 | A | A |
| 14 | B | |
| 15 | A | B |
| 16 | A | B |
| 17 | A | A |
| 18 | A | A |
| 19 | B | |
| 20 | A | A |
| 21 | B | B |
| 22 | A | A |
| 23 | C | |
| 24 | C | |
| 25 | B | |
| 26 | A | A |
| 27 | B | |
| 28 | B | |
| 29 | A | A |
| 30 | B | |
| 31 | D | D |
| 32 | A | A |
| 33 | B | |
| 34 | B | B |
| 35 | A | B |
| 36 | B | B |
| 37 | A | A |
| 38 | B | B |
| 39 | B | C |
| 40 | A | A |
| 41 | A | A |
| 42 | A | A |
| 43 | A | A |
| 44 | B | B |
| 45 | A | B |
| 46 | B | |
| 47 | B | |
| 48 | B | |
| 49 | A | A |
| 50 | | B |
| 51 | A | |
| 52 | A | A |
| 53 | A | A |
| 54 | A | A |
| 55 | A | |
| 56 | A | |
| 57 | A | |
| 58 | A | |
| 59 | C | |
| 60 | A | |
| 61 | B | |
| 62 | A | |
| 63 | C | |
| 64 | B | |
| 65 | B | |
| 66 | A | |
| 67 | A | |
| 68 | A | |
| 69 | A | |
| 70 | A | |
| 71 | B | |
| 72 | A | |
| 73 | A | |
| 74 | A | |
| 75 | A | |
| 76 | B | |
| 77 | A | |
| 78 | B | |
| 79 | C | |
| 80 | A | |
| 81 | A | |

TABLE 12-continued

Cell Proliferation Assay IC$_{50}$ Summary
A < 100 nM ≤ B < 500 nM ≤ C < 1000 nM ≤ D

| Compound # | Ba/F3 HER2-YVMA | NCI-H1781 |
|---|---|---|
| 82 | A | |
| 83 | A | |
| 84 | A | |
| 85 | A | |
| 86 | A | |
| 92 | A | |
| 93 | A | |
| 94 | A | |
| 95 | A | |
| 96 | B | |
| 97 | A | |
| 98 | A | |
| 99 | A | |
| 100 | A | |

Pharmacokinetics Assay

Rat pharmacokinetic studies: male Han Wistar rats are dosed with a test compound at 1 mg/kg by IV administration and/or 10 mg/kg by oral gavage in a suitable vehicle (for example, 20% HP-b-CD in DI water). Blood samples are collected from the jugular vein at multiple timepoints post dose. Approximately 0.2 mL of blood is collected at each time point and transferred into plastic micro centrifuge tubes containing EDTA-K2. The collection of tubes with blood samples and anti-coagulant are inverted several times for proper mixing and placed on wet ice prior to centrifugation. The blood samples are centrifuged at 4000 g for 5 min at 4 degrees Celsius to isolate the plasma. The plasma is stored at −75 degrees Celsius prior to analysis. Concentrations of a test compound in the plasma samples are analyzed using a LC-MS/MS method. WinNonlin (Phoenix™, version 8.3) or other similar software is used for pharmacokinetic calculations. The exemplified pharmacokinetic parameters that can be calculated from the plasma concentration versus time data are as follows:

IV Bolus administration: T½, C0, AUClast, AUCinf, MRTlast, Cl, Vss, Number of Points for Regression.

PO administration: F, T½, Cmax, Tmax, MRTlast, AUCinf, AUClast, Number of Points for Regression.

Mouse pharmacokinetic studies: female Balb/C mice are dosed with a test compound at 1 mg/kg IV and/or 10 mg/kg orally in a suitable vehicle (for example 20% HP-b-CD in DI water). Blood samples are collected from the dorsal metatarsal vein or heart puncture at multiple timepoints post dose. Approximately 0.03 mL of blood sample was collected at each time point and transferred into plastic micro centrifuge tubes containing Heparin-Na. Collection tubes with blood samples and anti-coagulant are inverted several times for proper mixing and placed on wet ice prior to centrifugation. Blood samples are centrifuged at 4000 g for 5 min at 4 degrees Celsius to obtain plasma. Plasma is stored at −75 degrees Celsius prior to analysis. Concentrations of the compound in the plasma samples are analyzed using a LC-MS/MS method. WinNonlin (Phoenix™, version 8.3) or other similar software was used for pharmacokinetic calculations. The exemplified pharmacokinetic parameters that can be calculated from the plasma concentration versus time data are as follows:

IV Bolus administration: T1/2, C0, AUClast, AUCinf, MRTlast, Cl, Vss, Number of Points for Regression.

PO administration: F, T1/2, Cmax, Tmax, MRTlast, AUCinf, AUClast, Number of Points for Regression.

Bidirectional Permeability in NIH-MDCKII-MDR1 Cells

MDCKII-MDR1 cells from the National Institutes of Health (NIH) are seeded onto membranes in 96-well Transwell plates to form a confluent cell monolayer. Test and reference compounds are prepared in transport buffer (HBSS, HEPES, pH 7.4) at 1 µM and added to either the apical compartment (for A→B) or the basolateral compartment (for B→A). The plates are shaken and then incubated. Aliquots are taken from both the apical and basolateral sides and transferred to a new plate with quenching buffer. These plates are vortexed and centrifuged, and aliquots of the supernatant are mixed with water and analyzed by LC/MS/MS. All incubations are performed in duplicate. Monolayer integrity is confirmed with the marker Lucifer Yellow.

The apparent permeability coefficient ($P_{app}$), in units of centimeter per second, can be calculated for MDCK-MDR1 drug transport assays using the following equation:

$$P_{app}=(V_A \times [drug]_{acceptor})/(Area \times Time \times [drug]_{initial,donor})$$

Where $V_A$ is the volume (in mL) in the acceptor well, Area is the surface area of the membrane (0.143 cm$^2$ for Transwell-96 Well Permeable Supports), and time is the total transport time in seconds.

Efflux ratio can be determined using the following equation:

$$\text{Efflux Ratio} = \frac{P_{app(B-A)}}{P_{app(A-B)}}$$

Where Papp (B-A) indicates the apparent permeability coefficient in basolateral to apical direction, and Papp (A-B) indicates the apparent permeability coefficient in apical to basolateral direction.

Mass balance (% recovery) can be determined using the following equation:

$$\text{Recovery \%} = \frac{[drug]_{acceptor} \times V_A + [drug]_{donor} \times V_D}{[drug]_{initial,donor} \times V_D} \times 100$$

Where VA is the volume (in mL) in the acceptor well (0.235 mL for Ap→Bl flux, and 0.075 mL for Bl→Ap), VD is the volume (in mL) in the donor well (0.075 mL for Ap→Bl flux, and 0.235 mL for Bl→Ap).

The leakage of Lucifer Yellow, in unit of percentage (%), can be calculated using the following equation:

% LY leakage=100×[LY]$_{acceptor}$/([LY]$_{donor}$+[LY]$_{acceptor}$)

Leakage of <1% is acceptable to indicate a well-qualified MDCK-MDR1 monolayer.

Kp and Kpuu Measurements in Rat and Mouse

The target dose (e.g., 10 mg/kg) of the test compound is prepared in a suitable formulation (e.g., 20% HP-b-CD in DI water) and administered PO to male Wistar Han rats or BALB/c mice. After a pre-specified amount of time (e.g., 1 h) the animals are sacrificed, and brain and blood samples are collected. The concentrations of test compound in plasma, brain homogenate and CSF samples (for rat only) are analyzed using LC/MS/MS. Binding measurements in plasma and brain can be conducted using a Rapid Equilibrium Dialysis Device.

The unbound fraction in plasma and brain homogenate, unbound fraction in brain, and free concentration in plasma and brain of test article can be calculated as follows:

Fu mea(%)=Peak Area Ratio acceptor chamber/Peak Area Ratio donor chamber*100%

Fu plasma (%)=Fu mea (%)
Fu brain (%)=1/D/((1/Fu mea−1)+1/D)*100%
D is the dilute factor of the homogenate.

Alternatively, the unbound fraction in plasma and brain homogenate can be measured in separate in vitro experiments. For brain binding, brain tissue is obtained from exsanguinated rats or mice, weighed, and homogenized with buffer by brain weight (g) to water volume (mL) ratio 1:4. Brain homogenate and test compound is added to each vial of a new plastic plate or separate plastic tube and vortexed. An aliquot is removed and transferred to a 96-well plate to act as a control sample. The remaining sample is incubated in the $CO_2$ incubator. After incubation, an aliquot of the spiked brain homogenate is transferred to the 96-well plate for analysis. Dialysis cells are loaded with brain homogenate sample and dialyzed against equal volume of dialysis buffer (PBS). After dialysis, aliquots from both buffer and brain homogenate chambers are added to separate tubes for analysis. All test compounds are tested in duplicate in the brain homogenate assay.

For plasma protein binding, a similar procedure is followed, using plasma from either rat or mouse. Plasma and test compound are added to each vial of a new plastic plate or separate plastic tube and vortexed. An aliquot is removed and transferred to a 96-well plate to act as a control sample. The remaining sample is incubated in the $CO_2$ incubator. After incubation, an aliquot of the spiked plasma is transferred to the 96-well plate for analysis. Dialysis cells are loaded with plasma sample and dialyzed against equal volume of dialysis buffer (PBS). After dialysis, aliquots from both buffer and plasma chambers are added to separate tubes for analysis. All test compounds are tested in duplicate in the plasma protein binding assay.

% Unbound=(Area ratio buffer chamber/Area ratio homogenate or plasma chamber)×100%

% Bound=100%−% Free

% Recovery=(Area ratio buffer chamber+Area ratio homogenate or plasma chamber)/(Area ratio Total sample)×100

Remaining %=Area ratio 6 hr/Area ratio 0 hr×100%

$$\text{Log} K = \text{Log}\left(\frac{\% \text{ Bound}}{100 - \% \text{ Bound}}\right)$$

% Unbound Brain=1/$D$/((1/(% Unbound/100)−1)+1/$D$)×100

D means the dilution factor when preparing the brain homogenate.
Conc. Free-plasma=Conc. plasma*Fu plasma
Conc. Free-brain=Conc. Brain*Fu brain
Kp=Conc. Brain/Conc. Plasma
Kpuu=Conc.free Brain/Conc.free Plasma Kinome Profiling Test compounds are evaluated in a panel of 381 kinases using the PhosphoSens CSox-Sensor Platform (AssayQuant Technologies Inc). This assay platform uses physiological ATP concentrations (1 mM) and measures kinase activity using a fluorogenic substrates with an optimized kinase recognition motif. Briefly, the test compound is mixed with the kinase, the fluorogenic peptide substrate, and ATP in reaction buffer, and fluorescence was recorded every 2 minutes for a total of 1.5-2 hours. When uninhibited, the kinase phosphorylates the substrate and induces fluorescence signal over time, the rate of which can be measured using the initial slope of fluorescence versus time (also called the initial velocity). Inhibition of kinase activity represses initial velocity. Inhibitory activity is calculated as the ratio between the initial velocity of the kinase in the presence and in the absence of the inhibitor, and is expressed as percent inhibition. Data are processed using GraphPad Prism or GeneData Mechanistic Action software.

PDX Study

Female athymic Nude-Foxn1nu mice are implanted subcutaneously in the left flank with tumor fragments from model CTG-2543 (Champions Oncology), a NSCLC tumor model harboring HER2$^{YVMA}$. In the efficacy study, mice are randomized to 5 mice per group based on tumor volume, and are administered with vehicle or test compounds. Tumor volume and body weight are measured twice per week. After the final dose, plasma samples are collected for PK analysis.

In a separate PK/PD study, CTG-2543 tumors are subcutaneously implanted in mice and allowed to grow before the mice are randomized based on tumor volume and administered with vehicle or test compounds by oral gavage. Tumor and blood samples are collected at multiple timepoints post the final dose for PK and PD analysis. Compound concentration in the plasma is determined by LC-MS/MS. Pharmacodynamic measurements include western blot, IHC assays, and transcript biomarker analysis.

N87-Luc Intracranial Efficacy Study

NCI-N87 cells stably expressing a luciferase reporter are stereotactically implanted into the right forebrains of 6- to 8-week-old female Balb/c nude mice. Two weeks after implantation, mice are randomized based on the mean bioluminescence signal into groups of n=10 mice each and received treatment of either appropriate vehicle or different dose levels of test compounds orally. Bioluminescence and body weight are measured at regular intervals until study endpoint. At study endpoint, blood and brain samples will be collected for PK measurements.

INCORPORATION BY REFERENCE

All U.S. and PCT patent publications and U.S. patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

The invention claimed is:
1. A compound of Formula (I-i):

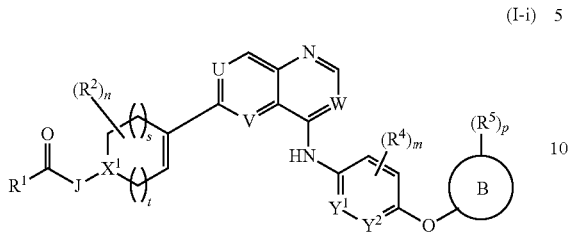

or a pharmaceutically acceptable salt, stereoisomer, or tautomer thereof,
wherein:
- $R^1$ is $C_{1-5}$ alkyl, $C_{2-5}$ alkenyl, $C_{2-5}$ alkynyl, or 3- to 6-membered heterocyclyl, wherein the $C_{1-5}$ alkyl, $C_{2-5}$ alkenyl, $C_{2-5}$ alkynyl, or 3- to 6-membered heterocyclyl is optionally substituted with one or more independently selected $R^a$ substituents;
- each $R^a$ is independently halo, CN, $C_{1-5}$ alkyl, $C(O)OC_{1-5}$ alkyl, $N(R^{n1})_2$, $OC_{1-5}$ alkyl, $OC_{1-5}$ alkylene-$OC_{1-5}$ alkyl, or 3- to 6-membered heterocyclyl, wherein each $C_{1-5}$ alkyl, $C(O)OC_{1-5}$ alkyl, $OC_{1-5}$ alkyl, $OC_{1-5}$ alkylene-$OC_{1-5}$ alkyl, and 3- to 6-membered heterocyclyl is optionally and independently substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;
- each $R^{n1}$ is independently H or $C_{1-5}$ alkyl;
- (i) J is $-NR^b-$;
  - $R^b$ is H or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl; and
  - $X^1$ is CH; or
- (ii) J is a bond; and
  - $X^1$ is N;
  - each $R^2$ is independently $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl; or
- two geminal $R^2$, taken together, form =O; or
- two non-geminal $R^2$, taken together, form a $C_{1-4}$ alkylene bridge;
- n is 0, 1, 2, or 3;
- s is 0, 1, or 2;
- t is 1 or 2;
- U is $CR^c$ or N;
- $R^c$ is H, halo, or $OC_{1-5}$ alkyl, wherein the $OC_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;
- V is $CR^d$ or N;
- $R^d$ is H, halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;
- W is $CR^e$ or N;
- $R^e$ is H, halo, or CN;
- $Y^1$ is CH, $CR^4$, or N;
- $Y^2$ is CH, $CR^4$, or N;
- each $R^4$ is independently halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)

$R^{40}$, $S(O)R^{38}$, $S(O)_2R^{39}$, $S(O)_2NR^{36}R^{37}$, $S(O)_2OH$, $S(O)_2O$(hydrocarbyl), cycloalkyl, heterocyclyl, aryl, and heteroaryl;

m is 0, 1, 2, 3, or 4;

ring B is 6- to 10-membered aryl or 5- to 10-membered heteroaryl;

each $R^5$ is independently halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(alkyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;

p is 0, 1, 2, or 3;

each $R^{36}$ is independently H or hydrocarbyl;

each $R^{37}$ is independently H or hydrocarbyl; or each $R^{36}$ and $R^{37}$, together with the nitrogen atom to which they are attached, independently forms a 4- to 8-membered heterocyclyl;

each $R^{38}$ is independently hydrocarbyl;

each $R^{39}$ is independently hydrocarbyl; and each $R^{40}$ is independently hydrocarbyl;

with the provisos that:
(1) at least one of U and V is N; and
(2) at least one of $Y^1$ and $Y^2$ is CH or CR$^4$.

2. The compound of claim 1, or a pharmaceutically acceptable salt, stereoisomer, or tautomer thereof, wherein $R^1$ is unsubstituted.

3. The compound of claim 1, or a pharmaceutically acceptable salt, stereoisomer, or tautomer thereof, wherein $R^1$ is substituted with one or more $R^a$ substituents independently selected from the group consisting of F, Cl, CN, CH$_3$, CH$_2$N(CH$_3$)$_2$, CH$_2$OCH$_3$, CH$_2$OCH$_2$CH$_2$OCH$_3$, CH$_2$-morpholino, CH$_2$CH$_2$N(CH$_3$)$_2$, C(O)OCH$_3$, N(CH$_3$)$_2$, or pyrrolidinyl.

4. The compound of claim 1, or a pharmaceutically acceptable salt, stereoisomer, or tautomer thereof, wherein $R^1$ is $C_{2-5}$ alkenyl, wherein the $C_{2-5}$ alkenyl is optionally substituted with one or more independently selected $R^a$ substituents.

5. The compound of claim 1, or a pharmaceutically acceptable salt, stereoisomer, or tautomer thereof, wherein $R^1$ is $C_{2-5}$ alkynyl, wherein the $C_{2-5}$ alkynyl is optionally substituted with one or more independently selected $R^a$ substituents.

6. The compound of claim 1, or a pharmaceutically acceptable salt, stereoisomer, or tautomer thereof, wherein $R^1$ is:

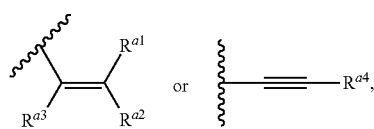

wherein:

$R^{a1}$ is H, halo, CN, $C_{1-5}$ alkyl, CH$_2$OC$_{1-5}$ alkyl, CH$_2$OCH$_2$OC$_{1-5}$ alkyl, CH$_2$OCH$_2$CH$_2$OC$_{1-5}$ alkyl, C(O)OC$_{1-5}$ alkyl, NH$_2$, NHC$_{1-5}$ alkyl, N(C$_{1-5}$ alkyl)$_2$, or 3- to 6-membered heterocyclyl;

wherein the $C_{1-5}$ alkyl is optionally substituted with one or more substituents independently selected from the group consisting of halo, CN, NO$_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl; and wherein the C(O)OC$_{1-5}$ alkyl or 3- to 6-membered heterocyclyl is optionally substituted with one or more substituents independently selected from the group consisting of halo, CN, NO$_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;

$R^{a2}$ is H, halo, CN, $C_{1-5}$ alkyl, CH$_2$OC$_{1-5}$ alkyl, CH$_2$OCH$_2$OC$_{1-5}$ alkyl, CH$_2$OCH$_2$CH$_2$OC$_{1-5}$ alkyl, C(O)OC$_{1-5}$ alkyl, NH$_2$, NHC$_{1-5}$ alkyl, N(C$_{1-5}$ alkyl)$_2$, or 3- to 6-membered heterocyclyl;

wherein the $C_{1-5}$ alkyl is optionally substituted with one or more substituents independently selected from the group consisting of halo, CN, NO$_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl; and wherein the C(O)OC$_{1-5}$ alkyl or 3- to 6-membered heterocyclyl is optionally substituted with one or more substituents independently selected from the group consisting of halo, CN, NO$_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;

$R^{a3}$ is H, halo, CN, $C_{1-5}$ alkyl, $CH_2OC_{1-5}$ alkyl, $CH_2OCH_2OC_{1-5}$ alkyl, $CH_2OCH_2CH_2OC_{1-5}$ alkyl, $C(O)OC_1s$ alkyl, $NH_2$, $NHC_{1-5}$ alkyl, $N(C_{1-5}$ alkyl$)_2$, or 3- to 6-membered heterocyclyl;

wherein the $C_{1-5}$ alkyl is optionally substituted with one or more substituents independently selected from the group consisting of halo, CN, $NO_2$, aralkyl, C(NH)H, C(NH)hydrocarbyl, $C(NH)NH_2$, C(NH)NH(hydrocarbyl), C(NH)N(hydrocarbyl)$_2$, C(O)H, C(O)hydrocarbyl, $C(O)NH_2$, C(O)NH(hydrocarbyl), C(O)N(hydrocarbyl)$_2$, C(O)OH, C(O)O(hydrocarbyl), $C(O)SR^{40}$, C(S)hydrocarbyl, C(S)OH, C(S)O(hydrocarbyl), $NH_2$, NH(hydrocarbyl), N(hydrocarbyl)$_2$, $N_3$, OH, $OS(O)_2OH$, $P(O)_{1-2}$hydrocarbyl, $P(O)_{1-2}OH$, $P(O)_{1-2}O$(hydrocarbyl), SH, S(hydrocarbyl), $SC(O)R^{40}$, $S(O)R^{38}$, $S(O)_2R^{39}$, $S(O)_2NR^{36}R^{37}$, $S(O)_2OH$, $S(O)_2O$(hydrocarbyl), cycloalkyl, heterocyclyl, aryl, and heteroaryl; and wherein the $C(O)OC_{1-5}$ alkyl or 3- to 6-membered heterocyclyl is optionally substituted with one or more substituents independently selected from the group consisting of halo, CN, $NO_2$, aralkyl, C(NH)H, C(NH)hydrocarbyl, $C(NH)NH_2$, C(NH)NH(hydrocarbyl), C(NH)N(hydrocarbyl)$_2$, C(O)H, C(O)hydrocarbyl, $C(O)NH_2$, C(O)NH(hydrocarbyl), C(O)N(hydrocarbyl)$_2$, C(O)OH, C(O)O(hydrocarbyl), $C(O)SR^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), $OS(O)_2OH$, $P(O)_{1-2}$hydrocarbyl, $P(O)_{1-2}OH$, $P(O)_{1-2}O$(hydrocarbyl), SH, S(hydrocarbyl), $SC(O)R^{40}$, $S(O)R^{38}$, $S(O)_2R^{39}$, $S(O)_2NR^{36}R^{37}$, $S(O)_2OH$, $S(O)_2O$(hydrocarbyl), cycloalkyl, heterocyclyl, aryl, and heteroaryl; and $R^{a4}$ is H, halo, CN, $C_{1-5}$ alkyl, $CH_2OC_{1-5}$ alkyl, $CH_2OCH_2OC_{1-5}$ alkyl, $CH_2OCH_2CH_2OC_{1-5}$ alkyl, $C(O)OC_{1-5}$ alkyl, $NH_2$, $NHC_{1-5}$ alkyl, $N(C_{1-5}$ alkyl$)_2$, or 3- to 6-membered heterocyclyl;

wherein the $C_{1-5}$ alkyl is optionally substituted with one or more substituents independently selected from the group consisting of halo, CN, $NO_2$, aralkyl, C(NH)H, C(NH)hydrocarbyl, $C(NH)NH_2$, C(NH)NH(hydrocarbyl), C(NH)N(hydrocarbyl)$_2$, C(O)H, C(O)hydrocarbyl, $C(O)NH_2$, C(O)NH(hydrocarbyl), C(O)N(hydrocarbyl)$_2$, C(O)OH, C(O)O(hydrocarbyl), $C(O)SR^{40}$, C(S)hydrocarbyl, C(S)OH, C(S)O(hydrocarbyl), $NH_2$, NH(hydrocarbyl), N(hydrocarbyl)$_2$, $N_3$, OH, $OS(O)_2OH$, $P(O)_{1-2}$hydrocarbyl, $P(O)_{1-2}OH$, $P(O)_{1-2}O$(hydrocarbyl), SH, S(hydrocarbyl), $SC(O)R^{40}$, $S(O)R^{38}$, $S(O)_2R^{39}$, $S(O)_2NR^{36}R^{37}$, $S(O)_2OH$, $S(O)_2O$(hydrocarbyl), cycloalkyl, heterocyclyl, aryl, and heteroaryl; and wherein the $C(O)OC_{1-5}$ alkyl or 3- to 6-membered heterocyclyl is optionally substituted with one or more substituents independently selected from the group consisting of halo, CN, $NO_2$, aralkyl, C(NH)H, C(NH)hydrocarbyl, $C(NH)NH_2$, C(NH)NH(hydrocarbyl), C(NH)N(hydrocarbyl)$_2$, C(O)H, C(O)hydrocarbyl, $C(O)NH_2$, C(O)NH(hydrocarbyl), C(O)N(hydrocarbyl)$_2$, C(O)OH, C(O)O(hydrocarbyl), $C(O)SR^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), $OS(O)_2OH$, $P(O)_{1-2}$hydrocarbyl, $P(O)_{1-2}OH$, $P(O)_{1-2}O$(hydrocarbyl), SH, S(hydrocarbyl), $SC(O)R^{40}$, $S(O)R^{38}$, $S(O)_2R^{39}$, $S(O)_2NR^{36}R^{37}$, $S(O)_2OH$, $S(O)_2O$(hydrocarbyl), cycloalkyl, heterocyclyl, aryl, and heteroaryl.

7. The compound of claim 1, or a pharmaceutically acceptable salt, stereoisomer, or tautomer thereof, wherein $R^1$ is:

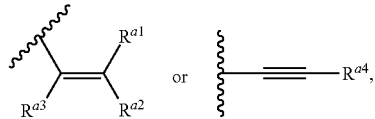

wherein:
$R^{a1}$ is H;
$R^{a2}$ is H;
$R^{a3}$ is H; and
$R^{a4}$ is H.

8. The compound of claim 1, or a pharmaceutically acceptable salt, stereoisomer, or tautomer thereof, wherein $R^1$ is $CH_3$, $CH_2CH_3$, $CH=CH_2$, $C\equiv CH$, or oxiranyl.

9. The compound of claim 1, or a pharmaceutically acceptable salt, stereoisomer, or tautomer thereof, wherein:
J is a bond; and
$X^1$ is N.

10. The compound of claim 1, or a pharmaceutically acceptable salt, stereoisomer, or tautomer thereof, wherein:
each $R^2$ is independently $CH_3$ or $CH_2F$; or
two geminal $R^2$, taken together, form =O; or
two non-geminal $R^2$, taken together, form a —$CH_2$— or —$CH_2CH_2$— bridge.

11. The compound of claim 1, or a pharmaceutically acceptable salt, stereoisomer, or tautomer thereof, wherein U is N.

12. The compound of claim 1, or a pharmaceutically acceptable salt, stereoisomer, or tautomer thereof, wherein V is N.

13. The compound of claim 1, or a pharmaceutically acceptable salt, stereoisomer, or tautomer thereof, wherein W is N.

14. The compound of claim 1, or a pharmaceutically acceptable salt, stereoisomer, or tautomer thereof, wherein:
$Y^1$ is $CR^4$; and
$Y^2$ is $CR^4$.

15. The compound of claim 14, or a pharmaceutically acceptable salt, stereoisomer, or tautomer thereof, wherein:
$Y^1$ is $CR^4$; and
$Y^2$ is N.

16. The compound of claim 1, or a pharmaceutically acceptable salt, stereoisomer, or tautomer thereof, wherein each $R^4$ is independently F, Cl, $CH_3$, $CHF_2$, or $OCH_3$.

17. The compound of claim 1, or a pharmaceutically acceptable salt, stereoisomer, or tautomer thereof, wherein ring B is:

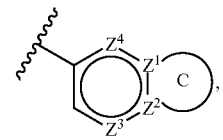

wherein:
$Z^1$ is C or N;
$Z^2$ is C or N;
$Z^3$ is C or N;
$Z^4$ is C or N; and
ring C is 5- or 6-membered heteroaryl;

with the provisos that:
(1) any atom of ring B is optionally substituted with $R^5$ as valency permits; and
(2) the number of optional $R^5$ substituents does not exceed 3.

18. The compound of claim 17, or a pharmaceutically acceptable salt, stereoisomer, or tautomer thereof, wherein ring B is:

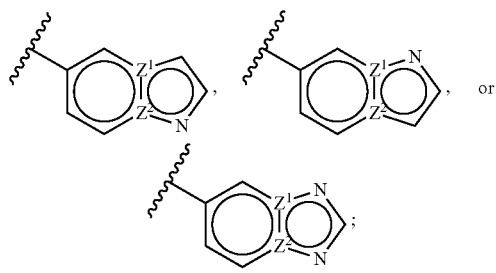

with the provisos that:
(1) any atom of ring B is optionally substituted with $R^5$ as valency permits; and
(2) the number of optional $R^5$ substituents does not exceed 3.

19. The compound of claim 17, or a pharmaceutically acceptable salt, stereoisomer, or tautomer thereof, wherein ring B is:

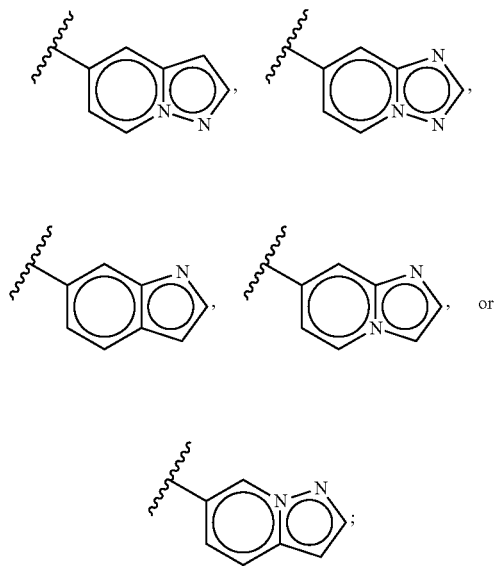

with the provisos that:
(1) any atom of ring B is optionally substituted with $R^5$ as valency permits; and
(2) the number of optional $R^5$ substituents does not exceed 3.

20. The compound of claim 1, or a pharmaceutically acceptable salt, stereoisomer, or tautomer thereof, wherein p is 0.

21. The compound of claim 1, wherein the compound is of Formula (I-i-a):

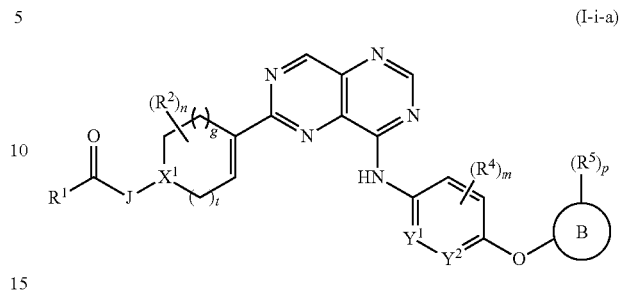

(I-i-a)

or a pharmaceutically acceptable salt, stereoisomer, or tautomer thereof.

22. The compound of claim 21, wherein the compound is of Formula (I-i-a0):

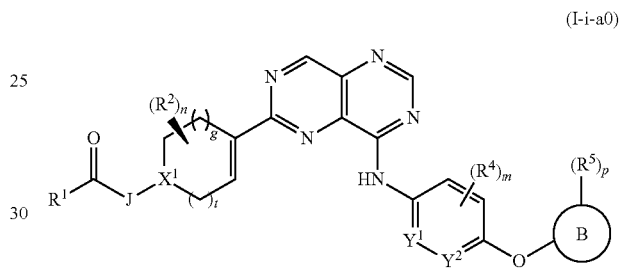

(I-i-a0)

or a pharmaceutically acceptable salt thereof.

23. The compound of claim 21, wherein the compound is of Formula (I-i-a1):

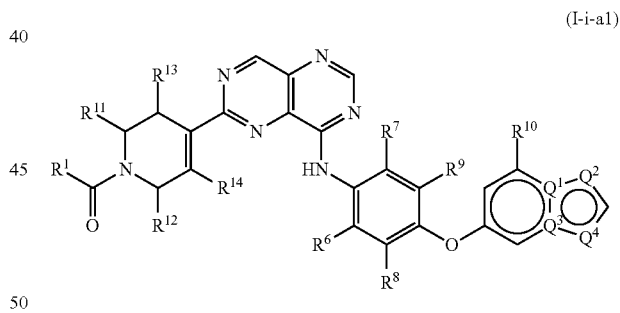

(I-i-a1)

or a pharmaceutically acceptable salt, stereoisomer, or tautomer thereof,
wherein:
$Q^1$ is $CR^g$ or $NR^f$;
$Q^2$ is $CR^g$ or $NR^f$;
$Q^3$ is $CR^g$ or $NR^f$;
$Q^4$ is $CR^g$ or $NR^f$;
each $R^f$ is independently absent, H, or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)$SR^{40}$, C(S)hydrocarbyl, C(S)OH, C(S)O (hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

each $R^g$ is independently absent, H, or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^6$ is H, halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^7$ is H, halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^8$ is H, halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^9$ is H, halo, $C_{1-5}$ alkyl, or $OC_{1-5}$ alkyl, wherein the $C_{1-5}$ alkyl or $OC_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$ hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^{10}$ is H, halo, or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl; and $R^{11}$ is H or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^{12}$ is H or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)S$R^{40}$, C(S)hydrocarbyl, C(S)OH, C(S)O(hydrocarbyl), $NH_2$, NH(hydrocarbyl), N(hydrocarbyl)$_2$, $N_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)$R^{40}$, S(O)$R^{38}$, S(O)$_2R^{39}$, S(O)$_2NR^{36}R^{37}$, S(O)$_2$OH, S(O)$_2$O(hydrocarbyl), cycloalkyl, heterocyclyl, aryl, and heteroaryl;

$R^{13}$ is H or $C_{1-5}$ alkyl, wherein the $C_{1-5}$ alkyl is optionally substituted with one or more substituents independently selected from the group consisting of halo, CN, $NO_2$, aralkyl, C(NH)H, C(NH)hydrocarbyl, C(NH)$NH_2$, C(NH)NH(hydrocarbyl), C(NH)N(hydrocarbyl)$_2$, C(O)H, C(O)hydrocarbyl, C(O)$NH_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl; and R$^{14}$ is H or C$_{1-5}$ alkyl, wherein the C$_{1-5}$ alkyl is optionally substituted with one or more substituents independently selected from the group consisting of halo, CN, NO$_2$, aralkyl, C(NH)H, C(NH)hydrocarbyl, C(NH)NH$_2$, C(NH)NH(hydrocarbyl), C(NH)N(hydrocarbyl)$_2$, C(O)H, C(O)hydrocarbyl, C(O)NH$_2$, C(O)NH(hydrocarbyl), C(O)N(hydrocarbyl)$_2$, C(O)OH, C(O)O(hydrocarbyl), C(O)SR$^{40}$, C(S)hydrocarbyl, C(S)OH, C(S)O(hydrocarbyl), NH$_2$, NH(hydrocarbyl), N(hydrocarbyl)$_2$, N$_3$, OH, O(hydrocarbyl), OS(O)$_2$OH, P(O)$_{1-2}$hydrocarbyl, P(O)$_{1-2}$OH, P(O)$_{1-2}$O(hydrocarbyl), SH, S(hydrocarbyl), SC(O)R$^{40}$, S(O)R$^{38}$, S(O)$_2$R$^{39}$, S(O)$_2$NR$^{36}$R$^{37}$, S(O)$_2$OH, S(O)$_2$O(hydrocarbyl), cycloalkyl, heterocyclyl, aryl, and heteroaryl;

with the provisos that:

(1) at least one of R$^{11}$, R$^{12}$, R$^{13}$, and R$^{14}$ is H; and (2) at least one of Q$^1$, Q$^2$, Q$^3$, and Q$^4$ is CR$^g$.

24. The compound of claim 23, wherein the compound is of Formula (I-i-a2):

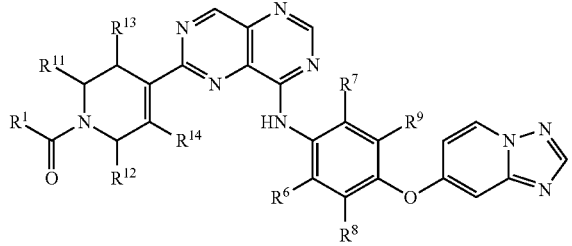

(I-i-a2)

or a pharmaceutically acceptable salt, stereoisomer, or tautomer thereof.

25. The compound of claim 23, wherein the compound is of Formula (I-i-a3):

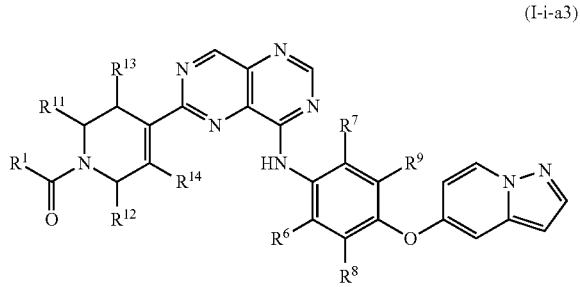

(I-i-a3)

or a pharmaceutically acceptable salt, stereoisomer, or tautomer thereof.

26. The compound of claim 23, wherein the compound is of Formula (I-i-a4):

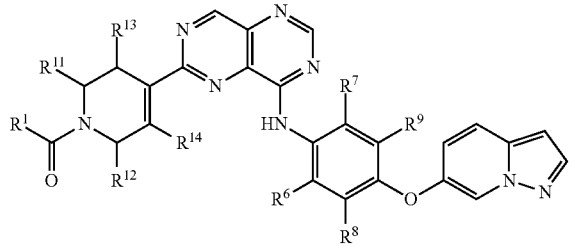

(I-i-a4)

or a pharmaceutically acceptable salt, stereoisomer, or tautomer thereof.

27. The compound of claim 23, wherein the compound is of Formula (I-i-a5):

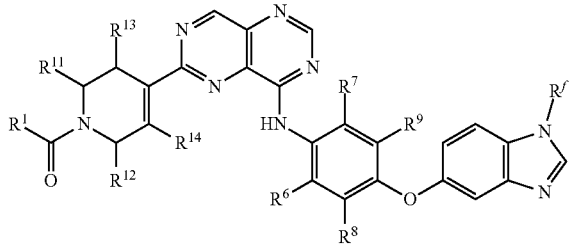

(I-i-a5)

or a pharmaceutically acceptable salt, stereoisomer, or tautomer thereof.

28. The compound of claim 23, wherein the compound is of Formula (I-i-a6):

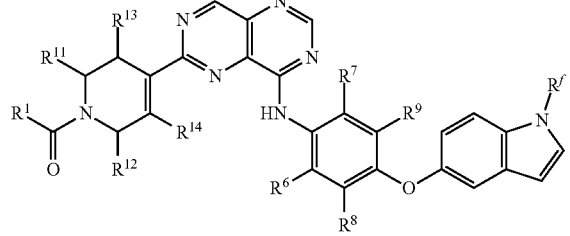

(I-i-a6)

or a pharmaceutically acceptable salt, stereoisomer, or tautomer thereof.

29. The compound of claim 1, wherein the compound is of Formula (I-i-b):

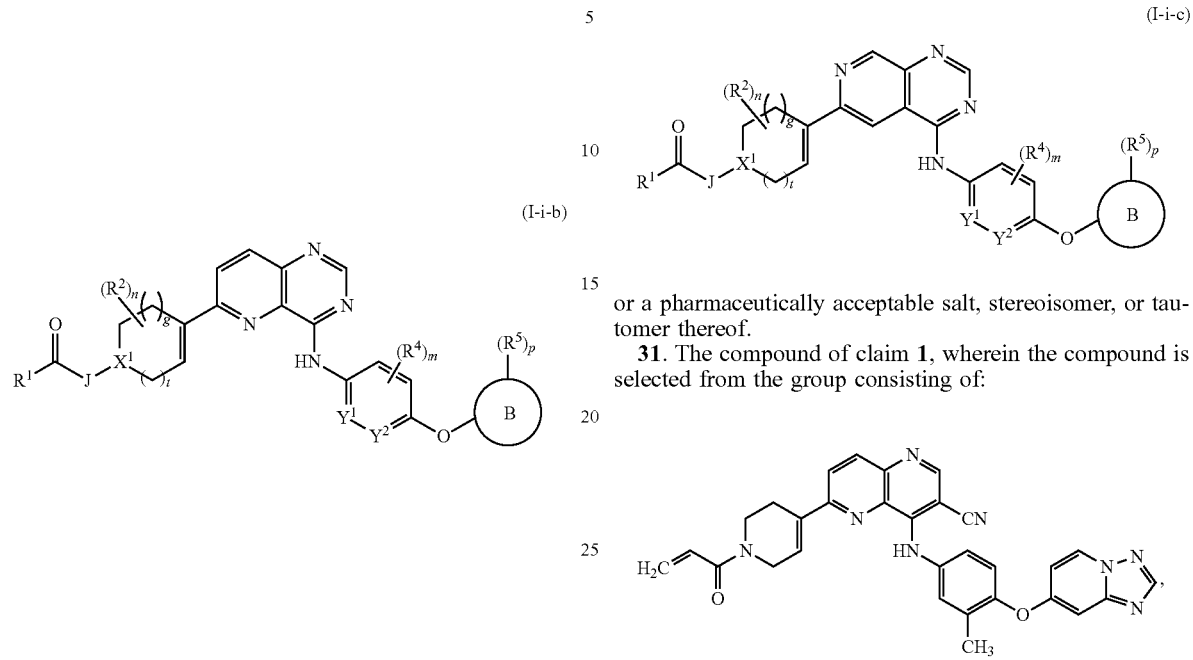

(I-i-b)

or a pharmaceutically acceptable salt, stereoisomer, or tautomer thereof.

30. The compound of claim 1, wherein the compound is of Formula (I-i-c):

(I-i-c)

or a pharmaceutically acceptable salt, stereoisomer, or tautomer thereof.

31. The compound of claim 1, wherein the compound is selected from the group consisting of:

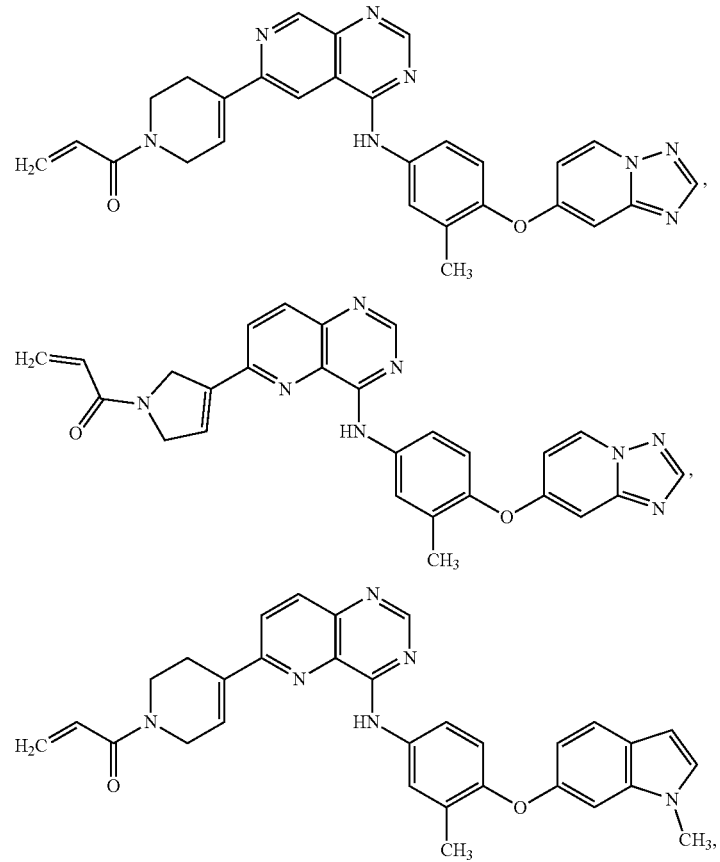

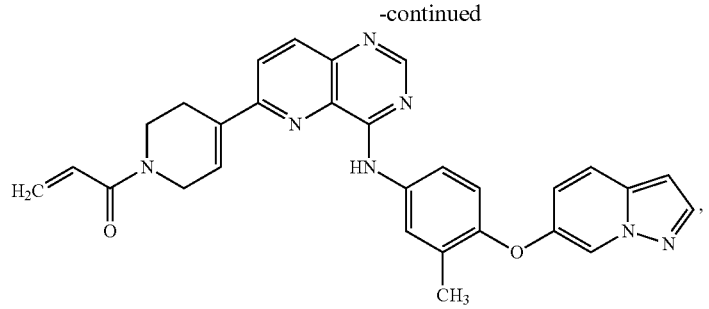,
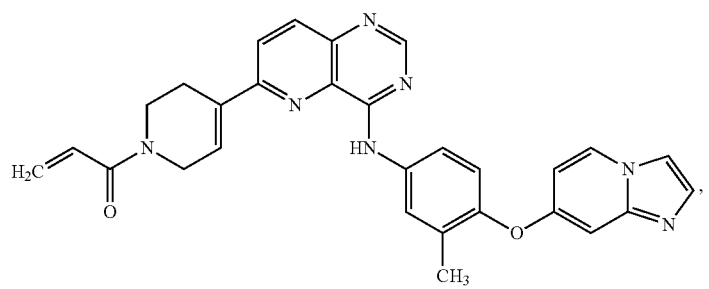,
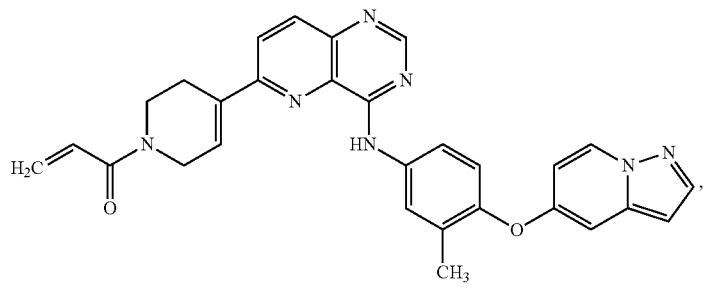,
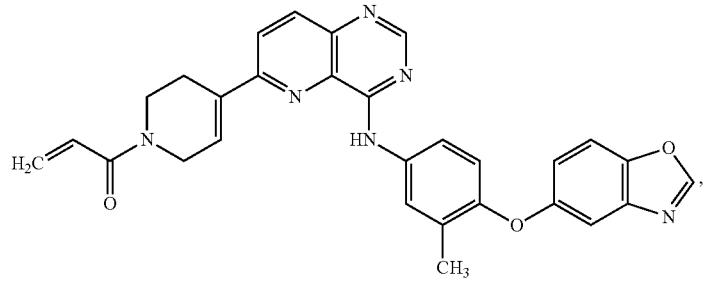,
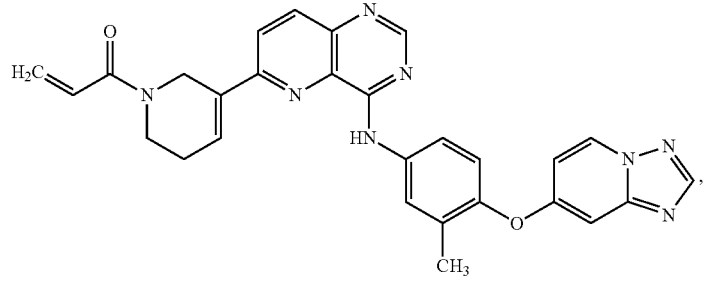,
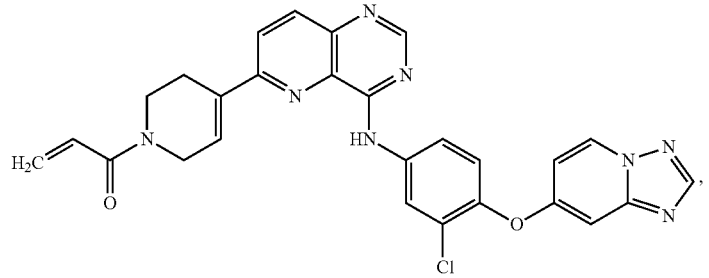,

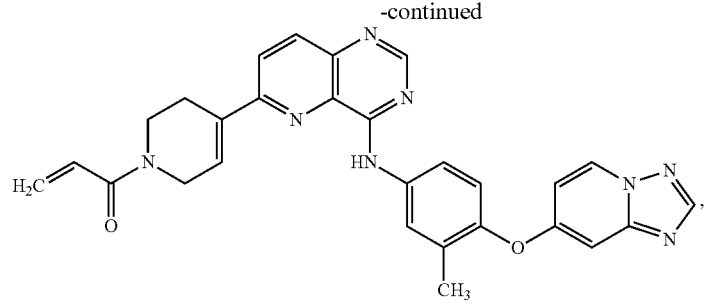
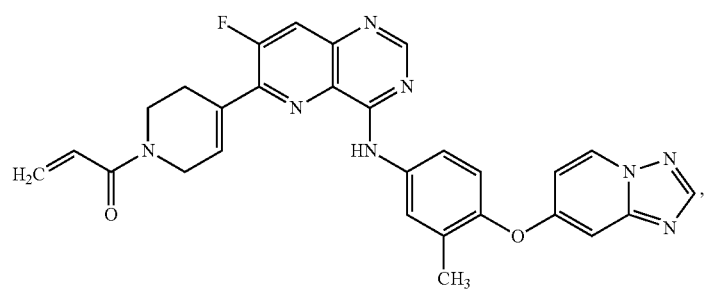
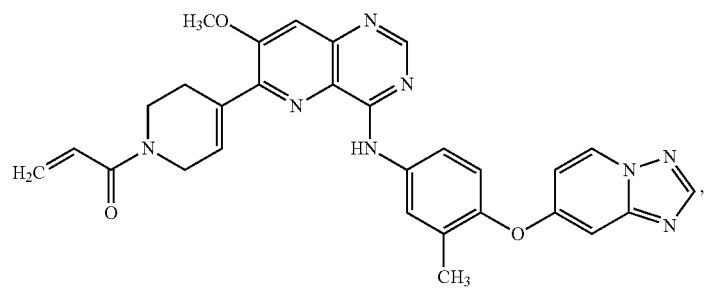
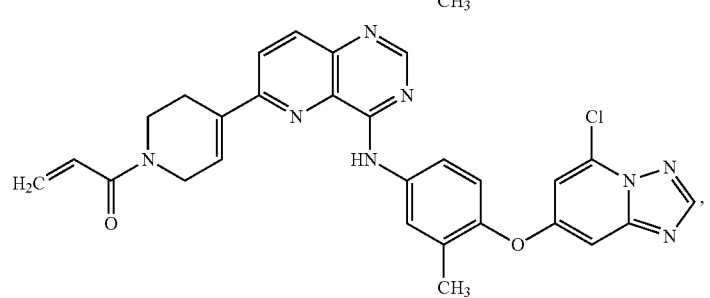
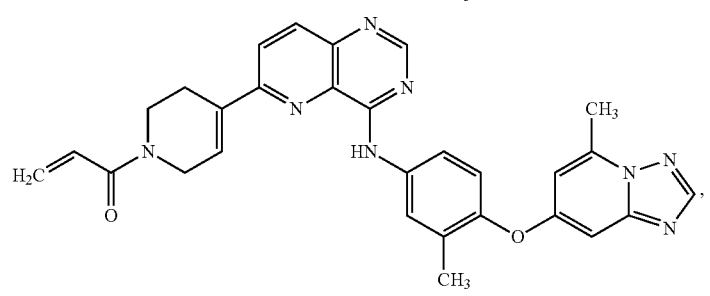
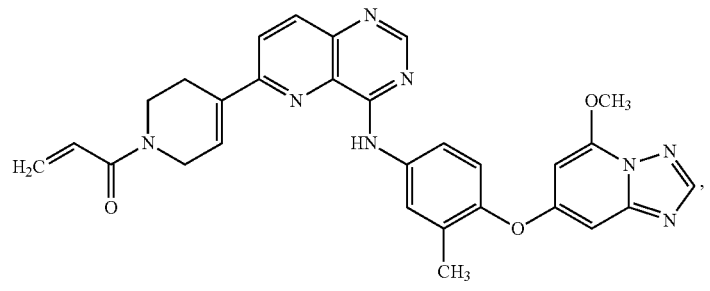

-continued
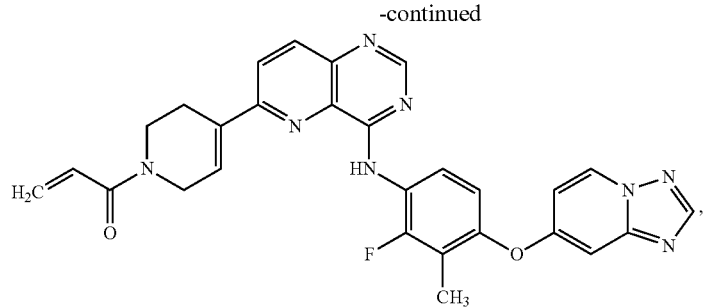
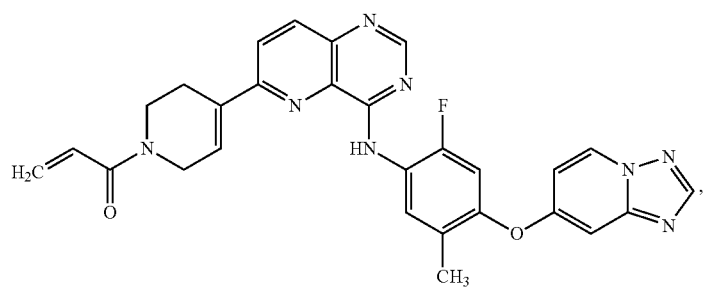
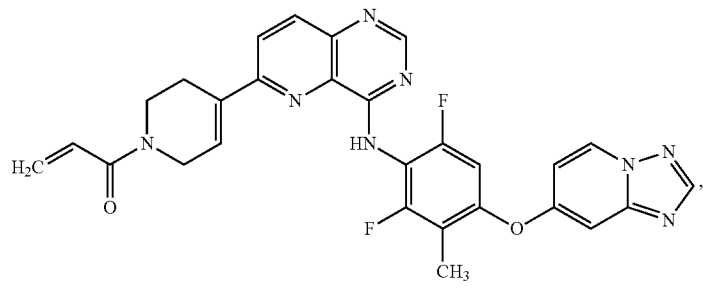
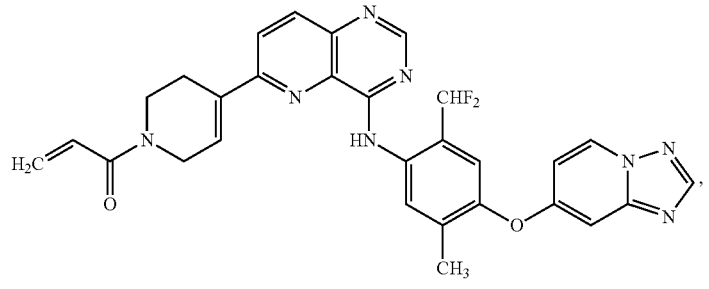
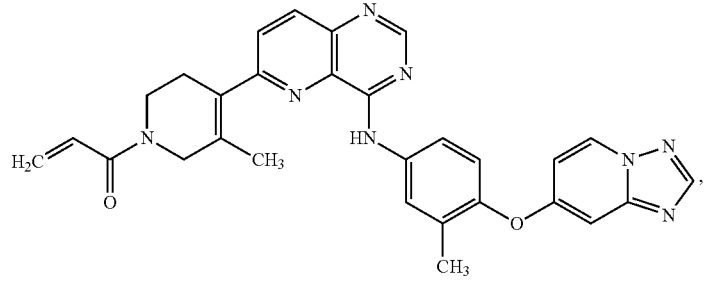
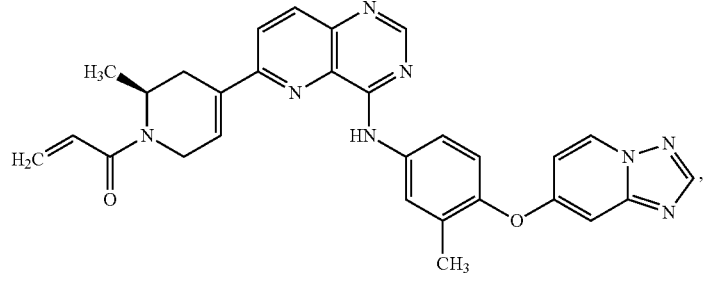

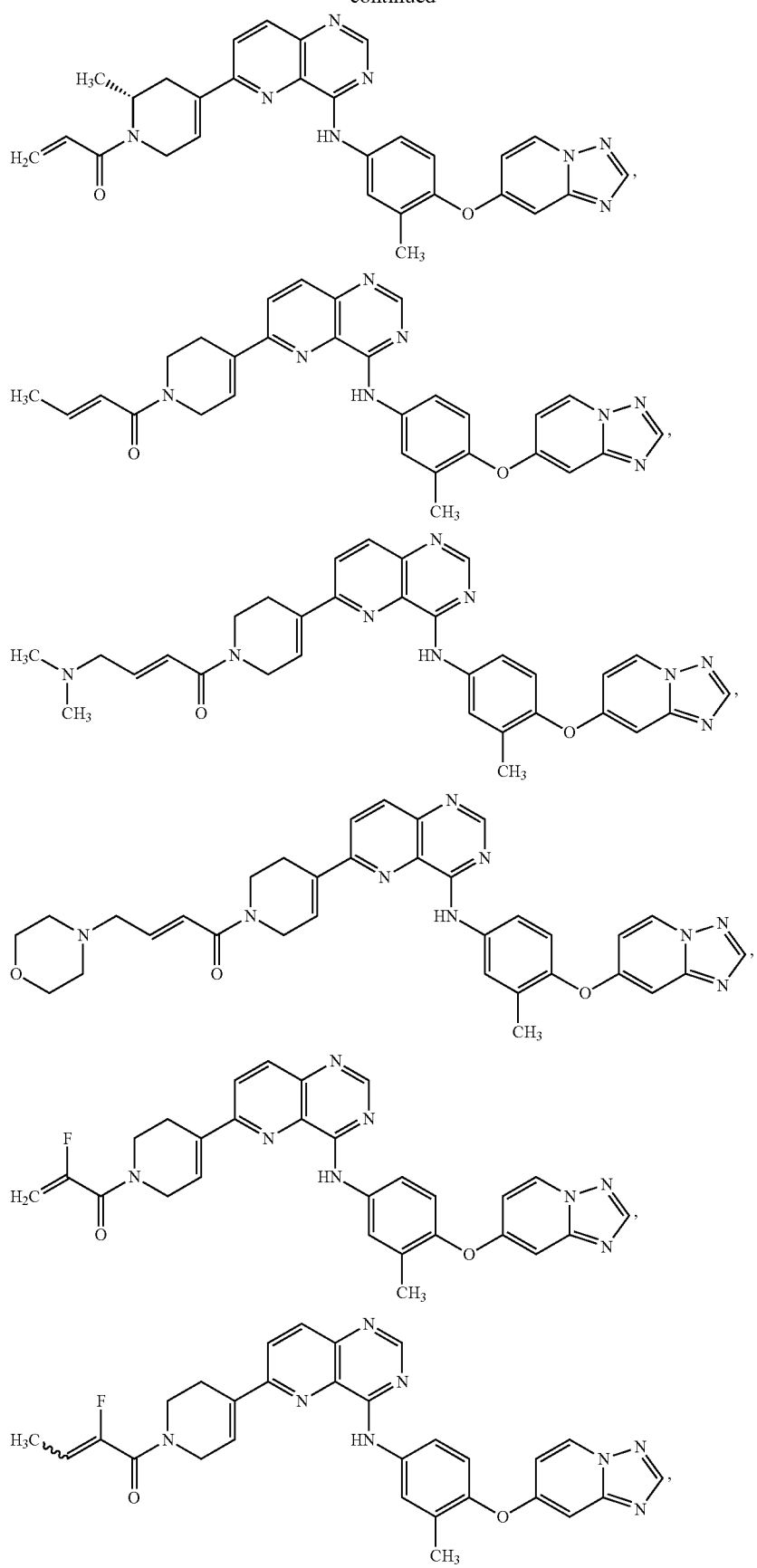

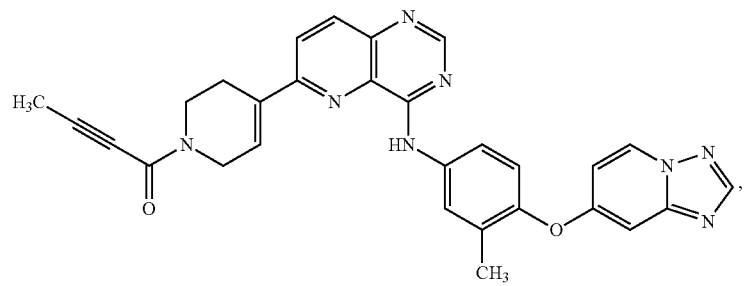
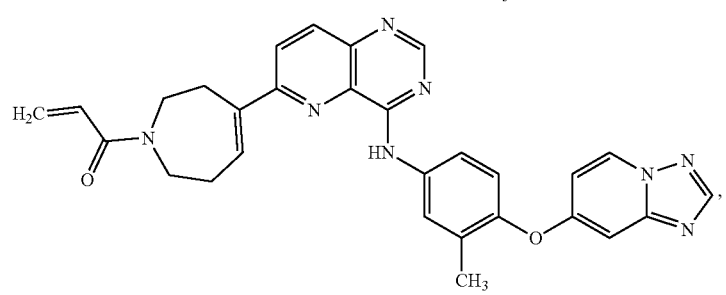
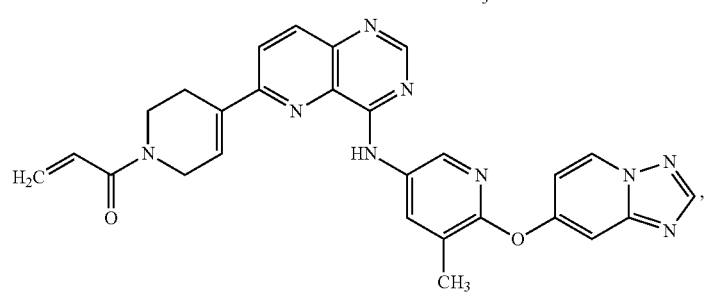
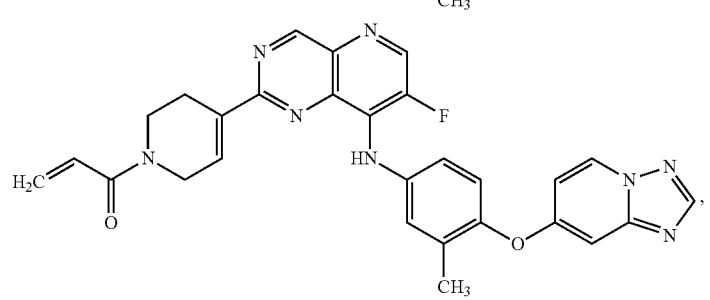
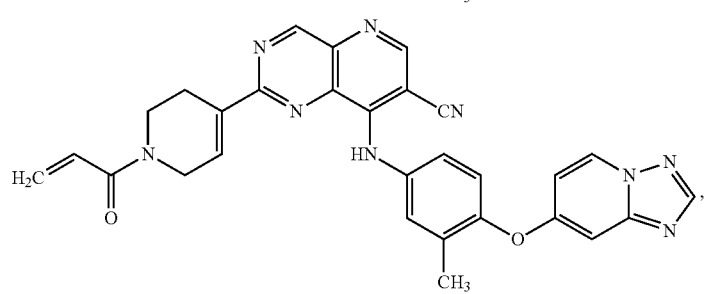
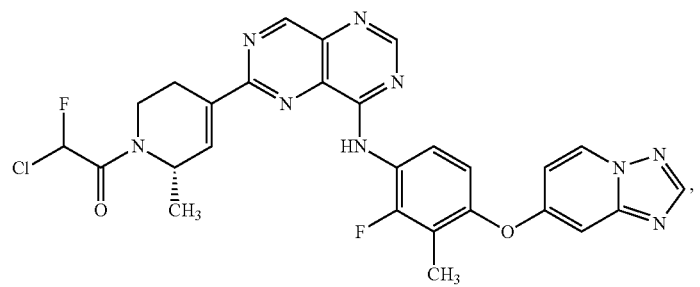

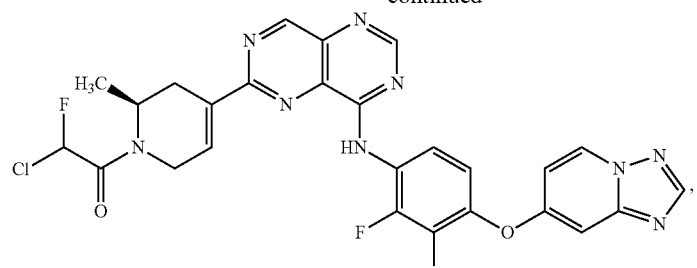
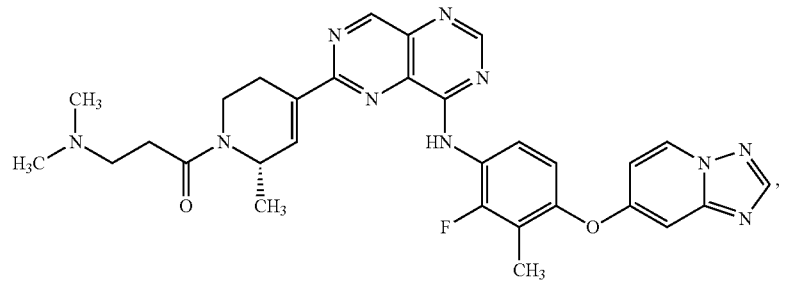
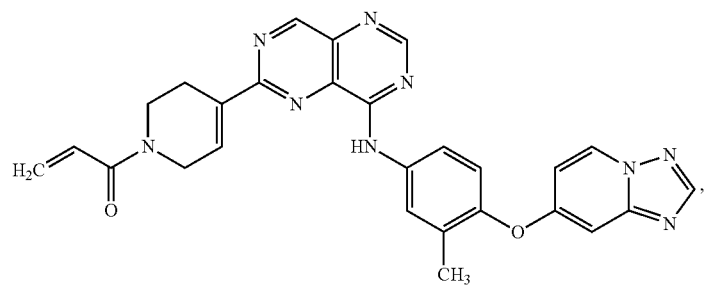
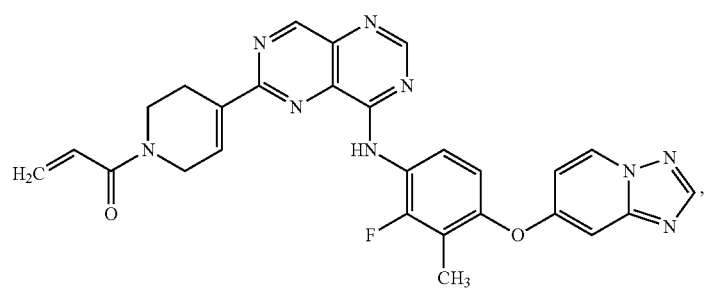
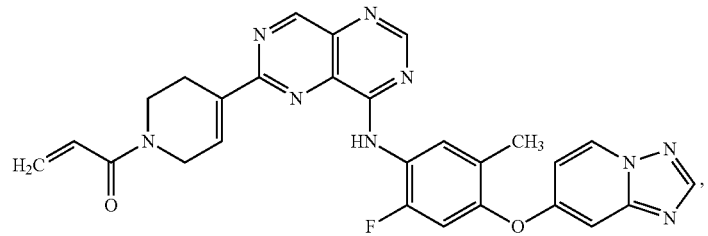
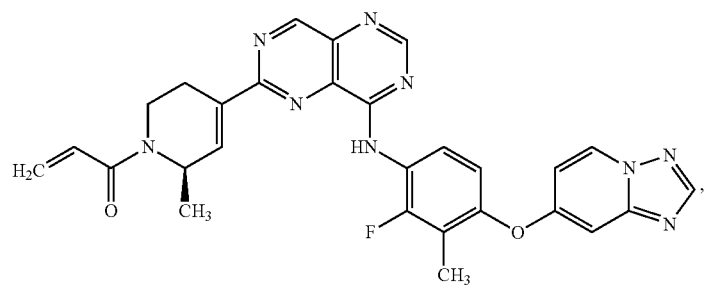

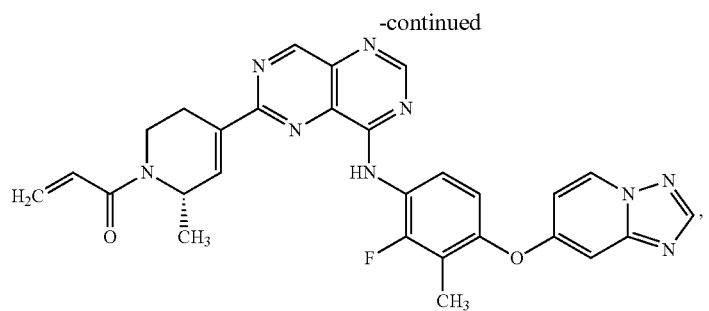
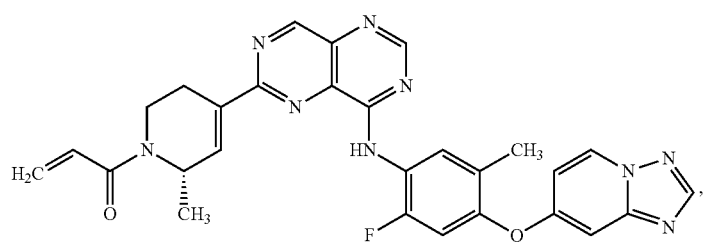
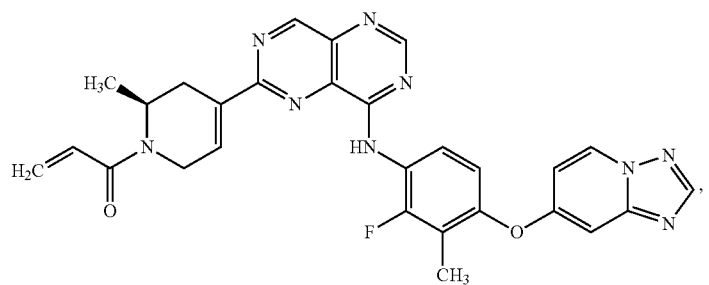
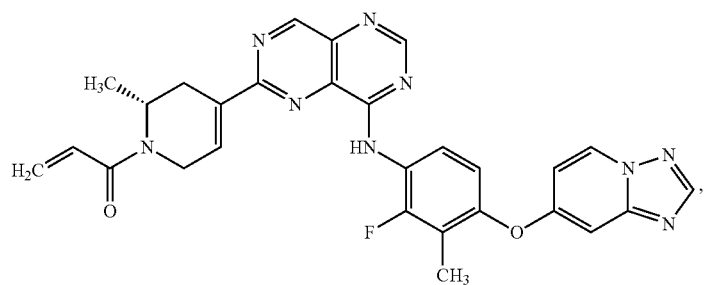
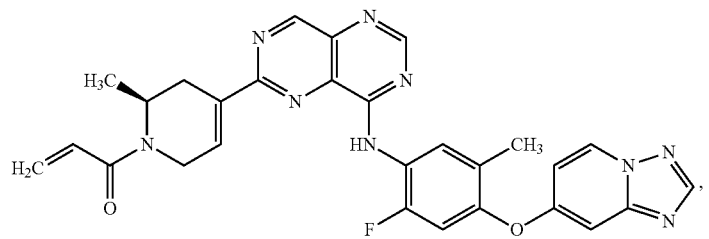
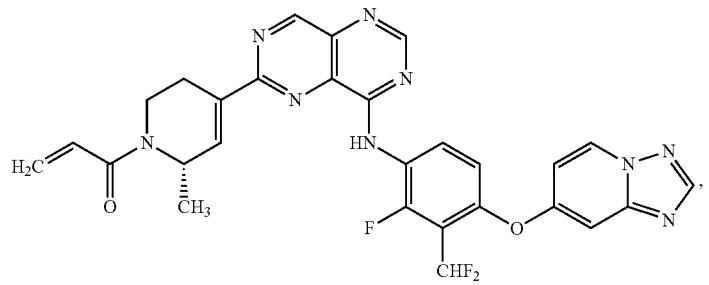

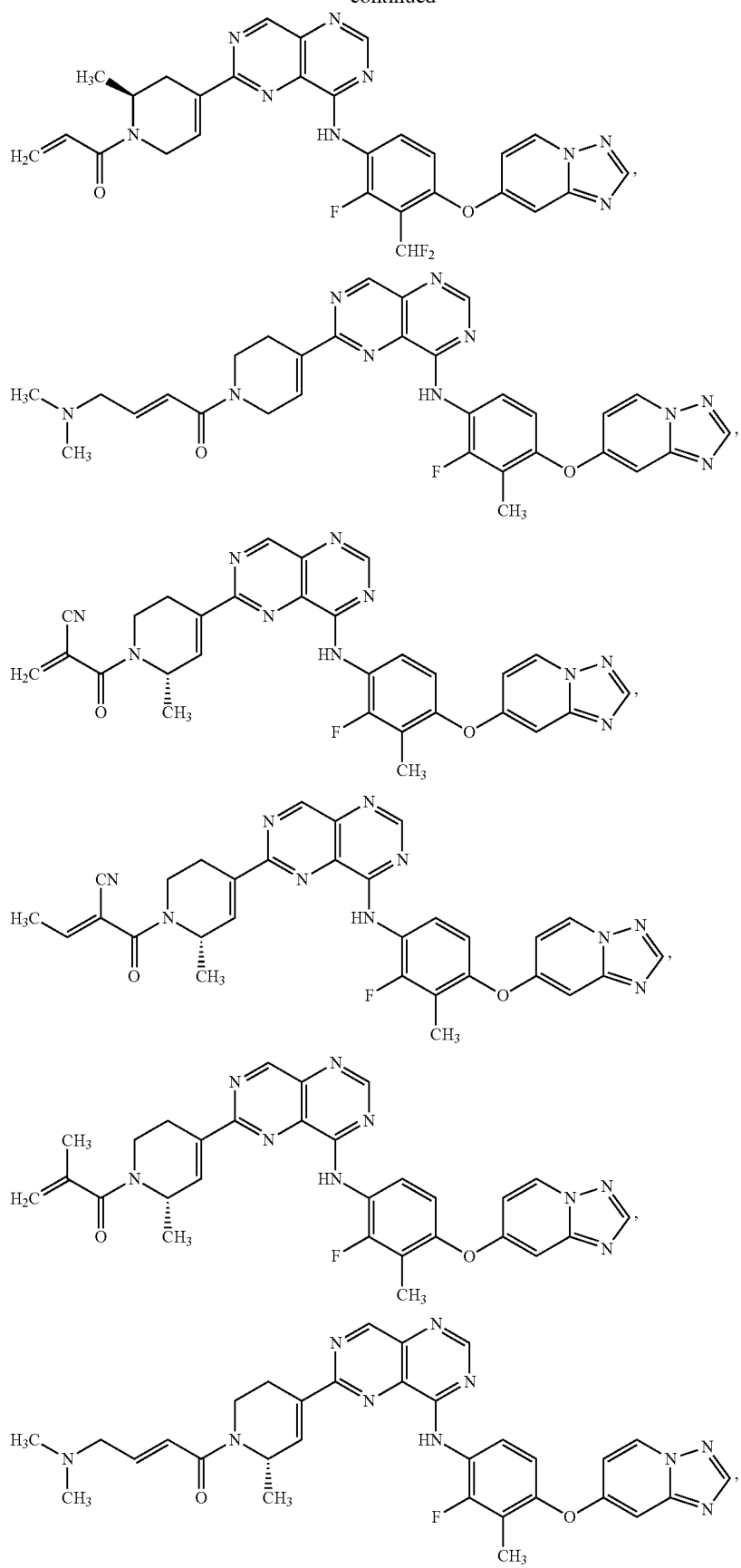

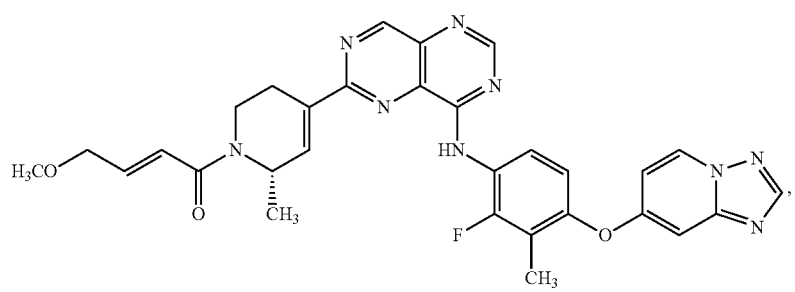
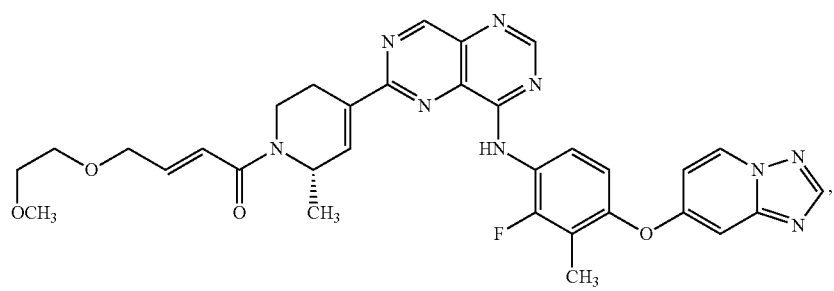
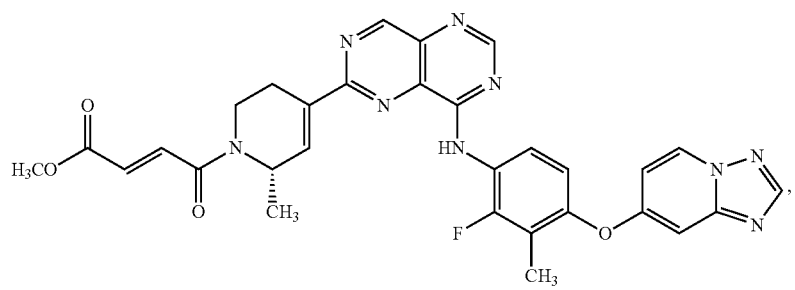
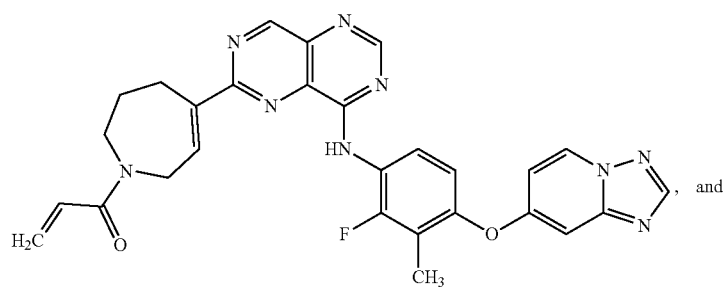
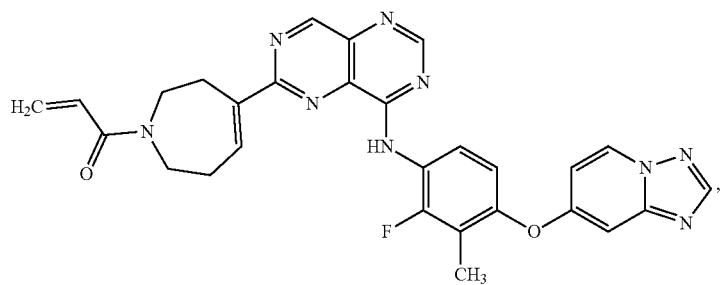
or a pharmaceutically acceptable salt or tautomer thereof.

32. The compound of claim 1, wherein the compound is:

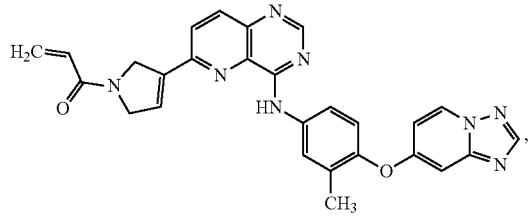 [SMILES: C=CC(=O)N1CC=C(c2ccc3ncnc(Nc4ccc(Oc5ccn6ncnc6c5)c(C)c4)c3n2)C1]

or a pharmaceutically acceptable salt thereof.

33. The compound of claim 1, wherein the compound is:

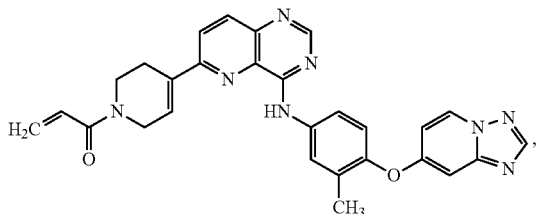

or a pharmaceutically acceptable salt thereof.

34. The compound of claim 1, wherein the compound is:

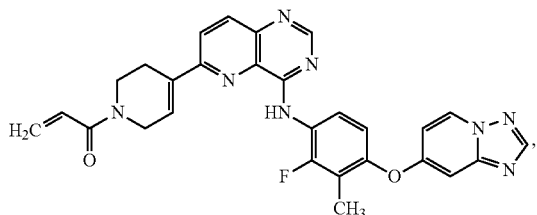

or a pharmaceutically acceptable salt thereof.

35. The compound of claim 1, wherein the compound is:

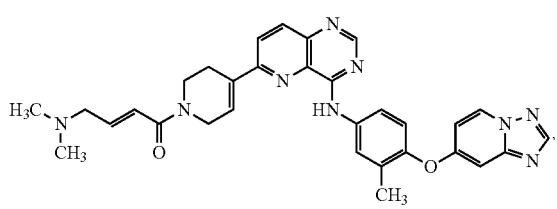 [SMILES: Cc1cc(Nc2ncnc3ccc(C4=CCN(C(=O)/C=C/CN(C)C)CC4)nc23)ccc1Oc1ccn2ncnc2c1]

or a pharmaceutically acceptable salt thereof.

36. The compound of claim 1, wherein the compound is:

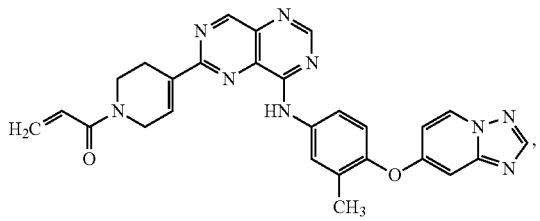 [SMILES: C=CC(=O)N1CC=C(c2ncc3ncnc(Nc4ccc(Oc5ccn6ncnc6c5)c(C)c4)c3n2)CC1]

or a pharmaceutically acceptable salt thereof.

37. The compound of claim 1, wherein the compound is:

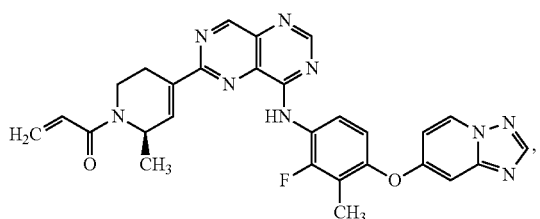

or a pharmaceutically acceptable salt thereof.

38. The compound of claim 1, wherein the compound is:

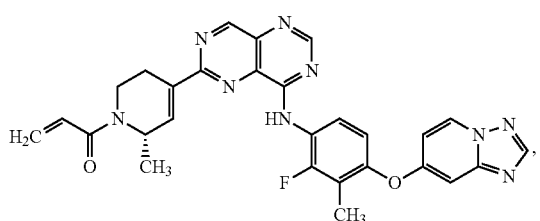

or a pharmaceutically acceptable salt thereof.

39. The compound of claim 1, wherein the compound is:

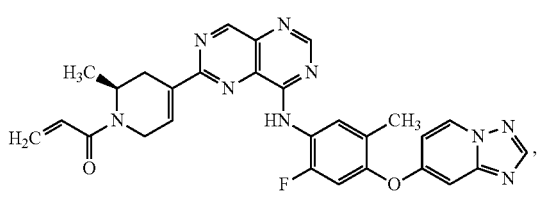 [SMILES: C=CC(=O)N1CC=C(c2ncc3ncnc(Nc4cc(C)c(Oc5ccn6ncnc6c5)cc4F)c3n2)C[C@@H]1C]

or a pharmaceutically acceptable salt thereof.

40. The compound of claim 1, wherein the compound is:

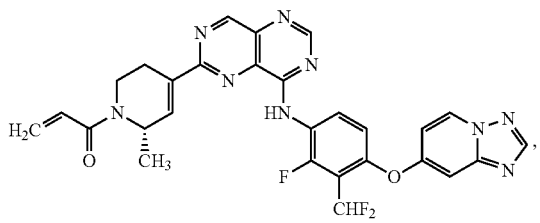 [SMILES: C=CC(=O)N1CCC(c2ncc3ncnc(Nc4ccc(Oc5ccn6ncnc6c5)c(C(F)F)c4F)c3n2)=C[C@@H]1C]

or a pharmaceutically acceptable salt thereof.

41. The compound of claim 1, wherein the compound is:

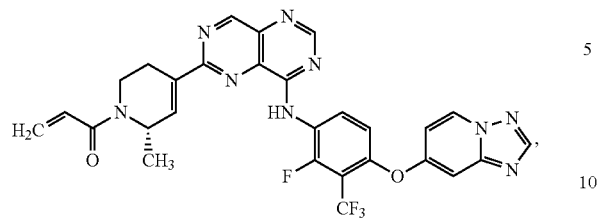

or a pharmaceutically acceptable salt thereof.

42. The compound of claim 1, wherein the compound is:

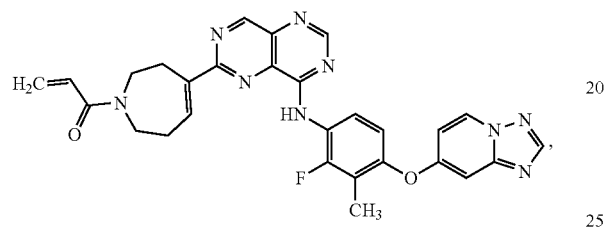

or a pharmaceutically acceptable salt thereof.

43. A pharmaceutical composition comprising a pharmaceutically acceptable excipient and the compound of claim 1, or a pharmaceutically acceptable salt, stereoisomer, or tautomer thereof.

* * * * *

UNITED STATES PATENT AND TRADEMARK OFFICE
CERTIFICATE OF CORRECTION

PATENT NO. : 12,037,346 B2
APPLICATION NO. : 17/718381
DATED : July 16, 2024
INVENTOR(S) : Kristin Lynne Andrews et al.

It is certified that error appears in the above-identified patent and that said Letters Patent is hereby corrected as shown below:

In the Claims

In Column 341, Line 63-64, Claim 1, replace "wherein the $C_{1-5}$ alkyl is optionally substituted" with --wherein each $C_{1-5}$ alkyl is optionally and independently substituted--.

In Column 342, Lines 56-57, Claim 1, replace "wherein the $C_{1-5}$ alkyl or $OC_{1-5}$ alkyl is optionally substituted" with --wherein each $C_{1-5}$ alkyl and $OC_{1-5}$ alkyl is optionally and independently substituted--.

In Column 343, Lines 8-9, Claim 1, replace "wherein the $C_{1-5}$ alkyl or $OC_{1-5}$ alkyl is optionally substituted" with --wherein each $C_{1-5}$ alkyl and $OC_{1-5}$ alkyl is optionally and independently substituted--.

In Column 348, Line 60, Claim 23, replace "wherein the $C_{1-5}$ alkyl is optionally substituted" with --wherein each $C_{1-5}$ alkyl is optionally and independently substituted--.

In Column 349, Line 8, Claim 23, replace "wherein the $C_{1-5}$ alkyl is optionally substituted" with --wherein each $C_{1-5}$ alkyl is optionally and independently substituted--.

Signed and Sealed this
Tenth Day of September, 2024

Katherine Kelly Vidal
*Director of the United States Patent and Trademark Office*